US010190108B2

(12) United States Patent
Mitchinson et al.

(10) Patent No.: US 10,190,108 B2
(45) Date of Patent: Jan. 29, 2019

(54) METHOD FOR REDUCING VISCOSITY IN SACCHARIFICATION PROCESS

(71) Applicant: Danisco US Inc., Palo Alto, CA (US)

(72) Inventors: Colin Mitchinson, Half Moon Bay, CA (US); Mian Li, Santa Clara, CA (US); Bradley R. Kelemen, Menlo Park, CA (US); Suzanne E. Lantz, San Carlos, CA (US); Keith D. Wing, Wilmington, DE (US); William D. Hitz, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 21 days.

(21) Appl. No.: 14/819,989

(22) Filed: Aug. 6, 2015

(65) Prior Publication Data

US 2017/0096651 A1 Apr. 6, 2017

Related U.S. Application Data

(63) Continuation of application No. 14/004,877, filed as application No. PCT/US2012/029445 on Mar. 16, 2012, now abandoned.

(60) Provisional application No. 61/453,923, filed on Mar. 17, 2011.

(51) Int. Cl.
C12N 9/42 (2006.01)
C12P 19/02 (2006.01)
C12P 19/14 (2006.01)

(52) U.S. Cl.
CPC ............ C12N 9/2437 (2013.01); C12P 19/02 (2013.01); C12P 19/14 (2013.01); C12Y 302/01004 (2013.01)

(58) Field of Classification Search
None
See application file for complete search history.

(56) References Cited

U.S. PATENT DOCUMENTS

| 4,797,361 | A | 1/1989 | Montenencourt |
| 5,405,769 | A | 4/1995 | Campbell et al. |
| 5,426,043 | A | 6/1995 | De Graaff et al. |
| 5,437,992 | A | 8/1995 | Bodie et al. |
| 5,536,325 | A | 7/1996 | Brink |
| 5,681,732 | A | 10/1997 | De Graaff et al. |
| 5,705,369 | A | 1/1998 | Torget et al. |
| 5,817,499 | A | 10/1998 | Dalboge et al. |
| 5,830,734 | A | 11/1998 | Christgau et al. |
| 5,997,913 | A | 12/1999 | Fowler et al. |
| 6,022,725 | A | 2/2000 | Fowler et al. |
| 6,132,727 | A | 10/2000 | Rohde, Jr. et al. |
| 6,409,841 | B1 | 6/2002 | Lombard |
| 6,423,145 | B1 | 7/2002 | Nguyen et al. |
| 6,509,171 | B1 | 1/2003 | Berka et al. |
| 6,555,335 | B1 | 4/2003 | Saloheimo et al. |
| 6,573,086 | B1 | 6/2003 | Emalfarb et al. |
| 6,660,506 | B2 | 12/2003 | Nguyen et al. |
| 6,768,001 | B2 | 7/2004 | Saloheimo et al. |
| 6,982,159 | B2 | 1/2006 | Dunn-Coleman et al. |
| 7,005,289 | B2 | 2/2006 | Dunn-Coleman et al. |
| 7,045,332 | B2 | 5/2006 | Dunn-Coleman et al. |
| 7,314,743 | B2 | 1/2008 | Clarkson et al. |
| 7,459,299 | B2 | 12/2008 | Goedegebuur et al. |
| 7,960,146 | B2 | 6/2011 | Dunn-Coleman et al. |
| 7,960,147 | B2 | 6/2011 | Danenberg et al. |
| 8,288,148 | B2 | 10/2012 | Cervin et al. |
| 8,476,048 | B2 * | 7/2013 | Caimi ...................... C12N 1/20 435/161 |
| 8,518,684 | B2 | 8/2013 | Brown et al. |
| 8,647,850 | B2 * | 2/2014 | Hitz ........................ C12N 1/20 435/161 |
| 8,673,618 | B2 | 3/2014 | Gusakov et al. |
| 8,721,794 | B2 | 5/2014 | Hennessey et al. |
| 8,906,235 | B2 | 12/2014 | Hennessey et al. |
| 9,175,275 | B2 * | 11/2015 | Gray ..................... C12N 9/2402 |
| 9,279,112 | B2 * | 3/2016 | Scott ....................... C12P 19/14 |
| 9,447,400 | B2 | 9/2016 | Bott et al. |
| 2002/0084046 | A1 | 7/2002 | Hsu et al. |
| 2003/0113732 | A1 | 6/2003 | Dunn-Coleman et al. |
| 2003/0113734 | A1 | 6/2003 | Dunn-Coleman et al. |
| 2003/0113735 | A1 | 6/2003 | Dunn-Coleman et al. |
| 2003/0114330 | A1 | 6/2003 | Dunn-Coleman et al. |
| 2004/0102619 | A1 | 5/2004 | Dunn-Coleman et al. |
| 2005/0191736 | A1 | 9/2005 | Brown et al. |
| 2006/0003408 | A1 | 1/2006 | Dunn-Coleman et al. |
| 2006/0075522 | A1 | 4/2006 | Cleveland et al. |
| 2006/0258554 | A1 | 11/2006 | Dunn-Coleman et al. |
| 2007/0031918 | A1 | 2/2007 | Dunson et al. |
| 2007/0031919 | A1 | 2/2007 | Dunson et al. |
| 2007/0031953 | A1 | 2/2007 | Dunson et al. |
| 2007/0037259 | A1 | 2/2007 | Hennessey et al. |
| 2007/0077630 | A1 | 4/2007 | Harris et al. |
| 2008/0076159 | A1 | 3/2008 | Baez-Vasquez et al. |
| 2008/0293109 | A1 | 11/2008 | Berka et al. |
| 2008/0299613 | A1 | 12/2008 | Merino et al. |

(Continued)

FOREIGN PATENT DOCUMENTS

DE 10043662 2/2001
EP 2397491 12/2011

(Continued)

OTHER PUBLICATIONS

Mach-Aigner et al., 'Transcriptional regulation of xyr1, encoding the main regulator of the xylanolytic and cellulolytic enzyme system in Hypocrea jecorina,' Applied and Environmental Microbiology, Nov. 2008, vol. 74, pp. 6554-6562.

(Continued)

Primary Examiner — Anand U Desai

(57) ABSTRACT

The present invention relates to compositions that can be used in hydrolyzing biomass such as compositions comprising a polypeptide having glycosyl hydrolase family 61/endoglucanase activity, methods for hydrolyzing biomass material, and methods for reducing viscosity of biomass mixture using a composition comprising a polypeptide having glycosyl hydrolase family 61/endoglucanase activity.

19 Claims, 122 Drawing Sheets

Specification includes a Sequence Listing.

(56) References Cited

U.S. PATENT DOCUMENTS

| | | |
|---|---|---|
| 2009/0050134 A1 | 2/2009 | Friend et al. |
| 2009/0099079 A1 | 4/2009 | Emalfarb et al. |
| 2009/0280541 A1 | 11/2009 | Jordan et al. |
| 2010/0124769 A1 | 5/2010 | Brown et al. |
| 2011/0039320 A1 | 2/2011 | Li et al. |
| 2011/0086408 A1 | 4/2011 | Power et al. |
| 2011/0136182 A1 | 6/2011 | Huang et al. |
| 2011/0212505 A1 | 9/2011 | Dunn-Coleman et al. |
| 2011/0318803 A1 | 12/2011 | Hitz et al. |
| 2012/0135499 A1 | 5/2012 | Bower et al. |
| 2013/0143277 A1 | 6/2013 | Gutierrez et al. |
| 2013/0143301 A1 | 6/2013 | Bott et al. |
| 2013/0177947 A1 | 7/2013 | Bower et al. |
| 2013/0337508 A1 | 12/2013 | Fujdala et al. |
| 2014/0073017 A1 | 3/2014 | Kaper et al. |
| 2014/0106408 A1 | 4/2014 | Mitchinson et al. |
| 2014/0134677 A1 | 5/2014 | Mitchinson et al. |
| 2014/0295475 A1 | 10/2014 | England et al. |
| 2015/0010981 A1 | 1/2015 | Yang et al. |
| 2016/0060665 A1 | 3/2016 | Power et al. |
| 2016/0177279 A1 | 6/2016 | Bower et al. |
| 2016/0272956 A1 | 9/2016 | Diez Garcia et al. |

FOREIGN PATENT DOCUMENTS

| | | |
|---|---|---|
| WO | 9700964 | 1/1997 |
| WO | 9815633 | 4/1998 |
| WO | 9902693 | 1/1999 |
| WO | 0149859 A1 | 7/2001 |
| WO | 02095014 A2 | 11/2002 |
| WO | 03027306 A2 | 4/2003 |
| WO | 03052118 A2 | 6/2003 |
| WO | 03093420 | 11/2003 |
| WO | 2004016760 A2 | 2/2004 |
| WO | 2004033646 A2 | 4/2004 |
| WO | 2004043980 A2 | 5/2004 |
| WO | 2004078919 A2 | 9/2004 |
| WO | 2004081185 A2 | 9/2004 |
| WO | 2005001036 A2 | 1/2005 |
| WO | 2005001065 A2 | 1/2005 |
| WO | 2005028636 A2 | 3/2005 |
| WO | 2005074647 A2 | 8/2005 |
| WO | 2005074656 A2 | 8/2005 |
| WO | 2005093050 A2 | 10/2005 |
| WO | 2005093073 A1 | 10/2005 |
| WO | 2005118769 | 12/2005 |
| WO | 2006074005 A2 | 7/2006 |
| WO | 2006110901 A2 | 10/2006 |
| WO | 2006110902 | 10/2006 |
| WO | 2006114095 | 11/2006 |
| WO | 2007071818 | 6/2007 |
| WO | 2007089290 A2 | 8/2007 |
| WO | 2007094852 A2 | 8/2007 |
| WO | 2008025165 | 3/2008 |
| WO | 2008039370 A1 | 4/2008 |
| WO | 2008045977 A2 | 4/2008 |
| WO | 2008140749 A2 | 11/2008 |
| WO | 2008147396 A2 | 12/2008 |
| WO | 2008151079 A2 | 12/2008 |
| WO | 2008153712 A2 | 12/2008 |
| WO | 2008153903 A2 | 12/2008 |
| WO | 2009003167 A1 | 12/2008 |
| WO | 2009009142 A2 | 1/2009 |
| WO | 2009033071 A2 | 3/2009 |
| WO | 2009035537 A1 | 3/2009 |
| WO | 2009045627 A2 | 4/2009 |
| WO | 2009074685 A1 | 6/2009 |
| WO | 2009076676 A2 | 6/2009 |
| WO | 2009085859 A2 | 7/2009 |
| WO | 2009108941 A2 | 9/2009 |
| WO | 2009117689 A1 | 9/2009 |
| WO | 2009132008 A2 | 10/2009 |
| WO | 2009149202 A2 | 12/2009 |
| WO | 2010096673 A1 | 8/2010 |
| WO | 2010138754 A1 | 12/2010 |
| WO | 2010141779 A1 | 12/2010 |
| WO | 2010148148 A2 | 12/2010 |
| WO | 2011038019 A2 | 3/2011 |
| WO | 2011063308 A2 | 5/2011 |
| WO | 2011079048 A2 | 6/2011 |
| WO | 2011137150 A1 | 11/2011 |
| WO | 2011153276 A2 | 12/2011 |
| WO | 2011161063 A1 | 12/2011 |
| WO | 2012030845 A2 | 3/2012 |
| WO | 2012125925 A2 | 9/2012 |
| WO | 2012125937 A2 | 9/2012 |
| WO | 2012125951 A1 | 9/2012 |
| WO | 2012154735 A2 | 11/2012 |
| WO | 2013090053 A1 | 6/2013 |
| WO | 2014070837 A1 | 5/2014 |
| WO | 2014070841 A1 | 5/2014 |
| WO | 2014093275 | 6/2014 |
| WO | 2015017254 A1 | 2/2015 |
| WO | 2015017255 A1 | 2/2015 |
| WO | 2015017256 A1 | 2/2015 |
| WO | 2015084596 A1 | 6/2015 |

OTHER PUBLICATIONS

Machida et al., 'Nucelotide sequences of Saccharomycopsis fibuligera genes for extracellular β-glucosidases as expressed in Saccharomyces cerevisiae,' Appl. Environ. Microbiol., 1988, vol. 54, pp. 3147-3155.

Mamma et al., 'Fungal multienzyme production on industrial by-products of the citrus-processing industry,' Bioresource Tech., Jun. 2007, vol. 99, pp. 2373-2383.

Mandels, Cellulases Annu. Rep. Ferment. Process., 1982, 5, 35.

Margolles et al., 'Purificationa nd functional characterization of a novel α-l-arabinofuranosidase from bifidobacterium longum B66,' Appl. Environ. Microbiol., 2003, vol. 69, pp. 5096-5103.

Margolles-Clark, 'Cloning of genes encoding alpha-L-arabinofuranosidase and beta-xylosidase from Trichoderma reesei by expression in Saccharomyces cerevisiae,' Appl. Environ. Microbiol., 1996, vol. 62, No. 10, pp. 3840-3846.

Margolles-Clark, 'Expression patterns of ten hemicellulase genes of the filamentous fungus Trichoderma reesei on various carbon sources' Journal of Biotechnology, Sep. 16, 1997, vol. 57, pp. 167-179.

Matsuo. M., et al., "Four Types of β-Xylosidases from Penicillium wortmanni IFO 7237," Agricultural and Biological Chemistry, 1987, vol. 51, No. 9, pp. 2367-2379.

Megazyme, 1,4-β-D-xylohexaose (Lot 121206), 2013.

Miyazaki et al., 'Hyperthermophilic α-L-arabinofuranosidase from thermotoga maritima MSB8: molecular cloning, gene expression, and characterization of the recombinant protein,' Extremophiles, 2005, vol. 9, pp. 399-406.

Morosoli et al., 'Purification and properties of a xylanase from Streptomyces lividans,' Biochem. J., 1986, vol. 239, pp. 587-592.

Nagendran et al., 'Reduced genomic potential for secreted plant cell-wall-degrading enzymes in the ectomycorrhizal fungus Amanita bisporigera, based on the secretome of Trichoderma reesei,' Funal Genetics Biol., 2009, vol. 46, pp. 427-435.

Numan et al., 'α-L-arabinofuranosidases: the potential applications in biotechnology,' J. Ind. Microbiol. Biotechnol., 2006, vol. 33, pp. 247-260.

Nuyens et al., Heterologous expression of the bacillus pumilus endo-β-xylanase (xynA) gene in the yeast Saccharomyces cerevisiae, Applied Microbiology and Biotechnology, 2001, vol. 56, pp. 431-434.

Ogasawara et al., 'Cloning, Functional Expression and Promoter Analysis of Xylanase III Gene from Trichoderma reesei,' Applied Microbiology and Biotechnology, 2006, vol. 72:5, pp. 995-1003.

Oguntimein et al., 'Properties of soluble and immobilized Aspergillus niger β-xylosidase,' Biotechnol. Bioeng., 1980, vol. 22, pp. 1143-1154.

Olofsson et al., 'A short review on SSF—an interesting process option for ethanol production from lignocellulosic feedstocks,' Biotech Biofuels, 2008, 1, 7.

(56) References Cited

OTHER PUBLICATIONS

Olsson et al., 'Fermentation of lignocellulosic hydrolysates for ethanol production,' Enzyme Microb Technol., 1996, vol. 18, pp. 312-331.
Oshima et al., 'Purification and characterization of an Exo-1,5-alpha-L-arabinanase from Aspergillus sojae,' Journal of Applied Glycoscience, 2005, vol. 52, pp. 261-265.
Pace et al., 'How to measure and predict the molar absorption coefficient of a protein,' Protein Science, 1995, vol. 4, pp. 2411-2423.
Panagiotou et al., 'Induction, purification and characterization of two extracellular-L-arabinofuranosidases from Fusarium oxysporum,' Can. J. Microbiol., 2003, vol. 49, pp. 639-644.
Pearson et al., 'Improved tools for biological sequence comparison,' Proc. Natl. Acad. Sci. USA, 1988, 85, pp. 2444-2448.
Pentilla et al., 'A versatile transformation system for the cellulolytic filamentous fungus *Trichoderma reesei*,' Gene, 1987, vol. 61, pp. 155-164.
Persson et al., 'Fungal cellulolytic enzyme production: a review,' Process Biochemistry, 1991, vol. 26, pp. 65-74.
Pinphanichakarn et al., 'Purification and characterization of β-xylosidase from *Streptomyces* sp. CH7 and its gene sequence analysis,' World J. Microbiol. Biotechnol., 2004, vol. 20, pp. 727-733.
Pollet et al., 'Structural determinants of the substrate specificities of xylanases from different glycoside hydrolase families,' Critical Reviews in Biotechnology, 2010, vol. 30:3, pp. 176-191.
Pozzo et al., 'Structural and functional analysis of β-glucosidase 3B from thermotoga neapolitana: a thermostable three-domain representative of glycoside hydrolase 3,' J. Mol. Biol., 2010, vol. 397, pp. 724-739.
Prior et al., 'Hydrolysis of Ammonia-pretreated Sugar Cane Bagasse with Cellulase, β-Glucosidase and Hemicellulase Preparations,' Applied Biochemistry and Biotechnology, Mar. 2008, vol. 146, Issue 1-3, pp. 151-164.
Rahman et al., 'A role of xylanase,-L-arabinofuranosidase and xylosidase in xylan degradation,' Can. J. Microbiol., 2003, vol. 49, pp. 58-64.
Rahman et al., 'Substrate specificity of the α-L-arabinofuranosidase from Rhizomucor pusillus HHT-1,' Carbohydrate Research, 2003, vol. 338, pp. 1469-1476.
Reen et al., 'Molecular characterization and expression analysis of the first hemicellulase gene (bxl1) encoding β-xylosidase from the thermophilic fungus *Talaromyces emersonii*,' Biochem. Biophys. Res. Commun., 2003, vol. 305, No. 3, pp. 579-585.
Rose et al., 'Crystallization and preliminary x-ray diffraction study of a xylanase from trichoderma harzianum,' J. Mol. Biol., 1987, vol. 194, No. 4, pp. 755-756.
Sader et al., 'Application of Kjeldahl and Dumas combustion methods for nitrogen analysis,' Archives of Veterinary Science, 2004, vol. 9, No. 2, pp. 73-79.
Saha et al., 'a-L-Arabinofuranosidases: biochemistry, molecular biology and application in biotechnology,' Biotechnology Advances, 2000, vol. 18, pp. 403-423.
Saha, B.C., "Xylanase from a newly isolated Fusarium verticillioides capable of utilizing corn fiber xylan," Applied Microbiol and Biotechnol, Sep. 1, 2001, vol. 56, No. 5-6, pp. 762-766.
Saha et al., 'Purification and characterization of an extracellular β-xylosidase from a newly isolated Fusarium verticilloides,' J Indust. Microbiol. Biotechnol., 2001, vol. 27, pp. 241-245.
Sakamoto et al., 'Purification and properties of two type-B α-L-arabinofuranosidases produced by Penicillum chrysogenum,' Biochimic et Biophys. Acta, 2003, vol. 1621, pp. 204-210.
Schmidt et al., 'Xylanases and β-xylosidase of trichoderma lignorum,' Methods in Enzymology, 1988, vol. 160, pp. 662-671.
Schulein et al., 'Cellulases of trichoderma reesei,' Methods in Enzymology, 1988, vol. 160, pp. 234-242.
Schulte et al., UniProt, Accession No. Q9P3R7, version 15, Apr. 14, 2009.
Shallom et al., 'Microbial Hemicellulases,' Current Opinion in Microbiology, 2003, vol. 6:3, pp. 219-228.
Shallom et al., 'Biochemical characterization and identification of the catalytic residues of a family 43 beta-D-Xylosidase from Geobacillus stearothermophilus T-6,' Biochemistry, 2005, vol. 44, pp. 387-397.
Shallom et al., 'Detailed kinetic analysis and identification of the nucleophile in α-L-arabinofuranosidase from Geobacillus stearothermophilus T-6, a family 51 glycoside hydrolase,' J. Biol. Chem., 2002, vol. 277, pp. 43667-43673.
Shareck et al., 'Sequences of three genes specifying xylanases in Streptomyces lividans,' Gene, 1991, vol. 107, pp. 75-82.
Sheir-Neiss et al., 'Characterization of the secreted cellulases of Trichoderma reesei wild type and mutants during controlled fermentations,' Appl. Microbiol. Biotechnology, 1984, vol. 20, pp. 46-53.
Shin et al., 'Purification and characterization of α-L-arabinopyranosidase and α-L-arabinofuranosidase from bifidobacterium breve K-110, a human intestinal anaerobic bacterium metabolizing ginsenoside Rb2 and Rc,' Appl. Environ. Microbiol., 2003, vol. 69, pp. 7116-7123.
Shinoyama, Hirofumi, et al., "Enzymatic Synthesis of Alkyl β-Xylosides from Xylobiose by Application of the Transxylosyl Reaction of Aspergillus niger β-Xylosidase," Agricultural and Biological Chemistry, Jan. 1, 1988, vol. 52, No. 9, pp. 2197-2202.
Shirkot et al., 'Effect of Dithiocarbamates on Cellulase Activity in Culture Filtrates of Trichoderma reesei,' Biotechnology and Bioengineering, 1982, vol. XXIV, pp. 1233-1240.
Simpson et al., 'An extremely thermostable xylanase from the thermophilic eubacterium thermotoga,' Biochem. J., 1991, vol. 277, pp. 413-417.
Sluiter et al., 'Determination of structural carbohydrates and lignin in biomass,' National Renewable Energy Laboratory, 2008, Golden, CO, pp. 1-15.
Abdelkader et al., 'In-vitro studies on wood degradation in soil by soft-rot fungi: *Aspergillus niger* and *Penicillium chrysogenum*,' International Biodeterioration & Biodegradation, 2013, vol. 78, pp. 98-108.
Akel, Eda, "Molecular Regulation of Arabinan and I-Arabinose Metabolism in Hypocrea jecorina (Trichoderma reesei)," Eukaryotic Cell, Dec. 1, 2009, vol. 8, No. 12, pp. 1837-1844.
Altschul et al., 'BLAST Manual,' J. Mol. Biol., 1990, vol. 215, pp. 403-410.
Altschul et al., 'Gapped BLAST and PSI-BLAST: a new generation of protein database search programs,' Nucleic Acids Research, 1997, vol. 25:17, pp. 3389-3402.
Andrade et al., 'Effect of carbon source on the biochemical properties of β-xylosidases produced by Aspergillus versicolor,' Process Biochem., 2004, vol. 39, pp. 1931-1938.
Ausubel et al., (eds.) 'Current Protocols in Molecular Biology,' 1987, Supplement 30, Section 7.7.18 (Book Not Included).
Barnett et al., 'Cloning and amplification of the gene encoding an extracellular β-glucosidase from Trichoderma reesei: evidence for improved rates of saccharification of cellulosic substrates,' Biotechnology, 1991, vol. 9, No. 6, pp. 562-567.
Berka et al., 'Molecular cloning and deletion of the gene encoding aspergillopepsin A from Aspergillus awamori,' Gene, 1990, vol. 86, pp. 153-162.
Bernier et al., 'Molecular cloning of a Bacillus subtilis xylanase gene in *Escherichia coli*.' Gene, 1983, vol. 26, No. 1, pp. 59-65.
Biely et al., 'Proceedings of the second TRICEL symposium on Trichoderma reesei Cellulases and other Hydrolases,' Espoo, Finland 1993, Souminen, P. and Reinikainen, R. (eds.), Foundation for Biotechnical and Industrial Fermentation Research, 1993, vol. 8, pp. 125-135.
Brown, et al., "Comparative Analysis of 87,000 Expressed Sequence Tags from the Fumonisin-producingfungus *Fusarium verticillioides*," Fungal Genetics and Biology, CA, US, San Diego, vol. 42, No. 10, Oct. 1, 2005, pp. 848-861.
Brüx, Christian, et al., "Crystallization and preliminary crystallographic analysis of a family 43 β-D-xylosidase from Geobacillus stearothermophilus T-6," Acta Crystallographica, Section F., Nov. 12, 2005, pp. 1054-1057.

(56) References Cited

OTHER PUBLICATIONS

Brüx et al., The structure of an inverting GH43 β-xylosidase from geobacillus stearothermophilus with its substrate reveals the role of the three catalytic residues, J. Mol. Biol., 2006, vol. 359, pp. 97-109.
Campbell et al., 'Improved transformation efficiency of Aspergillus niger using the homologous niaD gene for nitrate reductase,' Current Genetics, 1989, vol. 16, pp. 53-56.
Canals et al., 'Structure of xylanase Xys1 from Steptomyces halstedii,' Acta Crystalogr. Section D Biological Chrystallography, 2003, vol. 59, pp. 1447-1453.
Cantarel et al., 'The carbohydrate-active enzymes database (CAZy): an expert resource for Glycogenomics,' Nucleic Acids Res., 2009, vol. 37, pp. D233-D238.
Chacon-Martinez et al., 'Identification and characterization of the α-L-arabinofuranosidase B of *Fusarium oxysporum* f. sp. Dianthi,' Physiol. Mol. Plant Pathol., 2004, vol. 64, pp. 201-208.
Chen et al., 'Potential of agricultural residues and hay for bioethanol production,' Appl Biochem Biotechnol., Sep. 2007, vol. 142(3), pp. 276-290.
Chen et al., 'Purification and characterization of two extracellular β-glucosidases from Trichoderma reesei,' Biochimica et Biophysica Acta, 1992, vol. 1121, pp. 54-60.
Clarke et al., 'A modular xylanase from mesophilic Cellulomonas fimi contains the same cellulose-binding and thermostabilizing domains as xylanases from thermophilic bacteria,' Fems Microbiology Letters, 1996, vol. 139, pp. 27-35.
Coutinho et al., 'The modular structure of cellulases and other carbohydrate-active enzymes: an integrated database approach,' Genetics, Biochemistry, and Ecology of Cellulse Degradation, UNI Publishers Co., 1999, pp. 15-23.
Cuomo et al., 'The Fusarium Graminearum Genome Reveals a link between localized polymorphism and pathogen specialization,' Science, 2007, vol. 317, pp. 1400-1402.
Database EMBL [Online], Database Accession No. DR631218 sequence, Jul. 12, 2005, "EST1021346 Fvl Gibberella moniliformis cDNA clone FVIE185, mRNA sequence," retrieved from EBI Accession No. EMBL: DR631218.
Database EMBL [Online], Database Accession No. DR628222 sequence, Jul. 12, 2005, "EST1018350 Fvl Gibberella moniliformis cDNA clone FVICQ42, mRNA sequence," retrieved from EBI Accession No. EM EST: DR628222.
Database EMBL [Online] Database Accession No. DR630608 sequence, Jul. 12, 2005, "EST1020736 Fvl Gibberella moniliformis cDNA clone FVIDS84, mRNA sequence," retrieved from EBI Accession No. EM EST: DR630608.
Database UniProt [Online], Database Accession No. Q09LXO sequence, Oct. 17, 2006, "SubName: Full=Beta-xylosidase", retrieved from EBI Accession No. UNIPROT: Q09LXO.
Database UniProt [Online], Database Accession No. A4UVM8 Sequence, May 15, 2007, retrieved from EBI Accession No. UNIPROT: A4UVM8.
Database Geneseq [Online] Database Accession No. AXR37961 sequence, Nov. 26, 2009, "Plant biomass degradation related protein SEQ ID No. 107," retrieved from EBI Accession No. GSP: AXR37961 xp002672566.
Database Geneseq [Online], Database Accession No. AXR38055 sequence, Nov. 26, 2009, "Plant biomass degradation related SEQ 1D No. 199," retrieved from EBI Accession No. GSP: AXR38055.
Database Geneseq [Online], Accession No. AXR38027, Nov. 26, 2009, "Plant biomass degradation related SEQ 1D No. I72," retrieved from EBI Accession No. GSP: AXR38027.
Database Geneseq [Online], Database Accession No. AXR38047 sequence, Nov. 26, 2009, "Plant biomass degradation related SEQ 1D No. 192," retrieved from EBI Accession No. GSP: AXR38047.
Database Geneseq ID: AXR39051 )Plant biomass degrading enzyme encoding DNA #271): SEQ ID No. 2785 from International Patent Application Publication No. WO2009108941-A2, published Sep. 3, 2009, printed Mar. 18, 2016, pp. 1-2.
Database EMBL, Database Accession No. AB093564, 'Penicillium herquei mRNA for xylosidase, complete cds.', Apr. 15, 2003, XP002633644.
Database EMBL, Database Accession No. EF490448, 'Penicillium purpurogenum alpha-L-arabinofuranosidase 2 (abf2) gene, complete cds.', Apr. 19, 2007, XP002633645.
Database REFSEQ, Database Accession No. XP_383785, NCBI reference sequence collection Hypothetical protein FG03609 [Giberella zeae PH-1], Apr. 9, 2008, XP002660306.
Database REFSEQ, Database Accession No. XP 386639.1, NCBI reference sequence collection Hypothetical protein FG06463.1 [Giberella zeae PH-1], Apr. 9, 2008, XP002660307.
Database EMBL, Database Accession No. FJ040192, '*Trichoderma* sp. SSL endoglucanase IV mRNA, complete cds.', Sep. 22, 2008, XP002683383.
Database EMBL, Database Accession No. GY256384, 'Sequence 1 from U.S. Pat. No. 7,960,146,' Jun. 21, 2011.
Debeche et al., 'Probing the catalytically residues of the α-L-arabinofuranosidase from Thermobacillus kylanilyticus,' Protein Engineering, 2002, vol. 15, No. 1, pp. 21-28.
Deog et al., 'Construction and characterization of novel chimeric beta-glucosidases with Cellvibrio gilvus (CG) and thermotoga maritima TM by overlapping PCR,' Biotechnology and Bioprocess Engineering, Jun. 1, 2009, vol. 14, No. 3, pp. 266-273.
Dogaris, Ioannis, et al. Induction of Cellulases and hemicellulases from Neurospora crassa under solid-state cultivated for bioconversion of sorghum bagasse into alcohol, Industrial Crops and Products, Mar. 2009, vol. 29, No. 2-3, pp. 404-411.
Dominguez et al., 'A common protein fold and similar active site in two distinct families of β-glycanases,' Nature Structural Biology, Jul. 1995, vol. 2, No. 7, pp. 569-576.
Drouet, Philippe, et al., "Production of Alkyl β-D-Xylosides with the Trichoderma reesei β-Xylosidase," Annals of the New York Academy of Sciences, Mar. 1, 1995, vol. 750, pp. 306-311.
Drouet et al., 'Enzymatic synthesis of alkyl β-D-xylosides by transylosylation and reverse hydrolysis,' Biotech Bioeng., 1994, vol. 43, pp. 1075-1080.
Emsley et al., 'Features and development of Coot,' ACTA Cryst., 2010, vol. D66, pp. 486-501.
Foreman et al., 'Transcirptional regulation of biomass-degrading enzymes in the filamentous fungus *Trichoderma reesei*,' Journal of Biological Chemistry, Aug. 22, 2003, vol. 278, No. 34, pp. 31988-31997.
Fusarium Comparative Genome Project, Broad Institute, pp. 1-6; www.broadinstitute.org/scientific-community/science/projects/fungal-genome-initiative/fusarium-comparative-genome-project; printed Mar. 3, 2017.
Galbe et al., 'A review of the production of ethanol from softwood,' Appl. Microbiol. Biotechnol., 2002, vol. 59, pp. 618-628.
Gargouri, Mohamed, et al., "Fungus β-glycosidases: immobilization and use in alkyl-β-glycoside synthesis," Journal of Molecular Catalysis B: Enzymatic, Jun. 1, 2004, vol. 29, No. 1-6, pp. 89-94.
Geneseq Accession No. AXR37961 (Plant biomass degradation related protein; SEQ ID No. 107 from WO2009108941-A2, published Sep. 3, 2009), printed Mar. 29, 2012.
GenBank Accession No. EGU86020 (hypothetical protein FOXB_03424 [Fusarium oxysporum Fo5176]): Aug. 5, 2011, last modification date Aug. 5, 2011; printed on Mar. 9, 2016, pp. 1-2, XP002672563.
GenBank Accession No. CAK96229 (unnamed protein product [Aspergillus niger]): Feb. 17, 2011, last modification date Mar. 14, 2015); printed on Mar. 9, 2016, pp. 1-2, XP002672561.
GenBank Accession No. AAD13106 (beta-xylosidase [Aspergillus niger]]): Dec. 4, 2001, last modification date Dec. 4, 2001; printed on Mar. 9, 2016, pp. 1-2, XP002672562.
GenBank Accession No. KNA97832, Beta-glucosidase, *Fusarium oxysporum* F. Sp. Lycopersici 4287), last modification date Jul. 23, 2015; printed on Mar. 3, 2017, pp. 1-2.
GenbankAccession No. XM_018379766, *Fusarium oxysporum* F. Sp. Lycopersici 4287 beta glucosidase mRNA, last modification date Sep. 26, 2016; printed on Mar. 3, 2017, pp. 1-2.

(56) References Cited

OTHER PUBLICATIONS

Genbank Accession No. XM_018893759, Fusarium Verticilloides 7600 beta-glucosidase mRNA, last modification date Oct. 27, 2016; printed on Mar. 3, 2017, pp. 1-2.
Genbank Accession No. XP_018235880, Beta glucosidase *Fusarium oxysporum* f. sp. Lycopersici 4287, last modification date Sep. 26, 2016; printed on Mar. 3, 2017; pp. 1-2.
Genbank Accession No. XP_018750667, Beta-glucosidase fusarium verticilloides 7600, last modification date Oct. 27, 2016; printed on Mar. 3, 2017; pp. 1-2.
Genbank Accession No. XM_018379764, *Fusarium oxysporum* f. sp. Lycopersici 4287 beta glucosidase mRNA, last modification date Sep. 26, 2016; printed on Mar. 3, 2017, pp. 1-2.
Genbank Accession No. AY281374.1, Trichoderma reesei strain QM6a Cel3b (cel3b) mRNA, Last modification date Mar. 25, 2015; printed on Mar. 17, 2016; pp. 1-2.
Genbank Accession No. XM_006965219, Trichoderma reesei QM6a glycosidase hydolase family 3 (TRIREDRAFT_121735), Mma, Last modification date Mar. 15, 2014; printed on Mar. 18, 2016; pp. 1-3.
Genbank Accession No. XP_386781, Hypothetical protein FG06605.1, [Fusarium graminearum PH-1], Last modification date Oct. 19, 2010; printed Mar. 18, 2016, p. 1.
Genbank Accession No. XP_001912683, Hypothetical protein [Podospora anserina S mat+], last modification date May 5, 2010; printed on Nov. 24, 2015, pp. 1-2.
Genbank Accession No. XP_003045443, Hypothetical protein NECHADRAFT_39290 [Nectria haematococca mpVI77-13-4], last modification date Aug. 14, 2010; printed on Nov. 24, 2015, pp. 1-2.
Genbank Accession No. CAK48740, beta-glucosidase bgl1-Aspergillus niger, last modification date Mar. 14, 2015; printed on Nov. 24, 2015, pp. 1-2.
Genbank Accession No. AAL69548, beta-glucosidase [Rasamsonia emersonii], last modification date Jul. 10, 2003; printed on Nov. 25, 2015; pp. 1-2.
Genbank Accession No. AAP57755, Cel3b [Trichoderma reese]), last modification date Mar. 26, 2003; printed on Nov. 25, 2015; pp. 1-2.
Genbank Accession No. AAA18473, beta-D-glucoside glucohydrolase [Trichoderma reesei], last modification date May 26, 1994; printed on Nov. 25, 2015; pp. 1-2.
Genbank Accession No. QOGC07, Beta-glucosidase) last modification date Nov. 28, 2006; printed on Nov. 25, 2015, pp. 1-2.
Genbank Accession No. Q7Z9M5, Cel3b, last modification date Oct. 31, 2006; printed on Nov. 25, 2015, pp. 1-2.
Ghose, 'International union of pure and applied chemistry,' Pure and Applied Chemistry, 1987, vol. 59, No. 2, pp. 257-268.
Gilbert et al., 'Molecular cloning of multiple xylanase genes from *Pseudomonas fluorescens* subsp. Cellulosa,' Journal of General Microbiology, 1988, vol. 134, pp. 3239-3247.
Gornall et al., 'Determination of serum proteins by means of the biuret reaction,' J. Biol. Chem., 1949, vol. 177, pp. 752-766.
Gould et al., 'Alkaline peroxide delignification of agricultural residues to enhance enzymatic saccharification,' Biotech and Bioeng., 1984, vol. 26, pp. 46-52.
Goyal et al., 'Enhancement of transglycosylation activity by construction by chimeras between mesophilic and thermophilic beta-glucosidase,' Archives of Biochemistry and Biophysics, Nov. 1, 2002, vol. 407, No. 1, pp. 125-134.
Harris et al., 'Stimulation of lignocellulosic biomass hydrolysis by proteins of glycoside hydrolase family 61: structure and function of a large, enigmatic family,' Biochemistry, American Chemical Society, Us, vol. 49, No. 15, Apr. 1, 2010, pp. 3305-3316, XP002608645, Issn: 0006-2960, Doi: 10.1021/Bi100009p [Retrieved on Mar. 15, 2010].
Henrissat et al., 'A scheme for designating enzymes that hydrolyse the polysaccharides in the cell walls of plants,' Febs Letters, 1998, vol. 425, No. 2, pp. 352-354.

Herpoel-Gimbert et al., 'Comparative secretome analysis of two Trichoderma reesei RUT-C30 and CL847 hypersecretory strains,' Biotechnology for Biofuels, 2008, 1:18 doi:10.1186/1754-6834-1-18.
Iwashita et al., 'The bglA gene of Aspergillus kawachii encodes both extracellular and cell wall-bound βglucosidases,' Appl. Environ. Microbiol., 1999, vol. 65, pp. 5546-5553.
Jung et al., 'Purification and characterization of α-L-arabinosidase from *Trichoderma* sp. SY,' Agric. Chem. Biotechnol., 2005, vol. 48, pp. 7-10.
Juturu et al., 'Insight into microbial hemicellulases other than xylanases: a review,' J Chem Technol Biotechnol, 2013, vol. 88, pp. 353-363.
Karlsson et al., 'Homologous expression and characterization of Cel61A (EG IV) reesei,' Eur. J. Biochem., 2001, vol. 268, pp. 6498-6507.
Kawaguchi et al., 'Cloning and sequencing of the cDNA encoding β-glucosidase 1 from Aspergillus aculeatus,' Gene, 1996, vol. 173, pp. 287-288.
Kim et al., 'Characterization of the arfA gene from Bacillus stearothermophilus No. 236 and its protein product, α-L-arabinofuranosidase,' J. Microbiol. Biotechnol., 2004, vol. 14, pp. 474-482.
Kim et al., 'Purification and characterization of β-xylosidase from *Trichoderma* sp. SY,' J. Microbiol. Biotechnol., 2004, vol. 14, pp. 643-645.
Kinoshita et al., 'Cloning of the xynNB gene encoding xylanase B from Aspergillus niger and its expression in Aspergillus kawachii,' Journal of Fermentation and Bioengineering, 1995, vol. 79, No. 5, pp. 422-428.
Kitamoto, et al., "Sequence Analysis, Overexpression, and Antisense Inhibition of a b-Xylosidase Gene, xylA,from ASpergillus orvzae KBN616," Applied and Environmenta Microbiology, Jan. 1999, pp. 20-24.
Kluepfel et al., 'Purification and characterization of a new xylanase (xylanase B) produced by Streptomyces lividans 66,' Biochem J., 1990, vol. 287, pp. 45-50.
Knob et al., 'β-xylosidases from filamentous fungi,' World J. Microbiol. Biotechnol., Oct. 2009, vol. 226, pp. 389-407.
Knowles et al., 'Cellulase families and their genes,' Trends in Biotechnology, 1987, vol. 5, No. 9, pp. 255-261.
Kosecki et al., 'Mutational analysis of N-glycosylation recognition sites on the biochemical properties of Aspergillus kawachii α-L-arabinofuranosidase 54,' Biochim. Biophys. Acta, 2006, vol. 1760, pp. 1458-1464.
Kotake et al., 'An α-L-arabinofuranosidase/β-D-xylosidase from immature seeds of radish (*Raphanus sativus* L),' J. Exp. Botany, 2006, vol. 57, pp. 2353-2362.
Kurakake et al., 'Characteristics of transxylosylation by β-xylosidase from Aspergillus awamori K4,' Biochim. Biophys. Acta, 2005, vol. 1726, pp. 272-279.
Lee et al., 'Bifunctional family of 3 glycoside hydrolases from barley with α-L-arabinofuranosidase and β-D-xylosidase activity. Characterization, primary structures and COOH-terminal processing,' J. Biol. Chem., 2003, vol. 278, pp. 5377-5387.
Li et al., 'Catalytic mechanism of a family 3 β-glucosidase and mutagenesis study on residue Asp-24,' Biochem. J., 2001, vol. 355, pp. 835-840.
Luthi et al., 'Xylanase from the extremely thermophilic bacterium "Caldocellum saccharolyticum": overexpression of the gene in *Escherichia coli* and characterization of the gene product,' Appl. Environ. Microbiol., 1990, vol. 56, No. 9, pp. 2677-2683.
Ma et al., 'Comparative genomics reveals mobile pathogenicity chromosomes in Fusarium,' Nature, Mar. 18, 2010, vol. 464, pp. 367-373.
Supplementary Information, Figures S1-S20, from Ma et al. Comparative genomics reveals mobile pathogenicity chromosomes in Fusarium, Nature, 2010, vol. 464, pp. 367-373.
Supplementary Information, pp. 1-31, from Ma et al. Comparative genomics reveals mobile pathogenicity chromosomes in Fusarium, Nature, 2010, vol. 464, pp. 367-373.

(56) References Cited

OTHER PUBLICATIONS

Supplementary Information, Tables S1-S25, from Ma et al. Comparative genomics reveals mobile pathogenicity chromosomes in Fusarium, Nature, 2010, vol. 464, pp. 367-373.
Smaali et al., "Biocatalytic conversion of wheat bran hydrolysate using an immobilized GH43 beta-xylosidase", Bioresource Technology, Jan. 1, 2009, vol. 100, No. 1, pp. 338-344.
Smaali et al., 'Expression in *Escherichaia coli* and characterization of β-xylosidase GH39 and GH-43 from Bacillus halodurans C-125,' Appl. Microbiol. Biotechnol., 2006, vol. 73, pp. 582-590.
Sorensen et al., 'Enzymatic hydrolysis of water-soluble wheat arabinoxylan. 1.Synergy between alpha-L-arabinofuranosidases, endo-1,4-beta-xylanases, and beta-xlyosidase activities,' Biotechnology and Bioengineering, 2003, 81:6, pp. 726-731.
Sorensen, HR, et al., "Enzymatic Hydrolysis of Wheat Arabinoxylan by a Recombinant "Minimal" Enzyme Cocktail Containing β-Xylosidase and Novel endo-1,4-β-Xylanase and α-L-Arabinofuranosidase Activities," Biotechnology Progress, Jan. 1, 2007, vol. 23, No. 1, pp. 100-107.
Sunna et al. 'Xylanolytic Enzymes from Fungi and Bacteria,' Critical Reviews in Biotechnology, 1997, vol. 17(1), pp. 39-67.
Tabka et al., 'Enzymatic Saccharification of wheat straw for bioethanol production by a combined cellulase xylanase and feruloyl esterase treatment,' Enzyme and Microbial Technology, 2006, vol. 39, pp. 897-902.
Tangnu et al., 'Enhanced production of cellulase, hemicellulase, and P-Glucosidase by Trichoderma reesei (Rut C-30),' Biotechnology and Bioengineering, 1981, vol. XXIII, pp. 1837-1849.
Taylor et al., 'Structural insight into the ligand specificity of a thermostable family 51 arabinofuranosidase, Araf51, from Clostridium thermocellum,' Biochem. J., 2006, vol. 395, pp. 31-37.
Teixeira et al., 'Alkaline and peracetic acid pretreatments of biomass for ethanol production,' Appl. Biochem and Biotech., 1999, vol. 77, pp. 19-34.
Tenkanen et al., 'Two major xylaneses of trichoderma reesei,' Enzyme Microb. Technol., 1992, 14:566-574.
Teymouri et al., 'Ammonia fiber explosion treatment of corn stover,' Applied Biochemistry and Biotechnology, 2004, vol. 113-116, pp. 951-963.
Thygesen et al., 'Production of cellulose and hemicellulose-degrading enzymes by filamentous fungi cultivated on wet-oxidised wheat straw,' Enzyme and Microbial Technology, 2003, 32:5, pp. 606-615.
Torronen et al., 'The two major xylanases from trichoderma reesei: characterizationof both enzymes and gens,' Biotechnology, 1992, vol. 10, pp. 1461-1465.
Tuncer et al., 'Purification and partial characterization of α-L-arabinofuranosidase produced by thermonospora fusca,' Folia Microbiol., 2008, vol. 48, No. 2, pp. 168-172.
Xu et al., 'A third xylanase from trichoderma reesei PC-3-7,' Appl. Microbiol. Biotechnol. 1998, 49:718-724.
Wakiyama, M. et al, "Purification and Properties of an Extracellular β-Xylosidase from Aspergillus japonicus and Sequence Analysis of the Encoding Gene," Journal of Bioscience and Bioengineering, Oct. 1, 2008, vol. 106, No. 4, pp. 398-404.
Walseth et al., 'Occurrence of cellulases in enzyme preparations from microorganisms,' TAPPI, May 1952, vol. 35, No. 5, pp. 228-233.
Weichselbaum et al., 'An accurate and rapid method for the determination of proteins in small amounts of blood serum and plasma,' American Journal of Clinical Pathology, Mar. 1946, pp. 40-49.
Winterhalter et al., 'Two extremely thermostable xylanases of the hyperthermophilic bacterium thermotoga maritima MSB8,' Appl. Environ. Microbiol., 1995, vol. 61, No. 5, pp. 1810-1815.
Wong et al., 'The cloning, expression and characterization of a cellobiase gene encoding a secretory enzyme from cellulomonas biazotea,' Gene, 1998, vol. 207, pp. 79-86.
Wood et al., 'The genome sequence of Schizosaccharomyces Pombe,' Nature, 2002, vol. 415, pp. 871-880.
Wood et al., 'The cellulase of fusarium solani,' Biochem. J. 1971, vol. 121, pp. 353-362.
Xue et al., 'Expression and characterization of a thermostable β-xylosidase from the hyperthermophile, thermotoga maritima,' Biotechnol. Lett., 2004, vol. 26, pp. 1511-1515.
Yang et al., 'Nucleotide sequence of a bacillus circulans xylanese gene,' Nucleic Acids Res., 1988, vol. 16, No. 14, p. 7187.
Zaldivar et al., 'Fuel ethanol production from lignocellulose: a challenge for metabolic engineering and process integration,' Appl. Microbiol. Biotechnol., 2001, vol. 56, pp. 17-34.
Zanoelo et al., 'Purification and biochemical properties of a thermostable xylose-tolerant β-D-xylosidase from Scytalidium thermophilum,' J. Ind. Microbiol. Biotechnol., 2004, vol. 31, pp. 170-176.
Zappe et al., 'Nucleotide sequence of a clostridium acetobutylicum P262 xylanase gene (xynB),' Nucleic Acids Res., 1990, vol. 18, No. 8, p. 2179.
Zhang, et al., "Formation of Ethyl β-xylopyranoside during simultaneous saccharification and co-fermation of papers sludge," Enzyme and Microbial Technology, Apr. 2009, vol. 44, No. 4, pp. 196-202.
UniProt Acc# Q9P973 from Ogasawara et al., Appl Microbiol Biotechnol, 2006, 72: 995-1003, Alignment with SEQ ID No. 2.
UniProt Acc# Q92458 from Margolles-Clark et al., Appl. Environ. Microbiol., vol. 62, No. 10 Oct. 1996, pp. 3840-3846, Alignment with SEQ ID No. 17.
UniProt Acc# Q92455 from Margolles-Clark et al., Appl. Environ. Microbiol., vol. 62, No. 10 Oct. 1996, pp. 3840-3846, Alignment with SEQ ID No. 3.
UniProtKB/Swiss-Prot: Accession No. Q4X0K2 (Xylosidase : arabinofuranosidase): last modification date Oct. 31, 2006; printed on Mar. 10, 2016, pp. 1-2.
UniProtKB/Swiss-Prot: Accession No. P45702 (RecName: Full=Beta-xylosidase; AltName: Full=1,4-beta-D-xylan xylohydrolase; AltName: Full=Xylan 1,4-beta-xylosidase; Flags: Precursor): last modification date Jan. 7, 2015, printed Mar. 10, 2016, pp. 1-2.
UniProtKB/Swiss-Prot: Accession No. P36906 (RecName: Full=Beta-xylosidase; AltName: Full=1,4-beta-D-xylan xylohydrolase; AltName: Full=Xylan 1,4-beta-xylosidase): last modification date Oct. 14, 2015, printed Mar. 10, 2016, pp. 1-7.
UniProtKB/Swiss-Prot: Accession No. P48792 (RecName: Full=Arabinofuranosidase/B-xylosidase; Includes: RecName: Full=Alpha-L-arabinofuranosidase; Short=Arabinosidase; Includes: RecName: Full=Beta-xylosidase; AltName: Full=1,4-beta-D-xylan xylohydrolase; AltName: Full=Xylan 1,4-beta-xylosidase; Flags: Precursor): last modification date Dec. 9, 2015, printed Mar. 10, 2016, pp. 1-2.
UniProt, Accession No. N1S321, 2013, www.uniprot.org.
UniProt Accession No. Q9ZFM2, (Recname: Full=Beta-Xylosidase; Altname: Full=1,4-Beta-D-Xylan Xylohydrolase; Altname: Full=Xylan 1, 4-Beta-Xylosidase), last modification date Nov. 2, 2016; printed on Feb. 28, 2017, pp. 1-2.
Genbank Accession No. XP018761619, alpha-N-arabinofuranosidase [Fusarium verticilloides 7600], last modification date Oct. 27, 2016.
Genbank Accession No. XM_018902798, Fusarium verticilloides 7600 alpha-N-arabinofuranosidase partial mRNA, last modification date Oct. 27, 2016.
Genbank Accession No. AY690618.1, 2004, www.ncbi.nlm.nih.gov.
Genbank Accession No. XM_018379765, *Fusarium oxysporum* F. Sp. Lycopersici 4287 Beta-Glucosidase, mRNA, last modification date Sep. 26, 2016; printed on Feb. 28, 2017, pp. 1-2.
Genbank Accession No. XP_018235878, Beta-Glucosidase [*Fusarium oxysporum* F. Sp. Lycopersici 4287]), last modification date Sep. 26, 2016; printed on Feb. 28, 2017, pp. 1-2.
*Fusarium oxysporum* F. Sp. Lycopersici Genome, *Fusarium oxysporum* f. sp. Lycopersici Ensembl Genomes 34, p. 1-2; fungi.ensembl.org/Fusarium_oxysporum/Info/Annotation/; printed Mar. 3, 2017.
PCT International Search Report issued for PCT/US2009/037853, dated Jul. 16, 2009.
PCT Written Opinion issued for PCT/US2009/037853, dated Jul. 16, 2009.
U.S. Appl. No. 61/245,273, filed Sep. 23, 2009.
PCT International Search Report issued for PCT/US2010/049849, dated Sep. 30, 2011.

(56) References Cited

OTHER PUBLICATIONS

PCT Written Opinion issued for PCT/US2010/049849, dated Sep. 30, 2011.
PCT International Search Report issued for PCT/US2010/061082, dated May 7, 2012.
PCT Written Opinion issued for PCT/US2010/061082, dated May 7, 2012.
IPRP issued for PCT/US2012/029445 dated Sep. 17, 2013.
PCT International Search Report issued for PCT/US2012/029445 dated Oct. 22, 2012.
PCT Written Opinion issued for PCT/US2012/029445 dated Oct. 22, 2012.
PCT International Search Report issued for PCT/US2012/029470, dated Sep. 14, 2012.
PCT Written Opinion issued for PCT/US2012/029470, dated Sep. 14, 2012.
Pending U.S. Appl. No. 15/647,775, filed Jul. 12, 2017.
Pending U.S. Appl. No. 15/440,341, filed Feb. 23, 2017.
PCT International Search Report issued for PCT/US2012/029498 dated May 8, 2012.
PCT Written Opinion issued for PCT/US2012/029498 dated May 8, 2012.

* cited by examiner

GH61 Endoglucanase homologs and sequences:

GenBank Accession No. CAB97283.2 [*Neurospora crassa*] (SEQ ID NO:1)
mrfdllalsafaplvaahgavtsyiidgttypgyegfspasspktiqfqwpnydptmtvsdakmrcng
gtsaqlsatvqagsnvtavwkqwtheqgpvqvwlfkcpgafgssckqdgkgwfkidemgmwggklnsa
nwgtalivknhqwsseipknmapgnylirhellalhqantpqfyaecaqivvqgsgnavppsdylysi
ptyapqndpgvtltrdfkidiyssksattytppggrvwsgfqf

GenBank Accession No. CAD21296.1 [*Neurospora crassa*] (SEQ ID NO:2)
mkvlaplvlasaasahtifsslevngvnqglgegvrvptyngpiedvtsasiacngspntvastskvi
tvqagtnvtaiwrymlsttgdspadvmdsshkgptiaylkkvdnaatasgvgngwfkiqqdgmdssgv
wgtervingkgrhsikipeciapgqyllraemialhaasnypgaqfymecaqlnvvggtgaktpstvs
fpgaysgsdpgvkisiywppvtsytvpgpsvftc

GenBank Accession No. CAD70347.1 [*Neurospora crassa*] (SEQ ID NO:3)
mlpsislllaaalgtsahytfpkvwansgttadwqyvrradnwqnngfvdnvnsqqircfqsthspaq
stlsvaagttitygaapsvyhpgpmqfylarvpdgqdinswtgegavwfkiyheqptfgsqltwssng
kssfpvkipsciksgsyllraehiglhvaqssgaaqfyiscaqlsitgggstepganykvsfpgayka
sdpgilininypvptsyknpgpsvftc

GenBank Accession No. CAE81966.1 [*Neurospora crassa*] (SEQ ID NO:4)
mkssllvvltaglavrdaiahaifqqlwvdgvdygstcnrlptsnspvtnvgsrdvvcnagtrgvsgk
cpvkaggtvtvemhqqpgdrsckseaiggahwgpvqiylskvsdastadgssggwfkifsdawskksg
grvgdddnwgtrdlnaccgrmdvlipkdlpsgdyllraealalhtagqsggaqfyiscyqitvsgggs
anyatvkfpgayrasdpgiqinihavvsnyvapgpavvaggvtkqagsgcigcestckvgsspsavap
ggkpasggsdgnapevaepsggegspsapgacevaaygqcggdqysgctcasgytckavsppyysqc
apts

GenBank Accession No. CAF05857.1 [*Neurospora crassa*] (SEQ ID NO:5)
mkfssalaflaaagaqahytfpkgystgavsgeyehirmtenhynrgpvadvtsesmtcyelnpgkga
pktlsvaagsnytfvvgdnighpgplhfymakvpegktaatfdgkgavwfkiyqdgpmglgtgqltwp
sagatevsvklpsclesgeyllrvehiglhsagsvggaqlyiacaqlnvtggtgtintsgklvsfpga
ykatdpgllfnlyypaptsytnpgpavatcdgasapaapapapssaapsapaasapsatvpavsatsa
aavgkasstpkkgckraarkh

GenBank Accession No. EAA26873.1 [*Neurospora crassa*] (SEQ ID NO:6)
mrstlvtgliaglIsqqaaahatfqalwvdgadygsqcarvppsnspvtdvtsnamrcntgtspvakk
cpvkagstvtvemhqshppvptltykqqandrscsseaiggahygpvlvymskvsdaasadgssgwfk
ifedtwakkpssssgdddfwgvkdlnsccgkmqvkipsdipagdyllraevialhtaasaggaqlymt
cyqisvtgggsatpatvsfpgaykssdpgilvdihsamstyvapgpavysggsskkagsgcvgcestc
kvgsgptgtasavpvastsaaaggggggsggcsvakyqqcggtgytgctscasgstcsavsppyysq
cv

GenBank Accession No. EAA29132.1 [*Neurospora crassa*] (SEQ ID NO:7)
mvralrllascamfsqalahshilyliingqqyrgfnphapdaitnsigwstsavddgfvtpsnysnp
diichrdgkpakahapvkagdkiqiqwngwpqshkgpvlsylapcanttdgcasvdkrklswtkidds
spvlldekggppgrwatdvliaqnntwllglpndlepgpyvlrhelialhyanlkngaqnypqcvnlw
vegpgpkaitvgkeevvvagqkegvpatalykatdpgvaidiytavlstyvipgptlapeakpvpvte
qglkstitavgtpvivtratstvpmpngetaaafkg

*FIG. 1A*

**GenBank Accession No. EAA30263.1 [*Neurospora crassa*] (SEQ ID NO:8)**
mkvlsllaaasaasahtifvqleadgttypvsygirtpsydgpitdvtsndlacnggpnpttpsdkii
tvnagstvkaiwrhtltsgaddvmdashkgptlaylkkvddaltdtgigggwfkiqedgynngqwgts
tvitnggfqyidipacipsgqyllraemialhaasstagaqlymecaqinivggtggtalpsttysip
giykatdpgllvniysmspsstytipgpakftcpagngggagggstttakpasssttskaaitsavtt
lktsvvapqptggctaaqwaqcggmgfsgcttcaspytckkmndyysqcs

**GenBank Accession No. EAA33178.1 [*Neurospora crassa*] (SEQ ID NO:9)**
mktfatllasiglvaahgfvdnatiggqfyqfyqpyqdpymgsppdrisrkipgngpvedvtslaiqc
nadsapaklhasaaagstvtlrwtiwpdshvgpvitymarcpdtgcqdwtpsasdkvwfkikeggreg
tsnvwaatplmtapanyeyaipsclkpgyylvrheiialhsaysypgaqfypgchqlqvtgsgtktps
sglvsfpgaykstdpgvtydayqaatytipgpavftc

**GenBank Accession No. EAA33408.1 [*Neurospora crassa*] (SEQ ID NO:10)**
mrsttvlaglatvlaplasahtvlttvfvndknqgdgtgvrmpmdgnianapvinmnsddmicgrdgl
kkvnyaipatagskmtfefrtyvdgsrpqfidkshqgpisvyakavsdfdqspggsgwfkiwhdgyde
stgkwavqkvidtngllsislptgmptgayllrteviamqnvttkadgnwycepqfyvncaqvyvqgs
ssgplsipkdketsipghvhpsdkglnfnmydmkgllpyqipgpvpfrpassssgsnakaalttptnf
pgavpdncllknanwcgfevpdytnedgcwasadncwaqskkcfdsappsgikgckiweqekcqalan
scdakqftgppnkgkrwgdvteqssvqpgvmkgadlvdtpvvdttsnqkaaannnvvsipaatattf
ittssaapskpvttvpsvaittttsaavaiptetaaqntlircgrgdknqrramhinrhkradf

**GenBank Accession No. EAA34466.1 [*Neurospora crassa*] (SEQ ID NO:11)**
mklsvaaalslaaseasahyifqqvgagtsvnpvwkyirkhtnynspvtdltskdlvcnvgasaegve
tlsvaagsqvtfktdtavyhqgptsvylskadgslsdydgsggwfkikdwgatfpggewtlsdtytft
ipscipsgdyllriqqigihnpwpagvpqfylscahisvtgggsaspatvsipgafketdpgytvniy
snfnnytvpgpevftcsgsgsgsgsgsgsgstppsqpttsttlptsstvvattlktstvvattkssss
ttssasssgsqptspsgctvakygqcggigysgctscasgstckvgndyysqcl

**GenBank Accession No. EAA36362.1 [*Neurospora crassa*] (SEQ ID NO:12)**
mktgsilaalvasasahtifqkvsvngadqgqlkgirapannnpvtdvmssdiicnavtmkdsnvltv
pagakvghfwgheiggaagpndadnpiaashkgpimvylakvdnaattgtsglkwfkvaeaglsngkw
avddlianngwsyfdmptciapgqylmraelialhnagsqagaqfyigcaqinvtgqgsaspsntvsf
pgaysasdpgiliniyggsgktdnggkpyqipgpalftcpaggsggsspapattastpkptsasapkp
vsttastpkptngsgsgtgaahstkcggskpaattkasnpqptnggnsavraaalygqcggkgwtgpt
scasqtckfsndwysqclp

**GenBank Accession No. EAA29018.1 [*Neurospora crassa*] (SEQ ID NO:13)**
marmsiltalagaslvaahghvskvivngveyqnydptsfpynsnpptvigwtidqkdngfvspdafd
sgdiichksakpagghatvkagdkislqwdqwpeshkgpvidylaacdgdcesvdktalkffkidgag
ydatngwasdtlikdgnswvveipesikpgnyvlrheiialhsagqangaqnypqcfnlkvegsgstv
pagvagtelykatdagilfdiykndisypvpgpsliagasssiaqskmaatatasatlpgatggsnsp
atsaaaaapatsaaaatsqvqaapattlvtstkaaapatsaaapaapatsaaaggagqvqakqtkwgq
cggngftgptecesgstctkyndwysqcv

**St61 *Sporotrichum thermophilum* 24630 >jgi|Spoth1|24630|gw1.4.2027.1 (SEQ ID NO:14)**
ALGHSHLGYIIINGEVYQGFDPRPEQANSPLRVGWSTGAIDDGFVAPANYSSPDIICHIEGASPPAHA
PVRAGDRVHVQWNGWPLGHVGPVLSYLAPCGGLEGSESGCAGVDKRQLRWTKVDDSLPAMELRWATDV
LIAANNSWQVEIPRGLRDGPYVLRHEIVALHYAAEPGGAQNYPLCVNLWVEGGDGSMELDHFDATQFY
RPDDPGILLNVTAGLRSYAVPGPTLAAGATPVPYAQQNISSARADGTPVIVTRSTETVPFTAAPTPA

*FIG. 1B*

**St61A *Sporotrichum thermophilum* 23839c**
>jgi|Spoth1|23839|gw1.5.2084.1 (SEQ ID NO:15)

MSSFTSKGLLSALMGAATVAAHGHVTNIVINGVSYQNFDPFTHPYMQNPPTVVGWTASNTDNGFVGPE
SFSSPDIICHKSATNAGGHAVVAAGDKVFIQWDTWPESHHGPVIDYLADCGDAGCEKVDKTTLKFFKI
SESGLLDGTNAPGKWASDTLIANNNSWLVQIPPNIAPGNYVLRHEIIALHSAGQQNGAQNYPQCFNLQ
VTGSGTQKPSGVLGTELYKATDAGILANIYTSPVTYQIPGPAIISGASAVQQTTSAITASASAITGSA
TAAPTAATTTAAAATTTTTAGSGATATPSTGGSPSSAQPAPTTAAATSSPARPTRCA

**St61B *Sporotrichum thermophilum* 46583**
>jgi|Spoth1|46583|e_gw1.3.729.1 (SEQ ID NO:16)

MSKASALLAGLTGAALVAAHGHVSHIVVNGVYYRNYDPTTDWYQPNPPTVIGWTAADQDNGFVEPNSF
GTPDIICHKSATPGGCHATVAAGDKINIVWTPEWPESHIGPVIDYLAACNGDCETVDKSSLRWFKIDG
AGYDKAAGRWAADALRANGNSWLVQIPSDLKAGNYVLRHEIIALHGAQSPNGAQAYPQCINLRVTGGG
SNLPSGVAGTSLYKATDPGILFNPYVSSPDYTVPGPALIAGAASSIAQSTSVATATGTATVPGGGAN
PTATTTAATSAAPSTTLRTTTTTSAAQTTAPPSGDVQTKYGQCGGNGWTGPTVCAPGSSCSVLNEWYSQ
CL*

**St61D *Sporotrichum thermophilum* 80312**
>jgi|Spoth1|80312|estExt_Genewise1Plus.C_40585 (SEQ ID NO:17)

MKSFTLTTLAALAGNAAAHATFQALWVDGVDYGAQCARLPASNSPVTDVTSNAIRCNANPSPARGKCP
VKAGSTVTVEMHQQPGDRSCSSEAIGGAHYGPVMVYMSKVSDAASADGSSGWFKVFEDGWAKNPSGGS
GDDDYWGTKDLNSCCGKMNVKIPADLPSGDYLLRAEALALHTAGSAGGAQFYMTCYQLTVTGSGSASP
PTVSFPGAYKATDPGILVNIHAPLSGYTVPGPAVYSGGSTKKAGSACTGCESTCAVGSGPTATVSQSP
GSTATSAPGGGGGCTVQKYQQCGGQGYTGCTNCASGSTCSAVSPPYYSQCV*

**GenBank Accession No. EAA29347.1 [*Neurospora crassa* OR74A] (SEQ ID NO:18)**

mpsftsksllavlagaasvaahghvsnivingeyyrgfdsslnymanppavvgwkannqdngfvgpda
fsspdiichkdatnakghavvkagdkisiqwetwpeshkgpvidylancgasgcetvdktsleffkid
evglvdgqkwgsdqliannnswlveipptiapgfyvlrheiialhsagqpngaqnypqcfniqvtgsg
tekpagvkgtalykpddagisvniyqslssysipgpalikgavsvaqshsavtatataitglgdapaa
taapaattapaaapavttapaaaaptkpattaaapqptkpaksgcqkrraarraaalarrhardvafl
d

**Afu61a *Aspergillus fumigatus* Afu3g03870 [NCBI Ref: XP_748707] (SEQ ID NO:19)**

mrhvqstqllaallttrvtahghvtnivingvsyrgwnidsdpynpdppvvvawqtpntangfispd
aygtndiichlnatnarghavvaagdkisiqwtawpdshhgpvidylarcgsscetvdkttleffkid
gvglvdgsnppgvwgddqliadnnswlveipptiapgyyvlrheliialhgagsqngaqnypqcfnlqi
tgsgtaqpsgvkgtelyspdpgilvniynalstyivpgptlipgavsvvqssstitasgtpvtgsgs
apttsatttlstttratttttttagssstsvqsvygqcggsgwsgptacvtgatctsynsyysqcipt
as

Aspergillus fumigatus Afu6g09540 [NCBI Ref: XP_750843.1] (SEQ ID NO:20)

mkltasilfslasvtplvsghyvfsklivdgkptqdfeyirrntnnymptlpseilsndfrcnkgsmq
saantkvykvapgtelgfqlaygaemkhpgplqiymskapgdvrsydgsgdwfkvhqeglcadtskgi
kdedwctwgkdtasfkipqdtpagqylvrvehiglhrgflgeaefyftcaqievtgsgsgspsptvki
pgvykpddpnvhfniwyptptayslpgpsvwtggsaggasptapavnnnavqaapttmttvsspanpt
agaeaeadcgssesssavapegtlkkweqcgglnwtgsgsceearttchqynpyyyqci

*FIG. 1C*

*Aspergillus fumigatus* EDP47167 (SEQ ID NO:21)

msqtktlsllaallsatrvaahghvtnvvvngvsyagfdinsypymsdppkvaawttpntgngfiaps
aynspdiichqnatnaqayieiaagdriqlqwtawpeshhgpvidmlascgescttvdktslkffkid
gvglvdnsavpgtwgddqliansnswmveipksiapgnyvlrhelialhsafetggaqnypqcfnlkv
tgsgtdspagtlgtelytesdpgllvdiyksiasyavpgpamytgavsitqstsaitatgtatvgsga
dstpvpssaasseystvavqvpttkaqytpvpssspstfvtspapttsvpsgssvpvtsntaaplpta
apggtqtvygqcggqnwtgptyiv

*Thielavia terrestris* 16380 >jgi|Thite1|16380|gw1.5.932.1 (SEQ ID NO:22)

LLSTLAGAASVAAHGHVSNIVINGVSYQGYDPTSFPYMQNPPIVVGWTAADTDNGFVAPDAFASGDII
CHKNATNAKGHAVVAAGDKIFIQWNTWPESHHGPVIDYLASCGSASCETVDKTKLEFFKIDEVGLVDG
SSAPGVWGSDQLIANNNSWLVEIPPTIAPGNYVLRHEIIALHSAENADGAQNYPQCFNLQITGTGTAT
PSGVPGTSLYTPTDPGILVNIYSAPITYTVPGPALISGAVSIAQSSSAITASGTALTGSATAPAAA

*Thielavia terrestris* 155418 >jgi|Thite1|155418|genemark.4336_g (SEQ ID NO:23)

MPPALPQLLTTVLTALTLGSTALAHSHLAYIIVNGKLYQGFDPRPHQANYPSRVGWSTGAVDDGFVTP
ANYSTPDIICHIAGTSPAGHAPVRPGDRIHVQWNGWPVGHIGPVLSYLARCESDTGCTGQNKTALRWT
KIDDSSPTMQNVAGAGTQGEGTPGKRWATDVLIAANNSWQVAVPAGLPTGAYVLRNEIIALHYAARKN
GAQNYPLCMNLWVDASGDNSSVAATTAAVTAGGLQMDAYDARGFYKENDPGVLVNVTAALSSYVVPGP
TVAAGATPVPYAQQSPSVSTAAGTPVVVTRTSETAPYTGAMTPTVAARMKGRGYDRRG

*Thielavia terrestris* 68900
>jgi|Thite1|68900|estExt_Genewise1Plus.C_15411 (SEQ ID NO:24)

MRTTFAAALAAFAAQEVAGHAIFQQLWVDGTDYIRAPLFLFGKCPVKAGGTVTVEMHQQPGDRSCNNE
AIGGAHWGPVQVYLSKVEDASTADGSTGWFKIFADTWSKKAGSSVGDDDNWGTRDLNACCGKMQVKIP
ADIPSGDYLLRAEALALHTAGQVGGAQFYMSCYQITVSGGGSASPATVKFPGAYSANDPGIHINIHAA
VSNYVAPGPAVYSGGTTKVAGSGCQGCENTCKVGSSPTATAPSGKSGAGSDGGAGTDGGSSSSSPDTG
SACSVQAYGQCGGNGYSGCTQCAPGYTCKAVSPPYYSQCAPSS*

ABC2132 *Chaetomium globosum* Cg61A [ EAQ86340.1] (SEQ ID NO:25)

mskasallatltgaalvaahghvshiivngvyyenydptthwyqpnppptvigwkaaqqdngfvepnnf
gtsdiichksgspggghatvaagdkisivwdpewpeshigpvidylaacngdcetvdkaslrffkidg
agydktagrwaadtlrangnswlvqipadlkagnyvlrheiialhgasspngaqaypqcinlrvtgsg
tnapsgvagtslyrasdagilfnpyvaspnypvpgpaliagaassvaqsksvatatasatlpgnnngg
gpnpqpttatttanpgvsttlrtstststsaqvtppptggnaqtkygqcggsgwtgptacaagsscsv
lndwyaqcv

*T. reesei* Eg7 (SEQ ID NO:26)

MKSCAILAALGCLAGSVLGHGQVQNFTINGQYNQGFILDYYYQKQNTGHFPNVAGWYAEDLDLGFISP
DQYTTPDIVCHKNAAPGAISATAAAGSNIVFQWGPGVWPHPYGPIVTYVVECSGSCTTVNKNNLRWVK
IQEAGINYNTQVWAQQDLINQGNKWTVKIPSSLRPGNYVFRHELLAAHGASSANGMQNYPQCVNIAVT
GSGTKALPAGTPATQLYKPTDPGILFNPYTTITSYTIPGPALWQG

*T. reesei* Eg4 (SEQ ID NO:27)

MIQKLSNLLVTALAVATGVVGHGHINDIVINGVWYQAYDPTTFPYESNPPIVVGWTAADLDNGFVSPD
AYQNPDIICHKNATNAKGHASVKAGDTILFQWVPVPWHPGPIVDYLANCGDCETVDKTTLEFFKID
GVGLLSGGDPGTWASDVLISNNNTWVVKIPDNLAPGNYVLRHEIIALHSAGQANGAQNYPQCFNIAVS
GSGSLQPSGVLGTDLYHATDPGVLINIYTSPLNYIIPGPTVVSGLPTSVAQGSSAATATASATVPGGG
SGPTSRTTTARTTQASSRPSSTPPATTSAPAGGPTQTLYGQCGGSGYSGPTRCAPPATCSTLNPYYA
QCLN

FIG. 1D

*Aspergillus fumigatus* Af293, GenBank Accession: XP_752040 (SEQ ID NO:28)

mtlskitsiaglłasaslvaghgfvsgivadgkyyggylvnqypymsnppdtiawsttatdlgfvdgt
gyqspdiichrdakngkltatvaagsqiefqwttwpeshhgplitylapcngdcatvdkttlkfvkia
aqglidgsnppgvwaddemianntatvtipasyapgnyvlrheiialhsagnlngaqnypqcfniqi
tgggsaqgsgtagtslykntdpgikfdiysdlsggypipgpalfna TtEG, from *Thielavia terrestris* (SEQ ID NO:29)

MLANGAIVFLAAALGVSGHYTWPRVNDGADWQQVRKADNWQDNGYVGDVTSPQIRCFQATPSPAPSVL
NTTAGSTVTYWANPDVYHPGPVQFYMARVPDGEDINSWNGDGAVWFKVYEDHPTFGAQLTWPSTGKSS
FAVPIPPCIKSGYYLLRAEQIGLHVAQSVGGAQFYISCAQLSVTGGGSTEPPNKVAFPGAYSATDPGI
LINIYYPVPTSYQNPGPAVFSC

Ta61A, a GH61A polypeptide from *Thermoascus aurantiacus* (SEQ ID NO:148)

MSFSKIIATAGVLASASLVAGHGFVQNIVIDGKKYYGGYLVNQYPYMSNPPEVIAWSTTATDLGFVDG
TGYQTPDIICHRGAKPGALTAPVSPGGTVELQWTPWPDSHHGPVINYLAPCNGDCSTVDKTQLEFFKI
AESGLINDDNPPGIWASDNLIAANNSWTVTIPTTIAPGNYVLRHEIIALHSAQNQDGAQNYPQCINLQ
VTGGGSDNPAGTLGTALYHDTDPGILINIYQKLSSYIIPGPPLYTG

| | FIG. 2A | FIG. 2B |
|---|---|---|
| | FIG. 2C | FIG. 2D |

FIG. 2A

Percent Identity

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1 | | 26.1 | 21.2 | 19.5 | 21.5 | 17.5 | 20.3 | 23.2 | 26.1 | 15.0 | 20.3 | 19.9 | 23.6 | 17.5 | 24.4 | 22.8 | 21.5 | 25.2 |
| 2 | 162.2 | | 31.6 | 31.5 | 33.6 | 32.4 | 24.4 | 53.8 | 29.0 | 26.1 | 27.3 | 40.8 | 26.1 | 18.9 | 24.4 | 22.7 | 31.9 | 24.4 |
| 3 | 215.0 | 124.5 | | 26.0 | 47.2 | 29.0 | 19.5 | 30.7 | 27.3 | 13.9 | 32.5 | 30.7 | 25.5 | 18.6 | 21.6 | 22.1 | 30.3 | 19.9 |
| 4 | 183.3 | 106.7 | 116.3 | | 23.5 | 59.9 | 18.8 | 31.7 | 24.1 | 16.3 | 31.9 | 31.1 | 21.5 | 21.4 | 20.1 | 25.4 | 63.8 | 22.9 |
| 5 | 222.0 | 107.3 | 79.3 | 136.3 | | 24.6 | 21.8 | 29.4 | 29.0 | 15.7 | 27.5 | 27.3 | 23.2 | 19.9 | 21.8 | 23.9 | 26.6 | 22.2 |
| 6 | 204.0 | 117.6 | 112.5 | 47.2 | 130.2 | | 16.9 | 33.2 | 29.0 | 16.4 | 32.2 | 31.6 | 26.6 | 21.8 | 21.9 | 25.4 | 75.2 | 22.3 |
| 7 | 155.8 | 196.0 | 227.0 | 211.0 | 203.0 | 214.0 | | 20.1 | 29.9 | 13.6 | 13.3 | 22.7 | 34.7 | 50.2 | 33.4 | 31.8 | 18.2 | 34.1 |
| 8 | 166.5 | 59.6 | 118.1 | 116.4 | 118.4 | 115.8 | 202.0 | | 27.4 | 22.0 | 35.4 | 41.6 | 27.6 | 17.7 | 23.6 | 25.2 | 32.3 | 21.7 |
| 9 | 129.0 | 156.1 | 170.0 | 187.8 | 144.4 | 166.8 | 123.3 | 157.2 | | 19.5 | 24.9 | 26.6 | 32.8 | 22.8 | 35.7 | 32.8 | 31.5 | 31.1 |
| 10 | 258.0 | 166.7 | 189.6 | 279.0 | 220.0 | 243.0 | 294.0 | 232.0 | 260.0 | | 17.5 | 22.8 | 15.4 | 13.3 | 13.2 | 16.0 | 18.6 | 17.9 |
| 11 | 182.1 | 111.1 | 112.2 | 109.3 | 137.6 | 105.2 | 255.0 | 97.8 | 176.9 | 265.0 | | 31.9 | 25.8 | 15.1 | 20.9 | 26.4 | 33.1 | 18.7 |
| 12 | 195.0 | 84.5 | 110.4 | 117.4 | 138.3 | 114.9 | 193.2 | 85.5 | 156.7 | 208.0 | 113.2 | | 27.6 | 18.8 | 25.6 | 28.3 | 30.7 | 24.0 |
| 13 | 136.1 | 174.4 | 171.5 | 196.9 | 196.0 | 182.1 | 100.9 | 178.3 | 108.8 | 294.0 | 197.0 | 150.4 | | 38.4 | 49.1 | 58.9 | 29.1 | 51.0 |
| 14 | 167.4 | 201.0 | 204.0 | 205.0 | 204.0 | 206.0 | 59.2 | 214.0 | 137.5 | 294.0 | 281.0 | 206.0 | 107.5 | | 38.0 | 36.5 | 22.9 | 41.0 |
| 15 | 128.4 | 174.8 | 179.4 | 229.0 | 194.8 | 217.0 | 103.4 | 211.0 | 103.2 | 311.0 | 239.0 | 158.8 | 73.5 | 99.3 | | 49.9 | 23.5 | 62.5 |
| 16 | 149.4 | 181.0 | 166.5 | 166.4 | 173.7 | 160.4 | 96.9 | 175.9 | 99.1 | 303.0 | 173.0 | 150.4 | 46.8 | 94.4 | 70.9 | | 28.2 | 45.7 |
| 17 | 197.2 | 99.7 | 110.4 | 44.7 | 125.4 | 26.1 | 209.0 | 108.4 | 154.3 | 236.0 | 101.4 | 103.1 | 164.0 | 183.0 | 189.2 | 144.1 | | 23.2 |
| 18 | 127.1 | 166.6 | 187.2 | 188.6 | 193.7 | 195.0 | 90.3 | 197.5 | 107.1 | 291.0 | 236.0 | 165.4 | 66.6 | 89.1 | 51.3 | 64.8 | 180.9 | |

Divergence

FIG. 2B

| | 19 | 20 | 21 | 22 | 23 | 24 | 25 | 26 | 27 | 28 | | |
|---|---|---|---|---|---|---|---|---|---|---|---|---|
| 25.2 | | 18.3 | 24.8 | 22.8 | 26.0 | 16.7 | 17.1 | 23.2 | 21.5 | 23.6 | 1 | Ncrassa CAB97283.2 |
| 24.8 | 19 | 25.2 | 22.7 | 23.1 | 24.4 | 21.0 | 23.5 | 21.4 | 19.3 | 23.9 | 2 | Ncrassa CAD21296.1 |
| 22.9 | 20 | 28.1 | 21.2 | 20.3 | 20.8 | 19.5 | 23.8 | 21.2 | 19.0 | 21.2 | 3 | Ncrassa CAD70347.1 |
| 24.6 | 21 | 21.8 | 22.1 | 20.4 | 21.8 | 17.9 | 71.1 | 23.3 | 18.9 | 25.3 | 4 | Ncrassa CAE81966.1 |
| 19.5 | 22 | 25.6 | 20.8 | 22.8 | 24.2 | 20.5 | 23.9 | 20.8 | 18.1 | 21.2 | 5 | Ncrassa CAF05857.1 |
| 26.0 | 23 | 23.3 | 23.1 | 20.8 | 24.3 | 20.9 | 59.0 | 24.6 | 21.3 | 24.3 | 6 | Ncrassa EAA26873.1 |
| 38.0 | 24 | 13.6 | 31.5 | 40.4 | 32.5 | 46.4 | 16.9 | 32.1 | 28.5 | 36.0 | 7 | Ncrassa EAA29132.1 |
| 24.5 | 25 | 23.0 | 20.8 | 23.2 | 22.0 | 20.2 | 27.9 | 25.5 | 20.5 | 23.3 | 8 | Ncrassa EAA30263.1 |
| 32.8 | 26 | 18.7 | 31.1 | 34.4 | 35.7 | 24.1 | 19.1 | 31.1 | 29.5 | 29.5 | 9 | Ncrassa EAA33178.1 |
| 13.7 | 27 | 17.0 | 14.8 | 13.6 | 15.2 | 16.7 | 12.1 | 16.0 | 14.1 | 14.8 | 10 | Ncrassa EAA33408.1 |
| 25.5 | 28 | 26.7 | 23.6 | 18.4 | 21.8 | 15.6 | 32.1 | 24.5 | 18.1 | 24.2 | 11 | Ncrassa EAA34466.1 |
| 27.2 | | 23.0 | 24.2 | 26.4 | 25.1 | 17.6 | 27.0 | 26.1 | 21.7 | 25.9 | 12 | Ncrassa EAA36362.1 |
| 49.1 | | 22.1 | 45.9 | 49.6 | 50.1 | 33.6 | 22.2 | 59.6 | 38.6 | 53.5 | 13 | Ncrassa EAA29018.1 |
| 36.9 | | 16.2 | 34.7 | 32.0 | 38.0 | 65.7 | 19.6 | 35.4 | 31.3 | 35.8 | 14 | St61 Sporotrichum thermophilum 24630 |
| 55.3 | | 18.8 | 47.8 | 51.6 | 63.1 | 32.1 | 22.5 | 47.0 | 37.8 | 51.2 | 15 | St61A Sporotrichum thermophilum 23839 c |
| 49.7 | | 20.6 | 45.5 | 48.0 | 50.1 | 32.4 | 24.8 | 80.5 | 44.6 | 52.8 | 16 | St61B Sporotrichum thermophilum 46583 c |
| 28.2 | | 25.7 | 25.7 | 22.0 | 24.8 | 22.0 | 62.2 | 28.5 | 23.3 | 28.8 | 17 | St61D Sporotrichum thermophilum 80312 |
| 53.7 | | 18.2 | 49.3 | 49.2 | 65.1 | 32.7 | 22.5 | 44.9 | 39.4 | 47.2 | 18 | Ncrassa EAA29347.1 |

| | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 19 | 127.3 | 155.9 | 172.0 | 189.7 | 195.0 | 197.6 | 101.8 | 202.0 | 109.8 | 298.0 | 200.0 | 181.9 | 90.2 | 99.5 | 64.5 | 79.4 | 162.9 | 55.0 |
| 20 | 233.0 | 142.5 | 114.7 | 148.2 | 147.5 | 139.1 | 279.0 | 154.4 | 173.0 | 248.0 | 135.6 | 139.7 | 210.0 | 268.0 | 252.0 | 197.6 | 126.1 | 218.0 |
| 21 | 138.5 | 160.9 | 186.3 | 197.6 | 109.5 | 183.4 | 106.9 | 191.7 | 115.3 | 313.0 | 214.0 | 154.0 | 77.5 | 100.1 | 85.6 | 76.6 | 177.5 | 66.7 |
| 22 | 146.7 | 183.1 | 206.0 | 196.0 | 185.4 | 199.0 | 84.6 | 182.8 | 108.2 | 273.0 | 194.9 | 141.7 | 69.9 | 97.3 | 69.3 | 74.5 | 201.0 | 66.7 |
| 23 | 125.4 | 155.9 | 187.4 | 197.6 | 186.4 | 196.8 | 99.7 | 188.4 | 102.6 | 317.0 | 219.0 | 178.8 | 66.8 | 92.8 | 54.5 | 65.8 | 170.6 | 40.9 |
| 24 | 197.4 | 206.0 | 196.0 | 217.0 | 223.0 | 223.0 | 72.7 | 192.8 | 148.0 | 274.0 | 250.0 | 230.0 | 112.3 | 38.2 | 119.0 | 99.3 | 200.0 | 110.2 |
| 25 | 171.7 | 109.1 | 114.8 | 31.5 | 143.1 | 45.3 | 194.4 | 114.9 | 183.2 | 277.0 | 107.4 | 116.0 | 174.6 | 182.7 | 199.0 | 155.5 | 43.7 | 173.5 |
| 26 | 149.4 | 184.8 | 189.4 | 175.3 | 192.0 | 181.1 | 99.1 | 192.6 | 106.8 | 309.0 | 194.4 | 162.6 | 49.0 | 96.8 | 76.8 | 18.6 | 158.4 | 69.3 |
| 27 | 148.5 | 191.9 | 215.0 | 219.0 | 182.2 | 210.0 | 100.6 | 180.7 | 112.8 | 250.0 | 197.2 | 179.3 | 90.2 | 96.4 | 90.5 | 77.6 | 183.8 | 88.7 |
| 28 | 131.6 | 178.3 | 173.5 | 154.9 | 187.6 | 177.6 | 85.8 | 181.6 | 115.3 | 303.0 | 167.7 | 159.7 | 61.6 | 92.8 | 68.7 | 60.5 | 148.7 | 66.3 |

Column headers (left to right, SEQ ID 19–28):
- 19: Afu61A Aspergillus fumigatus Afu3g03870
- 20: Afu61B Aspergillus fumigatus Afu6g09540
- 21: Afu61C Aspergillus fumigatus EDP47167 w
- 22: Afumigatus XP_752040
- 23: Tt61A Thielavia terrestris 16380 JGI wo
- 24: Tt61B Thielavia terrestris 155418 JGI w
- 25: Tt61C Thielavia terrestris 68900 JGI wC
- 26: ABC2132 Cg61A Chaetomium globosum TrEgl
- 27: Treesei egl7 proteinID120961 from JGI
- 28: Treesei egl4 GH61

| | 19 | 20 | 21 | 22 | 23 | 24 | 25 | 26 | 27 | 28 |
|---|---|---|---|---|---|---|---|---|---|---|
| 19 | 246.0 | 18.8 | 56.4 | 52.8 | 62.3 | 34.2 | 26.0 | 47.7 | 39.0 | 52.3 |
| 20 | 60.6 | 220.0 | 17.6 | 20.0 | 17.6 | 13.3 | 22.9 | 20.0 | 18.5 | 21.8 |
| 21 | 68.7 | 226.0 | 71.6 | 51.6 | 51.9 | 30.0 | 21.9 | 41.3 | 38.2 | 45.9 |
| 22 | 47.4 | 246.0 | 67.9 | 62.9 | 54.4 | 32.4 | 20.4 | 45.6 | 37.8 | 50.4 |
| 23 | 115.2 | 289.0 | 115.9 | 120.8 | 116.2 | 32.4 | 21.6 | 46.1 | 41.4 | 51.5 |
| 24 | 166.0 | 128.2 | 165.4 | 181.6 | 182.0 | 200.0 | 19.0 | 31.8 | 26.5 | 33.0 |
| 25 | 83.3 | 196.8 | 90.6 | 81.0 | 71.2 | 105.8 | 166.9 | 23.5 | 18.1 | 27.6 |
| 26 | 91.7 | 237.0 | 93.8 | 89.3 | 83.8 | 117.4 | 196.0 | 42.2 | 83.3 | 50.9 |
| 27 | 71.6 | 186.6 | 77.4 | 69.6 | 62.3 | 101.3 | 139.6 | 65.3 | 83.3 | 43.0 |
| 28 | | | | | | | | | | 28 |

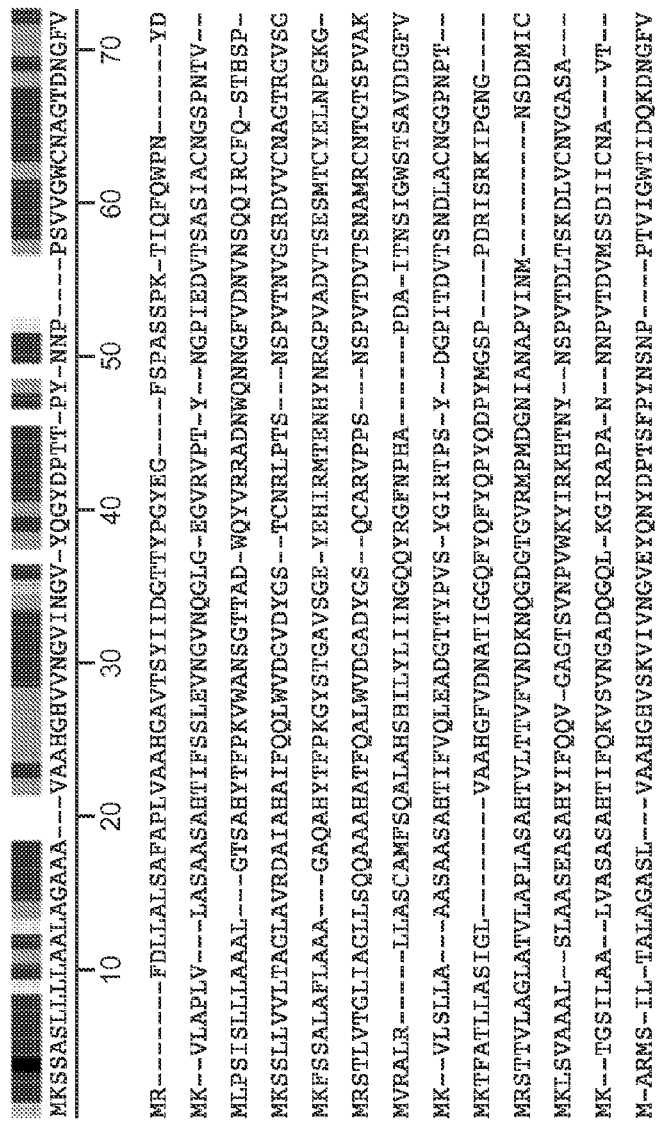

FIG. 3B

```
                                                                                                                         140
                          80              90             100            110            120            130
                          |               |              |              |              |              |
                      --PDAYASPDIICHKGATNAKGHATVAAGDKISIQWT-----WPESHKGPVIDYLAKC----------GGCT---
PTMTVSDAKMRCN--GGTSAQLSATVQAGSNVTAVWK--QWTHEQ--GPVQVWLFKCPG---AFGSSCKG-           116
----ASTSKVITVQAGTNVTAIWRYMLSTTGDS-----PADVMDSSHKGPTIAYLKK-------VDNAATA-          117
-------AQSTLSVAAGTT--------ITTYGAAPS--------VYHPGPMQFYLAR-------VPDGQDIN          107
KCPVKAGGTVTVEMHQ------------QPGDRSCKSEAIGGAHWGPVQIYLSK---------VSDASTA--         117
-------APKTLSVAAGSN--------YTFVVGDN--------IGHPGPLHFYMAK----------VPEGKTAA-      108
KCPVKAGSTVTVEMHQSHPPVPTLTYKQQANDRSCSSEAIGGAHYGPVLVYMSK----------VSDAASA-         129
TPSNYSNPDIICHRDGKPAKAHAPVKAGDKIQIQWNG---WPQSHKGPVLSYLAPCAN----TTDGCA---          122
----TPSDKITTVNAGSTVKAIWRHTLTSGAD----DVMDASHKGPTLAYLKK-------VDDALTD-             114
PVEDVTSLAIQCNADSAPAKLHASAAAGSTVTLRWT--IWPDSHVGPVITYMARC-------PDTGCQDW           117
GRDGLKKVNYAIPATAGSKMTEFRTEYVDGSRPQFIDK-----SHQGPISVYAKAVSDFDQSPGGSG---           126
------EGVETSLV---------AAGSQVTFKTDTA--------VYHQGPTSVYLSK---------ADGSLSD-       106
-----MKDSNVLTVPAGAKVGHFWGHEIGGAAGPND--ADNPIAASHKGPIMVYLAK-------VDNAATT-         117
SPDAFDSGDIICHKSAKPAGGHATVKAGDKISLQWD---QWPESHKGPVIDYLAAC--D-------GDCE---        121
```

FIG. 3C

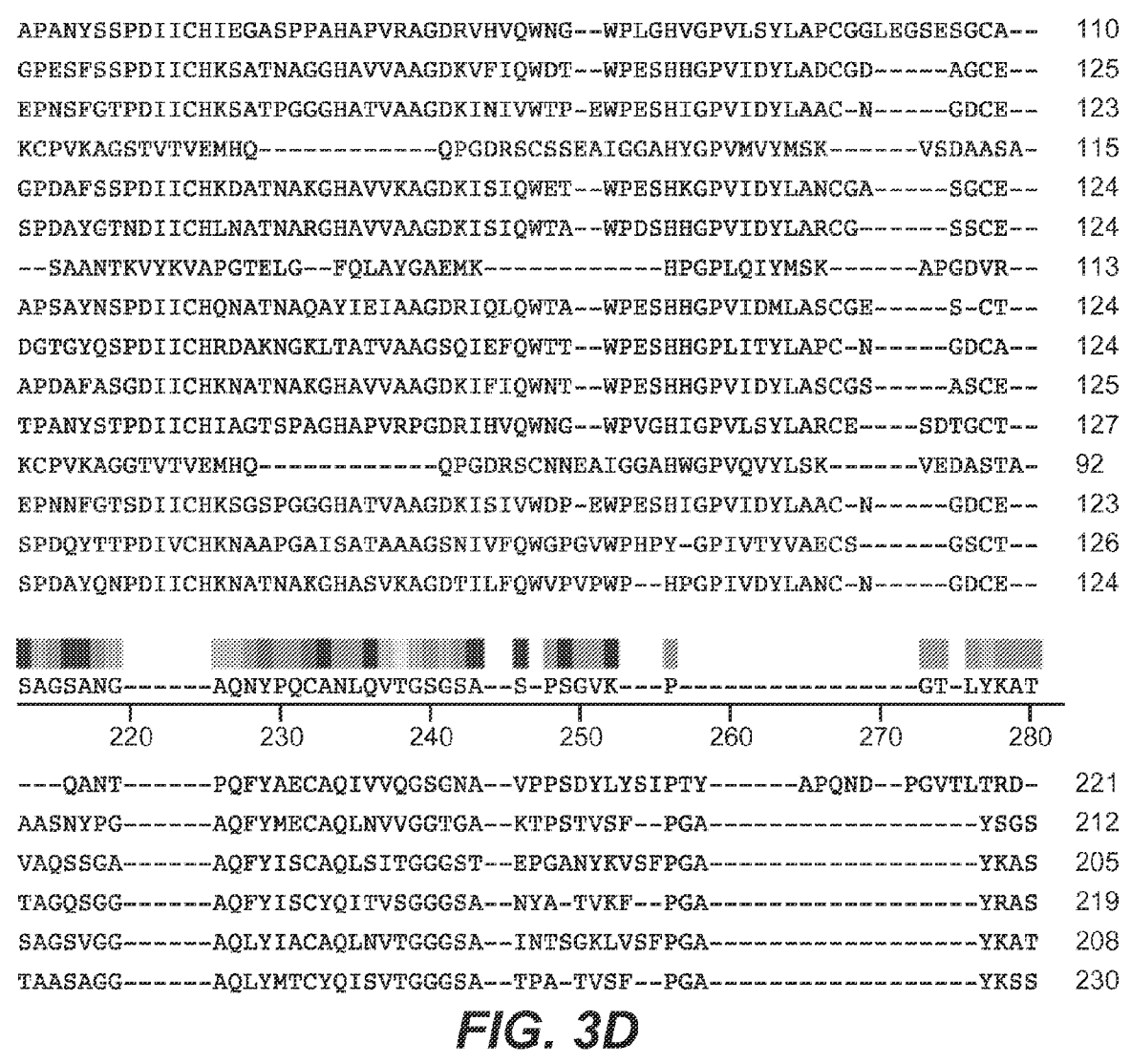

```
APANYSSPDIICHIEGASPPAHAPVRAGDRVHVQWNG---WPLGHVGPVLSYLAPCGGLEGSESGCA---                110
GPESFSSPDIICHKSATNAGGHAVVAAGDKVFIQWDT---WPESHHGPVIDYLADCGD-------AGCE---              125
EPNSFGTPDIICHKSATPGGGHATVAAGDKINIVWTP-EWPESHIGPVIDYLAAC-N-------GDCE---               123
KCPVKAGSTVTVEMHQ-------QPGDRSCSSEAIGGAHYGPVMVYMSK-----------VSDAASA-                  115
GPDAFSSPDIICHKDATNAKGHAVVKAGDKISIQWET---WPESHKGPVIDYLANCGA-------SGCE---              124
SPDAYGTNDIICHLNATNARGHAVVAAGDKISIQWTA---WPDSHHGPVIDYLARCG-------SSCE---               124
---SAANTKVYKVAPGTELG---FQLAYGAEMK------------------HPGPLQIYMSK-------APGDVR---        113
APSAYNSPDIICHQNATNAQAYIEIAAGDRIQLQWTA---WPESHHGPVIDMLASCGE-------S-CT---              124
DGTGYQSPDIICHRDAKNGKLTATVAAGSQIEFQWTT---WPESHHGPLITYLAPC-N-------GDCA---              124
APDAFASGDIICHKNATNAKGHAVVAAGDKIFIQWNT---WPESHHGPVIDYLASCGS-------ASCE---              125
TPANYSTPDIICHIAGTSPAGHAPVRPGDRIHVQWNG---WPVGHIGPVLSYLARCE-------SDTGCT---             127
KCPVKAGGTVTVEMHQ-------QPGDRSCNNEAIGGAHWGPVQVYLSK-----------VEDASTA-                  92
EPNNFGTSDIICHKSGSPGGGHATVAAGDKISIVWDP-EWPESHIGPVIDYLAAC-N-------GDCE---               123
SPDQYTTPDIVCHKNAAPGAISATAAAGSNIVFQWGPGVWPHPY-GPIVTYVAECS-------GSCT---                126
SPDAYQNPDIICHKNATNAKGHASVKAGDTILFQWVPVPWP--HPGPIVDYLANC-N-------GDCE---               124

SAGSANG------AQNYPQCANLQVTGSGSA---S-PSGVK---P-----------------GT-LYKAT
         220          230          240          250          260          270          280
---QANT-------PQFYAECAQIVVQGSGNA---VPPSDYLYSIPTY------APQND---PGVTLTRD-               221
AASNYPG------AQFYMECAQLNVVGGTGA---KTPSTVSF-PGA------------------YSGS                  212
VAQSSCA------AQFYISCAQLSITGGGST---EPGANYKVSFPGA-----------------YKAS                  205
TAGQSGG------AQFYISCYQITVSGGGSA---NYA-TVKF-PGA------------------YRAS                  219
SAGSVGG------AQLYIACAQLNVTGGGSA---INTSGKLVSFPGA-----------------YKAT                  208
TAASAGG------AQLYMTCYQISVTGGGSA---TPA-TVSF-PGA------------------YKSS                  230
```

*FIG. 3D*

```
Ncrassa EAA29132.1                         SVDKRRKLSWTKIDDSSPVLL------------DEKGGPPGRWATDVLIAQNNTWLLGLPNDLEPGPYVLRHELIALH
Ncrassa EAA30263.1                         ---TGIGGGWKFIQEDG-----------YN--------N-GQWGTSTVITNGGFQYIDIPACIPSGQYLLRAEMIALH
Ncrassa EAA33178.1                         TPSASDKVWFKIKEGGR----------------------EGTSNVWAATPLMTAPANYEYAIPSCLKPGYYLVRHEIIALH
Ncrassa EAA33408.1                         -------WFKIWHDGY---------------------DESTGKWAVQKVIDTNGLLSISLPTGMPTGAYLLRTEVIAMQ
Ncrassa EAA34466.1                         ---YDGSGGWFKI---KDW--------GATF---------PGGEWTLSD---------TYTFTIPSCIPSGDYLLRIQQIGIH
Ncrassa EAA36362.1                         ---GTSGLKWFKVAEAG------------L----------SNGKWAVDDLIANNGWSYFDMPTCIAPGQYLMRAELIALH
Ncrassa EAA29018.1                         SVDKTALKFFKID-----------GAGY---D-ATNG-WASDTLIKDGNSWVVEIPESIKPGNYVLRHEIIALH
St61 Sporotrichum thermophilum 2463        GVDKRQLRWTKVDDSLPAMEL-----------------RWATDVLIAANNSWQVEIPRGLRDGPYVLRHEIVALH
St61A Sporotrichum thermophilum 238        KVDKTTLKFFKIS-----------ESGLLDGTNAPGKWASDTLIANNNSWLVQIPPNIAPGNYVLRHEIIALH
St61B Sporotrichum thermophilum 465        TVDKSSLRWFKID-----------GAGY---D-KAAGRWAADALRANGNSWLVQIPSDLKAGNYVLRHEIIALH
St61D Sporotrichum thermophilum 803        --DGSSG-WFKVFEDGWAKNPSGGSG------DDDYWGTKDLNSCCGKMNVKIPADLPSGDYLLRAEALALH
Ncrassa EAA29347.1                         TVDKTSLEFFKID-----------EVGLVDGQK------WGSDQLIANNSWLVEIPPTIAPGFYVLRHEIIALH
Afu61A Aspergillus fumigatus Afu3g0        TVDKTTLEFFKID-----------GVGLVDGSNPPGVWGDDQLIADNNSWLVEIPPTIAPGYYVLRHELIALH
Afu61B Aspergillus fumigatus Afu6g0        SYDG--SGDWFKVHQEGLCADTSKGIK------DED--WCTWGKDTAS------FKIPQDTPAGQYLVRVEHIGLH
Afu61C Aspergillus fumigatus EDP471        TVDKTSLKFFKID-----------GVGLVDNSAVPGTWGDDQLIANSNWMVEIPKSIAPGNYVLRHEIIALH
Afumigatus XP_752040                       TVDKTTLKFVKIA-----------AQGLIDGSNPPGVWADDEMIANNNTATVTIPASYAPGNYVLRHEIIALH
Tt61A Thielavia terrestris 16380 JG        TVDKTKLEFFKID-----------EVGLVDGSSAPGVWGSDQLIANNNSWLVEIPPTIAPGNYVLRHEIIALH
Tt61B Thielavia terrestris 155418 J        GQNKTALRWTKIDDSSPTMQNVAGAGTQGEGTPGKRWATDVLIAANNSWQVAVPAGLPTGAYLRNEIIALH
Tt61C Thielavia terrestris 68900 JG        --DGSTG-WFKIFADTWSKKAGSVG-------DDDNWGTRDLNACCGKMQVKIPADIPSGDYLLRAEALALH
ABC2132 Cg61A Chaetomium globosum T        TVDKASLRFFKID-----------GAGY---D-KTAGRWAADTLRANGNSWLVQIPADLKAGNYVLRHEIIALH
Treesei eg17 proteinID120961 from J        TVNKNNLRWVKIQ-----------EAGINYNTQ-----VWAQQDLINQGNKWTVKIPSSLRPGNYVFRHELLAAH
Treesei eg14 GH61                          TVDKTTLEFFKID-----------GVGLLSG--GDPGTWASDVLISNNNTWVVKIPDNLAPGNYVLRHEIIALH
```

*FIG. 3E*

```
YANLKNG--------AQNYPQCVNLWVEGPGPK---AITVGKEEVVVAG--------QKEGVPATALYKAT 238
AASSTAG--------AQLYMECAQINIVGGTGG---TALPSTTYSIPGI----------------YKAT 210
SAYSYPG--------AQFYPGCHQLQVTGSGTK---TPSSGLVS-------------------FPGA---YKST 217
NVTTKADGNWYCEPQFYVNCAQVYVQGSSSGPLSIPKDKETSIPGHVHPSDKGLNFNMYDMKGLLPYQ 244
NPWPAGV--------PQFLYSCAHISVTGGGSA---SPA-TVSI---PGA---------------------FKET 195
NAGSQAG--------AQFYIGCAQINVTGGGSA---SPSNTVSF---PGA----------------YSAS 211
SAGQANG--------AQFYPQCFNLKVEGSGST---V-PAGVA------------------GTELYKAT 217
YAAEPGG--------AQNYPLCVNLWVEGGD-----------------G--------SMELDHFDATQFYRPD 207
SAGQQNG--------AQFYPQCFNLQVTGSGTQ---K-PSGVL------------------GTELYKAT 225
GAQSPNG--------AQAYPQCINLRVTGGGSN---L-PSGVA------------------GTSLYKAT 220
TAGSAGG--------AQFYMTCYQLTVTGSGSA---SPP-TVSF---PGA----------------YKAT 216
SAGQPNG--------AQNYPQCFNIQVTGSGTE---K-PAGVK------------------GTALYKPD 220
GAGSQNG--------AQNYPQCFNLQITGSGTA---Q-PSGVK------------------GTELYSPT 224
R-GFLGE--------AEFYFTCAQIEVTGSGSG---SPSPTVK---IPGV---------------YKPD 211
SAFETGG--------AQNYPQCFNLKVTGSGTD---S-PAGTL------------------GTELYTES 224
SAGNLNG--------AQNYPQCFNIQITGGGSA---Q-GSGTA------------------GTSLYKNT 224
SAENADG--------AQNYPQCFNLQITGTGTA---T-PSGVP------------------GTSLYTPT 225
YAARKNG--------AQNYPLCMNLWVDASGDN---SSVAATTAAVTAG--------GLQMDAYDARGFYKEN 252
TAGQVGG--------AQFYMSCYQITVSGGGSA---SPA-TVKF---PGA----------------YSAN 193
GASSPNG--------AQAYPQCINLRVTGSGTN---A-PSGVA------------------GTSLYRAS 220
GASSANG--------MQNYPQCVNIAVTGSGTK---ALPAGTP------------------ATQLYKPT 224
SAGQANG--------AQNYPQCFNIAVSGSGSL---Q-PSGVL------------------GTDLYHAT 223
```

*FIG. 3F*

```
            290         300         310         320         330         340         350
            |           |           |           |           |           |           |
            DPGILVNIY--------A---S--YTVPGPAVITG-ASSVAQS-SA-------------TAT--AV-PGGTAPAP-A

Ncrassa CAB97283.2    ---FKIDIY-------SSKATTYTPPGGRV--------------------------------------------
Ncrassa CAD21296.1    DPGVKISIYW-PPVT------SYTVPGPSVFTC-----------------------------------------
Ncrassa CAD70347.1    DPGILININYPVPTS------YKNPGPSVFTC------------------------------------------
Ncrassa CAE81966.1    DPGIQINIH-------AVVSNYVAPGPAVVAGGVTKQAGSGCI--------GCESTCKVGSSPSAVAPGG
Ncrassa CAF05857.1    DPGLLFNLYYPAPTS------YTNPGPAVATCDGASAPAA--------------PAPAPSSAAPSA
Ncrassa EAA26873.1    DPGILVDIH-------SAMSTYVAPGPAVYSGGSSKKAGSGCV--------GCESTCKVGSGPTGTASAV
Ncrassa EAA29132.1    DPGVAIDIY-------TAVLSTYVIPGPTL---------------------------APEAKPVPVT
Ncrassa EAA30263.1    DPGLLVNIYSMSPSS-------TYTIPGPAKFTCPAGNGGAGGG-------GSTT---TAKPASSTTSKAA
Ncrassa EAA33178.1    DPGVTYDAY-------QA--ATYTIPGPAV--------------------------------------------
St61 Sporotrichum thermophilum 2463    IPGPV--PFRPASSSGSNAKAALTTPTNFPGAVPDNCLLKNANWCGFEVPDYTNEDGCWASADNCWAQSKK
St61A Sporotrichum thermophilum 238    DPGYTVNIY-------SNFNNYTVPGPEVFTCSGSGSGSGSGS-------GSGSTPPSQPTTSTTLPTS
St61B Sporotrichum thermophilum 465    DPGILINIYGGSGKTDNGGKPYQIPGPALFTCPAGGSGSSPA---------PATTASTPKPTSASAPKPV
St61D Sporotrichum thermophilum 803    DAGILFDIY-------KNDIS--YPVPGPSLIAGASSSIAQSKMA------ATATASATLPGATGGSNSP
Ncrassa EAA29347.1    DPGILLNV--------TAGLRSYAVPGPTL-----------------------------AAGATPVPYA
Afu61A Aspergillus fumigatus Afu3g0    DAGILANIY-------TSPVT-YQIPGPALISG-ASAVQQTTSA-------ITASASAITGSATAAPTAA
Afu61B Aspergillus fumigatus Afu6g0    DPGILFNPY-------VSSPD-YTVPGPALIAGAASSIAQSTSV-------ATATGTATVPG---G----
Afu61C Aspergillus fumigatus EDP471    DPGILVNIH-------APLSGVTVPGPAVYSGGSTKKAGSACT--------GCESTCAVGSGPTATVSQS
Ncrassa EAA29347.1    DAGISVNIY-------QSLSS-YSIPGPALIKG-AVSVAQSHSA-------VTATATAITGLGDAPAATA
Afu61A Aspergillus fumigatus Afu3g0    DPGILVNIY-------NALST-VIVPGPTLIPG-AVSVVQSSST-------ITASGTPVTGSGSAPTTSA
Afu61B Aspergillus fumigatus Afu6g0    DPNVHFNIWPTPTA-------YSLPGPSVWTGGSAGGASP-----------------TAPAVNNAVQAAPTT
Afu61C Aspergillus fumigatus EDP471    DPGLLVDIY-------KSIAS-YAVPGPAMYTG-AVSITQSTSA-------ITATGTATVGSGADSTPVP
```

*FIG. 3G*

```
        ▓▓         ▓        ▓         ▓▓▓     ▓▓▓  ▓▓▓
  -T-AST----T------T--------A---G-SAP------C---A-----
        360       370       380       390      400       410       420
KPASGGS------------------DGN------APEVAEPSGGEGSPSAPGACEVAA--------------------- 241
PAASAPSATVPAVSATSAAA---------------------VGKASSTPKKGCKRAAR-------------------- 238
PVASTS----------------------------AAAGGGGGGSGGCSVAK-------------------------- 231
EQGLKSTITAVGTPVIVTRATSTVPMPNGETAA-------------------------------------------- 309
ITSAVT------------------------TLKTISVVAPQPTGGCTAAQWA------------------------- 292
CFDSAPPSGIKGCKIWEQEKCQALANSCDAKQFTGPPNKGKRWGDVTEQSSVQVPGVMKGADLVDTPV 310
STVATTLKTSTVVATTKSS------SSTTSASSSGSQPTSPSGCTVAK----------------------------- 305
STTASTPKPTNGSGSGTGAAHSTKCGGSKPAATTKASNPQPTNGGNSAVRAAAL----------------------- 293
ATSAAAAAPATSAAAATSQVQAAPATTLVTSTKAAAPATSAAAPATSAAAGGAGVQAKQTK---- 239
QQNISSA--RADGTPVIVTRSTETVPFTAAPTPA------------------------------------------ 382
TTTAAAA--ATTTTAGSGATATPSTGGSPSSAQPAPTTAAATSSPARPTRCAGLKKRRHARDVKVAL 295
------GGANPTATTTAATS-----AAPSTTLRTTTTTSA---AQTTAPPSG--DV----------QTK------- 328
PGSTAT--------------------------SAPGGGG--------CTVQK----------------------- 338
APAATTA--PAAAPAVT-TAPAAAAAPTKPATTAAAPQPTKPAKS-------------------------------- 271
TTTLSTT--TRATTTTTTTTAGSSTSVQSVYGQCGGGSWSGPTACVTGATCTSYNS-------------------- 346
MTTVSSP------ANPTAGAEAEADCGS---------SESSSAVAPEGTLKKW----------------------- 311
SSAASSEYSTVAVQVPTTKAQYTPVPSSSPSTFVTSPAPTTSVPSGSSVPVTS-------NTAAPL 291
                                                                            316
                                                                            333
                                                                            300
                                                                            337
```

*FIG. 3H*

```
Afumigatus XP_752040                    DPGIKDDIY-------SDLSGGYPIPGPALFNA
Tt61A Thielavia terrestris 16380 JG     DPGILVNIY-------SAPIT-YTVPGPALISG-AVSIAQSSSA----------------ITASGTALTGSATAPAAAA
Tt61B Thielavia terrestris 155418 J     DPGVLVNV--------TAALSSYVVPGPTV----------------------------------------AAGATPVPYA
Tt61C Thielavia terrestris 68900 JG     DPGIHINIH-------AAVSNYVAPGPAVYSGGTTKVAGSGCQ------------------GCENTCKVGSSPTATAPSG
ABC2132 Cg61A Chaetomium globosum T     DAGILFNPY-------VASPN-YPVPGPALIAGAASSVAQSKSV--------------------ATATASATLPGNNNG-
Treesei eg17 proteinID120961 from J     DPGILFNPY-------TTI-TSYTIPGPAL
Treesei eg14 GH61                       DPGVLINIY-------TSPLN-YIIPGPTVVSGLPTSVAQGSSA-----------------------ATATASATVPG--

YGQCGG-G-----TG-T--CA-G-T-
                                             430       440       450       460       470       480       490
                                                                                     W

Ncrassa CAB97283.2                                                           YGQCGGDQY---SGCTQ-CASGYT-
Ncrassa CAD21296.1
Ncrassa CAD70347.1                                                           YQQCGGTGY---TGCTS-CASGST-
Ncrassa CAE81966.1
Ncrassa CAF05857.1                                                              QCGGMGF---SGCTT-CASPYT-
Ncrassa EAA26873.1
Ncrassa EAA29132.1
Ncrassa EAA30263.1
Ncrassa EAA33178.1
Ncrassa EAA33408.1   VDTTSNQKAAANNNNVVSI-----------PAATATTFITTSSAAPSKPVTTVPSVAITTTTSAAVAIPTETAAQ
Ncrassa EAA34466.1                                                           YGQCGGIGY---SGCTS-CASGST-
Ncrassa EAA36362.1                                                           YGQCGGKGW---TGPTS-CASG-T-
Ncrassa EAA29018.1                                                           WGQCGGKGF---TGPTE-CESGST-
St61 Sporotrichum thermophilum 2463
```

*FIG. 3I*

```
ATTTSTT-NAAAAATSAAAAAGTSTTTTSAAAVVQTSSSSSAPSSAA----------------AAATTTAA  250
QQSPSVS--TAAGTPVVVTRTSETAPYTGAMTPTVAA-------------------------------  334
KSGAGSD---------------GGA------G------TDGGSSSSPDTGSACSVQA-----------  320
-------GGPNPQPTTATTTA--NPGVSTTLRTSTSTSAQVTPPPTGGNA-----------QTK----  280
--------------------------------------------------------------------  318
-------GGSGPTSRTTTTARTTQASSRP--------SSTPPATTSAPAGGPT-----------QTL--  247
                                                                     312
            ┌────┬────┐
            │    YYSQ      │
            500  510  520
-------C-----------------------
--------SGFQF---------------------                                246
-----------CKAVS----P-----PYYSQCAPTS                              238
--------------------------------KH                                231
-----------CSAVS----P-----PYYSQCV                                 344
--------------------------AF----KG                                293
--------CKKMN------D------YYSQC-S                                 342
----FTC                                                           308
NTLIRCGRGDKNQRRAMHINRHKRADF                                       322
--------CK-VG-----N----DYYSQCL                                    241
--------CKFSN----D------WYSQCLP                                   472
--------CT------KYN----DWYS---QC-V                                326
                                                                  359
                                                                  369
                                                                  271
```

*FIG. 3J*

| | | |
|---|---|---|
| St61A Sporotrichum thermophilum 238 | -.KKRSDNQSVDIIHVIPFFFFCTAVRSLC-VEAWLITSPA-RGRRPFLLHWVHGLMLPLD--VVKRRRRK | |
| St61B Sporotrichum thermophilum 465 | YGQCGNGW---TGPTV-CAPGSS------------------- | |
| St61D Sporotrichum thermophilum 803 | YQQCGGQGY---TGCTN-CASGST------------------- | |
| Ncrassa EAA29347.1 | ---------G----------------ARRAAALA-----------------RRHAR | |
| Afu61A Aspergillus fumigatus Afu3g0 | -------------------YYSQ------CQKRRA---------------------- | |
| Afu61B Aspergillus fumigatus Afu6g0 | EQCGGLNW---TGSGS-CEARTT------------------- | |
| Afu61C Aspergillus fumigatus EDP471 | PTAAPGGT---------------QTVYGQCGGQNW---TGPT---------------- | |
| Afumigatus XP_752040 | ASARPTG-----------------------CSSGRS------------------RKQP-----------RRHAR | |
| Tt61A Thielavia terrestris 16380 JG | ------------------------------------------------RMKGR | |
| Tt61B Thielavia terrestris 155418 J | YGQCGGNGY---SGCTQ-CAPGYT------------------- | |
| Tt61C Thielavia terrestris 68900 JG | YGQCGGSGW---TGPTA-CAAGSS------------------- | |
| ABC2132 Cg61A Chaetomium globosum T | | |
| Treesei eg17 proteinID120961 from J | ----------------------w----------------------- | |
| Treesei eg14 GH61 | YGQCGGSGY---SGPTR-CAPPAT------------------- | |

*FIG. 3K*

```
SSLIYVCIYIGFVL-----PFFFV-YDIF.        438
-------CS-----VLM-----EWYS---QCL.     343
------CSAVS----P------PYYSQCV         323
DVAFL---------------------------D     341
-------CI-------------------PTAS      342
-------CBQYW----------PYYYQCI         330
----------------YIV                   364
                                      250
DMVVA----RG-----------AE-BAN.         369
-----------------------GY-DRRG        330
------CKAVS----P------PYYSQCAPSS      315
-------CS-----VLM-----DWTA---QC-V     349
-----------------------------QG       249
-------CS-----TLM-----PYVA---QCLN     344
```

FIG. 3L

SEQ ID NO:30
Nucleic acid sequence of Eg4, an endoglucanase from *Trichoderma reesei* atgatccagaagctttccaaccttcttctcaccgcactagcggtggcaaccggtgttgttggacacggac
acatcaacaacattgtcgtcaacggagtgtactaccagggatatgatcctacatcgttcccatatgaatc
tgacccgccatagtggtgggctggacggctgccgatcttgacaacggcttcgtctcaccgacgcatat
cagagcccggacatcatctgccacaagaatgccaccaacgccaaaggacacgcgtccgtcaaggccggag
acactattcccctccagtgggtgccagttccttggccgcacccaggcccatcgtcgactacctggccaa
ctgcaacggcgactgcgagaccgtggacaagacgtcccttgagttcttcaagattgacggcgtcggtctc
atcagcggcggagatccgggcaactgggcctcggacgtgttgattgccaacaacaacacctgggttgtca
agatccccgaggatctcgccccgggcaactacgtgcttcgccacgagatcatcgccttgcacagcgccgg
gcaggcggacggcgctcagaactaccctcagtgcttcaacctcgccgtcccaggctccggatctctgcag
ccgagcggcgtcaagggaaccgcgctctaccactccgatgacccggtgtcctcatcaacatctacacca
gccctcttgcgtacaccattcctggaccttccgtggtatcaggcctccccacgagtgtcgcccagggcag
ctccgccgcgacggccactgccagcgccactgttcctggcggtagcggaccgggaaacccgaccagtaag
actacgacgacggcgaggacgacacaggcctcctctagcagggccagctctactcctcctgctactacgt
cggcacctggtggaggcccaacccagactttgtacggccagtgtggtggcagcggctacagtggtcctac
tcgatgcgcgccgccggccacttgctctaccttgaacccatactacgccagtgccttaactag

FIG. 4A

SEQ ID NO:27
Protein sequence of Eg4, an endoglucanase from *Trichoderma reesei*

<u>MIQKLSNLLVTALAVATGVVG</u>hghindivingvwyqaydpttfpyesnppivvgwtaadldngfvspday
qnpdiichknatnakghasvkagdtilfqwvpvpwphpgpivdylancngdcetvdkttleffkidgvgl
lsggdpgtwasdvlisnnntwvvkipdnlapgnyvlrheiialhsagqangaqnypqcfniavsgsgslq
psgvlgtdlyhatdpgvliniytsplnyiipgptvvsglptsvaq *gssaatatasatvpgggsgptsrtt
ttarttqassrpsstppattsapagg*ptqtlygqcggsgysgptrcappatcstlnpyyaqcl n

FIG. 4B

Alignment of *T. reesei* Eg4 with TrEGb (or TrEG7, or *T. reesei* Eg7) (SEQ ID NO:80) and TtEG from *Thielavia terrestris* (SEQ ID NO:81). Alignment was made in Muscle (Edgar R.C. BMC Bioinformatics, 2004, 5: 113) using default parameters.

```
                 *        20         *        40         *
TtEG  : ----MLANGAIVFLAAALG-VSGHYTWPRVNDGADWQQVRKADNWQ----- :  41
TrEg4 : MIQKLSNLLVTALAVATG-VVGHGHINDIVINGVWYQAYDPTTFPYESNP :  49
TrEGb : ---MKSCAILAALGCLAGSVLGHGQVQNFTINGQYNQGFILDYYYQKQNT :  47

60         *        80         *        100
TtEG  : ---------------DNGYVG---DVTSPQIRCFQATPSPAPSVLNTTAGST :  75
TrEg4 : ----PIVVGWTAADLDNGFVSPDAYQNPDIICHK-NATNAKGHASVKAGDT :  95
TrEGb : GHFPNVAGWYAEDLDLGFISPDQYTTPDIVCHK-NAAPGAISATAAAGSN :  96

*        120        *        140        *
TtEG  : VTY-WANPDVY-HP-GPVQFYMARVPDGEDINSWNGDGAVWFKVYEDHPT : 122
TrEg4 : ILFQWV-PVPWPHP-GPIVDYLANC--NGDCETVDKTTLEFFKIDGVGLL : 141
TrEGb : IVFQWG-PGVWPHPYGPIVTYVVEC--SGSCTTVNKNNLRWVKIQEAGIN : 143

160        *        180        *        200
TtEG  : FGAQL-TWPS-----TGKSSFAVPIPPCIKSGYYLLRAEQIGLHVAQSVGG : 167
TrEg4 : SGGDPGTWASDVLISNNNTWVVKIPDNLAPGNYVLRHEIIALHSAGQANG : 191
TrEGb : YNTQV--WAQQDLINQGNKWTVKIPSSLRPGNYVFRHELLAAHGASSANG : 191

*        220        *        240        *
TtEG  : AQFYISCAQLSVTGGGSTEPPNKVAFPGAYSATDPGILINIYYPVPTSYQ : 217
TrEg4 : AQNYPQCFNIAVSGSGSLQ-PSGVLGTDLYHATDPGVLINI-YTSPLNYI : 239
TrEGb : MQNYPQCVNIAVTGSGTKALPAGTPATQLYKPTDPGILFNP-YTTITSYT : 240

260        *        280        *        300
TtEG  : NPGPAVFSC----------------------------------------- : 226
TrEg4 : IPGPTVVSGLPTSVAQGSSAATATASATVPGGGSGPTSRTTTTARTTQAS : 289
TrEGb : IPGPALWQG----------------------------------------- : 249

*        320        *        340        *
TtEG  : -------------------------------------------------- :  -
TrEg4 : SRPSSTPPATTSAPAGGPTQTLYGQCGGSGYSGPTRCAPPATCSTLNPYY : 339
TrEGb : -------------------------------------------------- :  -

TtEG  : -----  :  -
TrEg4 : AQCLN  : 344
TrEGb : -----  :  -
```

*FIG. 5*

Conserved residues inferred from alignment and structures
of TrEGb (or *T. reesei* Eg7, or TrEG7) (pdb: 2vtc) and TtEG (pdb: 3EII)

| Protein | TtEG | TrEGb | TrEg4 |
|---|---|---|---|
| Metal coordination | H19 | H20 | H22 |
| Conserved surface patch | D42 | D62 | D61 |
| Conserved surface patch | G44 | G64 | G63 |
| Metal coordination | H86 | H108 | H107 |
| Buried salt bridge | R153 | R177 | R177 |
| Buried salt bridge | E155 | E179 | E179 |
| Metal coordination | H160 | H184 | H184 |
| Metal coordination | Q169 | Q193 | Q193 |
| Metal coordination | Y171 | Y195 | Y195 |
| Involved in activity | Y210 | Y233 | Y232 |
| Disulfide | C56 | C77 | C77 |
| Disulfide | C174 | C197 | C198 |

FIG. 6A

Conserved amino acids of CBM1 domains of TrEg4, Tr6A and Tr7A
inferred from alignment (Full length numbering)

| CBM1 | TrEg4 | Tr6A | Tr7A |
|---|---|---|---|
| | G313 | G32 | G483 |
| | Q314 | Q33 | Q484 |
| | C315 | C34 | C485 |
| | G316 | G35 | G486 |
| | G317 | G36 | G487 |
| | S321 | S40 | S491 |
| | G322 | G41 | G492 |
| | P323 | P42 | P493 |
| | T324 | T43 | T494 |
| | C326 | C45 | C496 |
| | A327 | A46 | A497 |
| | T331 | T50 | T501 |
| | C332 | C51 | C502 |
| | N336 | N55 | N506 |
| | Y338 | Y57 | Y508 |
| | Y339 | Y58 | Y509 |
| | Q341 | Q60 | Q511 |
| | C342 | C61 | C512 |
| | L343 | L62 | L513 |

FIG. 6B

GH61 endoglucanase motifs of the disclosure:

Motif 1 of GH61 Family Endoglucanases:
SEQ ID NO:84: (I/L/M/V)-P-a-a-a-G-a-Y-(I/L/M/V)-a-R-a-(E/Q)-a-a-a-(H/N/Q)

Motif 2 of GH61 Family Endoglucanases:
SEQ ID NO:85: (I/L/M/V)-p-a-a-a-a-a-G-a-Y-(I/L/M/V)-a-R-a-(E/Q)-a-a-a-(H/N/Q)

Motif 3 of GH61 Family Endoglucanases:
SEQ ID NO:86: (I/L/M/V)-p-a-a-a-G-a-Y-(I/L/M/V)-a-R-a-(E/Q)-a-a-a-(H/N/Q)

Motif 4 of GH61 Family Endoglucanases:
SEQ ID NO:87: (I/L/M/V)-p-a-a-a-a-G-a-Y-(I/L/M/V)-a-R-a-(E/Q)-a-a-a-A-(H/N/Q)

Motif 5 of GH61 Family Endoglucanases:
SEQ ID NO:88: (F/W)-(T/F)-K-(A/I/V)

Motif 6 of GH61 Family Endoglucanases:
SEQ ID NO:89: H-a-a-G-P-a-a-a-(Y/W)-(A/I/L/M/V)

Motif 7 of GH61 Family Endoglucanases:
SEQ ID NO:90: H-a-G-P-a-a-a-(Y/W)-(A/I/L/M/V)

Motif 8 of GH61 Family Endoglucanases:
SEQ ID NO:91: (E/Q)-a-Y-a-a-C-a-(E/H/Q/N)-(F/I/L/V)-a-(I/L/V)

FIG. 7

| Protein composition of T.reesei Integrated strain H3A ||
|---|---|
| Protein | % of Total Area |
| Fv3A | 9.6 |
| Fv51A+Fv43D | 14.8 |
| Xyn 3 | 12.6 |
| Bgl 1 | 7.5 |
| CBH1 | 36.4 |
| EGLs | 5.6 |
| CBH2 | 9.5 |
| Other | 4.0 |

*FIG. 9*

| Proteins added to T. reesei integrated strain H3A |||
|---|---|---|
| | Protein | Stock Protein Concentration (mg/ml) |
| 1 | Purified T. reesei CBH1 | 7.4 |
| 2 | Purified T. reesei CBH2 | 3.0 |
| 3 | Purified T. reesei EGI | 3.9 |
| 4 | -- | -- |
| 5 | Water | |
| 6 | Purified T. reesei EG4 | 1.1 |
| 7 | H3A UF concentrate | 102.8 |
| 8 | Purified T. reesei Bgl1 | 3.9 |
| 9 | Purified T. reesei Xyn2 | 2.6 |
| 10 | Purified T. reesei Xyn3 | 4.6 |
| 11 | Purified F. verticillioides Fv43D | 6.8 |
| 12 | Purified F. verticillioides Fv51A | 7.8 |

*FIG. 10*

Dosing chart for testing range of EG4 concentrations for improved saccharification of dilute ammonia pretreated corncob

| Vial | Water mL | 6N Sulfuric Acid (mL) | Substrate (g) | H3A or #27 (mL) | Purified EG4 (mL) | Volume (mL) | Sample Description |
|---|---|---|---|---|---|---|---|
| 1 | 2.931 | 0.026 | 1.866 | 0.177 | | 5 | 100% #27 |
| 2 | 2.982 | 0.026 | 1.866 | 0.127 | | 5 | 100% H3A |
| 3 | 2.874 | 0.026 | 1.866 | 0.114 | 0.120 | 5 | 90% H3A 10% EG4 |
| 4 | 2.766 | 0.026 | 1.866 | 0.101 | 0.241 | 5 | 80% H3A 20% EG4 |
| 5 | 2.551 | 0.026 | 1.866 | 0.076 | 0.482 | 5 | 60% H3A 40% EG4 |
| 6 | 2.335 | 0.026 | 1.866 | 0.051 | 0.723 | 5 | 40% H3A 60% EG4 |
| 7 | 2.119 | 0.026 | 1.866 | 0.025 | 0.963 | 5 | 20% H3A 80% EG4 |
| 8 | 2.896 | 0.026 | 1.866 | 0.127 | 0.086 | 5 | 14 H3A + 1 EG4 |
| 9 | 2.724 | 0.026 | 1.866 | 0.127 | 0.258 | 5 | 14 H3A + 3 EG4 |
| 10 | 2.551 | 0.026 | 1.866 | 0.127 | 0.430 | 5 | 14 H3A + 5 EG4 |
| 11 | 2.121 | 0.026 | 1.866 | 0.127 | 0.860 | 5 | 14 H3A + 10 EG4 |

*FIG. 15*

Dosing chart for testing range of EG4 concentrations (0.05 to 1.0 mg/g) for improved saccharification of dilute ammonia pretreated corncob

| Vial | Water mL | 6N Sulfuric Acid (mL) | Substrate (g) | H3A or #27 (mL) | Purified EG4 (mL) | Volume (mL) | Sample Description |
|---|---|---|---|---|---|---|---|
| 1 | 2.9 | 0.0261 | 1.87 | 0.177 | | 5.0 | 14 mg/g H3A/EG4#27 |
| 2 | 2.8 | 0.0261 | 1.87 | 0.177 | 0.086 | 5.0 | 14mg/g H3A/EG4#27 + 1 mg/g EG4 |
| 3 | 3.0 | 0.0261 | 1.87 | 0.127 | | 5.0 | 14mg/g H3A |
| 4 | 3.0 | 0.0261 | 1.87 | 0.127 | 0.004 | 5.0 | 14mg/g H3A + .05 mg/g EG4 |
| 5 | 3.0 | 0.0261 | 1.87 | 0.127 | 0.009 | 5.0 | 14mg/g H3A + 0.1 mg/g EG4 |
| 6 | 2.9 | 0.0261 | 1.87 | 0.127 | 0.043 | 5.0 | 14mg/g H3A + 0.5 mg/g EG4 |
| 7 | 2.9 | 0.0261 | 1.87 | 0.127 | 0.086 | 5.0 | 14mg/g H3A + 1.0 mg/g EG4 |

FIG. 17A

Dosing chart for testing range of EG4 concentrations (0.1 to 0.5 mg/g) for improved saccharification of dilute ammonia pretreated corncob

| Vial | Water mL | 6N Sulfuric Acid (mL) | Substrate (g) | H3A or #27 (mL) | Purified EG4 (mL) | Volume (mL) | Sample Description |
|---|---|---|---|---|---|---|---|
| 1 | 2.9 | 0.0261 | 1.87 | 0.177 | | 5.0 | 14 mg/g #27 |
| 2 | 3.0 | 0.0261 | 1.87 | 0.127 | | 5.0 | 14 mg/g H3A |
| 3 | 3.0 | 0.0261 | 1.87 | 0.127 | 0.009 | 5.0 | 14 mg/g H3A + 0.1 mg/g EG4 |
| 4 | 3.0 | 0.0261 | 1.87 | 0.127 | 0.017 | 5.0 | 14 mg/g H3A + 0.2 mg/g EG4 |
| 5 | 3.0 | 0.0261 | 1.87 | 0.127 | 0.026 | 5.0 | 14 mg/g H3A + 0.3 mg/g EG4 |
| 6 | 2.9 | 0.0261 | 1.87 | 0.127 | 0.034 | 5.0 | 14 mg/g H3A + 0.4 mg/g EG4 |
| 7 | 2.9 | 0.0261 | 1.87 | 0.127 | 0.043 | 5.0 | 14 mg/g H3A + 0.5 mg/g EG4 |

*FIG. 17B*

| Yield of Xylose Monomer released by EG4 on hydrolysis of dilute ammonia pretreated corncob | | | |
|---|---|---|---|
| mg/g Enzyme added per gram Glucan + Xylan | H3A | EG4 + 1.12 mg/g Xyn3 | H3A/EG4 #27 |
| 1.7 | 30.1% | 21.9% | 36.1% |
| 6.0 | 65.7% | 23.0% | 73.9% |
| 8.0 | 70.1% | 24.1% | 79.9% |
| 14.0 | 76.1% | 23.5% | 88.1% |
| 21.0 | 80.5% | 25.7% | 92.0% |

*FIG. 20*

| Percent Yield of Glucose Monomer released by EG4 on hydrolysis of dilute ammonia pretreated corncob | | | |
|---|---|---|---|
| mg/g Enzyme added per gram Glucan + Xylan | H3A | EG4 + 1.12 mg/g Xyn3 | H3A/EG4 #27 |
| 1.7 | 22.4% | 11.0% | 25.0% |
| 6.0 | 45.7% | 12.7% | 67.6% |
| 8.0 | 52.7% | 13.2% | 75.5% |
| 14.0 | 65.4% | 14.1% | 90.4% |
| 21.0 | 74.2% | 15.4% | 97.9% |

*FIG. 21*

| Total Fermentable Monomers (mg/ml) released by EG4 on hydrolysis of dilute ammonia pretreated corncob. | | | |
|---|---|---|---|
| mg/g Enzyme added per gram Glucan + Xylan | H3A | EG4 + 1.12 mg/g Xyn3 | H3A/EG4 #27 |
| 1.7 | 45 | 27 | 52 |
| 6.0 | 95 | 30 | 122 |
| 8.0 | 105 | 31 | 134 |
| 14.0 | 12 | 132 | 155 |
| 21.0 | 132 | 35 | 164 |

*FIG. 22*

| Table 6-1: Effect of addition of purified EG4 on glucose release from dilute ammonia pretreated corncob | | |
|---|---|---|
| EG4 added (mg/g) | Xyn3 added (mg/g) | Mg/mL Glucose monomer released |
| 0.53 | 0.53 | 3.4 |
| 0 | 0.53 | 0.77 |

*FIG. 23*

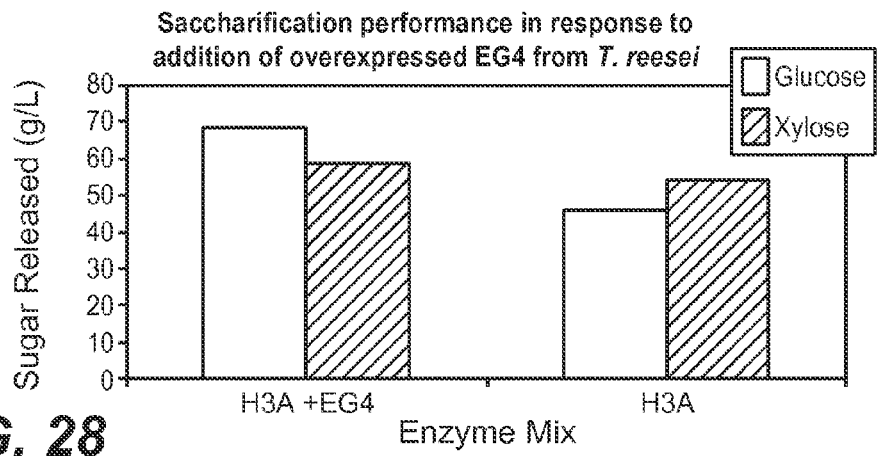
FIG. 28
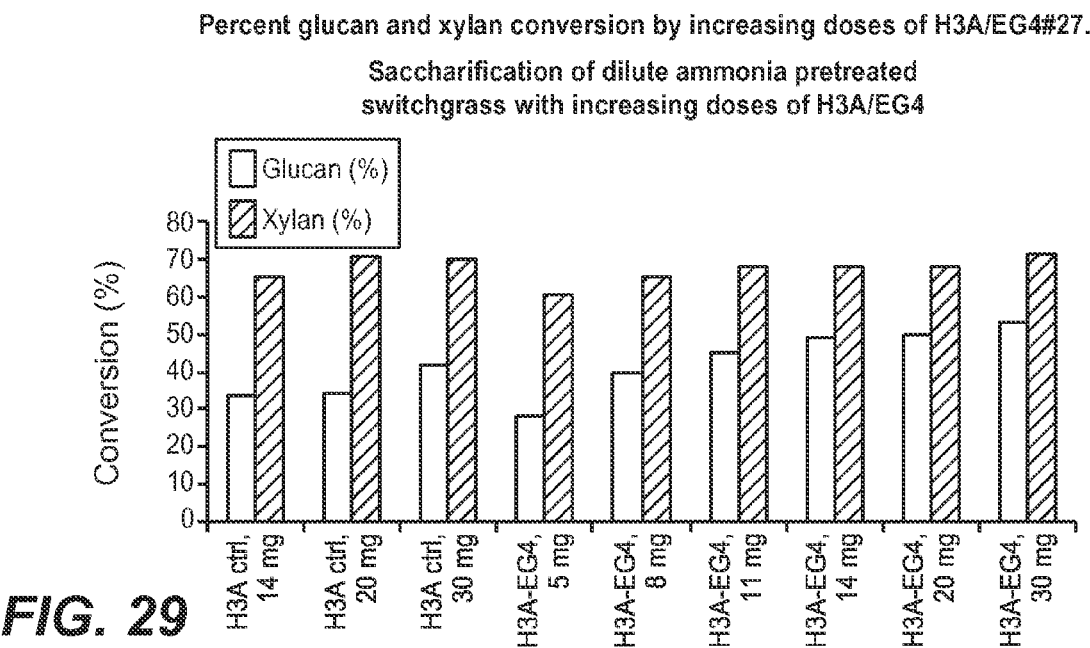
FIG. 29
Effect of *T. reesei* EG4 additions on corncob saccharification
| Protein Added (mg/g) | CBH1 background (5 mg/g) | | Without CBH1 background |
|---|---|---|---|
| | CBH1 | EG4 | EG4 |
| | % glucan conversion | | |
| 0 | 2.7 | 2.8 | 2.7 |
| 1 | 3.1 | 6.6 | 5.0 |
| 2 | 3.5 | 7.8 | 6.9 |
| 3 | 3.4 | 8.2 | 7.3 |
| 4 | 3.4 | 8.8 | 8.2 |
| 5 | 3.5 | 7.8 | 8.8 |
FIG. 30

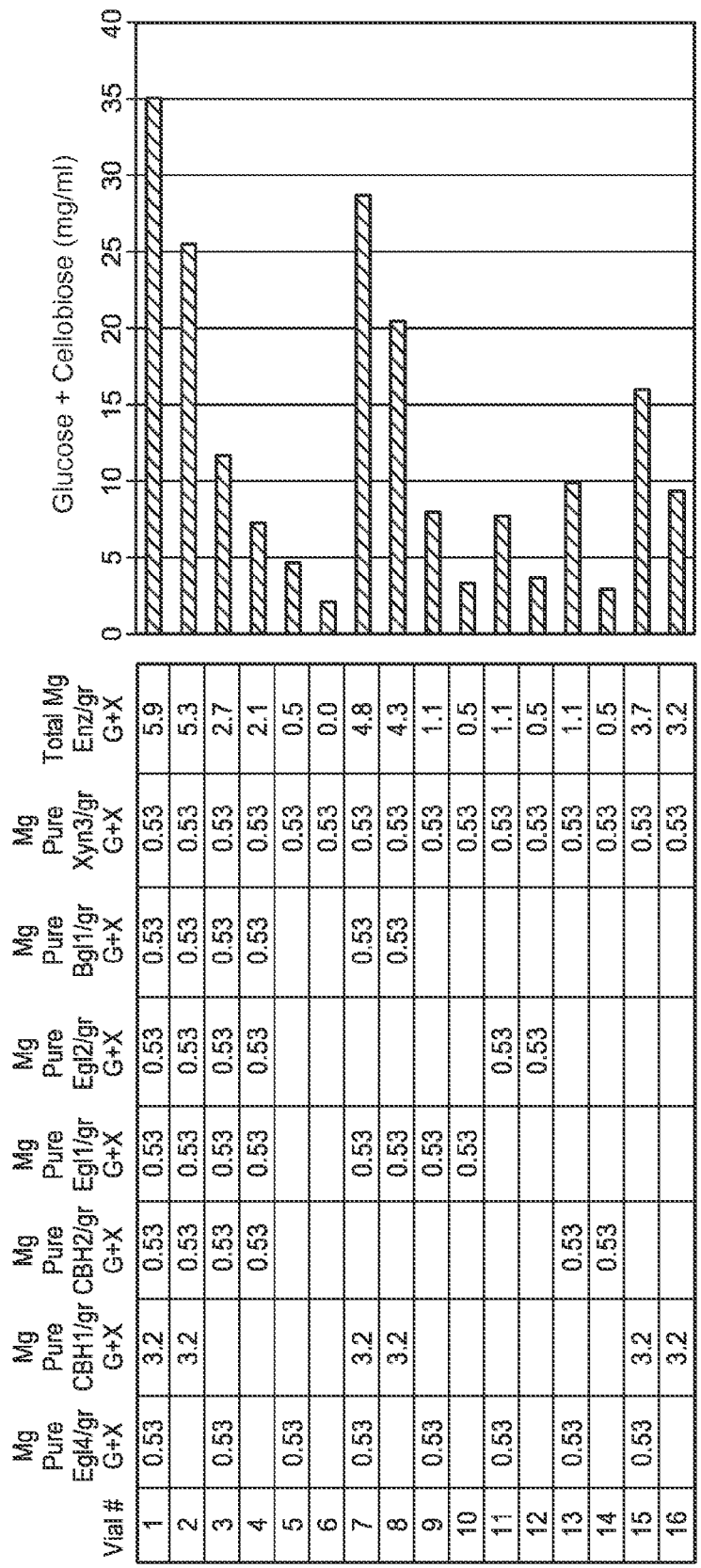

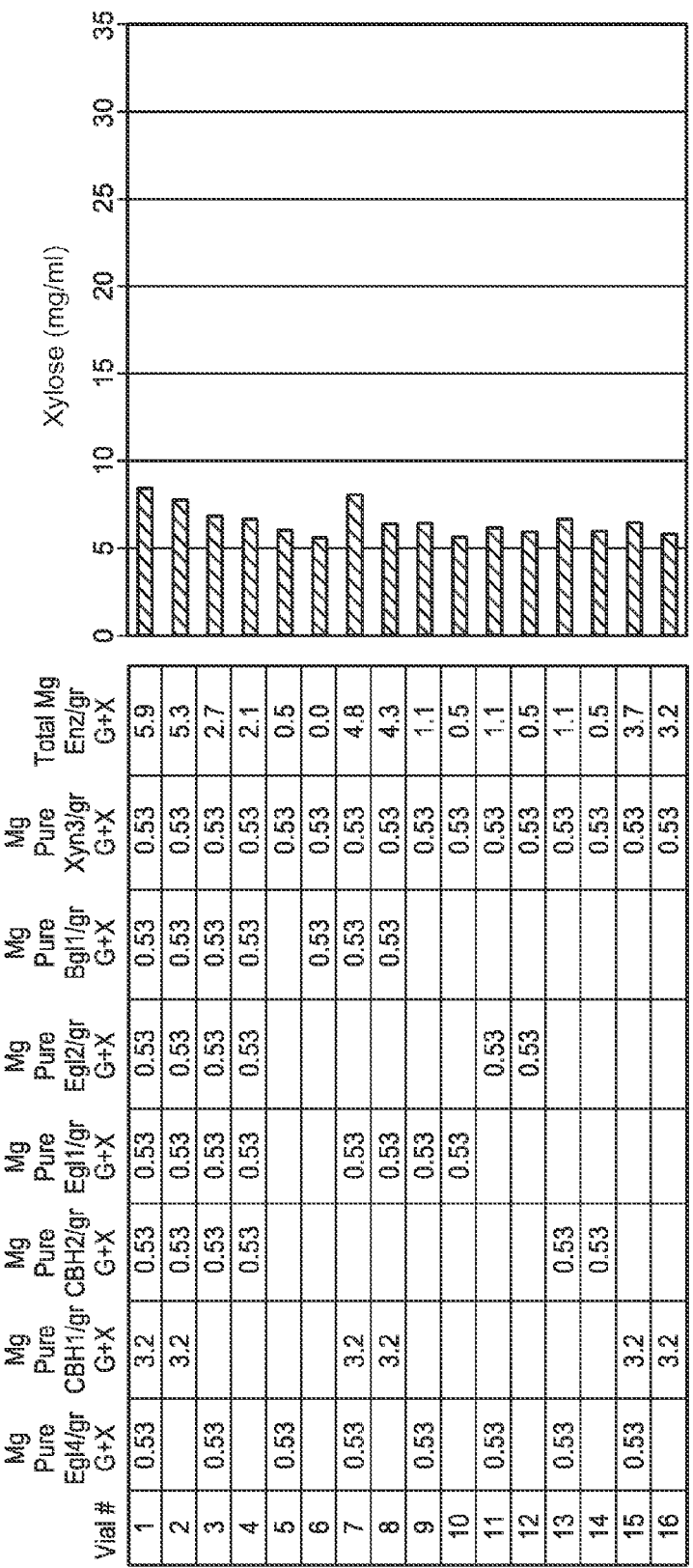

| CBH1 (mg/g glucan) | CBH2 (mg/g glucan) | EG2 (mg/g glucan) | EG4 (mg/g glucan) | Glucan Conversion (%) |
|---|---|---|---|---|
| | | | 20 | 18.6 |
| 1.25 | | | 18.75 | 42.7 |
| 2.5 | | | 17.5 | 46.9 |
| 5 | | | 15 | 59.1 |
| 10 | | | 10 | 74.8 |
| 20 | | | | 68.7 |
| | | | 20 | 18.3 |
| | 1.25 | | 18.75 | 32.1 |
| | 2.5 | | 17.5 | 38.2 |
| | 5 | | 15 | 35.9 |
| | 10 | | 10 | 41.7 |
| | 20 | | | 24.9 |
| | | | 20 | 17.6 |
| | | 1.25 | 18.75 | 24.3 |
| | | 2.5 | 17.5 | 26.3 |
| | | 5 | 15 | 24.3 |
| | | 10 | 10 | 29.2 |
| | | 20 | | 23.1 |
| | | | | 12.4 |
| 1.25 | | | | 28.1 |
| 2.5 | | | | 34.1 |
| 5 | | | | 40.0 |
| 10 | | | | 52.9 |
| 20 | | | | 68.2 |
| | | | | 12.5 |
| | 1.25 | | | 15.9 |
| | 2.5 | | | 17.3 |
| | 5 | | | 19.9 |
| | 10 | | | 22.1 |
| | 20 | | | 26.2 |
| | | | | 12.4 |
| | | 1.25 | | 15.0 |
| | | 2.5 | | 16.6 |
| | | 5 | | 17.0 |
| | | 10 | | 19.8 |
| | | 20 | | 22.1 |
| | | | 20 | 16.3 |
| | | | 18.75 | 17.4 |
| | | | 17.5 | 17.4 |
| | | | 15 | 16.2 |
| | | | 10 | 15.4 |
| | | | | 11.1 |

FIG. 36A

| CBH1 (mg/g glucan) | CBH2 (mg/g glucan) | EG2 (mg/g glucan) | EG4 (mg/g glucan) | Glucan Conversion (%) |
|---|---|---|---|---|
|  |  |  | 20 | 22.8 |
| 1 | 0.25 |  | 18.75 | 56.6 |
| 2 | 0.5 |  | 17.5 | 67.0 |
| 4 | 1 |  | 15 | 77.4 |
| 8 | 2 |  | 10 | 102.0 |
| 16 | 4 |  |  | 65.5 |
|  |  |  | 20 | 23.1 |
| 0.625 | 0.625 |  | 18.75 | 51.5 |
| 1.25 | 1.25 |  | 17.5 | 73.8 |
| 2.5 | 2.5 |  | 15 | 82.5 |
| 5 | 5 |  | 10 | 100.7 |
| 10 | 10 |  |  | 76.1 |
|  |  |  | 20 | 30.5 |
| 0.25 | 1 |  | 18.75 | 58.0 |
| 0.5 | 2 |  | 17.5 | 69.7 |
| 1 | 4 |  | 15 | 74.5 |
| 2 | 8 |  | 10 | 85.6 |
| 4 | 16 |  |  | 60.4 |
|  |  |  | 20 | 29.5 |
| 1.125 |  | 0.125 | 18.75 | 55.1 |
| 2.25 |  | 0.25 | 17.5 | 71.1 |
| 4.5 |  | 0.5 | 15 | 86.3 |
| 9 |  | 1 | 10 | 90.3 |
| 18 |  | 2 |  | 54.2 |
|  |  |  | 20 | 30.3 |
|  | 1.125 | 0.125 | 18.75 | 51.7 |
|  | 2.25 | 0.25 | 17.5 | 66.4 |
|  | 4.5 | 0.5 | 15 | 73.1 |
|  | 9 | 1 | 10 | 72.6 |

(units: µL of each added to the reaction mixture)

|  | 1 | 2 | 3 | 4 | 5 | 6 |
|---|---|---|---|---|---|---|
| Avicel | 50 | 50 | 50 | 50 | 50 | 50 |
| CBH1 | 3.4 | 0 | 0 | 3.4 | 0 | 3.4 |
| EG4 | 0 | 50 | 0 | 50 | 50 | 50 |
| Asc.Acid | 0 | 0 | 6 | 0 | 6 | 6 |
| $Mn^{2+}$ | 6 | 6 | 6 | 6 | 6 | 6 |
| Buffer | 240.6 | 194 | 238 | 190.6 | 188 | 184.6 |
| Total | 300 | 300 | 300 | 300 | 300 | 300 |

FIG. 39A (units: µL of each added to the reaction mixture)

|  | 1 | 2 | 3 | 4 | 5 | 6 | 7 | 8 | 9 |
|---|---|---|---|---|---|---|---|---|---|
| Avicel | 80 | 80 | 80 | 80 | 80 | 80 | 80 | 80 | 80 |
| CBH2 | 16.2 | 0 | 0 | 16.2 | 16.2 | 0 | 16.2 | 16.2 | 0 |
| EG4 | 0 | 21.3 | 0 | 21.3 | 0 | 21.3 | 21.3 | 21.3 | 0 |
| Asc.Acid | 0 | 0 | 10 | 0 | 10 | 10 | 10 | 10 | 10 |
| $Mn^{2+}$ | 10 | 10 | 10 | 10 | 10 | 10 | 10 | 0 | 10 |
| Buffer | 393.8 | 388.7 | 400 | 372.5 | 383.8 | 378.7 | 362.5 | 372.5 | 400 |
| Total | 500 | 500 | 500 | 500 | 500 | 500 | 500 | 500 | 500 |

FIG. 39B

| SEQ ID NO: | Nucleotide/ Amino Acid | Description |
|---|---|---|
| 1. | Amino acid | Protein sequence of a N. crassa GH61 endoglucanase [Accession #CAB97283.2] |
| 2. | Amino acid | Protein sequence of a 2nd N. crassa GH61 endoglucanase [Accession # CAD21296.1] |
| 3. | Amino acid | Protein sequence of a 3rd N. crassa GH61 endoglucanase [Accession # CAD70347.1] |
| 4. | Amino acid | Protein sequence a 4th N. crassa GH61 endoglucanase [Accession #CAE81966.1] |
| 5. | Amino acid | Protein sequence of a 5th N. crassa GH61 endoglucanase [Accession # CAF05857.1] |
| 6. | Amino acid | Protein sequence of a 6th N. crassa GH61 endoglucanase [Accession # EAA26873.1] |
| 7. | Amino acid | Protein sequence of a 7th N. crassa GH61 endoglucanase [Accession # EAA29132.1] |
| 8. | Amino acid | Protein sequence of an 8th N. crassa GH61 endoglucanase [Accession # EAA30263.1] |
| 9. | Amino acid | Protein sequence of a 9th N. crassa GH61 endoglucanase [Accession # EAA33178.1] |
| 10. | Amino acid | Protein sequence of a 10th N. crassa GH61 endoglucanase [Accession # EAA33408.1] |
| 11. | Amino acid | Protein sequence of an 11th N. crassa GH61 endoglucanase [Accession # EAA34466.1] |
| 12. | Amino acid | Protein sequence of a 12th N. crassa GH61 endoglucanase [Accession # EAA36362.1] |
| 13. | Amino acid | Protein sequence of a 13th N. crassa GH61 endoglucanase [Accession # EAA29018.1] |
| 14. | Amino acid | Protein sequence of a Sporotrichum thermophilum 24630 GH61 endoglucanase |
| 15. | Amino acid | Protein sequence of a Sporotrichum thermophilum 23839c GH61 endoglucanase |
| 16. | Amino acid | Protein sequence of a Sporotrichum thermophilum 46583 GH61 endoglucanase |
| 17. | Amino acid | Protein sequence for Sporotrichum thermophilum 80312 GH61 endoglucanase |
| 18. | Amino acid | Protein sequence of Neurospora crassa OR74A [Accession Number EAA29347.1] |
| 19. | Amino acid | Protein sequence of Aspergillus fumigatus Afu3g03870 GH61 endoglucanase |
| 20. | Amino acid | Protein sequence of Aspergillus fumigatus Afu6g09540 GH61 endoglucanase |
| 21. | Amino acid | Protein sequence of Aspergillus fumigatus EDP47167 GH61 endoglucanase |

*FIG. 49A*

| SEQ ID NO: | Nucleotide/ Amino Acid | Description |
|---|---|---|
| 22. | Amino acid | Protein sequence of *Thielavia terrestris* 16380 GH61 endoglucanase |
| 23. | Amino acid | Protein sequence of *Thielavia terrestris* 155418 GH61 endoglucanase |
| 24. | Amino acid | Protein sequence of *Thielavia terrestris* 68900 GH61 endoglucanase |
| 25. | Amino acid | Protein sequence of *C. globosum* Cg61A (Accession Number EAQ86340.1) |
| 26. | Amino acid | Protein sequence of *T. reesei* EG7 (or TrEGb) |
| 27. | Amino acid | Protein sequence of *T. reesei* Eg4 (or TrEG4) |
| 28. | Amino acid | Protein sequence of *A. fumigatus* Af293 GH61 endoglucanase (Accession Number XP_752040) |
| 29. | Amino acid | Protein sequence of *Thielavia terrestris* GH61 endoglucanase TtEG |
| 30. | Nucleotide | Nucleotide sequence encoding *T. reesei* EG4 |
| 31. | Amino acid | Protein sequence of Tr6A from *T. reesei* |
| 32. | Amino acid | Protein sequence of Tr7A from *T. reesei* |
| 33. | Amino acid | Protein sequence of Eg6 from *T. reesei* |
| 34. | Amino acid | Protein sequence of *S. coccosporum* endoglucanase |
| 35. | Nucleotide | Nucleotide sequence of Fv3A, a GH3 family enzyme from *F. verticillioides* |
| 36. | Amino acid | Protein sequence of Fv3A |
| 37. | Nucleotide | Nucleotide sequence of Pf43A, a GH43 family enzyme from *P. funiculosum* |
| 38. | Amino acid | Protein sequence of Pf43A |
| 39. | Nucleotide | Nucleotide sequence of Fv43E, a GH43 family enzyme from *F. verticillioides* |
| 40. | Amino acid | Protein sequence of Fv43E |
| 41. | Nucleotide | Nucleotide sequence of Fv39A, a GH39 family enzyme from *F. verticillioides* |
| 42. | Amino acid | Protein sequence of Fv39A |
| 43. | Nucleotide | Nucleotide sequence of Fv43A, a GH43 family enzyme from *F. verticillioides* |
| 44. | Amino acid | Protein sequence of Fv43A |
| 45. | Nucleotide | Nucleotide sequence of Fv43B, a GH43 family enzyme from *F. verticillioides* |
| 46. | Amino acid | Protein sequence of Fv43B |
| 47. | Nucleotide | Nucleotide sequence of Pa51A, a GH51 family enzyme from *P. anserina* |
| 48. | Amino acid | Protein sequence of Pa51A |
| 49. | Nucleotide | Nucleotide sequence of Gz43A, a GH43 family enzyme from *G. zeae* |
| 50. | Amino acid | Protein sequence of Gz43A |
| 51. | Nucleotide | Nucleotide sequence of Fo43A, a GH43 family enzyme from *F. oxysporum* |
| 52. | Amino acid | Protein sequence of Fo43A |
| 53. | Nucleotide | Nucleotide sequence of Af43A, a GH43 family enzyme from *A. fumigatus* |
| 54. | Amino acid | Protein sequence of Af43A |
| 55. | Nucleotide | Nucleotide sequence of Pf51A, a GH51 family enzyme from *P. funiculosum* |
| 56. | Amino acid | Protein sequence of Pf51A |

*FIG. 49B*

| SEQ ID NO: | Nucleotide/ Amino Acid | Description |
|---|---|---|
| 57. | Nucleotide | Nucleotide sequence of AfuXyn2, a GH11 family enzyme from *A. fumigatus* |
| 58. | Amino acid | Protein sequence of AfuXyn2 |
| 59. | Nucleotide | Nucleotide sequence of AfuXyn5, a GH11 family enzyme from *A. fumigatus* |
| 60. | Amino acid | Protein sequence of AfuXyn5 |
| 61. | Nucleotide | Nucleotide sequence of Fv43D, a GH43 family enzyme from *F. verticillioides* |
| 62. | Amino acid | Protein sequence of Fv43D |
| 63. | Nucleotide | Nucleotide sequence of Pf43B, a GH43 family enzyme from *P. funiculosum* |
| 64. | Amino acid | Protein sequence of Pf43B |
| 65. | Nucleotide | Nucleotide sequence of Fv51A, a GH51 family enzyme *F. verticillioides* |
| 66. | Amino acid | Protein sequence of Fv51A |
| 67. | Nucleotide | Nucleotide sequence of Cg51B, a GH51 family enzyme from *C. globosum* |
| 68. | Amino acid | Protein sequence of Cg51B |
| 69. | Nucleotide | Nucleotide sequence of Fv43C, a GH43 family enzyme from *F. verticillioides* |
| 70. | Amino acid | Fv43C protein sequence |
| 71. | Nucleotide | Nucleotide sequence of Fv30A, a GH30 family enzyme from *F. verticillioides* |
| 72. | Amino acid | Fv30A protein sequence |
| 73. | Nucleotide | Nucleotide sequence of Fv43F, a GH43 family enzyme from *F. verticillioides* |
| 74. | Amino acid | Fv43F protein sequence |
| 75. | Nucleotide | Nucleotide sequence of Xyn3, a GH10 family xylanase from *T. reesei* |
| 76. | Amino acid | Xyn3 protein sequence |
| 77. | Amino acid | Protein sequence of Xyn2, a GH11 xylanase from *Trichoderma reesei* |
| 78. | Amino acid | Protein sequence of Bxl1, a GH3 β-xylosidase from *Trichoderma reesei* |
| 79. | Amino acid | Protein sequence of Bgl1, a GH3 β-glucosidase from *Trichoderma reesei* |
| 80. | Nucleotide | Deduced cDNA of Pa51A. |
| 81. | Nucleotide | Codon optimized cDNA for Pa51A. |
| 82. | Nucleotide | Coding sequence of CBH1 signal sequence upstream of genomic DNA encoding mature Gz43A. |
| 83. | Nucleotide | Coding sequence of CBH1 signal sequence upstream of genomic DNA encoding mature Fo43A. |
| 84. | Amino acid | Motif 1 of GH61 family endoglucanses |
| 85. | Amino acid | Motif 2 of GH61 family endoglucanses |
| 86. | Amino acid | Motif 3 of GH61 family endoglucanses |
| 87. | Amino acid | Motif 4 of GH61 family endoglucanses |
| 88. | Amino acid | Motif 5 of GH61 family endoglucanses |
| 89. | Amino acid | Motif 6 of GH61 family endoglucanses |
| 90. | Amino acid | Motif 7 of GH61 family endoglucanses |

*FIG. 49C*

| SEQ ID NO: | Nucleotide/ Amino Acid | Description |
|---|---|---|
| 91. | Amino acid | Motif 6 of GH61 family endoglucanses |
| 92. | Nucleotide | Codon optimized nucleotide sequence for CBH1 signal sequence upstream of codon optimized DNA encoding mature Pf51A |
| 93. | Nucleotide | Nucleotide sequence of Pa3D, a GH3 family β-glucosidase from *P. anserina* |
| 94. | Amino acid | Protein sequence of Pa3D |
| 95. | Nucleotide | Nucleotide sequence of Fv3G, a GH3 family β-glucosidase from *F. vertiides* |
| 96. | Amino acid | Protein sequence of Fv3G |
| 97. | Nucleotide | Nucleotide sequence of Fv3D, a GH3 family β-glucosidase from *F. verticillioides* |
| 98. | Amino acid | Protein sequence of Fv3D |
| 99. | Nucleotide | Nucleotide sequence of Fv3C, a GH3 family β-glucosidase from *F. verticillioides* |
| 100. | Amino acid | Protein sequence of Fv3C |
| 101. | Nucleotide | Nucleotide sequence of Tr3A, a GH3 family β-glucosidase from *T. reesei* |
| 102. | Amino acid | Protein sequence of Tr3A |
| 103. | Nucleotide | Nucleotide sequence of Tr3B, a GH3 family β-glucosidase from *T. reesei* |
| 104. | Amino acid | Protein sequence of Tr3B |
| 105. | Nucleotide | Nucleotide sequenced of Te3A, a GH3 family β-glucosidase from *Talaromyces emersonii*, optimized for expression in *T.reesei* |
| 106. | Amino acid | Protein sequence of Te3A |
| 107. | Nucleotide | Nucleotide sequence of An3A, a GH3 family β-glucosidase from *A. niger* |
| 108. | Amino acid | Protein sequence of An3A |
| 109. | Nucleotide | Nucleotide sequence of Fo3A, a GH3 family β-glucosidase from *F. oxysporum* |
| 110. | Amino acid | Protein sequence of Fo3A |
| 111. | Nucleotide | Nucleotide sequence of Gz3A, a GH3 family β-glucosidase from *G. zeae* |
| 112. | Amino acid | Protein sequence of Gz3A |
| 113. | Nucleotide | Nucleotide sequence of Nh3A, a GH3 family β-glucosidase from *N. haematococca* |
| 114. | Amino acid | Protein sequence of Nh3A |
| 115. | Nucleotide | Nucleotide sequence of Vd3A, a GH3 family β-glucosidase from *V. dahlias* |
| 116. | Amino acid | Protein sequence of Vd3A |
| 117. | Nucleotide | Nucleotide sequence of Pa3G, a GH3 family β-glucosidase from *P. anserina* |
| 118. | Amino acid | Protein sequence of Pa3G |
| 119. | Amino acid | Protein sequence of Tn3B, a GH3 family β-glucosidase from *T.neapolitana* |

*FIG. 49D*

| SEQ ID NO: | Nucleotide/ Amino Acid | Description |
|---|---|---|
| 148. | Amino acid | Protein sequence of Ta61, a GH61A polypeptide from *T. aurantiacus* |
| 149. | Nucleotide | Nucleotide sequence of Ta61A, a GH61A polypeptide from *T. aurantiacus* |
| 150. | Amino acid | Protein sequence of Afu7Aa cellobiohydrolase 1 polypeptide from *A. fumigatus* |
| 151. | Amino acid | Protein sequence of Afu7B, a cellobiohydrolase 1 polypeptide from *A. fumigatus* |
| 152. | Amino acid | Protein sequence of Cg7A, a cellobiohydrolase 1 polypeptide from *C. globosum* |
| 153. | Amino acid | Protein sequence of Cg7B, a cellobiohydrolase 1 polypeptide from *C. globosum* |
| 154. | Amino acid | Protein sequence of Tt7A, a cellobiohydrolase 1 polypeptide from *T. terrestris* |
| 155. | Amino acid | Protein sequence of Tt7B, a cellobiohydrolase 1 polypeptide from *T. terrestris* |
| 156. | Amino acid | Protein sequence of St6A, a cellobiohydrolase 2 polypeptide from *S. thermophile* |
| 157. | Amino acid | Protein sequence of St6B, a cellobiohydrolase 2 polypeptide from *S. thermophile* |
| 158. | Amino acid | Protein sequence of Tt6A, a cellobiohydrolase 2 polypeptide from *T. terrestris* |
| 159. | Nucleotide | Nucleotide sequence encoding *T. reesei* Bxl1, a GH3 β-xylosidase |
| 160. | Nucleotide | Nucleotide sequence encoding *T. reesei* Xyn2, a GH11 xylanase |

*FIG. 49E*

SEQ ID NO:35

**Nucleotide sequence for Fv3A, a GH3 family enzyme from *Fusarium verticillioides*** atgctgctcaatcttcaggtcgctgccagcgctttgtcgctttctctttaggtggattggctgaggctg
ctacgcccatataccctcggactgtaccaaaggaccttgagcaagaatggaatctgcgatacttcgtt
atctccagctaaaagagcggctgctctagttgctgctctgacgcccgaagagaaggtgggcaatctggtc
aggtaaaatatacccccccccataatcactattcggagattggagctgacttaacgcagcaatgcaactg
gtgcaccaagaatcggacttccaaggtacaactggtggaacgaagcccttcatggcctcgctggatctcc
aggtggtcgctttgccgacactcctccctacgacgcggccacatcatttcccatgcctcttctcatggcc
gctgctttcgacgatgatctgatccacgatatcggcaacgtcgtcggcaccgaagcgcgtgcgttcacta
acggcggttggcgcggagtcgacttctggacacccaacgtcaaccctttaaagatcctcgctggggtcg
tggctccgaaactccaggtgaagatgcccttcatgtcagccggtatgctcgctatatcgtcaggggtctc
gaaggcgataaggagcaacgacgtattgttgctacctgcaagcactatgctggaaacgactttgaggact
ggggaggcttcacgcgtcacgactttgatgccaagattactcctcaggacttggctgagtactacgtcag
gcctttccaggagtgcacccgtgatgcaaaggttggttccatcatgtgcgcctacaatgccgtgaacggc
attcccgcatgcgcaaactcgtatctgcaggagacgatcctcagagggcactggaactggacgcgcgata
acaactggatcactagtgattgtggcgccatgcaggatatctggcagaatcacaagtatgtcaagaccaa
cgctgaaggtgcccaggtagctttcgagaacggcatggattctagctgcgagtatactactaccagcgat
gtctccgattcgtacaagcaaggcctcttgactgagaagctcatggatcgttcgttgaagcgccttttcg
aagggcttgttcatactggtttctttgacggtgccaaagcgcaatggaactcgctcagttttgcggatgt
caacaccaaggaagctcaggatcttgcactcagatctgctgtggagggtgctgttcttcttaagaatgac
ggcactttgcctctgaagctcaagaagaaggatagtgttgcaatgatcggattctgggccaacgatactt
ccaagctgcagggtggttacagtggacgtgctccgttcctccacagcccgctttatgcagctgagaagct
tggtcttgacaccaacgtggcttggggtccgacactgcagaacagctcatctcatgataactggaccacc
aatgctgttgctgcggcgaagaagtctgattacattctctactttggtggtcttgacgcctctgctgctg
gcgaggacagagatcgtgagaaccttgactggcctgagagccagctgacccttcttcagaagctctctag
tctcggcaagccactggttgttatccagcttggtgatcaagtcgatgacaccgctcttttgaagaacaag
aagattaacagtattctttgggtcaattaccctggtcaggatggcggcactgcagtcatggacctgctca
ctggacgaaagagtcctgctggccgactacccgtcacgcaatatcccagtaaatacactgagcagattgg
catgactgacatggacctcagacctaccaagtcgttgccagggagaacttatcgctggtactcaactcca
gttcttccctacggctttggcctccactacaccaagttccaagccaagttcaagtccaacaagttgacgt
ttgacatccagaagcttctcaagggctgcagtgctcaatactccgatacttgcgcgctgcccccatcca
agttagtgtcaagaacaccggccgcattacctccgactttgtctctctggtctttatcaagagtgaagtt
ggacctaagccttaccctctcaagacccttgcggcttatggtcgcttgcatgatgtcgcgccttcatcga
cgaaggatatctcactggagtggacgttggataacattgcgcgacggggagagaatggtgatttggttgt
ttatcctgggacttacactctgttgctggatgagcctacgcaagccaagatccaggttacgctgactgga
aagaaggctatttttggataagtggcctcaagaccccaagtctgcgtaa

*FIG. 50A*

SEQ ID NO:36

Protein sequence of Fv3A mllnlqvaasalslsllggla eaatpytlpdctkgplskngicdtslspakraaalvaaltpeekvgnlv
snATGAPRIGLPRYNWWNEALHGLAGSPGGRFADTPPYDAATSFPMPLLMAAAFDDDLIHDIGNVVGTEA
RAFTNGGWRGVDFWTPNVNPFKDPRWGRGSETPGEDALHVSRYARYIVRGLEGDKEQRRIVATCKHYAGN
DFEDWGGFTRHDFDAKITPQDLAEYYVRPFQECTRDAKVGSIMCAYNAVNGIPACANSYLQETILRGHWN
WTRDNNWITSDCGAMQDIWQNHKYVKTNAEGAQVAFENGMD ssceytttsdvsdsykqglltekl mdrsl
krlfeglvhtgffdgakaqwnslsfadvntkeaqdlalrsaveg AVLLKNDGTLPLKLKKKDSVAMIGFW
ANDTSKLQGGYSGRAPFLHSPLYAAEKLGLDTNVAWGPTLQNSSSHDNWTTNAVAAAKKSDYILYFGGLD
ASAAGEDRDRENLDWPESQLTLLQKLSSLGKPLVVIQLGDQVDDTALLKNKKINSILWVNYPGQDGGTAV
MDLLTGRKSPAGRLPVTQYPSKYTEQIGMTDMDLRPTKSLPGRTYRWYSTPVLPYGFGLHYT kfqakfks
nkltfdiqkllkgcsaqysdtcalppiqvsvkntgritsdfvslvfiksevgpkpyplktlaaygrlhdv
apsstkdislewtldniarrgengdlvvypgtytllldeptqakiqvtltgkkaildkwpqdpksa

*FIG. 50B*

SEQ ID NO:37
**Nucleotide sequence for Pf43A, a GH43 family enzyme from *Penicillium funiculosum*** atgcttcagcgatttgcttatattttaccactggtctattgagtgttggagtgaaagccgacaaccct
ttgtgcagagcatctacaccgctgatccggcaccgatggtatacaatgaccgcgtttatgtcttcatgga
ccatgacaacaccggagctacctactacaacatgacagactggcatctgttctcgtcagcagatatggcg
aattggcaagatcatggcattccaatgagcctggccaatttcacctggccaacgcgaatgcgtgggccc
cgcaagtcatcctcgcaacggccaattctacttttatgctcctgtccgacacaacgatggttctatggc
tatcggtgtgggagtgagcagcaccatcacaggtccataccatgatgctatcggcaaaccgctagtagag
aacaacgagattgatccaccgtgttcatcgacgatgacggtcaggcataccgtactggggaaatccag
acctgtggtacgtcaaattgaaccaagatatgatatcgtacagcgggagccctactcagattccactcac
cacggctggatttggtactcgaacgggcaatgctcaacggccgaccactttgaagaagctccatgggta
tacaaacgcaacggcatctactatatcgcctatgcagccgattgttgttctgaggatattcgctactcca
cgggaaccagtgccactggtccgtggacttatcgaggcgtcatcatgccgacccaaggtagcagcttcac
caatcacgagggtattatcgacttccagaacaactcctactttttctatcacaacggcgctcttcccggc
ggaggcggctaccaacgatctgtatgtgtggagcaattcaaatacaatgcagatggaaccattcgacga
tcgaaatgaccaccgccggtccagctcaaattggcactctcaaccttacgtgcgacaggaagccgaaac
ggcggcatggtcttcaggcatcactacgaggtttgtagcgaaggcggaattgacgtcggggttatcaac
aatggcgattacatcaaagttaaaggcgtagctttcggttcaggagcccattcttctcagcgcggggttg
cttctgcaaatagcggcggcactattgcaatacacctcggaagcacaactggtacgctcgtgggcacttg
tactgtcccagcactggcggttggcagacttggactaccgttactgttctgtcagtggcgcatctggg
acccaggatgtatattgttttcggtggtagcggaacaggatacctgttcaactttgattattggcagt
tcgcataa

FIG. 51A

SEQ ID NO:38
Protein sequence of Pf43A

<u>mlsrfavilplallsvqvka</u>dnpfvqsiytadpapmvyndrvyvfmdhdntgatyynmtdwhlfssadma
nwqdhgipmslanftwananawapqviprngqfyfyapvrhndgsmaigvgvsstitgpyhdaigkplve
nneidptvfidddgqaylywgnpdlwyvklnqdmisysgsptqiplttagfgtrtgnaqrpttfeeapwv
ykrngiyyiayaadccsediryrstgtsatgpwtyrgvimptqgssftnhegiidfqnnsyffyhngalpg
gggyqrsvcveqfkynadgti*ptiemttagpaqigtlnpyvrq*EAETAAWSSGITTEVCSEGGIDVGFIN
NGDYIKVKGVAFGSGAHSFSARVASANSGGTIAISLGSTTGTLVGTCTVPSTGGWQTWTTVTCSVSGASG
TQDVYFVFGGSGTGYLFNFDYWQFa

FIG. 51B

SEQ ID NO:39
**Nucleotide sequence for Fv43E, a GH43 family enzyme from *Fusarium verticillioides*** atgaaggtatactggctcgtggcgtgggccacttctttgacgccggcactggctggcttgattggacacc
gtcgcgccaccacttcaacaatcctatcatctactcagactttccagataacgatgtattcctcggtcc
agataactactactacttctctgcttccaacttccacttcagcccaggagcacccgttttgaagtctaaa
gatctgctaaactgggatctcatcggccattcaattccccgcctgaactttggcgacggctatgatctc
ctcctggctcacgttattaccgtggaggtacttgggcatcatccctcagatacagaaagagcaatggaca
gtggtactggatcggctgcatcaacttctggcagacctgggtatacactgcctcatcgccggaaggtcca
tggtacaacaagggaaacttcggtgataacaattgctactacgacaatggcatactgatcgatgacgatg
ataccatgtatgtcgtatacggttccggtgaggtcaaagtatctcaactatctcaggacggattcagcca
ggtcaaatctcaggtagttttcaagaacactgatattgggtccaagacttggagggtaaccgcatgtac
aagatcaacgggctctactatatcctaaacgatagcccaagtggcagtcagacctggatttggaagtcga
aatcaccctggggcccttatgagtctaaggtcctcgccgacaaagtcaccccgcctatctctggtggtaa
ctcgccgcatcagggtagtctcataaagactcccaatggtggctggtacttcatgtcattcacttgggcc
tatcctgccggccgtcttccggttcttgcaccgattacgtgggtagcgatggtttcccattcttgtca
aggtgctaatggcggatggggatcatcttacccaacacttcctggcacggatggtgtgacaaagaattg
gacaaggactgatacttccgcggaacctcacttgtccgtcctgggagtggaaccataatcggacgtc
aactccttcactgtcaacaacggcctgactctccgcactgctagcattacgaaggatatttaccaggcga
ggaacacgctatctcaccgaactcatggtgatcatccaacaggaatagtgaagattgatttctctccgat
gaaggaccgcgaccgggccggctttcagcgtttcgagaccaaagtgcatacatggtattcatcgagat
aacggaaagttcacaatcgctacgaagcatggatgaatatggatgagtggaacgaacaacaacagacc
tgggacaaataaaagccacagctaatgtgccttctggaaggaccaagatctggctgagacttcaacttga
taccaaccagcaggaactggcaacactatctttctcttacagttgggatggagtcaagtatgaaacactg
ggtcccaacttcaaactgtacaatggttgggcattctttattgcttaccgattggcatcttcaacttcg
ccgagacggctttaggaggctcgatcaaggttgagtctttcacagctgcatag

FIG. 52A

SEQ ID NO:40
Protein sequence of Fv43E mkvylvavatsltpalagllghrnattfnnpiiysdfpdndvflgpdnyyyfsaasnfhfspgapvlksk
dllnwdlighsiprlnfgdgydlppgsryyrggtwasslryrksngqwywigcinfwqtwvytasspegp
wynkgnfgdnncyydngiliddddtmyvvygsgevkvsqlsqdgfsqvksqvvfkntdigvqdlegnrmy
kinglyyilndspsgsqtwiwkskspwgpyeskvladkvtppisggnsphqgsliktpnggwyfmsftwa
ypagrlpvlapitwgsdgfpilvkganggwgssyptlpgtdgvtknwtrtdtfrqtslapswewnhnpdv
nsftvnqltlrtasitkdlyqarntlshrthgdhptgivkidfspmkdgdraglsafrdqsayigihrd
ngkftiatkhqmnmadewnqtttdlgqikatanvpsgrtkiwlrlqldtnpagtqntifsyewdgvkyetl
qpnfklyngwaffiayrfgifnfaetalggsikvesftaa

FIG. 52B

SEQ ID NO:41
Nucleotide sequence for Fv39A, a GH39 family enzyme from *Fusarium verticillioides* atgcactacgctaccctcaccactttggtgctggctctgaccaccaacgtcgctgcacagcaaggcacag
caactgtcgacctctccaaaaatcatggaccggcgaaggcccttggttcaggcttcatatacggctggcc
tgacaacggaacaagcgtcgacacctccataccagatttcttggtaactgacatcaaattcaactcaaac
cgcggcggtggcgcccaaatccatcactgggttgggccagaggtggctatgaaggatacctcggccgct
tcaactcaaccttatccaactatcgcaccacgcgcaagtataacgctgactttatcttgttgcctcatga
cctctggggtgcggatggcgggcagggttcaaactccccgtttcctggcgacaatggcaattggactgag
atggagttattctggaatcagcttgtgtctgacttgaaggctcataatatgctggaaggtcttgtgattg
atgtttggaatgagcctgatatigatatctttgggatcgcccgtggtcgcagtttcttgagtattacaa
tcgcgcgaccaaactacttcggtgagtctactactgatccatacgtatttacagtgagctgactggtcga
attagaaaaacacttcccaaaactcttctcagtggcccagccatggcacattctcccattctgtccgatg
ataaatggcatacctggcttcaatcagtagcgggtaacaagacagtccctgatatttactcctggcatca
gattggcgcttgggaacgtgagccggacagcactatccccgactttaccaccttgcgggcgcaatatggc
gttcccgagaagccaattgacgtcaatgagtacgctgcacgcgatgagcaaaatccagccaactccgtct
actacctctctcaactagagcgtcataaccttagaggtcttcgcgcaaactggggtagcggatctgacct
ccacaactggatgggcaacttgatttacagcactaccggtacctcggaggggacttactacccctaatggt
gaatggcaggcttacaagtactatgcggccatggcagggcagagacttgtgaccaaagcatcgtcggact
tgaagtttgatgtctttgccactaagcaaggccgtaagattaagattatagccggcacgaggaccgttca
agcaaagtataacatcaaaatcagcggtttggaagtagcaggacttcctaagatgggtacggtaaaggtc
cggacttatcggttcgactgggctgggccgaatggaaaggttgacgggcctgttgatttggggagaaga
agtatacttattcggccaatacggtgagcagccctctacttga

FIG. 53A

SEQ ID NO:42
Protein sequence of Fv39A mhyatlttlvlalttnvaaqqgtatvdlsknhqpakalgsgfiygwpdngtsvdtsipdflvtdikfnsn
rgggaqipslgwarggyegylgrfnstlsnyrttrkynadfillphdlwgadggqgsnspfpgdngnwte
melfwnqlvsdlkahnmleglvidvwnepdidifwdrpwsqfleyynratkllrktlpktllsgpamahs
pilsddkwhtwlqsvagnktvpdiyswhqigawerepdstipdfttlraqygvpekpidvneyaardeqn
pansvyylsqlerhnlrglranwgsgsdlhnwmgnliysttgtsegtyypngewqaykyyaamagqrlvt
kassdlkfdvfatkqgrkikiiagtrtvqakynikisglevaglpkmgtvkvrtyrfdwagpngkvdgpv
dlgekkytysantvsspst

FIG. 53B

SEQ ID NO:43
Nucleotide sequence for Fv43A, a GH43 family enzyme from *Fusarium verticillioides* atgtggctgacctccccattgctgttcgccagcaccctcctgggcctcactggcgttgctctagcagaca
accccatcgtccaagacatctacaccgcagacccagcaccaatggtctacaatggccgcgtctacctctt
cacaggccatgacaacgacggctctaccgacttcaacatgacagactggcgtctcttctcgtcagcagac
atggtcaactggcagcaccatggtgtccccatgagcttaaagaccttcagctgggccaacagcagagcct
gggctggtcaagtcgttgcccgaaacggaaagttttacttctatgttcctgtccgtaatgccaagacggg
tggaatggctattggtgtcggtgttagtaccaacatccttgggccctacactgatgcccttggaaagcca
ttggtcgagaacaatgagatcgacccaactgtctacatcgacactgatggccaggcctatctctactggg
gcaaccctggattgtactacgtcaagctcaaccaagacatgctctcctacagtggtagcatcaacaaagt
atcgctcacaacagctggattcggcagccgcccgaacaacgcgcagcgtcctactactttcgaggaagga
ccgtggctgtacaagcgtggaaatctctactacatgatctacgcagccaactgctgttccgaggacattc
gctactcaactggacccagcgccactggaccttggacttaccgcggtgtcgtgatgaacaaggcgggtcg
aagcttcaccaaccatcctggcatcatcgactttgagaacaactcgtacttcttttaccacaatggcgct
cttgatggaggtagcggttatactcggtctgtggctgtcgagagcttcaagtatggttcggacggtctga
tccccgagatcaagatgactacgcaaggcccagcgcagctcaagtctctgaacccatatgtcaagcagga
ggccgagactatcgcctggtctgagggtatcgagactgaggtctgcagcgaaggtggtctcaacgttgct
ttcatcgacaatggtgactacatcaaggtcaagggagtcgactttggcagcaccggtgcaaagacgttca
gcgcccgtgttgcttccaacagcagcggaggcaagattgagcttcgacttggtagcaagaccggtaagtt
ggttggtacctgcacggtaacgactacgggaaactggcagacttataagactgtggattgccccgtcagt
ggtgctactggtacgagcgatctattctttgtcttcacgggctctgggtctggctctctgttcaacttca
actggtggcagtttagctaa

*FIG. 54A*

SEQ ID NO:44
Protein sequence of Fv43A mwltspllfastllgltqvaladnpivqdiytadpapmvyngrvylftghdndgstdfnmtdwrlfssad
mvnwqhhgvpmslktfswansrawagqvvarngkfyfyvpvrnaktggmaigvgvstnilgpytdalgkp
lvenneidptvyidtdgqaylywgnpglyyvklnqdmlsysgsinkvslttagfgsrpnnaqrpttfeeg
pwlykrgnlyymiyaanccsedirystgpsatgpwtyrgvvmnkagrsftnhpgiidfennsyffyhnga
ldggsgytrsvavesfkygsdg *lipeikmttqgpaqlksl*NPYVKQEAETIAWSEGIETEVCSEGGLNVA
FIDNGDYIKVKGVDFGSTGAKTFSARVASNSSGGKIELRLGSKTGKLVGTCTVTTTGNWQTYKTVDCPVS
GATGTSDLFFVFTGSGSGSLFNFNWWQFs

*FIG. 54B*

SEQ ID NO:45
Nucleotide sequence for Fv43B, a GH43 family enzyme from *Fusarium verticillioides* atgcgcttctcttggctattgtgcccccttctagcgatgggaagtgctcttcctgaaacgaagacggatg
tttcgacatacaccaaccctgtccttccaggatggcactcggatccatcgtgtatccagaaagatggcct
cttcctctgcgtcacttcaacattcatctccttcccaggtcttcccgtctatgcctcaagggatctagtc
aactggcgtctcatcagccatgtctggaaccgcgagaaacagttgcctggcattagctggaagacggcag
gacagcaacagggaatgtatgcaccaaccattcgataccacaagggaacatactacgtcatctgcaata
cctgggcgttggagatattattggtgtcatcttcaagaccaccaatccgtgggacgagagtagctggagt
gaccctgttaccttcaagccaaatcacatcgaccccgatctgttctgggatgatgacggaaaggtttatt
gtgctacccatggcatcactctgcaggagattgatttggaaactggagagcttagcccggagcttaatat
ctggaacggcacaggaggtgtatggcctgagggtccccatatctacaagcgcgacggttactactatctc
atgattgccgagggtggaactgccgaagaccacgctatcacaatcgctcgggcccgcaagatcaccggcc
cctatgaagcctacaataacaacccaatcttgaccaacgcgggacatctgagtacttccagactgtcgg
tcacggtgatctgttccaagataccaagggcaactggtgggtctttgtcttgctactcgcatcacagca
cagggagtttcacccatgggccgtgaagctgttttgttcaatggcacatggaacaagggcgaatggccca
agttgcaaccagtacgaggtcgcatgcctggaaacctctcccaaagccgacgcgaaacgttccggaga
tgggcccttcaacgctgacccagacaactacaacttgaagaagactaagaagatccctcctcactttgtg
caccatagagtccccaagagacggtgccttctctttgtcttccaagggtctgcacatcgtgcctagtcgaa
acaacgttaccggtagtgtgttgccaggagatgagattgagctatcaggacagcgaggtctagctttcat
cggacgccgccaaactcacactctgttcaaatatagtgttgatatcgacttcaagcccaagtccgatgat
caggaagctggaatcaccgtttccgcacgcagttcgaccatatcgatcttggcattgttcgtcttccta
caaaccaaggcagcaacaagaaatctaagcttgccttccgattccgggccacaggagctcagaatgttcc
tgcaccgaaggtagtaccggtccccgatggctgggagaagggcgtaatcagtctacatatcgaggcagcc
aacgcgacgcactacaaccttggagcttcgagccacagaggcaagactctcgacatcgcgacagcatcag
caagtcttgtgagtggaggcacgggttcatttgttggtagtttgcttggacctatgctacctgcaacgg
caaaggatctggagtggaatgtcccaagggaggtgatgtctatgtgacccaatggacttataagcccgtg
gcacaagagattgatcatggtgttttgtgaaatcagaattgtag

*FIG. 55A*

SEQ ID NO:46
Protein sequence of Fv43B

<u>mrfswllcpllamqsal</u>petktdvst**ytnpvlpgwhsdpsciqkdglflcvtstfisfpglpvyasrdlv
nwrlishvwnrekqlpgiswktagqqqgmyaptiryhkgtyyviceylgvgdiigvifkttnpwdessws
dpvtfkpnhidpdlfwdddgkvycathgitlqeidletgelspelniwngtggvwpegphiykrdgyyyl
miaeggtaedhaitiararkitgpyeaynnnpiltnrgtseyfqtvghgdlfqdtkgnwwglclatrita
qgvspmgreavlfngtwnkgewp**klqpvrgrmpgnllpkptrnvpgdgpfnadpdnylkktkkipphfv
hhrvprdgafslsskqlhivpsrnnvtgsvlpgdeielsgqrqlafigrrqthtlfkysvdidfkpksdd
qeagitvfrtqfdhidlgivrlptnqgsnkksklafrfratgaqnvpapkvvpvpdgwekgvislhieaa
nathynlgasshrgktldiatasaslvsggtgsfvgsllgpyatcngkgsqvecpkggdvyv
tqwtykpvaqeidhgvfvksel

*FIG. 55B*

SEQ ID NO:47
Nucleotide sequence for Pa51A, a GH51 family enzyme from *Podospora anserina* atgatccacctcaagccagccctcgcggcgttgttggcgctgtcgacgcaatgtgtggctattgatttgt
ttgtcaagtcttcgggggggaataagacgactgatatcatgtatggtcttatgcacgaggtatgtgtttt
gcgagatctcccttttgtttttgcgcactgctgacatggagactgcaaacaggatatcaacaactccggc
gacggcggcatctacgccgagctaatctccaaccgcgcgttccaagggagtgagaagttcccctccaacc
tcgacaactggagcccgtcggtggcgctacccttacccttcagaagcttgccaagccccttcctctgc
gttgccttactccgtcaatgttgccaaccccaaggagggcaagggcaaggggcaaggacaccaaggggaag
aaggttggcttggccaatgctgggttttggggtatggatgtcaagaggcagaagtacactggtagcttcc
acgttactggtgagtacaagggtgactttgaggttagcttgcgcagcgcgattaccggggagacctttgg
caagaaggtggtgaaggtgggagtaagaaggggaagtggaccgagaaggagtttgagttggtgcctttc
aaggatgcgcccaacagcaacaacacctttgttgtgcagtgggatgccgaggtatgtgcttctttgatat
tggctgagatagaagttgggttgacatgatgtggtgcagggcgcaaaggacggatctttggatctcaact
tgatcagcttgttccctccgacattcaagggaaggaagaatgggctgagaattgatcttgcgcagacgat
ggttgagctcaagccggtaagtcctctctagtcagaaaagtagagcctttgttaacgcttgacagacctt
cttgcgcttccccggtggcaacatgctcgagggtaacaccttggacacttggtggaagtggtacgagacc
attggccctctgaaggatcgcccgggcatggctggtgtctgggagtaccagcaaaccttggcttgggtc
tggtcgagtacatggagtgggccgatgacatgaacttggagcccagtatgtgatcccattttctggagtg
acttctcttgctaacgtatccacagttgtcggtgtcttcgctggtcttgccctcgatggctcgttcgttc
ccgaatccgagatgggatgggtcatccaacaggctctcgacgaaatcgagttcctcactggcgatgctaa
gaccaccaaatggggtgccgtccgcgcgaagcttggtcaccccaagccttggaaggtcaagtgggttgag
atcggtaacgaggattggcttgccggacgccctgctggcttcgagtcgtacatcaactaccgcttcccca
tgatgatgaaggccttcaacgaaaagtaccccgacatcaagatcatcgcctcgcctccatcttcgacaa
catgacaatccccgcgggtgctgccggtgatcaccacccgtacctgactcccgatgagttcgttgagcga
ttcgccaagttcgataacttgagcaaggataacgtgacgctcatcggcgaggctgcgtcgacgcatccta
acggtggtatcgcttgggagggagatctcatgcccttgccttggtggggcggcagtgttgctgaggctat
cttcttgatcagcactgagagaaacggtgacaagatcatcggtgctacttacgcgcctggtcttcgcagc
ttggaccgctggcaatggagcatgacctgggtgcagcatgccgccgacccggccctcaccactcgctcga
ccagttggtatgtctggagaatcctcgcccaccacatcatccgtgagacgctcccggtcgatgccccggc
cggcaagcccaactttgaccctctgttctacgttgccggaaagagcgagagtggcaccggtatcttcaag
gctgccgtctacaactcgactgaatcgatcccggtgtcgttgaagtttgatggtctcaacgagggagcgg
ttgccaacttgacggtgcttactgggccggaggatccgtatggatacaacgacccccttcactggtatcaa
tgttgtcaaggagaagaccaccttcatcaaggccggaaagggcggcaagttcaccttcaccctgccgggc
ttgagtgttgctgtgttggagacggccgacgcggtcaagggtggcaaggaaagggcaagggcaagggaa
agggtaactga

*FIG. 56A*

SEQ ID NO:48
Protein sequence of Pa51A

<u>mihlkpalaaallalstgcva</u>idlfvkssggnkttdimyglmhedinnsgdggiyaelisnrafqgsekfp
snldnwspvggatltlqklakplssalpysvnvanpkegkgkgkdtkgkkvglanagfwgmdvkrqkytg
sfhvtgeykgdfevslrsaitgetfgkkvvkggskkgkwtekefelvpfkdapnsnntfvvqwdaegakd
gsldlnlislfpptfkgrknglridlaqtmvelkptflrfpggnmlegntldtwwkwyetigplkdrpgm
agvweyqqtlglglveymewaddmnlepivgvfaglaldgsfvpesemgwviqqaldeiefltgdakttk
wgavraklghpkpwkvkwveignedwlagrpagfesyinyrfpmmmkafnekypdikiiaspsifdnmti
pagaagdhhpyltpdefverfakfdnlskdnvtlligeaasthpnggia **wegdlmplpwwggsvaeaifli
sterngdkiigatyapglrsldrwqwsmtwvqhaadpalttrstswyvwrilahhiiretlpvdapagkp
nfdplfyvagksesgtgifkaavynstesipvslkfdglnegavanltvltgpedpygyndpftginvvk
ekttfikagkggkftftlpgls**vavletadavkggkgkgkgkgkgn

*FIG. 56B*

SEQ ID NO:49
Nucleotide sequence for Gz43A, a GH43 family enzyme from *Gibberella zeae* atgaagtccaagttgttattcccactcctctctttcgttggtcaaagtcttgccaccaacgacgactgtc
ctctcatcactagtagatggactgcggatccttcggctcatgtctttaacgacaccttgtggctctaccc
gtctcatgacatcgatgctggatttgagaatgatcctgatggaggccagtacgccatgagagattaccat
gtctactctatcgacaagatctacggttccctgccggtcgatcacggtacggccctgtcagtggaggatg
tcccctgggcctctcgacagatgtgggctcctgacgctgcccacaagaacggcaaatactacctatactt
ccctgccaaagacaaggatgatatcttcagaatcggcgttgctgtctcaccaaccccggcggaccatc
gtccccgacaagagttggatccctcacactttcagcatcgaccccgccagtttcgtcgatgatgatgaca
gagcctacttggcatggggtggtatcatgggtggccagcttaacgatggcaggataagaacaagtacaa
cgaatctggcactgagccaggaaacggcaccgctgccttgagccctcagattgccaagctgagcaaggac
atgcacactctggcagagaagcctcgcgacatgctcattcttgacccaagactggcaagccgctccttt
ctgaggatgaagaccgacgcttcttcgaaggacctggattcacaagcgcaacaagatttactacctcac
ctactctactggcacaacccactatcttgtctatgcgacttcaaagaccccctatggtccttacacctac
cagggcagaattctggagccagttgatgctggactactcactctagtatcgtcaagtaccagggtcagt
ggtggctattttatcacgatgccaagacatctggcaaggactatcttcgccaggtaaaggctaagaagat
ttggtacgatagcaaaggaaagatcttgacaagaagccttga

*FIG. 57A*

SEQ ID NO:50
Protein sequence of Gz43A mkskllfpllsfvqqslatnddcplitsrwtadpsahvfndtlwlypshdid agfendpdggqyamrdyh
vysidkiygslpvdhgtalsvedvpwasrqmwapdaahkngkyylyfpakdkddifrigvavsptpggpf
vpdkswiphtfsidpasfvddddraylawggimggqlqrwqdknkynesgtepgngtaalspqiaklskd
mhtlaekprdmlildpktgkpllsededrrffegpwihkrnkiyyltystgtthylvyatsktpygpyty
qgrilepvdgwtthssivkyqgqwwlfyhdaktsgkdylrqvkakkiwydskg kiltkkp

FIG. 57B

SEQ ID NO:51
Nucleotide sequence for Fo43A, a GH43 family enzyme from *Fusarium oxysporum* atgcagctcaagtttctgtcttcagcattgctgttctctctgaccagcaaatgcgctgcgcaagacacta
atgacattcctcccctgatcaccgacctctggtccgcagatccctcggctcatgttttcgaaggcaagct
ctgggtttacccatctcacgacatcgaagccaatgttgtcaacggcacaggaggcgctcaatacgccatg
agggattaccatacctactccatgaagagcatctatggtaaagatcccgttgtcgaccacggcgtcgctc
tctcagtcgatgacgttccctgggcgaagcagcaaatgtgggctcctgacgcagctcataagaacggcaa
atattatctgtacttccccgccaaggacaaggatgagatcttcagaattggagttgctgtctccaacaag
cccagcggtcctttcaaggccgacaagagctggatccctggcacgtacagtatcgatcctgctagctacg
tcgacactgataacgaggcctacctcatctggggcggtatctggggcggccagctccaagcctggcagga
taaaaagaactttaacgagtcgtggattggagacaaggctgctcctaacggcaccaatgccctatctcct
cagatcgccaagctaagcaaggacatgcacaagatcaccgaaacacccgcgatctcgtcattctcgccc
ccgagacaggcaagcctcttcaggctgaggacaacaagcgacgattcttcgagggcccttggatccacaa
gcgcggcaagctttactacctcatgtactccaccggtgatacccacttccttgtctacgctacttccaag
aacatctacggtccttatacctaccggggcaagattcttgatcctgttgatgggtggactactcatgga
gtattgttgagtataagggacagtggtggcttttctttgctgatgcgcatacgtctggtaaggattaccct
tcgacaggtgaaggcgaggaagatctggtatgacaagaacggcaagatcttgcttcaccgtccttag

FIG. 58A

SEQ ID NO:52
Protein sequence of Fo43A mqlkflssallfsltskcaaqdtndipplitdlwsadpsahvfegklwvypshdieanvvngtggaqyam
rdyhtysmksiygkdpvvdhgvalsvddvpwakqqmwapdaahkngkyylyfpakdkdeifrigvavsnk
psgpfkadkswipgtysidpasyvdtdneayliwggiwggqlqawqdkknfneswigdkaapngtnalsp
qiaklskdmhkitetprdlvilapetgkplqaednkrrffegpwihkrgklyylmystgdthflvyatsk
niygpytyrgkildpvdgwtthgsiveykgqwwlffadahtsgkdylrqvkarkiwydkng killhrp

FIG. 58B

SEQ ID NO:53
Nucleotide sequence for Af43A, a GH43 family enzyme from *Aspergillus fumigatus* atggcagctccaagtttatcctaccccacaggtatccaatcgtataccaatcctctcttccctggttggc
actccgatcccagctgtgcctacgtagcggagcaagacaccttttctgcgtgacgtccactttcattgc
cttccccggtcttcctctttatgcaagccgagatctgcagaactggaaactggcaagcaatattttcaat
cggcccagccagatccctgatcttcgcgtcacggatggacagcagtcgggtatctatgcgcccactctgc
gctatcatgagggccagttctacttgatcgtttcgtacctgggccgcagactaagggcttgctgttcac
ctcgtctgatccgtacgacgatgccgcgtggagcgatccgctcgaattcgcggtacatggcatcgacccg
gatatcttctgggatcacgacgggacggtctatgtcacgtccgccgaggaccagatgattaagcagtaca
cactcgatctgaagacgggggcgattggcccggttgactacctctggaacggcaccggaggagtctggcc
cgagggccccgcacatttacaagagagacggatactactacctcatgatcgcagagggaggtaccgagctc
ggccactcggagaccatggcgcgatctagaacccggacaggtccctgggagccataccccgcacaatccgc
tcttgtcgaacaagggcacctcggagtacttccagactgtgggccatgcggacttgttccaggatgggaa
cggcaactggtgggccgtggcgttgagcacccgatcagggcctgcatggaagaactatccatgggtcgg
gagacggtgctcgccccgccgcttgggagaagggtgagtggcctgtcattcagcctgtgagaggccaaa
tgcaggggccgtttccaccaccaaataagcgagttcctcgcggcgagggcggatggatcaagcaacccga
caaagtggatttcaggcccggatcgaagataccggcgcacttccagtactggcgatatcccaagacagag
gattttaccgtctccctcggggccacccgaatactcttcggctcacaccctccttttacaacctcaccg
gaactgcggacttcaagccgatgatggcctgtcgcttgttatgcgcaaacagaccgacaccttgttcac
gtacactgtggacgtgtcttttgaccccaaggttgccgatgaagaggcgggtgtgactgttttccttacc
cagcagcagcacatcgatcttggtattgtccttctccagacaaccgaggggctgtcgttgtccttccggt
tccgcgtggaaggccgcggtaactacgaaggtcctcttccagaagccaccgtgcctgttcccaaggaatg
gtgtggacagaccatccggcttgagattcaggccgtgagtgacaccgagtatgtctttgcggctgccccg
gctcggcaccctgcacagaggcaaatcatcagccgcgccaactcgttgattgtcagtggtgatacgggac
ggtttactggctcgcttgttggcgtgtatgccacgtcgaacggggtgccggatccacgcccgcatatat
cagcagatggagatacgaaggacggggccagatgattgattttggtcgagtggtcccgagctactga

FIG. 59A

SEQ ID NO:54
Protein sequence of Af43A maapslsyptgiqsytnplfpgwhsdpscayvaeqdtffcvtstfiafpglplyasrdlqnwklasnifn
rpsqipdlrvtdgqqsgiyaptlryhegqfylivsylgpqtkgllftssdpyddaawsdplefavhgidp
difwdhdgtvyvtsaedqmikqytldlktgaigpvdylwngtggvwpegphiykrdgyyylmiaeggtel
ghsetmarsrtrtgpwepyphnpllsnkgtseyfqtvghadlfqdgngnwwavalstrsgpawknypmgr
etvlapaawekgewpviqpvrgqmqgpfpppnkrvprgeggwikqpdkvdfrpgskipahfqywrypkte
dftvsprghpntlrltpsfynltgtadfkpddglslvmrkqtdtlftytvdvsfdpkvadeeagvtvflt
qqqhidlgivllqtteglslsfrfrvegrgnyegplpeatvpvpkewcgqtirleiqavsdteyvfaaap
arhpaqrqiisranslivsgdtgrftgslvgvyatsnggagstpayisrwryegrgqmidfgrvvpsy

FIG. 59B

SEQ ID NO:55
Nucleotide sequence for Pf51A, a GH51 family enzyme from *Penicillium funiculosum* atgggaaagatgtggcattcgatcttggttgtgttgggcttattgtctgtcgggcatgccatcactatca
acgtgtcccaaagtggcggcaataagaccagtcctttgcaatatggtctgatgttcgaggtaatccttct
cttataccacatataaaagttgcgtcatttctaagacaagtcaaggacataaatcacggcggtgatggcg
gtctgtatgcagagcttgttcgaaaccgagcattccaaggtagcaccgtctatccagcaaacctcgatgg
atacgactcggtcaatggagcaatcctagcgcttcagaatttgacaaaccctctatcaccctccatgcct
agctctctcaacgtcgccaaggggtccaacaatggaagcatcggtttcgcaaatgaaggctggtggggga
tagaagtcaagccgcaaagatacgcgggctcattctacgtccaggggggactatcaaggagatttcgacat
ctctcttcagtcgaaattgacacaagaagtcttcgcaacggcaaaagtcaggtcctcgggcaaacacgag
gactgggttcaatacaagtacgagttggtgcccaaaaaggcagcatcaaacaccaataacactctgacca
ttacttttgactcaaaggtatgttaaattttgggtttagttcgatgtctggcaattgtcttacgagaaac
gtagggattgaaagacggatccttgaacttcaacttgatcagcctatttcccccaacttacaacaatcgg
cccaatggcctaagaatcgacctggttgaagctatggctgaactagagggggtaagctcttacaaatcaa
ctttatctttacgaagactaatgtgaaaacttagaaatttctgcggtttccaggcggtagcgatgtggaa
ggtgtacaagctccttactggtataagtggaatgaaacggtaggagatctcaaggaccgttatagtaggc
ccagtgcatggacgtacgaagaaagcaatggaattggcttgattgagtacatgaattggtgtgatgacat
gggcttgagccgagtgagtgtattccattcagcgtcaaatccagtgttctaatcatacacatcagttct
tgccgtatgggatggacattaccttcgaacgaagtgatatcggaaaacgatttgcagccatatatcgac
gacaccctcaaccaactggaattcctgatgggtgccccagatacgccatatggtagttggcgtgcgtctc
tgggctatccgaagccgtggacgattaactacgtcgagattggaaacgaagacaatctatacgggggact
agaaacatacatcgcctaccggtttcaggcatattacgacgctataacagctaaatatccccatatgacg
gtcatggaatctttgacggagatgcctggtccggcggccgctgcaagcgattaccatcaatattctactc
ctgatgggtttgtttcccagttcaactactttgatcagatgccagtcactaatagaacactgaacggtat
gaaaaccccccctttttaaatatgcttttaatggtattaaccatctttcataggagagattgcaaccgt
ttatccaaataatcctagtaattcggtggcctggggaagcccattcccctgtatccttggtggattggg
tccgttgcagaagctgttttcctaattggtgaagagaggaattcgccaaagataatcggtgctagctacg
tacggaattctacttttcgagattttaacattggataagaaggactaacctcaatacaggctccaatgtt
cagaaatatcaacaattggcagtggtctccaacactcatcgcttttgacgctgactcgtcgcgtacaagt
cgttcaacaagctggcatgtgatcaaggtatgctaattttcctcctcattcaaacccgcagatgtgagct
aactttccgaagcttctctcgacaaacaaaatcacgcaaaatttacccacgacttggagtggcggtgaca
taggtccattatactgggtagctggacgaaacgacaatacaggatcgaacatattcaaggccgctgttta
caacagcacctcagacgtccctgtcaccgttcaatttgcaggatgcaacgcaaagagcgcaaatttgacc
atcttgtcatccgacgatccgaacgcatcgaactaccctggggggcccgaagttgtgaagactgagatcc
agtctgtcactgcaaatgctcatggagcatttgagttcagtctcccgaacctaagtgtggctgttctcaa
aacggagtaa

*FIG. 60A*

SEQ ID NO:56
Protein sequence of Pf51A mckmwhsilvvlgllsvghaitinvsqsggnktsplqyglmfedinhggdgglyaelvrnrafqgstvyp
anldgydsvngailalqnltnplspsmpsslnvakgsnngsigfanegwwgievkpqryagsfyvqgdyq
gdfdislqskltqevfatakvrssgkhedwvqykyelvpkkaasntnntltitfdskglkdgslnfnlis
lfpptynnrpnglridlveamaelegkflrfpggsdvegvqapywykwnetvgdlkdrysrpsawtyees
ngiglieymnwcddmglepilavwdghylsnevisendlqpyiddtlnqleflmgapdtpygswraslgy
pkpwtinyveignednlyggletyiayrfqayydaitakyphmtvmesltempgpaaaasdyhqystpdg
fvsqfnyfdqmpvtnrtlngeiatvyprnpsnsvawgspfplyp **wwigsvaeavfligeernspkiigas
yapmfrninnwqwsptliafdadssrtsrstswhvikllstnkitqnlpttwsggdigplywvagrndnt
gsnifkaavynstsdvpvtvqfagcnaksanltilssddpnasnypggpevvkteiqsvtanahgafefs
lpnlsvavlkte**

*FIG. 60B*

SEQ ID NO:57
**Nucleotide sequence for AfuXyn2, a GH11 family enzyme from *Aspergillus fumigatus*** atggtttctttctcctacctgctgctggcgtgctccgccattggagctctggctgcccccgtcgaacccg
agaccacctcgttcaatgagactgctcttcatgagttcgctgagcgcgccggcacccaagctccaccgg
ctggaacaacggctactactactccttctggactgatggcggcggcgacgtgacctacaccaatggcgcc
ggtggctcgtactccgtcaactggaggaacgtgggcaactttgtcggtggaaaggggctggaaccctggaa
gcgctaggtaccgagctttgtcaacgtcggatgtgcagacctgtggctgacagaagtagaaccatcaact
acggaggcagcttcaaccccagcggcaatggctacctggctgtctacggctggaccaccaaccccttgat
tgagtactacgttgttgagtcgtatggtacatacaaccccggcagcggcggtaccttcaggggcactgtc
aacaccgacggtggcacttacaacatctacacggccgttcgctacaatgctcctccatcgaaggcacca
agaccttcacccagtactggtctgtgcgcacctccaagcgtaccggcggcactgtcaccatggccaacca
cttcaacgcctggagcagactgggcatgaacctgggaactcacaactaccagattgtcgccactgagggt
taccagagcagcggatctgcttccatcactgtctactag

*FIG. 61A*

SEQ ID NO:58
Protein sequence of AfuXyn2 mvsfsvlllacsaigalaapvepettsfnetalhefaeragtpsst **gwnngyyysfwtdgggdvtytnga
ggsysvnwrnvgnfvggkgwnpgsartinyggsfnpsgngylavygwttnplieyyvvesygtynpgsgg
tfrgtvntdggtyniytavrynapsiegtktftqywsvrtskrtggtvtmanhfnawsrlgmnlgthnyq
ivategyqssgsasitvy**

*FIG. 61B*

SEQ ID NO:59
Nucleotide sequence for AfuXyn5, a GH11 family enzyme from *Aspergillus fumigatus* atgatctccatttcctcgctcagctttggactcgccgctatcgccggcgcatatgctcttccgagtgaca
aatccgtcagcttagcggaacgtcagacgatcacgaccagccagacaggcacaaacaatggctactacta
ttccttctggaccaacggtgccggatcagtgcaatatacaaatggtgctggtggcgaatatagtgtgacg
tgggcgaaccagaacggtggtgactttacctgtgggaaggctggaatccagggagtgaccagtaggcaa
cgcccgagaactatagaagaggacgcaaagaaagcactaaactctctactagtgacattaccttctctgg
cagcttcaatccttccggaaatgcttacctgtccgtgtatggatggactaccaaccccctagtcgaatac
tacatcctcgagaactatggcagttacaatcctggctcgggcatgacgcacaagggcaccgtcaccagcg
atggatccacctacgacatctatgagcaccaacaggtcaaccagccttcgatcgtcggcacggccacctt
caaccaatactggtccatccgccaaaacaagcgatccagcggcacagtcaccaccgcgaatcacttcaag
gctgggctagtctggggatgaacctgggtacccataactatcagattgtttccactgagggatatgaga
gcagcggtacctcgaccatcactgtctcgtctggtggttcttcttctggtggaagtggtggcagctcgtc
tactacttcctcaggcagctcccctactggtggctccggcagtgtaagtcttcttccatatggttgtggc
tttatgtgtattctgactgtgatagtgctctgctttgtggggccagtgcggtggaattggctggtctggt
cctacttgctgctcttcgggcacttgccaggtttcgaactcgtactactcccagtgcttgtagtaccttc
ttgcagggttatatccaagtga

FIG. 62A

SEQ ID NO:60
Protein sequence of AfuXyn5

MISISSLSFGLAAIAGAYALPSDKSVSLAERQTITTSQT GTNNGYYYSFWTNGAGSVQYTNGAGGEYSVT
WANQNGGDFTCGKGWNPGSDHDITFSGSFNPSGNAYLSVYGWTTNPLVEYYILENYGSYNPGSGMTHKGT
VTSDGSTYDIYEHQQVNQPSIVGTATFNQYWSIRQNKRSSGTVTTANHFKAWASLGMNLGTHNYQIVSTE
GYESSGTSTITV*SSGGSSSGGSGGSSSTTSSGSSPTGGSGSCSA*LWGQCGGIGWSGPTCCSSGTCQVSNS
YYSQCL

FIG. 62B

SEQ ID NO:61
Nucleotide sequence for Fv43D, GH43 family enzyme from *Fusarium verticillioides*

```
atgcagctcaagtttctgtcttcagcattgttgctgtctttgaccggcaattgcgctgcgcaagacacta
atgatatccctcctctgatcaccgacctctggtctgcggatccctcggctcatgttttcgagggcaaact
ctgggtttacccatctcacgacatcgaagccaatgtcgtcaacggcaccggaggcgctcagtacgccatg
agagattatcacacctattccatgaagaccatctatggaaaagatcccgttatcgaccatggcgtcgctc
tgtcagtcgatgatgtccatgggccaagcagcaaatgtgggctcctgacgcagcttacaagaacggcaa
atattatctctacttccccgccaaggataaagatgagatcttcagaattggagttgctgtctccaacaag
cccagcggtcctttcaaggccgacaagagctggatccccggtacttacagtatcgatcctgctagctatg
tcgacactaatggcgaggcatacctcatctggggcggtatctggggcggccagcttcaggcctggcagga
tcacaagaccttaatgagtcgtggctcggcgacaaagctgctcccaacggcaccaacgccctatctcct
cagatcgccaagctaagcaaggacatgcacaagatcaccgagacaccccgcgatctcgtcatcctggccc
ccgagacaggcaagcccttcaagcagaggacaataagcgacgattttcgaggggccctggttcacaa
gcgcggcaagctgtactacctcatgtactctaccggcgacacgcacttcctcgtctacgcgacttccaag
aacatctacggtccttatacctatcagggcaagattctcgacctgttgatgggtggactacgcatggaa
gtattgttgagtacaagggacagtggtggttgttctttgcggatgcgcatacttctggaaaggattatct
gagacaggttaaggcgaggaagatctggtatgacaaggatggcaagattttgcttactcgtcctaagatt
tag
```

FIG. 63A

SEQ ID NO:62
Protein sequence of Fv43D mqlkflssalllsltqncaaqdtndipplitdlwsadpsahvfegklwvypshdieanvvngtggaqyam
rdyhtysmktiygkdpvidhgvalsvddvpwakqqm**wapdaaykngkyylyfpakdkdeifrigvavsnk
psgpfkadkswipgtysidpasyvdtngeayliwggiwggqlqawqdhktfneswlgdkaapngtnalsp
qiaklskdmhkitetprdlvilapetgkplqaednkrrffegpwvhkrgklyylmystgdthflvyatsk
niygpytyqgkildpvdgwtthgsiveykgqwwlffadahtsgkdylrqvkarkiwydkdg** killtrpki

FIG. 63B

SEQ ID NO:63
Nucleotide sequence for Pf43B, GH43 family enzyme from *Penicillium funiculosum* atgagtcgcagcatccttccgtacgcctctgttttcgcctcctgggcggggctatcgccgaaccgttttt
tggttctcaatagcgattttcccgatcccagtctcatagagacatccagcggatactatgcattcggtac
caccggaaacggagtcaatgcgcaggttgcttcttccagactttaatacctggactttgctttccggc
acagatgccctcccgggaccatttccgtcatgggtagcttcgtctccacaaatctgggcgccagatgttt
tggttaaggtatgttcttatggaataacagttttaggagtaggtcagccaggatattgacaaaattataa
taggccgatggtacctatgtcatgtactttcggcatctgctgcgagtgactcgggcaaacactgcgttg
gtgccgcaactgcgacctcaccggaaggaccttacaccccggtcgatagcgctgttgcctgtccattaga
ccagggaggagctattgatgccaatggatttattgacaccgacggcactatatacgttgtatacaaaatt
gatggaaacagtctagacggtgatggaaccacacatcctaccccatcatgcttcaacaaatggaggcag
acggaacaaccccaaccggcagcccaatccaactcattgaccgatccgacctcgacggacctttgatcga
ggctcctagtttgctcctctccaatggaatctactacctcagtttctcttccaactactacaacactaat
tactacgacacttcatacgcctatgcctcgtcgattactggtccttggaccaaacaatctgcgccttatg
caccttgttggttactggaaccgagactagcaatgacggcgcattgagcgccctggtggtgccgattt
ctccgtcgatggcaccaagatgttgttccacgcaaacctcaatggacaagatatctcgggcggacgcgcc
ttatttgctgcgtcaattactgaggccagcgatgtggttacattgcagtag

FIG. 64A

SEQ ID NO:64
Protein sequence of Pf43B

<u>msrsilpyasvfallqgaia</u>epflvlnsdfpdpslietssgyyafgttgngvnaqvasspdfntwtllsg
tdalpgpfpswvasspqiwapdvlvkadgtyvmyfsasaasdsgkhcvgaatatspegpytpvdsavacp
ldqggaidangfidtdgtiyvvykidgnsldgdgtthptpimlqqmeadgttptgspiqlidrsdldgpl
ieapslllsngiyylsfssnyyntnyydtsyayassitgpwtkqsapyapllvtgtetsndgalsapgga
dfsvdgtkmlfhanlngqdisggralfaasiteasdvvtlq

FIG. 64B

SEQ ID NO:65
**Nucleotide sequence of Fv51A, a GH51 family enzyme from *Fusarium verticillioides*** atggttcgcttcagttcaatcctagcggctgcggcttgcttcgtggctgttgagtcagtcaacatcaagg
tcgacagcaagggcggaaacgctactagcggtcaccaatatggcttccttcacgaggttggtattgacac
accactggcgatgattgggatgctaacttggagctaggatatcaacaattccggtgatggtggcatctac
gctgagctcatccgcaatcgtgctttccagtacagcaagaaataccctgtttctctatctggctggagac
ccatcaacgatgctaagctctccctcaaccgtctcgacactcctctctccgacgctctccccgtttccat
gaacgtgaagcctggaaagggcaaggccaaggagattggtttcctcaacgagggttactggggaatggat
gtcaagaagcaaaagtacactggctctttctgggttaagggcgcttacaagggccactttacagcttctt
tgcgatctaaccttaccgacgatgtctttggcagcgtcaaggtcaagtccaaggccaacaagaagcagtg
ggttgagcatgagtttgtgcttactcctaacaagaatgcccctaacagcaacaacacttttgctatcacc
tacgatcccaaggtgagtaacaatcaaaactgggacgtgatgtatactgacaatttgtagggcgctgatg
gagctcttgacttcaacctcattagcttgttccctcccacctacaagggccgcaagaacggtcttcgagt
tgatcttgccgaggctctcgaaggtctccaccccgtaaggtttaccgtctcacgtgtatcgtgaacagtc
gctgacttgtagaaaagagcctgctgcgcttccccggtggtaacatgctcgagggcaacaccaacaagac
ctggtgggactggaaggataccctcggacctctccgcaaccgtcctggtttcgagggtgtctggaactac
cagcagacccatggtcttggaatcttggagtacctccagtgggctgaggacatgaaccttgaaatcagta
ggttctataaaattcagtgacggttatgtgcatgctaacagatttcagttgtcggtgtctacgctggcct
ctccctcgacggctccgtcaccccaaggaccaactccagcccctcatcgacgacgcgctcgacgagatc
gaattcatccgaggtcccgtcacttcaaagtggggaaagaagcgcgctgagctcggccaccccaagcctt
tcagactctcctacgttgaagtcggaaacgaggactggctcgctggttatcccactggctggaactctta
caaggagtaccgcttccccatgttcctcgaggctatcaagaaagctcaccccgatctcaccgtcatctcc
tctggtgcttctattgaccccgttggtaagaaggatgctggtttcgatattcctgctcctggaatcggtg
actaccacccttaccgcgagcctgatgttcttgttgaggagttcaacctgtttgataacaataagtatgg
tcacatcattggtgaggttgcttctacccaccccaacggtggaactggctggagtggtaaccttatgcct
taccccctggtggatctctggtgttggcgaggccgtcgctctctgcggttatgagcgcaacgccgatcgta
ttcccggaacattctacgctcctatcctcaagaacgagaaccgttggcagtgggctatcaccatgatcca
attcgccgccgactccgccatgaccacccgctccaccagctggtatgtctggtcactcttcgcaggccac
cccatgacccatactctccccaccaccgccgacttcgacccccctctactacgtcgctggtaagaacgagg
acaagggaactcttatctggaagggtgctgcgtataacaccaccaagggtgctgacgttcccgtgtctct
gtccttcaagggtgtcaagcccggtgctcaagctgagcttactcttctgaccaacaaggagaaggatcct
tttgcgttcaatgatcctcacaagggcaacaatgttgttgatactaagaagactgttctcaaggccgatg
gaaagggtgctttcaacttcaagcttcctaacctgagcgtcgctgttcttgagaccctcaagaagggaaa
gccttactctagctag

*FIG. 65A*

SEQ ID NO:66
Protein sequence of Fv51A

<u>mvrfssilaaaacfvaves</u>vnikvdskggnatsghqygflhedinnsgdggiyaelirnrafqyskkypv
slsgwrpindaklslnrldtplsdalpvsmnvkpgkgkakeigflnegywgmdvkkqkytgsfwvkgayk
ghftaslrsnltddvfgsvkvkskankkqwvehefvltpnknapnsnntfaitydpkgadgaldfnlisl
fpptykgrknglrvdlaealeglhpsllrfpggnmlegntnktwwdwkdtlgplrnrpgfegvwnyqqth
glgileylqwaedmnleiivgvyaglsldgsvtpkdqlqplidaldeiefirgpvtskwgkkraelghp
kpfrlsyvevgnedwlagyptgwnsykeyrfpmfleaikkahpdltvissgasidpvgkkdagfdipapg
igdyhpyrepdvlveefnlfdnnkyghii**gevasthpnggtgwsgnlmpypwwisgvgeavalcgyerna
dripgtfyapilknenrwqwaitmiqfaadsamttrstswyvwslfaghpmthtlpttadfdplyyvagk
nedkgtliwkgaaynttkgadvpvslsfkgvkpgaqaeltlltnkekdpfafndphkgnnvvdtkktvlk
adgkgafnfklpnls**vavletlkkgkpyss

*FIG. 65B*

**SEQ ID NO:67, Nucleotide sequence for Cg51B, a GH51 family enzyme from *Chaetomium globosum***

```
atggcgcccctttcgcttcgggccctctcgctgctcgcgctcacaggagccgcagccgcggtgaccctat
cggtcgcgaactctggcggtaatgatacgtctccgtacatgtatggcatcatgttcgaggacatcaatca
gagcggtgacggcgggctgtaagttctgtcgcggcttccctgacaagcttgcatgatgcttaactaaag
tccttaggtacgccgagctgattcgcaaccgagccttccataatagctccctccaggcctggaccgccgt
ggggacagcactctcgaggtcgtaacctctgcaccgttatcggatgccctgcctcgctcggtcaaggtc
acgagtggaaagggcaaggcgggcttgaagaatgccggctactggggaatggacgtccagaagaccgaca
agtatagcggcagcttctactcgtacggcgcctacgacgaaagtttaccctctctctggtgtcggacat
cacaaatgagaccctggccaccaccaagatcaagtccaggtcggtggagcatgcctggaccgagcacaag
ttcgagcttctcccgaccaagagcgcggcgaacagcaacaacagcttcgtgctggagttcgcccctgcc
accagacggagctccagttcaacctcatcagcttgttcccgccgacgtataagaacaggcccaacggcat
gcgccgagagctcatggagaagctcgcagacctcaagcccagtttccttcggattccaggaggcaacaac
ctgtaagtgcttccggcgaaactagcagtagttgcctgagagacactaatctcagcgaacaacagcgagg
gcaactatgctggcaactactggaactggtcaagcacacttggcccgctgaccgaccggcccggtcgtga
cggcgtgtggacgtacgccaacacggacggcatcggctggtcgagtacatgcactgggccgaggacctc
gacgtggaggttgtgctggcggtcgccgcaggcctgtacctgaacggcgatgtggtcccggaggaggagc
tgcacgtcttcgtggaggatgcgctgaacgagctcgagttcctcatgggcgacgtctcgacccctttggg
cgcgcgccgcgctaagctcggctaccccaagccgtggaacatcaagttcgtcgaggtcggcaacgaggac
aacctgtggggcggcctcgactcgtacaagagctaccggctgaagactttctacgacgccatcaaggcga
agtaccccgacatctccatcttttcgtcgaccgacgagtttgtgtacaaggagtcgggccaggactacca
caagtacacccggccggactactccgtgtcccagttcgacctgtttgacaactgggccgacggccacccc
atcatcatcggagagtgagtgaacggcgaccccacctcccctaacgcgggatcgcgagctgatagatc
acccccaggtatgcgaccatccagaacaacacgggcaagctcgaggacacggactgggacgcgcccaagaa
caagtggtccaactggatcggctccgtcgccgaggccgtcttcatcctcggagccgagcgcaacggcgac
cgggtctggggcaccacctttgcgccgatcctccagaacctcaacagctaccaatgggctgtaagtacat
acatacataccgcaccccaaccccaaccccccaaagcgcacctccacccacccacccaaacacaccac
aactacctagctaacccgccacacaaacaaacagcccgacctaatctccttcaccgccaacccggccgac
accacgccagcgtctcgtacccgatcatccagctgctcgcctcgcacgcatcacgcacaccctccccg
tcagcagcgccgacgccttcggcccggcctactgggtggccggtcgcggcgccgacgacggctcgtacat
cctcaaggcggccgtgtacaacagcacggggggtgcggatgtaccggtgagggtgcagtttgaggcgggg
ggtggtggtggtggtggtggtggtggtggtggtggtggtgatgggaagggaagggtaaagggaagg
gaggggagggtggtgagggtgtgaagaagggtgaccgcgcgcagttgaccgtgttgacggcgccggaggg
gccctgggcgcataatacgccggagaataaggggcggtcaagacgacagtgacgacgttgaaggccggg
aggggtggggtgtttgagtttagtctgccggatttgtcggtggcggtgttggtggtggagggggagaagt
ga
```

*FIG. 66A*

SEQ ID NO:68, Protein sequence of Cg51B

<u>maplslralslllaltgaaaa</u>vtlsvansggndtspymygimfedinqsgdgglyaelirnrafhnsslqa
wtavgdstlevvtsaplsdalprsvkvtsgkgkaglknagywgmdvqktdkysqsfysygaydgkftlsl
vsditnetlattkiksrsvehawtehkfellptksaansnnsfvlefrpchqtelqfnlislfpptyknr
pngmrrelmekladlkpsflripggnnlegnyagnywnwsstlgpltdrpgrdqvwtyantdgiglveym
hwaedldvevvlavaaglylngdvvpeeelhvfvedalneleflmgdvstpwgarraklgypkpwnikfv
evgnednlwggldsyksyrlktfydaikakypdisifsstdefvykesgqdyhkytrpdysvsqfdlfdn
wadghpiii**geyatiqnntgkledtdwdapknkwsnwigsvaeavfilgaerngdrvwgttfapilqnln
syqwapdlisftanpadttpsvsypiiqllashrithtlpvssadafgpaywvagrgaddgsyilkaavy
nstggadvpvrvqfeagggggggggggggggdgkgkgkgkggeggegvkkgdraqltvltapegpwahnt
penkgavkttvttlkagrggvfefslpdls**vavlvvegek

*FIG. 66B*

**SEQ ID NO:69, Nucleotide sequence for Fv43C, a GH43 family enzyme from *Fusarium verticillioides*** atgcgtcttctatcgtttcccagccatctcctcgtggccttcctaaccctcaaagaggcttcatccctcg
ccctcagcaaacgggatagccctgtcctccccggcctctggcggaccccaacatcgccatcgtcgacaa
gacatactacatcttccctaccaccgacggtttcgaaggctggggcggcaacgtcttctactggtggaaa
tcaaaagatctcgtatcatggacaaagagcgacaagccattccttactctcaatggtacgaatggcaacg
ttccctgggctacaggtaatgcctgggctcctgctttcgctgctcgcggaggcaagtattacttctacca
tagtgggaataatccctctgtgagtgatggcataagagtattggtgcggcggtggctgatcatcctgag
gggccgtggaaggcacaggataagccgatgatcaagggaacttctgatgaggagattgtcagcaaccagg
ctatcgatcccgctgcctttgaagaccctgagactggaaagtggtatatctactggggaaacggtgtccc
cattgtcgcagagctcaacgacgacatggtctctctcaaagcaggctggcacaaaatcacaggtcttcag
aatttccgcgagggtcttttcgtcaactatcgcgatggaacatatcatctgacatactctatcgacgata
cgggctcagagaactatcgcgttgggtacgctacggcggataacccattggaccttggacatatcgtgg
tgttcttctggagaaggacgaatcgaagggcattcttgctacgggacataactccatcatcaacattcct
ggaacggatgagtggtatatcgcgtatcatcgcttccatattcccgatggaaatggctataataggggaga
ctacgattgataggtacccatcgacaaggatacgggttgtttggaaaggttacgccgactttgcagag
tgttgatcctaggcctttgtag

*FIG. 67A*

SEQ ID NO:70, Protein sequence for Fv43C

<u>mrllsfpshllvafltlkeass</u>lalskrdspvlpglwadpniaivdktyyifpttdgfegwggnv
fywwkskdlvswtksdkpfltlngtngnvpwatgnawapafaarggkyyfyhsgnnpsvsdghks
igaavadhpegpwkaqdkpmikgtsdeeivsnqaidpaafedpetgkwyiywgngvpivaelndd
mvslkagwhkitglqnfreglfvnyrdgtyhltysiddtgsenyrvgyatadnpigpwtyrgvll
ekdeskgilatghnsiinipgtdewyiayhrfhipdgngynrettidrvpidkd**tglfgkvtptl
qsvdprpl**

*FIG. 67B*

**SEQ ID NO:71, Nucleotide sequence for Fv30A, a GH30 family enzyme from *Fusarium verticillioides*** atgctcttctcgctcgttcttcctacccttgcctttcaagccagcctggcgctcggcgatacatccgtta
ctgtcgacaccagccagaaactccaggtcatcgatggctttggtgtctcagaagcctacggccacgccaa
acaattccaaaacctcggtcctggaccacagaaagagggcctcgatcttctcttcaacactacaaccggc
gcaggcttatccatcatccgaaacaagatcggctgcgacgcctccaactccatcaccagcaccaacaccg
acaacccagataagcaggctgtttaccattttgacggcgatgatgatggtcaggtatggtttagcaaaca
ggccatgagctatggtgtagatactatctacgctaatgcttggtctgcgcctgtatacatgaagtcagcc
cagagtatgggccgtctctgcggtacacctggtgtgtcgtgctcctctggagattggagacatcgttacg
ttgagatgatagctgagtacctctcctactacaagcaggctggcatcccagtgtcgcacgttggattcct
caatgagggtgacggctcggactttatgctctcaactgccgaacaggctgcagatgtcattcctcttcta
cacagcgctttgcagtccaagggccttggcgatatcaagatgacgtgctgtgataacatcggttggaagt
cacagatggactataccgccaagctggctgagcttgaggtggagaagtatctatctgtcatcacatccca
cgagtactccagcagccccaaccagcctatgaacactacattgccaacctggatgtccgagggagctgcc
aatgaccaggcatttgccacagcgtggtacgtcaacggcggttccaacgaaggtttcacatgggcagtca
agatcgcacaaggcatcgtcaatgccgacctctcagcgtatatctactgggagggcgttgagaccaacaa
caaggggtctctatctcacgtcatcgacacggacggtaccaagtttaccatatcctcgattctctgggcc
attgctcactggtcgcgccatattcgccctggtgcgcatagactttcgacttcaggtgttgtgcaagata
cgattgttggtgcgtttgagaacgttgatggcagtgtcgtcatggtgctcaccaactctggcactgctgc
tcagactgtggacctgggtgtttcgggaagtagcttctcaacagctcaggctttcacttcggatgctgag
gcgcagatggtcgataccaaggtgactctgtccgacggtcgtgtcaaggttacggtcccggtgcacggtg
tcgtcactgtgaagctcacaacagcaaaaagctccaaaccggtctcaactgctgtttctgcgcaatctgc
ccccactccaactagtgttaagcacaccttgactcaccagaagacttcttcaacaacactctcgaccgcc
aaggccccaacctccactcagactacctctgtagttgagtcagccaaggcggtgaaataccctgtccccc
ctgtagcatccaagggatcctcgaagagtgctcccaagaagggtaccaagaagaccactacgaagaaggg
ctcccaccaatcgcacaaggcgcatagtgctactcatcgtcgatgccgccatggaagttaccgtcgtggc
cactgcaccaactaa

*FIG. 68A*

SEQ ID NO:72, Protein sequence of Fv30A mlfslvlptlafqaslalgdtsvtvdtsqklqvidgfgvseayghakqfqnlgpgpqkegldllfntttg
aglsiirnkigcdasnsitstntdnpdkqavyhfdgdddgqsaqsmgrlcgtpgvscssgdwrhryvemi
aeylsyykqagipvshvgflnegdgsdfmlstaeqaadvipllhsalqskglgdikmtccdnigwksqmd
ytaklaelevekylsvitsheyssspnqpmnttlptwmsegaandqafatawyvnggsnegftwavkiaq
givnadlsayiywegvetnnkgslshvidtdgtkftissilwaiahwsrhirpgahrlstsgvvqdtivg
afenvdgsvvmvltnsgtaaqtvdlgvsgssfstaqaftsdaeaqmvdtkvtlsdgrvkvtvpvhgvvtv
klttaksskpvstavsaqsaptptsvkhtlthqktssttlstakaptstqttsvvesakavkypvppvas
kgssksapkkgtkktttkkgshqshkahsathrrcrhgsyrrghctn

*FIG. 68B*

**SEQ ID NO:73, Nucleotide sequence for Fv43F, a GH43 family enzyme from *Fusarium verticillioides*** atgtggaaactcctcgtcagcggtcttgtcgccgtcgcgtccctcagcggcgtgaacgctgcttatccta
accctggtcccgtcaccggcgatactcgtgttcacgaccctacggttgtcaagactcccagcggtggata
cttgctggctcatactggcgataacgtttcgctcaagacttcttctgatcgaactgcttggaaggatgca
ggtgctgttttccccaacggtgcgccttggactacgcagtacaccaagggcgacaagaacctctgggccc
ctgatatctcctaccacaacggccagtactatctgtactactccgcctcttccttcggtcagcgtacctc
tgccattttctcgctaccagcaagaccggtgcatccggctcgtggaccaaccaaggcgtcgtcgtcgag
tccaacaacaacaacgactacaatgccattgacggaaatctctttgtcgactctgatggaaaatggtggc
tctccttcggctctttctggtccggcatcaagctcatccaactcgacccaagaccggcaagcgcaccgg
ctcaagcatgtactccctcgccaaacgcgacgcctccgtcgaaggcgccgtcgagctccgttcatcacc
aaacgcggaagcacctactacctctgggtgtcgttcgacaagtgttgccagggcgctgctagcacgtacc
gtgtcatggttggacggtcgagcagcattactggtccttatgttgacaaggctggtaagcagatgatgtc
tggtggaggaacggagattatggctagtcacggatctattcatggaccgggacataatgctgttttcact
gataacgatgcggacgttcttgtctatcattactacgataacgctggcacagcgctgttgggcatcaact
tgctcagatatgacaatggctggcctgttgcttattag

FIG. 69A

SEQ ID NO:74, Protein sequence for Fv43F mwkllvsqlvavaslsqvnaaypnpgpvtgdtrvhdptvvktpsggyllahtgdnvslktssdrtawkda
gavfpngapwttqytkgdknlwapdisyhngqyylyysassfgqrtsaiflatsktgasgswtnqgvvve
snnnndynaidgnlfvdsdgkwwlsfgsfwsgikliqldpktgkrtgssmyslakrdasvegaveapfit
krgstyylwvsfdkccqgaastyrvmvgrsssitgpyvdkagkqmmsgggteimashgsihgpghnavft
dndadvlvyhyydnagtallginllrydngwpvay

FIG. 69B

**SEQ ID NO:75, Nucleotide sequence for Xyn3, a GH10 xylanase from *Trichoderma reesei*** atgaaagcaaacgtcatcttgtgcctcctggccccctggtcgccgctctccccaccgaaaccatccacc
tcgaccccgagctcgccgctctccgcgccaacctcaccgagcgaacagccgacctctgggaccgccaagc
ctctcaaagcatcgaccagctcatcaagagaaaaggcaagctctactttggcaccgccaccgaccgcggc
ctcctccaacgggaaaagaacgcggccatcatccaggcagacctcggccaggtgacgccggagaacagca
tgaagtggcagtcgctcgagaacaaccaaggccagctgaactggggagacgccgactatctcgtcaactt
tgcccagcaaaacggcaagtcgatacgcggccacactctgatctggcactcgcagctgcctgcgtgggtg
aacaatatcaacaacgcggatactctgcgcggcaagtcatccgcacccatgtctctactgtggttgggcggt
acaagggcaagattcgtgcttgggtgagttttgaacaccacatgccccttttcttagtccgctcctcctc
ctcttggaacttctcacagttatagccgtatacaacattcgacaggaaatttaggatgacaactactgac
tgacttgtgtgtgtgatggcgataggacgtggtcaatgaaatcttcaacgaggatggaacgctgcgctct
tcagtcttttccaggctcctcggcgaggagtttgtctcgattgcctttcgtgctgctcgagatgctgacc
cttctgcccgtctttacatcaacgactacaatctcgaccgcgccaactatggcaaggtcaacgggttgaa
gacttacgtctccaagtggatctctcaaggagttcccattgacggtattggtgagccacgaccctaaat
gtccccattagagtctctttctagagccaaggcttgaagccattcagggactgacacgagagccttctc
tacaggaagccagtccatctcagcggcggcggaggctctggtacgctgggtgcgctccagcagctggca
acggtacccgtcaccgagctggccattaccgagctggacattcaggggcaccgacgacggattacaccc
aagttgttcaagcatgcctgagcgtctccaagtgcgtcggcatcaccgtgtgggcatcagtgacaaggt
aagttgcttcccctgtctgtgcttatcaactgtaagcagcaacaactgatgctgtctgtctttacctagg
actcgtggcgtgccagcaccaaccctcttctgtttgacgcaaacttcaacccaagccggcatataacag
cattgttggcatcttacaatag

FIG. 70A

SEQ ID NO:76, Protein sequence for Xyn3

<u>mkanvilcllaplvaal</u>ptetihldpelaalranltertadlwdrqasq sidqlikrkgklyfgtatdrg
llqreknaaiiqadlgqvtpensmkwqslennqgqlnwgdadylvnfaqqngksirghtliwhsqlpawv
nninnadtlrqvirthvstvvgrykgkirawdvvneifnedgtlrssvfsrllgeefvsiafraardadp
sarlyindynldranygkvnglktyvskwisqgvpidgigsqshlsggggsgtlgalqqlatvpvtelai
teldiqgapttdytqvvqaclsvskcvgitvwgisdkdswrastnpllfdanfnpkpaynsivgil q

FIG. 70B

**SEQ ID NO:77, Protein sequence of Xyn2, a GH11 family xylanase from *Trichoderma reesei***

<u>mvsftsllaaspps</u><u>rascrpaaevesvavekr</u>qtiqpgt gynngyfysywndghggvtytngpggqfsvn
wsnsgnfvggkgwqpgtknkvinfsgsynpngnsylsvygwsrnplieyyivenfgtynpstgatklgev
tsdgsvydiyrtqrvnqpsiigtatfyqywsvrrnhrssgsvntanhfnawaqqgltlgtmdyqivaveg
yfssgsasitvs

FIG. 71A

**SEQ ID NO:160, Nucleotide sequence encoding *T. reesei* Xyn2**

ATGGTCTCCTTCACCTCCCTCCTCGCCGGCGTCGCCGCCATCTCGGGCGTCTTGGCCGCTCCCGCCGCCG
AGGTCGAATCCGTGGCTGTGTGGAGAAGCGCCAGACGATTCAGCCCGGCACGGGCTACAACAACGGCTACTT
CTACTCGTACTGGAACGATGGCCACGGCGGCGTGACGTACACCAATGGTCCCGGCGGGCAGTTCTCCGTC
AACTGGTCCAACTCGGGCAACTTTGTCGGCGGCAAGGGATGGCAGCCCGGGACCAAGAACAAGTAAGACT
ACCTACTCTTACCCCCTTTGACCAACACAGCACAACACAATACAACACATGTGACTACCAATCATGGAAT
CGGATCTAACAGCTGTGTTTAAAAAAAAGGGTCATCAACTTCTCGGGAAGCTACAACCCCAACGGCAAC
AGCTACCTCTCCGTGTACGGCTGGTCCCGCAACCCCCTGATCGAGTACTACATCGTCGAGAACTTTGGCA
CCTACAACCCGTCCACGGGCGCCACCAAGCTGGGCGAGGTCACCTCCGACGGCAGCGTCTACGACATTTA
CCGCACGCAGCGCGTCAACCAGCCGTCCATCATCGGCACCGCCACCTTTTACCAGTACTGGTCCGTCCGC
CGCAACCACCGCTCGAGCGGCTCCGTCAACACGGCGAACCACTTCAACGCGTGGGCTCAGCAAGGCCTGA
CGCTCGGGACGATGGATTACCAGATTGTTGCCGTGGAGGGTTACTTTAGCTCTGGCTCTGCTTCCATCAC
CGTCAGCTAA

FIG. 71B

**SEQ ID NO:78, Protein sequence of Bxl1, a GH3 family β-xylosidase from *Trichoderma reesei***

<u>mvnnaallaalsallptala</u>qnnqtyanysaqgqpdlypetlatltlsfpdcehgplknnlvcdssagyv
eraqalislftleelilntqnsgpgvprlglpnyqvwnealhgldranfatkggqfewatsfpmpiltta
alnrtlihqiadiistqarafsnsgrygldvyapnvngfrsplwgrgqetpgedafflssaytyeyitgi
qggvdpehlkvaatvkhfagydlenwnnqsrlgfdaiitqqdlseyytpqflaaaryaksrslmcaynsv
ngvpscansfflqtllreswgfpewgyvssdcdavynvfnphdyasnqssaaasslragtd idcgqtypw
hlnesfvagevsrgeiersvtrlyanlvrlgyfdkknqyrslgwkdvvktdawnisyeaavegivllknd
gtlplskkvrsialigpwanattqmqgnyygpapylispleaakkagyhvnfelgteiagnsttgfakai
aaakksdaiiylggidntieqegadrtdiawpgnqldlikqlsevgkplvvlqmgggqvdssslksnkkv
nslvwggypgqsggvalfdilsgkrapagrlvttqypaeyvhqfpqndmnlrpdgksnpgqtyiwytgkp
vyefgsglfyttfketlashpkslkfntssilsaphpgytyseqipvftfeaniknsgktespytamlfv
rtsnagpapypnkwlvgfdrladikpghssklsipipvsalarvdshgnrivypgkyelalntdesvkle
felvgeevtienwpleeqqikdatpda

FIG. 72A

**SEQ ID NO:159, Nucleotide sequence encoding *T. reesei* Bxl1**

```
atggtgaataacgcagctcttctcgccgccctgtcggctctcctgcccacggccctggcgcagaacaatc
aaacatacgccaactactctgctcagggccagcctgatctctaccccgagacacttgccacgctcacact
ctcgttccccgactgcgaacatggcccctcaagaacaatctcgtctgtgactcatcggccggctatgta
gagcgagcccaggccctcatctcgctcttcaccctcgaggagctcattctcaacacgcaaaactcgggcc
ccggcgtgcctcgcctgggtcttccgaactaccaagtctggaatgaggctctgcacggcttggaccgcgc
caacttcgccaccaagggcggccagttcgaatgggcgacctcgttccccatgcccatcctcactacggcg
gccctcaaccgcacattgatccaccagattgccgacatcatctcgacccaagctcgagcattcagcaaca
gcggccgttacggtctcgacgtctatgcgccaaacgtcaatggcttccgaagcccctctggggccgtgg
ccaggagacgcccggcgaagacgcctttttcctcagctccgcctatacttacgagtacatcacgggcatc
cagggtggcgtcgaccctgagcacctcaaggttgccgccacggtgaagcactttgccggatacgacctcg
agaactggaacaaccagtcccgtctcggtttcgacgccatcataactcagcaggacctctccgaatacta
cactccccagttcctcgctgcggcccgttatgcaaagtcacgcagcttgatgtgcgcatacaactccgtc
aacggcgtgcccagctgtgccaacagcttcttcctgcagacgcttttgcgcgagagctgggcttccccg
aatggggatacgtctcgtccgattgcgatgccgtctacaacgttttcaaccctcatgactacgccagcaa
ccagtcgtcagccgccgccagctcactgcgagccggcaccgatatcgactgcggtcagacttacccgtgg
cacctcaacgagtcctttgtggccggcgaagtctcccgcggcgagatcgagcggtccgtcacccgtctgt
acgccaacctcgtccgtctcggatacttcgacaagaagaaccagtaccgctcgctcggttggaaggatgt
cgtcaagactgatgcctggaacatctcgtacgaggctgctgttgagggcatcgtcctgctcaagaacgat
ggcactctccctctgtccaagaaggtgcgcagcattgctctgatcggaccatgggccaatgccacaaccc
aaatgcaaggcaactactatggccctgccccataactcatcagccctctggaagctgctaagaaggccgg
ctatcacgtcaactttgaactcggcacagagatcgccggcaacagcaccactggctttgccaaggccatt
gctgccgccaagaagtcggatgccatcatctacctcggtggaattgacaacaccattgaacaggagggcg
ctgaccgcacggacattgcttggcccggtaatcagctggatctcatcaagcagctcagcgaggtcggcaa
acccctgtcgtcctgcaaatgggcggtggtcaggtagactcatcctcgctcaagagcaacaagaaggtc
aactccctcgtctggggcggatatcccggccagtcgggaggcgttgccctcttcgacattctctctggca
agcgtgctcctgccggccgactggtcaccactcagtacccggctgagtatgttcaccaattcccccagaa
tgacatgaacctccgacccgatggaaagtcaaaccctggacagacttacatctggtacaccggcaaaccc
gtctacgagtttggcagtggtctcttctacaccaccttcaaggagactctcgccagccacccaagagcc
tcaagttcaacacctcatcgatcctctctgctcctcacccggatacacttacagcgagcagattcccgt
cttcaccttcgaggccaacatcaagaactcgggcaagacggagtccccatatacggccatgctgtttgtt
cgcacaagcaacgctggcccagccccgtacccgaacaagtggctcgtcggattcgaccgacttgccgaca
tcaagcctggtcactcttccaagctcagcatccccatccctgtcagtgctctcgcccgtgttgattctca
cggaaaccggattgtataccccggcaagtatgagctagccttgaacaccgacgagtctgtgaagcttgag
tttgagttggtgggagaagaggtaacgattgagaactggccgttggaggagcaacagatcaaggatgcta
cacctgacgcataa
```

*FIG. 72B*

**SEQ ID NO:79, Protein sequence of Bgl1, a GH3 family β-glucosidase from *Trichoderma reesei*** mryrtaaalalatgpfaradshstsgasaeavvppagtpwgtaydkakaalaklnlqdkvgivsgv gwng
gpcvgntspaskisypslclqdgplgvrystgstaftpgvqaastwdvnlirergqfigeevkasgihvi
lgpvagplgktpqggrnwegfgvdpyltgiamgqtingiqsvgvqatakhyilneqelnretissnpddr
tlhelytwpfadavqanvasvmcsynkvnttwacedqytlqtvlkdqlgfpgyvmtdwnaqhttvqsans
gldmsmpgtdfngnnr lwgpaltnavnsnqvptsrvddmvtrilaawyltgqdqagypsfnisrnvqgnh
ktnvraiardgivllk ndanilplkkpasiavvgsaaiignharnspscndkgcddgalgmgwgsgavny
pyfvapydaintrassqgtqvtlsntdntssgasaargkdvaivfitadsgegyitvegnagdrnnldpw
hngnalvqavagansnvivvvhsvgaiileqilalpqvkavvwaglpsqesgnalvdvlwgdvspsgklv
ytiakspndyntrivsggsdsfseglfidykhfddanitpryefgyglsyt kfnysrlsvlstaksgpat
gavvpggpsdlfqnvatvtvdiansgqvtgaevaqlyitypssaprtppkqlrgfaklnltpgqsgtatf
nirrrdlsywdtasqkwvvpsgsfgisvgassrdirltstlsva

*FIG. 73A*

**SEQ ID NO:80, Nucleotide sequence for Pa51A, a GH51 family enzyme from *Podospora anserina*** atgatccacctcaagccagccctcgcggcgttgttggcgctgtcgacgcaatgtgtggctattgatttgt
ttgtcaagtcttcggggggaataagacgactgatatcatgtatggtcttatgcacgaggatatcaacaa
ctccggcgacggcggcatctacgccgagctaatctccaaccgcgcgttccaagggagtgagaagttcccc
tccaacctcgacaactggagccccgtcggtggcgctaccttacccttcagaagcttgccaagcccttt
cctctgcgttgccttactccgtcaatgttgccaaccccaaggagggcaagggcaaggcaaggacaccaa
ggggaagaaggttggcttggccaatgctgggttttggggtatggatgtcaagaggcagaagtacactggt
agcttccacgttactggtgagtacaaggggtgactttgaggttagcttgcgcagcgcgattaccggggaga
cctttggcaagaaggtggtgaaggtgggagtaagaagggaagtggaccgagaaggagtttgagttggt
gcctttcaaggatgcgcccaacagcaacaacaccttttgttgtgcagtgggatgccgagggcgcaaaggac
ggatctttggatctcaacttgatcagcttgttccctccgacattcaagggaaggaagaatgggctgagaa
ttgatcttgcgcagacgatggttgagctcaagccgaccttcttgcgcttccccggtggcaacatgctcga
gggtaacaccttggacacttggtggaagtggtacgagaccattggccctctgaaggatcgcccgggcatg
gctggtgtctgggagtaccagcaaacccttggcttgggtctggtcgagtacatggagtgggccgatgaca
tgaacttggagcccattgtcggtgtcttcgctggtcttgccctcgatggctcgttcgttcccgaatccga
gatgggatgggtcatccaacaggctctcgacgaaatcgagttcctcactggcgatgctaagaccaccaaa
tggggtgccgtccgcgcgaagcttggtcaccccaagccttggaaggtcaagtgggttgagatcggtaacg
aggattggcttgccggacgccctgctggcttcgagtcgtacatcaactaccgcttccccatgatgatgaa
ggccttcaacgaaaagtaccccgacatcaagatcatcgcctcgcctccatcttcgacaacatgacaatc
cccgcgggtgctgccggtgatcaccacccgtacctgactcccgatgagttcgttgagcgattcgccaagt
tcgataacttgagcaaggataacgtgacgctcatcggcgaggctgcgtcgacgcatcctaacggtggtat
cgcttgggagggagatctcatgcccttgccttggtgggcggcagtgttgctgagctatcttcttgatc
agcactgagagaaacggtgacaagatcatcggtgctacttacgcgcctggtcttcgcagcttggaccgct
ggcaatggagcatgacctgggtgcagcatgccgccgacccggccctcaccactcgctcgaccagttggta
tgtctggagaatcctcgcccaccacatcatccgtgagacgctcccggtcgatgccccggccggcaagccc
aactttgaccctctgttctacgttgccggaaagagcgagagtggcaccggtatcttcaaggctgccgtct
acaactcgactgaatcgatcccggtgtcgttgaagtttgatggtctcaacgagggagcggttgccaactt
gacggtgcttactgggccggaggatccgtatggatacaacgaccccttcactggtatcaatgttgtcaag
gagaagaccaccttcatcaaggccggaaaggcggcaagttcaccttcaccctgccgggcttgagtgttg
ctgtgttggagacggccgacgcggtcaagggtggcaagggaaagggcaagggcaagggaaagggtaactg
a

*FIG. 73B*

SEQ ID NO:81
Codon optimized cDNA for Pa51A, a GH51 family enzyme from *Podospora anserina* atgatccacctcaagcccgccctcgccgccctcctcgccctcagcacccaatgcgtcgccatcgacctct
tcgtcaagagcagcggcggcaacaagaccaccgacatcatgtacggcctcatgcacgaggacatcaacaa
cagcggcgacggcggcatctacgccgagctgatcagcaaccgcgccttccagggcagcgagaagttcccc
agcaacctcgacaactggtccccgtcggcggcgccaccctcaccctccagaagctcgccaagcccctgt
cctctgccctcccctactccgtcaacgtcgccaacccaaggagggtaagggtaagggcaaggacaccaa
gggcaagaaggtcggcctcgccaacgccggcttttggggcatggacgtcaagcgccagaaatacaccggc
agcttccacgtcaccggcgagtacaagggcgacttcgaggtcagcctccgcagcgccattaccggcgaga
ccttcggcaagaaggtcgtcaagggcggcagcaagaagggcaagtggaccgagaaggagttcgagctggt
cccttcaaggacgccccaacagcaacaacaccttcgtcgtccagtgggacgccgagggcgccaaggac
ggcagcctcgacctcaacctcatcagcctcttcccgcccaccttcaagggccgcaagaacggcctccgca
tcgacctcgcccagaccatggtcgagctgaagcccaccttcctccgctttccggcggcaacatgctcga
gggcaacaccctcgacacctggtggaagtggtacgagaccatcggcccctgaaggaccgccctggcatg
gccggcgtctgggagtaccagcagacgctgggcctcggcctggtcgagtacatggagtgggccgacgaca
tgaacctcgagcccatcgtcggcgtctttgctggcctggcctggatggcagctttgtccccgagagcga
gatgggctgggtcatccagcaggctctcgatgagatcgagttcctcaccggcgacgccaagaccaccaag
tggggcgccgtccgcgccaagctcggccaccctaagccctggaaggtcaaatgggtcgagatcggcaacg
aggactggctcgccggccgacctgccggcttcgagagctacatcaactaccgcttccccatgatgatgaa
ggccttcaacgagaaataccccgacatcaagatcattgccagccccctccatcttcgacaacatgaccatt
ccagccggtgctgccggtgaccaccacccctacctcacccccgacgaatttgtcgagcgcttcgccaagt
tcgacaacctcagcaaggacaacgtcaccctcattggcgaggccgccagcacccaccccaacggcggcat
tgcctgggagggcgacctcatgccctgccctggtggggcggcagcgtcgccgaggccatcttcctcatc
agcaccgagcgcaacggcgacaagatcatcggcgccacctacgccctggcctccgatctctcgaccgct
ggcagtggagcatgacctgggtccagcacgccgccgacctgccctcaccacccgcagcaccagctggta
cgtctggcgcatcctcgccaccacatcattcgcgagaccctcccgtcgacgccccgccggcaagccc
aacttcgaccccctcttctacgtcgctggcaagtcggagagcggcaccggcatcttcaaggccgccgtct
acaacagcaccgagagcatccccgtcagcctcaagttcgacggcctcaacgagggcgccgtcgccaacct
caccgtcctcaccggccccgaggaccctacggctacaacgacccttcaccggcatcaacgtcgtcaag
gaaagaccaccttcatcaaggccggcaagggcggcaagttcacctttaccctccccggcctctctgtcg
ccgtcctcgagaccgccgacgccgtgaaggtggcaagggaaagggaaagggcaagggtaagggtaacta
a

SEQ ID NO:82
**Nucleotide sequence for Gz43A, a GH43 family enzyme from *Gibberella zeae*** atgtatcggaagttggccgtcatctcggccttcttggccacagctcgtgctaccaacgacgactgtcctc
tcatcactagtagatggactgcggatccttcggctcatgtctttaacgacaccttgtggctctaccgtc
tcatgacatcgatgctggatttgagaatgatcctgatggaggccagtacgccatgagagattaccatgtc
tactctatcgacaagatctacggttccctgccggtcgatcacggtacggccctgtcagtggaggatgtcc
cctgggcctctcgacagatgtgggctcctgacgctgcccacaagaacggcaaatactacctatacttccc
tgccaaagacaaggatgatatcttcagaatcggcgttgctgtctccaaccccggcggaccattcgtc
cccgacaagagttggatccctcacactttcagcatcgacccgccagtttcgtcgatgatgatgacagag
cctacttggcatggggtggtatcatgggtggccagcttcaacgatggcaggataagaacaagtacaacga
atctggcactgagccaggaaacggcaccgctgccttgagccctcagattgccaagctgagcaaggacatg
cacactctggcagagaagcctcgcgacatgctcattcttgacccaagactggcaagccgctcctttctg
aggatgaagaccgacgcttcttcgaaggaccctggattcacaagcgcaacaagatttactacctcaccta
ctctactggcacaacccactatcttgtctatgcgacttcaaagacccctatggtccttacacctaccag
ggcagaattctggagccagttgatggctggactactcactctagtatcgtcaagtaccagggtcagtggt
ggctattttatcacgatgccaagacatctggcaaggactatcttcgccaggtaaaggctaagaagatttg
gtacgatagcaaaggaaagatcttgacaagaagccttga

FIG. 73D

SEQ ID NO:83
**Nucleotide sequence for Fo43A, a GH43 family enzyme from *Fusarium oxysporum*** atgtatcggaagttggccgtcatctcggccttcttggccacagctcgtgctcaagacactaatgacattc
ctccctgatcaccgacctctggtccgcagatccctcggctcatgttttcgaaggcaagctctgggttta
cccatctcacgacatcgaagccaatgttgtcaacggcacaggaggcgctcaatacgccatgagggattac
catacctactccatgaagagcatctatggtaaagatcccgttgtcgaccacggcgtcgctctctcagtcg
atgacgttccctgggcgaagcagcaaatgtgggctcctgacgcagctcataagaacggcaaatattatct
gtacttccccgccaaggacaaggatgagatcttcagaattggagttgctgtctccaacaagccagcggt
cctttcaaggccgacaagagctggatccctggcacgtacagtatcgatcctgctagctacgtcgacactg
ataacgaggcctacctcatctggggcggtatctggggcggccagctccaagcctggcaggataaaaagaa
ctttaacgagtcgtggattggagacaaggctgctcctaacggcaccaatgccctatctcctcagatcgcc
aagctaagcaaggacatgcacaagatcaccgaaacacccgcgatctcgtcattctcgccccgagacag
gcaagcctcttcaggctgaggacaacaagcgacgattcttcgagggccttggatccacaagcgcggcaa
gctttactacctcatgtactccaccggtgatacccacttccttgtctacgctacttccaagaacatctac
ggtccttatacctaccggggcaagattcttgatcctgttgatggtggactactcatggaagtattgttg
agtataagggacagtggtggcttttctttgctgatgcgcatacgtctggtaaggattaccttcgacaggt
gaaggcgaggaagatctggtatgacaagaacggcaagatcttgcttcaccgtccttag

FIG. 73E

SEQ ID NO:92
Nucleotide sequence for Pf51A, a GH51 family enzyme from *Penicillium funiculosum* atgtaccggaagctcgccgtgatcagcgccttcctggcgactgctcgcgccatcaccatcaacgtcagcc
agagcggcggcaacaagaccagcccgctccagtacggcctcatgttcgaggacatcaaccacggcggcga
cggcggcctctacgccgagctggtccggaaccgggccttccagggcagcaccgtctacccggccaacctc
gacggctacgactcggtgaacggcgcgattctcgcgctccagaacctcaccaaccgctcagcccgagca
tgccctcgtcgctgaacgtcgccaagggctcgaacaacggcagcatcggcttcgccaacgaggggtggtg
gggcatcgaggtcaagccgcagcggtacgccggcagcttctacgtccagggcgactaccagggcgacttc
gacatcagcctccagagcaagctcacccaggaggtcttcgcgacggcgaaggtccggtcgagcggcaagc
acgaggactgggtccagtacaagtacgagctggtcccgaagaaggccgccagcaacaccaacaacaccct
caccatcaccttcgacagcaagggcctcaaggacggcagcctcaacttcaacctcatcagcctcttcccg
ccgacctacaacaaccggccgaacggcctccggatcgacctcgtcgaggccatggcggagctggagggca
agttcctccgcttcccggcggctcggacgtggagggcgtccaggccccgtactggtacaagtggaacga
gaccgtcggcgacctcaaggaccgctactcgcgcccgagcgcctggacctacgaggagagcaacggcatc
ggcctcatcgagtacatgaactggtgcgacgacatgggcctcgagccgatcctcgccgtctgggacggcc
actacctcagcaacgaggtcatcagcgagaacgacctccagccgtacatcgacgacaccctcaaccagct
cgagttcctcatgggcgccccggacactccctacggggtcttggagggctagcctcggctacccgaagccg
tggaccatcaactacgtcgagatcggcaacgaggacaacctctacgcggcctcgagacctacatcgcct
accggttccaggcctactacgacgccatcaccgccaagtacccgcacatgacgtcatggagagcctcac
cgagatgcccggccccgctgccgcggcgtcggactaccaccagtactcgacgcccgacggcttcgtcagc
cagttcaactacttcgaccagatgccggtcaccaaccgcacgctgaacggcgagatcgccaccgtctacc
ccaacaacccgagcaactcggtggcgtggggcagcccgttcccgctctaccgtggtggatcgggtccgt
ggctgaggccgtcttcctcatcggcgaggagcggaacagcccgaagatcatcggcgccagctacgccccc
atgttccgcaacattaacaactggcagtggagcccgaccctgatcgccttcgacgccgacagcagccgga
cgtcgcgctctacttcctggcacgtcatcaagctcctcagcaccaacaagatcacccagaacctgcccac
gacgtggtctggggggacatcggcccgctctactgggtcgccggccggaacgacaacaccggcagcaac
atcttcaaggccgccgtctacaacagcaccagcgacgtcccggtcaccgtccagttcgccggctgcaacg
ccaagagcgccaacctcaccatcctctcgtcggacgacccaacgccagcaactaccgggcggccccga
ggtcgtcaagaccgagatccagagcgtcaccgccaacgcccacggcgccttcgagttcagcctcccgaac
ctgtcggtggctgtgctgaagacggagtag

*FIG. 73F*

SEQ ID NO:93
Nucleic acid sequence of Pa3D, a GH3 family β-glucosidase from *Podospora anserina* atggctcttcaaaccttcttcctgctggcggcagccatgctggccaacgcagagacaacaggcgaaagg
tctctcggcaagcaccgtctggcgctcaagcatgggccgccgcccactccaggctgccgccactctggc
cagaatgtcacagcaagacaagatcaacatggtcacgggcattggctgggacagagggccttgcgtggga
aacacagctgccatcagctccatcaactatcctcaaatctgtcttcaggatggaccattgggcattcgct
tcggcactggtaccaccgccttcacacctggcgtccaagctgcttcgacatgggacgttgatctgatccg
gcagcgcggtgcttacctgggcgccgaagccaagggctgcggcattcacatcctttttggggcccgttgcc
ggtgccctgggcaagattccccacggcggtcgcaactgggagggatttggcgccgaccctaccttgccg
gtattgccatgaaggagaccatcgagggtattcagtcagcaggcgtccaggccaacgccaagcactacat
tgcaaacgaacaagagctcaaccgcgagaccatgagcagcaatgtggatgaccgcactcagcacgagctc
tacctctggcctttgccgacgccgtgcacgccaacgtcgccagcgtcatgtgcagttacaacaagctca
atggcacgtgggcttgcgagaatgacaaggctctgaatcagatcttgaagaaggagctcggattccaggg
ctacgttctcagcgactggaatgctcagcacagcactgctctgtctgctaacagtggtctggacatgact
atgcccggtaccgatttcaacggccgcaatgtctactggggccctcaactgaacaacgctgtcaacgccg
gccaggttcagagatccagactagacgacatgtgcaagagaatcttggctggctggtacttgctcggtca
gaaccagggctatcccgccatcaacatcagggccaacgttcagggcaaccataaggagaacgtacgtgct
gttgccagagacggcatcgtcttgctgaagaacgatggaattctgccgctttccaagccgagaaagattg
ctgtcgtgggctcccactccgtcaacaatccccagggaatcaacgcctgtgttgacaagggctgcaatgt
tggcaccctttggcatgggctggggttcaggcagcgtcaactaccctatctcgtgtccccgtacgatgct
ctccggactcgtgctcaggccgatggcacacaaatcagcctccacaacactgacagcaccaacggtgtgt
caaacgttgtgtctgacgctgatgctgttgttgttgtcatcactgccgattctggtgaagggtacatcac
tgtcgagggccacgctggcgaccgcagccaccttgacccgtggcacaatggcaaccaacttgttcaggct
gccgcggctgccaacaagaacgtcatcgttgttgtgcacagtgttggccagatcaccctggagactatcc
tcaacaccaatggagtccgcgcgattgtgtgggctggtcttccgggccaagagaatggcaacgctcttgt
tgatgttctctacggcttggtttcgccatctggaaagcttccctacaccattggcaagagggagtcggac
tatggcacagccgttgttcgtggggatgataacttcaggggagggccttttttgttgactaccgtcactttg
acaatgccaggatcgagccgcgctatgagtttggctttggtctttgtaagttccagcggcggagttgggt
ttgatttcaagctttcctaacctgataaaacagcttacaccaatttcaccttctccgacatcaagattac
ttccaatgtcaagccggggcccgctactggccagaccattcccggcggacctgccgacctgtgggaggac
gttgcgacagtcactgcaaccatcaccaactcgggtgctgtcgagggcgctgaggttgcccagctttaca
tcggcctgccgtcctcggctcctgcctctccccgaagcagctgcgtggattttccaagctgaagctggc
cccgggtgccagcggcactgccacattcaacctcagacgcagagatctcagctattgggatacccgcctc
cagaactgggtcgtgcccagcggcaactttgtcgtcagcgtcggcgccagctcgagagatatccgcttga
cgggcaccatcacggcgtag

*FIG. 74A*

SEQ ID NO:94
Protein sequence of Pa3D, a GH3 family β-glucosidase from *Podospora anserina* malqtffllaaamlanaettgekvsrqapsgaqawaaahsqaaatlarmsqqdkinmvtgigwdrgpcvg
ntaaissinypqiclqdgplgirfgtgttaftpgvqaastwdvdlirqrgaylgaeakgcgihillgpva
galgkiphggrnwegfgadpylagiamketiegiqsagvqanakhyianeqelnretmssnvddrtqhel
ylwpfadavhanvasvmcsynklngtwacendkalnqilkkelgfqgyvlsdwnaqhstalsansgldmt
mpgtdfngrnvywgpqlnnavnagqvqrsrlddmckrilagwyllgqnqgypainiranvqgnhkenvra
vardgivllkndgilplskprkiavvgshsvnnpqginacvdkgcnvgtlgmgwgsgsvnypylvspyda
lrtraqadgtqislhntdstngvsnvvsdadavvvvitadsgegyitveghagdrshldpwhngnqlvqa
aaaanknvivvvhsvgqitletilntngvraivwaglpgqengnalvdvlyglvspsgklpytigkresd
ygtavvrgddnfreglfvdyrhfdnariepryefgfglsytnftfsdikitsnvkpgpatgqtipggpad
lwedvatvtatitnsgavegaevaqlyiglpssapasppkqlrgfsklklapgasgtatfnlrrrdlsyw
dtrlqnwvvpsgnfvvsvgassrdirltgtita

FIG. 74B

SEQ ID NO:95

**Nucleotide sequence of Fv3G, a GH3 family β-glucosidase from *Fusarium verticillioides*** atgtttccttcttccatatcttgtttggcggccctgagtctgatgagccagggtctactagctcagagcc
aaccggaaaatgtcatcaccgatgatacctacttctacggtcaatcgccaccagtgtatcctacacgtaa
gcactctctctgatttcccaacgaaagcaatactgatctcttgaccagcggaacaggtagacaccggctc
atgggctgccgctgtagccaaagccaagaacttggtgtcccagttgactcttgaagagaaagtcaacttg
actacaggaggccagacgaccaccggctgctctggcttcatccctggcattccccgtgtaggctttccag
gactgtgtttagcagacgctggcaacggtgtccgcaacacagattatgtgagctcgtttccctccgggat
tcatgtcggtgcaagctggaatccggagttgacctacagccggagctactacatgggtgctgaggccaaa
gccaagggcgttaacatccttctcggtccagtatttggacctttgggccgagtagttgaaggtggacgca
actgggaggggtttccaatgatccctacctggcgggtaaattagggcatgaagctgtcgccggtatcca
agacgccggagttgttgcatgcggaaaacatttccttgctcaagagcaggagacccatagacttgcggcg
tctgtcactggggctgatgcaatctcatcaaatctcgatgacaagacactccatgaattatatctctggt
aagcacatcatatcttggctgagtagatgaaccttactaacacccgaactgggcttttcgctgatgcagt
ccacgccggacttgccagtgtgatgtgcagctacaacagagcaaacaattcacacgcctgccaaaactcg
aagcttctcaatggccttctcaagggcgagttaggattccagggttttgtcgtctcggactggggcgcac
agcaatctggtatggcttcagcattggctggcctggatgttgtcatgcccagctcgatcttgtggggtgc
caaccttacccttggtgtgaacaacggaactattcccgagtcacaggttgacaatatggttacacggtac
gcgaagtctcagccttacttctcaattcttttgaactgacaatcgtgtaggctccttgcaacttggtatc
agttgaaccaggaccaagacaccgaagccccaggtcacggactcgctgccaagctttgggagcctcaccc
agtagtcgacgctcgcaacgcaagctccaagcctactatctgggacggtgcagtcgagggccatgttctt
gttaagaacaccaacaacgcactgccattcaagcccaacatgaaactcgtttctttgttcggatactctc
acaaagctcctgataagaacatcccagaccccgcccaaggcatgttctccgcttggtctatcggtgccca
atccgccaacatcactgagctgaacctcggctttctcggaaatttgagtctcacatactccgccatcgcg
cccaacggaaccatcatctcgggtggaggctcgggtgccagcgcttggactctgttcagctcacccttcg
atgcattcgtttctcgggcgaagaaagagggtactgcgcttttctgggattttgagagctgggatcctta
tgtgaaccctacatctgaagcttgcatcgttgctggtaatgcatgggctagcgaaggctgggatagacct
gcaacctatgatgcctatactgatgagctcatcaataacgtcgctgacaagtgcgctaacactattgttg
ttcttcacaatgctggaacacgacttgtggatggcttctttggtcaccccaacgtcaccgctattatcta
cgctcatctcccaggtcaggatagtggagatgctctggtatctttgctctatggcgatgagaacccatct
ggtcgcctcccttacaccgttgcccgcaacgagacggattatggtcacctgctgaagccagacttgactc
tcgcccccaaccagtaccaacactttccccagtccgacttctccgagggtattttcattgactaccgaca
tttcgatgctaagaacatcacgcctcgcttcgagtttggtttcggcttgagctacacaacctttgagtac
gctagtctccagatctcaaagtcccaggcccagacaccggaatacccagctggtgctcttaccgagggag
gccgttcagatttgtgggacgtcgttgctactgtcacagcaagcgtcaggaacactgggtctgtcgacgg
caaggaggttgcacagctatacgttggtgttccaggtggtcctatgagacagctacgtggctttacgaaa
ccagctattaaggctggagagacggctacagtgacctttgagcttactcgccgcgacttgagtgtctggg
atgttaatgcgcaggagtggcaacttcagcaaggcaactatgctatctacgttggccgaagtagtcgaga
tttgcctctgcaaagtaccttgagcatctag

*FIG. 75A*

SEQ ID NO:96
Protein sequence of Fv3G, a GH3 family β-glucosidase from *Fusarium verticillioides*

<u>mfpssisclaalslmsqqllaq</u>sqpenvitddtyfygqsppvypthtgswaaavakaknlvsqltleekv
nlttggqtttgcsgfipgiprvgfpglcladagngvrntdyvssfpsgihvgaswnpeltysrsyymgae
akakgvnillgpvfgplgrvveggrnwegfsndpylagklgheavagiqdagvvacgkhflaqeqethrl
aasvtgadaissnlddktlhelylcvmcsynrannshacqnskllngllkgelqfqgfvvsdwgaqqsgm
asalagldvvmp*ssilwganltlgvnngtipesqvdnmvtrllatwyqlnqdqdteapghglaaklweph
pvvdarnasskptiwdgaveghv*lvkntnnalpfkpnmklvslfgyshkapdknipdpaqgmfsawsiga
qsanitelnlgflgnlsltysaiapngtiisgggsgasawtlfsspfdafvsrakkegtalfwdfeswdp
yvnptseacivagnawasegwdrpatydaytdelinnvadkcantivvlhnagtrlvdgffghpnvtaii
yahlpgqdsgdalvsllygdenpsgrlpytvarnetdyghllkpdltlapnqyqhfpqsdfsegifidy r
hfdaknitprfefgfglsyttfeyaslqisksqaqtpeypagalteggrsdlwdvvatvtasvrntgsvd
gkevaqlyvgvpgqpmrqlrgftkpaikaqetatvtfeltrrdlsvwdvnaqewqlqqgnyaiyvgrssr
dlplqstlsi

*FIG. 75B*

SEQ ID NO:97
Nucleotide sequence of Fv3D, a GH3 family β-glucosidase from *Fusarium verticillioides*

```
atggctagcattcgatctgtgttggtctcgggtcttttggccgcgggtgtcaatgccaagcctacgatg
cgagtgatcgcgctgaagatgctttcagctgggtccagcccaagaacaccactattcttggacagtacgg
ccattcgcctcattaccctgccagtatgttcaccaactacaccaagtgacactgaggctgtactgacatt
ctagacaatgctactggcaagggctgggaagatgccttcgccaaggctcaaaactttgtctcccaactaa
ccctcgaggaaaaggccgacatggtcacaggaactccaggtccttgcgtcggcaacatcgtcgccattcc
ccgtctcaacttcaacggtctctgtcttcacgacggcccctcgccatccgagtagcagactacgccagt
gttttccccgctggtgtatcagccgcttcatcgtgggacaaggacctcctctaccagcgcggtctcgcca
tgggtcaagagttcaaggccaagggtgctcacatcctcctcggccccgtcgccggtcctcttggccgctc
ggcatactctggtcgtaactggggagggtttctcgccggaccccttacctcactggtattgcgatggaggag
actatcatgggacatcaagatgctggtgttcaggctactgcgaagcactttatcggtaatgagcaggagg
tcatgcgaaaccctacttttgtcaaggatgggtatattggtgaggttgacaaggaggctctttcgtctaa
catggatgatcgaaccatgcacgagctttacctctggcccttgccaatgctgttcatgccaaggcttcc
agcatgatgtgctcgtaccagcgtctcaacggctcctacgcctgccagaactcaaaggtcctcaacggaa
ttctgcgtgatgagcttggtttccagggctacgtcatgtcagattggggtgccacccacgccggtgttgc
tgccatcaacagcggtctcgacatggacatgcccggtggtatcggtgcctacggaacatactttaccaag
tccttcttcggcggcaacctcacccgcgccgtcaccaacggcaccctcgacgagacccgcgtcaacgaca
tgatcaccgcatcatgactccctacttctggctcggccaggacaaggactatcctccgtcgacccctc
cagcggtgatctcaacaccttcagccccaagagctcctggttccgcgagttcaacctcaccggcgagcgc
agccgtgacgtccgcggtaaccacggcgacttgatccgcaagcacggcgccgagtctaccgtccttctca
agaacgagaagaacgcccttcccctcaagaagcccaagtccatcgctgtctttggcaacgatgctggtga
tatcactgagggtttctacaaccagaatgactacgaatttggcactcttgttgctggtggtggctctgga
actggtcgtttgacataccttgtttcgcctctagccgccatcaatgctcgtgctaagcaggacggtactc
ttgttcagcagtggatgaacaacactcttattgctaccaccaacgtcactgatctctggatccctgctac
tcccgatgtctgcctcgttttcttgaagacttgggctgaggaggctgctgatcgtgagcacctctccgtt
gactgggacggtaatgatgttgttgagtctgttgccaagtactgcaataacactgtcgtcgtcactcact
cttctggtatcaacactcttccttgggctgaccaccccaacgtcaccgctattctcgctgcccacttccc
cggtcaggagtctggcaactccctcgttgacctcctctacggcgatgtcaaccctctggtcgtcttccc
tacaccatcgccttcaacggcaccgactacaacgctcccccaccactgccgtcaacaccaccggcaagg
aggactggcagtcttggttcgacgagaagctcgagattgactaccgctacttcgacgcgcacaacatctc
cgtccgctacgaattcggcttcggtctctcctactccaccttcgaaatctccgacatctccgctgagcca
ctcgcatccgacattacctccagccgaggatctcccgtgcagccggcggcaaccccgcctctggg
agaccgtctacaacgtgaccgtctccgtctcaacacgggcaaggtcgacggcgccactgtccccagct
atacgtgacattccccgacagcgcgcctgccggtacaccacccaagcagctccgtgggttcgacaaggtc
ttccttgaggctggcgagagcaagagtgtcagctttgagctgatgcgccgtgatctgagctactgggata
tcatttctcagaagtggctcatccctgagggagagtttactattcgtgttggattcagcagtcgggactt
gaaggaggagacaaaggttactgttgttgaggcgtaa
```

*FIG. 76A*

SEQ ID NO:98

**Protein sequence of Fv3D, a GH3 family β-glucosidase from *Fusarium verticillioides*** masirsvlvsqllaaqvnaqaydasdraedafswvqpknttilgqyghsphypannatgkgwedafaka
qnfvsqltleekadmvtgtpgpcvgnivaiprlnfnglclhdgplairvadyasvfpagvsaasswdkd
llyqrglamgqefkakgahillgpvagplgrsaysgrnwegfspdpyltgiameetimghqdagvqata
khfigneqevmrnptfvkdgyigevdkealssnmddrtmhelylwpfanavhakassmmcsyqrlngsy
acqnskvlngilrdelgfqgyvmsdwgathagvaainsgldmdmp *ggigaygtyftksffggnltravt*
*ngtldetrvndmitrimtpyfwlgqdkdypsvdpssgdlntfspksswfrefnltgersrdvrgnhgdl*
*irkhgaes*tvllkneknalplkkpksiavfgndagditegfynqndyefgtlvagggsgtgrltylvsp
laainarakqdgtlvqqwmnntliattnvtdlwipatpdvclvflktwaeeaadrehlsvdwdgndvve
svakycnntvvvthssgintlpwadhpnvtailaahfpgqesgnslvdllygdvnpsgrlpytiafngt
dynappttavnttgkedwqswfdekleidyryfdahnisvryefgfglsystfeisdisaeplasdits
qpedlpvqpggnpalwetvynvtvsvsntgkvdgatvpqlyvtfpdsapagtppkqlrgfdkvfleage
sksvsfelmrrdlsywdiisqkwlipegeftirvgfssrdlkeetkvtvvea

FIG. 76B

SEQ ID NO:99
**Nucleotide sequence of Fv3C, a GH3 family β-glucosidase from *Fusarium verticillioides***

```
atgaagctgaattgggtcgccgcagccctgtctataggtgctgctggcactgacagcgcagttgctcttg
cttctgcagttccagacactttggctggtgtaaaggtcagttttttttcaccattcctcgtctaatctc
agccttgttgccatatcgccttgttcgctcggacgccacgcaccagatcgcgatcatttcctcccttgc
agccttggttcctcttacgatcttcctccgcaattatcagcgcccttagtctacacaaaaaccccgag
acagtctttcattgagtttgtcgacatcaagttgcttctcaactgtgcatttgcgtggctgtctacttct
gcctctagacaaccaaatctgggcgcaattgaccgctcaaaccttgttcaaataaccttttttattcgag
acgcacatttataaatatgcgcctttcaataataccgactttatgcgcggcggctgctgtggcggttgat
cagaaagctgacgctcaaaaggttgtcacgagagatacactcgcatactcgccgcctcattatccttcac
catggatggacctaatgctgttggctgggaggaagcttacgccaaagccaagagctttgtgtcccaact
cactctcatggaaaaggtcaacttgaccactggtgttgggtaagcagctccttgcaaacagggtatctca
atcccctcagctaacaacttctcagatggcaaggcgaacgctgtgtaggaaacgtgggatcaattcctcg
tctcggtatgcgaggtctctgtctccaggatggtcctcttggaattcgtctgtccgactacaacagcgct
tttccgctggcaccacagctggtgcttcttggagcaagtctctctggtatgagagaggtctcctgatgg
gcactgagttcaaggagaagggtatcgatatcgctcttggtcctgctactggacctcttggtcgcactgc
tgctggtggacgaaactgggaaggcttcaccgttgatccttatatggctggccacgccatggccgaggcc
gtcaagggtattcaagacgcaggtgtcattgcttgtgctaagcattacatcgcaaacgagcagggtaagc
cacttggacgatttgaggaattgacagagaactgaccctcttgtagagcacttccgacagagtggcgagg
tccagtcccgcaagtacaacatctccgagtctctctcctccaacctggatgacaagactatgcacgagct
ctacgcctggcccttcgctgacgccgtccgcgccggcgtcggttccgtcatgtgctcgtacaaccagatc
aacaactcgtacggttgccagaactccaagctcctcaacggtatcctcaaggacgagatgggcttccagg
gtttcgtcatgagcgattgggcggcccagcataccggtgccgcttctgccgtcgctggtctcgatatgag
catgcctggtgacactgccttcgacagcggatacagcttctggggcggaaacttgactctggctgtcatc
aacggaactgttcccgcctggcgagttgatgacatggctctgcgaatcatgtctgccttcttcaaggttg
gaaagacgatagaggatcttcccgacatcaacttctcctcctggacccgcgacaccttcggcttcgtgca
tacatttgctcaagagaaccgcgagcaggtcaactttggagtcaacgtccagcacgaccacaagagccac
atccgtgaggccgctgccaagggaagcgtcgtgctcaagaacaccgggtcccttcccctcaagaacccaa
agttcctcgctgtcattggtgaggacgccggtcccaaccctgctggacccaatggttgtggtgaccgtgg
ttgcgataatggtaccctggctatggcttggggctcgggaacttccaattcccttacttgatcaccccc
gatcaagggctctctaatcgagctactcaagacggaactcgatatgagagcatcttgaccaacaacgaat
gggcttcagtacaagctcttgtcagccagcctaacgtgaccgctatcgttttcgccaatgccgactctgg
tgagggatacattgaagtcgacggaaactttggtgatcgcaagaacctcaccctctggcagcagggagac
gagctcatcaagaacgtgtcgtccatatgccccaacaccattgtagttctgcacaccgtcggccctgtcc
tactcgccgactacgagaagaacccaacatcactgccatcgtctgggctggtcttccggccaagagtc
aggcaatgccatcgctgatctcctctacggcaaggtcagccctggccgatctccttcacttggggccgc
accgcgagagctacggtactgaggttctttatgaggcgaacaacggccgtggccgctcctcaggatgact
tctctgagggtgtcttcatcgactaccgtcacttcgaccgacgatctccaagcaccgatggaaagagctc
tcccaacaacaccgctgctcctctctacgagttcggtcacggtctatcttggtccacctttgagtactct
gacctcaacatccagaagaacgtcgagaaccctactctcctcccgctggccagaccatcccgcccaa
cctttggcaacttcagcaagaacctcaacgactacgtgttcccaagggcgtccgatacatctacaagtt
catctacccctttcctcaacacctcctcatccgccagcgaggcatccaacgatggtggccagtttggtaag
actgccgaagagttcctccctcccaacgccctcaacggctcagccagcctcgtcttccgcctctggtg
cccaggtggtaaccctcaattgtgggacatcttgtacaccgtcacagccacaatcaccaacacaggcaa
cgccacctccgacgagattcccagctgtatgtcagcctcggtggcgagaacgagcccatccgtgttctc
cgcggtttcgaccgtatcgagaacattgctcccggccagagcgccatcttcaacgctcaattgaccgtc
gcgatctgagtaactgggatacaaatgcccagaactgggtcatcactgaccatcccaagactgtctgggt
tggaagcagctctcgcaagctgcctctcagcgccaagttggagtaagaaagccaaacaagggttgttttt
tggactgcaattttttgggaggacatagtagccgcgcgccagttacgtc
```

*FIG. 77A*

SEQ ID NO:100
Protein sequence of Fv3C, a GH3 family β-glucosidase from *Fusarium verticillioides*

<u>mklnwvaaalsigaaqtds</u>avalasavpdtlagvkkadaqkvvtrdtlayspphypspwmdpnavgweea
yakaksfvsqltlmekvnlttgvgwqgercvgnv**gsiprlgmrglclqdgplgirlsdynsafpagttag
aswskslwyergllmgtefkekgidialgpatgplgrtaaggrnwegftvdpymaghamaeavkgiqdag
viacakhyianeqehfrqsgevqsrkynisesIssnlddktmhelyawpfadavragvgsvmcsynqinn
sygcqnsklIngilkdemgfqgfvmsdwaaqhtgaasavagldmsmp** *gdtafdsgysfwggnltlaving
tvpawrvddmalrimsaffkvgktiedlpdinfsswtrdtfgfvhtfaqenreqvnfgvnvqhdhkshir
eaaakgsvvlkntgslplknpkflavigedagpnpagpngcgdrgcdngtlamawgsgtsqfpylitpdq
glsnratqdgtryesiltnnewasvqalvsqpnvtaivfanadsgegyievdgnfgdrknltlwqqgdel
iknvssicpntivvlhtvgpvlladyeknpnitaivwaglpgqesgnaiadllygkvspgrspftwgrtr
esygtevlyeanngrgapqddfsegvfidy*rhfdrrspstdgksspnnt

SEQ ID NO:101
Nucleotide sequence of Tr3A, a GH3 family β-glucosidase from *Trichoderma reesei*

```
atgcgttaccgaacagcagctgcgctggcacttgccactgggcctttgctagggcagacagtcagtata
gctggtcccatactgggatgtgatatgtatcctggagacaccatgctgactcttgaatcaaggtagctca
acatcggggggcctcggctgaggcagttgtacctcctgcagggactccatggggaaccgcgtacgacaagg
cgaaggccgcattggcaaagctcaatctccaagataaggtcggcatcgtgagcggtgtcggctggaacgg
cggtccttgcgttggaaacacatctccggcctccaagatcagctatccatcgctatgccttcaagacgga
cccctcggtgttcgatactcgacaggcagcacagcctttacgccgggcgttcaagcggcctcgacgtggg
atgtcaatttgatccgcgaacgtggacagttcatcggtgaggaggtgaaggcctcggggattcatgtcat
acttggtcctgtggctgggccgctgggaaagactccgcagggcggtcgcaactgggagggcttcggtgtc
gatccatatctcacgggcattgccatgggtcaaaccatcaacggcatccagtcggtaggcgtgcaggcga
cagcgaagcactatatcctcaacgagcaggagctcaatcgagaaaccatttcgagcaacccagatgaccg
aactctccatgagctgtatacttggccatttgccgacgcggttcaggccaatgtcgcttctgtcatgtgc
tcgtacaacaaggtcaataccacctgggcctgcgaggatcagtacacgctgcagactgtgctgaaagacc
agctgggggttcccaggctatgtcatgacggactggaacgcacagcacacgactgtccaaagcgcgaattc
tgggcttgacatgtcaatgcctggcacagacttcaacggtaacaatcggctctggggtccagctctcacc
aatgcggtaaatagcaatcaggtccccacgagcagagtcgacgatatggtgactcgtatcctcgccgcat
ggtacttgacaggccaggaccaggcaggctatccgtcgttcaacatcagcagaaatgttcaaggaaacca
caagaccaatgtcagggcaattgccagggacggcatcgttctgctcaagaatgacgccaacatcctgccg
ctcaagaagcccgctagcattgccgtcgttggatctgccgcaatcattggtaaccacgccagaaactcgc
cctcgtgcaacgacaaaggctgcgacgacggggccttgggcatgggttggggttccggcgccgtcaacta
tccgtacttcgtcgcgccctacgatgccatcaataccagagcgtcttcgcagggcacccaggttaccttg
agcaacaccgacaacacgtcctcaggcgcatctgcagcaagaggaaaggacgtcgccatcgtcttcatca
ccgccgactcgggtgaaggctacatcaccgtggagggcaacgcgggcgatcgcaacaacctggatccgtg
gcacaacggcaatgccctggtccaggcggtggccggtgccaacagcaacgtcattgttgttgtccactcc
gttggcgccatcattctggagcagattcttgctcttccgcaggtcaaggccgttgtctgggcgggtcttc
cttctcaggagagcggcaatgcgctcgtcgacgtgctgtggggagatgtcagcccttctggcaagctggt
gtacaccattgcgaagagccccaatgactataacactcgcatcgtttccggcggcagtgacagcttcagc
gagggactgttcatcgactataagcacttcgacgacgccaatatcacgccgcggtacgagttcggctatg
gactgtgtaagtttgctaacctgaacaatctattagacaggttgactgacggatgactgtggaatgatag
cttacaccaagttcaactactcacgcctctccgtcttgtcgaccgccaagtctggtcctgcgactggggc
cgttgtgccgggaggccgagtgatctgttccagaatgtcgcgacagtcaccgttgacatcgcaaactct
ggccaagtgactggtgccgaggtagcccagctgtacatcacctacccatcttcagcacccaggacccctc
cgaagcagctgcgaggctttgccaagctgaacctcacgcctggtcagagcggaacagcaacgttcaacat
ccgacgacgagatctcagctactgggacacggcttcgcagaaatggtggtgccgtcggggtcgtttggc
atcagcgtgggagcgagcagccgggatatcaggctgacgagcactctgtcggtagcgtag
```

*FIG. 78A*

SEQ ID NO:102
Protein sequence of Tr3A, a GH3 family β-glucosidase from *Trichoderma reesei*

MRYRTAAALALATGPFARADSHSTSGASAEAVVPPAGTPWGTAYDKAKAALAKLNLQDKVGIVSGVGWNG
GPCVGNTSPASKISYPSLCLQDGPLGVRYSTGSTAFTPGVQAASTWDVNLIRERGQFIGEEVKASGIHVI
LGPVAGPLGKTPQGGRNWEGFGVDPYLTGIAMGQTINGIQSVGVQATAKHYILNEQELNRETISSNPDDR
TLHELYTWPFADAVQANVASVMCSYNKVNTTWACEDQYTLQTVLKDQLGFPGYVMTDWNAQHTTVQSANS
GLDMSMP *GTDFNGNNRLWGPALTNAVNSNQVPTSRVDDMVTRILAAWYLTGQDQAGYPSFNISRNVQGNH
KTNVRAIARDG* IVLLKNDANILPLKKPASIAVVGSAAIIGNHARNSPSCNDKGCDDGALGMGWGSGAVNY
PYFVAPYDAINTRASSQGTQVTLSNTDNTSSGASAARGKDVAIVFITADSGEGYITVEGNAGDRNNLDPW
HNGNALVQAVAGANSNVIVVVHSVGAIILEQILALPQVKAVVWAGLPSQESGNALVDVLWGDVSPSGKLV
YTIAKSPNDYNTRIVSGGSDSFSEGLFIDYKHFDDANITPRYEFGYGLSYT KFNYSRLSVLSTAKSGPAT
GAVVPGGPSDLFQNVATVTVDIANSGQVTGAEVAQLYITYPSSAPRTPPKQLRGFAKLNLTPGQSGTATF
NIRRRDLSYWDTASQKWVVPSGSFGISVGASSRDIRLTSTLSVA

FIG. 78B

SEQ ID NO:103
Nucleotide sequence of Tr3B, a GH3 family β-glucosidase from *Trichoderma reesei*

```
atgaagacgttgtcagtgtttgctgccgccttttggcggccgtagctgaggccaatccctacccgcctc
ctcactccaaccaggcgtactcgcctcctttctaccottcgccatggatggaccccagtgctccaggctg
ggagcaagcctatgcccaagctaaggagttcgtctcgggcttgactctcttggagaaggtcaacctcacc
acgggtgttggctggatgggtgagaagtgcgttggaaacgttggtaccgtgcctcgcttgggcatgcgaa
gtctttgcatgcaggacggccccctgggtctccgattcaacacgtacaacagcgctttcagcgttggctt
gacggccgccgccagctggagccgacacctttggttgaccgcggtaccgctctgggctccgaggcaaag
ggcaagggtgtcgatgttcttctcggacccgtggctggcctctcggtcgcaaccccaacggaggccgta
acgtcgagggtttcggctcggatccctatctggcgggtttggctctggccgataccgtgacggaatcca
gaacgcgggcaccatcgcctgtgccaagcacttcctcctcaacgagcaggagcatttccgccaggtcggc
gaagctaacggttacggatacccatcaccgaggctctgtcttccaacgttgatgacaagacgattcacg
aggtgtacggctggcccttccaggatgctgtcaaggctggtgtcgggtccttcatgtgctcgtacaacca
ggtcaacaactcgtacgcttgccaaaactccaagctcatcaacggcttgctcaaggaggagtacggtttc
caaggctttgtcatgagcgactggcaggccagcacacgggtgtcgcgtctgctgttgccggtctcgata
tgaccatgcctggtgacaccgccttcaacaccggcgcatcctactttggaagcaacctgacgcttgctgt
tctcaacggcaccgtccccgagtggcgcattgacgacatggtgatgcgtatcatggctcccttcttcaag
gtgggcaagacggttgacagcctcattgacaccaactttgattcttggaccaatggcgagtacggctacg
ttcaggccgccgtcaatgagaactgggagaaggtcaactacggcgtcgatgtccgcgccaaccatgcgaa
ccacatccgcgaggttggcgccaagggaactgtcatcttcaagaacaacggcatcctgcccttaagaag
cccaagttcctgaccgtcattggtgaggatgctggcggcaaccctgccggccccaacggctgcggtgacc
gcggctgtgacgacggcactcttgccatggagtggggatctggtactaccaacttccctacctcgtcac
ccccgacgcggccctgcagagccaggctctccaggacggcacccgctacgagagcatcctgtccaactac
gccatctcgcagacccaggcgctcgtcagccagcccgatgccattgccattgtctttgccaactcggata
gcggcgagggctacatcaacgtcgatggcaacgagggcgaccgcaagaacctgacgctgtggaagaacgg
cgacgatctgatcaagactgttgctgctgtcaaccccaagacgattgtcgtcatccactcgaccggcccc
gtgattctcaaggactacgccaaccaccccaacatctctgccattctgtgggccggtgctcctggccagg
agtctggcaactcgctggtcgacattctgtacggcaagcagagcccgggccgcactccttcacctgggg
cccgtcgctggagagctacggagttagtgttatgaccacgccaacaacggcaacggcgctccccaggat
aacttcaacgagggcgccttcatcgactaccgctactttgacaaggtggctcccggcaagcctcgcagct
cggacaaggctcccacgtacgagtttggcttcggactgtcgtggtcgacgttcaagttctccaacctcca
catccagaagaacaatgtcggccccatgagcccgcccaacggcaagacgattgcggctccctctctgggc
agcttcagcaagaaccttaaggactatggcttccccaagaacgttcgccgcatcaaggagtttatctacc
cctacctgagccaccactacctctggcaaggaggcgtcgggtgacgctcactacggccagactgcgaagga
gttcctccccgccggtgccctggacggcagccctcagcctcgctctgcggcctctggcgaaccggcggc
aaccgccagctgtacgacattctctacaccgtgacggccaccattaccaacacgggctcggtcatggacg
acgccgttcccagctgtacctgagccacggcggtcccaacgagccgcccaaggtgctgcgtggcttcga
ccgcatcgagcgcattgctcccggccagagcgtcacgttcaaggcagacctgacgcgccgtgacctgtcc
aactgggacacgaagaagcagcagtgggtcattaccgactaccccaagactgtgtacgtgggcagctcct
cgcgcgacctgccgctgagcgcccgcctgccatga
```

*FIG. 79A*

SEQ ID NO:104
Protein sequence of Tr3B, a GH3 family β-glucosidase from *Trichoderma reesei* mktlsvfaaallaavaeanpyppphsnqaysppfypspwmdpsapgweqayaqakefvsgltllekvnl
ttgvgwmgekcvgnvgtvprlgmrslcmqdgplglrfntynsafsvgltaaaswsrhlwvdrgtalgse
akgkgvdvllgpvagplgrnpnggrnvegfgsdpylaglaladtvtgiqnagtiacakhfllneqehfr
qvgeangygypitealssnvddktihevygwpfqdavkagvgsfmcsynqvnnsyacqnsklingllke
eygfqgfvmsdwqaqhtgvasavagldmtmp*gdtafntgasyfgsnltlavlngtvpewriddmvmrim
apffkvgktvdslidtnfdswtngeygyvqaavnenwekvnygvdvranhanhirevgakg*tvifknng
ilplkkpkfltvigedaggnpagpngcgdrgcddgtlamewgsgttnfpylvtpdaalqsqalqdgtry
esilsnyaisqtqalvsqpdaiaivfansdsgegyinvdgnegdrknltlwkngddliktvaavnpkti
vvihstgpvilkdyanhpnisailwagapgqesgnslvdilygkqspgrtpftwgpslesygvsvmttp
nngngapqdnfnegafidyryfdkvapgkprssdkaptyefgfglswstfkfsnlhiqknnvgpmsppn
gktiaapslgsfsknlkdygfpknvrrikefiypylstttsgkeasgdahygqtakeflpagaldgspq
prsaasgepggnrqlydilytvtatitntgsvmddavpqlylshggpneppkvlrgfdrieriapgqsv
tfkadltrrdlsnwdtkkqqwvitdypktvyvgsssrdlplsarlp

FIG. 79B

SEQ ID NO:105
Nucleotide sequence of Te3A, a GH3 family β-glucosidase from *Talaromyces emersonii*, codon-optimized for expression in *T.reesei*

```
atgcgcaacggcctcctcaaggtcgccgccttagccgctgccagcgccgtcaacggcgagaacctcgcct
acagccccccttctaccccagccctgggccaacggccagggcgactgggccgaggcctaccagaaggc
cgtccagttcgtcagccagctcaccctcgccgagaaggtcaacctcaccaccggcaccggctgggagcag
gaccgctgcgtcggccaggtcggcagcatccccgcttaggcttccccggcctctgcatgcaggacagcc
cctcggcgtccgcgacaccgactacaacagcgccttccctgccggcgttaacgtcgccgccacctggga
ccgcaacttagcctaccgcagaggcgtcgccatgggcgaggaacaccgcggcaagggcgtcgacgtccag
ttaggccccgtcgccggcccttaggccgctctcctgatgccggccgcaactgggagggcttcgccccg
accccgtcctcaccggcaacatgatggccagcaccatccagggcatccaggatgctggcgtcattgcctg
cgccaagcacttcatcctctacgagcaggaacacttccgccagggcgcccaggacggctacgacatcagc
gacagcatcagcgccaacgccgacgacaagaccatgcacgagttatacctctggcccttcgccgatgccg
tccgcgccggtgtcggcagcgtcatgtgcagctacaaccaggtcaacaacagctacgcctgcagcaacag
ctacaccatgaacaagctcctcaagagcgagttaggcttccagggcttcgtcatgaccgactggggcggc
caccacagcggcgtcggctctgccctcgccggcctcgacatgagcatgcccggcgacattgccttcgaca
gcggcacgtctttctggggcaccaacctcaccgttgccgtcctcaacggctccatcccgagtggcgcgt
cgacgacatggccgtccgcatcatgagcgcctactacaaggtcggccgcgaccgctacagcgtccccatc
aacttcgacagctggaccctcgacacctacggccccgagcactacgccgtcggccagggccagaccaaga
tcaacgagcacgtcgacgtccgcggcaaccacgccgagatcatccacgagatcggcgccgcctccgccgt
cctcctcaagaacaagggcggcctcccctcactggcaccgagcgcttcgtcggtgtctttggcaaggat
gctggcagcaacccctggggcgtcaacggctgcagcgaccgcggctgcgacaacggcaccctcgccatgg
gctggggcagcggcaccgccaactttccctacctcgtcaccccgagcaggccatccagcgcgaggtcct
cagccgcaacggcaccttcaccggcatcaccgacaacggcgccttagccgagatggccgctgccgcctct
caggccgacacctgcctcgtctttgccaacgccgactccggcgagggctacatcaccgtcgatggcaacg
agggcgaccgcaagaacctcaccctctggcagggcgccgaccaggtcatccacaacgtcagcgccaactg
caacaacaccgtcgtcgtcttacacaccgtcggccccgtcctcatcgacgactggtacgaccacccaac
gtcaccgccatcctctgggccggtttaccggtcaggaaagcggcaacagcctcgtcgacgtcctctacg
gccgcgtcaacccggcaagacccccttcacctggggcagagcccgcgacgactatggcgcccctctcat
cgtcaagcctaacaacggcaagggcgccccccagcaggacttcaccgagggcatcttcatcgactaccgc
cgcttcgacaagtacaacatcaccccatctacgagttcggcttcggcctcagctacaccaccttcgagt
tcagccagttaaacgtccagcccatcaacgcccctccctacaccccgccagcggctttacgaaggccgc
ccagagcttcggccagccctccaatgccagcgacaacctctaccctagcgacatcgagcgcgtccccctc
tacatctacccctggctcaacagcaccgacctcaaggccagcgccaacgacccgactacggcctcccca
ccgagaagtacgtccccccaacgccaccaacggcgaccccagccattgaccctgccggcggtgcccc
tggcggcaaccccagcctctacgagcccgtcgccgcgtcaccaccatcatcaacaccggcaaggtc
accggcgacgaggtccccagctctatgtcagcttaggcggccctgacgacgcccccaaggtcctccgcg
gcttcgaccgcatcaccctcgccctggccagcagtacctctggaccaccaccctcactcgccgcgacat
cagcaactgggacccgtcacccagaactgggtcgtcaccaactacaccaagaccatctacgtcggcaac
agcagccgcaacctccccctccaggccccctcaagccctaccccggcatctgatga
```

*FIG. 80A*

SEQ ID NO:106
Protein sequence of Te3A, a GH3 family β-glucosidase from *Talaromyces emersonii*

<u>mrnqllkvaalaaasavnq</u>enlaysppfypspwangqgdwaeayqkavqfvsqltlaekvnlttgtqweq
drcvgqvgsiprlgfpglcmqdsplgvrdtdynsafpagvnvaatwdrnlayrrgvamgeehrgkgvdvq
lgpvagplgrspdagrnwegfapdpvltgnmmastiqgiqdagviacakhfilyeqehfrqgaqdgydis
dsisanaddktmhelylwpfadavragvgsvmcsynqvnnsyacsnsytmnkllkselgfqgfvmtdwgg
hhsgvgsalagldmsmp*gdiafdsgtsfwgtnltvavlngsipewrvddmavrimsayykvgrdrysvpi
nfdswtldtygpehyavgqgqtkinehvdvrgnhaeiiheigaas*avllknkgglpltgterfvgvfgkd
agsnpwgvngcsdrgcdngtlamgwgsgtanfpylvtpeqaiqrevlsrngtftgitdngalaemaaaas
qadtclvfanadsgegyitvdgnegdrknltlwqgadqvihnvsancnntvvvlhtvgpvliddwydhpn
vtailwaglpgqesgnslvdvlygrvnpgktpftwgrarddygaplivkpnngkgapqqdftegifidy r
rfdkynitpiyefgfglsyttfefsqlnvqpinappytpasgftkaaqsfgqpsnasdnlypsdiervpl
yiypwlnstdlkasandpdyglptekyvppnatngdpqpidpaggapggnpslyepvarvttiitntgkv
tgdevpqlyvslggpddapkvlrgfdritlapgqqylwttltrrdisnwdpvtqnwvvtnytktiyvgn
ssrnlplqaplkpypgi

*FIG. 80B*

SEQ ID NO:107
Nucleotide sequence of An3A, a GH3 family β-glucosidase from *Aspergillus niger* atgcgcttcaccagcatcgaggccgtcgccctcaccgccgtcagcctcgccagcgccgacgagttagcct
acagccccctactaccccagccctggggccaacggccagggcgactgggccgaggcctaccagcgcgc
cgtcgacatcgtcagccagatgaccctcgccgagaaggtcaacctcaccaccggcaccggctgggagtta
gagttatgcgtcggccagactggtggcgtccccgcctcggcatcccggcatgtgcgccaggacagcc
cctcggcgtccgcgacagcgactacaacagcgccttcctgccggcgtcaacgtcgccgccacctggga
caagaacctcgcctacctccgcggccaggccatgggccaggaattcagcgacaagggcgccgacatccag
ttaggccccgctgccggcccttaggccgctctcccgacggcggcagaaactgggagggcttcagcccg
accccgctctcagcggcgtcctcttcgccgagactatcaagggcatccaggatgctggcgtcgtcgccac
cgccaagcactacattgcctacgagcaggaacacttccgccaggccccgaggcccagggctacggcttc
aacatcaccgagagcggcagcgccaacctcgacgacaagaccatgcacgagttatacctctggcccttcg
ccgacgccattagagctggcgctggtgctgtcatgtgcagctacaaccagatcaacaacagctacggctg
ccagaacagctacaccctcaacaagctcctcaaggccgagttaggcttccagggcttcgtcatgtccgac
tgggccgccaccacgccggcgtcagcggcgccttagccggcctcgacatgagcatgccggcgacgtcg
actacgacagcggcaccagctactgggcaccaacctcaccatcagcgtcctcaacggcaccgtccccca
gtggcgcgtcgacgacatggccgtccgcatcatggccgcctactacaaggtcggccgcgaccgcctctgg
accccccccaacttcagcagctggaccccgcgacgagtacggcttcaagtactactacgtcagcgagggcc
cctatgagaaggtcaaccagttcgtcaacgtccagcgcaaccacagcgagttaatccgccgcatcggcgc
cgacagcaccgtcctcctcaagaacgacggcgccctccccctcaccggcaaggaacgcctcgtcgcctc
atcggcgaggacgccggcagcaacccctacggcgccaacggctgcagcgaccgcggctgcgacaacggca
cctcgccatgggctggggcagcggcaccgccaacttccttacctcgtcaccccgagcaggccatcag
caacgaggtcctcaagaacaagaacggcgtctttaccgccaccgacaactgggccatcgaccagatcgag
gccttagccaagaccgcctctgtcagcctcgtctttgtcaacgccgacagcggcgagggctacatcaacg
tcgacggcaacctcggcgaccgccgcaacctcaccctctggcgcaacggcgacaacgtcatcaaggccgc
cgccagcaactgcaacaacaccatcgtcatcatccacagcgtcggccccgtcctcgtcaacgagtggtac
gacaaccccaacgtcaccgccatcctctggggcggcttaccggccaggaaagcggcaacagcctcgccg
acgtcctctacggccgcgtcaaccctggcgccaagagccccttcacctggggcaagacccgcgaggccta
tcaggactacctctacaccgagccaacaacggcaacggcgcccccaggaagatttcgtcgagggcgtc
tttatcgactaccgcggctttgacaagcgcaacgagactcccatctacgagttcggctacggcctcagct
acaccaccttcaactacagcaacctccaggtcgaggtcctcagcgcccctgcctacgagcccgccagcgg
cgagactgaggccgccccaccttcggcgaggtcggcaacgccagcgactacttataccccgacggcctc
cagcgcatcaccaagttcatctaccctggctcaacagcaccgacctcgaggccagcagcggcgacgcct
cttacggccaggacgcctccgactacctccccgagggtgccaccgacggcagcgctcagccatcttacc
tgccggtggcggtgctggcggcaaccccagactctacgacgagctgatccgcgtcagcgtcaccatcaag
aacaccggcaaggtcgctggtgacgaggtccccagctctacgcagcttaggcggccctaacgagcca
agatcgtcctccgccagttcgagcgcatcaccctccagcccagcaaggaaactcagtggagcaccacct
cactcgccgcgacctcgccaactggaacgtcgagactcaggactgggagatcaccagctaccccaagatg
gtctttgccggcagcagcagccgcaagctccccctccgcgccagcctcccaccgtccactgatga

*FIG. 81A*

SEQ ID NO:108
Protein sequence of An3A, a GH3 family β-glucosidase from *Aspergillus niger*

<u>mrftsieavaltavslasa</u>delaysppyypspwangqgdwaeayqravdivsqmtlaekvnlttgtgwel
elcvgqtggvprlgipgmcaqdsplgvrdsdynsafpagvnvaatwdknlaylrgqamgqefsdkgadiq
lgpaagplgrspdggrnwegfspdpalsgvlfaetikgiqdagvvatakhyiayeqehfrqapeaqgygf
nitesgsanlddktmhelylwpfadairagagavmcsynqinnsygcqnsytlnkllkaelgfqgfvmsd
waahhagvsgalagldmsmp*gdvdydsgtsywgtnltisvlngtvpqwrvddmavrimaayykvgrdrlw*
*tppnfsswtrdeygfkyyyvseqpyekvnqfvnvqrnhselirrigads*tvllkndgalpltgkerlval
igedagsnpygangcsdrgcdngtlamgwgsgtanfpylvtpeqaisnevlknkngvftatdnwaidqie
alaktasvslvfvnadsgegyinvdgnlgdrrnltlwrngdnvikaaasncnntiviihsvgpvlvnewy
dnpnvtailwgglpgqesgnsladvlygrvnpgakspftwgktreayqdylytepnngngapqedfvegv
fi*dy*rgfdkrnetpiyefgyglsyttfnysnlqvevlsapayepasgeteaaptfgevgnasdylypdgl
qritkfiypwlnstdleassgdasygqdasdylpegatdgsaqpilpagggaggnprlydelirvsvtik
ntgkvagdevpqlyvslggpnepkivlrqferitlqpsketqwstttltrrdlanwnvetqdweitsypkm
vfagsssrklplraslptvh

*FIG. 81B*

SEQ ID NO:109
Nucleotide sequence of Fo3A, a GH3 family β-glucosidase from *Fusarium oxysporum* atgaagctgaactgggtcgccgcagccctctctataggtgctgctggcactgatggtgcagttgctcttg
cttctgaagttccaggcactttggctggtgtaaaggtcggttttttttaccatttcctcacctaatctcag
ccttgttgccatatcgcccttattcgctcggacgctacgcaccaaatcgcgatcatttcctcccttgcag
ccttgttttcttttttcgatcttccctccgcaatcgccagcaccctagcctacacaaaaacccccgaga
cagtctcattgagtttgtcgacatcaagttgcttctcaagtgtgcatttgcgtggctgtctacttctgcc
tctagaccaccaaatctgggcgcaattgatcgctcaaaccttgttcgaataagccttttattcgagacgt
ccaattttacagagaatgtaccttcaataataccgacgttatgcgcggcggtggctgctgtgatggtt
gttgatcagaatactgacgctcaaaaggttgtcacgagagatacactcgcacactcacctcctcactatc
cttcaccatggatggatcctaatgccattggctgggaggaagcttacgccaaagcaaagaactttgtgtc
ccagctcactctcctcgaaaaggtcaacttgaccactggtgttgggtaagtagctccttgcgaacagtgc
atctcggtctccttgactaacgactctctcaggtggcaaggcgaacgctgtaggaaacgtgggatcaa
ttcctcgtcttggtatgcgaggtctttgtcttcaggatggtcctcttggaattcgtctgtccgattacaa
cagtgcttttccgctggcaccacagctggtgcttcttggagcaagtctctctggtatgagaggggtctt
ctgatgggaactgagttcaaggggaagggtatcgatatcgctcttggccctgctactggtcctcttgcc
gcactgctgctggtggacgaaactgggagggcttaccgttgatcctatatggctggccatgccatggc
cgaggccgtcaagggcatccaagacgcagtgtcattgcttgtgctaagcattacatcgcaaacgagcaa
ggtaagccaattggacggtttgggaaatcgacagagaactgaccccccttgtagagcacttccgacagagt
ggcgaggtccagtcccgcaagtacaacatctccgagtctctcctccaacctggacgacaagactttgc
acgagctctacgctggccctttgctgatgccgtccgcgctggcgtcggttcagtcatgtgctcttacaa
tcagatcaacaactcgtacggttgccagaactccaagctcctcaacggtatcctcaaggacgagatggct
ttccagggcttcgtcatgagcgattgggcggcccagcacaccggtgctgcttctgccgtcgctggtcttg
atatgagcatgcctggtgacaccgcgttcgacagtggatatagcttctggggtggaaacctgactcttgc
tgtcatcaacggaactgttccgcctggcgagttgatgacatggctctgcgaatcatgtcggccttcttc
aaggttggaaagacggtagaggacctccccgacatcaacttctcctcctggaccgcgacaccttcggct
tcgtccaaacatttgctcaagagaaccgcgaacaagtcaactttggagttaacgtccagcacgaccacaa
gaaccacatccgtgagtctgccgccaagggaagcgtcatcctcaagaacaccggctcccttccctcaac
aatcccaagttcctcgctgtcattggtgaggacgccggtcccaaccctgctggacccaatggttgcggcg
accgtggttgcgacaatggtaccctggctatggcttggggctcgggaacttctcaattcccttacttgat
cacaccgaccaaggtctccagaaccgagctgccaagacggaactcgatatgagagcatcttgaccaac
aacgaatgggcccagacacaggctcttgtcagccaacccaacgtgaccgctatcgttttgccaacgccg
actctggtgagggttacattgaagtcgacggaaacttcggtgatcgcaagaacctcaccctctggcaaca
gggagacgagctcatcaagaacgtctcgtccatctgcccaacaccattgtcgttctgcataccgtcggc
cctgtcctgctcgccgactacgagaagaacccaacatcaccgccatcgtctgggctggtcttcccggcc
aagagtctggcaatgccatcgctgatctcctctacggcaaggtaagcctggccgatctcccttcacttg
gggccgcaccgtgagagctacggtaccgaggttctttatgaggcgaacaacggccgtggcgctcctcag
gatgacttctcggagggtgtcttcattgactaccgtcactttgatcgacatctccagcacgatggca
agagcgctccaacaacaccgctgtcctctctacgagttcggtcatggtctgtcttggactaccttga
gtattcagacctcaacatccagaagaacgttaactccacctactctcctcctgctggtcagaccattcct
gccccaacctttggcaacttcagcaagaacctcaacgactacgtgttccctaagggtgtccgatacatct
acaagttcatctaccccttcctgaacacttcctcatccgccagcgaggcatctaacgacggcggccagtt
tggtaagactgccgaagagttcctacctccaaacgccctcaacggctcagccagcctcgtcttccctct
tctggtgcccaggcggtaaccctcaattgtgggatatcctgtacaccgtcacagccacaatcaccaaca
caggcaacgccacctccgacgagattccccagctgtatgtcagcctcggtggcgagaacgaacccgttcg
tgtcctccgcggtttcgaccgtatcgagaacattgctcccggccagagcgccatcttcaacgctcaattg
acccgtcgcgatctgagcaactgggatgtggatgcccagaactggttatcaccgaccatccaaagacgg
tgtgggttggaagtagttctcgcaagctgcctctcagcgccaagttggaataa

*FIG. 82A*

SEQ ID NO:110
Protein sequence of Fo3A, a GH3 family β-glucosidase from *Fusarium oxysporum* mklnwvaaalsiqaagtdqavalasevpgtlagvkntdaqkvvtrdtlahspphypspwmdpnaigweea
yakaknfvsqltllekvnlttgvgwqgercvgnvgsiprlgmrglclqdgplgirlsdynsafpagttag
aswskslwyergllmgtefkgkgidialgpatgplgrtaaggrnwegftvdpymaghamaeavkgiqdag
viacakhyianeqehfrqsgevqsrkyniseslssnlddktlhelyawpfadavragvgsvmcsynqinn
sygcqnsktlngilkdemgfqgfvmsdwaaqhtgaasavagldmsmp *gdtafdsgysfwggnltlaving
tvpawrvddmalrimsaffkvgktvedlpdinfsswtrdtfgfvqtfaqenreqvnfgvnvqhdhknhir
esaakgsvilkntgslplnnpkflavigedagpnpagpngcgdrgcdngtlamawgsgtsqfpylitpdq
glqnraaqdgtryesiltnnewaqtqalvsqpnvtaivfanadsgegyievdgnfgdrknltlwqqgdel
iknvssicpntivvlhtvgpvlladyeknpnitaivwaglpgqesgnaiadllygkvspgrspftwgrtr
esygtevlyeanngrgapqddfsegvfidy* rhfdrrspstdgksapnntaaplyefghglswttfeysdl
niqknvnstysppagqtipaptfgnfsknlndyvfpkgvryiykfiypflntsssaseasndggqfgkta
eeflppnalngsaqprlpssgapggnpqlwdilytvtatitntgnatsdeipqlyvslggenepvrvlrg
fdrieniapgqsaifnaqltrrdlsnwdvdaqnwvitdhpktvwvgsssrklplsakle

*FIG. 82B*

SEQ ID NO:111

**Nucleotide sequence of Gz3A, a GH3 family β-glucosidase from *Gibberella zeae***

```
ATGAAGGCCAATTGGCTTGCCGCGGCCGTTTATTTGGCTGCTGGCACCGATGCTGCAGTCCCTGACACTT
TGGCAGGAGTCAATGTAAGCTACTCTTCAATTTCATCTCATCTCAACTTTGCCAGGCCACAACAACTTTT
CTTCACTCACGATCTTTTCACCATAAACGCAACAGTTTCACAAAAAATAAAGCCCAAATCATGTCTCTGA
TCGTTGAACTCGCCATCTTCGTTTACATCGCGGTTGTCTTTTTCTTCTTGTACTTCTCATTCGTTGTTGT
TCTCTACATTTTCGACTGGCTGTTTAGCCTTGAGATTCTTCTCACTCCCCGTGATGCCTAGATCACTCTC
TGAGGCGTTTAATCTACTTGTAGAGATGCGCCTCTCATTTGTTGTGTCGCTAGTCGCGATAGTTGCTGGA
ATTGCAGTCCTTGATCTTCCTACTGACACTCAAAAGCTCGTTGCGCGGGACACACTCGCTCACTCTCCTC
CTCACTATCCCTCGCCATGGATGGACCCTAACGCTGTCGGCTGGGAGGACGCCTACGCCAAGGCCAAGGA
CTTTGTCTCCCAGATGACTCTCCTAGAAAAGGTCAACTTGACCACTGGTGTTGGGTAAGTAACGAGCGAC
AAGACGTCTACAATCCACTAACACGATCTCTAGATGGCAGGGCGAACGTTGTGTTGGAAACGTGGGATCT
ATCCCTCGTCTCGGTATGCGAGGCCTCTGTCTCCAGGATGGTCCTCTCGGAATTCGCTTCTCCGACTACA
ACAGCGCTTTCCCTACTGGTGTCACCGCTGGTGCTTCTTGGAGTAAGGCCCTTTGGTACGAGCGAGGACG
ATTGATGGGTACCGAGTTTAAGGAGAAGGGTATCGATATTGCTCTCGGCCCTGCAACTGGTCCTCTCGGT
CGCCACGCTGCTGGTGGACGAAACTGGGAAGGCTTCACTGTCGACCCCTACGCCGCTGGCCATGCTATGG
CTGAGACTGTCAAGGGTATCCAAGATTCTGGAGTCATTGCTTGTGCTAAGCATTACATCGCAAACGAGCA
AGGTATGTACAGGCCCATTCAATGGCTTCAGGAACGAAAACTAACTCTTAATAGAACACTTCCGTCAACG
AGGCGATGTCATGTCTCAAAAGTTCAACATTTCCGAGTCTCTGTCTTCCAACCTTGACGATAAGACTATG
CACGAGCTCTACAACTGGCCTTTCGCCGACGCCGTCCGCGCCGGTGTTGGCTCCATTATGTGCTCTTACA
ACCAGGTCAACAACTCATATGCTTGCCAGAACTCCAAGCTCCTCAACGGCATCCTCAAGGACGAGATGGG
TTTCCAGGGTTTCGTCATGAGCGATTGGCAGGCTCAGCACACCGGTGCCGCCTCCGCTGTTGCCGGTCTT
GACATGACCATGCCTGGTGACACCGAGTTCAACACTGGCTTCAGCTTCTGGGGTGGAAACCTGACCCTCG
CTGTTATCAACGGTACTGTTCCGCCTGGAGAATCGACGACATGGCTACCCGAATTATGGCTGCTTTCTT
CAAGGTTGGCCGATCTGTTGAGGAGGAACCCGACATCAACTTCTCAGCTTGGACTCGTGATGAGTATGGC
TTCGTCCAGACCTACGCCCAAGAGAACCGAGAAAAGGTCAACTTTGCTGTTAATGTCCAGCACGACCACA
AGCGCCACATTCGCGAGGCTGGCGCAAAGGGATCCGTCGTCCTCAAGAACACTGGCTCACTTCCTCTTAA
GAAGCCCCAGTTCCTCGCTGTCATTGGAGAGGACGCTGGTTCCAACCCTGCCGGACCCAACGGTTGCGCT
GACCGTGGATGCGACAACGGTACTCTTGCCATGGCATGGGGTTCCGGAACCTCTCAATTCCCCTACCTTG
TCACCCCCGACCAAGGCATCTCGCTCCAGGCTATTCAGGACGGTACTCGTTATGAGAGCATCCTCAACAA
CAACCAGTGGCCCCAGACACAAGCTCTTGTCAGCCAGCCCAACGTCACCGCCATTGTCTTTGCCAATGCC
GATTCTGGTGAGGGCTACATCGAGTTGACGGCAACTACGGCGACCGCAAGAACCTCACTCTGTGGAAGC
AAGGCGATGAGCTCATCAAGAACGTCTCTGCTATCTGCCCCAACACCATTGTGGTCCTTCACACCGTTGG
CCCCGTCCTTCTAACCGAGTGGCACAACAACCCCAACATCACCGCCATTGTTTGGGCTGGTGTGCCTGGA
CAGGAGTCCGGTAACGCCATCGCCGACATCCTCTACGGCAAGACCAGCCCTGGACGTTCTCCCTTCACCT
GGGGTCGCACTTATGACAGCTATGGCACCAAGGTTCTCTACAAGGCCAACAATGGAGAGGGTGCCCCTCA
AGAGGACTTTGTCGAGGGCAACTTCATCGACTACCGCCACTTTGACCGACAATCCCCCAGCACCAACGGA
AAGAGTGCCACCAACGACTCTTCTGCTCCTCTCTACGAGTTCGGTTTCGGTCTGTCCTGGACTACCTTTG
AGTACTCTGATCTCAAAGTCGAGTCTGTCAGCAACGCCTCTTACAGCCCCTCTGTCGGAAACACCATTCC
TGCCCCTACCTACGGCAACTTCAGCAAGAACCTGGACGATTACACATTCCCCTCAGGTGTCCGATACCTC
TACAAGTTCATCTACCCCTACCTCAACACCTCTTCCTCCGCTGAGAAGGCTTCCGGCGATGTCAAGGGCA
GATTGGTGAGACCGGCGACGAGTTCCTCCCTCCCAACGCTCTCAACGGTTCATCGCAGCCTCGTCTTCC
TTCCAGTGGTGCTCCCGGCGGTAACCCTCAGCTCTGGGACATTATGTACACCGTCACTGCCACCATCACC
AACACTGGTGACGCTACCTCGGATGAGGTTCCCCAGCTGTACGTCAGCCTCGGTGGTGAGGGCGAGCCTG
TCCGTGTCCTCCGTGGCTTCGAGCGTCTTGAAAACATTGCTCCTGGTGAGAGTGCCACATTCACCGCTCA
GCTTACTCGCCGTGACCTGAGCAACTGGGACGTCAACGTCCAGAACTGGGTCATCACCGATCACGCCAAG
AAGATCTGGGTCGGCAGCAGCTCTCGCAATCTGCCCCTCAGCGCCGACCTGTAG
```

*FIG. 83A*

SEQ ID NO:112
Protein sequence of Gz3A, a GH3 family β-glucosidase from *Gibberella zeae* mkanwlaaavylaagtdaavpdtlagvnlvardtlahspphypspwmdpnavgwedayakakdfvsqmtl
lekvnlttgvgwqgercvgnvgsiprlgmrglclqdgplgirfsdynsafptgvtagaswskalwyergr
lmgtefkekgidialgpatgplgrhaaggrnwegftvdpyaaghamaetvkgiqdsgviacakhyianeq
ehfrqrgdvmsqkfniseslssnlddktmhelynwpfadavragvgsimcsynqvnnsyacqnskllngi
lkdemgfqgfvmsdwqaqhtgaasavagldmtmp*gdtefntgfsfwggnltlavingtvpawriddmatr
imaaffkvgrsveeepdinfsawtrdeygfvqtyaqenrekvnfavnvqhdhkrhireagakgs*vvlknt
gslplkkpqflavigedagsnpagpngcadrgcdngtlamawgsgtsqfpylvtpdqgislqaiqdgtry
esilnnnqwpqtqalvsqpnvtaivfanadsgegyievdgnygdrknltlwkqgdeliknvsaicpntiv
vlhtvgpvlltewhnnpnitaivwagvpgqesgnaiadilygktspgrspftwgrtydsygtkvlykann
gegapqedfvegnfidy*rhfdrqspstngksatndssaplyefgfglswttfeysdlkvesvsnasysps
vgntipaptygnfsknlddytfpsgvrylykfiypylntsssaekasgdvkgrfgetgdeflppnalngs
sqprlpssgapggnpqlwdimytvtatitntgdatsdevpqlyvslggegepvrvlrgferleniapges
atftaqltrrdlsnwdvnvqnwvitdhakkiwvgsssrnlplsadl

FIG. 83B

SEQ ID NO:113
Nucleotide sequence of Nh3A, a GH3 family β-glucosidase from *Nectria haematococca* atgcggttcaccgtccttctcgcggcattttcggggcttgtcccatggttggttcgcaagctgaccaga
aaccactacagctcggtgtgaacaataacactctggcgcattcacctcctcactatccttcgccatggat
ggatcctgctgctcctggctgggaggaagcctatctcaaggcgaaagattttgtttcacagcttacccctt
cttgaaaaggtcaacttgaccactggtgttgggtgagtcacttgttttcctctctcctgacgtgacactt
tgctttggcctgcttcctatatcgtctactagcattgctaacactcgaggcagatggatgggcgaacgtt
gcgtcggcaacgtgggttcactccctcgttttggaatgcgtggtctctgcatgcaggatggcccctcgg
catccgcttgtctgactataactctgccttttcctactggtattacagctggtgcctcttggagccgtgcc
ctttggtaccaacgtggcctcctgatgggcaccgagcatcgtgaaaaaggcatcgacgttgcacttgggc
ctgctactggtcctcttggtcgtactcctactggcggccgcaactgggagggtttctcggttgatccta
cgttgctggcgttgccatggccgagactgttagcggcattcaagatggtggtactatcgcctgtgctaag
cactacatcggcaacgaacaaggtatgcctcttcacttctcctcgctgataaatctgctcacaacaacct
agagcaccatcgccaagcccccgaatccattggccgcggctacaacatcaccgagtccctgtcgtcgaac
gttgatgacaagaccctccacgagctctatctctggccgttcgcagatgccgtcaaggctggtgttggtg
ctatcatgtgttcctaccagcagctgaacaactcttacggttgccaaaactctaagcttctcaacggaat
tctcaaggacgagctaggattccagggcttcgtcatgagtgactggcaagcccaacatgctggagctgct
accgctgttgcaggccttgacatgaccatgcccggtgacactttgttcaacaccggatacagcttctggg
gtggtaacctgaccctcgctgtagtcaatggcactgttcccgactggcgtattgacgacatggctatgag
aatcatggcagctttcttcaaggttggcaagactgttgaggaccttcctgacatcaacttttcttcttgg
tctcgagacacttttggctacgttcaagccgctgcccaagagaactgggaacagatcaacttcggagttg
atgttcgtcacgaccacagcgaacacattcgactctcggccgccaagggcaccgtcctccttaagaactc
tggctcattgcctctgaagaagcccaagttccttgccgtcgttggcgaggacgccggcccgaaccctgct
ggccccaacggctgtaacgaccgcggatgtaacaacggcactctggccatgtcctggggctcaggaacag
cccagttcccttacctcgttactcccgactcagcgctacagaaccaggctgtcctcgacggcactcgcta
cgagagtgtcttgcggaacaaccagtgggaacagacacgcagtctcattagccaacctaacgtgacggct
attgtgtttgccaatgccaattccggagagggatatatcgatgttgacggcaacgaaggcgatcggaaga
atttgaccttgtggaacgagggtgatgacctaattaagaacgtctcctcaatctgccccaacaccattgt
tgttctgcacactgttggccctgtcatcctgacggaatggtatgacaacccgaacattaccgccatagtg
tgggctggtgtacctggacaggagtccggcaatgctcttgtggacatcctttatggcaaaacaagccctg
gtcgctctcccttcacatggggtcgcacccgaaagagttacggcactgatgtcctatacgagcccaacaa
tggtcagggtgctcctcaagatgatttcacggagggagtctttatcgactatcgtcattttgaccaggtt
tctcctagcaccgacggcagcaagtctaatgatgagtccagtccatctacgagtttggccatggtctgt
cctggaccacgtttgagtactctgaactcaacattcaagctcacaacaagattcccttcgatcctcctat
tggcgagacgattgccgctccggtccttggcaactacagtaccgaccttgccgattacacgttccccgat
ggaattcgctacatctaccagttcatctatccctggttgaatacttcttcttccggaagagaggcttctg
gcgatcccgactacggaaagacggccgaagagttcctgcccccggagctctcgacgggtcagctcagcc
gcgacctccatcctctggtgctccaggtggaaaccctcatctttgggatgtgttgtacactgttagtgct
atcatcaccaacactggcaacgccacctcggacgagatcccgcagctctacgttagtctcggtggcgaga
acgagcccgtccgcgtccttcgcgggttcgaccgaattgagaacattgcgcctggccagagtgtcagatt
cacaactgacatcactcgccgcgacctgagcaactgggacgtcgtctctcagaactgggtcattacagac
tacgagaagaccgtatatgtcgggagcagctcccgcaacctgcctctcaaggcaaccctgaagtaa

*FIG. 84A*

SEQ ID NO:114
Protein sequence of Nh3A, a GH3 family β-glucosidase from *Nectria haematococca*

<u>mrftvllaafsqlvpmvqs</u>qadqkplqlgvnnntlahspphypspwmdpaapgweeaylkakdfvsqltl
lekvnlttgvgwmgercvgnv<u>gslprfgmrglcmqdgplgirlsdynsafptgitagaswsralwyqrgl
lmgtehrekgidvalgpatgplgrtptggrnwegfsvdpyvagvamaetvsgiqdggtiacakhyigneq
ehhrqapesigrgyniteslssnvddktlhelylwpfadavkagvgaimcsyqqlnnsygcqnskllngi
lkdelgfqgfvmsdw</u>qaqhagaatavagldmtmpgdtlfntgysfwggnltlavvngtvpdwriddmamr
imaaffkvgktvedlpdinfsswsrdtfgyvqaaaqenweqinfgvdvrhdhsehirlsaakg<u>tvllkns
gslplkkpkflavvgedagpnpagpngcndrgcnngtlamswgsgtaqfpylvtpdsalqnqavldgtry
esvlrnnqweqtrslisqpnvtaivfanansgegyidvdgnegdrknltlwnegddliknvssicpntiv
vlhtvgpviltewydnpnitaivwagvpgqesgnalvdilygktspgrspftwgrtrksygtdvlyepnn
gqgapqddftegvfidy</u>rhfdqvspstdgsksndesspiyefghglswttfeyselniqahnkipfdppi
getiaapvlgnystdladytfpdgiryiyqfiypwlntsssgreasgdpdygktaeeflppgaldgsaqp
rppssgapggnphlwdvlytvsaiitntgnatsdeipqlyvslggenepvrvlrgfdrieniapgqsvrf
ttditrrdlsnwdvvsqnwvitdyektvyvgsssrnlplk

*FIG. 84B*

SEQ ID NO:115

**Nucleotide sequence of Vd3A, a GH3 family β-glucosidase from *Verticillium dahliae***

ATGAAGCTGACCCTCGCTACTGCCTTACTGGCAGCCAGCGGGTGTGTCTCTGCGGGACAACCCAAGCTCA
AGGTACGTACTTGCCTCTTTTTCACAAGGAAACCAAACCCGCACCATAATGGTGATTGAGCAGTCGTGCT
TTCCTCAACCCGAATCAAACCCATGCCGTGTTCGCGCATGCCCTTTCGATCGTCTGTTGTGTGTGAACCC
ACGCTCTTCAAGCATCGCACATAGCACCACTCCATCTTCATTTTCGAGCAATTTCGGGCCGCAGAGAGCG
GTCTTTCACTTCACCACAATCGTTCATGCCTCGTGCCCCACTGCCATGTTTCTTCCCAGTATTCTACTTC
TGAGAGCCTTGACCACCGTTGTCGACATCTCGTCGCCAAGGCTCGTTGACACGGACTCTGTTTCCCTTGG
AATTAATATTCGAAACAATGCTGACCAGCATCCTCAGCGCCAGACTAACAGCTCTAGCGAGCTCGCCTTT
TCCCCTCCGCACTACCCTTCTCCATGGATGAACCCCCAAGCGACTGGGTGGGAGGACGCCTACGCCCGTG
CCAGAGAGGTGGTAGAGCAGATGACTCTGCTCGAAAAGGTCAACCTGACGACAGGTGTCGGGTAAGCTTC
ACAGACCCCGTCTTGCCATCCAAAGTCATCTGACAGAATCCTAGCTGGAGCGGTGATCTCTGCGTCGGAA
ACGTCGGCTCGATCCCCCGAATCGGCTGGAGGGGGCTTTGTTTGCAGGATGGCCCACAGGGTATCCGTTT
CGCGGACTACGTCTCGTACTTCACTTCGAGCCAGACAGCCGGCGCTACCTGGGACCGAGGGCTTCTGTAC
CAGCGCGCTCACGCCATTGGCGCCGAAGGAGTAGCCAAGGGCGTCGACGTCGTCCTCGGGCCCGCCATTG
GCCCTCTAGGTCGCCTTCCCGCCGGAGGTCGTAACTGGGAGGGTTTCGCCGTGGACCCTTACCTCAGTGG
CGTTGCTGTCGCCGAATCCGTCAGGGGCATCCAGGATGCTGGTGCTATTGCCAACGTCAAGCACTACATC
GTCAATGAGCAGGAACATTTCCGCCAGGCTGGCGAGGCTCAAGGTTACGGCTACGATGTCGACGAGGCAT
TATCGTCGAACGTTGACGACAAGACCATGCATGAGCTTTACCTTTGGCCATTTGCAGACGCTGTCCGTGC
TGGAGCCGGCAGTGTCATGTGTTCTTATCAACAGGTGGGGGCAATACCATTCTCTCCTCTTTCCTTGCAG
ACAGTGCACTGACCGACCTTTTTTGCCCAAGATCAACAACAGTTACGGCTGTCAAAACTCACATCTTCTG
AATGGGCTCCTCAAGGACGAACTCGGCTTTCAGGGGTTCGTCCTCAGCGATTGGCAAGCGCAGCATGCTG
GTGCTGCCACTGCCGTTGCTGGACTTGACATGGCCATGCCCGGTGACACTCGCTTCAACACCGGAGTCGC
CTTCTGGGGCGCTAACCTTACCAATGCCATTTTGAACGGCACCGTTCCCGAATATCGGCTCGATGACATG
GCCATGCGTATTATGGCGGCCTTTTTCAAAGTTGGAAAGACCCTGGACGATGTTCCTGACATCAACTTCT
CGTCTTGGACAAAAGACACCATCGGCCCGCTGCACTGGGCGGCCCAGGACAATGTGCAGGTCATCAACCA
ACACGTTGATGTCCGTCAAGACCACGGCGCCCTCATTCGCACCATCGCTGCCCGCGGTACTGTCTTACTA
AAAAATGAGGGATCACTGCCTCTGAACAAGCCGAAATTTGTTGCTGTCATTGGTGAAGATGCTGGCCCTC
GTCCTGTTGGTCCCAATGGCTGCCCTGATCAGGGTTGCAATAACGGCACTCTGGCTGCTGGATGGGGATC
TGGCACCGCCAGTTTCCCTTATCTCATCACTCCTGATAGTGCTCTTCAGTTTCAAGCCGTTTCGGATGGC
TCGCGATACGAAAGCATCCTCAGCAACTGGGATTATGAGCGCACAGAGGCCTTGGTTTCCCAGGCGGATG
CTACTGCTCTGGTTTTCGTCAATGCAAACTCTGGCGAAGGATATATCAGCGTTGATGGAAACGAAGGTGA
TCGCAAGAACCTCACTCTCTGGAATGGAGGAGACGAGCTTATTCAACGAGTCGCTGCGGCCAACAACAAC
ACCATCGTCATCATCCATTCGGTTGGTCCCGTTCTAGTCACTGACTGGTACGAGAATCCCAATATCACGG
CTATCATCTGGGCCGGCTTACCCGGACAGGAGTCTGGCAACTCTATCGCCGATATTCTTTACGGCCGCGT
GAACCCTGGTGGCAAGACACCTTTCACCTGGGGTCCAACTGTTGAGAGCTACGGCGTTGACGTCCTGAGA
GAGCCCAACAATGGCAATGGTGCTCCCCAGAGCGATTTCGACGAGGGAGTCTTCATCGATTACCGTTGGT
TTGACCGGCAGTCGGGTGTTGATAACAATGCATCAGCGCCGAGGAACAGCAGCAGCAGCCACGCCCCAAT
CTTCGAGTTTGGCTATGGCCTTTCGTACACAACCTTTGAATTCTCCAATCTTCAGATTGAGAGGCATGAC
GTTCACGATTACGTCCCTACCACTGGGCAGACGAGCCCTGCGCCGAGATTTGGTGCTAACTACAGTACGA
ACTACGACGACTACGTCTTTCCCGAGGGCGAAATCCGTTACATCTATCAACACATCTACCCATACCTCAA
TTCCTCAGACCCAAAGGAGGCATTGGCTGATCCTAAATACGGCCAAACTGCAGAAGAGTTCCTCCCAGAG
GGCGCTCTTGATGCCTCACCGCAGCCTAGGCTCCCAGCTTCTGGAGGGCCCGGAGGCAACCCAATGCTTT
GGGACGTCATATTCACGGTCACCGCGACCGTGACCAACACGGGTAAGGTTGCTGGGGACGAAGTGGCACA
GCTTTACGTTTCTCTTGGTGGACCTGACGATCCGATTCGAGTCCTCCGTGGGTTCGACCGCATTCACATC
GCGCCTGGAGCCTCGCAAACCTTCCGTGCGGAACTCACGCGCCGGGACCTCAGCAACTGGGATGTTGTCA
CGCAAAATTGGTTCATCAGCCAGTACGAAAAGACGGTCTTTGTCGGGAGCTCATCCCGAAACCTCCCTCT
CAGCACTCGCCTCGAATAG

*FIG. 85A*

SEQ ID NO:116
**Protein sequence of Vd3A, a GH3 family β-glucosidase from *Verticillium dahliae*** mkltlatallaasqcvsagqpklkhpqrqtnssselafspphypspwmnpqatgwedayararevveqmt
llekvnlttgvgwsgdlcvgnvgsiprigwrglclqdgpqgirfadyvsyftssqtagatwdrgllyqra
haigaegvakgvdvvlgpaigplgrlpaggrnwegfavdpylsgvavaesvrgiqdagaianvkhyivne
qehfrqageaqgygydvdealssnvddktmhelylwpfadavragagsvmcsyqqinnsygcqnshllng
llkdelgfqgfvlsdw*qaqhagaatavagldmampgdtrfntgvafwganltnailngtvpeyrlddmam*
*rimaaffkvgktlddvpdinfsswtkdtigplhwaaqdnvqvinqhvdvrqdhgalirtiaarg*tvllkn
egslplnkpkfvavigedagprpvgpngcpdqgcnngtlaagwgsgtasfpylitpdsalqfqavsdgsr
yesilsnwdyertealvsqadatalvfvnansgegyisvdgnegdrknltlwnggdeliqrvaaannnti
viihsvgpvlvtdwyenpnitaiiwaglpgqesgnsiadilygrvnpggktpftwgptvesygvdvlrep
nngngapqsdfdegvfidyrwfdrqsgvdnnasaprnsssshapifefgyglsyttfefsnlqierhdvh
dyvpttgqtspaprfganystnyddyvfpegeiryiyqhiypylnssdpkealadpkygqtaeeflpega
ldaspqprlpasggpggnpmlwdviftvtatvtntgkvagdevaqlyvslggpddpirvlrgfdrihiap
gasqtfraeltrrdlsnwdvvtqnwfisqyektvfvgsssrnlplstrle

*FIG. 85B*

SEQ ID NO:117
Nucleotide sequence of Pa3G, a GH3 family β-glucosidase from *Podospora anserina*

ATGAAACTCAATAAGCCATTCCTGGCCATTTATTTGGCTTTCAACTTGGCCGACGCTTCGAAAACTCCGG
ATTGCATCAGTGGTCCGCTGGCAAAGACCTTGGCATGTGATACAACGGCGTCACCTCCTGCGCGAGCAGC
TGCTCTTGTGCAGGCTTTAAATATCACGGAAAAGCTTGTGAATCTAGTGGAGTATGTCAAGTCAAGAGAA
GCTCCTTTAGGGATTTCAATTCAGCTAATCACTCCTCATAGCATGAGCCTCGGTGCAGAAAGGATCGGCC
TTCCAGCTTATGCTTGGTGGAACGAAGCTCTTCATGGTGTTGCCGCGTCGCCTGGGGTCTCCTTCAATCA
GGCCGGACAAGAATTCTCACACGCTACTTCATTTGCGAATACTATTACGCTAGCAGCCGCCTTTGACAAT
GACCTGGTTTACGAGGTGGCGGATACCATCAGCACTGAAGCGCGAGCGTTCAGCAATGCCGAGCTCGCTG
GACTGGATTACTGGACGCCTAACATCAACCCGTACAAAGATCCGAGATGGGGGAGGGGCCATGAGGTTTG
TTACCTTAGCCTTCTTTTCCGTGCCGTGCAGTTGCTGAGAACTCAAAAGACACCCGGAGAAGATCCGGTA
CACATCAAAGGCTACGTCCAAGCACTTCTCGAGGGTCTAGAAGGGAGAGACAAGATCAGAAAGGTGATTG
CCACTTGTAAACACTTTGCAGCCTATGATTTGGAGAGATGGCAAGGGGCTCTTAGATACAGGTTCAATGC
TGTTGTGACCTCGCAGGATCTTTCGGAGTACTACCTCCAACCGTTTCAACAATGCGCTCGAGACAGCAAG
GTCGGGTCTTTCATGTGCTCATATAATGCGCTCAACGGAACACCGGCATGTGCAAGCACGTATTTGATGG
ACGACATCCTTCGAAAACACTGGAATTGGACCGAGCACAACAACTATATAACGAGCGACTGTAATGCTAT
TCAGGACTTCCTCCCCAACTTTCACAACTTCAGCCAAACTCCAGCTCAAGCCGCCGCTGATGCTTATAAC
GCCGGTACAGACACCGTCTGTGAGGTGCCTGGATACCCCCACTCACAGATGTAATCGGAGCATACAATC
AGTCTCTGCTGTCAGAGGAAATTATCGACCGAGCACTTCGCAGATTATACGAAGGCCTCATCCGAGCTGG
CTATCTCGACTCAGCCTCCCCACATCCATACACCAAAATCTCATGGTCCAAGTAAACACCCCAAAGCC
CAAGCCCTGGCTCTCCAGTCCGCCACCGACGGGATAGTCCTTCTCAAAAACAACGGCCTCCTTCCCCTAG
ACCTCACCAACAAAACCATAGCCCTCATAGGCCACTGGGCCAATGCAACCCGCCAAATGCTAGGCGGCTA
CAGCGGTATCCCCCCTTACTACGCCAACCCAATCTATGCAGCCACCCAGCTCAACGTCACTTTTCATCAC
GCCCCAGGACCGGTGAACCAGTCATCTCCCTCCACAAATGACACCTGGACCTCCCCGCCCTCTCCGCGG
CTTCCAAATCGGATATCATCCTCTACCTCGGCGGCACCGACCTCTCCATCGCAGCCGAAGACCGAGACAG
AGACTCCATCGCCTGGCCATCCGCTCAACTTTCCTTGTTAACCTCCCTCGCCCAGATGGGAAAACCCACA
ATCGTAGCAAGACTAGGCGACCAAGTAGACGACACCCCCTGCTCTCCAACCCAAACATCTCCTCCATCC
TATGGGTAGGCTACCCAGGCCAATCAGGCGGAACAGCCCTCTTGAACATCATCACCGGAGTCAGCTCCCC
CGCCGCTCGACTGCCCGTCACAGTCTACCCAGAAACTTACACCTCCCTCATCCCCCTGACAGCCATGTCC
CTCCGCCCAACCTCCGCCCGCCCAGGCCGGACTTACAGGTGGTACCCCTCCCCCGTGCTCCCCTTCGGCC
ACGGCCTCCACTACACAACCTTTACCGCCAAATTCGGCGTCTTTGAGTCCCTCACCATCAACATTGCCGA
ACTCGTTTCCAACTGTAACGAACGATACCTCGACCTCTGCCGGTTCCCGCAGGTGTCCGTCTGGGTGTCG
AATACGGGAGAACTCAAATCTGACTATGTCGCCCTTGTTTTTGTCAGGGGTGAGTACGGACCGGAGCCGT
ACCCGATCAAGACGCTGGTGGGTACAAGCGGATAAGGGATATCGAGCCGGGGACTACGGGGCGGCGCC
GGTGGGGGTGGTGGTGGGGATTTGGCTAGGGTGGATTTGGGGGGAATAGGGTTTTGTTTCCGGGGAAG
TATGAGTTTCTGCTGGATGTGGAGGGGGGAGGGATAGGGTTGTGATCGAGTTGGTTGGGGAGGAGGTGG
TGTTGGAGAAGTTCCCTCAGCCGCCTGCGGCGGGTTGA

*FIG. 86A*

SEQ ID NO:118
Protein sequence of Pa3G, a GH3 family β-glucosidase from *Podospora anserina*

<u>mklnkpflaiylafnlae</u>asktpdcisgplaktlacdttaspparaaalvqalniteklvnlveyvksre
aplgisiqlitphsmslgaeriglpayawwnealhgvaaspgvsfnqagqefshatsfantitlaaafdn
dlvyevadtistearafsnaelagldywtpninpykdprwgrghevcylsllfravqllrtqktpgedpv
hikgyvqalleglegrdkirkviatckhfaaydlerwqgalryrfnavvtsqdlseyylqpfqqcardsk
vgsfmcsynalngtpacastylmddilrkhwmwtehnnyitsdcnaiqdflpnfhnfsqtpaqaaadayn
agtd*tvcevpgyppltdvigaynqsllseeiidralrrlyegliragyldsasphpytkiswsqvntpka
qalalqsatdgivllknngllpldltnk*tialighwanatrqmlggysgippyyanpiyaatqlnvtfhh
apgpvnqsspstndtwtspalsaasksdiilylggtdlsiaaedrdrdsiawpsaqlslltslaqmgkpt
ivarlgdqvddtpllsnpnissilwvgypgqsggtallniitgvsspaarlpvtvypetytslipltams
lrptsarpgrtyrwypspvlpfghglhyttftakfgvfesltiniaelvsncneryldlcrfpqvsvwvs
ntgelksdyvalvfvrgeygpepypiktlvgykrirdiepgttgaapvgvvvgdlarvdlggnrvlfpgk
yeflldveggrdrvvielvgeevvlekfpqppaag

*FIG. 86B*

SEQ ID NO:119
Protein sequence of Tn3B, a GH3 family β-glucosidase from *Thermotoga neapolitana*

MEKVNEILSQLTLEEKVKLVVGVGLPGLFGNPHSRVAGAAGETHPVPRVGLPAFVLADGPAGLRINPTRE
NDENTYYTTAFPVEIMLASTWNRELLEEVGKAMGEEVREYGVDVLLAPAMNIHRNPLCGRNFEYYSEDPV
LSGEMASSFVKGVQSQGVGACIKHFVANNQETNRMVVDTIVSERALREIYLRGFEIAVKKSKPWSVMSAY
NKLNGKYCSQNEWLLKKVLREEWGFEGFVMSDWYAGDNPVEQLKAGNDLIMPGKAYQVNTERRDEIEEIM
EALKEGKLSEEVLDECVRNILKVLVNAPSFKNYRYSNKPDLEKHAKVAYEAGAEGVVLLRNEEALPLSEN
SKIALFGTGQIETIKGGTGSGDTHPRYAISILEGIKERGLNFDEELAKTYEDYIKKMRETEEYKPRRDSW
GTIIKPKLPENFLSEKEIHKLAKKNDVAVIVISRISGEGYDRKPVKGDFYLSDDETDLIKTVSREFHEQG
KKVIVLLNIGSPVEVVSWRDLVDGILLVWQAGQETGRIVADVLTGRINPSGKLPTTFPRDYSDVPSWTFP
GEPKDNPQKVVYEEDIYVGYRYYDTFGVEPAYEFGYGLSYTTFEYSDLNVSFDGETLRVQYRIENTGGRA
GKEVSQVYIKAPKGKIDKPFQELKAFHKTRLLNPGESEEVVLEIPVRDLASFNGEEWVVEAGEYEVRVGA
SSRNIKLKGTFSVGEERRFKP

*FIG. 87*

Partial amino acid alignment of the CBM1 domains of Eg4 with Tr6A from *T. reesei* (SEQ ID NO:82); and Tr7A from *T. reesei* (SEQ ID NO:83). Partial amino acid alignment was made in Muscle (Edgar R.C. (2004) MUSCLE: a multiple sequence alignment method with reduced time and space complexity. BMC Bioinformatics 5: 113) using default parameters.

```
                        *         20         *
Tr6A-CBM1  :  QACSSVWGQCGGQNWSGPTCCASGSTCVYSNDYYSQCLP  :  63
TrEg4-CBM1 :  -PTQTLYGQCGGSGYSGPTRCAPPATCSTLNPYYAQCLN  : 343
Tr7A-CBM1  :  -PTQSHYGQCGGIGYSGPTVCASGTTCQVLNPYYSQCL-  : 513
```

SEQ ID NO:31
**Protein sequence of Tr6A from *T. reesei***

MIVGILTTLATLATLAASVPLEERQACSSVWGQCGGQNWSGPTCCASGSTCVYSNDYYSQ
CLPGAASSSSSTRAASTTSRVSPTTSRSSSATPPPGSTTTRVPPVGSGTATYSGNPFVGV
TPWANAYYASEVSSLAIPSLTGAMATAAAAVAKVPSFMWLDTLDKTPLMEQTLADIRTAN
KNGGNYAGQFVVYDLPDRDCAALASNGEYSIADGGVAKYKNYIDTIRQIVVEYSDIRTLL
VIEPDSLANLVTNLGTPKCANAQSAYLECINYAVTQLNLPNVAMYLDAGHAGWLGWPANQ
DPAAQLFANVYKNASSPRALRGLATNVANYNGWNITSPPSYTQGNAVYNEKLYIHAIGPL
LANHGWSNAFFITDQGRSGKQPTGQQQWGDWCNVIGTGFGIRPSANTGDSLLDSFVWVKP
GGECDGTSDSSAPRFDSHCALPDALQPAPQAGAWFQAYFVQLLTNANPSFL

SEQ ID NO:32
**Protein sequence of Tr7A from *T. reesei***

MYRKLAVISAFLATARAQSACTLQSETHPPLTWQKCSSGGTCTQQTGSVVIDANWRWTHA
TNSSTNCYDGNTWSSTLCPDNETCAKNCCLDGAAYASTYGVTTSGNSLSIGFVTQSAQKN
VGARLYLMASDTTYQEFTLLGNEFSFDVDVSQLPCGLNGALYFVSMDADGGVSKYPTNTA
GAKYGTGYCDSQCPRDLKFINGQANVEGWEPSSNNANTGIGGHGSCCSEMDIWEANSISE
ALTPHPCTTVGQEICEGDGCGGTYSDNRYGGTCDPDGCDWNPYRLGNTSFYGPGSSFTLD
TTKKLTVVTQFETSGAINRYYVQNGVTFQQPNAELGSYSGNELNDDYCTAEEAEFGGSSF
SDKGGLTQFKKATSGGMVLVMSLWDDYYANMLWLDSTYPTNETSSTPGAVRGSCSTSSGV
PAQVESQSPNAKVTFSNIKFGPIGSTGNPSGGNPPGGNRGTTTTRRPATTTGSSPGPTQS
HYGQCGGIGYSGPTVCASGTTCQVLNPYYSQCL

*FIG. 88*

**Protein sequence of Eg6 from *T. reesei* (SEQ ID NO:33)**

MKVSRVLALVLGAVIPAHAAFSWKNVKLGGGGGFVPGIIFHPKTKGVAYARTDIGGLYRLNADDSWTAVT
DGIADNAGWHNWGIDAVALDPQDDQKVYAAVGMYTNSWDPSNGAIIRSSDRGATWSFTNLPFKVGGNMPG
RGAGERLAVDPANSNIIYFGARSGNGLWKSTDGGVTFSKVSSFTATGTYIPDPSDSNGYNSDKQGLMWVT
FDSTSSTTGGATSRIFVGTADNITASVYVSTNAGSTWSAVPGQPGKYFPHKAKLQPAEKALYLTYSDGTG
PYDGTLGSVWRYDIAGGTWKDITPVSGSDLYFGFGGLGLDLQKPGTLVVASLNSWWPDAQLFRSTDSGTT
WSPIWAWASYPTETYYYSISTPKAPWIKNNFIDVTSESPSDGLIKRLGWMIESLEIDPTDSNHWLYGTGM
TIFGCHDLTNWDTRHNVSIQSLADGIEEFSVQDLASAPGGSELLAAVGDDNGFTFASRNDLGTSPQTVWA
TPTWATSTSVDYAGNSVKSVVRVGNTAGTQVAISSDGGATWSIDYAADTSMNGGTVAYSADGDTILWSTA
SSGVQRSQFQGSFASVSSLPAGAVIASDKKTNSVFYAGSGSTFYVSKDTGSSFTRGPKLGSAGTIRDIAA
HPTTAGTLYVSTDVGIFRSTDSGTTFGQVSTALTNTYQIALGVGSGSNWNLYAFGTGPSGARLYASGDSG
ASWTDIQGSQGFGSIDSTKVAGSGSTAGQVYVGTNGRGVFYAQGTVGGGTGGTSSSTKQSSSSTSSASSS
TTLRSSVVSTTRASTVTSSRTSSAAGPTGSGVAGHYAQCGGIGWTGPTQCVAPYVCQKQNDYYYQCV

*FIG. 89A*

**Protein sequence of *S. coccosporum* endoglucanase (SEQ ID NO:34)**

```
  1   MRSSPFLRAA  LAAALPLSAH  ALDGKSTRYW  DCCKPSCGWP  GKASVNQPVF  SCSADWQRIS
 61   DFNAKSGCDG  GSAYSCADQT  PWAVNDNFSY  GFAATAIAGG  SESSWCCACY  ALTFNSGPVA
121   GKTMVVQSTS  TGGDLGSNQF  DLAIPGGGVG  IFNGCASQFG  GLPGAQYGGI  SDRSQCSSFP
181   APLQPGCQWR  FDWFQNADNP  TFTFQRVQCP  SELTSRTGCK  RDDDASYPVF  NPPSGGSPST
241   TSTTTSSPSG  PTGNPPGGGG  CTAQKWAQCG  GTGFTGCTTC  VSGTTCQVQN  QWYSQCL
```

*FIG. 89B*

**Nucleotide sequence of Ta61A, a GH61A polypeptide from *Thermoascus aurantiacus* (SEQ ID NO:149)**

ATGTCCTTTTCCAAGATAATTGCTACTGCCGGCGTTCTTGCCTCTGCTTCTCTAGTGGCTGGCCATGGCT
TCGTTCAGAACATCGTGATTGATGGTAAAAAGTATGTCATTGCAAGACGCACATAAGCGGCAACAGCTGA
CAATCGACAGTTATGGCGGGTATCTAGTGAACCAGTATCCATACATGTCCAATCCTCCAGAGGTCATCGC
CTGGTCTACTACGGCAACTGATCTTGGATTTGTGGACGGTACTGGATACCAAACCCCAGATATCATCTGC
CATAGGGGCGCCAAGCCTGGAGCCCTGACTGCTCCAGTCTCTCCAGGAGGAACTGTTGAGCTTCAATGGA
CTCCATGGCCTGATTCTCACCATGGCCCAGTTATCAACTACCTTGCTCCGTGCAATGGTGATTGTTCCAC
TGTGGATAAGACCCAATTAGAATTCTTCAAAATTGCCGAGAGCGGTCTCATCAATGATGACAATCCTCCT
GGGATCTGGGCTTCAGACAATCTGATAGCAGCCAACAACAGCTGGACTGTCACCATTCCAACCACAATTG
CACCTGGAAACTATGTTCTGAGGCATGAGATTATTGCTCTTCACTCAGCTCAGAACCAGGATGGTGCCCA
GAACTATCCCCAGTGCATCAATCTGCAGGTCACTGGAGGTGGTTCTGATAACCCTGCTGGAACTCTTGGA
ACGGCACTCTACCACGATACCGATCCTGGAATTCTGATCAACATCTATCAGAAACTTTCCAGCTATATCA
TCCCTGGTCCTCCTCTGTATACTGGTTAA

*FIG. 89C*

Amino acid sequence of Afu7A (SEQ ID NO:150)

MLASTFSYRMYKTALILAALLGSGQAQQVGTSQAEVHPSMTWQSCTACGSCTTNNGKVVIDANWRWVHKV
GDYTNCYTGNTWDTTICPDDATCASNCALEGANYESTYGVTASGNSLRLNFVTTSQQKNIGSRLYMMKDD
STYEMFKLLNQEFTFDVDVSNLPCGLNGALYFVAMDADGGMSKYPTNKAGAKYGTGYCDSQCPRDLKFIN
GQANVEGWQPSSNDANAGTGNHGSCCAEMDIWEANSISTAFTPHPCDTPGQVMCTGDACGGTYSSDRYGG
TCDPDGCDFNSFRQGNKTFYGPGMTVDTKSKFTVVTQFITDDGTSSGTLKEIKRFYVQNGKVIPNSESTW
TGVSGNSITTEYCTAQKSLFQDQNVFEKHGGLEGMGAALAQGMVLVMSLWDDHSANMLWLDSNYPTTASS
TTPGVARGTCDISSGVPADVEANHPDAYVVYSNIKVGPIGSTFNSGGSNPGGGTTTTTTQPTTTTTTAG
NPGGTGVAQHYGQCGGIGWTGPTTCASPYTCQKLNDYYSQCL

*FIG. 90A*

Amino acid sequence of Afu7B (SEQ ID NO:151)

MHQRALLFSALAVAANAQQVGTQTPETHPPLTWQKCTAAGSCSQQSGSVVIDANWRWLHSTKDTTNCYTG
NTWNTELCPDNESCAQNCALDGADYAGTYGVTTSGSELKLSFVTGANVGSRLYLMQDDETYQHFNLLNHE
FTFDVDVSNLPCGLNGALYFVAMDADGGMSKYPSNKAGAKYGTGYCDSQCPRDLKFINGMANVEGWEPSS
SDKNAGVGGHGSCCPEMDIWEANSISTAVTPHPCDDVSQTMCSGDACGGTYSESRYAGTCDPDGCDFNPF
RMGNESFYGPGKIVDTKSKMTVVTQFITADGTDSGALSEIKRLYVQNGKVIANSVSNVAGVSGNSITSDF
CTAQKKAFGDEDIFAKHGGLSGMGKALSEMVLIMSIWDDHHSSMMWLDSTYPTDADPSKPGVARGTCEHG
AGDPENVESQHPDASVTFSNIKFGPIGSTYEG

*FIG. 90B*

Amino acid sequence of Cg7A (SEQ ID NO:152)

MKQYLQYLAAALPLMSLVSAQGVGTSTSETHPKITWKKCSSGGSCSTVNAEVVIDANWRWLHNADSKNCY
DGNEWTDACTSSDDCTSKCVLEGAEYGKTYGASTSGDSLSLKFLTKHEYGTNIGSRFYLMNGASKYQMFT
LMNNEFAFDVDLSTVECGLNSALYFVAMEEDGGMASYSTNKAGAKYGTGYCDAQCARDLKFVGGKANYDG
WTPSSNDANAGVGALGGCCAEIDVWESNAHAFAFTPHACENNNYHVCEDTTCGGTYSEDRFAGDCDANGC
DYNPYRVGNTDFYGKGMTVDTSKKFTVVSQFQENKLTQFFVQNGKKIEIPGPKHEGLPTESSDITPELCS
AMPEVFGDRDRFAEVGGFDALNKALAVPMVLVMSIWDDHYANMLWLDSSYPPEKAGTPGGDRGPCAQDSG
VPSEVESQYPDATVVWSNIRFGPIGSTVQV

*FIG. 90C*

Amino acid sequence of Cg7B (SEQ ID NO:153)

MYRQVATALSFASLVLGQQVGTLTAETHPSLPIEVCTAPGSCTKEDTTVVLDANWRWTHVTDGYTNCYTG
NAWNETACPDGKTCAANCAIDGAEYEKTYGITTPEEGALRLNFVTESNVGSRVYLMAGEDKYRLFNLLNK
EFTMDVDVSNLPCGLNGAVYFSEMDEDGGMSRFEGNKAGAKYGTGYCDSQCPRDIKFINGEANSEGWGGE
DGNSGTGKYGTCCAEMDIWEANLDATAYTPHPCKVTEQTRCEDDTECGAGDARYEGLCDRDGCDFNSFRL
GNKEFYGPEKTVDTSKPFTLVTQFVTADGTDTGALQSIRRFYVQDGTVIPNSETVVEGVDPTNEITDDFC
AQQKTAFGDNNHFKTIGGLPAMGKSLEKMVLVLSIWDDHAVYMNWLDSNYPTDADPTKPGVARGRCDPEA
GVPETVEAAHPDAYVIYSNIKIGALNSTFAAA

*FIG. 90D*

Amino acid sequence of Tt7A (SEQ ID NO:154)
MHAKPATLAALVASAAQQACTLTAENHPTLSWSKCTSGGSCTSVSGSVTIDANWRWTHQVSSSTNCYTCNE
WDTSICTDGASCAAACCLDGADYSGTYGITTSGNALSLQFVTQGPYSTNIGSRTYLMASDTKYQMFTLLGNE
FTFDVDVSGLGCGLNGALYFVSMDEDGGLSKYSGNKAGAKYGTGYCDSQCPRDLKFINGEANNVGWTPSSND
KNAGLGNYGSCCSEMDVWEANSISAAYTPHPCTTIGQTRCEGDDCGGTYSTDRYAGECDPDGCDFNSYPMGN
TTPYGKGMTVDTSKKFTVVTQFLTLSSGNLSEIKRFYVQNGVVIPNSNSNIAGVSGNSITQAFCDAQKTAFG
DTNVFDQKGGLAQSGKALAQPMVLVMSLWDDHAVNMLWLDSTYPTDAAGKPGAARGTCPTTSGVPADVESQA
PNSKVIYSNIRPGPIGSTVSGLFGGGSNPGGGSSSTTTTRPATSTFSSASSGPTGGGTAASWGQCGGIGWT
GPTVCASPYTCQKLNDWYYQCL

*FIG. 90E*

Amino acid sequence of Tt7B (SEQ ID NO:155)
MLSFILALGALAGAAVAQQAGTQTAENHPKMSWQKCSSGGSCTTVQGEVVIDSNWRWVHDKNGYTNCYTGNE
WRTTICSDAKSCAANCALDGADYSGTYGVTTSGNALTLKFVTKGSYSTNIGSRLYMMASSTKYQMFTLLGNE
FTFDVDVSKLGCGLNGALYFVAMDEDGGMSKYSANKAGAKYGTGYCDAQCPRDLKFINGQANSAQWTPSSND
QNAGVGQYGSCCAEMDIWYANSISAAVTPHPCETVEQHQCEGDSCGGTYSGDRYGGDCDPDGCDFNAYRQGV
KDPYGPSMTVDTTEKFTVVTQFIKGSDGELSEIKRFYVQDGKVIENANSTIPNNPGNSITPDFCKAQKVAFG
DRDVFNEKGGFPQFSKAVQTPMVLVMSLWDDHYANMLWLDSTYPVDADPSEPGKARGTCDTSSGVPKDVEAN
QASNQVIYSNIKFGPIGSTFRQS

*FIG. 90F*

Amino acid sequence of St6A (SEQ ID NO:156)
MAKKLFITAALAAAVLAAPVIEERQNCGAVWTQCGGNGWQGPTCCASGSTCVAQNEWYSQCLPNSQVTSSTT
PSSTSTSQRSTSTSSSTTRSGSSSSSSTTPPPVSSPVTSIPGGATSTASYSGNPFSGVRLFANDYYRSEVHN
LAIPSMTGTLAAKASAVAEVPSFQWLDRNVTIDTLMVQTLSQVRALNKAGANPPYAAQLVVYDLPDRDCAAA
ASNGEFSIANGGAANYRSYIDAIRKHIIEYSDIRIILVIEPDSMANMVTNMNVAKCSNAASTYHELTVYALK
QLNLPNVAMYLDAGHAGWLGWPANIQFAAELFAGIYNDAGKPAAVRGLATNVANYNAWSIASAPSYTSPNPN
YDEKHYIEAFSPLLNSAGFPARFIVDTGRNGKQPTGQQQWGDWCNVKGTGFGVRPTANTGHELVDAFVWVKP
GGESDGTSDTSAARYDYHCGLSDALQPAPEAGQWFQAYFEQLLTNANPPF

*FIG. 90G*

Amino acid sequence of St6B (SEQ ID NO:157)
MKFVQSAFLAPAATALAAPSRTTPQKFRQASAGCASAVTLDASTNVFQQYTLHPNMFYRAEVEAAAEAISDS
ALAEKAPKVADVGTPLWLDTTIENIGRLEPALEDVPCENIVGLVIYDLPGRDCAAKASNGELKVGELDRYKTE
YIDKIAEILKAHSNTAFALVIEPDSLPNLVTNSDLQTCQQSASGYRSGVAYALKQLNLPNVVMYIDAGHGGW
LGWDANLKPGAQELASVYKSAGSPSQVRGISTNVAGWNAWDQEPGEFSDASDAQYNKCQNEKIYINTFGAEL
KSAGMPNHAIIDTGRNGVTGLRDEWGDWCNVNGAGFGVRPTANTGDELADAFVWVKPGGESDGTSDSSAARY
DSFCGKPDAFKPSPEAGTWNQAYFEMLLKNANPSF

*FIG. 90H*

Amino acid sequence of Tt6A (SEQ ID NO:158)
MAQKLLLAAALAASALAAPVVEERQNCGSVWSQCGGIGWSGATCCASGNTCVELNPYYSQCLPNSQVTTSTS
KFTSTFTRSSTTSSSSGPTSTSTTTSSPVVTTPPSTSIPGGASSTASWSGNPFSGVQMWANDYYASEVSSL
AIPSMTGAMATKAAEVAKVPSFQWLDRNVTIDTLFAHPLSQIRAANQKGANPPYAGIFVVYDLPDRDCAAAA
SNGEFSIANKGAANYKTYIDAIRSLVIQYSDIRIIFVIEPDSLANMVTNLNVAKCANAESTYKELTVYALQQ
LNLPNVAMYLDAGHAGWLGWPANIQPAANLFAEIYTSAGKPAAVRGLATNVANYNGWSLATPPSYTQGDPNY
DESHYVQALAPLLTANGFPAHFITDTGRNGKQPTGQRQWGDWCNVIGTGFGVRPTTNTGLDIEDAFVWVKPG
GECDGTSNTTSPRYDYHCGLSDALQPAPEAGTWFQAYFEQLLTNANPPF

*FIG. 90I*

SEQUENCE LISTING

```
<160> NUMBER OF SEQ ID NOS: 162

<210> SEQ ID NO 1
<211> LENGTH: 246
<212> TYPE: PRT
<213> ORGANISM: Neurospora crassa

<400> SEQUENCE: 1

Met Arg Phe Asp Leu Leu Ala Leu Ser Ala Phe Ala Pro Leu Val Ala
1               5                   10                  15

Ala His Gly Ala Val Thr Ser Tyr Ile Ile Asp Gly Thr Thr Tyr Pro
            20                  25                  30
```

```
Gly Tyr Glu Gly Phe Ser Pro Ala Ser Ser Pro Lys Thr Ile Gln Phe
            35                  40                  45

Gln Trp Pro Asn Tyr Asp Pro Thr Met Thr Val Ser Asp Ala Lys Met
 50                  55                  60

Arg Cys Asn Gly Thr Ser Ala Gln Leu Ser Ala Thr Val Gln Ala
 65                  70                  75                  80

Gly Ser Asn Val Thr Ala Val Trp Lys Gln Trp Thr His Glu Gln Gly
                 85                  90                  95

Pro Val Gln Val Trp Leu Phe Lys Cys Pro Gly Ala Phe Gly Ser Ser
                100                 105                 110

Cys Lys Gly Asp Gly Lys Gly Trp Phe Lys Ile Asp Glu Met Gly Met
            115                 120                 125

Trp Gly Gly Lys Leu Asn Ser Ala Asn Trp Gly Thr Ala Leu Ile Val
130                 135                 140

Lys Asn His Gln Trp Ser Ser Glu Ile Pro Lys Asn Met Ala Pro Gly
145                 150                 155                 160

Asn Tyr Leu Ile Arg His Glu Leu Leu Ala Leu His Gln Ala Asn Thr
                165                 170                 175

Pro Gln Phe Tyr Ala Glu Cys Ala Gln Ile Val Val Gln Gly Ser Gly
            180                 185                 190

Asn Ala Val Pro Pro Ser Asp Tyr Leu Tyr Ser Ile Pro Thr Tyr Ala
            195                 200                 205

Pro Gln Asn Asp Pro Gly Val Thr Leu Thr Arg Asp Phe Lys Ile Asp
            210                 215                 220

Ile Tyr Ser Ser Lys Ala Thr Thr Tyr Thr Pro Pro Gly Gly Arg Val
225                 230                 235                 240

Trp Ser Gly Phe Gln Phe
                245

<210> SEQ ID NO 2
<211> LENGTH: 238
<212> TYPE: PRT
<213> ORGANISM: Neurospora crassa

<400> SEQUENCE: 2

Met Lys Val Leu Ala Pro Leu Val Leu Ala Ser Ala Ser Ala His
 1               5                  10                  15

Thr Ile Phe Ser Ser Leu Glu Val Asn Gly Val Asn Gln Gly Leu Gly
                 20                  25                  30

Glu Gly Val Arg Val Pro Thr Tyr Asn Gly Pro Ile Glu Asp Val Thr
            35                  40                  45

Ser Ala Ser Ile Ala Cys Asn Gly Ser Pro Asn Thr Val Ala Ser Thr
 50                  55                  60

Ser Lys Val Ile Thr Val Gln Ala Gly Thr Asn Val Thr Ala Ile Trp
 65                  70                  75                  80

Arg Tyr Met Leu Ser Thr Thr Gly Asp Ser Pro Ala Asp Val Met Asp
                 85                  90                  95

Ser Ser His Lys Gly Pro Thr Ile Ala Tyr Leu Lys Lys Val Asp Asn
            100                 105                 110

Ala Ala Thr Ala Ser Gly Val Gly Asn Gly Trp Phe Lys Ile Gln Gln
            115                 120                 125

Asp Gly Met Asp Ser Ser Gly Val Trp Gly Thr Glu Arg Val Ile Asn
130                 135                 140

Gly Lys Gly Arg His Ser Ile Lys Ile Pro Glu Cys Ile Ala Pro Gly
145                 150                 155                 160
```

```
Gln Tyr Leu Leu Arg Ala Glu Met Ile Ala Leu His Ala Ala Ser Asn
                165                 170                 175

Tyr Pro Gly Ala Gln Phe Tyr Met Glu Cys Ala Gln Leu Asn Val Val
            180                 185                 190

Gly Gly Thr Gly Ala Lys Thr Pro Ser Thr Val Ser Phe Pro Gly Ala
        195                 200                 205

Tyr Ser Gly Ser Asp Pro Gly Val Lys Ile Ser Ile Tyr Trp Pro Pro
    210                 215                 220

Val Thr Ser Tyr Thr Val Pro Gly Pro Ser Val Phe Thr Cys
225                 230                 235

<210> SEQ ID NO 3
<211> LENGTH: 231
<212> TYPE: PRT
<213> ORGANISM: Neurospora crassa

<400> SEQUENCE: 3

Met Leu Pro Ser Ile Ser Leu Leu Leu Ala Ala Ala Leu Gly Thr Ser
1               5                   10                  15

Ala His Tyr Thr Phe Pro Lys Val Trp Ala Asn Ser Gly Thr Thr Ala
            20                  25                  30

Asp Trp Gln Tyr Val Arg Arg Ala Asp Asn Trp Gln Asn Asn Gly Phe
        35                  40                  45

Val Asp Asn Val Asn Ser Gln Gln Ile Arg Cys Phe Gln Ser Thr His
    50                  55                  60

Ser Pro Ala Gln Ser Thr Leu Ser Val Ala Ala Gly Thr Thr Ile Thr
65                  70                  75                  80

Tyr Gly Ala Ala Pro Ser Val Tyr His Pro Gly Pro Met Gln Phe Tyr
                85                  90                  95

Leu Ala Arg Val Pro Asp Gly Gln Asp Ile Asn Ser Trp Thr Gly Glu
            100                 105                 110

Gly Ala Val Trp Phe Lys Ile Tyr His Glu Gln Pro Thr Phe Gly Ser
        115                 120                 125

Gln Leu Thr Trp Ser Ser Asn Gly Lys Ser Ser Phe Pro Val Lys Ile
    130                 135                 140

Pro Ser Cys Ile Lys Ser Gly Ser Tyr Leu Leu Arg Ala Glu His Ile
145                 150                 155                 160

Gly Leu His Val Ala Gln Ser Ser Gly Ala Ala Gln Phe Tyr Ile Ser
                165                 170                 175

Cys Ala Gln Leu Ser Ile Thr Gly Gly Gly Ser Thr Glu Pro Gly Ala
            180                 185                 190

Asn Tyr Lys Val Ser Phe Pro Gly Ala Tyr Lys Ala Ser Asp Pro Gly
        195                 200                 205

Ile Leu Ile Asn Ile Asn Tyr Pro Val Pro Thr Ser Tyr Lys Asn Pro
    210                 215                 220

Gly Pro Ser Val Phe Thr Cys
225                 230

<210> SEQ ID NO 4
<211> LENGTH: 344
<212> TYPE: PRT
<213> ORGANISM: Neurospora crassa

<400> SEQUENCE: 4

Met Lys Ser Ser Leu Leu Val Val Leu Thr Ala Gly Leu Ala Val Arg
1               5                   10                  15
```

Asp Ala Ile Ala His Ala Ile Phe Gln Gln Leu Trp Val Asp Gly Val
            20                  25                  30

Asp Tyr Gly Ser Thr Cys Asn Arg Leu Pro Thr Ser Asn Ser Pro Val
        35                  40                  45

Thr Asn Val Gly Ser Arg Asp Val Val Cys Asn Ala Gly Thr Arg Gly
50                  55                  60

Val Ser Gly Lys Cys Pro Val Lys Ala Gly Thr Val Thr Val Glu
65                  70                  75                  80

Met His Gln Gln Pro Gly Asp Arg Ser Cys Lys Ser Glu Ala Ile Gly
                85                  90                  95

Gly Ala His Trp Gly Pro Val Gln Ile Tyr Leu Ser Lys Val Ser Asp
            100                 105                 110

Ala Ser Thr Ala Asp Gly Ser Ser Gly Gly Trp Phe Lys Ile Phe Ser
        115                 120                 125

Asp Ala Trp Ser Lys Lys Ser Gly Gly Arg Val Gly Asp Asp Asn
130                 135                 140

Trp Gly Thr Arg Asp Leu Asn Ala Cys Cys Gly Arg Met Asp Val Leu
145                 150                 155                 160

Ile Pro Lys Asp Leu Pro Ser Gly Asp Tyr Leu Leu Arg Ala Glu Ala
                165                 170                 175

Leu Ala Leu His Thr Ala Gly Gln Ser Gly Gly Ala Gln Phe Tyr Ile
            180                 185                 190

Ser Cys Tyr Gln Ile Thr Val Ser Gly Gly Ser Ala Asn Tyr Ala
        195                 200                 205

Thr Val Lys Phe Pro Gly Ala Tyr Arg Ala Ser Asp Pro Gly Ile Gln
210                 215                 220

Ile Asn Ile His Ala Val Val Ser Asn Tyr Val Ala Pro Gly Pro Ala
225                 230                 235                 240

Val Val Ala Gly Gly Val Thr Lys Gln Ala Gly Ser Gly Cys Ile Gly
                245                 250                 255

Cys Glu Ser Thr Cys Lys Val Gly Ser Ser Pro Ser Ala Val Ala Pro
            260                 265                 270

Gly Gly Lys Pro Ala Ser Gly Gly Ser Asp Gly Asn Ala Pro Glu Val
        275                 280                 285

Ala Glu Pro Ser Gly Gly Glu Gly Ser Pro Ser Ala Pro Gly Ala Cys
290                 295                 300

Glu Val Ala Ala Tyr Gly Gln Cys Gly Gly Asp Gln Tyr Ser Gly Cys
305                 310                 315                 320

Thr Gln Cys Ala Ser Gly Tyr Thr Cys Lys Ala Val Ser Pro Pro Tyr
                325                 330                 335

Tyr Ser Gln Cys Ala Pro Thr Ser
            340

<210> SEQ ID NO 5
<211> LENGTH: 293
<212> TYPE: PRT
<213> ORGANISM: Neurospora crassa

<400> SEQUENCE: 5

Met Lys Phe Ser Ser Ala Leu Ala Phe Leu Ala Ala Gly Ala Gln
1               5                   10                  15

Ala His Tyr Thr Phe Pro Lys Gly Tyr Ser Thr Gly Ala Val Ser Gly
            20                  25                  30

Glu Tyr Glu His Ile Arg Met Thr Glu Asn His Tyr Asn Arg Gly Pro

-continued

```
                35                  40                  45
Val Ala Asp Val Thr Ser Glu Ser Met Thr Cys Tyr Glu Leu Asn Pro
             50                  55                  60
Gly Lys Gly Ala Pro Lys Thr Leu Ser Val Ala Ala Gly Ser Asn Tyr
 65                  70                  75                  80
Thr Phe Val Val Gly Asp Asn Ile Gly His Pro Gly Pro Leu His Phe
                 85                  90                  95
Tyr Met Ala Lys Val Pro Glu Gly Lys Thr Ala Ala Thr Phe Asp Gly
                100                 105                 110
Lys Gly Ala Val Trp Phe Lys Ile Tyr Gln Asp Gly Pro Met Gly Leu
            115                 120                 125
Gly Thr Gly Gln Leu Thr Trp Pro Ser Ala Gly Ala Thr Glu Val Ser
        130                 135                 140
Val Lys Leu Pro Ser Cys Leu Glu Ser Gly Tyr Leu Leu Arg Val
145                 150                 155                 160
Glu His Ile Gly Leu His Ser Ala Gly Ser Val Gly Gly Ala Gln Leu
                165                 170                 175
Tyr Ile Ala Cys Ala Gln Leu Asn Val Thr Gly Gly Thr Gly Thr Ile
                180                 185                 190
Asn Thr Ser Gly Lys Leu Val Ser Phe Pro Gly Ala Tyr Lys Ala Thr
            195                 200                 205
Asp Pro Gly Leu Leu Phe Asn Leu Tyr Tyr Pro Ala Pro Thr Ser Tyr
        210                 215                 220
Thr Asn Pro Gly Pro Ala Val Ala Thr Cys Asp Gly Ala Ser Ala Pro
225                 230                 235                 240
Ala Ala Pro Ala Pro Ala Pro Ser Ser Ala Ala Pro Ser Ala Pro Ala
                245                 250                 255
Ala Ser Ala Pro Ser Ala Thr Val Pro Ala Val Ser Ala Thr Ser Ala
                260                 265                 270
Ala Ala Val Gly Lys Ala Ser Ser Thr Pro Lys Lys Gly Cys Lys Arg
            275                 280                 285
Ala Ala Arg Lys His
        290

<210> SEQ ID NO 6
<211> LENGTH: 342
<212> TYPE: PRT
<213> ORGANISM: Neurospora crassa

<400> SEQUENCE: 6

Met Arg Ser Thr Leu Val Thr Gly Leu Ile Ala Gly Leu Leu Ser Gln
 1               5                  10                  15
Gln Ala Ala Ala His Ala Thr Phe Gln Ala Leu Trp Val Asp Gly Ala
                20                  25                  30
Asp Tyr Gly Ser Gln Cys Ala Arg Val Pro Pro Ser Asn Ser Pro Val
            35                  40                  45
Thr Asp Val Thr Ser Asn Ala Met Arg Cys Asn Thr Gly Thr Ser Pro
        50                  55                  60
Val Ala Lys Lys Cys Pro Val Lys Ala Gly Ser Thr Val Thr Val Glu
 65                  70                  75                  80
Met His Gln Ser His Pro Pro Val Pro Thr Leu Thr Tyr Lys Gln Gln
                85                  90                  95
Ala Asn Asp Arg Ser Cys Ser Ser Glu Ala Ile Gly Gly Ala His Tyr
                100                 105                 110
```

```
Gly Pro Val Leu Val Tyr Met Ser Lys Val Ser Asp Ala Ser Ala
            115                 120                 125

Asp Gly Ser Ser Gly Trp Phe Lys Ile Phe Glu Asp Thr Trp Ala Lys
130                 135                 140

Lys Pro Ser Ser Ser Gly Asp Asp Phe Trp Gly Val Lys Asp
145                 150                 155                 160

Leu Asn Ser Cys Cys Gly Lys Met Gln Val Lys Ile Pro Ser Asp Ile
                165                 170                 175

Pro Ala Gly Asp Tyr Leu Leu Arg Ala Glu Val Ile Ala Leu His Thr
            180                 185                 190

Ala Ala Ser Ala Gly Gly Ala Gln Leu Tyr Met Thr Cys Tyr Gln Ile
        195                 200                 205

Ser Val Thr Gly Gly Gly Ser Ala Thr Pro Ala Thr Val Ser Phe Pro
    210                 215                 220

Gly Ala Tyr Lys Ser Ser Asp Pro Gly Ile Leu Val Asp Ile His Ser
225                 230                 235                 240

Ala Met Ser Thr Tyr Val Ala Pro Gly Pro Ala Val Tyr Ser Gly Gly
                245                 250                 255

Ser Ser Lys Lys Ala Gly Ser Gly Cys Val Gly Cys Glu Ser Thr Cys
            260                 265                 270

Lys Val Gly Ser Gly Pro Thr Gly Thr Ala Ser Ala Val Pro Val Ala
275                 280                 285

Ser Thr Ser Ala Ala Ala Gly Gly Gly Gly Gly Ser Gly Gly
        290                 295                 300

Cys Ser Val Ala Lys Tyr Gln Gln Cys Gly Gly Thr Gly Tyr Thr Gly
305                 310                 315                 320

Cys Thr Ser Cys Ala Ser Gly Ser Thr Cys Ser Ala Val Ser Pro Pro
                325                 330                 335

Tyr Tyr Ser Gln Cys Val
            340

<210> SEQ ID NO 7
<211> LENGTH: 308
<212> TYPE: PRT
<213> ORGANISM: Neurospora crassa

<400> SEQUENCE: 7

Met Val Arg Ala Leu Arg Leu Leu Ala Ser Cys Ala Met Phe Ser Gln
1               5                   10                  15

Ala Leu Ala His Ser His Ile Leu Tyr Leu Ile Ile Asn Gly Gln Gln
            20                  25                  30

Tyr Arg Gly Phe Asn Pro His Ala Pro Asp Ala Ile Thr Asn Ser Ile
        35                  40                  45

Gly Trp Ser Thr Ser Ala Val Asp Asp Gly Phe Val Thr Pro Ser Asn
    50                  55                  60

Tyr Ser Asn Pro Asp Ile Ile Cys His Arg Asp Gly Lys Pro Ala Lys
65                  70                  75                  80

Ala His Ala Pro Val Lys Ala Gly Asp Lys Ile Gln Ile Gln Trp Asn
                85                  90                  95

Gly Trp Pro Gln Ser His Lys Gly Pro Val Leu Ser Tyr Leu Ala Pro
            100                 105                 110

Cys Ala Asn Thr Thr Asp Gly Cys Ala Ser Val Asp Lys Arg Lys Leu
        115                 120                 125

Ser Trp Thr Lys Ile Asp Asp Ser Pro Val Leu Leu Asp Glu Lys
    130                 135                 140
```

```
Gly Gly Pro Pro Gly Arg Trp Ala Thr Asp Val Leu Ile Ala Gln Asn
145                 150                 155                 160

Asn Thr Trp Leu Leu Gly Leu Pro Asn Asp Leu Glu Pro Gly Pro Tyr
                165                 170                 175

Val Leu Arg His Glu Leu Ile Ala Leu His Tyr Ala Asn Leu Lys Asn
            180                 185                 190

Gly Ala Gln Asn Tyr Pro Gln Cys Val Asn Leu Trp Val Glu Gly Pro
        195                 200                 205

Gly Pro Lys Ala Ile Thr Val Gly Lys Glu Val Val Ala Gly
    210                 215                 220

Gln Lys Glu Gly Val Pro Ala Thr Ala Leu Tyr Lys Ala Thr Asp Pro
225                 230                 235                 240

Gly Val Ala Ile Asp Ile Tyr Thr Ala Val Leu Ser Thr Tyr Val Ile
                245                 250                 255

Pro Gly Pro Thr Leu Ala Pro Glu Ala Lys Pro Val Pro Val Thr Glu
                260                 265                 270

Gln Gly Leu Lys Ser Thr Ile Thr Ala Val Gly Thr Pro Val Ile Val
            275                 280                 285

Thr Arg Ala Thr Ser Thr Val Pro Met Pro Asn Gly Glu Thr Ala Ala
    290                 295                 300

Ala Phe Lys Gly
305

<210> SEQ ID NO 8
<211> LENGTH: 322
<212> TYPE: PRT
<213> ORGANISM: Neurospora crassa

<400> SEQUENCE: 8

Met Lys Val Leu Ser Leu Leu Ala Ala Ala Ser Ala Ala Ser Ala His
1               5                   10                  15

Thr Ile Phe Val Gln Leu Glu Ala Asp Gly Thr Thr Tyr Pro Val Ser
            20                  25                  30

Tyr Gly Ile Arg Thr Pro Ser Tyr Asp Gly Pro Ile Thr Asp Val Thr
        35                  40                  45

Ser Asn Asp Leu Ala Cys Asn Gly Gly Pro Asn Pro Thr Thr Pro Ser
50                  55                  60

Asp Lys Ile Ile Thr Val Asn Ala Gly Ser Thr Val Lys Ala Ile Trp
65                  70                  75                  80

Arg His Thr Leu Thr Ser Gly Ala Asp Asp Val Met Asp Ala Ser His
                85                  90                  95

Lys Gly Pro Thr Leu Ala Tyr Leu Lys Lys Val Asp Asp Ala Leu Thr
            100                 105                 110

Asp Thr Gly Ile Gly Gly Gly Trp Phe Lys Ile Gln Glu Asp Gly Tyr
        115                 120                 125

Asn Asn Gly Gln Trp Gly Thr Ser Thr Val Ile Thr Asn Gly Gly Phe
    130                 135                 140

Gln Tyr Ile Asp Ile Pro Ala Cys Ile Pro Ser Gly Gln Tyr Leu Leu
145                 150                 155                 160

Arg Ala Glu Met Ile Ala Leu His Ala Ala Ser Ser Thr Ala Gly Ala
                165                 170                 175

Gln Leu Tyr Met Glu Cys Ala Gln Ile Asn Ile Val Gly Gly Thr Gly
            180                 185                 190

Gly Thr Ala Leu Pro Ser Thr Thr Tyr Ser Ile Pro Gly Ile Tyr Lys
```

```
                195                 200                 205
Ala Thr Asp Pro Gly Leu Leu Val Asn Ile Tyr Ser Met Ser Pro Ser
210                 215                 220

Ser Thr Tyr Thr Ile Pro Gly Pro Ala Lys Phe Thr Cys Pro Ala Gly
225                 230                 235                 240

Asn Gly Gly Gly Ala Gly Gly Gly Ser Thr Thr Ala Lys Pro
                245                 250                 255

Ala Ser Ser Thr Thr Ser Lys Ala Ala Ile Thr Ser Ala Val Thr Thr
                260                 265                 270

Leu Lys Thr Ser Val Val Ala Pro Gln Pro Thr Gly Gly Cys Thr Ala
                275                 280                 285

Ala Gln Trp Ala Gln Cys Gly Gly Met Gly Phe Ser Gly Cys Thr Thr
290                 295                 300

Cys Ala Ser Pro Tyr Thr Cys Lys Lys Met Asn Asp Tyr Tyr Ser Gln
305                 310                 315                 320

Cys Ser

<210> SEQ ID NO 9
<211> LENGTH: 241
<212> TYPE: PRT
<213> ORGANISM: Neurospora crassa

<400> SEQUENCE: 9

Met Lys Thr Phe Ala Thr Leu Leu Ala Ser Ile Gly Leu Val Ala Ala
1               5                   10                  15

His Gly Phe Val Asp Asn Ala Thr Ile Gly Gly Gln Phe Tyr Gln Phe
                20                  25                  30

Tyr Gln Pro Tyr Gln Asp Pro Tyr Met Gly Ser Pro Pro Asp Arg Ile
                35                  40                  45

Ser Arg Lys Ile Pro Gly Asn Gly Pro Val Glu Asp Val Thr Ser Leu
50                  55                  60

Ala Ile Gln Cys Asn Ala Asp Ser Ala Pro Ala Lys Leu His Ala Ser
65                  70                  75                  80

Ala Ala Ala Gly Ser Thr Val Thr Leu Arg Trp Thr Ile Trp Pro Asp
                85                  90                  95

Ser His Val Gly Pro Val Ile Thr Tyr Met Ala Arg Cys Pro Asp Thr
                100                 105                 110

Gly Cys Gln Asp Trp Thr Pro Ser Ala Ser Asp Lys Val Trp Phe Lys
                115                 120                 125

Ile Lys Glu Gly Gly Arg Glu Gly Thr Ser Asn Val Trp Ala Ala Thr
130                 135                 140

Pro Leu Met Thr Ala Pro Ala Asn Tyr Glu Tyr Ala Ile Pro Ser Cys
145                 150                 155                 160

Leu Lys Pro Gly Tyr Tyr Leu Val Arg His Glu Ile Ile Ala Leu His
                165                 170                 175

Ser Ala Tyr Ser Tyr Pro Gly Ala Gln Phe Tyr Pro Gly Cys His Gln
                180                 185                 190

Leu Gln Val Thr Gly Ser Gly Thr Lys Thr Pro Ser Ser Gly Leu Val
                195                 200                 205

Ser Phe Pro Gly Ala Tyr Lys Ser Thr Asp Pro Gly Val Thr Tyr Asp
                210                 215                 220

Ala Tyr Gln Ala Ala Thr Tyr Thr Ile Pro Gly Pro Ala Val Phe Thr
225                 230                 235                 240

Cys
```

<210> SEQ ID NO 10
<211> LENGTH: 472
<212> TYPE: PRT
<213> ORGANISM: Neurospora crassa

<400> SEQUENCE: 10

Met Arg Ser Thr Thr Val Leu Ala Gly Leu Ala Thr Val Leu Ala Pro
1               5                   10                  15

Leu Ala Ser Ala His Thr Val Leu Thr Thr Val Phe Val Asn Asp Lys
            20                  25                  30

Asn Gln Gly Asp Gly Thr Gly Val Arg Met Pro Met Asp Gly Asn Ile
        35                  40                  45

Ala Asn Ala Pro Val Ile Asn Met Asn Ser Asp Asp Met Ile Cys Gly
    50                  55                  60

Arg Asp Gly Leu Lys Lys Val Asn Tyr Ala Ile Pro Ala Thr Ala Gly
65                  70                  75                  80

Ser Lys Met Thr Phe Glu Phe Arg Thr Tyr Val Asp Gly Ser Arg Pro
                85                  90                  95

Gln Phe Ile Asp Lys Ser His Gln Gly Pro Ile Ser Val Tyr Ala Lys
            100                 105                 110

Ala Val Ser Asp Phe Asp Gln Ser Pro Gly Gly Ser Gly Trp Phe Lys
        115                 120                 125

Ile Trp His Asp Gly Tyr Asp Glu Ser Thr Gly Lys Trp Ala Val Gln
130                 135                 140

Lys Val Ile Asp Thr Asn Gly Leu Leu Ser Ile Ser Leu Pro Thr Gly
145                 150                 155                 160

Met Pro Thr Gly Ala Tyr Leu Leu Arg Thr Glu Val Ile Ala Met Gln
                165                 170                 175

Asn Val Thr Thr Lys Ala Asp Gly Asn Trp Tyr Cys Glu Pro Gln Phe
            180                 185                 190

Tyr Val Asn Cys Ala Gln Val Tyr Val Gln Gly Ser Ser Ser Gly Pro
        195                 200                 205

Leu Ser Ile Pro Lys Asp Lys Glu Thr Ser Ile Pro Gly His Val His
    210                 215                 220

Pro Ser Asp Lys Gly Leu Asn Phe Asn Met Tyr Asp Met Lys Gly Leu
225                 230                 235                 240

Leu Pro Tyr Gln Ile Pro Gly Pro Val Pro Phe Arg Pro Ala Ser Ser
                245                 250                 255

Ser Ser Gly Ser Asn Ala Lys Ala Ala Leu Thr Thr Pro Thr Asn Phe
            260                 265                 270

Pro Gly Ala Val Pro Asp Asn Cys Leu Leu Lys Asn Ala Asn Trp Cys
        275                 280                 285

Gly Phe Glu Val Pro Asp Tyr Thr Asn Glu Asp Gly Cys Trp Ala Ser
    290                 295                 300

Ala Asp Asn Cys Trp Ala Gln Ser Lys Lys Cys Phe Asp Ser Ala Pro
305                 310                 315                 320

Pro Ser Gly Ile Lys Gly Cys Lys Ile Trp Glu Gln Glu Lys Cys Gln
                325                 330                 335

Ala Leu Ala Asn Ser Cys Asp Ala Lys Gln Phe Thr Gly Pro Pro Asn
            340                 345                 350

Lys Gly Lys Arg Trp Gly Asp Val Thr Glu Gln Ser Ser Val Gln Val
        355                 360                 365

Pro Gly Val Met Lys Gly Ala Asp Leu Val Asp Thr Pro Val Val Asp

```
                370             375             380
Thr Thr Ser Asn Gln Lys Ala Ala Asn Asn Asn Val Val Ser Ile
385                 390             395                 400

Pro Ala Ala Thr Ala Thr Thr Phe Ile Thr Thr Ser Ala Ala Pro
                405             410             415

Ser Lys Pro Val Thr Thr Val Pro Ser Val Ala Ile Thr Thr Thr
            420             425             430

Ser Ala Ala Val Ala Ile Pro Thr Glu Thr Ala Ala Gln Asn Thr Leu
            435             440             445

Ile Arg Cys Gly Arg Gly Asp Lys Asn Gln Arg Arg Ala Met His Ile
    450             455             460

Asn Arg His Lys Arg Ala Asp Phe
465             470

<210> SEQ ID NO 11
<211> LENGTH: 326
<212> TYPE: PRT
<213> ORGANISM: Neurospora crassa

<400> SEQUENCE: 11

Met Lys Leu Ser Val Ala Ala Leu Ser Leu Ala Ala Ser Glu Ala
1               5               10                  15

Ser Ala His Tyr Ile Phe Gln Gln Val Gly Ala Gly Thr Ser Val Asn
            20              25              30

Pro Val Trp Lys Tyr Ile Arg Lys His Thr Asn Tyr Asn Ser Pro Val
            35              40              45

Thr Asp Leu Thr Ser Lys Asp Leu Val Cys Asn Val Gly Ala Ser Ala
50              55              60

Glu Gly Val Glu Thr Leu Ser Val Ala Ala Gly Ser Gln Val Thr Phe
65              70              75              80

Lys Thr Asp Thr Ala Val Tyr His Gln Gly Pro Thr Ser Val Tyr Leu
            85              90              95

Ser Lys Ala Asp Gly Ser Leu Ser Asp Tyr Asp Gly Ser Gly Gly Trp
            100             105             110

Phe Lys Ile Lys Asp Trp Gly Ala Thr Phe Pro Gly Gly Glu Trp Thr
            115             120             125

Leu Ser Asp Thr Tyr Thr Phe Thr Ile Pro Ser Cys Ile Pro Ser Gly
130             135             140

Asp Tyr Leu Leu Arg Ile Gln Gln Ile Gly Ile His Asn Pro Trp Pro
145             150             155             160

Ala Gly Val Pro Gln Phe Tyr Leu Ser Cys Ala His Ile Ser Val Thr
            165             170             175

Gly Gly Gly Ser Ala Ser Pro Ala Thr Val Ser Ile Pro Gly Ala Phe
            180             185             190

Lys Glu Thr Asp Pro Gly Tyr Thr Val Asn Ile Tyr Ser Asn Phe Asn
            195             200             205

Asn Tyr Thr Val Pro Gly Pro Glu Val Phe Thr Cys Ser Gly Ser Gly
            210             215             220

Ser Gly Ser Gly Ser Gly Ser Gly Ser Thr Pro Pro Ser Gln
225             230             235             240

Pro Thr Thr Ser Thr Thr Leu Pro Ser Ser Thr Val Val Ala Thr
            245             250             255

Thr Leu Lys Thr Ser Thr Val Val Ala Thr Thr Lys Ser Ser Ser
            260             265             270
```

Thr Thr Ser Ser Ala Ser Ser Gly Ser Gln Pro Thr Ser Pro Ser
            275                 280                 285

Gly Cys Thr Val Ala Lys Tyr Gly Gln Cys Gly Ile Gly Tyr Ser
            290                 295                 300

Gly Cys Thr Ser Cys Ala Ser Gly Ser Thr Cys Lys Val Gly Asn Asp
305                 310                 315                 320

Tyr Tyr Ser Gln Cys Leu
                325

<210> SEQ ID NO 12
<211> LENGTH: 359
<212> TYPE: PRT
<213> ORGANISM: Neurospora crassa

<400> SEQUENCE: 12

Met Lys Thr Gly Ser Ile Leu Ala Ala Leu Val Ala Ser Ala Ser Ala
1               5                   10                  15

His Thr Ile Phe Gln Lys Val Ser Val Asn Gly Ala Asp Gln Gly Gln
            20                  25                  30

Leu Lys Gly Ile Arg Ala Pro Ala Asn Asn Pro Val Thr Asp Val
            35                  40                  45

Met Ser Ser Asp Ile Ile Cys Asn Ala Val Thr Met Lys Asp Ser Asn
    50                  55                  60

Val Leu Thr Val Pro Ala Gly Ala Lys Val Gly His Phe Trp Gly His
65                  70                  75                  80

Glu Ile Gly Gly Ala Ala Gly Pro Asn Asp Ala Asp Asn Pro Ile Ala
                85                  90                  95

Ala Ser His Lys Gly Pro Ile Met Val Tyr Leu Ala Lys Val Asp Asn
                100                 105                 110

Ala Ala Thr Thr Gly Thr Ser Gly Leu Lys Trp Phe Lys Val Ala Glu
            115                 120                 125

Ala Gly Leu Ser Asn Gly Lys Trp Ala Val Asp Asp Leu Ile Ala Asn
        130                 135                 140

Asn Gly Trp Ser Tyr Phe Asp Met Pro Thr Cys Ile Ala Pro Gly Gln
145                 150                 155                 160

Tyr Leu Met Arg Ala Glu Leu Ile Ala Leu His Asn Ala Gly Ser Gln
                165                 170                 175

Ala Gly Ala Gln Phe Tyr Ile Gly Cys Ala Gln Ile Asn Val Thr Gly
            180                 185                 190

Gly Gly Ser Ala Ser Pro Ser Asn Thr Val Ser Phe Pro Gly Ala Tyr
        195                 200                 205

Ser Ala Ser Asp Pro Gly Ile Leu Ile Asn Ile Tyr Gly Gly Ser Gly
    210                 215                 220

Lys Thr Asp Asn Gly Gly Lys Pro Tyr Gln Ile Pro Gly Pro Ala Leu
225                 230                 235                 240

Phe Thr Cys Pro Ala Gly Gly Ser Gly Gly Ser Ser Pro Ala Pro Ala
                245                 250                 255

Thr Thr Ala Ser Thr Pro Lys Pro Thr Ser Ala Ser Ala Pro Lys Pro
            260                 265                 270

Val Ser Thr Thr Ala Ser Thr Pro Lys Pro Thr Asn Gly Ser Gly Ser
    275                 280                 285

Gly Thr Gly Ala Ala His Ser Thr Lys Cys Gly Gly Ser Lys Pro Ala
        290                 295                 300

Ala Thr Thr Lys Ala Ser Asn Pro Gln Pro Thr Asn Gly Gly Asn Ser
305                 310                 315                 320

Ala Val Arg Ala Ala Ala Leu Tyr Gly Gln Cys Gly Lys Gly Trp
            325                 330                 335

Thr Gly Pro Thr Ser Cys Ala Ser Gly Thr Cys Lys Phe Ser Asn Asp
            340                 345                 350

Trp Tyr Ser Gln Cys Leu Pro
            355

<210> SEQ ID NO 13
<211> LENGTH: 369
<212> TYPE: PRT
<213> ORGANISM: Neurospora crassa

<400> SEQUENCE: 13

Met Ala Arg Met Ser Ile Leu Thr Ala Leu Ala Gly Ala Ser Leu Val
1               5                   10                  15

Ala Ala His Gly His Val Ser Lys Val Ile Val Asn Gly Val Glu Tyr
                20                  25                  30

Gln Asn Tyr Asp Pro Thr Ser Phe Pro Tyr Asn Ser Asn Pro Pro Thr
            35                  40                  45

Val Ile Gly Trp Thr Ile Asp Gln Lys Asp Asn Gly Phe Val Ser Pro
50                  55                  60

Asp Ala Phe Asp Ser Gly Asp Ile Ile Cys His Lys Ser Ala Lys Pro
65                  70                  75                  80

Ala Gly Gly His Ala Thr Val Lys Ala Gly Asp Lys Ile Ser Leu Gln
                85                  90                  95

Trp Asp Gln Trp Pro Glu Ser His Lys Gly Pro Val Ile Asp Tyr Leu
            100                 105                 110

Ala Ala Cys Asp Gly Asp Cys Glu Ser Val Asp Lys Thr Ala Leu Lys
        115                 120                 125

Phe Phe Lys Ile Asp Gly Ala Gly Tyr Asp Ala Thr Asn Gly Trp Ala
130                 135                 140

Ser Asp Thr Leu Ile Lys Asp Gly Asn Ser Trp Val Val Glu Ile Pro
145                 150                 155                 160

Glu Ser Ile Lys Pro Gly Asn Tyr Val Leu Arg His Glu Ile Ile Ala
                165                 170                 175

Leu His Ser Ala Gly Gln Ala Asn Gly Ala Gln Asn Tyr Pro Gln Cys
            180                 185                 190

Phe Asn Leu Lys Val Glu Gly Ser Gly Ser Thr Val Pro Ala Gly Val
        195                 200                 205

Ala Gly Thr Glu Leu Tyr Lys Ala Thr Asp Ala Gly Ile Leu Phe Asp
    210                 215                 220

Ile Tyr Lys Asn Asp Ile Ser Tyr Pro Val Pro Gly Pro Ser Leu Ile
225                 230                 235                 240

Ala Gly Ala Ser Ser Ile Ala Gln Ser Lys Met Ala Ala Thr Ala
                245                 250                 255

Thr Ala Ser Ala Thr Leu Pro Gly Ala Thr Gly Gly Ser Asn Ser Pro
            260                 265                 270

Ala Thr Ser Ala Ala Ala Ala Pro Ala Thr Ser Ala Ala Ala Ala
        275                 280                 285

Thr Ser Gln Val Gln Ala Ala Pro Ala Thr Thr Leu Val Thr Ser Thr
    290                 295                 300

Lys Ala Ala Ala Pro Ala Thr Ser Ala Ala Pro Ala Ala Pro Ala
305                 310                 315                 320

Thr Ser Ala Ala Ala Gly Gly Ala Gly Gln Val Gln Ala Lys Gln Thr

```
                    325                 330                 335
Lys Trp Gly Gln Cys Gly Gly Asn Gly Phe Thr Gly Pro Thr Glu Cys
                340                 345                 350

Glu Ser Gly Ser Thr Cys Thr Lys Tyr Asn Asp Trp Tyr Ser Gln Cys
            355                 360                 365

Val
```

<210> SEQ ID NO 14
<211> LENGTH: 271
<212> TYPE: PRT
<213> ORGANISM: Sporotrichum thermophilum

<400> SEQUENCE: 14

```
Ala Leu Gly His Ser His Leu Gly Tyr Ile Ile Ile Asn Gly Glu Val
1               5                   10                  15

Tyr Gln Gly Phe Asp Pro Arg Pro Glu Gln Ala Asn Ser Pro Leu Arg
            20                  25                  30

Val Gly Trp Ser Thr Gly Ala Ile Asp Asp Gly Phe Val Ala Pro Ala
        35                  40                  45

Asn Tyr Ser Ser Pro Asp Ile Ile Cys His Ile Glu Gly Ala Ser Pro
50                  55                  60

Pro Ala His Ala Pro Val Arg Ala Gly Asp Arg Val His Val Gln Trp
65                  70                  75                  80

Asn Gly Trp Pro Leu Gly His Val Gly Pro Val Leu Ser Tyr Leu Ala
                85                  90                  95

Pro Cys Gly Gly Leu Glu Gly Ser Glu Ser Gly Cys Ala Gly Val Asp
            100                 105                 110

Lys Arg Gln Leu Arg Trp Thr Lys Val Asp Asp Ser Leu Pro Ala Met
        115                 120                 125

Glu Leu Arg Trp Ala Thr Asp Val Leu Ile Ala Ala Asn Asn Ser Trp
130                 135                 140

Gln Val Glu Ile Pro Arg Gly Leu Arg Asp Gly Pro Tyr Val Leu Arg
145                 150                 155                 160

His Glu Ile Val Ala Leu His Tyr Ala Ala Glu Pro Gly Gly Ala Gln
                165                 170                 175

Asn Tyr Pro Leu Cys Val Asn Leu Trp Val Glu Gly Gly Asp Gly Ser
            180                 185                 190

Met Glu Leu Asp His Phe Asp Ala Thr Gln Phe Tyr Arg Pro Asp Asp
        195                 200                 205

Pro Gly Ile Leu Leu Asn Val Thr Ala Gly Leu Arg Ser Tyr Ala Val
    210                 215                 220

Pro Gly Pro Thr Leu Ala Ala Gly Ala Thr Pro Val Pro Tyr Ala Gln
225                 230                 235                 240

Gln Asn Ile Ser Ser Ala Arg Ala Asp Gly Thr Pro Val Ile Val Thr
                245                 250                 255

Arg Ser Thr Glu Thr Val Pro Phe Pro Thr Ala Ala Pro Thr Pro Ala
            260                 265                 270
```

<210> SEQ ID NO 15
<211> LENGTH: 330
<212> TYPE: PRT
<213> ORGANISM: Sporotrichum thermophilum

<400> SEQUENCE: 15

```
Met Ser Ser Phe Thr Ser Lys Gly Leu Leu Ser Ala Leu Met Gly Ala
1               5                   10                  15
```

Ala Thr Val Ala Ala His Gly His Val Thr Asn Ile Val Ile Asn Gly
            20                  25                  30

Val Ser Tyr Gln Asn Phe Asp Pro Phe Thr His Pro Tyr Met Gln Asn
            35                  40                  45

Pro Pro Thr Val Val Gly Trp Thr Ala Ser Asn Thr Asp Asn Gly Phe
 50                  55                  60

Val Gly Pro Glu Ser Phe Ser Ser Pro Asp Ile Ile Cys His Lys Ser
 65                  70                  75                  80

Ala Thr Asn Ala Gly Gly His Ala Val Val Ala Ala Gly Asp Lys Val
                85                  90                  95

Phe Ile Gln Trp Asp Thr Trp Pro Glu Ser His His Gly Pro Val Ile
            100                 105                 110

Asp Tyr Leu Ala Asp Cys Gly Asp Ala Gly Cys Glu Lys Val Asp Lys
            115                 120                 125

Thr Thr Leu Lys Phe Phe Lys Ile Ser Glu Ser Gly Leu Leu Asp Gly
            130                 135                 140

Thr Asn Ala Pro Gly Lys Trp Ala Ser Asp Thr Leu Ile Ala Asn Asn
145                 150                 155                 160

Asn Ser Trp Leu Val Gln Ile Pro Pro Asn Ile Ala Pro Gly Asn Tyr
                165                 170                 175

Val Leu Arg His Glu Ile Ile Ala Leu His Ser Ala Gly Gln Gln Asn
            180                 185                 190

Gly Ala Gln Asn Tyr Pro Gln Cys Phe Asn Leu Gln Val Thr Gly Ser
            195                 200                 205

Gly Thr Gln Lys Pro Ser Gly Val Leu Gly Thr Glu Leu Tyr Lys Ala
            210                 215                 220

Thr Asp Ala Gly Ile Leu Ala Asn Ile Tyr Thr Ser Pro Val Thr Tyr
225                 230                 235                 240

Gln Ile Pro Gly Pro Ala Ile Ile Ser Gly Ala Ser Ala Val Gln Gln
                245                 250                 255

Thr Thr Ser Ala Ile Thr Ala Ser Ala Ile Thr Gly Ser Ala
            260                 265                 270

Thr Ala Ala Pro Thr Ala Ala Thr Thr Ala Ala Ala Ala Thr
            275                 280                 285

Thr Thr Thr Thr Ala Gly Ser Gly Ala Thr Ala Thr Pro Ser Thr Gly
            290                 295                 300

Gly Ser Pro Ser Ser Ala Gln Pro Ala Pro Thr Thr Ala Ala Ala Thr
305                 310                 315                 320

Ser Ser Pro Ala Arg Pro Thr Arg Cys Ala
                325                 330

<210> SEQ ID NO 16
<211> LENGTH: 342
<212> TYPE: PRT
<213> ORGANISM: Sporotrichum thermophilum

<400> SEQUENCE: 16

Met Ser Lys Ala Ser Ala Leu Leu Ala Gly Leu Thr Gly Ala Ala Leu
1               5                   10                  15

Val Ala Ala His Gly His Val Ser His Ile Val Val Asn Gly Val Tyr
            20                  25                  30

Tyr Arg Asn Tyr Asp Pro Thr Thr Asp Trp Tyr Gln Pro Asn Pro Pro
            35                  40                  45

Thr Val Ile Gly Trp Thr Ala Ala Asp Gln Asp Asn Gly Phe Val Glu

```
                50             55             60
Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro Glu Ser His Ile Gly Pro Val Ile Asp
            100                 105                 110

Tyr Leu Ala Ala Cys Asn Gly Asp Cys Glu Thr Val Asp Lys Ser Ser
        115                 120                 125

Leu Arg Trp Phe Lys Ile Asp Gly Ala Gly Tyr Asp Lys Ala Ala Gly
    130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
            165                 170                 175

Ile Ile Ala Leu His Gly Ala Gln Ser Pro Asn Gly Ala Gln Ala Tyr
        180                 185                 190

Pro Gln Cys Ile Asn Leu Arg Val Thr Gly Gly Ser Asn Leu Pro
    195                 200                 205

Ser Gly Val Ala Gly Thr Ser Leu Tyr Lys Ala Thr Asp Pro Gly Ile
210                 215                 220

Leu Phe Asn Pro Tyr Val Ser Pro Asp Tyr Thr Val Pro Gly Pro
225                 230                 235                 240

Ala Leu Ile Ala Gly Ala Ser Ser Ile Ala Gln Ser Thr Ser Val
            245                 250                 255

Ala Thr Ala Thr Gly Thr Ala Thr Val Pro Gly Gly Gly Ala Asn
                260                 265                 270

Pro Thr Ala Thr Thr Thr Ala Ala Thr Ser Ala Ala Pro Ser Thr Thr
            275                 280                 285

Leu Arg Thr Thr Thr Thr Ser Ala Ala Gln Thr Thr Ala Pro Pro Ser
    290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
            340

<210> SEQ ID NO 17
<211> LENGTH: 323
<212> TYPE: PRT
<213> ORGANISM: Sporotrichum thermophilum

<400> SEQUENCE: 17

Met Lys Ser Phe Thr Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
                20                  25                  30

Gly Ala Gln Cys Ala Arg Leu Pro Ala Ser Asn Ser Pro Val Thr Asp
            35                  40                  45

Val Thr Ser Asn Ala Ile Arg Cys Asn Ala Asn Pro Ser Pro Ala Arg
        50                  55                  60

Gly Lys Cys Pro Val Lys Ala Gly Ser Thr Val Thr Val Glu Met His
65                  70                  75                  80
```

Gln Gln Pro Gly Asp Arg Ser Cys Ser Ser Glu Ala Ile Gly Gly Ala
                85                  90                  95

His Tyr Gly Pro Val Met Val Tyr Met Ser Lys Val Ser Asp Ala Ala
            100                 105                 110

Ser Ala Asp Gly Ser Ser Gly Trp Phe Lys Val Phe Glu Asp Gly Trp
            115                 120                 125

Ala Lys Asn Pro Ser Gly Gly Ser Gly Asp Asp Asp Tyr Trp Gly Thr
            130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Ala Gln Phe Tyr Met Thr Cys Tyr
            180                 185                 190

Gln Leu Thr Val Thr Gly Ser Gly Ser Ala Ser Pro Pro Thr Val Ser
            195                 200                 205

Phe Pro Gly Ala Tyr Lys Ala Thr Asp Pro Gly Ile Leu Val Asn Ile
            210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
            260                 265                 270

Gly Ser Thr Ala Thr Ser Ala Pro Gly Gly Gly Gly Cys Thr Val
            275                 280                 285

Gln Lys Tyr Gln Gln Cys Gly Gly Gln Gly Tyr Thr Gly Cys Thr Asn
            290                 295                 300

Cys Ala Ser Gly Ser Thr Cys Ser Ala Val Ser Pro Pro Tyr Tyr Ser
305                 310                 315                 320

Gln Cys Val

<210> SEQ ID NO 18
<211> LENGTH: 341
<212> TYPE: PRT
<213> ORGANISM: Neurospora crassa

<400> SEQUENCE: 18

Met Pro Ser Phe Thr Ser Lys Ser Leu Leu Ala Val Leu Ala Gly Ala
1               5                   10                  15

Ala Ser Val Ala Ala His Gly His Val Ser Asn Ile Val Ile Asn Gly
            20                  25                  30

Glu Tyr Tyr Arg Gly Phe Asp Ser Ser Leu Asn Tyr Met Ala Asn Pro
            35                  40                  45

Pro Ala Val Val Gly Trp Lys Ala Asn Asn Gln Asp Asn Gly Phe Val
            50                  55                  60

Gly Pro Asp Ala Phe Ser Ser Pro Asp Ile Ile Cys His Lys Asp Ala
65                  70                  75                  80

Thr Asn Ala Lys Gly His Ala Val Val Lys Ala Gly Asp Lys Ile Ser
                85                  90                  95

Ile Gln Trp Glu Thr Trp Pro Glu Ser His Lys Gly Pro Val Ile Asp
            100                 105                 110

Tyr Leu Ala Asn Cys Gly Ala Ser Gly Cys Glu Thr Val Asp Lys Thr
            115                 120                 125

```
Ser Leu Glu Phe Phe Lys Ile Asp Glu Val Gly Leu Val Asp Gly Gln
    130                 135                 140

Lys Trp Gly Ser Asp Gln Leu Ile Ala Asn Asn Ser Trp Leu Val
145                 150                 155                 160

Glu Ile Pro Pro Thr Ile Ala Pro Gly Phe Tyr Val Leu Arg His Glu
                165                 170                 175

Ile Ile Ala Leu His Ser Ala Gly Gln Pro Asn Gly Ala Gln Asn Tyr
            180                 185                 190

Pro Gln Cys Phe Asn Ile Gln Val Thr Gly Ser Gly Thr Glu Lys Pro
        195                 200                 205

Ala Gly Val Lys Gly Thr Ala Leu Tyr Lys Pro Asp Asp Ala Gly Ile
    210                 215                 220

Ser Val Asn Ile Tyr Gln Ser Leu Ser Ser Tyr Ser Ile Pro Gly Pro
225                 230                 235                 240

Ala Leu Ile Lys Gly Ala Val Ser Val Ala Gln Ser His Ser Ala Val
                245                 250                 255

Thr Ala Thr Ala Thr Ala Ile Thr Gly Leu Gly Asp Ala Pro Ala Ala
            260                 265                 270

Thr Ala Pro Ala Ala Thr Thr Ala Pro Ala Ala Pro Ala Val
        275                 280                 285

Thr Thr Ala Pro Ala Ala Ala Pro Thr Lys Pro Ala Thr Thr Ala
    290                 295                 300

Ala Ala Pro Gln Pro Thr Lys Pro Ala Lys Ser Gly Cys Gln Lys Arg
305                 310                 315                 320

Arg Ala Ala Arg Arg Ala Ala Ala Leu Ala Arg Arg His Ala Arg Asp
                325                 330                 335

Val Ala Phe Leu Asp
            340

<210> SEQ ID NO 19
<211> LENGTH: 342
<212> TYPE: PRT
<213> ORGANISM: Aspergillus fumigatus

<400> SEQUENCE: 19

Met Arg His Val Gln Ser Thr Gln Leu Leu Ala Ala Leu Leu Leu Thr
1               5                   10                  15

Thr Arg Val Thr Ala His Gly His Val Thr Asn Ile Val Ile Asn Gly
                20                  25                  30

Val Ser Tyr Arg Gly Trp Asn Ile Asp Ser Asp Pro Tyr Asn Pro Asp
            35                  40                  45

Pro Pro Val Val Val Ala Trp Gln Thr Pro Asn Thr Ala Asn Gly Phe
    50                  55                  60

Ile Ser Pro Asp Ala Tyr Gly Thr Asn Asp Ile Ile Cys His Leu Asn
65                  70                  75                  80

Ala Thr Asn Ala Arg Gly His Ala Val Val Ala Ala Gly Asp Lys Ile
                85                  90                  95

Ser Ile Gln Trp Thr Ala Trp Pro Asp Ser His His Gly Pro Val Ile
            100                 105                 110

Asp Tyr Leu Ala Arg Cys Gly Ser Ser Cys Glu Thr Val Asp Lys Thr
        115                 120                 125

Thr Leu Glu Phe Phe Lys Ile Asp Gly Val Gly Leu Val Asp Gly Ser
    130                 135                 140

Asn Pro Pro Gly Val Trp Gly Asp Asp Gln Leu Ile Ala Asp Asn Asn
145                 150                 155                 160
```

Ser Trp Leu Val Glu Ile Pro Pro Thr Ile Ala Pro Gly Tyr Tyr Val
            165                 170                 175

Leu Arg His Glu Leu Ile Ala Leu His Gly Ala Gly Ser Gln Asn Gly
            180                 185                 190

Ala Gln Asn Tyr Pro Gln Cys Phe Asn Leu Gln Ile Thr Gly Ser Gly
            195                 200                 205

Thr Ala Gln Pro Ser Gly Val Lys Gly Thr Glu Leu Tyr Ser Pro Thr
    210                 215                 220

Asp Pro Gly Ile Leu Val Asn Ile Tyr Asn Ala Leu Ser Thr Tyr Ile
225                 230                 235                 240

Val Pro Gly Pro Thr Leu Ile Pro Gly Ala Val Ser Val Val Gln Ser
                245                 250                 255

Ser Ser Thr Ile Thr Ala Ser Gly Thr Pro Val Thr Gly Ser Gly Ser
            260                 265                 270

Ala Pro Thr Thr Ser Ala Thr Thr Thr Leu Ser Thr Thr Thr Arg Ala
            275                 280                 285

Thr Thr Thr Thr Thr Thr Thr Thr Ala Gly Ser Ser Thr Ser Val Gln
    290                 295                 300

Ser Val Tyr Gly Gln Cys Gly Gly Ser Gly Trp Ser Gly Pro Thr Ala
305                 310                 315                 320

Cys Val Thr Gly Ala Thr Cys Thr Ser Tyr Asn Ser Tyr Tyr Ser Gln
                325                 330                 335

Cys Ile Pro Thr Ala Ser
            340

<210> SEQ ID NO 20
<211> LENGTH: 330
<212> TYPE: PRT
<213> ORGANISM: Aspergillus fumigatus

<400> SEQUENCE: 20

Met Lys Leu Thr Ala Ser Ile Leu Phe Ser Leu Ala Ser Val Thr Pro
1               5                   10                  15

Leu Val Ser Gly His Tyr Val Phe Ser Lys Leu Ile Val Asp Gly Lys
            20                  25                  30

Pro Thr Gln Asp Phe Glu Tyr Ile Arg Arg Asn Thr Asn Asn Tyr Met
            35                  40                  45

Pro Thr Leu Pro Ser Glu Ile Leu Ser Asn Asp Phe Arg Cys Asn Lys
        50                  55                  60

Gly Ser Met Gln Ser Ala Ala Asn Thr Lys Val Tyr Lys Val Ala Pro
65                  70                  75                  80

Gly Thr Glu Leu Gly Phe Gln Leu Ala Tyr Gly Ala Glu Met Lys His
                85                  90                  95

Pro Gly Pro Leu Gln Ile Tyr Met Ser Lys Ala Pro Gly Asp Val Arg
            100                 105                 110

Ser Tyr Asp Gly Ser Gly Asp Trp Phe Lys Val His Gln Glu Gly Leu
        115                 120                 125

Cys Ala Asp Thr Ser Lys Gly Ile Lys Asp Glu Asp Trp Cys Thr Trp
    130                 135                 140

Gly Lys Asp Thr Ala Ser Phe Lys Ile Pro Gln Asp Thr Pro Ala Gly
145                 150                 155                 160

Gln Tyr Leu Val Arg Val Glu His Ile Gly Leu His Arg Gly Phe Leu
                165                 170                 175

Gly Glu Ala Glu Phe Tyr Phe Thr Cys Ala Gln Ile Glu Val Thr Gly

```
            180                 185                 190
Ser Gly Ser Gly Ser Pro Ser Pro Thr Val Lys Ile Pro Gly Val Tyr
            195                 200                 205
Lys Pro Asp Asp Pro Asn Val His Phe Asn Ile Trp Tyr Pro Thr Pro
            210                 215                 220
Thr Ala Tyr Ser Leu Pro Gly Pro Ser Val Trp Thr Gly Gly Ser Ala
225                 230                 235                 240
Gly Gly Ala Ser Pro Thr Ala Pro Ala Val Asn Asn Asn Ala Val Gln
                245                 250                 255
Ala Ala Pro Thr Thr Met Thr Thr Val Ser Ser Pro Ala Asn Pro Thr
            260                 265                 270
Ala Gly Ala Glu Ala Glu Ala Asp Cys Gly Ser Ser Glu Ser Ser Ser
            275                 280                 285
Ala Val Ala Pro Glu Gly Thr Leu Lys Lys Trp Glu Gln Cys Gly Gly
            290                 295                 300
Leu Asn Trp Thr Gly Ser Gly Ser Cys Glu Ala Arg Thr Thr Cys His
305                 310                 315                 320
Gln Tyr Asn Pro Tyr Tyr Tyr Gln Cys Ile
                325                 330

<210> SEQ ID NO 21
<211> LENGTH: 364
<212> TYPE: PRT
<213> ORGANISM: Aspergillus fumigatus

<400> SEQUENCE: 21

Met Ser Gln Thr Lys Thr Leu Ser Leu Leu Ala Ala Leu Leu Ser Ala
1               5                   10                  15
Thr Arg Val Ala Ala His Gly His Val Thr Asn Val Val Asn Gly
            20                  25                  30
Val Ser Tyr Ala Gly Phe Asp Ile Asn Ser Tyr Pro Tyr Met Ser Asp
                35                  40                  45
Pro Pro Lys Val Ala Ala Trp Thr Thr Pro Asn Thr Gly Asn Gly Phe
        50                  55                  60
Ile Ala Pro Ser Ala Tyr Asn Ser Pro Asp Ile Cys His Gln Asn
65                  70                  75                  80
Ala Thr Asn Ala Gln Ala Tyr Ile Glu Ile Ala Ala Gly Asp Arg Ile
                85                  90                  95
Gln Leu Gln Trp Thr Ala Trp Pro Glu Ser His His Gly Pro Val Ile
            100                 105                 110
Asp Met Leu Ala Ser Cys Gly Glu Ser Cys Thr Thr Val Asp Lys Thr
            115                 120                 125
Ser Leu Lys Phe Phe Lys Ile Asp Gly Val Gly Leu Val Asp Asn Ser
            130                 135                 140
Ala Val Pro Gly Thr Trp Gly Asp Asp Gln Leu Ile Ala Asn Ser Asn
145                 150                 155                 160
Ser Trp Met Val Glu Ile Pro Lys Ser Ile Ala Pro Gly Asn Tyr Val
                165                 170                 175
Leu Arg His Glu Leu Ile Ala Leu His Ser Ala Phe Glu Thr Gly Gly
            180                 185                 190
Ala Gln Asn Tyr Pro Gln Cys Phe Asn Leu Lys Val Thr Gly Ser Gly
                195                 200                 205
Thr Asp Ser Pro Ala Gly Thr Leu Gly Thr Glu Leu Tyr Thr Glu Ser
            210                 215                 220
```

```
Asp Pro Gly Leu Leu Val Asp Ile Tyr Lys Ser Ile Ala Ser Tyr Ala
225                 230                 235                 240

Val Pro Gly Pro Ala Met Tyr Thr Gly Ala Val Ser Ile Thr Gln Ser
            245                 250                 255

Thr Ser Ala Ile Thr Ala Thr Gly Thr Ala Thr Val Gly Ser Gly Ala
            260                 265                 270

Asp Ser Thr Pro Val Pro Ser Ser Ala Ala Ser Ser Glu Tyr Ser Thr
            275                 280                 285

Val Ala Val Gln Val Pro Thr Thr Lys Ala Gln Tyr Thr Pro Val Pro
            290                 295                 300

Ser Ser Ser Pro Ser Thr Phe Val Thr Ser Pro Ala Pro Thr Thr Ser
305                 310                 315                 320

Val Pro Ser Gly Ser Ser Val Pro Val Thr Ser Asn Thr Ala Ala Pro
            325                 330                 335

Leu Pro Thr Ala Ala Pro Gly Gly Thr Gln Thr Val Tyr Gly Gln Cys
            340                 345                 350

Gly Gly Gln Asn Trp Thr Gly Pro Thr Tyr Ile Val
            355                 360

<210> SEQ ID NO 22
<211> LENGTH: 270
<212> TYPE: PRT
<213> ORGANISM: Thielavia terrestris

<400> SEQUENCE: 22

Leu Leu Ser Thr Leu Ala Gly Ala Ala Ser Val Ala Ala His Gly His
1               5                   10                  15

Val Ser Asn Ile Val Ile Asn Gly Val Ser Tyr Gln Gly Tyr Asp Pro
            20                  25                  30

Thr Ser Phe Pro Tyr Met Gln Asn Pro Pro Ile Val Val Gly Trp Thr
            35                  40                  45

Ala Ala Asp Thr Asp Asn Gly Phe Val Ala Pro Asp Ala Phe Ala Ser
        50                  55                  60

Gly Asp Ile Ile Cys His Lys Asn Ala Thr Asn Ala Lys Gly His Ala
65                  70                  75                  80

Val Val Ala Ala Gly Asp Lys Ile Phe Ile Gln Trp Asn Thr Trp Pro
                85                  90                  95

Glu Ser His His Gly Pro Val Ile Asp Tyr Leu Ala Ser Cys Gly Ser
            100                 105                 110

Ala Ser Cys Glu Thr Val Asp Lys Thr Lys Leu Glu Phe Phe Lys Ile
            115                 120                 125

Asp Glu Val Gly Leu Val Asp Gly Ser Ser Ala Pro Gly Val Trp Gly
        130                 135                 140

Ser Asp Gln Leu Ile Ala Asn Asn Asn Ser Trp Leu Val Glu Ile Pro
145                 150                 155                 160

Pro Thr Ile Ala Pro Gly Asn Tyr Val Leu Arg His Glu Ile Ile Ala
                165                 170                 175

Leu His Ser Ala Glu Asn Ala Asp Gly Ala Gln Asn Tyr Pro Gln Cys
            180                 185                 190

Phe Asn Leu Gln Ile Thr Gly Thr Gly Thr Ala Thr Pro Ser Gly Val
            195                 200                 205

Pro Gly Thr Ser Leu Tyr Thr Pro Asp Pro Gly Ile Leu Val Asn
        210                 215                 220

Ile Tyr Ser Ala Pro Ile Thr Tyr Thr Val Pro Gly Pro Ala Leu Ile
225                 230                 235                 240
```

```
Ser Gly Ala Val Ser Ile Ala Gln Ser Ser Ala Ile Thr Ala Ser
            245                 250                 255

Gly Thr Ala Leu Thr Gly Ser Ala Thr Ala Pro Ala Ala Ala
            260                 265                 270

<210> SEQ ID NO 23
<211> LENGTH: 330
<212> TYPE: PRT
<213> ORGANISM: Thielavia terrestris

<400> SEQUENCE: 23

Met Pro Pro Ala Leu Pro Gln Leu Leu Thr Thr Val Leu Thr Ala Leu
1               5                   10                  15

Thr Leu Gly Ser Thr Ala Leu Ala His Ser His Leu Ala Tyr Ile Ile
            20                  25                  30

Val Asn Gly Lys Leu Tyr Gln Gly Phe Asp Pro Arg Pro His Gln Ala
        35                  40                  45

Asn Tyr Pro Ser Arg Val Gly Trp Ser Thr Gly Ala Val Asp Asp Gly
    50                  55                  60

Phe Val Thr Pro Ala Asn Tyr Ser Thr Pro Asp Ile Ile Cys His Ile
65                  70                  75                  80

Ala Gly Thr Ser Pro Ala Gly His Ala Pro Val Arg Pro Gly Asp Arg
                85                  90                  95

Ile His Val Gln Trp Asn Gly Trp Pro Val Gly His Ile Gly Pro Val
            100                 105                 110

Leu Ser Tyr Leu Ala Arg Cys Glu Ser Asp Thr Gly Cys Thr Gly Gln
        115                 120                 125

Asn Lys Thr Ala Leu Arg Trp Thr Lys Ile Asp Asp Ser Ser Pro Thr
    130                 135                 140

Met Gln Asn Val Ala Gly Ala Gly Thr Gln Gly Glu Gly Thr Pro Gly
145                 150                 155                 160

Lys Arg Trp Ala Thr Asp Val Leu Ile Ala Ala Asn Asn Ser Trp Gln
                165                 170                 175

Val Ala Val Pro Ala Gly Leu Pro Thr Gly Ala Tyr Val Leu Arg Asn
            180                 185                 190

Glu Ile Ile Ala Leu His Tyr Ala Ala Arg Lys Asn Gly Ala Gln Asn
        195                 200                 205

Tyr Pro Leu Cys Met Asn Leu Trp Val Asp Ala Ser Gly Asp Asn Ser
    210                 215                 220

Ser Val Ala Ala Thr Thr Ala Val Thr Ala Gly Gly Leu Gln Met
225                 230                 235                 240

Asp Ala Tyr Asp Ala Arg Gly Phe Tyr Lys Glu Asn Asp Pro Gly Val
                245                 250                 255

Leu Val Asn Val Thr Ala Ala Leu Ser Ser Tyr Val Val Pro Gly Pro
            260                 265                 270

Thr Val Ala Ala Gly Ala Thr Pro Val Pro Tyr Ala Gln Gln Ser Pro
        275                 280                 285

Ser Val Ser Thr Ala Ala Gly Thr Pro Val Val Thr Arg Thr Ser
    290                 295                 300

Glu Thr Ala Pro Tyr Thr Gly Ala Met Thr Pro Thr Val Ala Ala Arg
305                 310                 315                 320

Met Lys Gly Arg Gly Tyr Asp Arg Arg Gly
                325                 330
```

```
<210> SEQ ID NO 24
<211> LENGTH: 315
<212> TYPE: PRT
<213> ORGANISM: Thielavia terrestris

<400> SEQUENCE: 24

Met Arg Thr Thr Phe Ala Ala Leu Ala Phe Ala Ala Gln Glu
1               5                   10                  15

Val Ala Gly His Ala Ile Phe Gln Gln Leu Trp Val Asp Gly Thr Asp
            20                  25                  30

Tyr Ile Arg Ala Pro Leu Phe Leu Phe Gly Lys Cys Pro Val Lys Ala
            35                  40                  45

Gly Gly Thr Val Thr Val Glu Met His Gln Gln Pro Gly Asp Arg Ser
        50                  55                  60

Cys Asn Asn Glu Ala Ile Gly Ala His Trp Gly Pro Val Gln Val
65                  70                  75                  80

Tyr Leu Ser Lys Val Glu Asp Ala Ser Thr Ala Asp Gly Ser Thr Gly
                85                  90                  95

Trp Phe Lys Ile Phe Ala Asp Thr Trp Ser Lys Ala Gly Ser Ser
                100                 105                 110

Val Gly Asp Asp Asp Asn Trp Gly Thr Arg Asp Leu Asn Ala Cys Cys
            115                 120                 125

Gly Lys Met Gln Val Lys Ile Pro Ala Asp Ile Pro Ser Gly Asp Tyr
        130                 135                 140

Leu Leu Arg Ala Glu Ala Leu Ala Leu His Thr Ala Gly Gln Val Gly
145                 150                 155                 160

Gly Ala Gln Phe Tyr Met Ser Cys Tyr Gln Ile Thr Val Ser Gly Gly
                165                 170                 175

Gly Ser Ala Ser Pro Ala Thr Val Lys Phe Pro Gly Ala Tyr Ser Ala
            180                 185                 190

Asn Asp Pro Gly Ile His Ile Asn Ile His Ala Ala Val Ser Asn Tyr
        195                 200                 205

Val Ala Pro Gly Pro Ala Val Tyr Ser Gly Gly Thr Thr Lys Val Ala
    210                 215                 220

Gly Ser Gly Cys Gln Gly Cys Glu Asn Thr Cys Lys Val Gly Ser Ser
225                 230                 235                 240

Pro Thr Ala Thr Ala Pro Ser Gly Lys Ser Gly Ala Gly Ser Asp Gly
                245                 250                 255

Gly Ala Gly Thr Asp Gly Gly Ser Ser Ser Ser Pro Asp Thr Gly
            260                 265                 270

Ser Ala Cys Ser Val Gln Ala Tyr Gly Gln Cys Gly Gly Asn Gly Tyr
        275                 280                 285

Ser Gly Cys Thr Gln Cys Ala Pro Gly Tyr Thr Cys Lys Ala Val Ser
    290                 295                 300

Pro Pro Tyr Tyr Ser Gln Cys Ala Pro Ser Ser
305                 310                 315

<210> SEQ ID NO 25
<211> LENGTH: 349
<212> TYPE: PRT
<213> ORGANISM: Chaetomium globosum

<400> SEQUENCE: 25

Met Ser Lys Ala Ser Ala Leu Leu Ala Thr Leu Thr Gly Ala Ala Leu
1               5                   10                  15

Val Ala Ala His Gly His Val Ser His Ile Ile Val Asn Gly Val Tyr
```

```
                20                  25                  30
Tyr Glu Asn Tyr Asp Pro Thr Thr His Trp Tyr Gln Pro Asn Pro Pro
            35                  40                  45

Thr Val Ile Gly Trp Lys Ala Ala Gln Gln Asp Asn Gly Phe Val Glu
        50                  55                  60

Pro Asn Asn Phe Gly Thr Ser Asp Ile Ile Cys His Lys Ser Gly Ser
65                  70                  75                  80

Pro Gly Gly His Ala Thr Val Ala Ala Gly Asp Lys Ile Ser Ile
                85                  90                  95

Val Trp Asp Pro Glu Trp Pro Glu Ser His Ile Gly Pro Val Ile Asp
            100                 105                 110

Tyr Leu Ala Ala Cys Asn Gly Asp Cys Glu Thr Val Asp Lys Ala Ser
            115                 120                 125

Leu Arg Phe Phe Lys Ile Asp Gly Ala Gly Tyr Asp Lys Thr Ala Gly
            130                 135                 140

Arg Trp Ala Ala Asp Thr Leu Arg Ala Asn Gly Asn Ser Trp Leu Val
145                 150                 155                 160

Gln Ile Pro Ala Asp Leu Lys Ala Gly Asn Tyr Val Leu Arg His Glu
            165                 170                 175

Ile Ile Ala Leu His Gly Ala Ser Ser Pro Asn Gly Ala Gln Ala Tyr
            180                 185                 190

Pro Gln Cys Ile Asn Leu Arg Val Thr Gly Ser Gly Thr Asn Ala Pro
            195                 200                 205

Ser Gly Val Ala Gly Thr Ser Leu Tyr Arg Ala Ser Asp Ala Gly Ile
            210                 215                 220

Leu Phe Asn Pro Tyr Val Ala Ser Pro Asn Tyr Pro Val Pro Gly Pro
225                 230                 235                 240

Ala Leu Ile Ala Gly Ala Ala Ser Val Ala Gln Ser Lys Ser Val
            245                 250                 255

Ala Thr Ala Thr Ala Ser Ala Thr Leu Pro Gly Asn Asn Gly Gly
            260                 265                 270

Gly Pro Asn Pro Gln Pro Thr Thr Ala Thr Thr Ala Asn Pro Gly
            275                 280                 285

Val Ser Thr Thr Leu Arg Thr Ser Thr Ser Thr Ser Thr Ser Ala Gln
            290                 295                 300

Val Thr Pro Pro Thr Gly Asn Ala Gln Thr Lys Tyr Gly Gln
305                 310                 315                 320

Cys Gly Gly Ser Gly Trp Thr Gly Pro Thr Ala Cys Ala Ala Gly Ser
            325                 330                 335

Ser Cys Ser Val Leu Asn Asp Trp Tyr Ala Gln Cys Val
            340                 345

<210> SEQ ID NO 26
<211> LENGTH: 249
<212> TYPE: PRT
<213> ORGANISM: Trichoderma reesei

<400> SEQUENCE: 26

Met Lys Ser Cys Ala Ile Leu Ala Ala Leu Gly Cys Leu Ala Gly Ser
1               5                   10                  15

Val Leu Gly His Gly Gln Val Gln Asn Phe Thr Ile Asn Gly Gln Tyr
            20                  25                  30

Asn Gln Gly Phe Ile Leu Asp Tyr Tyr Gln Lys Gln Asn Thr Gly
            35                  40                  45
```

```
His Phe Pro Asn Val Ala Gly Trp Tyr Ala Glu Asp Leu Asp Leu Gly
 50                  55                  60

Phe Ile Ser Pro Asp Gln Tyr Thr Thr Pro Asp Ile Val Cys His Lys
 65                  70                  75                  80

Asn Ala Ala Pro Gly Ala Ile Ser Ala Thr Ala Ala Gly Ser Asn
                 85                  90                  95

Ile Val Phe Gln Trp Gly Pro Gly Val Trp Pro His Pro Tyr Gly Pro
                100                 105                 110

Ile Val Thr Tyr Val Val Glu Cys Ser Gly Ser Cys Thr Thr Val Asn
                115                 120                 125

Lys Asn Asn Leu Arg Trp Val Lys Ile Gln Glu Ala Gly Ile Asn Tyr
130                 135                 140

Asn Thr Gln Val Trp Ala Gln Gln Asp Leu Ile Asn Gln Gly Asn Lys
145                 150                 155                 160

Trp Thr Val Lys Ile Pro Ser Ser Leu Arg Pro Gly Asn Tyr Val Phe
                165                 170                 175

Arg His Glu Leu Leu Ala Ala His Gly Ala Ser Ser Ala Asn Gly Met
                180                 185                 190

Gln Asn Tyr Pro Gln Cys Val Asn Ile Ala Val Thr Gly Ser Gly Thr
                195                 200                 205

Lys Ala Leu Pro Ala Gly Thr Pro Ala Thr Gln Leu Tyr Lys Pro Thr
210                 215                 220

Asp Pro Gly Ile Leu Phe Asn Pro Tyr Thr Thr Ile Thr Ser Tyr Thr
225                 230                 235                 240

Ile Pro Gly Pro Ala Leu Trp Gln Gly
                245

<210> SEQ ID NO 27
<211> LENGTH: 344
<212> TYPE: PRT
<213> ORGANISM: Trichoderma reesei

<400> SEQUENCE: 27

Met Ile Gln Lys Leu Ser Asn Leu Leu Val Thr Ala Leu Ala Val Ala
1                   5                  10                  15

Thr Gly Val Val Gly His Gly His Ile Asn Asp Ile Val Ile Asn Gly
                 20                  25                  30

Val Trp Tyr Gln Ala Tyr Asp Pro Thr Thr Phe Pro Tyr Glu Ser Asn
                 35                  40                  45

Pro Pro Ile Val Val Gly Trp Thr Ala Ala Asp Leu Asp Asn Gly Phe
 50                  55                  60

Val Ser Pro Asp Ala Tyr Gln Asn Pro Asp Ile Ile Cys His Lys Asn
 65                  70                  75                  80

Ala Thr Asn Ala Lys Gly His Ala Ser Val Lys Ala Gly Asp Thr Ile
                 85                  90                  95

Leu Phe Gln Trp Val Pro Val Pro Trp Pro His Pro Gly Pro Ile Val
                100                 105                 110

Asp Tyr Leu Ala Asn Cys Asn Gly Asp Cys Glu Thr Val Asp Lys Thr
                115                 120                 125

Thr Leu Glu Phe Phe Lys Ile Asp Gly Val Gly Leu Leu Ser Gly Gly
                130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175
```

-continued

Arg His Glu Ile Ile Ala Leu His Ser Ala Gly Gln Ala Asn Gly Ala
            180                 185                 190

Gln Asn Tyr Pro Gln Cys Phe Asn Ile Ala Val Ser Gly Ser Gly Ser
        195                 200                 205

Leu Gln Pro Ser Gly Val Leu Gly Thr Asp Leu Tyr His Ala Thr Asp
    210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
                260                 265                 270

Ser Gly Pro Thr Ser Arg Thr Thr Thr Ala Arg Thr Thr Gln Ala
            275                 280                 285

Ser Ser Arg Pro Ser Ser Thr Pro Pro Ala Thr Thr Ser Ala Pro Ala
    290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
            340

<210> SEQ ID NO 28
<211> LENGTH: 250
<212> TYPE: PRT
<213> ORGANISM: Aspergillus fumigatus

<400> SEQUENCE: 28

Met Thr Leu Ser Lys Ile Thr Ser Ile Ala Gly Leu Leu Ala Ser Ala
1               5                   10                  15

Ser Leu Val Ala Gly His Gly Phe Val Ser Gly Ile Val Ala Asp Gly
                20                  25                  30

Lys Tyr Tyr Gly Gly Tyr Leu Val Asn Gln Tyr Pro Tyr Met Ser Asn
            35                  40                  45

Pro Pro Asp Thr Ile Ala Trp Ser Thr Thr Ala Thr Asp Leu Gly Phe
    50                  55                  60

Val Asp Gly Thr Gly Tyr Gln Ser Pro Asp Ile Ile Cys His Arg Asp
65                  70                  75                  80

Ala Lys Asn Gly Lys Leu Thr Ala Thr Val Ala Ala Gly Ser Gln Ile
                85                  90                  95

Glu Phe Gln Trp Thr Thr Trp Pro Glu Ser His His Gly Pro Leu Ile
            100                 105                 110

Thr Tyr Leu Ala Pro Cys Asn Gly Asp Cys Ala Thr Val Asp Lys Thr
        115                 120                 125

Thr Leu Lys Phe Val Lys Ile Ala Ala Gln Gly Leu Ile Asp Gly Ser
    130                 135                 140

Asn Pro Pro Gly Val Trp Ala Asp Asp Glu Met Ile Ala Asn Asn
145                 150                 155                 160

Thr Ala Thr Val Thr Ile Pro Ala Ser Tyr Ala Pro Gly Asn Tyr Val
                165                 170                 175

Leu Arg His Glu Ile Ile Ala Leu His Ser Ala Gly Asn Leu Asn Gly
            180                 185                 190

Ala Gln Asn Tyr Pro Gln Cys Phe Asn Ile Gln Ile Thr Gly Gly Gly

```
              195                 200                 205
Ser Ala Gln Gly Ser Gly Thr Ala Gly Thr Ser Leu Tyr Lys Asn Thr
        210                 215                 220

Asp Pro Gly Ile Lys Phe Asp Ile Tyr Ser Asp Leu Ser Gly Gly Tyr
225                 230                 235                 240

Pro Ile Pro Gly Pro Ala Leu Phe Asn Ala
                245                 250

<210> SEQ ID NO 29
<211> LENGTH: 226
<212> TYPE: PRT
<213> ORGANISM: Thielavia terrestris

<400> SEQUENCE: 29

Met Leu Ala Asn Gly Ala Ile Val Phe Leu Ala Ala Leu Gly Val
1               5                   10                  15

Ser Gly His Tyr Thr Trp Pro Arg Val Asn Asp Gly Ala Asp Trp Gln
                20                  25                  30

Gln Val Arg Lys Ala Asp Asn Trp Gln Asp Asn Gly Tyr Val Gly Asp
            35                  40                  45

Val Thr Ser Pro Gln Ile Arg Cys Phe Gln Ala Thr Pro Ser Pro Ala
        50                  55                  60

Pro Ser Val Leu Asn Thr Thr Ala Gly Ser Thr Val Thr Tyr Trp Ala
65                  70                  75                  80

Asn Pro Asp Val Tyr His Pro Gly Pro Val Gln Phe Tyr Met Ala Arg
                85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
    130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
                165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225

<210> SEQ ID NO 30
<211> LENGTH: 1044
<212> TYPE: DNA
<213> ORGANISM: Trichoderma reesei

<400> SEQUENCE: 30
atgatccaga agctttccaa ccttcttctc accgcactag cggtggcaac cggtgttgtt      60
ggacacggac acatcaacaa cattgtcgtc aacggagtgt actaccaggg atatgatcct     120
acatcgttcc catatgaatc tgacccgccc atagtggtgg gctggacggc tgccgatctt     180
gacaacggct tcgtctcacc cgacgcatat cagagcccgg acatcatctg ccacaagaat     240
```

-continued

```
gccaccaacg ccaaaggaca cgcgtccgtc aaggccggag acactattcc cctccagtgg    300
gtgccagttc cttggccgca cccaggcccc atcgtcgact acctggccaa ctgcaacggc    360
gactgcgaga ccgtggacaa gacgtccctt gagttcttca agattgacgg cgtcggtctc    420
atcagcggcg gagatccggg caactgggcc tcggacgtgt tgattgccaa caacaacacc    480
tgggttgtca agatccccga ggatctcgcc ccgggcaact acgtgcttcg ccacgagatc    540
atcgccttgc acagcgccgg gcaggcggac ggcgctcaga actaccctca gtgcttcaac    600
ctcgccgtcc caggctccgg atctctgcag ccgagcggcg tcaagggaac cgcgctctac    660
cactccgatg accccggtgt cctcatcaac atctacacca gccctcttgc gtacaccatt    720 cctggaccttt ccgtggtatc aggcctcccc acgagtgtcg cccagggcag ctccgccgcg    780
acggccactg ccagcgccac tgttcctggc ggtagcggac cgggaaaccc gaccagtaag    840
actacgacga cggcgaggac gacacaggcc tcctctagca gggccagctc tactcctcct    900
gctactacgt cggcacctgg tggaggccca acccagactt tgtacggcca gtgtggtggc    960
agcggctaca gtggtcctac tcgatgcgcg ccgccggcca cttgctctac cttgaaccca   1020
tactacgccc agtgccttaa ctag                                           1044
```

<210> SEQ ID NO 31
<211> LENGTH: 471
<212> TYPE: PRT
<213> ORGANISM: Trichoderma reesei

<400> SEQUENCE: 31

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Gly
                85                  90                  95

Ser Thr Thr Thr Arg Val Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220
```

Thr Ile Arg Gln Ile Val Glu Tyr Ser Asp Ile Arg Thr Leu Leu
225                 230                 235                 240

Val Ile Glu Pro Asp Ser Leu Ala Asn Leu Val Thr Asn Leu Gly Thr
            245                 250                 255

Pro Lys Cys Ala Asn Ala Gln Ser Ala Tyr Leu Glu Cys Ile Asn Tyr
        260                 265                 270

Ala Val Thr Gln Leu Asn Leu Pro Asn Val Ala Met Tyr Leu Asp Ala
    275                 280                 285

Gly His Ala Gly Trp Leu Gly Trp Pro Ala Asn Gln Asp Pro Ala Ala
290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Ser Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 32
<211> LENGTH: 513
<212> TYPE: PRT
<213> ORGANISM: Trichoderma reesei

<400> SEQUENCE: 32

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

```
Ala Ser Asp Thr Thr Tyr Gln Glu Phe Thr Leu Leu Gly Asn Glu Phe
        130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Arg Gly Thr Thr Thr Thr
    450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
                485                 490                 495

Ala Ser Gly Thr Thr Cys Gln Val Leu Asn Pro Tyr Tyr Ser Gln Cys
            500                 505                 510

Leu

<210> SEQ ID NO 33
<211> LENGTH: 837
<212> TYPE: PRT
```

<213> ORGANISM: Trichoderma reesei

<400> SEQUENCE: 33

```
Met Lys Val Ser Arg Val Leu Ala Leu Val Leu Gly Ala Val Ile Pro
1               5                   10                  15

Ala His Ala Ala Phe Ser Trp Lys Asn Val Lys Leu Gly Gly Gly Gly
            20                  25                  30

Gly Phe Val Pro Gly Ile Ile Phe His Pro Lys Thr Lys Gly Val Ala
        35                  40                  45

Tyr Ala Arg Thr Asp Ile Gly Gly Leu Tyr Arg Leu Asn Ala Asp Asp
50                  55                  60

Ser Trp Thr Ala Val Thr Asp Gly Ile Ala Asp Asn Ala Gly Trp His
65                  70                  75                  80

Asn Trp Gly Ile Asp Ala Val Ala Leu Asp Pro Gln Asp Asp Gln Lys
                85                  90                  95

Val Tyr Ala Ala Val Gly Met Tyr Thr Asn Ser Trp Asp Pro Ser Asn
            100                 105                 110

Gly Ala Ile Ile Arg Ser Ser Asp Arg Gly Ala Thr Trp Ser Phe Thr
        115                 120                 125

Asn Leu Pro Phe Lys Val Gly Gly Asn Met Pro Gly Arg Gly Ala Gly
    130                 135                 140

Glu Arg Leu Ala Val Asp Pro Ala Asn Ser Asn Ile Ile Tyr Phe Gly
145                 150                 155                 160

Ala Arg Ser Gly Asn Gly Leu Trp Lys Ser Thr Asp Gly Gly Val Thr
                165                 170                 175

Phe Ser Lys Val Ser Ser Phe Thr Ala Thr Gly Thr Tyr Ile Pro Asp
            180                 185                 190

Pro Ser Asp Ser Asn Gly Tyr Asn Ser Asp Lys Gln Gly Leu Met Trp
        195                 200                 205

Val Thr Phe Asp Ser Thr Ser Ser Thr Thr Gly Gly Ala Thr Ser Arg
    210                 215                 220

Ile Phe Val Gly Thr Ala Asp Asn Ile Thr Ala Ser Val Tyr Val Ser
225                 230                 235                 240

Thr Asn Ala Gly Ser Thr Trp Ser Ala Val Pro Gly Gln Pro Gly Lys
                245                 250                 255

Tyr Phe Pro His Lys Ala Lys Leu Gln Pro Ala Glu Lys Ala Leu Tyr
            260                 265                 270

Leu Thr Tyr Ser Asp Gly Thr Gly Pro Tyr Asp Gly Thr Leu Gly Ser
        275                 280                 285

Val Trp Arg Tyr Asp Ile Ala Gly Gly Thr Trp Lys Asp Ile Thr Pro
    290                 295                 300

Val Ser Gly Ser Asp Leu Tyr Phe Gly Phe Gly Gly Leu Gly Leu Asp
305                 310                 315                 320

Leu Gln Lys Pro Gly Thr Leu Val Val Ala Ser Leu Asn Ser Trp Trp
                325                 330                 335

Pro Asp Ala Gln Leu Phe Arg Ser Thr Asp Ser Gly Thr Thr Trp Ser
            340                 345                 350

Pro Ile Trp Ala Trp Ala Ser Tyr Pro Thr Glu Thr Tyr Tyr Tyr Ser
        355                 360                 365

Ile Ser Thr Pro Lys Ala Pro Trp Ile Lys Asn Asn Phe Ile Asp Val
    370                 375                 380

Thr Ser Glu Ser Pro Ser Asp Gly Leu Ile Lys Arg Leu Gly Trp Met
385                 390                 395                 400
```

```
Ile Glu Ser Leu Glu Ile Asp Pro Thr Asp Ser Asn His Trp Leu Tyr
                405                 410                 415
Gly Thr Gly Met Thr Ile Phe Gly Gly His Asp Leu Thr Asn Trp Asp
            420                 425                 430
Thr Arg His Asn Val Ser Ile Gln Ser Leu Ala Asp Gly Ile Glu Glu
        435                 440                 445
Phe Ser Val Gln Asp Leu Ala Ser Ala Pro Gly Gly Ser Glu Leu Leu
    450                 455                 460
Ala Ala Val Gly Asp Asp Asn Gly Phe Thr Phe Ala Ser Arg Asn Asp
465                 470                 475                 480
Leu Gly Thr Ser Pro Gln Thr Val Trp Ala Thr Pro Thr Trp Ala Thr
                485                 490                 495
Ser Thr Ser Val Asp Tyr Ala Gly Asn Ser Val Lys Ser Val Val Arg
                500                 505                 510
Val Gly Asn Thr Ala Gly Thr Gln Val Ala Ile Ser Ser Asp Gly Gly
                515                 520                 525
Ala Thr Trp Ser Ile Asp Tyr Ala Ala Asp Thr Ser Met Asn Gly Gly
            530                 535                 540
Thr Val Ala Tyr Ser Ala Asp Gly Asp Thr Ile Leu Trp Ser Thr Ala
545                 550                 555                 560
Ser Ser Gly Val Gln Arg Ser Gln Phe Gln Gly Ser Phe Ala Ser Val
                565                 570                 575
Ser Ser Leu Pro Ala Gly Ala Val Ile Ala Ser Asp Lys Lys Thr Asn
                580                 585                 590
Ser Val Phe Tyr Ala Gly Ser Gly Ser Thr Phe Tyr Val Ser Lys Asp
                595                 600                 605
Thr Gly Ser Ser Phe Thr Arg Gly Pro Lys Leu Gly Ser Ala Gly Thr
            610                 615                 620
Ile Arg Asp Ile Ala Ala His Pro Thr Thr Ala Gly Thr Leu Tyr Val
625                 630                 635                 640
Ser Thr Asp Val Gly Ile Phe Arg Ser Thr Asp Ser Gly Thr Thr Phe
                645                 650                 655
Gly Gln Val Ser Thr Ala Leu Thr Asn Thr Tyr Gln Ile Ala Leu Gly
                660                 665                 670
Val Gly Ser Gly Ser Asn Trp Asn Leu Tyr Ala Phe Gly Thr Gly Pro
                675                 680                 685
Ser Gly Ala Arg Leu Tyr Ala Ser Gly Asp Ser Gly Ala Ser Trp Thr
            690                 695                 700
Asp Ile Gln Gly Ser Gln Gly Phe Gly Ser Ile Asp Ser Thr Lys Val
705                 710                 715                 720
Ala Gly Ser Gly Ser Thr Ala Gly Gln Val Tyr Val Gly Thr Asn Gly
                725                 730                 735
Arg Gly Val Phe Tyr Ala Gln Gly Thr Val Gly Gly Thr Gly Gly
            740                 745                 750
Thr Ser Ser Ser Thr Lys Gln Ser Ser Ser Thr Ser Ser Ala Ser
            755                 760                 765
Ser Ser Thr Thr Leu Arg Ser Ser Val Ser Thr Thr Arg Ala Ser
    770                 775                 780
Thr Val Thr Ser Ser Arg Thr Ser Ser Ala Ala Gly Pro Thr Gly Ser
785                 790                 795                 800
Gly Val Ala Gly His Tyr Ala Gln Cys Gly Gly Ile Gly Trp Thr Gly
                805                 810                 815
Pro Thr Gln Cys Val Ala Pro Tyr Val Cys Gln Lys Gln Asn Asp Tyr
```

```
          820                 825                 830

Tyr Tyr Gln Cys Val
        835

<210> SEQ ID NO 34
<211> LENGTH: 297
<212> TYPE: PRT
<213> ORGANISM: Staphylotrichum coccosporum

<400> SEQUENCE: 34

Met Arg Ser Ser Pro Phe Leu Arg Ala Ala Leu Ala Ala Ala Leu Pro
1               5                   10                  15

Leu Ser Ala His Ala Leu Asp Gly Lys Ser Thr Arg Tyr Trp Asp Cys
            20                  25                  30

Cys Lys Pro Ser Cys Gly Trp Pro Gly Lys Ala Ser Val Asn Gln Pro
        35                  40                  45

Val Phe Ser Cys Ser Ala Asp Trp Gln Arg Ile Ser Asp Phe Asn Ala
    50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
    130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
    210                 215                 220

Ala Ser Tyr Pro Val Phe Asn Pro Pro Ser Gly Gly Ser Pro Ser Thr
225                 230                 235                 240

Thr Ser Thr Thr Thr Ser Ser Pro Ser Gly Pro Thr Gly Asn Pro Pro
                245                 250                 255

Gly Gly Gly Gly Cys Thr Ala Gln Lys Trp Ala Gln Cys Gly Gly Thr
            260                 265                 270

Gly Phe Thr Gly Cys Thr Thr Cys Val Ser Gly Thr Thr Cys Gln Val
        275                 280                 285

Gln Asn Gln Trp Tyr Ser Gln Cys Leu
    290                 295

<210> SEQ ID NO 35
<211> LENGTH: 2358
<212> TYPE: DNA
<213> ORGANISM: Fusarium verticillioides

<400> SEQUENCE: 35
atgctgctca atcttcaggt cgctgccagc gctttgtcgc tttctctttt aggtggattg      60
```

```
gctgaggctg ctacgccata tacccttccg gactgtacca aaggaccttt gagcaagaat      120
ggaatctgcg atacttcgtt atctccagct aaaagagcgg ctgctctagt tgctgctctg      180
acgcccgaag agaaggtggg caatctggtc aggtaaaata tacccccccc cataatcact      240
attcggagat tggagctgac ttaacgcagc aatgcaactg gtgcaccaag aatcggactt      300
ccaaggtaca actggtggaa cgaagcccct tcatggcctcg ctggatctcc aggtggtcgc      360
tttgccgaca ctcctcccta cgacgcggcc acatcatttc ccatgcctct tctcatggcc      420
gctgctttcg acgatgatct gatccacgat atcggcaacg tcgtcggcac cgaagcgcgt      480
gcgttcacta acggcggttg gcgcggagtc gacttctgga cacccaacgt caacccttt      540 aaagatcctc gctggggtcg tggctccgaa actccaggtg aagatgccct tcatgtcagc      600
cggtatgctc gctatatcgt caggggtctc gaaggcgata aggagcaacg acgtattgtt      660
gctacctgca agcactatgc tggaaacgac tttgaggact ggggaggctt cacgcgtcac      720
gactttgatg ccaagattac tcctcaggac ttggctgagt actacgtcag gcctttccag      780
gagtgcaccc gtgatgcaaa ggttggttcc atcatgtgcg cctacaatgc cgtgaacggc      840
attcccgcat gcgcaaactc gtatctgcag gagacgatcc tcagagggca ctggaactgg      900
acgcgcgata caactggat cactagtgat tgtggcgcca tgcaggatat ctggcagaat      960
cacaagtatg tcaagaccaa cgctgaaggt gcccaggtag cttttgagaa cggcatggat     1020
tctagctgcg agtatactac taccagcgat gtctccgatt cgtacaagca aggcctcttg     1080
actgagaagc tcatggatcg ttcgttgaag cgcctttcg aagggcttgt tcatactggt     1140
ttctttgacg gtgccaaagc gcaatggaac tcgctcagtt ttgcggatgt caacaccaag     1200
gaagctcagg atcttgcact cagatctgct gtggagggtg ctgttcttct taagaatgac     1260
ggcactttgc ctctgaagct caagaagaag gatagtgttg caatgatcgg attctgggcc     1320
aacgatactt ccaagctgca gggtggttac agtggacgtg ctccgttcct ccacagcccg     1380
ctttatgcag ctgagaagct tggtcttgac accaacgtgg cttggggtcc gacactgcag     1440
aacagctcat ctcatgataa ctggaccacc aatgctgttg ctgcggcgaa gaagtctgat     1500
tacattctct actttggtgg tcttgacgcc tctgctgctg gcgaggacag agatcgtgag     1560
aaccttgact ggcctgagag ccagctgacc cttcttcaga agctctctag tctcggcaag     1620
ccactggttg ttatccagct tggtgatcaa gtcgatgaca ccgctctttt gaagaacaag     1680
aagattaaca gtattctttg ggtcaattac cctggtcagg atggcggcac tgcagtcatg     1740
gacctgctca ctggacgaaa gagtcctgct ggccgactac ccgtcacgca atatcccagt     1800
aaatacactg agcagattgg catgactgac atggacctca gacctaccaa gtcgttgcca     1860
gggagaactt atcgctggta ctcaactcca gttcttccct acggctttgg cctccactac     1920
accaagttcc aagccaagtt caagtccaac aagttgacgt ttgacatcca gaagcttctc     1980
aagggctgca gtgctcaata ctccgatact gcgcgctgc ccccccatcca agttagtgtc     2040 aagaacaccg gccgcattac ctccgacttt gtctctctgg tctttatcaa gagtgaagtt     2100
ggacctaagc cttaccctct caagacccct gcggcttatg gtcgcttgca tgatgtcgcg     2160
ccttcatcga cgaaggatat ctcactggag tggacgttgg ataacattgc gcgacgggga     2220
gagaatggtg atttggttgt ttatcctggg acttacactc tgttgctgga tgagcctacg     2280
caagccaaga tccaggttac gctgactgga aagaaggcta ttttggataa gtggcctcaa     2340
gaccccaagt ctgcgtaa                                                   2358
```

<210> SEQ ID NO 36
<211> LENGTH: 766
<212> TYPE: PRT
<213> ORGANISM: Fusarium verticillioides

<400> SEQUENCE: 36

```
Met Leu Leu Asn Leu Gln Val Ala Ala Ser Ala Leu Ser Leu Ser Leu
1               5                   10                  15

Leu Gly Gly Leu Ala Glu Ala Ala Thr Pro Tyr Thr Leu Pro Asp Cys
            20                  25                  30

Thr Lys Gly Pro Leu Ser Lys Asn Gly Ile Cys Asp Thr Ser Leu Ser
        35                  40                  45

Pro Ala Lys Arg Ala Ala Ala Leu Val Ala Ala Leu Thr Pro Glu Glu
    50                  55                  60

Lys Val Gly Asn Leu Val Ser Asn Ala Thr Gly Ala Pro Arg Ile Gly
65                  70                  75                  80

Leu Pro Arg Tyr Asn Trp Trp Asn Glu Ala Leu His Gly Leu Ala Gly
                85                  90                  95

Ser Pro Gly Gly Arg Phe Ala Asp Thr Pro Pro Tyr Asp Ala Ala Thr
            100                 105                 110

Ser Phe Pro Met Pro Leu Leu Met Ala Ala Ala Phe Asp Asp Asp Leu
        115                 120                 125

Ile His Asp Ile Gly Asn Val Val Gly Thr Glu Ala Arg Ala Phe Thr
130                 135                 140

Asn Gly Gly Trp Arg Gly Val Asp Phe Trp Thr Pro Asn Val Asn Pro
145                 150                 155                 160

Phe Lys Asp Pro Arg Trp Gly Arg Gly Ser Glu Thr Pro Gly Glu Asp
                165                 170                 175

Ala Leu His Val Ser Arg Tyr Ala Arg Tyr Ile Val Arg Gly Leu Glu
            180                 185                 190

Gly Asp Lys Glu Gln Arg Arg Ile Val Ala Thr Cys Lys His Tyr Ala
        195                 200                 205

Gly Asn Asp Phe Glu Asp Trp Gly Gly Phe Thr Arg His Asp Phe Asp
    210                 215                 220

Ala Lys Ile Thr Pro Gln Asp Leu Ala Glu Tyr Tyr Val Arg Pro Phe
225                 230                 235                 240

Gln Glu Cys Thr Arg Asp Ala Lys Val Gly Ser Ile Met Cys Ala Tyr
                245                 250                 255

Asn Ala Val Asn Gly Ile Pro Ala Cys Ala Asn Ser Tyr Leu Gln Glu
            260                 265                 270

Thr Ile Leu Arg Gly His Trp Asn Trp Thr Arg Asp Asn Asn Trp Ile
        275                 280                 285

Thr Ser Asp Cys Gly Ala Met Gln Asp Ile Trp Gln Asn His Lys Tyr
    290                 295                 300

Val Lys Thr Asn Ala Glu Gly Ala Gln Val Ala Phe Glu Asn Gly Met
305                 310                 315                 320

Asp Ser Ser Cys Glu Tyr Thr Thr Ser Asp Val Ser Asp Ser Tyr
                325                 330                 335

Lys Gln Gly Leu Leu Thr Glu Lys Leu Met Asp Arg Ser Leu Lys Arg
            340                 345                 350

Leu Phe Glu Gly Leu Val His Thr Gly Phe Phe Asp Gly Ala Lys Ala
        355                 360                 365

Gln Trp Asn Ser Leu Ser Phe Ala Asp Val Asn Thr Lys Glu Ala Gln
    370                 375                 380
```

Asp Leu Ala Leu Arg Ser Ala Val Glu Gly Ala Val Leu Leu Lys Asn
385                 390                 395                 400

Asp Gly Thr Leu Pro Leu Lys Leu Lys Lys Lys Asp Ser Val Ala Met
            405                 410                 415

Ile Gly Phe Trp Ala Asn Asp Thr Ser Lys Leu Gln Gly Gly Tyr Ser
            420                 425                 430

Gly Arg Ala Pro Phe Leu His Ser Pro Leu Tyr Ala Ala Glu Lys Leu
        435                 440                 445

Gly Leu Asp Thr Asn Val Ala Trp Gly Pro Thr Leu Gln Asn Ser Ser
    450                 455                 460

Ser His Asp Asn Trp Thr Thr Asn Ala Val Ala Ala Lys Lys Ser
465                 470                 475                 480

Asp Tyr Ile Leu Tyr Phe Gly Leu Asp Ala Ser Ala Ala Gly Glu
                485                 490                 495

Asp Arg Asp Arg Glu Asn Leu Asp Trp Pro Glu Ser Gln Leu Thr Leu
            500                 505                 510

Leu Gln Lys Leu Ser Ser Leu Gly Lys Pro Leu Val Val Ile Gln Leu
        515                 520                 525

Gly Asp Gln Val Asp Asp Thr Ala Leu Leu Lys Asn Lys Lys Ile Asn
530                 535                 540

Ser Ile Leu Trp Val Asn Tyr Pro Gly Gln Asp Gly Gly Thr Ala Val
545                 550                 555                 560

Met Asp Leu Leu Thr Gly Arg Lys Ser Pro Ala Gly Arg Leu Pro Val
            565                 570                 575

Thr Gln Tyr Pro Ser Lys Tyr Thr Glu Gln Ile Gly Met Thr Asp Met
            580                 585                 590

Asp Leu Arg Pro Thr Lys Ser Leu Pro Gly Arg Thr Tyr Arg Trp Tyr
        595                 600                 605

Ser Thr Pro Val Leu Pro Tyr Gly Phe Gly Leu His Tyr Thr Lys Phe
    610                 615                 620

Gln Ala Lys Phe Lys Ser Asn Lys Leu Thr Phe Asp Ile Gln Lys Leu
625                 630                 635                 640

Leu Lys Gly Cys Ser Ala Gln Tyr Ser Asp Thr Cys Ala Leu Pro Pro
            645                 650                 655

Ile Gln Val Ser Val Lys Asn Thr Gly Arg Ile Thr Ser Asp Phe Val
            660                 665                 670

Ser Leu Val Phe Ile Lys Ser Glu Val Gly Pro Lys Pro Tyr Pro Leu
        675                 680                 685

Lys Thr Leu Ala Ala Tyr Gly Arg Leu His Asp Val Ala Pro Ser Ser
    690                 695                 700

Thr Lys Asp Ile Ser Leu Glu Trp Thr Leu Asp Asn Ile Ala Arg Arg
705                 710                 715                 720

Gly Glu Asn Gly Asp Leu Val Val Tyr Pro Gly Thr Tyr Thr Leu Leu
            725                 730                 735

Leu Asp Glu Pro Thr Gln Ala Lys Ile Gln Val Thr Leu Thr Gly Lys
        740                 745                 750

Lys Ala Ile Leu Asp Lys Trp Pro Gln Asp Pro Lys Ser Ala
    755                 760                 765

<210> SEQ ID NO 37
<211> LENGTH: 1338
<212> TYPE: DNA
<213> ORGANISM: Penicillium funiculosum

<400> SEQUENCE: 37

```
atgcttcagc gatttgctta tattttacca ctggctctat tgagtgttgg agtgaaagcc      60
gacaacccct ttgtgcagag catctacacc gctgatccgg caccgatggt atacaatgac     120
cgcgtttatg tcttcatgga ccatgacaac accggagcta cctactacaa catgacagac     180
tggcatctgt tctcgtcagc agatatggcg aattggcaag atcatggcat tccaatgagc     240
ctggccaatt tcacctgggc caacgcgaat gcgtgggccc cgcaagtcat ccctcgcaac     300
ggccaattct acttttatgc tcctgtccga cacaacgatg gttctatggc tatcggtgtg     360
ggagtgagca gcaccatcac aggtccatac catgatgcta tcggcaaacc gctagtagag     420
aacaacgaga ttgatcccac cgtgttcatc gacgatgacg gtcaggcata cctgtactgg     480
ggaaatccag acctgtggta cgtcaaattg aaccaagata tgatatcgta cagcgggagc     540
cctactcaga ttccactcac cacggctgga tttggtactc gaacgggcaa tgctcaacgg     600
ccgaccactt ttgaagaagc tccatgggta tacaaacgca acggcatcta ctatatcgcc     660
tatgcagccg attgttgttc tgaggatatt cgctactcca cgggaaccag tgccactggt     720
ccgtggactt atcgaggcgt catcatgccg acccaaggta gcagcttcac caatcacgag     780
ggtattatcg acttccagaa caactcctac tttttctatc acaacggcgc tcttcccggc     840
ggaggcggct accaacgatc tgtatgtgtg gagcaattca aatacaatgc agatggaacc     900
attccgacga tcgaaatgac caccgccggt ccagctcaaa ttgggactct caacccttac     960
gtgcgacagg aagccgaaac ggcggcatgg tcttcaggca tcactacgga ggtttgtagc    1020
gaaggcggaa ttgacgtcgg gtttatcaac aatggcgatt acatcaaagt taaaggcgta    1080
gctttcggtt caggagccca ttctttctca gcgcgggttg cttctgcaaa tagcggcggc    1140
actattgcaa tacacctcgg aagcacaact ggtacgctcg tgggcacttg tactgtcccc    1200
agcactggcg gttggcagac ttggactacc gttacctgtt ctgtcagtgg cgcatctggg    1260
acccaggatg tgtattttgt tttcggtggt agcggaacag gatacctgtt caactttgat    1320
tattggcagt tcgcataa                                                   1338
```

<210> SEQ ID NO 38
<211> LENGTH: 445
<212> TYPE: PRT
<213> ORGANISM: Penicillium funiculosum

<400> SEQUENCE: 38

```
Met Leu Gln Arg Phe Ala Tyr Ile Leu Pro Leu Ala Leu Leu Ser Val
1               5                   10                  15

Gly Val Lys Ala Asp Asn Pro Phe Val Gln Ser Ile Tyr Thr Ala Asp
            20                  25                  30

Pro Ala Pro Met Val Tyr Asn Asp Arg Val Tyr Val Phe Met Asp His
        35                  40                  45

Asp Asn Thr Gly Ala Thr Tyr Tyr Asn Met Thr Asp Trp His Leu Phe
    50                  55                  60

Ser Ser Ala Asp Met Ala Asn Trp Gln Asp His Gly Ile Pro Met Ser
65                  70                  75                  80

Leu Ala Asn Phe Thr Trp Ala Asn Ala Asn Ala Trp Ala Pro Gln Val
                85                  90                  95

Ile Pro Arg Asn Gly Gln Phe Tyr Phe Tyr Ala Pro Val Arg His Asn
            100                 105                 110

Asp Gly Ser Met Ala Ile Gly Val Gly Val Ser Ser Thr Ile Thr Gly
        115                 120                 125
```

Pro Tyr His Asp Ala Ile Gly Lys Pro Leu Val Glu Asn Asn Glu Ile
     130                 135                 140

Asp Pro Thr Val Phe Ile Asp Asp Gly Gln Ala Tyr Leu Tyr Trp
145                 150                 155                 160

Gly Asn Pro Asp Leu Trp Tyr Val Lys Leu Asn Gln Asp Met Ile Ser
                165                 170                 175

Tyr Ser Gly Ser Pro Thr Gln Ile Pro Leu Thr Thr Ala Gly Phe Gly
            180                 185                 190

Thr Arg Thr Gly Asn Ala Gln Arg Pro Thr Thr Phe Glu Glu Ala Pro
        195                 200                 205

Trp Val Tyr Lys Arg Asn Gly Ile Tyr Ile Ala Tyr Ala Ala Asp
210                 215                 220

Cys Cys Ser Glu Asp Ile Arg Tyr Ser Thr Gly Thr Ser Ala Thr Gly
225                 230                 235                 240

Pro Trp Thr Tyr Arg Gly Val Ile Met Pro Thr Gln Gly Ser Ser Phe
                245                 250                 255

Thr Asn His Glu Gly Ile Ile Asp Phe Gln Asn Asn Ser Tyr Phe Phe
            260                 265                 270

Tyr His Asn Gly Ala Leu Pro Gly Gly Gly Tyr Gln Arg Ser Val
        275                 280                 285

Cys Val Glu Gln Phe Lys Tyr Asn Ala Asp Gly Thr Ile Pro Thr Ile
290                 295                 300

Glu Met Thr Thr Ala Gly Pro Ala Gln Ile Gly Thr Leu Asn Pro Tyr
305                 310                 315                 320

Val Arg Gln Glu Ala Glu Thr Ala Ala Trp Ser Ser Gly Ile Thr Thr
                325                 330                 335

Glu Val Cys Ser Glu Gly Gly Ile Asp Val Gly Phe Ile Asn Asn Gly
            340                 345                 350

Asp Tyr Ile Lys Val Lys Gly Val Ala Phe Gly Ser Gly Ala His Ser
        355                 360                 365

Phe Ser Ala Arg Val Ala Ser Ala Asn Ser Gly Gly Thr Ile Ala Ile
370                 375                 380

His Leu Gly Ser Thr Thr Gly Thr Leu Val Gly Thr Cys Thr Val Pro
385                 390                 395                 400

Ser Thr Gly Gly Trp Gln Thr Trp Thr Thr Val Thr Cys Ser Val Ser
                405                 410                 415

Gly Ala Ser Gly Thr Gln Asp Val Tyr Phe Val Phe Gly Gly Ser Gly
            420                 425                 430

Thr Gly Tyr Leu Phe Asn Phe Asp Tyr Trp Gln Phe Ala
        435                 440                 445

<210> SEQ ID NO 39
<211> LENGTH: 1593
<212> TYPE: DNA
<213> ORGANISM: Fusarium verticillioides

<400> SEQUENCE: 39
atgaaggtat actggctcgt ggcgtgggcc acttctttga cgccggcact ggctggcttg     60
attggacacc gtcgcgccac caccttcaac aatcctatca tctactcaga ctttccagat    120
aacgatgtat tcctcggtcc agataactac tactacttct ctgcttccaa cttccacttc    180
agcccaggag cacccgtttt gaagtctaaa gatctgctaa actgggatct catcggccat    240
tcaattcccc gcctgaactt tggcgacggc tatgatcttc ctcctggctc acgttattac    300

```
cgtggaggta cttgggcatc atccctcaga tacagaaaga gcaatggaca gtggtactgg    360
atcggctgca tcaacttctg gcagacctgg gtatacactg cctcatcgcc ggaaggtcca    420
tggtacaaca agggaaactt cggtgataac aattgctact acgacaatgg catactgatc    480
gatgacgatg ataccatgta tgtcgtatac ggttccggtg aggtcaaagt atctcaacta    540
tctcaggacg gattcagcca ggtcaaatct caggtagttt tcaagaacac tgatattggg    600
gtccaagact tggagggtaa ccgcatgtac aagatcaacg ggctctacta tatcctaaac    660
gatagcccaa gtggcagtca gacctggatt tggaagtcga aatcaccctg ggcccttat     720
gagtctaagg tcctcgccga caaagtcacc ccgcctatct ctggtggtaa ctcgccgcat    780
cagggtagtc tcataaagac tcccaatggt ggctggtact catgtcatt cacttgggcc     840
tatcctgccg gccgtcttcc ggttcttgca ccgattacgt ggggtagcga tggtttcccc    900
attcttgtca agggtgctaa tggcggatgg ggatcatctt acccaacact tcctggcacg    960
gatggtgtga caaagaattg gacaaggact gataccttcc gcggaacctc acttgctccg   1020
tcctgggagt ggaaccataa tccggacgtc aactccttca ctgtcaacaa cggcctgact   1080
ctccgcactg ctagcattac gaaggatatt taccaggcga ggaacacgct atctcaccga   1140
actcatggta atcatccaac aggaatagtg aagattgatt ctctccgat gaaggacggc    1200
gaccgggccg ggcttccagc gtttcgagac caaagtgcat acatcggtat tcatcgagat   1260
aacgaaaagt tcacaatcgc tacgaagcat gggatgaata tggatgagtg aacggaaca    1320
acaacagacc tgggacaaat aaaagccaca gctaatgtgc cttctggaag gaccaagatc   1380
tggctgagac ttcaacttga taccaaccca gcaggaactg gcaacactat cttttcttac   1440
agttgggatg gagtcaagta tgaaacactg ggtcccaact tcaaactgta caatggttgg   1500
gcattcttta ttgcttaccg attcggcatc ttcaacttcg ccgagacggc tttaggaggc   1560
tcgatcaagg ttgagtcttt cacagctgca tag                                1593
```

<210> SEQ ID NO 40
<211> LENGTH: 530
<212> TYPE: PRT
<213> ORGANISM: Fusarium verticillioides

<400> SEQUENCE: 40

```
Met Lys Val Tyr Trp Leu Val Ala Trp Ala Thr Ser Leu Thr Pro Ala
1               5                   10                  15

Leu Ala Gly Leu Ile Gly His Arg Arg Ala Thr Thr Phe Asn Asn Pro
            20                  25                  30

Ile Ile Tyr Ser Asp Phe Pro Asp Asn Asp Val Phe Leu Gly Pro Asp
        35                  40                  45

Asn Tyr Tyr Tyr Phe Ser Ala Ser Asn Phe His Phe Ser Pro Gly Ala
    50                  55                  60

Pro Val Leu Lys Ser Lys Asp Leu Leu Asn Trp Asp Leu Ile Gly His
65                  70                  75                  80

Ser Ile Pro Arg Leu Asn Phe Gly Asp Gly Tyr Asp Leu Pro Pro Gly
                85                  90                  95

Ser Arg Tyr Tyr Arg Gly Gly Thr Trp Ala Ser Ser Leu Arg Tyr Arg
            100                 105                 110

Lys Ser Asn Gly Gln Trp Tyr Trp Ile Gly Cys Ile Asn Phe Trp Gln
        115                 120                 125

Thr Trp Val Tyr Thr Ala Ser Ser Pro Glu Gly Pro Trp Tyr Asn Lys
    130                 135                 140
```

```
Gly Asn Phe Gly Asp Asn Asn Cys Tyr Tyr Asp Asn Gly Ile Leu Ile
145                 150                 155                 160

Asp Asp Asp Asp Thr Met Tyr Val Val Tyr Gly Ser Gly Glu Val Lys
            165                 170                 175

Val Ser Gln Leu Ser Gln Asp Gly Phe Ser Gln Val Lys Ser Gln Val
        180                 185                 190

Val Phe Lys Asn Thr Asp Ile Gly Val Gln Asp Leu Glu Gly Asn Arg
    195                 200                 205

Met Tyr Lys Ile Asn Gly Leu Tyr Tyr Ile Leu Asn Asp Ser Pro Ser
210                 215                 220

Gly Ser Gln Thr Trp Ile Trp Lys Ser Lys Ser Pro Trp Gly Pro Tyr
225                 230                 235                 240

Glu Ser Lys Val Leu Ala Asp Lys Val Thr Pro Ile Ser Gly Gly
            245                 250                 255

Asn Ser Pro His Gln Gly Ser Leu Ile Lys Thr Pro Asn Gly Gly Trp
            260                 265                 270

Tyr Phe Met Ser Phe Thr Trp Ala Tyr Pro Ala Gly Arg Leu Pro Val
        275                 280                 285

Leu Ala Pro Ile Thr Trp Gly Ser Asp Gly Phe Pro Ile Leu Val Lys
    290                 295                 300

Gly Ala Asn Gly Gly Trp Gly Ser Ser Tyr Pro Thr Leu Pro Gly Thr
305                 310                 315                 320

Asp Gly Val Thr Lys Asn Trp Thr Arg Thr Asp Thr Phe Arg Gly Thr
                325                 330                 335

Ser Leu Ala Pro Ser Trp Glu Trp Asn His Asn Pro Asp Val Asn Ser
            340                 345                 350

Phe Thr Val Asn Asn Gly Leu Thr Leu Arg Thr Ala Ser Ile Thr Lys
        355                 360                 365

Asp Ile Tyr Gln Ala Arg Asn Thr Leu Ser His Arg Thr His Gly Asp
    370                 375                 380

His Pro Thr Gly Ile Val Lys Ile Asp Phe Ser Pro Met Lys Asp Gly
385                 390                 395                 400

Asp Arg Ala Gly Leu Ser Ala Phe Arg Asp Gln Ser Ala Tyr Ile Gly
                405                 410                 415

Ile His Arg Asp Asn Gly Lys Phe Thr Ile Ala Thr Lys His Gly Met
            420                 425                 430

Asn Met Asp Glu Trp Asn Gly Thr Thr Thr Asp Leu Gly Gln Ile Lys
        435                 440                 445

Ala Thr Ala Asn Val Pro Ser Gly Arg Thr Lys Ile Trp Leu Arg Leu
    450                 455                 460

Gln Leu Asp Thr Asn Pro Ala Gly Thr Gly Asn Thr Ile Phe Ser Tyr
465                 470                 475                 480

Ser Trp Asp Gly Val Lys Tyr Glu Thr Leu Gly Pro Asn Phe Lys Leu
                485                 490                 495

Tyr Asn Gly Trp Ala Phe Phe Ile Ala Tyr Arg Phe Gly Ile Phe Asn
            500                 505                 510

Phe Ala Glu Thr Ala Leu Gly Gly Ser Ile Lys Val Glu Ser Phe Thr
        515                 520                 525

Ala Ala
530

<210> SEQ ID NO 41
<211> LENGTH: 1374
<212> TYPE: DNA
```

<213> ORGANISM: Fusarium verticillioides

<400> SEQUENCE: 41

```
atgcactacg ctaccctcac cactttggtg ctggctctga ccaccaacgt cgctgcacag      60
caaggcacag caactgtcga cctctccaaa aatcatggac cggcgaaggc ccttggttca     120
ggcttcatat acggctggcc tgacaacgga acaagcgtcg acacctccat accagatttc     180
ttggtaactg acatcaaatt caactcaaac cgcggcggtg gcgcccaaat cccatcactg     240
ggttgggcca gaggtggcta tgaaggatac ctcggccgct tcaactcaac cttatccaac     300
tatcgcacca cgcgcaagta taacgctgac tttatcttgt tgcctcatga cctctggggt     360
gcggatggcg ggcagggttc aaactccccg tttcctggcg acaatggcaa ttggactgag     420
atggagttat tctggaatca gcttgtgtct gacttgaagg ctcataatat gctggaaggt     480
cttgtgattg atgtttggaa tgagcctgat attgatatct tttgggatcg cccgtggtcg     540
cagtttcttg agtattacaa tcgcgcgacc aaactacttc ggtgagtcta ctactgatcc     600
atacgtattt acagtgagct gactggtcga attagaaaaa cacttcccaa aactcttctc     660
agtggcccag ccatggcaca ttctcccatt ctgtccgatg ataaatggca tacctggctt     720
caatcagtag cgggtaacaa gacagtccct gatatttact cctggcatca gattggcgct     780
tgggaacgtg agccggacag cactatcccc gactttacca ccttgcgggc gcaatatggc     840
gttcccgaga agccaattga cgtcaatgag tacgctgcac gcgatgagca aaatccagcc     900
aactccgtct actacctctc tcaactagag cgtcataacc ttagaggtct tcgcgcaaac     960
tggggtagcg gatctgacct ccacaactgg atgggcaact tgatttacag cactaccggt    1020
acctcggagg ggacttacta ccctaatggt gaatggcagg cttacaagta ctatgcggcc    1080
atggcagggc agagacttgt gaccaaagca tcgtcggact tgaagtttga tgtctttgcc    1140
actaagcaag gccgtaagat taagattata gccggcacga ggaccgttca agcaaagtat    1200
aacatcaaaa tcagcggttt ggaagtagca ggacttccta agatgggtac ggtaaaggtc    1260
cggacttatc ggttcgactg ggctgggccg aatggaaagg ttgacgggcc tgttgatttg    1320
gggagaaga agtatactta ttcggccaat acggtgagca gcccctctac ttga           1374
```

<210> SEQ ID NO 42
<211> LENGTH: 439
<212> TYPE: PRT
<213> ORGANISM: Fusarium verticillioides

<400> SEQUENCE: 42

```
Met His Tyr Ala Thr Leu Thr Thr Leu Val Leu Ala Leu Thr Thr Asn
1               5                   10                  15

Val Ala Ala Gln Gln Gly Thr Ala Thr Val Asp Leu Ser Lys Asn His
            20                  25                  30

Gly Pro Ala Lys Ala Leu Gly Ser Gly Phe Ile Tyr Gly Trp Pro Asp
        35                  40                  45

Asn Gly Thr Ser Val Asp Thr Ser Ile Pro Asp Phe Leu Val Thr Asp
    50                  55                  60

Ile Lys Phe Asn Ser Asn Arg Gly Gly Gly Ala Gln Ile Pro Ser Leu
65                  70                  75                  80

Gly Trp Ala Arg Gly Gly Tyr Glu Gly Tyr Leu Gly Arg Phe Asn Ser
                85                  90                  95

Thr Leu Ser Asn Tyr Arg Thr Thr Arg Lys Tyr Asn Ala Asp Phe Ile
            100                 105                 110
```

| | | | | | | | | | | | |
|---|---|---|---|---|---|---|---|---|---|---|---|
|Leu|Leu|Pro|His|Asp|Leu|Trp|Gly|Ala|Asp|Gly|Gln|Gly|Ser|Asn|
| | |115| | | |120| | | |125| | | | |

Leu Leu Pro His Asp Leu Trp Gly Ala Asp Gly Gln Gly Ser Asn
            115                 120                 125

Ser Pro Phe Pro Gly Asp Asn Gly Asn Trp Thr Glu Met Glu Leu Phe
    130                 135                 140

Trp Asn Gln Leu Val Ser Asp Leu Lys Ala His Asn Met Leu Glu Gly
145                 150                 155                 160

Leu Val Ile Asp Val Trp Asn Glu Pro Asp Ile Asp Ile Phe Trp Asp
                165                 170                 175

Arg Pro Trp Ser Gln Phe Leu Glu Tyr Tyr Asn Arg Ala Thr Lys Leu
            180                 185                 190

Leu Arg Lys Thr Leu Pro Lys Thr Leu Leu Ser Gly Pro Ala Met Ala
        195                 200                 205

His Ser Pro Ile Leu Ser Asp Asp Lys Trp His Thr Trp Leu Gln Ser
    210                 215                 220

Val Ala Gly Asn Lys Thr Val Pro Asp Ile Tyr Ser Trp His Gln Ile
225                 230                 235                 240

Gly Ala Trp Glu Arg Glu Pro Asp Ser Thr Ile Pro Asp Phe Thr Thr
                245                 250                 255

Leu Arg Ala Gln Tyr Gly Val Pro Glu Lys Pro Ile Asp Val Asn Glu
            260                 265                 270

Tyr Ala Ala Arg Asp Glu Gln Asn Pro Ala Asn Ser Val Tyr Tyr Leu
        275                 280                 285

Ser Gln Leu Glu Arg His Asn Leu Arg Gly Leu Arg Ala Asn Trp Gly
    290                 295                 300

Ser Gly Ser Asp Leu His Asn Trp Met Gly Asn Leu Ile Tyr Ser Thr
305                 310                 315                 320

Thr Gly Thr Ser Glu Gly Thr Tyr Tyr Pro Asn Gly Glu Trp Gln Ala
                325                 330                 335

Tyr Lys Tyr Tyr Ala Ala Met Ala Gly Gln Arg Leu Val Thr Lys Ala
            340                 345                 350

Ser Ser Asp Leu Lys Phe Asp Val Phe Ala Thr Lys Gln Gly Arg Lys
        355                 360                 365

Ile Lys Ile Ile Ala Gly Thr Arg Thr Val Gln Ala Lys Tyr Asn Ile
370                 375                 380

Lys Ile Ser Gly Leu Glu Val Ala Gly Leu Pro Lys Met Gly Thr Val
385                 390                 395                 400

Lys Val Arg Thr Tyr Arg Phe Asp Trp Ala Gly Pro Asn Gly Lys Val
                405                 410                 415

Asp Gly Pro Val Asp Leu Gly Glu Lys Lys Tyr Thr Tyr Ser Ala Asn
            420                 425                 430

Thr Val Ser Ser Pro Ser Thr
        435

<210> SEQ ID NO 43
<211> LENGTH: 1350
<212> TYPE: DNA
<213> ORGANISM: Fusarium verticillioides

<400> SEQUENCE: 43

```
atgtggctga cctcccccatt gctgttcgcc agcaccctcc tgggcctcac tggcgttgct    60
ctagcagaca accccatcgt ccaagacatc tacaccgcag acccagcacc aatggtctac   120
aatggccgcg tctacctctt cacaggccat gacaacgacg gctctaccga cttcaacatg   180
acagactggc gtctcttctc gtcagcagac atggtcaact ggcagcacca tggtgtcccc   240
```

```
atgagcttaa agaccttcag ctgggccaac agcagagcct gggctggtca agtcgttgcc    300
cgaaacggaa agttttactt ctatgttcct gtccgtaatg ccaagacggg tggaatggct    360
attggtgtcg gtgttagtac caacatcctt gggccctaca ctgatgccct tggaaagcca    420
ttggtcgaga caatgagatc gacccaact gtctacatcg acactgatgg ccaggcctat     480
ctctactggg gcaaccctgg attgtactac gtcaagctca accaagacat gctctcctac    540
agtggtagca tcaacaaagt atcgctcaca acagctggat cggcagccg cccgaacaac     600
gcgcagcgtc ctactacttt cgaggaagga ccgtggctgt acaagcgtgg aaatctctac    660
tacatgatct acgcagccaa ctgctgttcc gaggacattc gctactcaac tggacccagc    720
gccactggac cttggactta ccgcggtgtc gtgatgaaca aggcgggtcg aagcttcacc    780
aaccatcctg gcatcatcga ctttgagaac aactcgtact tcttttacca caatggcgct    840
cttgatggag gtagcggtta tactcggtct gtggctgtcg agagcttcaa gtatggttcg    900
gacggtctga tccccgagat caagatgact acgcaaggcc cagcgcagct caagtctctg    960
aacccatatg tcaagcagga ggccgagact atcgcctggt ctgagggtat cgagactgag   1020
gtctgcagcg aaggtggtct caacgttgct ttcatcgaca atggtgacta catcaaggtc   1080
aagggagtcg actttggcag caccggtgca agacgttca gcgcccgtgt tgcttccaac    1140
agcagcggag gcaagattga gcttcgactt ggtagcaaga ccggtaagtt ggttggtacc   1200
tgcacggtaa cgactacggg aaactggcag acttataaga ctgtggattg ccccgtcagt   1260
ggtgctactg gtacgagcga tctattcttt gtcttcacgg gctctgggtc tggctctctg   1320
ttcaacttca actggtggca gtttagctaa                                    1350
```

<210> SEQ ID NO 44
<211> LENGTH: 449
<212> TYPE: PRT
<213> ORGANISM: Fusarium verticillioides

<400> SEQUENCE: 44

Met Trp Leu Thr Ser Pro Leu Leu Phe Ala Ser Thr Leu Leu Gly Leu
1               5                   10                  15

Thr Gly Val Ala Leu Ala Asp Asn Pro Ile Val Gln Asp Ile Tyr Thr
            20                  25                  30

Ala Asp Pro Ala Pro Met Val Tyr Asn Gly Arg Val Tyr Leu Phe Thr
        35                  40                  45

Gly His Asp Asn Asp Gly Ser Thr Asp Phe Asn Met Thr Asp Trp Arg
    50                  55                  60

Leu Phe Ser Ser Ala Asp Met Val Asn Trp Gln His His Gly Val Pro
65                  70                  75                  80

Met Ser Leu Lys Thr Phe Ser Trp Ala Asn Ser Arg Ala Trp Ala Gly
                85                  90                  95

Gln Val Val Ala Arg Asn Gly Lys Phe Tyr Phe Tyr Val Pro Val Arg
            100                 105                 110

Asn Ala Lys Thr Gly Gly Met Ala Ile Gly Val Gly Val Ser Thr Asn
        115                 120                 125

Ile Leu Gly Pro Tyr Thr Asp Ala Leu Gly Lys Pro Leu Val Glu Asn
    130                 135                 140

Asn Glu Ile Asp Pro Thr Val Tyr Ile Asp Thr Asp Gly Gln Ala Tyr
145                 150                 155                 160

Leu Tyr Trp Gly Asn Pro Gly Leu Tyr Tyr Val Lys Leu Asn Gln Asp
                165                 170                 175

```
Met Leu Ser Tyr Ser Gly Ser Ile Asn Lys Val Ser Leu Thr Thr Ala
            180                 185                 190
Gly Phe Gly Ser Arg Pro Asn Asn Ala Gln Arg Pro Thr Thr Phe Glu
        195                 200                 205
Glu Gly Pro Trp Leu Tyr Lys Arg Gly Asn Leu Tyr Tyr Met Ile Tyr
    210                 215                 220
Ala Ala Asn Cys Cys Ser Glu Asp Ile Arg Tyr Ser Thr Gly Pro Ser
225                 230                 235                 240
Ala Thr Gly Pro Trp Thr Tyr Arg Gly Val Val Met Asn Lys Ala Gly
            245                 250                 255
Arg Ser Phe Thr Asn His Pro Gly Ile Ile Asp Phe Glu Asn Asn Ser
        260                 265                 270
Tyr Phe Phe Tyr His Asn Gly Ala Leu Asp Gly Gly Ser Gly Tyr Thr
    275                 280                 285
Arg Ser Val Ala Val Glu Ser Phe Lys Tyr Gly Ser Asp Gly Leu Ile
290                 295                 300
Pro Glu Ile Lys Met Thr Thr Gln Gly Pro Ala Gln Leu Lys Ser Leu
305                 310                 315                 320
Asn Pro Tyr Val Lys Gln Glu Ala Glu Thr Ile Ala Trp Ser Glu Gly
            325                 330                 335
Ile Glu Thr Glu Val Cys Ser Glu Gly Gly Leu Asn Val Ala Phe Ile
        340                 345                 350
Asp Asn Gly Asp Tyr Ile Lys Val Lys Gly Val Asp Phe Gly Ser Thr
    355                 360                 365
Gly Ala Lys Thr Phe Ser Ala Arg Val Ala Ser Asn Ser Ser Gly Gly
370                 375                 380
Lys Ile Glu Leu Arg Leu Gly Ser Lys Thr Gly Lys Leu Val Gly Thr
385                 390                 395                 400
Cys Thr Val Thr Thr Thr Gly Asn Trp Gln Thr Tyr Lys Thr Val Asp
            405                 410                 415
Cys Pro Val Ser Gly Ala Thr Gly Thr Ser Asp Leu Phe Phe Val Phe
        420                 425                 430
Thr Gly Ser Gly Ser Gly Ser Leu Phe Asn Phe Asn Trp Trp Gln Phe
    435                 440                 445
Ser

<210> SEQ ID NO 45
<211> LENGTH: 1725
<212> TYPE: DNA
<213> ORGANISM: Fusarium verticillioides

<400> SEQUENCE: 45
atgcgcttct cttggctatt gtgccccctt ctagcgatgg gaagtgctct tcctgaaacg     60
aagacggatg tttcgacata caccaaccct gtccttccag gatggcactc ggatccatcg    120
tgtatccaga aagatggcct ctttctctgc gtcacttcaa cattcatctc ttcccaggt    180 cttcccgtct atgcctcaag ggatctagtc aactggcgtc tcatcagcca tgtctggaac    240
cgcgagaaac agttgcctgg cattagctgg aagacggcag acagcaaca gggaatgtat    300 gcaccaacca ttcgatacca caagggaaca tactacgtca tctgcgaata cctgggcgtt    360
ggagatatta ttggtgtcat cttcaagacc accaatccgt gggacgagag tagctggagt    420
gaccctgtta ccttcaagcc aaatcacatc gaccccgatc tgttctggga tgatgacgga    480
aaggtttatt gtgctaccca tggcatcact ctgcaggaga ttgatttgga aactggagag    540
```

-continued

```
cttagcccgg agcttaatat ctggaacggc acaggaggtg tatggcctga gggtccccat    600
atctacaagc gcgacggtta ctactatctc atgattgccg agggtggaac tgccgaagac    660
cacgctatca caatcgctcg ggcccgcaag atcaccggcc cctatgaagc ctacaataac    720
aacccaatct tgaccaaccg cgggacatct gagtacttcc agactgtcgg tcacggtgat    780
ctgttccaag ataccaaggg caactggtgg ggtctttgtc ttgctactcg catcacagca    840
cagggagttt cacccatggg ccgtgaagct gttttgttca atggcacatg gaacaagggc    900
gaatggccca agttgcaacc agtacgaggt cgcatgcctg gaaacctcct cccaaagccg    960
acgcgaaacg ttcccggaga tgggcccttc aacgctgacc cagacaacta caacttgaag   1020
aagactaaga agatccctcc tcactttgtg caccatagag tcccaagaga cggtgccttc   1080
tctttgtctt ccaagggtct gcacatcgtg cctagtcgaa acaacgttac cggtagtgtg   1140
ttgccaggag atgagattga gctatcagga cagcgaggtc tagctttcat cggacgccgc   1200
caaactcaca ctctgttcaa atatagtgtt gatatcgact tcaagcccaa gtccgatgat   1260
caggaagctg gaatcaccgt tttccgcacg cagttcgacc atatcgatct tggcattgtt   1320
cgtcttccta caaaccaagg cagcaacaag aaatctaagc ttgccttccg attccgggcc   1380
acaggagctc agaatgttcc tgcaccgaag gtagtaccgg tccccgatgg ctgggagaag   1440
ggcgtaatca gtctacatat cgaggcagcc aacgcgacgc actacaacct tggagcttcg   1500
agccacagag gcaagactct cgacatcgcg acagcatcag caagtcttgt gagtggaggc   1560
acgggttcat tgttggtag tttgcttgga ccttatgcta cctgcaacgg caaaggatct   1620
ggagtggaat gtcccaaggg aggtgatgtc tatgtgaccc aatggactta taagcccgtg   1680
gcacaagaga ttgatcatgg tgttttgtg aaatcagaat tgtag               1725
```

<210> SEQ ID NO 46
<211> LENGTH: 574
<212> TYPE: PRT
<213> ORGANISM: Fusarium verticillioides

<400> SEQUENCE: 46

```
Met Arg Phe Ser Trp Leu Leu Cys Pro Leu Leu Ala Met Gly Ser Ala
1               5                   10                  15

Leu Pro Glu Thr Lys Thr Asp Val Ser Thr Tyr Thr Asn Pro Val Leu
            20                  25                  30

Pro Gly Trp His Ser Asp Pro Ser Cys Ile Gln Lys Asp Gly Leu Phe
        35                  40                  45

Leu Cys Val Thr Ser Thr Phe Ile Ser Phe Pro Gly Leu Pro Val Tyr
    50                  55                  60

Ala Ser Arg Asp Leu Val Asn Trp Arg Leu Ile Ser His Val Trp Asn
65                  70                  75                  80

Arg Glu Lys Gln Leu Pro Gly Ile Ser Trp Lys Thr Ala Gly Gln Gln
                85                  90                  95

Gln Gly Met Tyr Ala Pro Thr Ile Arg Tyr His Lys Gly Thr Tyr Tyr
            100                 105                 110

Val Ile Cys Glu Tyr Leu Gly Val Gly Asp Ile Ile Gly Val Ile Phe
        115                 120                 125

Lys Thr Thr Asn Pro Trp Asp Glu Ser Trp Ser Asp Pro Val Thr
    130                 135                 140

Phe Lys Pro Asn His Ile Asp Pro Asp Leu Phe Trp Asp Asp Gly
145                 150                 155                 160

Lys Val Tyr Cys Ala Thr His Gly Ile Thr Leu Gln Glu Ile Asp Leu
```

```
            165                 170                 175
Glu Thr Gly Glu Leu Ser Pro Glu Leu Asn Ile Trp Asn Gly Thr Gly
                180                 185                 190
Gly Val Trp Pro Glu Gly Pro His Ile Tyr Lys Arg Asp Gly Tyr Tyr
            195                 200                 205
Tyr Leu Met Ile Ala Glu Gly Thr Ala Glu Asp His Ala Ile Thr
        210                 215                 220
Ile Ala Arg Ala Arg Lys Ile Thr Gly Pro Tyr Glu Ala Tyr Asn Asn
225                 230                 235                 240
Asn Pro Ile Leu Thr Asn Arg Gly Thr Ser Glu Tyr Phe Gln Thr Val
                245                 250                 255
Gly His Gly Asp Leu Phe Gln Asp Thr Lys Gly Asn Trp Trp Gly Leu
            260                 265                 270
Cys Leu Ala Thr Arg Ile Thr Ala Gln Gly Val Ser Pro Met Gly Arg
        275                 280                 285
Glu Ala Val Leu Phe Asn Gly Thr Trp Asn Lys Gly Glu Trp Pro Lys
    290                 295                 300
Leu Gln Pro Val Arg Gly Arg Met Pro Gly Asn Leu Leu Pro Lys Pro
305                 310                 315                 320
Thr Arg Asn Val Pro Gly Asp Gly Pro Phe Asn Ala Asp Pro Asp Asn
                325                 330                 335
Tyr Asn Leu Lys Lys Thr Lys Lys Ile Pro Pro His Phe Val His His
            340                 345                 350
Arg Val Pro Arg Asp Gly Ala Phe Ser Leu Ser Ser Lys Gly Leu His
        355                 360                 365
Ile Val Pro Ser Arg Asn Asn Val Thr Gly Ser Val Leu Pro Gly Asp
    370                 375                 380
Glu Ile Glu Leu Ser Gly Gln Arg Gly Leu Ala Phe Ile Gly Arg Arg
385                 390                 395                 400
Gln Thr His Thr Leu Phe Lys Tyr Ser Val Asp Ile Asp Phe Lys Pro
                405                 410                 415
Lys Ser Asp Asp Gln Glu Ala Gly Ile Thr Val Phe Arg Thr Gln Phe
            420                 425                 430
Asp His Ile Asp Leu Gly Ile Val Arg Leu Pro Thr Asn Gln Gly Ser
        435                 440                 445
Asn Lys Lys Ser Lys Leu Ala Phe Arg Phe Arg Ala Thr Gly Ala Gln
    450                 455                 460
Asn Val Pro Ala Pro Lys Val Val Pro Val Pro Asp Gly Trp Glu Lys
465                 470                 475                 480
Gly Val Ile Ser Leu His Ile Glu Ala Ala Asn Ala Thr His Tyr Asn
                485                 490                 495
Leu Gly Ala Ser Ser His Arg Gly Lys Thr Leu Asp Ile Ala Thr Ala
            500                 505                 510
Ser Ala Ser Leu Val Ser Gly Gly Thr Gly Ser Phe Val Gly Ser Leu
        515                 520                 525
Leu Gly Pro Tyr Ala Thr Cys Asn Gly Lys Gly Ser Gly Val Glu Cys
    530                 535                 540
Pro Lys Gly Gly Asp Val Tyr Val Thr Gln Trp Thr Tyr Lys Pro Val
545                 550                 555                 560
Ala Gln Glu Ile Asp His Gly Val Phe Val Lys Ser Glu Leu
                565                 570

<210> SEQ ID NO 47
```

<211> LENGTH: 2251
<212> TYPE: DNA
<213> ORGANISM: Podospora anserina

<400> SEQUENCE: 47

```
atgatccacc tcaagccagc cctcgcggcg ttgttggcgc tgtcgacgca atgtgtggct      60
attgatttgt ttgtcaagtc ttcgggggggg aataagacga ctgatatcat gtatggtctt     120
atgcacgagg tatgtgtttt gcgagatctc ccttttgttt ttgcgcactg ctgacatgga     180
gactgcaaac aggatatcaa caactccggc gacggcggca tctacgccga gctaatctcc     240
aaccgcgcgt tccaagggag tgagaagttc ccctccaacc tcgacaactg agccccgtc      300
ggtggcgcta cccttaccct tcagaagctt gccaagcccc tttcctctgc gttgccttac     360
tccgtcaatg ttgccaaccc caaggagggc aagggcaagg gcaaggacac caaggggaag     420
aaggttggct tggccaatgc tgggttttgg ggtatggatg tcaagaggca gaagtacact     480
ggtagcttcc acgttactgg tgagtacaag ggtgactttg aggttagctt gcgcagcgcg     540
attaccgggg agacctttgg caagaaggtg gtgaaggggtg gagtaagaa ggggaagtgg     600
accgagaagg agtttgagtt ggtgcctttc aaggatgcgc ccaacagcaa caacaccttt     660
gttgtgcagt gggatgccga ggtatgtgct tctttgatat tggctgagat agaagttggg     720
ttgacatgat gtggtgcagg gcgcaaagga cggatctttg gatctcaact tgatcagctt     780
gttccctccg acattcaagg gaaggaagaa tgggctgaga attgatcttg cgcagacgat     840
ggttgagctc aagccggtaa gtcctctcta gtcagaaaag tagagccttt gttaacgctt     900
gacagacctt cttgcgcttc cccggtggca acatgctcga gggtaacacc ttggacactt     960
ggtggaagtg gtacgagacc attggccctc tgaaggatcg cccgggcatg gctggtgtct    1020
gggagtacca gcaaacccctt ggcttgggtc tggtcgagta catggagtgg gccgatgaca    1080
tgaacttgga gcccagtatg tgatcccatt ttctggagtg acttctcttg ctaacgtatc    1140
cacagttgtc ggtgtcttcg ctggtcttgc cctcgatggc tcgttcgttc ccgaatccga    1200
gatgggatgg gtcatccaac aggctctcga cgaaatcgag ttcctcactg gcgatgctaa    1260
gaccaccaaa tggggtgccg tccgcgcgaa gcttggtcac cccaagcctt ggaaggtcaa    1320
gtgggttgag atcggtaacg aggattggct tgccggacgc cctgctggct tcgagtcgta    1380
catcaactac cgcttcccca tgatgatgaa ggccttcaac gaaaagtacc ccgacatcaa    1440
gatcatcgcc tcgccctcca tcttcgacaa catgacaatc cccgcgggtg ctgccggtga    1500
tcaccacccg tacctgactc ccgatgagtt cgttgagcga ttcgccaagt tcgataactt    1560
gagcaaggat aacgtgacgc tcatcggcga ggctgcgtcg acgcatccta acggtggtat    1620
cgcttgggag ggagatctca tgcccttgcc ttggtgggc ggcagtgttg ctgaggctat    1680
cttcttgatc agcactgaga gaaacggtga caagatcatc ggtgctactt acgcgcctgg    1740
tcttcgcagc tttggaccgct ggcaatggag catgacctgg gtgcagcatg ccgccgaccc    1800
ggccctcacc actcgctcga ccagttggta tgtctggaga atcctcgccc accacatcat    1860
ccgtgagacg ctcccggtcg atgccccggc cggcaagccc aactttgacc ctctgttcta    1920
cgttgccgga aagagcgaga gtggcaccgg tatcttcaag gctgccgtct acaactcgac    1980
tgaatcgatc ccggtgtcgt tgaagtttga tggtctcaac gagggagcgg ttgccaactt    2040
gacggtgctt actgggccgg aggatccgta tggatacaac gacccccttca ctggtatcaa    2100
tgttgtcaag gagaagacca ccttcatcaa ggccggaaag gcggcaagt tcaccttcac    2160
cctgccgggc ttgagtgttg ctgtgttgga gacggccgac gcggtcaagg gtggcaaggg    2220
```

-continued aaagggcaag ggcaagggaa agggtaactg a  2251

<210> SEQ ID NO 48
<211> LENGTH: 676
<212> TYPE: PRT
<213> ORGANISM: Podospora anserina

<400> SEQUENCE: 48

| | | | | | | | | | | | | | | |
|---|---|---|---|---|---|---|---|---|---|---|---|---|---|---|
| Met | Ile | His | Leu | Lys | Pro | Ala | Leu | Ala | Ala | Leu | Leu | Ala | Leu | Ser | Thr |
| 1 | | | | 5 | | | | | 10 | | | | | 15 | |
| Gln | Cys | Val | Ala | Ile | Asp | Leu | Phe | Val | Lys | Ser | Ser | Gly | Gly | Asn | Lys |
| | | | 20 | | | | | 25 | | | | | 30 | | |
| Thr | Thr | Asp | Ile | Met | Tyr | Gly | Leu | Met | His | Glu | Asp | Ile | Asn | Asn | Ser |
| | | | 35 | | | | | 40 | | | | | 45 | | |
| Gly | Asp | Gly | Gly | Ile | Tyr | Ala | Glu | Leu | Ile | Ser | Asn | Arg | Ala | Phe | Gln |
| | | 50 | | | | | 55 | | | | | 60 | | | |
| Gly | Ser | Glu | Lys | Phe | Pro | Ser | Asn | Leu | Asp | Asn | Trp | Ser | Pro | Val | Gly |
| 65 | | | | | 70 | | | | | 75 | | | | | 80 |
| Gly | Ala | Thr | Leu | Thr | Leu | Gln | Lys | Leu | Ala | Lys | Pro | Leu | Ser | Ser | Ala |
| | | | | 85 | | | | | 90 | | | | | 95 | |
| Leu | Pro | Tyr | Ser | Val | Asn | Val | Ala | Asn | Pro | Lys | Glu | Gly | Lys | Gly | Lys |
| | | | 100 | | | | | 105 | | | | | 110 | | |
| Gly | Lys | Asp | Thr | Lys | Gly | Lys | Lys | Val | Gly | Leu | Ala | Asn | Ala | Gly | Phe |
| | | | 115 | | | | | 120 | | | | | 125 | | |
| Trp | Gly | Met | Asp | Val | Lys | Arg | Gln | Lys | Tyr | Thr | Gly | Ser | Phe | His | Val |
| | | 130 | | | | | 135 | | | | | 140 | | | |
| Thr | Gly | Glu | Tyr | Lys | Gly | Asp | Phe | Glu | Val | Ser | Leu | Arg | Ser | Ala | Ile |
| 145 | | | | | 150 | | | | | 155 | | | | | 160 |
| Thr | Gly | Glu | Thr | Phe | Gly | Lys | Lys | Val | Val | Lys | Gly | Gly | Ser | Lys | Lys |
| | | | | 165 | | | | | 170 | | | | | 175 | |
| Gly | Lys | Trp | Thr | Glu | Lys | Glu | Phe | Glu | Leu | Val | Pro | Phe | Lys | Asp | Ala |
| | | | 180 | | | | | 185 | | | | | 190 | | |
| Pro | Asn | Ser | Asn | Asn | Thr | Phe | Val | Val | Gln | Trp | Asp | Ala | Glu | Gly | Ala |
| | | | 195 | | | | | 200 | | | | | 205 | | |
| Lys | Asp | Gly | Ser | Leu | Asp | Leu | Asn | Leu | Ile | Ser | Leu | Phe | Pro | Pro | Thr |
| | | 210 | | | | | 215 | | | | | 220 | | | |
| Phe | Lys | Gly | Arg | Lys | Asn | Gly | Leu | Arg | Ile | Asp | Leu | Ala | Gln | Thr | Met |
| 225 | | | | | 230 | | | | | 235 | | | | | 240 |
| Val | Glu | Leu | Lys | Pro | Thr | Phe | Leu | Arg | Phe | Pro | Gly | Gly | Asn | Met | Leu |
| | | | | 245 | | | | | 250 | | | | | 255 | |
| Glu | Gly | Asn | Thr | Leu | Asp | Thr | Trp | Trp | Lys | Trp | Tyr | Glu | Thr | Ile | Gly |
| | | | 260 | | | | | 265 | | | | | 270 | | |
| Pro | Leu | Lys | Asp | Arg | Pro | Gly | Met | Ala | Gly | Val | Trp | Glu | Tyr | Gln | Gln |
| | | | 275 | | | | | 280 | | | | | 285 | | |
| Thr | Leu | Gly | Leu | Gly | Leu | Val | Glu | Tyr | Met | Glu | Trp | Ala | Asp | Asp | Met |
| | | 290 | | | | | 295 | | | | | 300 | | | |
| Asn | Leu | Glu | Pro | Ile | Val | Gly | Val | Phe | Ala | Gly | Leu | Ala | Leu | Asp | Gly |
| 305 | | | | | 310 | | | | | 315 | | | | | 320 |
| Ser | Phe | Val | Pro | Glu | Ser | Glu | Met | Gly | Trp | Val | Ile | Gln | Gln | Ala | Leu |
| | | | | 325 | | | | | 330 | | | | | 335 | |
| Asp | Glu | Ile | Glu | Phe | Leu | Thr | Gly | Asp | Ala | Lys | Thr | Thr | Lys | Trp | Gly |
| | | | 340 | | | | | 345 | | | | | 350 | | |
| Ala | Val | Arg | Ala | Lys | Leu | Gly | His | Pro | Lys | Pro | Trp | Lys | Val | Lys | Trp |
| | | | 355 | | | | | 360 | | | | | 365 | | |

Val Glu Ile Gly Asn Glu Asp Trp Leu Ala Gly Arg Pro Ala Gly Phe
    370                 375                 380

Glu Ser Tyr Ile Asn Tyr Arg Phe Pro Met Met Lys Ala Phe Asn
385                 390                 395                 400

Glu Lys Tyr Pro Asp Ile Lys Ile Ile Ala Ser Pro Ser Ile Phe Asp
                405                 410                 415

Asn Met Thr Ile Pro Ala Gly Ala Gly Asp His His Pro Tyr Leu
            420                 425                 430

Thr Pro Asp Glu Phe Val Glu Arg Phe Ala Lys Phe Asp Asn Leu Ser
            435                 440                 445

Lys Asp Asn Val Thr Leu Ile Gly Glu Ala Ala Ser Thr His Pro Asn
450                 455                 460

Gly Gly Ile Ala Trp Glu Gly Asp Leu Met Pro Leu Pro Trp Trp Gly
465                 470                 475                 480

Gly Ser Val Ala Glu Ala Ile Phe Leu Ile Ser Thr Glu Arg Asn Gly
                485                 490                 495

Asp Lys Ile Ile Gly Ala Thr Tyr Ala Pro Gly Leu Arg Ser Leu Asp
                500                 505                 510

Arg Trp Gln Trp Ser Met Thr Trp Val Gln His Ala Ala Asp Pro Ala
            515                 520                 525

Leu Thr Thr Arg Ser Thr Ser Trp Tyr Val Trp Arg Ile Leu Ala His
530                 535                 540

His Ile Ile Arg Glu Thr Leu Pro Val Asp Ala Pro Ala Gly Lys Pro
545                 550                 555                 560

Asn Phe Asp Pro Leu Phe Tyr Val Ala Gly Lys Ser Glu Ser Gly Thr
                565                 570                 575

Gly Ile Phe Lys Ala Ala Val Tyr Asn Ser Thr Glu Ser Ile Pro Val
                580                 585                 590

Ser Leu Lys Phe Asp Gly Leu Asn Glu Gly Ala Val Ala Asn Leu Thr
            595                 600                 605

Val Leu Thr Gly Pro Glu Asp Pro Tyr Gly Tyr Asn Asp Pro Phe Thr
610                 615                 620

Gly Ile Asn Val Val Lys Glu Lys Thr Thr Phe Ile Lys Ala Gly Lys
625                 630                 635                 640

Gly Gly Lys Phe Thr Phe Thr Leu Pro Gly Leu Ser Val Ala Val Leu
                645                 650                 655

Glu Thr Ala Asp Ala Val Lys Gly Gly Lys Gly Lys Gly Lys
            660                 665                 670

Gly Lys Gly Asn
        675

<210> SEQ ID NO 49
<211> LENGTH: 1023
<212> TYPE: DNA
<213> ORGANISM: Gibberella zeae

<400> SEQUENCE: 49
atgaagtcca agttgttatt cccactcctc tctttcgttg gtcaaagtct tgccaccaac      60
gacgactgtc ctctcatcac tagtagatgg actgcggatc cttcggctca tgtctttaac 120
gacaccttgt ggctctaccc gtctcatgac atcgatgctg gatttgagaa tgatcctgat 180
ggaggccagt acgccatgag agattaccat gtctactcta tcgacaagat ctacggttcc 240
ctgccggtcg atcacggtac ggccctgtca gtggaggatg tcccctgggc ctctcgacag 300

```
atgtgggctc ctgacgctgc ccacaagaac ggcaaatact acctatactt ccctgccaaa    360
gacaaggatg atatcttcag aatcggcgtt gctgtctcac caaccccgg cggaccattc     420 gtccccgaca agagttggat ccctcacact ttcagcatcg accccgccag tttcgtcgat    480
gatgatgaca gagcctactt ggcatggggt ggtatcatgg gtggccagct tcaacgatgg    540
caggataaga acaagtacaa cgaatctggc actgagccag gaaacggcac cgctgccttg    600
agccctcaga ttgccaagct gagcaaggac atgcacactc tggcagagaa gcctcgcgac    660
atgctcattc ttgaccccaa gactggcaag ccgctccttt ctgaggatga agaccgacgc    720
ttcttcgaag acccctggat tcacaagcgc aacaagattt actacctcac ctactctact    780
ggcacaaccc actatcttgt ctatgcgact tcaaagaccc cctatggtcc ttacacctac    840
cagggcagaa ttctggagcc agttgatggc tggactactc actctagtat cgtcaagtac    900
cagggtcagt ggtggctatt ttatcacgat gccaagacat ctggcaagga ctatcttcgc    960
caggtaaagg ctaagaagat ttggtacgat agcaaggaa agatcttgac aaagaagcct    1020
tga                                                                  1023
```

<210> SEQ ID NO 50
<211> LENGTH: 340
<212> TYPE: PRT
<213> ORGANISM: Gibberella zeae

<400> SEQUENCE: 50

```
Met Lys Ser Lys Leu Leu Phe Pro Leu Leu Ser Phe Val Gly Gln Ser
1               5                   10                  15

Leu Ala Thr Asn Asp Asp Cys Pro Leu Ile Thr Ser Arg Trp Thr Ala
            20                  25                  30

Asp Pro Ser Ala His Val Phe Asn Asp Thr Leu Trp Leu Tyr Pro Ser
        35                  40                  45

His Asp Ile Asp Ala Gly Phe Glu Asn Asp Pro Asp Gly Gly Gln Tyr
    50                  55                  60

Ala Met Arg Asp Tyr His Val Tyr Ser Ile Asp Lys Ile Tyr Gly Ser
65                  70                  75                  80

Leu Pro Val Asp His Gly Thr Ala Leu Ser Val Glu Asp Val Pro Trp
                85                  90                  95

Ala Ser Arg Gln Met Trp Ala Pro Asp Ala Ala His Lys Asn Gly Lys
            100                 105                 110

Tyr Tyr Leu Tyr Phe Pro Ala Lys Asp Lys Asp Ile Phe Arg Ile
        115                 120                 125

Gly Val Ala Val Ser Pro Thr Pro Gly Gly Pro Phe Val Pro Asp Lys
    130                 135                 140

Ser Trp Ile Pro His Thr Phe Ser Ile Asp Pro Ala Ser Phe Val Asp
145                 150                 155                 160

Asp Asp Asp Arg Ala Tyr Leu Ala Trp Gly Gly Ile Met Gly Gly Gln
                165                 170                 175

Leu Gln Arg Trp Gln Asp Lys Asn Lys Tyr Asn Glu Ser Gly Thr Glu
            180                 185                 190

Pro Gly Asn Gly Thr Ala Ala Leu Ser Pro Gln Ile Ala Lys Leu Ser
        195                 200                 205

Lys Asp Met His Thr Leu Ala Glu Lys Pro Arg Asp Met Leu Ile Leu
    210                 215                 220

Asp Pro Lys Thr Gly Lys Pro Leu Leu Ser Glu Asp Glu Asp Arg Arg
225                 230                 235                 240
```

Phe Phe Glu Gly Pro Trp Ile His Lys Arg Asn Lys Ile Tyr Tyr Leu
            245                 250                 255

Thr Tyr Ser Thr Gly Thr Thr His Tyr Leu Val Tyr Ala Thr Ser Lys
        260                 265                 270

Thr Pro Tyr Gly Pro Tyr Thr Tyr Gln Gly Arg Ile Leu Glu Pro Val
    275                 280                 285

Asp Gly Trp Thr Thr His Ser Ser Ile Val Lys Tyr Gln Gly Gln Trp
290                 295                 300

Trp Leu Phe Tyr His Asp Ala Lys Thr Ser Gly Lys Asp Tyr Leu Arg
305                 310                 315                 320

Gln Val Lys Ala Lys Lys Ile Trp Tyr Asp Ser Lys Gly Lys Ile Leu
                325                 330                 335

Thr Lys Lys Pro
            340

<210> SEQ ID NO 51
<211> LENGTH: 1047
<212> TYPE: DNA
<213> ORGANISM: Fusarium oxysporum

<400> SEQUENCE: 51

```
atgcagctca agtttctgtc ttcagcattg ctgttctctc tgaccagcaa atgcgctgcg      60
caagacacta tgacattcc tcccctgatc accgacctct ggtccgcaga tccctcggct     120
catgttttcg aaggcaagct ctgggtttac ccatctcacg acatcgaagc caatgttgtc     180
aacggcacag gaggcgctca atacgccatg agggattacc ataccactc catgaagagc     240
atctatggta aagatcccgt tgtcgaccac ggcgtcgctc tctcagtcga tgacgttccc     300
tgggcgaagc agcaaatgtg ggctcctgac gcagctcata gaacggcaa atattatctg     360
tacttccccg ccaaggacaa ggatgagatc ttcagaattg agttgctgt ctccaacaag     420
cccagcggtc ctttcaaggc cgacaagagc tggatccctg gcacgtacag tatcgatcct     480
gctagctacg tcgacactga taacgaggcc tacctcatct ggggcggtat ctggggcggc     540
cagctccaag cctggcagga taaaaagaac tttaacgagt cgtggattgg agacaaggct     600
gctcctaacg gcaccaatgc cctatctcct cagatcgcca agctaagcaa ggacatgcac     660
aagatcaccg aaacaccccg cgatctcgtc attctcgccc ccgagacagg caagcctctt     720
caggctgagg acaacaagcg acgattcttc gagggcccctt ggatccacaa gcgcggcaag     780
ctttactacc tcatgtactc caccggtgat acccacttcc ttgtctacgc tacttccaag     840
aacatctacg tccttatac ctaccggggc aagattcttg atcctgttga tgggtggact     900
actcatggaa gtattgttga gtataaggga cagtggtggc tttctttgc tgatgcgcat     960
acgtctggta aggattacct tcgacaggtg aaggcgagga agatctggta tgacaagaac    1020
ggcaagatct tgcttcaccg tccttag                                         1047
```

<210> SEQ ID NO 52
<211> LENGTH: 348
<212> TYPE: PRT
<213> ORGANISM: Fusarium oxysporum

<400> SEQUENCE: 52

Met Gln Leu Lys Phe Leu Ser Ser Ala Leu Leu Phe Ser Leu Thr Ser
1               5                  10                  15

Lys Cys Ala Ala Gln Asp Thr Asn Asp Ile Pro Pro Leu Ile Thr Asp
            20                  25                  30

```
Leu Trp Ser Ala Asp Pro Ser Ala His Val Phe Glu Gly Lys Leu Trp
            35                  40                  45

Val Tyr Pro Ser His Asp Ile Glu Ala Asn Val Val Asn Gly Thr Gly
 50                  55                  60

Gly Ala Gln Tyr Ala Met Arg Asp Tyr His Thr Tyr Ser Met Lys Ser
 65                  70                  75                  80

Ile Tyr Gly Lys Asp Pro Val Val Asp His Gly Val Ala Leu Ser Val
                 85                  90                  95

Asp Asp Val Pro Trp Ala Lys Gln Gln Met Trp Ala Pro Asp Ala Ala
            100                 105                 110

His Lys Asn Gly Lys Tyr Tyr Leu Tyr Phe Pro Ala Lys Asp Lys Asp
        115                 120                 125

Glu Ile Phe Arg Ile Gly Val Ala Val Ser Asn Lys Pro Ser Gly Pro
130                 135                 140

Phe Lys Ala Asp Lys Ser Trp Ile Pro Gly Thr Tyr Ser Ile Asp Pro
145                 150                 155                 160

Ala Ser Tyr Val Asp Thr Asp Asn Glu Ala Tyr Leu Ile Trp Gly Gly
                165                 170                 175

Ile Trp Gly Gly Gln Leu Gln Ala Trp Gln Asp Lys Lys Asn Phe Asn
            180                 185                 190

Glu Ser Trp Ile Gly Asp Lys Ala Ala Pro Asn Gly Thr Asn Ala Leu
        195                 200                 205

Ser Pro Gln Ile Ala Lys Leu Ser Lys Asp Met His Lys Ile Thr Glu
    210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Ile His
                245                 250                 255

Lys Arg Gly Lys Leu Tyr Tyr Leu Met Tyr Ser Thr Gly Asp Thr His
            260                 265                 270

Phe Leu Val Tyr Ala Thr Ser Lys Asn Ile Tyr Gly Pro Tyr Thr Tyr
        275                 280                 285

Arg Gly Lys Ile Leu Asp Pro Val Asp Gly Trp Thr Thr His Gly Ser
290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asn Gly Lys Ile Leu Leu His Arg Pro
            340                 345
```

<210> SEQ ID NO 53
<211> LENGTH: 1677
<212> TYPE: DNA
<213> ORGANISM: Aspergillus fumigatus

<400> SEQUENCE: 53

```
atggcagctc caagtttatc ctaccccaca ggtatccaat cgtataccaa tcctctcttc    60
cctggttggc actccgatcc cagctgtgcc tacgtagcgg agcaagacac cttttctgc   120 gtgacgtcca ctttcattgc cttccccggt cttcctcttt atgcaagccg agatctgcag   180
aactggaaac tggcaagcaa tattttcaat cggcccagcc agatccctga tcttcgcgtc   240
acggatggac agcagtcggg tatctatgcg cccactctgc gctatcatga gggccagttc   300
tacttgatcg tttcgtacct gggcccgcag actaagggct tgctgttcac ctcgtctgat   360
```

```
ccgtacgacg atgccgcgtg gagcgatccg ctcgaattcg cggtacatgg catcgacccg    420
gatatcttct gggatcacga cgggacggtc tatgtcacgt ccgccgagga ccagatgatt    480
aagcagtaca cactcgatct gaagacgggg gcgattggcc cggttgacta cctctggaac    540
ggcaccggag gagtctggcc cgagggcccg cacatttaca agagagacgg atactactac    600
ctcatgatcg cagagggagg taccgagctc ggccactcgg agaccatggc gcgatctaga    660
acccggacag gtccctggga gccataccccg cacaatccgc tcttgtcgaa caagggcacc    720
tcggagtact tccagactgt gggccatgcg gacttgttcc aggatgggaa cggcaactgg    780
tgggccgtgg cgttgagcac ccgatcaggg cctgcatgga agaactatcc catgggtcgg    840
gagacggtgc tcgccccccgc cgcttgggag aagggtgagt ggcctgtcat tcagcctgtg    900
agaggccaaa tgcaggggcc gtttccacca ccaaataagc gagttcctcg cggcgagggc    960
ggatggatca agcaacccga caaagtggat ttcaggcccg gatcgaagat accggcgcac   1020
ttccagtact ggcgatatcc caagacagag gattttaccg tctccccctcg gggccacccg   1080
aatactcttc ggctcacacc ctccttttac aacctcaccg gaactgcgga cttcaagccg   1140
gatgatggcc tgtcgcttgt tatgcgcaaa cagaccgaca ccttgttcac gtacactgtg   1200
gacgtgtctt ttgaccccaa ggttgccgat gaagaggcgg gtgtgactgt tttccttacc   1260
cagcagcagc acatcgatct tggtattgtc cttctccaga caaccgaggg gctgtcgttg   1320
tccttccggt tccgcgtgga aggccgcggt aactacgaag gtcctcttcc agaagccacc   1380
gtgcctgttc ccaaggaatg gtgtggacag accatccggc ttgagattca ggccgtgagt   1440
gacaccgagt atgtctttgc ggctgccccg gctcggcacc ctgcacagag gcaaatcatc   1500
agccgcgcca actcgttgat tgtcagtggt gatacgggac ggtttactgg ctcgcttgtt   1560
ggcgtgtatg ccacgtcgaa cggggtgcc ggatccacgc ccgcatatat cagcagatgg   1620
agatacgaag gacggggcca gatgattgat tttggtcgag tggtcccgag ctactga     1677
```

<210> SEQ ID NO 54  
<211> LENGTH: 558  
<212> TYPE: PRT  
<213> ORGANISM: Aspergillus fumigatus

<400> SEQUENCE: 54

```
Met Ala Ala Pro Ser Leu Ser Tyr Pro Thr Gly Ile Gln Ser Tyr Thr
1               5                   10                  15

Asn Pro Leu Phe Pro Gly Trp His Ser Asp Pro Ser Cys Ala Tyr Val
            20                  25                  30

Ala Glu Gln Asp Thr Phe Phe Cys Val Thr Ser Thr Phe Ile Ala Phe
        35                  40                  45

Pro Gly Leu Pro Leu Tyr Ala Ser Arg Asp Leu Gln Asn Trp Lys Leu
    50                  55                  60

Ala Ser Asn Ile Phe Asn Arg Pro Ser Gln Ile Pro Asp Leu Arg Val
65                  70                  75                  80

Thr Asp Gly Gln Gln Ser Gly Ile Tyr Ala Pro Thr Leu Arg Tyr His
                85                  90                  95

Glu Gly Gln Phe Tyr Leu Ile Val Ser Tyr Leu Gly Pro Gln Thr Lys
            100                 105                 110

Gly Leu Leu Phe Thr Ser Ser Asp Pro Tyr Asp Ala Ala Trp Ser
        115                 120                 125

Asp Pro Leu Glu Phe Ala Val His Gly Ile Asp Pro Asp Ile Phe Trp
    130                 135                 140
```

-continued

```
Asp His Asp Gly Thr Val Tyr Val Thr Ser Ala Glu Asp Gln Met Ile
145                 150                 155                 160

Lys Gln Tyr Thr Leu Asp Leu Lys Thr Gly Ala Ile Gly Pro Val Asp
                165                 170                 175

Tyr Leu Trp Asn Gly Thr Gly Gly Val Trp Pro Glu Gly Pro His Ile
            180                 185                 190

Tyr Lys Arg Asp Gly Tyr Tyr Tyr Leu Met Ile Ala Glu Gly Gly Thr
            195                 200                 205

Glu Leu Gly His Ser Glu Thr Met Ala Arg Ser Arg Thr Arg Thr Gly
210                 215                 220

Pro Trp Glu Pro Tyr Pro His Asn Pro Leu Leu Ser Asn Lys Gly Thr
225                 230                 235                 240

Ser Glu Tyr Phe Gln Thr Val Gly His Ala Asp Leu Phe Gln Asp Gly
                245                 250                 255

Asn Gly Asn Trp Trp Ala Val Ala Leu Ser Thr Arg Ser Gly Pro Ala
            260                 265                 270

Trp Lys Asn Tyr Pro Met Gly Arg Glu Thr Val Leu Ala Pro Ala Ala
            275                 280                 285

Trp Glu Lys Gly Glu Trp Pro Val Ile Gln Pro Val Arg Gly Gln Met
290                 295                 300

Gln Gly Pro Phe Pro Pro Asn Lys Arg Val Pro Arg Gly Glu Gly
305                 310                 315                 320

Gly Trp Ile Lys Gln Pro Asp Lys Val Asp Phe Arg Pro Gly Ser Lys
            325                 330                 335

Ile Pro Ala His Phe Gln Tyr Trp Arg Tyr Pro Lys Thr Glu Asp Phe
            340                 345                 350

Thr Val Ser Pro Arg Gly His Pro Asn Thr Leu Arg Leu Thr Pro Ser
            355                 360                 365

Phe Tyr Asn Leu Thr Gly Thr Ala Asp Phe Lys Pro Asp Asp Gly Leu
370                 375                 380

Ser Leu Val Met Arg Lys Gln Thr Asp Thr Leu Phe Thr Tyr Thr Val
385                 390                 395                 400

Asp Val Ser Phe Asp Pro Lys Val Ala Asp Glu Glu Ala Gly Val Thr
                405                 410                 415

Val Phe Leu Thr Gln Gln Gln His Ile Asp Leu Gly Ile Val Leu Leu
            420                 425                 430

Gln Thr Thr Glu Gly Leu Ser Leu Ser Phe Arg Phe Arg Val Glu Gly
            435                 440                 445

Arg Gly Asn Tyr Glu Gly Pro Leu Pro Glu Ala Thr Val Pro Val Pro
450                 455                 460

Lys Glu Trp Cys Gly Gln Thr Ile Arg Leu Glu Ile Gln Ala Val Ser
465                 470                 475                 480

Asp Thr Glu Tyr Val Phe Ala Ala Pro Ala Arg His Pro Ala Gln
                485                 490                 495

Arg Gln Ile Ile Ser Arg Ala Asn Ser Leu Ile Val Ser Gly Asp Thr
            500                 505                 510

Gly Arg Phe Thr Gly Ser Leu Val Gly Val Tyr Ala Thr Ser Asn Gly
            515                 520                 525

Gly Ala Gly Ser Thr Pro Ala Tyr Ile Ser Arg Trp Arg Tyr Glu Gly
            530                 535                 540

Arg Gly Gln Met Ile Asp Phe Gly Arg Val Val Pro Ser Tyr
545                 550                 555
```

<210> SEQ ID NO 55
<211> LENGTH: 2320
<212> TYPE: DNA
<213> ORGANISM: Penicillium funiculosum

<400> SEQUENCE: 55

| | | | | | |
|---|---|---|---|---|---|
| atgggaaaga | tgtggcattc | gatcttggtt | gtgttgggct | tattgtctgt | cgggcatgcc | 60 |
| atcactatca | acgtgtccca | aagtggcggc | aataagacca | gtcctttgca | atatggtctg | 120 |
| atgttcgagg | taatccttct | cttataccac | atataaaagt | tgcgtcattt | ctaagacaag | 180 |
| tcaaggacat | aaatcacggc | ggtgatggcg | gtctgtatgc | agagcttgtt | cgaaaccgag | 240 |
| cattccaagg | tagcaccgtc | tatccagcaa | acctcgatgg | atacgactcg | gtcaatggag | 300 |
| caatcctagc | gcttcagaat | ttgacaaacc | ctctatcacc | ctccatgcct | agctctctca | 360 |
| acgtcgccaa | ggggtccaac | aatggaagca | tcggtttcgc | aaatgaaggc | tggtgggga | 420 |
| tagaagtcaa | gccgcaaaga | tacgcgggct | cattctacgt | ccaggggac | tatcaaggag | 480 |
| atttcgacat | ctctcttcag | tcgaaattga | cacaagaagt | cttcgcaacg | gcaaaagtca | 540 |
| ggtcctcggg | caaacacgag | gactgggttc | aatacaagta | cgagttggtg | cccaaaaagg | 600 |
| cagcatcaaa | caccaataac | actctgacca | ttacttttga | ctcaaaggta | tgttaaattt | 660 |
| tgggtttagt | tcgatgtctg | gcaattgtct | tacgagaaac | gtagggattg | aaagacggat | 720 |
| ccttgaactt | caacttgatc | agccatatttc | ccccaactta | caacaatcgg | cccaatggcc | 780 |
| taagaatcga | cctggttgaa | gctatggctg | aactagaggg | ggtaagctct | tacaaatcaa | 840 |
| ctttatcttt | acgaagacta | atgtgaaaac | ttagaaattt | ctgcggtttc | caggcggtag | 900 |
| cgatgtggaa | ggtgtacaag | ctccttactg | gtataagtgg | aatgaaacgg | taggagatct | 960 |
| caaggaccgt | tatagtaggc | ccagtgcatg | gacgtacgaa | gaaagcaatg | gaattggctt | 1020 |
| gattgagtac | atgaattggt | gtgatgacat | ggggcttgag | ccgagtgagt | gtattccatt | 1080 |
| cagcgtcaaa | tccagtgttc | taatcataca | catcagttct | tgccgtatgg | gatggacatt | 1140 |
| acctttcgaa | cgaagtgata | tcggaaaacg | atttgcagcc | atatatcgac | gacaccctca | 1200 |
| accaactgga | attcctgatg | ggtgccccag | atacgccata | tggtagttgg | cgtgcgtctc | 1260 |
| tgggctatcc | gaagccgtgg | acgattaact | acgtcgagat | tggaaacgaa | gacaatctat | 1320 |
| acggggact | agaaacatac | atcgcctacc | ggtttcaggc | atattacgac | gctataacag | 1380 |
| ctaaatatcc | ccatatgacg | gtcatggaat | ctttgacgga | gatgcctggt | ccggcggccg | 1440 |
| ctgcaagcga | ttaccatcaa | tattctactc | ctgatgggtt | tgtttcccag | ttcaactact | 1500 |
| ttgatcagat | gccagtcact | aatagaacac | tgaacggtat | gaaaaccccc | ccttttttaa | 1560 |
| atatgctttt | aatggtatta | accatctttc | ataggagaga | ttgcaaccgt | ttatccaaat | 1620 |
| aatcctagta | attcggtggc | ctggggaagc | ccattcccct | tgtatccttg | gtggattggg | 1680 |
| tccgttgcag | aagctgtttt | cctaattggt | gaagagagga | attcgccaaa | gataatcggt | 1740 |
| gctagctacg | tacggaattc | tacttttcga | gattttaaca | ttggataaga | aggactaacc | 1800 |
| tcaatacagg | ctccaatgtt | cagaaatatc | aacaattggc | agtggtctcc | aacactcatc | 1860 |
| gcttttgacg | ctgactcgtc | gcgtacaagt | cgttcaacaa | gctggcatgt | gatcaaggta | 1920 |
| tgctaatttt | cctcctcatt | caaacccgca | gatgtgagct | aactttccga | agcttctctc | 1980 |
| gacaaacaaa | atcacgcaaa | atttacccac | gacttggagt | ggcggtgaca | taggtccatt | 2040 |
| atactgggta | gctggacgaa | acgacaatac | aggatcgaac | atattcaagg | ccgctgttta | 2100 |
| caacagcacc | tcagacgtcc | ctgtcaccgt | tcaatttgca | ggatgcaacg | caaagagcgc | 2160 |

```
aaatttgacc atcttgtcat ccgacgatcc gaacgcatcg aactaccctg gggggcccga   2220
agttgtgaag actgagatcc agtctgtcac tgcaaatgct catggagcat ttgagttcag   2280
tctcccgaac ctaagtgtgg ctgttctcaa aacggagtaa                         2320
```

<210> SEQ ID NO 56
<211> LENGTH: 642
<212> TYPE: PRT
<213> ORGANISM: Penicillium funiculosum

<400> SEQUENCE: 56

```
Met Gly Lys Met Trp His Ser Ile Leu Val Val Leu Gly Leu Leu Ser
1               5                   10                  15

Val Gly His Ala Ile Thr Ile Asn Val Ser Gln Ser Gly Gly Asn Lys
            20                  25                  30

Thr Ser Pro Leu Gln Tyr Gly Leu Met Phe Glu Asp Ile Asn His Gly
        35                  40                  45

Gly Asp Gly Gly Leu Tyr Ala Glu Leu Val Arg Asn Arg Ala Phe Gln
    50                  55                  60

Gly Ser Thr Val Tyr Pro Ala Asn Leu Asp Gly Tyr Asp Ser Val Asn
65                  70                  75                  80

Gly Ala Ile Leu Ala Leu Gln Asn Leu Thr Asn Pro Leu Ser Pro Ser
                85                  90                  95

Met Pro Ser Ser Leu Asn Val Ala Lys Gly Ser Asn Asn Gly Ser Ile
            100                 105                 110

Gly Phe Ala Asn Glu Gly Trp Trp Gly Ile Glu Val Lys Pro Gln Arg
        115                 120                 125

Tyr Ala Gly Ser Phe Tyr Val Gln Gly Asp Tyr Gln Gly Asp Phe Asp
    130                 135                 140

Ile Ser Leu Gln Ser Lys Leu Thr Gln Glu Val Phe Ala Thr Ala Lys
145                 150                 155                 160

Val Arg Ser Ser Gly Lys His Glu Asp Trp Val Gln Tyr Lys Tyr Glu
                165                 170                 175

Leu Val Pro Lys Lys Ala Ala Ser Asn Thr Asn Asn Thr Leu Thr Ile
            180                 185                 190

Thr Phe Asp Ser Lys Gly Leu Lys Asp Gly Ser Leu Asn Phe Asn Leu
        195                 200                 205

Ile Ser Leu Phe Pro Pro Thr Tyr Asn Asn Arg Pro Asn Gly Leu Arg
    210                 215                 220

Ile Asp Leu Val Glu Ala Met Ala Glu Leu Glu Gly Lys Phe Leu Arg
225                 230                 235                 240

Phe Pro Gly Gly Ser Asp Val Glu Gly Val Gln Ala Pro Tyr Trp Tyr
                245                 250                 255

Lys Trp Asn Glu Thr Val Gly Asp Leu Lys Asp Arg Tyr Ser Arg Pro
            260                 265                 270

Ser Ala Trp Thr Tyr Glu Glu Ser Asn Gly Ile Gly Leu Ile Glu Tyr
        275                 280                 285

Met Asn Trp Cys Asp Asp Met Gly Leu Glu Pro Ile Leu Ala Val Trp
    290                 295                 300

Asp Gly His Tyr Leu Ser Asn Glu Val Ile Ser Glu Asn Asp Leu Gln
305                 310                 315                 320

Pro Tyr Ile Asp Asp Thr Leu Asn Gln Leu Glu Phe Leu Met Gly Ala
                325                 330                 335

Pro Asp Thr Pro Tyr Gly Ser Trp Arg Ala Ser Leu Gly Tyr Pro Lys
```

|     |     |     |     | 340 |     |     |     | 345 |     |     |     | 350 |     |     |
| --- | --- | --- | --- | --- | --- | --- | --- | --- | --- | --- | --- | --- | --- | --- |
| Pro | Trp | Thr | Ile | Asn | Tyr | Val | Glu | Ile | Gly | Asn | Glu | Asp | Asn | Leu | Tyr |
|     |     |     |     | 355 |     |     |     |     |     | 360 |     |     |     | 365 |     |

Gly Gly Leu Glu Thr Tyr Ile Ala Tyr Arg Phe Gln Ala Tyr Tyr Asp
    370                 375                 380

Ala Ile Thr Ala Lys Tyr Pro His Met Thr Val Met Glu Ser Leu Thr
385                 390                 395                 400

Glu Met Pro Gly Pro Ala Ala Ala Ser Asp Tyr His Gln Tyr Ser
                405                 410                 415

Thr Pro Asp Gly Phe Val Ser Gln Phe Asn Tyr Phe Asp Gln Met Pro
            420                 425                 430

Val Thr Asn Arg Thr Leu Asn Gly Glu Ile Ala Thr Val Tyr Pro Asn
            435                 440                 445

Asn Pro Ser Asn Ser Val Ala Trp Gly Ser Pro Phe Pro Leu Tyr Pro
            450                 455                 460

Trp Trp Ile Gly Ser Val Ala Glu Ala Val Phe Leu Ile Gly Glu Glu
465                 470                 475                 480

Arg Asn Ser Pro Lys Ile Ile Gly Ala Ser Tyr Ala Pro Met Phe Arg
                485                 490                 495

Asn Ile Asn Asn Trp Gln Trp Ser Pro Thr Leu Ile Ala Phe Asp Ala
                500                 505                 510

Asp Ser Ser Arg Thr Ser Arg Ser Thr Ser Trp His Val Ile Lys Leu
            515                 520                 525

Leu Ser Thr Asn Lys Ile Thr Gln Asn Leu Pro Thr Thr Trp Ser Gly
            530                 535                 540

Gly Asp Ile Gly Pro Leu Tyr Trp Val Ala Gly Arg Asn Asp Asn Thr
545                 550                 555                 560

Gly Ser Asn Ile Phe Lys Ala Ala Val Tyr Asn Ser Thr Ser Asp Val
                565                 570                 575

Pro Val Thr Val Gln Phe Ala Gly Cys Asn Ala Lys Ser Ala Asn Leu
            580                 585                 590

Thr Ile Leu Ser Ser Asp Asp Pro Asn Ala Ser Asn Tyr Pro Gly Gly
            595                 600                 605

Pro Glu Val Val Lys Thr Glu Ile Gln Ser Val Thr Ala Asn Ala His
        610                 615                 620

Gly Ala Phe Glu Phe Ser Leu Pro Asn Leu Ser Val Ala Val Leu Lys
625                 630                 635                 640

Thr Glu

<210> SEQ ID NO 57
<211> LENGTH: 739
<212> TYPE: DNA
<213> ORGANISM: Aspergillus fumigatus

<400> SEQUENCE: 57

| | | |
|---|---|---|
| atggtttctt tctcctacct gctgctggcg tgctccgcca ttggagctct ggctgccccc | 60 |
| gtcgaacccg agaccacctc gttcaatgag actgctcttc atgagttcgc tgagcgcgcc | 120 |
| ggcaccccaa gctccaccgg ctggaacaac ggctactact actccttctg gactgatggc | 180 |
| ggcggcgacg tgacctacac caatggcgcc ggtggctcgt actccgtcaa ctggaggaac | 240 |
| gtgggcaact tgtcggtgg aaagggctgg aaccctggaa gcgctaggta ccgagctttg | 300 |
| tcaacgtcgg atgtgcagac ctgtggctga cagaagtaga accatcaact acggaggcag | 360 |
| cttcaacccc agcggcaatg ctacctggc tgtctacggc tggaccacca cccccttgat | 420 |

```
tgagtactac gttgttgagt cgtatggtac atacaacccc ggcagcggcg gtaccttcag    480
gggcactgtc aacaccgacg gtggcactta caacatctac acggccgttc gctacaatgc    540
tccctccatc gaaggcacca agaccttcac ccagtactgg tctgtgcgca cctccaagcg    600
taccggcggc actgtcacca tggccaacca cttcaacgcc tggagcagac tgggcatgaa    660
cctgggaact cacaactacc agattgtcgc cactgagggt taccagagca gcggatctgc    720
ttccatcact gtctactag                                                  739
```

<210> SEQ ID NO 58
<211> LENGTH: 228
<212> TYPE: PRT
<213> ORGANISM: Aspergillus fumigatus

<400> SEQUENCE: 58

```
Met Val Ser Phe Ser Tyr Leu Leu Ala Cys Ser Ala Ile Gly Ala
1               5                   10                  15

Leu Ala Ala Pro Val Glu Pro Glu Thr Thr Ser Phe Asn Glu Thr Ala
            20                  25                  30

Leu His Glu Phe Ala Glu Arg Ala Gly Thr Pro Ser Ser Thr Gly Trp
        35                  40                  45

Asn Asn Gly Tyr Tyr Tyr Ser Phe Trp Thr Asp Gly Gly Asp Val
    50                  55                  60

Thr Tyr Thr Asn Gly Ala Gly Gly Ser Tyr Ser Val Asn Trp Arg Asn
65                  70                  75                  80

Val Gly Asn Phe Val Gly Gly Lys Gly Trp Asn Pro Gly Ser Ala Arg
                85                  90                  95

Thr Ile Asn Tyr Gly Gly Ser Phe Asn Pro Ser Gly Asn Gly Tyr Leu
            100                 105                 110

Ala Val Tyr Gly Trp Thr Thr Asn Pro Leu Ile Glu Tyr Tyr Val Val
        115                 120                 125

Glu Ser Tyr Gly Thr Tyr Asn Pro Gly Ser Gly Gly Thr Phe Arg Gly
    130                 135                 140

Thr Val Asn Thr Asp Gly Gly Thr Tyr Asn Ile Tyr Thr Ala Val Arg
145                 150                 155                 160

Tyr Asn Ala Pro Ser Ile Glu Gly Thr Lys Thr Phe Thr Gln Tyr Trp
                165                 170                 175

Ser Val Arg Thr Ser Lys Arg Thr Gly Gly Thr Val Thr Met Ala Asn
            180                 185                 190

His Phe Asn Ala Trp Ser Arg Leu Gly Met Asn Leu Gly Thr His Asn
        195                 200                 205

Tyr Gln Ile Val Ala Thr Glu Gly Tyr Gln Ser Ser Gly Ser Ala Ser
    210                 215                 220

Ile Thr Val Tyr
225
```

<210> SEQ ID NO 59
<211> LENGTH: 1002
<212> TYPE: DNA
<213> ORGANISM: Aspergillus fumigatus

<400> SEQUENCE: 59

```
atgatctcca tttcctcgct cagctttgga ctcgccgcta tcgccggcgc atatgctctt     60
ccgagtgaca aatccgtcag cttagcggaa cgtcagacga tcacgaccag ccagacaggc    120
acaaacaatg gctactacta ttccttctgg accaacggtg ccggatcagt gcaatataca    180
```

| | |
|---|---|
| aatggtgctg gtggcgaata tagtgtgacg tgggcgaacc agaacggtgg tgactttacc | 240 |
| tgtgggaagg gctggaatcc agggagtgac cagtaggcaa cgcccgagaa ctatagaaga | 300 |
| ggacgcaaag aaagcactaa actctctact agtgacatta ccttctctgg cagcttcaat | 360 |
| ccttccggaa atgcttacct gtccgtgtat ggatggacta ccaaccccct agtcgaatac | 420 |
| tacatcctcg agaactatgg cagttacaat cctggctcgg gcatgacgca aagggcacc | 480 |
| gtcaccagcg atggatccac ctacgacatc tatgagcacc aacaggtcaa ccagccttcg | 540 |
| atcgtcggca cggccacctt caaccaatac tggtccatcc gccaaaacaa gcgatccagc | 600 |
| ggcacagtca ccaccgcgaa tcacttcaag gcctgggcta gtctggggat gaacctgggt | 660 |
| acccataact atcagattgt ttccactgag ggatatgaga gcagcggtac ctcgaccatc | 720 |
| actgtctcgt ctggtggttc ttcttctggt ggaagtggtg gcagctcgtc tactacttcc | 780 |
| tcaggcagct cccctactgg tggctccggc agtgtaagtc ttcttccata tggttgtggc | 840 |
| tttatgtgta ttctgactgt gatagtgctc tgctttgtgg ggccagtgcg gtggaattgg | 900 |
| ctggtctggt cctacttgct gctcttcggg cacttgccag gtttcgaact cgtactactc | 960 |
| ccagtgcttg tagtaccttc ttgcagggtt atatccaagt ga | 1002 |

<210> SEQ ID NO 60
<211> LENGTH: 286
<212> TYPE: PRT
<213> ORGANISM: Aspergillus fumigatus

<400> SEQUENCE: 60

```
Met Ile Ser Ile Ser Ser Leu Ser Phe Gly Leu Ala Ala Ile Ala Gly
1               5                   10                  15

Ala Tyr Ala Leu Pro Ser Asp Lys Ser Val Ser Leu Ala Glu Arg Gln
            20                  25                  30

Thr Ile Thr Thr Ser Gln Thr Gly Thr Asn Asn Gly Tyr Tyr Tyr Ser
        35                  40                  45

Phe Trp Thr Asn Gly Ala Gly Ser Val Gln Tyr Thr Asn Gly Ala Gly
    50                  55                  60

Gly Glu Tyr Ser Val Thr Trp Ala Asn Gln Asn Gly Gly Asp Phe Thr
65                  70                  75                  80

Cys Gly Lys Gly Trp Asn Pro Gly Ser Asp His Asp Ile Thr Phe Ser
                85                  90                  95

Gly Ser Phe Asn Pro Ser Gly Asn Ala Tyr Leu Ser Val Tyr Gly Trp
            100                 105                 110

Thr Thr Asn Pro Leu Val Glu Tyr Tyr Ile Leu Glu Asn Tyr Gly Ser
        115                 120                 125

Tyr Asn Pro Gly Ser Gly Met Thr His Lys Gly Thr Val Thr Ser Asp
    130                 135                 140

Gly Ser Thr Tyr Asp Ile Tyr Glu His Gln Gln Val Asn Gln Pro Ser
145                 150                 155                 160

Ile Val Gly Thr Ala Thr Phe Asn Gln Tyr Trp Ser Ile Arg Gln Asn
                165                 170                 175

Lys Arg Ser Ser Gly Thr Val Thr Thr Ala Asn His Phe Lys Ala Trp
            180                 185                 190

Ala Ser Leu Gly Met Asn Leu Gly Thr His Asn Tyr Gln Ile Val Ser
        195                 200                 205

Thr Glu Gly Tyr Glu Ser Ser Gly Thr Ser Thr Ile Thr Val Ser Ser
    210                 215                 220
```

```
Gly Gly Ser Ser Ser Gly Gly Ser Gly Gly Ser Ser Thr Thr Ser
225                 230                 235                 240

Ser Gly Ser Ser Pro Thr Gly Gly Ser Gly Ser Cys Ser Ala Leu Trp
                245                 250                 255

Gly Gln Cys Gly Gly Ile Gly Trp Ser Gly Pro Thr Cys Cys Ser Ser
            260                 265                 270

Gly Thr Cys Gln Val Ser Asn Ser Tyr Tyr Ser Gln Cys Leu
        275                 280                 285

<210> SEQ ID NO 61
<211> LENGTH: 1053
<212> TYPE: DNA
<213> ORGANISM: Fusarium verticillioides

<400> SEQUENCE: 61
atgcagctca agtttctgtc ttcagcattg ttgctgtctt tgaccggcaa ttgcgctgcg      60
caagacacta tgatatccc tcctctgatc accgacctct ggtctgcgga tccctcggct      120
catgttttcg agggcaaact ctgggtttac ccatctcacg acatcgaagc caatgtcgtc     180
aacggcaccg gaggcgctca gtacgccatg agagattatc acacctattc catgaagacc     240
atctatggaa aagatcccgt tatcgaccat ggcgtcgctc tgtcagtcga tgatgtccca     300
tgggccaagc agcaaatgtg gctcctgac gcagcttaca gaacggcaa atattatctc       360 tacttccccg ccaaggataa agatgagatc ttcagaattg gagttgctgt ctccaacaag     420
cccagcggtc ctttcaaggc cgacaagagc tggatccccg gtacttacag tatcgatcct     480
gctagctatg tcgacactaa tggcgaggca tacctcatct ggggcggtat ctggggcggc     540
cagcttcagg cctggcagga tcacaagacc tttaatgagt cgtggctcgg cgacaaagct     600
gctcccaacg gcaccaacgc cctatctcct cagatcgcca agctaagcaa ggacatgcac     660
aagatcaccg agacaccccg cgatctcgtc atcctggccc ccgagacagg caagccccctt    720 caagcagagg acaataagcg acgatttttc gaggggccct gggttcacaa gcgcggcaag     780
ctgtactacc tcatgtactc taccggcgac acgcacttcc tcgtctacgc gacttccaag     840
aacatctacg tccttatac ctatcagggc aagattctcg accctgttga tgggtggact      900
acgcatggaa gtattgttga gtacaaggga cagtggtggt tgttctttgc ggatgcgcat     960
acttctggaa aggattatct gagacaggtt aaggcgagga gatctggta tgacaaggat      1020 ggcaagattt tgcttactcg tcctaagatt tag                                 1053

<210> SEQ ID NO 62
<211> LENGTH: 350
<212> TYPE: PRT
<213> ORGANISM: Fusarium verticillioides

<400> SEQUENCE: 62

Met Gln Leu Lys Phe Leu Ser Ser Ala Leu Leu Leu Ser Leu Thr Gly
1               5                   10                  15

Asn Cys Ala Ala Gln Asp Thr Asn Asp Ile Pro Pro Leu Ile Thr Asp
                20                  25                  30

Leu Trp Ser Ala Asp Pro Ser Ala His Val Phe Glu Gly Lys Leu Trp
            35                  40                  45

Val Tyr Pro Ser His Asp Ile Glu Ala Asn Val Val Asn Gly Thr Gly
        50                  55                  60

Gly Ala Gln Tyr Ala Met Arg Asp Tyr His Thr Tyr Ser Met Lys Thr
65                  70                  75                  80
```

```
Ile Tyr Gly Lys Asp Pro Val Ile Asp His Gly Val Ala Leu Ser Val
                 85                  90                  95

Asp Asp Val Pro Trp Ala Lys Gln Gln Met Trp Ala Pro Asp Ala Ala
            100                 105                 110

Tyr Lys Asn Gly Lys Tyr Tyr Leu Tyr Phe Pro Ala Lys Asp Lys Asp
            115                 120                 125

Glu Ile Phe Arg Ile Gly Val Ala Val Ser Asn Lys Pro Ser Gly Pro
        130                 135                 140

Phe Lys Ala Asp Lys Ser Trp Ile Pro Gly Thr Tyr Ser Ile Asp Pro
145                 150                 155                 160

Ala Ser Tyr Val Asp Thr Asn Gly Glu Ala Tyr Leu Ile Trp Gly Gly
            165                 170                 175

Ile Trp Gly Gly Gln Leu Gln Ala Trp Gln Asp His Lys Thr Phe Asn
        180                 185                 190

Glu Ser Trp Leu Gly Asp Lys Ala Ala Pro Asn Gly Thr Asn Ala Leu
            195                 200                 205

Ser Pro Gln Ile Ala Lys Leu Ser Lys Asp Met His Lys Ile Thr Glu
        210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Val His
            245                 250                 255

Lys Arg Gly Lys Leu Tyr Tyr Leu Met Tyr Ser Thr Gly Asp Thr His
            260                 265                 270

Phe Leu Val Tyr Ala Thr Ser Lys Asn Ile Tyr Gly Pro Tyr Thr Tyr
        275                 280                 285

Gln Gly Lys Ile Leu Asp Pro Val Asp Gly Trp Thr Thr His Gly Ser
        290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
            325                 330                 335

Tyr Asp Lys Asp Gly Lys Ile Leu Leu Thr Arg Pro Lys Ile
            340                 345                 350

<210> SEQ ID NO 63
<211> LENGTH: 1031
<212> TYPE: DNA
<213> ORGANISM: Penicillium funiculosum

<400> SEQUENCE: 63
atgagtcgca gcatccttcc gtacgcctct gttttcgccc tcctgggcgg ggctatcgcc      60
gaaccgtttt tggttctcaa tagcgatttt cccgatccca gtctcataga gcatccagc     120 ggatactatg cattcggtac caccggaaac ggagtcaatg cgcaggttgc ttcttcacca     180
gactttaata cctggacttt gctttccggc acagatgccc tcccgggacc atttccgtca     240
tgggtagctt cgtctccaca aatctgggcg ccagatgttt tggttaaggt atgttcttat     300
ggaataacag ttttaggagt aggtcagcca ggatattgac aaaattataa taggccgatg     360
gtacctatgt catgtacttt tcggcatctg ctgcgagtga ctcgggcaaa cactgcgttg     420
gtgccgcaac tgcgacctca ccggaaggac cttacacccc ggtcgatagc gctgttgcct     480
gtccattaga ccagggagga gctattgatg ccaatggatt tattgacacc gacggcacta     540
tatacgttgt atacaaaatt gatggaaaca gtctagacgg tgatggaacc acacatccta     600
```

```
cccccatcat gcttcaacaa atggaggcag acggaacaac cccaaccggc agcccaatcc    660
aactcattga ccgatccgac ctcgacggac ctttgatcga ggctcctagt ttgctcctct    720
ccaatggaat ctactacctc agtttctctt ccaactacta caacactaat tactacgaca    780
cttcatacgc ctatgcctcg tcgattactg gtccttggac caaacaatct gcgccttatg    840 caccccttgtt ggttactgga accgagacta gcaatgacgg cgcattgagc gcccctggtg    900
gtgccgattt ctccgtcgat ggcaccaaga tgttgttcca cgcaaacctc aatggacaag    960
atatctcggg cggacgcgcc ttatttgctg cgtcaattac tgaggccagc gatgtggtta   1020
cattgcagta g                                                        1031

<210> SEQ ID NO 64
<211> LENGTH: 321
<212> TYPE: PRT
<213> ORGANISM: Penicillium funiculosum

<400> SEQUENCE: 64

Met Ser Arg Ser Ile Leu Pro Tyr Ala Ser Val Phe Ala Leu Leu Gly
1               5                   10                  15

Gly Ala Ile Ala Glu Pro Phe Leu Val Leu Asn Ser Asp Phe Pro Asp
            20                  25                  30

Pro Ser Leu Ile Glu Thr Ser Ser Gly Tyr Tyr Ala Phe Gly Thr Thr
        35                  40                  45

Gly Asn Gly Val Asn Ala Gln Val Ala Ser Ser Pro Asp Phe Asn Thr
    50                  55                  60

Trp Thr Leu Leu Ser Gly Thr Asp Ala Leu Pro Gly Pro Phe Pro Ser
65                  70                  75                  80

Trp Val Ala Ser Ser Pro Gln Ile Trp Ala Pro Asp Val Leu Val Lys
                85                  90                  95

Ala Asp Gly Thr Tyr Val Met Tyr Phe Ser Ala Ser Ala Ala Ser Asp
            100                 105                 110

Ser Gly Lys His Cys Val Gly Ala Ala Thr Ala Thr Ser Pro Glu Gly
        115                 120                 125

Pro Tyr Thr Pro Val Asp Ser Ala Val Ala Cys Pro Leu Asp Gln Gly
    130                 135                 140

Gly Ala Ile Asp Ala Asn Gly Phe Ile Asp Thr Asp Gly Thr Ile Tyr
145                 150                 155                 160

Val Val Tyr Lys Ile Asp Gly Asn Ser Leu Asp Gly Asp Gly Thr Thr
                165                 170                 175

His Pro Thr Pro Ile Met Leu Gln Gln Met Glu Ala Asp Gly Thr Thr
            180                 185                 190

Pro Thr Gly Ser Pro Ile Gln Leu Ile Asp Arg Ser Asp Leu Asp Gly
        195                 200                 205

Pro Leu Ile Glu Ala Pro Ser Leu Leu Leu Ser Asn Gly Ile Tyr Tyr
    210                 215                 220

Leu Ser Phe Ser Ser Asn Tyr Tyr Asn Thr Asn Tyr Tyr Asp Thr Ser
225                 230                 235                 240

Tyr Ala Tyr Ala Ser Ser Ile Thr Gly Pro Trp Thr Lys Gln Ser Ala
                245                 250                 255

Pro Tyr Ala Pro Leu Leu Val Thr Gly Thr Glu Thr Ser Asn Asp Gly
            260                 265                 270

Ala Leu Ser Ala Pro Gly Gly Ala Asp Phe Ser Val Asp Gly Thr Lys
        275                 280                 285

Met Leu Phe His Ala Asn Leu Asn Gly Gln Asp Ile Ser Gly Gly Arg
```

Ala Leu Phe Ala Ala Ser Ile Thr Glu Ala Ser Asp Val Val Thr Leu
305                 310                 315                 320

Gln

<210> SEQ ID NO 65
<211> LENGTH: 2186
<212> TYPE: DNA
<213> ORGANISM: Fusarium verticillioides

<400> SEQUENCE: 65

| | | | | | |
|---|---|---|---|---|---|
| atggttcgct | tcagttcaat | cctagcggct | gcggcttgct | tcgtggctgt | tgagtcagtc | 60 |
| aacatcaagg | tcgacagcaa | gggcggaaac | gctactagcg | gtcaccaata | tggcttcctt | 120 |
| cacgaggttg | gtattgacac | accactggcg | atgattggga | tgctaacttg | gagctaggat | 180 |
| atcaacaatt | ccggtgatgg | tggcatctac | gctgagctca | tccgcaatcg | tgctttccag | 240 |
| tacagcaaga | ataccctgt | ttctctatct | ggctggagac | ccatcaacga | tgctaagctc | 300 |
| tccctcaacc | gtctcgacac | tcctctctcc | gacgctctcc | ccgtttccat | gaacgtgaag | 360 |
| cctggaaagg | gcaaggccaa | ggagattggt | ttcctcaacg | agggttactg | gggaatggat | 420 |
| gtcaagaagc | aaaagtacac | tggctctttc | tgggttaagg | gcgcttacaa | gggccacttt | 480 |
| acagcttctt | tgcgatctaa | ccttaccgac | gatgtctttg | gcagcgtcaa | ggtcaagtcc | 540 |
| aaggccaaca | agaagcagtg | ggttgagcat | gagtttgtgc | ttactcctaa | caagaatgcc | 600 |
| cctaacagca | acaacacttt | tgctatcacc | tacgatccca | aggtgagtaa | caatcaaaac | 660 |
| tgggacgtga | tgtatactga | caatttgtag | ggcgctgatg | gagctcttga | cttcaacctc | 720 |
| attagcttgt | tccctcccac | ctacaagggc | cgcaagaacg | gtcttcgagt | tgatcttgcc | 780 |
| gaggctctcg | aaggtctcca | ccccgtaagg | tttaccgtct | cacgtgtatc | gtgaacagtc | 840 |
| gctgacttgt | agaaaagagc | ctgctgcgct | tccccggtgg | taacatgctc | gagggcaaca | 900 |
| ccaacaagac | ctggtgggac | tggaaggata | ccctcggacc | tctccgcaac | cgtcctggtt | 960 |
| tcgagggtgt | ctggaactac | cagcagaccc | atggtcttgg | aatcttggag | tacctccagt | 1020 |
| gggctgagga | catgaaccct | gaaatcagta | ggttctataa | aattcagtga | cggttatgtg | 1080 |
| catgctaaca | gatttcagtt | gtcggtgtct | acgctggcct | ctccctcgac | ggctccgtca | 1140 |
| cccccaagga | ccaactccag | cccctcatcg | acgacgcgct | cgacgagatc | gaattcatcc | 1200 |
| gaggtcccgt | cacttcaaag | tggggaaaga | agcgcgctga | gctcggccac | cccaagcctt | 1260 |
| tcagactctc | ctacgttgaa | gtcggaaacg | aggactggc | cgctggttat | cccactggct | 1320 |
| ggaactctta | caaggagtac | cgcttcccca | tgttcctcga | ggctatcaag | aaagctcacc | 1380 |
| ccgatctcac | cgtcatctcc | tctggtgctt | ctattgaccc | cgttggtaag | aaggatgctg | 1440 |
| gtttcgatat | tcctgctcct | ggaatcggtg | actaccaccc | ttaccgcgag | cctgatgttc | 1500 |
| ttgttgagga | gttcaacctg | tttgataaca | ataagtatgg | tcacatcatt | ggtgaggttg | 1560 |
| cttctaccca | ccccaacggt | ggaactggct | ggagtggtaa | ccttatgcct | tacccctggt | 1620 |
| ggatctctgg | tgttggcgag | gccgtcgctc | tctgcggtta | tgagcgcaac | gccgatcgta | 1680 |
| ttcccggaac | attctacgct | cctatcctca | gaacgagaa | ccgttggcag | tgggctatca | 1740 |
| ccatgatcca | attcgccgcc | gactccgcca | tgaccacccg | ctccaccagc | tggtatgtct | 1800 |
| ggtcactctt | cgcaggccac | cccatgaccc | atactctccc | caccaccgcc | gacttcgacc | 1860 |
| ccctctacta | cgtcgctggt | aagaacgagg | acaagggaac | tcttatctgg | aagggtgctg | 1920 |

```
cgtataacac caccaagggt gctgacgttc ccgtgtctct gtccttcaag ggtgtcaagc    1980
ccggtgctca agctgagctt actcttctga ccaacaagga gaaggatcct tttgcgttca    2040
atgatcctca aagggcaac aatgttgttg atactaagaa gactgttctc aaggccgatg    2100
gaaagggtgc tttcaacttc aagcttccta acctgagcgt cgctgttctt gagaccctca    2160
agaagggaaa gccttactct agctag                                        2186
```

<210> SEQ ID NO 66
<211> LENGTH: 660
<212> TYPE: PRT
<213> ORGANISM: Fusarium verticillioides

<400> SEQUENCE: 66

```
Met Val Arg Phe Ser Ser Ile Leu Ala Ala Ala Cys Phe Val Ala
1               5                   10                  15

Val Glu Ser Val Asn Ile Lys Val Asp Ser Lys Gly Gly Asn Ala Thr
                20                  25                  30

Ser Gly His Gln Tyr Gly Phe Leu His Glu Asp Ile Asn Asn Ser Gly
            35                  40                  45

Asp Gly Gly Ile Tyr Ala Glu Leu Ile Arg Asn Arg Ala Phe Gln Tyr
        50                  55                  60

Ser Lys Lys Tyr Pro Val Ser Leu Ser Gly Trp Arg Pro Ile Asn Asp
65                  70                  75                  80

Ala Lys Leu Ser Leu Asn Arg Leu Asp Thr Pro Leu Ser Asp Ala Leu
                85                  90                  95

Pro Val Ser Met Asn Val Lys Pro Gly Lys Gly Lys Ala Lys Glu Ile
            100                 105                 110

Gly Phe Leu Asn Glu Gly Tyr Trp Gly Met Asp Val Lys Lys Gln Lys
        115                 120                 125

Tyr Thr Gly Ser Phe Trp Val Lys Gly Ala Tyr Lys Gly His Phe Thr
    130                 135                 140

Ala Ser Leu Arg Ser Asn Leu Thr Asp Asp Val Phe Gly Ser Val Lys
145                 150                 155                 160

Val Lys Ser Lys Ala Asn Lys Lys Gln Trp Val Glu His Glu Phe Val
                165                 170                 175

Leu Thr Pro Asn Lys Asn Ala Pro Asn Ser Asn Asn Thr Phe Ala Ile
            180                 185                 190

Thr Tyr Asp Pro Lys Gly Ala Asp Gly Ala Leu Asp Phe Asn Leu Ile
        195                 200                 205

Ser Leu Phe Pro Pro Thr Tyr Lys Gly Arg Lys Asn Gly Leu Arg Val
    210                 215                 220

Asp Leu Ala Glu Ala Leu Glu Gly Leu His Pro Ser Leu Leu Arg Phe
225                 230                 235                 240

Pro Gly Gly Asn Met Leu Glu Gly Asn Thr Asn Lys Thr Trp Trp Asp
                245                 250                 255

Trp Lys Asp Thr Leu Gly Pro Leu Arg Asn Arg Pro Gly Phe Glu Gly
            260                 265                 270

Val Trp Asn Tyr Gln Gln Thr His Gly Leu Gly Ile Leu Glu Tyr Leu
        275                 280                 285

Gln Trp Ala Glu Asp Met Asn Leu Glu Ile Ile Val Gly Val Tyr Ala
    290                 295                 300

Gly Leu Ser Leu Asp Gly Ser Val Thr Pro Lys Asp Gln Leu Gln Pro
305                 310                 315                 320

Leu Ile Asp Asp Ala Leu Asp Glu Ile Glu Phe Ile Arg Gly Pro Val
```

325                 330                 335
Thr Ser Lys Trp Gly Lys Lys Arg Ala Glu Leu Gly His Pro Lys Pro
            340                 345                 350
Phe Arg Leu Ser Tyr Val Glu Val Gly Asn Glu Asp Trp Leu Ala Gly
            355                 360                 365
Tyr Pro Thr Gly Trp Asn Ser Tyr Lys Glu Tyr Arg Phe Pro Met Phe
    370                 375                 380
Leu Glu Ala Ile Lys Lys Ala His Pro Asp Leu Thr Val Ile Ser Ser
385                 390                 395                 400
Gly Ala Ser Ile Asp Pro Val Gly Lys Lys Asp Ala Gly Phe Asp Ile
                405                 410                 415
Pro Ala Pro Gly Ile Gly Asp Tyr His Pro Tyr Arg Glu Pro Asp Val
            420                 425                 430
Leu Val Glu Glu Phe Asn Leu Phe Asp Asn Asn Lys Tyr Gly His Ile
            435                 440                 445
Ile Gly Glu Val Ala Ser Thr His Pro Asn Gly Gly Thr Gly Trp Ser
    450                 455                 460
Gly Asn Leu Met Pro Tyr Pro Trp Trp Ile Ser Gly Val Gly Glu Ala
465                 470                 475                 480
Val Ala Leu Cys Gly Tyr Glu Arg Asn Ala Asp Arg Ile Pro Gly Thr
                485                 490                 495
Phe Tyr Ala Pro Ile Leu Lys Asn Glu Asn Arg Trp Gln Trp Ala Ile
            500                 505                 510
Thr Met Ile Gln Phe Ala Ala Asp Ser Ala Met Thr Thr Arg Ser Thr
            515                 520                 525
Ser Trp Tyr Val Trp Ser Leu Phe Ala Gly His Pro Met Thr His Thr
    530                 535                 540
Leu Pro Thr Thr Ala Asp Phe Asp Pro Leu Tyr Tyr Val Ala Gly Lys
545                 550                 555                 560
Asn Glu Asp Lys Gly Thr Leu Ile Trp Lys Gly Ala Ala Tyr Asn Thr
                565                 570                 575
Thr Lys Gly Ala Asp Val Pro Val Ser Leu Ser Phe Lys Gly Val Lys
            580                 585                 590
Pro Gly Ala Gln Ala Glu Leu Thr Leu Leu Thr Asn Lys Glu Lys Asp
            595                 600                 605
Pro Phe Ala Phe Asn Asp Pro His Lys Gly Asn Asn Val Val Asp Thr
    610                 615                 620
Lys Lys Thr Val Leu Lys Ala Asp Gly Lys Gly Ala Phe Asn Phe Lys
625                 630                 635                 640
Leu Pro Asn Leu Ser Val Ala Val Leu Glu Thr Leu Lys Lys Gly Lys
                645                 650                 655
Pro Tyr Ser Ser
            660

<210> SEQ ID NO 67
<211> LENGTH: 2312
<212> TYPE: DNA
<213> ORGANISM: Chaetomium globosum

<400> SEQUENCE: 67
atggcgcccc tttcgcttcg ggccctctcg ctgctcgcgc tcacaggagc cgcagccgcg    60 gtgacccctat cggtcgcgaa ctctggcggt aatgatacgt ctccgtacat gtatggcatc   120
atgttcgagg acatcaatca gagcggtgac ggcgggctgt aagttctgtc gcggcttccc   180

| | | |
|---|---|---|
| ctgacaagct tgcatgatgc ttaactaaag tccttaggta cgccgagctg attcgcaacc | 240 | |
| gagccttcca taatagctcc ctccaggcct ggaccgccgt gggggacagc actctcgagg | 300 | |
| tcgtaacctc tgcaccgtta tcggatgccc tgcctcgctc ggtcaaggtc acgagtggaa | 360 | |
| agggcaaggc gggcttgaag aatgccggct actggggaat ggacgtccag aagaccgaca | 420 | |
| agtatagcgg cagcttctac tcgtacggcg cctacgacgg aaagtttacc ctctctctgg | 480 | |
| tgtcggacat cacaaatgag accctggcca ccaccaagat caagtccagg tcggtggagc | 540 | |
| atgcctggac cgagcacaag ttcgagcttc tcccgaccaa gagcgcggcg aacagcaaca | 600 | |
| acagcttcgt gctggagttc cgcccctgcc accagacgga gctccagttc aacctcatca | 660 | |
| gcttgttccc gccgacgtat aagaacaggc ccaacggcat gcgccgagag ctcatggaga | 720 | |
| agctcgcaga cctcaagccc agtttccttc ggattccagg aggcaacaac ctgtaagtgc | 780 | |
| ttccggcgaa actagcagta gttgcctgag agacactaat ctcagcgaac aacagcgagg | 840 | |
| gcaactatgc tggcaactac tggaactggt caagcacact ggcccgctg accgaccggc | 900 | |
| ccggtcgtga cggcgtgtgg acgtacgcca acacggacgg catcgggctg gtcgagtaca | 960 | |
| tgcactgggc cgaggacctc gacgtggagg ttgtgctggc ggtcgccgca ggcctgtacc | 1020 | |
| tgaacggcga tgtggtcccg gaggaggagc tgcacgtctt cgtggaggat gcgctgaacg | 1080 | |
| agctcgagtt cctcatgggc gacgtctcga ccccttgggg cgcgcgccgc gctaagctcg | 1140 | |
| gctaccccaa gccgtggaac atcaagttcg tcgaggtcgg caacgaggac aacctgtggg | 1200 | |
| gcggcctcga ctcgtacaag agctaccggc tgaagacttt ctacgacgcc atcaaggcga | 1260 | |
| agtaccccga catctccatc ttttcgtcga ccgacgagtt tgtgtacaag gagtcgggcc | 1320 | |
| aggactacca caagtacacc cggccggact actccgtgtc ccagttcgac ctgtttgaca | 1380 | |
| actgggccga cggccacccc atcatcatcg gagagtgagt gaacggcgac ccccaccttc | 1440 | |
| ccctaacgcg ggatcgcgag ctgatagatc accccaggta tgcgaccatc cagaacaaca | 1500 | |
| cgggcaagct cgaggacacg gactgggacg cgcccaagaa caagtggtcc aactggatcg | 1560 | |
| gctccgtcgc cgaggccgtc ttcatcctcg gagccgagcg caacggcgac cgggtctggg | 1620 | |
| gcaccacctt tgcgccgatc ctccagaacc tcaacagcta ccaatgggct gtaagtacat | 1680 | |
| acatacatac cgcacccca accccaaccc ccccaaagcg cacctccacc cacccaccca | 1740 | |
| aacacaccac aactacctag ctaacccgcc acacaaacaa acagcccgac ctaatctcct | 1800 | |
| tcaccgccaa cccggccgac accacgccca gcgtctcgta cccgatcatc cagctgctcg | 1860 | |
| cctcgcaccg catcacgcac accctccccg tcagcagcgc cgacgccttc ggcccggcct | 1920 | |
| actgggtggc cggtcgcggc gccgacgacg gctcgtacat cctcaaggcg gccgtgtaca | 1980 | |
| acagcacggg gggtgcggat gtaccggtga gggtgcagtt tgaggcgggg ggtggtggtg | 2040 | |
| gtggtggtgg tggtggtggt ggtggtggtg gtgatgggaa ggggaagggt aaagggaagg | 2100 | |
| gaggggaggg tggtgagggt gtgaagaagg gtgaccgcgc gcagttgacc gtgttgacgg | 2160 | |
| cgccggaggg gccctgggcg cataatacgc cggagaataa ggggcggtc aagacgacag | 2220 | |
| tgacgacgtt gaaggccggg aggggtgggg tgtttgagtt tagtctgccg gatttgtcgg | 2280 | |
| tggcggtgtt ggtggtggag ggggagaagt ga | 2312 | |

<210> SEQ ID NO 68
<211> LENGTH: 670
<212> TYPE: PRT
<213> ORGANISM: Chaetomium globosum

<400> SEQUENCE: 68

```
Met Ala Pro Leu Ser Leu Arg Ala Leu Ser Leu Leu Ala Leu Thr Gly
1               5                   10                  15

Ala Ala Ala Ala Val Thr Leu Ser Val Ala Asn Ser Gly Gly Asn Asp
                20                  25                  30

Thr Ser Pro Tyr Met Tyr Gly Ile Met Phe Glu Asp Ile Asn Gln Ser
        35                  40                  45

Gly Asp Gly Gly Leu Tyr Ala Glu Leu Ile Arg Asn Arg Ala Phe His
    50                  55                  60

Asn Ser Ser Leu Gln Ala Trp Thr Ala Val Gly Asp Ser Thr Leu Glu
65                  70                  75                  80

Val Val Thr Ser Ala Pro Leu Ser Asp Ala Leu Pro Arg Ser Val Lys
                85                  90                  95

Val Thr Ser Gly Lys Gly Lys Ala Gly Leu Lys Asn Ala Gly Tyr Trp
                100                 105                 110

Gly Met Asp Val Gln Lys Thr Asp Lys Tyr Ser Gly Ser Phe Tyr Ser
        115                 120                 125

Tyr Gly Ala Tyr Asp Gly Lys Phe Thr Leu Ser Leu Val Ser Asp Ile
    130                 135                 140

Thr Asn Glu Thr Leu Ala Thr Thr Lys Ile Lys Ser Arg Ser Val Glu
145                 150                 155                 160

His Ala Trp Thr Glu His Lys Phe Glu Leu Leu Pro Thr Lys Ser Ala
                165                 170                 175

Ala Asn Ser Asn Asn Ser Phe Val Leu Glu Phe Arg Pro Cys His Gln
                180                 185                 190

Thr Glu Leu Gln Phe Asn Leu Ile Ser Leu Phe Pro Pro Thr Tyr Lys
        195                 200                 205

Asn Arg Pro Asn Gly Met Arg Arg Glu Leu Met Glu Lys Leu Ala Asp
    210                 215                 220

Leu Lys Pro Ser Phe Leu Arg Ile Pro Gly Gly Asn Asn Leu Glu Gly
225                 230                 235                 240

Asn Tyr Ala Gly Asn Tyr Trp Asn Trp Ser Ser Thr Leu Gly Pro Leu
                245                 250                 255

Thr Asp Arg Pro Gly Arg Asp Gly Val Trp Thr Tyr Ala Asn Thr Asp
        260                 265                 270

Gly Ile Gly Leu Val Glu Tyr Met His Trp Ala Glu Asp Leu Asp Val
    275                 280                 285

Glu Val Val Leu Ala Val Ala Ala Gly Leu Tyr Leu Asn Gly Asp Val
    290                 295                 300

Val Pro Glu Glu Glu Leu His Val Phe Val Glu Asp Ala Leu Asn Glu
305                 310                 315                 320

Leu Glu Phe Leu Met Gly Asp Val Ser Thr Pro Trp Gly Ala Arg Arg
                325                 330                 335

Ala Lys Leu Gly Tyr Pro Lys Pro Trp Asn Ile Lys Phe Val Glu Val
                340                 345                 350

Gly Asn Glu Asp Asn Leu Trp Gly Leu Asp Ser Tyr Lys Ser Tyr
                355                 360                 365

Arg Leu Lys Thr Phe Tyr Asp Ala Ile Lys Ala Lys Tyr Pro Asp Ile
    370                 375                 380

Ser Ile Phe Ser Ser Thr Asp Glu Phe Val Tyr Lys Glu Ser Gly Gln
385                 390                 395                 400

Asp Tyr His Lys Tyr Thr Arg Pro Asp Tyr Ser Val Ser Gln Phe Asp
                405                 410                 415
```

Leu Phe Asp Asn Trp Ala Asp Gly His Pro Ile Ile Gly Glu Tyr
            420                 425                 430

Ala Thr Ile Gln Asn Asn Thr Gly Lys Leu Glu Asp Thr Asp Trp Asp
        435                 440                 445

Ala Pro Lys Asn Lys Trp Ser Asn Trp Ile Gly Ser Val Ala Glu Ala
    450                 455                 460

Val Phe Ile Leu Gly Ala Glu Arg Asn Gly Asp Arg Val Trp Gly Thr
465                 470                 475                 480

Thr Phe Ala Pro Ile Leu Gln Asn Leu Asn Ser Tyr Gln Trp Ala Pro
                485                 490                 495

Asp Leu Ile Ser Phe Thr Ala Asn Pro Ala Asp Thr Thr Pro Ser Val
            500                 505                 510

Ser Tyr Pro Ile Ile Gln Leu Leu Ala Ser His Arg Ile Thr His Thr
        515                 520                 525

Leu Pro Val Ser Ser Ala Asp Ala Phe Gly Pro Ala Tyr Trp Val Ala
    530                 535                 540

Gly Arg Gly Ala Asp Asp Gly Ser Tyr Ile Leu Lys Ala Ala Val Tyr
545                 550                 555                 560

Asn Ser Thr Gly Gly Ala Asp Val Pro Val Arg Val Gln Phe Glu Ala
                565                 570                 575

Gly Gly Gly Gly Gly Gly Gly Gly Gly Gly Gly Gly Gly Gly Gly Asp
            580                 585                 590

Gly Lys Gly Lys Gly Lys Lys Gly Gly Glu Gly Glu Gly Val
        595                 600                 605

Lys Lys Gly Asp Arg Ala Gln Leu Thr Val Leu Thr Ala Pro Glu Gly
    610                 615                 620

Pro Trp Ala His Asn Thr Pro Glu Asn Lys Gly Ala Val Lys Thr Thr
625                 630                 635                 640

Val Thr Thr Leu Lys Ala Gly Arg Gly Val Phe Glu Phe Ser Leu
                645                 650                 655

Pro Asp Leu Ser Val Ala Val Leu Val Val Glu Gly Glu Lys
            660                 665                 670

<210> SEQ ID NO 69
<211> LENGTH: 1002
<212> TYPE: DNA
<213> ORGANISM: Fusarium verticillioides

<400> SEQUENCE: 69
atgcgtcttc tatcgtttcc cagccatctc ctcgtggcct tcctaaccct caaagaggct        60
tcatccctcg ccctcagcaa acgggatagc cctgtcctcc ccggcctctg ggcggacccc       120
aacatcgcca tcgtcgacaa gacatactac atcttcccta ccaccgacgg tttcgaaggc       180
tggggcggca acgtcttcta ctggtggaaa tcaaaagatc tcgtatcatg acaaagagc        240 gacaagccat tccttactct caatggtacg aatggcaacg ttccctgggc tacaggtaat       300
gcctgggctc ctgctttcgc tgctcgcgga ggcaagtatt acttctacca tagtgggaat       360
aatccctctg tgagtgatgg gcataagagt attggtgcgg cggtggctga tcatcctgag       420
gggccgtgga aggcacagga taagccgatg atcaagggaa cttctgatga ggagattgtc       480
agcaaccagg ctatcgatcc cgctgccttt gaagaccctg agactggaaa gtggtatatc       540
tactggggaa acggtgtccc cattgtcgca gagctcaacg acgacatggt ctctctcaaa       600
gcaggctggc acaaaatcac aggtcttcag aattccgcg agggtctttt cgtcaactat        660
cgcgatggaa catatcatct gacatactct atcgacgata cgggctcaga gaactatcgc       720

```
gttgggtacg ctacggcgga taacccatt ggaccttgga catatcgtgg tgttcttctg    780
gagaaggacg aatcgaaggg cattcttgct acgggacata actccatcat caacattcct    840
ggaacggatg agtggtatat cgcgtatcat cgcttccata ttcccgatgg aaatgggtat    900
aataggagga ctacgattga tagggtaccc atcgacaagg atacgggttt gtttggaaag    960
gttacgccga ctttgcagag tgttgatcct aggcctttgt ag                     1002
```

<210> SEQ ID NO 70
<211> LENGTH: 333
<212> TYPE: PRT
<213> ORGANISM: Fusarium verticillioides

<400> SEQUENCE: 70

```
Met Arg Leu Leu Ser Phe Pro Ser His Leu Leu Val Ala Phe Leu Thr
1               5                   10                  15

Leu Lys Glu Ala Ser Ser Leu Ala Leu Ser Lys Arg Asp Ser Pro Val
            20                  25                  30

Leu Pro Gly Leu Trp Ala Asp Pro Asn Ile Ala Ile Val Asp Lys Thr
        35                  40                  45

Tyr Tyr Ile Phe Pro Thr Thr Asp Gly Phe Glu Gly Trp Gly Gly Asn
    50                  55                  60

Val Phe Tyr Trp Trp Lys Ser Lys Asp Leu Val Ser Trp Thr Lys Ser
65                  70                  75                  80

Asp Lys Pro Phe Leu Thr Leu Asn Gly Thr Asn Gly Asn Val Pro Trp
                85                  90                  95

Ala Thr Gly Asn Ala Trp Ala Pro Ala Phe Ala Ala Arg Gly Gly Lys
            100                 105                 110

Tyr Tyr Phe Tyr His Ser Gly Asn Asn Pro Ser Val Ser Asp Gly His
        115                 120                 125

Lys Ser Ile Gly Ala Ala Val Ala Asp His Pro Glu Gly Pro Trp Lys
    130                 135                 140

Ala Gln Asp Lys Pro Met Ile Lys Gly Thr Ser Asp Glu Glu Ile Val
145                 150                 155                 160

Ser Asn Gln Ala Ile Asp Pro Ala Ala Phe Glu Asp Pro Glu Thr Gly
                165                 170                 175

Lys Trp Tyr Ile Tyr Trp Gly Asn Gly Val Pro Ile Val Ala Glu Leu
            180                 185                 190

Asn Asp Asp Met Val Ser Leu Lys Ala Gly Trp His Lys Ile Thr Gly
        195                 200                 205

Leu Gln Asn Phe Arg Glu Gly Leu Phe Val Asn Tyr Arg Asp Gly Thr
    210                 215                 220

Tyr His Leu Thr Tyr Ser Ile Asp Asp Thr Gly Ser Glu Asn Tyr Arg
225                 230                 235                 240

Val Gly Tyr Ala Thr Ala Asp Asn Pro Ile Gly Pro Trp Thr Tyr Arg
                245                 250                 255

Gly Val Leu Leu Glu Lys Asp Glu Ser Lys Gly Ile Leu Ala Thr Gly
            260                 265                 270

His Asn Ser Ile Ile Asn Ile Pro Gly Thr Asp Glu Trp Tyr Ile Ala
        275                 280                 285

Tyr His Arg Phe His Ile Pro Asp Gly Asn Gly Tyr Asn Arg Glu Thr
    290                 295                 300

Thr Ile Asp Arg Val Pro Ile Asp Lys Asp Thr Gly Leu Phe Gly Lys
305                 310                 315                 320
```

```
Val Thr Pro Thr Leu Gln Ser Val Asp Pro Arg Pro Leu
                325                 330

<210> SEQ ID NO 71
<211> LENGTH: 1695
<212> TYPE: DNA
<213> ORGANISM: Fusarium verticillioides

<400> SEQUENCE: 71
atgctcttct cgctcgttct tcctaccctt gcctttcaag ccagcctggc gctcggcgat      60
acatccgtta ctgtcgacac cagccagaaa ctccaggtca tcgatggctt tggtgtctca     120
gaagcctacg gccacgccaa acaattccaa aacctcggtc ctggaccaca gaaagagggc     180
ctcgatcttc tcttcaacac tacaaccggc gcaggcttat ccatcatccg aaacaagatc     240
ggctgcgacg cctccaactc catcaccagc accaacaccg acaacccaga taagcaggct     300
gtttaccatt ttgacggcga tgatgatggt caggtatggt ttagcaaaca ggccatgagc     360
tatggtgtag atactatcta cgctaatgct tggtctgcgc ctgtatacat gaagtcagcc     420
cagagtatgg gccgtctctg cggtacacct ggtgtgtcgt gctcctctgg agattggaga     480
catcgttacg ttgagatgat agctgagtac ctctcctact acaagcaggc tggcatccca     540
gtgtcgcacg ttggattcct caatgagggt gacggctcgg actttatgct ctcaactgcc     600
gaacaggctg cagatgtcat tcctcttcta cacagcgctt tgcagtccaa gggccttggc     660
gatatcaaga tgacgtgctg tgataacatc ggttggaagt cacagatgga ctataccgcc     720
aagctggctg agcttgaggt ggagaagtat ctatctgtca tcacatccca cgagtactcc     780
agcagcccca accagcctat gaacactaca ttgccaacct ggatgtccga gggagctgcc     840
aatgaccagg catttgccac agcgtggtac gtcaacggcg gttccaacga aggtttcaca     900
tgggcagtca agatcgcaca aggcatcgtc aatgccgacc tctcagcgta tatctactgg     960
gagggcgttg agaccaacaa caaggggtct ctatctcacg tcatcgacac ggacggtacc    1020
aagtttacca tatcctcgat tctctgggcc attgctcact ggtcgcgcca tattcgccct    1080
ggtgcgcata gactttcgac ttcaggtgtt gtgcaagata cgattgttgg tgcgtttgag    1140
aacgttgatg gcagtgtcgt catggtgctc accaactctg gcactgctgc tcagactgtg    1200
gacctgggtg tttcgggaag tagcttctca acagctcagg ctttcacttc ggatgctgag    1260
gcgcagatgg tcgataccaa ggtgactctg tccgacggtc gtgtcaaggt tacggtcccg    1320
gtgcacggtg tcgtcactgt gaagctcaca acagcaaaaa gctccaaacc ggtctcaact    1380
gctgtttctg cgcaatctgc ccccactcca actagtgtta agcacacctt gactcaccag    1440
aagacttctt caacaacact ctcgaccgcc aaggccccaa cctccactca gactacctct    1500
gtagttgagt cagccaaggc ggtgaaatac cctgtccccc ctgtagcatc caagggatcc    1560
tcgaagagtg ctcccaagaa gggtaccaag aagaccacta cgaagaaggg ctcccaccaa    1620
tcgcacaagg cgcatagtgc tactcatcgt cgatgccgcc atggaagtta ccgtcgtggc    1680
cactgcacca actaa                                                     1695

<210> SEQ ID NO 72
<211> LENGTH: 537
<212> TYPE: PRT
<213> ORGANISM: Fusarium verticillioides

<400> SEQUENCE: 72

Met Leu Phe Ser Leu Val Leu Pro Thr Leu Ala Phe Gln Ala Ser Leu
1               5                   10                  15
```

```
Ala Leu Gly Asp Thr Ser Val Thr Val Asp Thr Ser Gln Lys Leu Gln
            20                  25                  30

Val Ile Asp Gly Phe Gly Val Ser Glu Ala Tyr Gly His Ala Lys Gln
        35                  40                  45

Phe Gln Asn Leu Gly Pro Gly Pro Gln Lys Glu Gly Leu Asp Leu Leu
50                  55                  60

Phe Asn Thr Thr Thr Gly Ala Gly Leu Ser Ile Ile Arg Asn Lys Ile
65                  70                  75                  80

Gly Cys Asp Ala Ser Asn Ser Ile Thr Ser Thr Asn Thr Asp Asn Pro
                85                  90                  95

Asp Lys Gln Ala Val Tyr His Phe Asp Gly Asp Asp Gly Gln Ser
                100                 105                 110

Ala Gln Ser Met Gly Arg Leu Cys Gly Thr Pro Gly Val Ser Cys Ser
            115                 120                 125

Ser Gly Asp Trp Arg His Arg Tyr Val Glu Met Ile Ala Glu Tyr Leu
    130                 135                 140

Ser Tyr Tyr Lys Gln Ala Gly Ile Pro Val Ser His Val Gly Phe Leu
145                 150                 155                 160

Asn Glu Gly Asp Gly Ser Asp Phe Met Leu Ser Thr Ala Glu Gln Ala
                165                 170                 175

Ala Asp Val Ile Pro Leu Leu His Ser Ala Leu Gln Ser Lys Gly Leu
            180                 185                 190

Gly Asp Ile Lys Met Thr Cys Cys Asp Asn Ile Gly Trp Lys Ser Gln
        195                 200                 205

Met Asp Tyr Thr Ala Lys Leu Ala Glu Leu Glu Val Glu Lys Tyr Leu
    210                 215                 220

Ser Val Ile Thr Ser His Glu Tyr Ser Ser Pro Asn Gln Pro Met
225                 230                 235                 240

Asn Thr Thr Leu Pro Thr Trp Met Ser Glu Gly Ala Ala Asn Asp Gln
                245                 250                 255

Ala Phe Ala Thr Ala Trp Tyr Val Asn Gly Gly Ser Asn Glu Gly Phe
            260                 265                 270

Thr Trp Ala Val Lys Ile Ala Gln Gly Ile Val Asn Ala Asp Leu Ser
        275                 280                 285

Ala Tyr Ile Tyr Trp Glu Gly Val Glu Thr Asn Asn Lys Gly Ser Leu
    290                 295                 300

Ser His Val Ile Asp Thr Asp Gly Thr Lys Phe Thr Ile Ser Ser Ile
305                 310                 315                 320

Leu Trp Ala Ile Ala His Trp Ser Arg His Ile Arg Pro Gly Ala His
                325                 330                 335

Arg Leu Ser Thr Ser Gly Val Val Gln Asp Thr Ile Val Gly Ala Phe
            340                 345                 350

Glu Asn Val Asp Gly Ser Val Val Met Val Leu Thr Asn Ser Gly Thr
        355                 360                 365

Ala Ala Gln Thr Val Asp Leu Gly Val Ser Gly Ser Ser Phe Ser Thr
    370                 375                 380

Ala Gln Ala Phe Thr Ser Asp Ala Glu Ala Gln Met Val Asp Thr Lys
385                 390                 395                 400

Val Thr Leu Ser Asp Gly Arg Val Lys Val Thr Val Pro Val His Gly
                405                 410                 415

Val Val Thr Val Lys Leu Thr Thr Ala Lys Ser Ser Lys Pro Val Ser
            420                 425                 430
```

```
Thr Ala Val Ser Ala Gln Ser Ala Pro Thr Pro Thr Ser Val Lys His
            435                 440                 445

Thr Leu Thr His Gln Lys Thr Ser Thr Thr Leu Ser Thr Ala Lys
    450                 455                 460

Ala Pro Thr Ser Thr Gln Thr Thr Ser Val Val Glu Ser Ala Lys Ala
465                 470                 475                 480

Val Lys Tyr Pro Val Pro Val Ala Ser Lys Gly Ser Ser Lys Ser
                485                 490                 495

Ala Pro Lys Lys Gly Thr Lys Lys Thr Thr Thr Lys Lys Gly Ser His
            500                 505                 510

Gln Ser His Lys Ala His Ser Ala Thr His Arg Arg Cys Arg His Gly
            515                 520                 525

Ser Tyr Arg Arg Gly His Cys Thr Asn
    530                 535

<210> SEQ ID NO 73
<211> LENGTH: 948
<212> TYPE: DNA
<213> ORGANISM: Fusarium verticillioides

<400> SEQUENCE: 73
atgtggaaac tcctcgtcag cggtcttgtc gccgtcgcgt ccctcagcgg cgtgaacgct      60
gcttatccta accctggtcc cgtcaccggc gatactcgtg ttcacgaccc tacggttgtc     120
aagactccca gcggtggata cttgctggct catactggcg ataacgtttc gctcaagact     180
tcttctgatc gaactgcttg gaaggatgca ggtgctgttt ccccaacggt gcgccttgg      240 actacgcagt acaccaaggg cgacaagaac ctctgggccc ctgatatctc ctaccacaac     300
ggccagtact atctgtacta ctccgcctct tccttcggtc agcgtacctc tgccattttt     360
ctcgctacca gcaagaccgg tgcatccggc tcgtggacca ccaaggcgt cgtcgtcgag     420 tccaacaaca caacgactca caatgccatt gacggaaatc tctttgtcga ctctgatgga     480
aaatggtggc tctccttcgg ctctttctgg tccggcatca agctcatcca actcgacccc     540
aagaccggca gcgcaccggc tcaagcatg tactccctcg ccaaacgcga cgcctccgtc     600
gaaggcgccg tcgaggctcc gttcatcacc aaacgcggaa gcacctacta cctctgggtg     660
tcgttcgaca gtgttgcca gggcgctgct agcacgtacc gtgtcatggt tggacggtcg     720
agcagcatta ctggtcctta tgttgacaag gctggtaagc agatgatgtc tggtggagga     780
acggagatta tggctagtca cggatctatt catggaccgg acataatgc tgttttcact     840 gataacgatg cggacgttct tgtctatcat tactacgata cgctggcac agcgctgttg     900 ggcatcaact tgctcagata tgacaatggc tggcctgttg cttattag               948

<210> SEQ ID NO 74
<211> LENGTH: 315
<212> TYPE: PRT
<213> ORGANISM: Fusarium verticillioides

<400> SEQUENCE: 74

Met Trp Lys Leu Leu Val Ser Gly Leu Val Ala Val Ala Ser Leu Ser
1               5                   10                  15

Gly Val Asn Ala Ala Tyr Pro Asn Pro Gly Pro Val Thr Gly Asp Thr
                20                  25                  30

Arg Val His Asp Pro Thr Val Val Lys Thr Pro Ser Gly Gly Tyr Leu
            35                  40                  45

Leu Ala His Thr Gly Asp Asn Val Ser Leu Lys Thr Ser Ser Asp Arg
```

```
            50                  55                  60
Thr Ala Trp Lys Asp Ala Gly Ala Val Phe Pro Asn Gly Ala Pro Trp
 65                  70                  75                  80

Thr Thr Gln Tyr Thr Lys Gly Asp Lys Asn Leu Trp Ala Pro Asp Ile
                 85                  90                  95

Ser Tyr His Asn Gly Gln Tyr Tyr Leu Tyr Tyr Ser Ala Ser Ser Phe
             100                 105                 110

Gly Gln Arg Thr Ser Ala Ile Phe Leu Ala Thr Ser Lys Thr Gly Ala
         115                 120                 125

Ser Gly Ser Trp Thr Asn Gln Gly Val Val Glu Ser Asn Asn Asn
     130                 135                 140

Asn Asp Tyr Asn Ala Ile Asp Gly Asn Leu Phe Val Asp Ser Asp Gly
145                 150                 155                 160

Lys Trp Trp Leu Ser Phe Gly Ser Phe Trp Ser Gly Ile Lys Leu Ile
                165                 170                 175

Gln Leu Asp Pro Lys Thr Gly Lys Arg Thr Gly Ser Ser Met Tyr Ser
            180                 185                 190

Leu Ala Lys Arg Asp Ala Ser Val Glu Gly Ala Val Glu Ala Pro Phe
        195                 200                 205

Ile Thr Lys Arg Gly Ser Thr Tyr Tyr Leu Trp Val Ser Phe Asp Lys
    210                 215                 220

Cys Cys Gln Gly Ala Ala Ser Thr Tyr Arg Val Met Val Gly Arg Ser
225                 230                 235                 240

Ser Ser Ile Thr Gly Pro Tyr Val Asp Lys Ala Gly Lys Gln Met Met
                245                 250                 255

Ser Gly Gly Gly Thr Glu Ile Met Ala Ser His Gly Ser Ile His Gly
            260                 265                 270

Pro Gly His Asn Ala Val Phe Thr Asp Asn Asp Ala Asp Val Leu Val
        275                 280                 285

Tyr His Tyr Tyr Asp Asn Ala Gly Thr Ala Leu Leu Gly Ile Asn Leu
    290                 295                 300

Leu Arg Tyr Asp Asn Gly Trp Pro Val Ala Tyr
305                 310                 315

<210> SEQ ID NO 75
<211> LENGTH: 1352
<212> TYPE: DNA
<213> ORGANISM: Trichoderma reesei

<400> SEQUENCE: 75
atgaaagcaa acgtcatctt gtgcctcctg gccccctgg tcgccgctct ccccaccgaa      60
accatccacc tcgaccccga gctcgccgct ctccgcgcca acctcaccga gcgaacagcc    120
gacctctggg accgccaagc tctctcaaagc atcgaccagc tcatcaagag aaaaggcaag    180
ctctactttg gcaccgccac cgaccgcggc ctcctccaac gggaaaagaa cgcggccatc    240
atccaggcag acctcggcca ggtgacgccg gagaacagca tgaagtggca gtcgctcgag    300
aacaaccaag gccagctgaa ctggggagac gccgactatc tcgtcaactt tgcccagcaa    360
aacggcaagt cgatacgcgg ccacactctg atctggcact cgcagctgcc tcgcgtgggtg    420 aacaatatca caacgcgga tactctgcgg caagtcatcc gcacccatgt ctctactgtg    480
gttgggcggt acaagggcaa gattcgtgct tgggtgagtt ttgaacacca catgccccct    540
ttcttagtcc gctcctcctc ctcttggaac ttctcacagt tatagccgta tacaacattc    600
gacaggaaat ttaggatgac aactactgac tgacttgtgt gtgtgatggc gataggacgt    660
```

```
ggtcaatgaa atcttcaacg aggatggaac gctgcgctct tcagtcttttt ccaggctcct    720
cggcgaggag tttgtctcga ttgccttttcg tgctgctcga gatgctgacc cttctgcccg    780
tctttacatc aacgactaca atctcgaccg cgccaactat ggcaaggtca acgggttgaa    840
gacttacgtc tccaagtgga tctctcaagg agttcccatt gacggtattg gtgagccacg    900
acccctaaat gtcccccatt agagtctctt tctagagcca aggcttgaag ccattcaggg    960
actgacacga gagccttctc tacaggaagc cagtcccatc tcagcggcgg cggaggctct   1020
ggtacgctgg gtgcgctcca gcagctggca acggtacccg tcaccgagct ggccattacc   1080
gagctggaca ttcaggggc accgacgacg gattacaccc aagttgttca agcatgcctg   1140
agcgtctcca gtgcgtcgg catcaccgtg tggggcatca gtgacaaggt aagttgcttc   1200
ccctgtctgt gcttatcaac tgtaagcagc aacaactgat gctgtctgtc tttacctagg   1260
actcgtggcg tgccagcacc aaccctcttc tgtttgacgc aaacttcaac cccaagccgg   1320
catataacag cattgttggc atcttacaat ag                                 1352
```

<210> SEQ ID NO 76
<211> LENGTH: 347
<212> TYPE: PRT
<213> ORGANISM: Trichoderma reesei

<400> SEQUENCE: 76

```
Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
```

```
                        245                 250                 255
Gly Gly Gly Gly Ser Gly Thr Leu Gly Ala Leu Gln Gln Leu Ala Thr
                260                 265                 270

Val Pro Val Thr Glu Leu Ala Ile Thr Glu Leu Asp Ile Gln Gly Ala
            275                 280                 285

Pro Thr Thr Asp Tyr Thr Gln Val Val Gln Ala Cys Leu Ser Val Ser
        290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345
```

<210> SEQ ID NO 77
<211> LENGTH: 222
<212> TYPE: PRT
<213> ORGANISM: Trichoderma reesei

<400> SEQUENCE: 77

```
Met Val Ser Phe Thr Ser Leu Leu Ala Ala Ser Pro Pro Ser Arg Ala
1               5                   10                  15

Ser Cys Arg Pro Ala Ala Glu Val Glu Ser Val Ala Val Glu Lys Arg
            20                  25                  30

Gln Thr Ile Gln Pro Gly Thr Gly Tyr Asn Asn Gly Tyr Phe Tyr Ser
        35                  40                  45

Tyr Trp Asn Asp Gly His Gly Gly Val Thr Tyr Thr Asn Gly Pro Gly
    50                  55                  60

Gly Gln Phe Ser Val Asn Trp Ser Asn Ser Gly Asn Phe Val Gly Gly
65                  70                  75                  80

Lys Gly Trp Gln Pro Gly Thr Lys Asn Lys Val Ile Asn Phe Ser Gly
                85                  90                  95

Ser Tyr Asn Pro Asn Gly Asn Ser Tyr Leu Ser Val Tyr Gly Trp Ser
            100                 105                 110

Arg Asn Pro Leu Ile Glu Tyr Tyr Ile Val Glu Asn Phe Gly Thr Tyr
        115                 120                 125

Asn Pro Ser Thr Gly Ala Thr Lys Leu Gly Glu Val Thr Ser Asp Gly
    130                 135                 140

Ser Val Tyr Asp Ile Tyr Arg Thr Gln Arg Val Asn Gln Pro Ser Ile
145                 150                 155                 160

Ile Gly Thr Ala Thr Phe Tyr Gln Tyr Trp Ser Val Arg Arg Asn His
                165                 170                 175

Arg Ser Ser Gly Ser Val Asn Thr Ala Asn His Phe Asn Ala Trp Ala
            180                 185                 190

Gln Gln Gly Leu Thr Leu Gly Thr Met Asp Tyr Gln Ile Val Ala Val
        195                 200                 205

Glu Gly Tyr Phe Ser Ser Gly Ser Ala Ser Ile Thr Val Ser
    210                 215                 220
```

<210> SEQ ID NO 78
<211> LENGTH: 797
<212> TYPE: PRT
<213> ORGANISM: Trichoderma reesei

<400> SEQUENCE: 78

```
Met Val Asn Asn Ala Ala Leu Leu Ala Ala Leu Ser Ala Leu Leu Pro
```

-continued

```
1               5                   10                  15
Thr Ala Leu Ala Gln Asn Asn Gln Thr Tyr Ala Asn Tyr Ser Ala Gln
                20                  25                  30

Gly Gln Pro Asp Leu Tyr Pro Glu Thr Leu Ala Thr Leu Thr Leu Ser
                35                  40                  45

Phe Pro Asp Cys Glu His Gly Pro Leu Lys Asn Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
                100                 105                 110

Gly Leu Asp Arg Ala Asn Phe Ala Thr Lys Gly Gly Gln Phe Glu Trp
                115                 120                 125

Ala Thr Ser Phe Pro Met Pro Ile Leu Thr Thr Ala Ala Leu Asn Arg
                130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
                180                 185                 190

Glu Asp Ala Phe Phe Leu Ser Ser Ala Tyr Thr Tyr Glu Tyr Ile Thr
                195                 200                 205

Gly Ile Gln Gly Gly Val Asp Pro Glu His Leu Lys Val Ala Ala Thr
                210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Gln Asp Leu Ser Glu Tyr
                245                 250                 255

Tyr Thr Pro Gln Phe Leu Ala Ala Ala Arg Tyr Ala Lys Ser Arg Ser
                260                 265                 270

Leu Met Cys Ala Tyr Asn Ser Val Asn Gly Val Pro Ser Cys Ala Asn
                275                 280                 285

Ser Phe Phe Leu Gln Thr Leu Leu Arg Glu Ser Trp Gly Phe Pro Glu
                290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ala Ser Ser Leu
                325                 330                 335

Arg Ala Gly Thr Asp Ile Asp Cys Gly Gln Thr Tyr Pro Trp His Leu
                340                 345                 350

Asn Glu Ser Phe Val Ala Gly Glu Val Ser Arg Gly Glu Ile Glu Arg
                355                 360                 365

Ser Val Thr Arg Leu Tyr Ala Asn Leu Val Arg Leu Gly Tyr Phe Asp
                370                 375                 380

Lys Lys Asn Gln Tyr Arg Ser Leu Gly Trp Lys Asp Val Lys Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ser Lys Lys Val Arg Ser Ile
                420                 425                 430
```

```
Ala Leu Ile Gly Pro Trp Ala Asn Ala Thr Thr Gln Met Gln Gly Asn
            435                 440                 445
Tyr Tyr Gly Pro Ala Pro Tyr Leu Ile Ser Pro Leu Glu Ala Ala Lys
    450                 455                 460
Lys Ala Gly Tyr His Val Asn Phe Glu Leu Gly Thr Glu Ile Ala Gly
465                 470                 475                 480
Asn Ser Thr Thr Gly Phe Ala Lys Ala Ile Ala Ala Lys Lys Ser
                485                 490                 495
Asp Ala Ile Ile Tyr Leu Gly Gly Ile Asp Asn Thr Ile Glu Gln Glu
                500                 505                 510
Gly Ala Asp Arg Thr Asp Ile Ala Trp Pro Gly Asn Gln Leu Asp Leu
            515                 520                 525
Ile Lys Gln Leu Ser Glu Val Gly Lys Pro Leu Val Val Leu Gln Met
        530                 535                 540
Gly Gly Gly Gln Val Asp Ser Ser Leu Lys Ser Asn Lys Lys Val
545                 550                 555                 560
Asn Ser Leu Val Trp Gly Gly Tyr Pro Gly Gln Ser Gly Gly Val Ala
                565                 570                 575
Leu Phe Asp Ile Leu Ser Gly Lys Arg Ala Pro Ala Gly Arg Leu Val
            580                 585                 590
Thr Thr Gln Tyr Pro Ala Glu Tyr Val His Gln Phe Pro Gln Asn Asp
        595                 600                 605
Met Asn Leu Arg Pro Asp Gly Lys Ser Asn Pro Gly Gln Thr Tyr Ile
    610                 615                 620
Trp Tyr Thr Gly Lys Pro Val Tyr Glu Phe Gly Ser Gly Leu Phe Tyr
625                 630                 635                 640
Thr Thr Phe Lys Glu Thr Leu Ala Ser His Pro Lys Ser Leu Lys Phe
                645                 650                 655
Asn Thr Ser Ser Ile Leu Ser Ala Pro His Pro Gly Tyr Thr Tyr Ser
            660                 665                 670
Glu Gln Ile Pro Val Phe Thr Phe Glu Ala Asn Ile Lys Asn Ser Gly
        675                 680                 685
Lys Thr Glu Ser Pro Tyr Thr Ala Met Leu Phe Val Arg Thr Ser Asn
    690                 695                 700
Ala Gly Pro Ala Pro Tyr Pro Asn Lys Trp Leu Val Gly Phe Asp Arg
705                 710                 715                 720
Leu Ala Asp Ile Lys Pro Gly His Ser Ser Lys Leu Ser Ile Pro Ile
                725                 730                 735
Pro Val Ser Ala Leu Ala Arg Val Asp Ser His Gly Asn Arg Ile Val
            740                 745                 750
Tyr Pro Gly Lys Tyr Glu Leu Ala Leu Asn Thr Asp Glu Ser Val Lys
        755                 760                 765
Leu Glu Phe Glu Leu Val Gly Glu Val Thr Ile Glu Asn Trp Pro
    770                 775                 780
Leu Glu Glu Gln Gln Ile Lys Asp Ala Thr Pro Asp Ala
785                 790                 795

<210> SEQ ID NO 79
<211> LENGTH: 744
<212> TYPE: PRT
<213> ORGANISM: Trichoderma reesei

<400> SEQUENCE: 79

Met Arg Tyr Arg Thr Ala Ala Ala Leu Ala Leu Ala Thr Gly Pro Phe
```

-continued

```
1               5                   10                  15
Ala Arg Ala Asp Ser His Ser Thr Ser Gly Ala Ser Ala Glu Ala Val
                20                  25                  30
Val Pro Pro Ala Gly Thr Pro Trp Gly Thr Ala Tyr Asp Lys Ala Lys
                35                  40                  45
Ala Ala Leu Ala Lys Leu Asn Leu Gln Asp Lys Val Gly Ile Val Ser
 50                 55                  60
Gly Val Gly Trp Asn Gly Gly Pro Cys Val Gly Asn Thr Ser Pro Ala
 65                 70                  75                  80
Ser Lys Ile Ser Tyr Pro Ser Leu Cys Leu Gln Asp Gly Pro Leu Gly
                85                  90                  95
Val Arg Tyr Ser Thr Gly Ser Thr Ala Phe Thr Pro Gly Val Gln Ala
                100                 105                 110
Ala Ser Thr Trp Asp Val Asn Leu Ile Arg Glu Arg Gly Gln Phe Ile
                115                 120                 125
Gly Glu Glu Val Lys Ala Ser Gly Ile His Val Ile Leu Gly Pro Val
130                 135                 140
Ala Gly Pro Leu Gly Lys Thr Pro Gln Gly Gly Arg Asn Trp Glu Gly
145                 150                 155                 160
Phe Gly Val Asp Pro Tyr Leu Thr Gly Ile Ala Met Gly Gln Thr Ile
                165                 170                 175
Asn Gly Ile Gln Ser Val Gly Val Gln Ala Thr Ala Lys His Tyr Ile
                180                 185                 190
Leu Asn Glu Gln Glu Leu Asn Arg Glu Thr Ile Ser Ser Asn Pro Asp
                195                 200                 205
Asp Arg Thr Leu His Glu Leu Tyr Thr Trp Pro Phe Ala Asp Ala Val
                210                 215                 220
Gln Ala Asn Val Ala Ser Val Met Cys Ser Tyr Asn Lys Val Asn Thr
225                 230                 235                 240
Thr Trp Ala Cys Glu Asp Gln Tyr Thr Leu Gln Thr Val Leu Lys Asp
                245                 250                 255
Gln Leu Gly Phe Pro Gly Tyr Val Met Thr Asp Trp Asn Ala Gln His
                260                 265                 270
Thr Thr Val Gln Ser Ala Asn Ser Gly Leu Asp Met Ser Met Pro Gly
                275                 280                 285
Thr Asp Phe Asn Gly Asn Asn Arg Leu Trp Gly Pro Ala Leu Thr Asn
                290                 295                 300
Ala Val Asn Ser Asn Gln Val Pro Thr Ser Arg Val Asp Asp Met Val
305                 310                 315                 320
Thr Arg Ile Leu Ala Ala Trp Tyr Leu Thr Gly Gln Asp Gln Ala Gly
                325                 330                 335
Tyr Pro Ser Phe Asn Ile Ser Arg Asn Val Gln Gly Asn His Lys Thr
                340                 345                 350
Asn Val Arg Ala Ile Ala Arg Asp Gly Ile Val Leu Leu Lys Asn Asp
                355                 360                 365
Ala Asn Ile Leu Pro Leu Lys Lys Pro Ala Ser Ile Ala Val Val Gly
370                 375                 380
Ser Ala Ala Ile Ile Gly Asn His Ala Arg Asn Ser Pro Ser Cys Asn
385                 390                 395                 400
Asp Lys Gly Cys Asp Asp Gly Ala Leu Gly Met Gly Trp Gly Ser Gly
                405                 410                 415
Ala Val Asn Tyr Pro Tyr Phe Val Ala Pro Tyr Asp Ala Ile Asn Thr
                420                 425                 430
```

Arg Ala Ser Ser Gln Gly Thr Gln Val Thr Leu Ser Asn Thr Asp Asn
         435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
             485                 490                 495

Val Gln Ala Val Ala Gly Ala Asn Ser Asn Val Ile Val Val Val His
             500                 505                 510

Ser Val Gly Ala Ile Ile Leu Glu Gln Ile Leu Ala Leu Pro Gln Val
             515                 520                 525

Lys Ala Val Val Trp Ala Gly Leu Pro Ser Gln Glu Ser Gly Asn Ala
             530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
             565                 570                 575

Gly Gly Ser Asp Ser Phe Ser Glu Gly Leu Phe Ile Asp Tyr Lys His
             580                 585                 590

Phe Asp Asp Ala Asn Ile Thr Pro Arg Tyr Glu Phe Gly Tyr Gly Leu
             595                 600                 605

Ser Tyr Thr Lys Phe Asn Tyr Ser Arg Leu Ser Val Leu Ser Thr Ala
             610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
             645                 650                 655

Gln Val Thr Gly Ala Glu Val Ala Gln Leu Tyr Ile Thr Tyr Pro Ser
             660                 665                 670

Ser Ala Pro Arg Thr Pro Pro Lys Gln Leu Arg Gly Phe Ala Lys Leu
             675                 680                 685

Asn Leu Thr Pro Gly Gln Ser Gly Thr Ala Thr Phe Asn Ile Arg Arg
             690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
             725                 730                 735

Leu Thr Ser Thr Leu Ser Val Ala
             740

<210> SEQ ID NO 80
<211> LENGTH: 2031
<212> TYPE: DNA
<213> ORGANISM: Podospora anserina

<400> SEQUENCE: 80
atgatccacc tcaagccagc cctcgcggcg ttgttggcgc tgtcgacgca atgtgtggct      60
attgatttgt tgtcaagtc ttcgggggg aataagacga ctgatatcat gtatggtctt     120
atgcacgagg atatcaacaa ctccggcgac ggcggcatct acgccgagct aatctccaac     180
cgcgcgttcc aagggagtga gaagttcccc tccaacctcg acaactggag ccccgtcggt     240
ggcgctaccc ttacccttca gaagcttgcc aagccccttt cctctgcgtt gccttactcc     300

| | |
|---|---|
| gtcaatgttg ccaaccccaa ggagggcaag gcaagggca aggacaccaa ggggaagaag | 360 |
| gttggcttgg ccaatgctgg gttttgggt atggatgtca agaggcagaa gtacactggt | 420 |
| agcttccacg ttactggtga gtacaagggt gactttgagg ttagcttgcg cagcgcgatt | 480 |
| accggggaga cctttggcaa gaaggtggtg aaggtggga gtaagaaggg gaagtggacc | 540 |
| gagaaggagt ttgagttggt gcctttcaag gatgcgccca acagcaacaa cacctttgtt | 600 |
| gtgcagtggg atgccgaggg cgcaaaggac ggatctttgg atctcaactt gatcagcttg | 660 |
| ttccctccga cattcaaggg aaggaagaat gggctgagaa ttgatcttgc gcagacgatg | 720 |
| gttgagctca agccgaccttt cttgcgcttc cccgtggca acatgctcga gggtaacacc | 780 |
| ttggacactt ggtggaagtg gtacgagacc attggccctc tgaaggatcg cccgggcatg | 840 |
| gctggtgtct gggagtacca gcaaacccctt ggcttgggtc tggtcgagta catggagtgg | 900 |
| gccgatgaca tgaacttgga gcccattgtc ggtgtcttcg ctggtcttgc cctcgatggc | 960 |
| tcgttcgttc ccgaatccga gatgggatgg gtcatccaac aggctctcga cgaaatcgag | 1020 |
| ttcctcactg gcgatgctaa gaccaccaaa tggggtgccg tccgcgcgaa gcttggtcac | 1080 |
| cccaagcctt ggaaggtcaa gtgggttgag atcggtaacg aggattggct gccggacgc | 1140 |
| cctgctggct tcgagtcgta catcaactac cgcttcccca tgatgatgaa ggccttcaac | 1200 |
| gaaaagtacc ccgacatcaa gatcatcgcc tcgccctcca tcttcgacaa catgacaatc | 1260 |
| cccgcgggtg ctgccggtga tcaccacccg tacctgactc ccgatgagtt cgttgagcga | 1320 |
| ttcgccaagt tcgataactt gagcaaggat aacgtgacgc tcatcggcga ggctgcgtcg | 1380 |
| acgcatccta acgtggtat cgcttgggag ggagatctca tgcccttgcc ttggtggggc | 1440 |
| ggcagtgttg ctgaggctat cttcttgatc agcactgaga gaaacggtga caagatcatc | 1500 |
| ggtgctactt acgcgcctgg tcttcgcagc ttggaccgct ggcaatggag catgacctgg | 1560 |
| gtgcagcatg ccgccgaccc ggccctcacc actcgctcga ccagttggta tgtctggaga | 1620 |
| atcctcgccc accacatcat ccgtgagacg ctccggtcg atgccccggc cggcaagccc | 1680 |
| aactttgacc ctctgttcta cgttgccgga agagcgaga gtggcaccgg tatcttcaag | 1740 |
| gctgccgtct acaactcgac tgaatcgatc ccggtgtcgt tgaagtttga tggtctcaac | 1800 |
| gagggagcgg ttgccaactt gacggtgctt actgggccgg aggatccgta tggatacaac | 1860 |
| gacccccttca ctggtatcaa tgttgtcaag gagaagacca ccttcatcaa ggccggaaag | 1920 |
| ggcggcaagt tcaccttcac cctgccgggc ttgagtgttg ctgtgttgga gacggccgac | 1980 |
| gcggtcaagg gtggcaaggg aaagggcaag gcaagggaa agggtaactg a | 2031 |

<210> SEQ ID NO 81
<211> LENGTH: 2031
<212> TYPE: DNA
<213> ORGANISM: Artificial Sequence
<220> FEATURE:
<223> OTHER INFORMATION: synthetic codon optimized cDNA

<400> SEQUENCE: 81

| | |
|---|---|
| atgatccacc tcaagcccgc cctcgccgcc ctcctcgccc tcagcaccca atgcgtcgcc | 60 |
| atcgacctct tcgtcaagag cagcggcggc aacaagacca ccgacatcat gtacggcctc | 120 |
| atgcacgagg acatcaacaa cagcggcgac ggcggcatct acgccgagct gatcagcaac | 180 |
| cgcgccttcc agggcagcga gaagttcccc agcaacctcg acaactggtc ccccgtcggc | 240 |
| ggcgccaccc tcaccctcca gaagctcgcc aagcccctgt cctctgccct cccctactcc | 300 |
| gtcaacgtcg ccaaccccaa ggagggtaag ggtaagggca aggacaccaa gggcaagaag | 360 |

| | |
|---|---:|
| gtcggcctcg ccaacgccgg cttttggggc atggacgtca agcgccagaa atacaccggc | 420 |
| agcttccacg tcaccggcga gtacaagggc gacttcgagg tcagcctccg cagcgccatt | 480 |
| accggcgaga ccttcggcaa gaaggtcgtc aagggcggca gcaagaaggg caagtggacc | 540 |
| gagaaggagt tcgagctggt ccccttcaag gacgccccca cagcaacaa caccttcgtc | 600 |
| gtccagtggg acgccgaggg cgccaaggac ggcagcctcg acctcaacct catcagcctc | 660 |
| ttcccgccca ccttcaaggg ccgcaagaac ggcctccgct cgacctcgc ccagaccatg | 720 |
| gtcgagctga agcccacctt cctccgcttt cccggcggca acatgctcga gggcaacacc | 780 |
| ctcgacacct ggtggaagtg gtacgagacc atcggccccc tgaaggaccg ccctggcatg | 840 |
| gccggcgtct gggagtacca gcagacgctg ggcctcggcc tggtcgagta catggagtgg | 900 |
| gccgacgaca tgaacctcga gcccatcgtc ggcgtctttg ctggcctggc cctggatggc | 960 |
| agctttgtcc ccgagagcga gatgggctgg gtcatccagc aggctctcga tgagatcgag | 1020 |
| ttcctcaccg cgacgccaa gaccaccaag tggggcgccg tccgcgccaa gctcggccac | 1080 |
| cctaagccct ggaaggtcaa atgggtcgag atcggcaacg aggactggct cgccggccga | 1140 |
| cctgccggct tcgagagcta catcaactac cgcttcccca tgatgatgaa ggccttcaac | 1200 |
| gagaaatacc ccgacatcaa gatcattgcc agcccctcca tcttcgacaa catgaccatt | 1260 |
| ccagccggtg ctgccggtga ccaccacccc tacctcaccc ccgacgaatt tgtcgagcgc | 1320 |
| ttcgccaagt tcgacaacct cagcaaggac aacgtcaccc tcattggcga ggccgccagc | 1380 |
| acccaccccca acggcggcat tgcctgggag ggcgacctca tgcccctgcc ctggtggggc | 1440 |
| ggcagcgtcg ccgaggccat cttcctcatc agcaccgagc gcaacggcga caagatcatc | 1500 |
| ggcgccacct acgccctgg cctccgatct ctcgaccgct ggcagtggag catgacctgg | 1560 |
| gtccagcacg ccgccgaccc tgccctcacc acccgcagca ccagctggta cgtctggcgc | 1620 |
| atcctcgccc accacatcat cgcgagacc ctccccgtcg acgccccgc cggcaagccc | 1680 |
| aacttcgacc ccctcttcta cgtcgctggc aagtcggaga gcggcaccgg catcttcaag | 1740 |
| gccgccgtct acaacagcac cgagagcatc cccgtcagcc tcaagttcga cggcctcaac | 1800 |
| gagggcgccg tcgccaacct caccgtcctc accggccccg aggacccta cggctacaac | 1860 |
| gacccccttca ccggcatcaa cgtcgtcaag gaaaagacca ccttcatcaa ggccggcaag | 1920 |
| ggcggcaagt tcacctttac cctccccggc ctctctgtcg ccgtcctcga ccgccgac | 1980 |
| gccgtgaagg gtggcaaggg aaagggaaag ggcaagggta agggtaacta a | 2031 |

<210> SEQ ID NO 82
<211> LENGTH: 1020
<212> TYPE: DNA
<213> ORGANISM: Gibberella zeae

<400> SEQUENCE: 82

| | |
|---|---:|
| atgtatcgga agttggccgt catctcggcc ttcttggcca cagctcgtgc taccaacgac | 60 |
| gactgtcctc tcatcactag tagatggact gcggatcctt cggctcatgt ctttaacgac | 120 |
| accttgtggc tctacccgtc tcatgacatc gatgctggat ttgagaatga tcctgatgga | 180 |
| ggccagtacg ccatgagaga ttaccatgtc tactctatcg acaagatcta cggttccctg | 240 |
| ccggtcgatc acggtacggc cctgtcagtg gaggatgtcc cctgggcctc tcgacagatg | 300 |
| tgggctcctg acgctgccca caagaacggc aaatactacc tatacttccc tgccaaagac | 360 |
| aaggatgata tcttcagaat cggcgttgct gtctcaccaa cccccggcgg accattcgtc | 420 |

```
cccgacaaga gttggatccc tcacactttc agcatcgacc ccgccagttt cgtcgatgat    480
gatgacagag cctacttggc atggggtggt atcatgggtg ccagcttca acgatggcag    540 gataagaaca agtacaacga atctggcact gagccaggaa acggcaccgc tgccttgagc    600
cctcagattg ccaagctgag caaggacatg cacactctgg cagagaagcc tcgcgacatg    660
ctcattcttg accccaagac tggcaagccg ctcctttctg aggatgaaga ccgacgcttc    720
ttcgaaggac cctggattca aagcgcaac aagatttact acctcaccta ctctactggc    780
acaacccact atcttgtcta tgcgacttca agaccccct atggtcctta cacctaccag    840
ggcagaattc tggagccagt tgatggctgg actactcact ctagtatcgt caagtaccag    900
ggtcagtggt ggctatttta tcacgatgcc aagacatctg gcaaggacta tcttcgccag    960
gtaaaggcta agaagatttg gtacgatagc aaaggaaaga tcttgacaaa gaagccttga   1020
```

<210> SEQ ID NO 83
<211> LENGTH: 1038
<212> TYPE: DNA
<213> ORGANISM: Fusarium oxysporum

<400> SEQUENCE: 83

```
atgtatcgga agttggccgt catctcggcc ttcttggcca cagctcgtgc tcaagacact     60
aatgacattc ctcccctgat caccgacctc tggtccgcag atccctcggc tcatgttttc    120
gaaggcaagc tctgggttta cccatctcac gacatcgaag ccaatgttgt caacggcaca    180
ggaggcgctc aatacgccat gagggattac catacctact ccatgaagag catctatggt    240
aaagatcccg ttgtcgacca cggcgtcgct ctctcagtcg atgacgttcc ctgggcgaag    300
cagcaaatgt gggctcctga cgcagctcat aagaacggca atattatct gtacttcccc    360 gccaaggaca aggatgagat cttcagaatt ggagttgctg tctccaacaa gcccagcggt    420
cctttcaagg ccgacaagag ctggatccct ggcacgtaca gtatcgatcc tgctagctac    480
gtcgacactg ataacgaggc ctacctcatc tggggcggta tctggggcgg ccagctccaa    540
gcctggcagg ataaaaagaa ctttaacgag tcgtggattg agacaaggc tgctcctaac    600 ggcaccaatg ccctatctcc tcagatcgcc aagctaagca aggacatgca caagatcacc    660
gaaacacccc gcgatctcgt cattctcgcc cccgagacag gcaagcctct tcaggctgag    720
gacaacaagc gacgattctt cgagggcct tggatccaca gcgcggcaa gctttactac    780 ctcatgtact ccaccggtga tacccacttc cttgtctacg ctacttccaa gaacatctac    840
ggtccttata cctaccgggg caagattctt gatcctgttg atgggtggac tactcatgga    900
agtattgttg agtataaggg acagtggtgg cttttctttg ctgatgcgca tacgtctggt    960
aaggattacc ttcgacaggt gaaggcgagg aagatctggt atgacaagaa cggcaagatc   1020
ttgcttcacc gtccttag                                                 1038
```

<210> SEQ ID NO 84
<211> LENGTH: 19
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: MISC_FEATURE
<222> LOCATION: (1)..(1)
<223> OTHER INFORMATION: Xaa can be Ile, Leu, Met, or Val
<220> FEATURE:
<221> NAME/KEY: misc_feature
<222> LOCATION: (3)..(6)
<223> OTHER INFORMATION: Xaa can be any naturally occurring amino acid -continued

```
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be Ile, Leu, Met, or Val
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa can be Glu or Gln
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: Xaa can be His, Asn, or Gln

<400> SEQUENCE: 84

Xaa Pro Xaa Xaa Xaa Xaa Gly Xaa Tyr Xaa Xaa Arg Xaa Xaa Xaa Xaa
1               5                   10                  15

Xaa Xaa Xaa

<210> SEQ ID NO 85
<211> LENGTH: 20
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: MISC_FEATURE
<222> LOCATION: (1)..(1)
<223> OTHER INFORMATION: Xaa can be Ile, Leu, Met, or Val
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be Ile, Leu, Met, or Val
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa can be Glu or Gln
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa can be His, Asn or Gln
```

<400> SEQUENCE: 85

Xaa Pro Xaa Xaa Xaa Xaa Xaa Gly Xaa Tyr Xaa Xaa Arg Xaa Xaa Xaa
1               5                   10                  15

Xaa Xaa Xaa Xaa
            20

<210> SEQ ID NO 86
<211> LENGTH: 19
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: MISC_FEATURE
<222> LOCATION: (1)..(1)
<223> OTHER INFORMATION: Xaa can be Ile, Leu, Met or Val
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be Ile, Leu, Met or Val
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa can be Glu or Gln
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: Xaa can be His, Asn or Gln

<400> SEQUENCE: 86

Xaa Pro Xaa Xaa Xaa Xaa Gly Xaa Tyr Xaa Xaa Arg Xaa Xaa Xaa Xaa
1               5                   10                  15

Xaa Ala Xaa

<210> SEQ ID NO 87
<211> LENGTH: 20
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: MISC_FEATURE
<222> LOCATION: (1)..(1)
<223> OTHER INFORMATION: Xaa can be Ile, Leu, Met or Val
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

```
<220> FEATURE:
<221> NAME/KEY: MISC_FEATURE
<222> LOCATION: (11)..(11)
<223> OTHER INFORMATION: Xaa can be Ile, Leu, Met or Val
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa can be Glu or Gln
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa can be His, Asn or Gln

<400> SEQUENCE: 87

Xaa Pro Xaa Xaa Xaa Xaa Xaa Gly Xaa Tyr Xaa Xaa Arg Xaa Xaa Xaa
1               5                   10                  15

Xaa Xaa Ala Xaa
            20

<210> SEQ ID NO 88
<211> LENGTH: 4
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: MISC_FEATURE
<222> LOCATION: (1)..(1)
<223> OTHER INFORMATION: Xaa can be Phe or Trp
<220> FEATURE:
<221> NAME/KEY: MISC_FEATURE
<222> LOCATION: (2)..(2)
<223> OTHER INFORMATION: Xaa can be Thr or Phe
<220> FEATURE:
<221> NAME/KEY: MISC_FEATURE
<222> LOCATION: (4)..(4)
<223> OTHER INFORMATION: Xaa can be Ala, Ile or Val

<400> SEQUENCE: 88

Xaa Xaa Lys Xaa
1

<210> SEQ ID NO 89
<211> LENGTH: 10
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be Tyr or Trp
<220> FEATURE:
<221> NAME/KEY: MISC_FEATURE
```

```
<222> LOCATION: (10)..(10)
<223> OTHER INFORMATION: Xaa can be Ala, Ile, Leu, Met or Val

<400> SEQUENCE: 89

His Xaa Xaa Gly Pro Xaa Xaa Xaa Xaa Xaa
1               5                   10

<210> SEQ ID NO 90
<211> LENGTH: 9
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be Tyr or Trp
<220> FEATURE:
<221> NAME/KEY: MISC_FEATURE
<222> LOCATION: (9)..(9)
<223> OTHER INFORMATION: Xaa can be Ala, Ile, Leu, Met or Val

<400> SEQUENCE: 90

His Xaa Gly Pro Xaa Xaa Xaa Xaa Xaa
1               5

<210> SEQ ID NO 91
<211> LENGTH: 11
<212> TYPE: PRT
<213> ORGANISM: Artificial Sequence
<220> FEATURE:
<223> OTHER INFORMATION: synthetic motif for GH61 endoglucanase family
<220> FEATURE:
<221> NAME/KEY: MISC_FEATURE
<222> LOCATION: (1)..(1)
<223> OTHER INFORMATION: Xaa can be Glu or Gln
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be Glu, His, Gln or Asn
<220> FEATURE:
<221> NAME/KEY: MISC_FEATURE
<222> LOCATION: (9)..(9)
<223> OTHER INFORMATION: Xaa can be Phe, Ile, Leu or Val
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be Ile, Leu or Val

<400> SEQUENCE: 91
```

Xaa Xaa Tyr Xaa Xaa Cys Xaa Xaa Xaa Xaa Xaa
1               5                   10

<210> SEQ ID NO 92
<211> LENGTH: 1920
<212> TYPE: DNA
<213> ORGANISM: Penicillium funiculosum

<400> SEQUENCE: 92

| | |
|---|---:|
| atgtaccgga agctcgccgt gatcagcgcc ttcctggcga ctgctcgcgc catcaccatc | 60 |
| aacgtcagcc agagcggcgg caacaagacc agcccgctcc agtacggcct catgttcgag | 120 |
| gacatcaacc acggcggcga cggcggcctc tacgccgagc tggtccggaa ccgggccttc | 180 |
| cagggcagca ccgtctaccc ggccaacctc gacggctacg actcggtgaa cggcgcgatt | 240 |
| ctcgcgctcc agaacctcac caacccgctc agcccgagca tgccctcgtc gctgaacgtc | 300 |
| gccaagggct cgaacaacgg cagcatcggc ttcgccaacg aggggtggtg gggcatcgag | 360 |
| gtcaagccgc agcggtacgc cggcagcttc tacgtccagg cgactacca gggcgacttc | 420 |
| gacatcagcc tccagagcaa gctcacccag gaggtcttcg cgacggcgaa ggtccggtcg | 480 |
| agcggcaagc acgaggactg ggtccagtac aagtacgagc tggtcccgaa gaaggccgcc | 540 |
| agcaacacca caacaccct caccatcacc ttcgacagca agggcctcaa ggacggcagc | 600 |
| ctcaacttca acctcatcag cctcttcccg ccgacctaca caaccggcc gaacggcctc | 660 |
| cggatcgacc tcgtcgaggc catggcggag ctggagggca agttcctccg cttcccggc | 720 |
| ggctcggacg tggagggcgt ccaggccccg tactggtaca agtggaacga gaccgtcggc | 780 |
| gacctcaagg accgctactc gcgcccgagc gcctggacct acgaggagag caacggcatc | 840 |
| ggcctcatcg agtacatgaa ctggtgcgac gacatgggcc tcgagccgat cctcgccgtc | 900 |
| tgggacggcc actacctcag caacgaggtc atcagcgaga cgacctcca gccgtacatc | 960 |
| gacgacaccc tcaaccagct cgagttcctc atgggcgccc cggacactcc ctacgggtct | 1020 |
| tggagggcta gcctcggcta cccgaagccg tggaccatca actacgtcga gatcggcaac | 1080 |
| gaggacaacc tctacggcgg cctcgagacc tacatcgcct accggttcca ggcctactac | 1140 |
| gacgccatca ccgccaagta cccgcacatg accgtcatgg agagcctcac cgagatgccc | 1200 |
| ggccccgctg ccgcggcgtc ggactaccac cagtactcga cgcccgacgg cttcgtcagc | 1260 |
| cagttcaact acttcgacca gatgccggtc accaaccgca cgctgaacgg cgagatcgcc | 1320 |
| accgtctacc ccaacaaccc gagcaactcg gtggcgtggg gcagcccgtt ccgctctac | 1380 |
| ccgtggtgga tcgggtccgt ggctgaggcc gtcttcctca tcggcgagga gcggaacagc | 1440 |
| ccgaagatca tcggcgccag ctacgccccc atgttccgca acattaacaa ctggcagtgg | 1500 |
| agcccgaccc tgatcgcctt cgacgccgac agcagccgga cgtcgcgctc tacttcctgg | 1560 |
| cacgtcatca agctcctcag caccaacaag atcacccaga acctgcccac gacgtggtct | 1620 |
| ggggggaca tcgcccgct ctactgggtc gccggccgga cgacaacac cggcagcaac | 1680 |
| atcttcaagg ccgccgtcta caacagcacc agcgacgtcc cggtcaccgt ccagttcgcc | 1740 |
| ggctgcaacg ccaagagcgc caacctcacc atcctctcgt cggacgaccc caacgccagc | 1800 |
| aactacccgg cgccccga ggtcgtcaag accgagatcc agagcgtcac cgccaacgcc | 1860 |
| cacggcgcct tcgagttcag cctcccgaac ctgtcggtgg ctgtgctgaa gacggagtag | 1920 |

<210> SEQ ID NO 93
<211> LENGTH: 2260
<212> TYPE: DNA

<213> ORGANISM: Podospora anserina

<400> SEQUENCE: 93

```
atggctcttc aaaccttctt cctgctggcg gcagccatgc tggccaacgc agagacaaca        60
ggcgaaaagg tctctcggca agcaccgtct ggcgctcaag catgggccgc cgcccactcc       120
caggctgccg ccactctggc cagaatgtca cagcaagaca agatcaacat ggtcacgggc       180
attggctggg acagagggcc ttgcgtggga acacagctg ccatcagctc catcaactat        240
cctcaaatct gtcttcagga tggaccattg gcattcgct tcggcactgg taccaccgcc        300
ttcacacctg cgtccaagc tgcttcgaca tgggacgttg atctgatccg gcagcgcggt        360
gcttacctgg gcgccgaagc caagggctgc ggcattcaca tccttttggg gcccgttgcc       420
ggtgccctgg gcaagattcc ccacggcggt cgcaactggg agggatttgg cgccgacccc       480
taccttgccg gtattgccat gaaggagacc atcgagggta ttcagtcagc aggcgtccag       540
gccaacgcca agcactacat tgcaaacgaa caagagctca accgcgagac catgagcagc       600
aatgtggatg accgcactca gcacgagctc tacctctggc cctttgccga cgccgtgcac       660
gccaacgtcg ccagcgtcat gtgcagttac aacaagctca atggcacgtg ggcttgcgag       720
aatgacaagg ctctgaatca gatcttgaag aaggagctcg gattccaggg ctacgttctc       780
agcgactgga atgctcagca cagcactgct ctgtctgcta acagtggtct ggacatgact       840
atgcccggta ccgatttcaa cggccgcaat gtctactggg ccctcaact gaacaacgct        900
gtcaacgccg ccaggttca gagatccaga ctagacgaca tgtgcaagag aatcttggct        960
ggctggtact tgctcggtca gaaccagggc tatcccgcca tcaacatcag gccaacgtt       1020
cagggcaacc ataaggagaa cgtacgtgct gttgccagag acggcatcgt cttgctgaag      1080
aacgatggaa ttctgccgct ttccaagccg agaaagattg ctgtcgtggg ctcccactcc      1140
gtcaacaatc cccagggaat caacgcctgt gttgacaagg gctgcaatgt tggcaccctt      1200
ggcatgggct ggggttcagg cagcgtcaac taccccctatc tcgtgtcccc gtacgatgct      1260
ctccggactc gtgctcaggc cgatggcaca caaatcagcc tccacaacac tgacagcacc      1320
aacggtgtgt caaacgttgt gtctgacgct gatgctgttg ttgttgtcat cactgccgat      1380
tctggtgaag ggtacatcac tgtcgagggc cacgctggcg accgcagcca ccttgacccg      1440
tggcacaatg caaccaact tgttcaggct gccgcggctg ccaacaagaa cgtcatcgtt       1500
gttgtgcaca gtgttggcca gatcaccctg gagactatcc tcaacaccaa tggagtccgc      1560
gcgattgtgt gggctggtct tccgggccaa gagaatggca acgctcttgt tgatgttctc      1620
tacggcttgg tttcgccatc tggaaagctt ccctacacca ttggcaagag ggagtcggac      1680
tatggcacag ccgttgttcg tggggatgat aacttcaggg agggccttt tgttgactac       1740
cgtcactttg acaatgccag gatcgagccg cgctatgagt ttggctttgg tctttgtaag      1800
ttccagcggc ggagttgggt ttgatttcaa gctttcctaa cctgataaaa cagcttacac      1860
caatttcacc ttctccgaca tcaagattac ttccaatgtc aagccggggc cgctactgg       1920
ccagaccatt cccggcggac ctgccgacct gtgggaggac gttgcgacag tcactgcaac      1980
catcaccaac tcgggtgctg tcagggcgc tgaggttgcc cagctttaca tcggcctgcc       2040
gtcctcggct cctgcctctc ccccgaagca gctgcgtgga ttttccaagc tgaagctggc      2100
cccgggtgcc agcggcactg ccacattcaa cctcagacgc agagatctca gctattggga      2160
tacccgcctc cagaactggg tcgtgcccag cggcaacttt gtcgtcagcg tcggcgccag      2220
ctcgagagat atccgcttga cgggcaccat cacggcgtag                            2260
```

<210> SEQ ID NO 94
<211> LENGTH: 733
<212> TYPE: PRT
<213> ORGANISM: Podospora anserina

<400> SEQUENCE: 94

```
Met Ala Leu Gln Thr Phe Phe Leu Leu Ala Ala Met Leu Ala Asn
1               5                   10                  15

Ala Glu Thr Thr Gly Glu Lys Val Ser Arg Gln Ala Pro Ser Gly Ala
                20                  25                  30

Gln Ala Trp Ala Ala Ala His Ser Gln Ala Ala Thr Leu Ala Arg
            35                  40                      45

Met Ser Gln Gln Asp Lys Ile Asn Met Val Thr Gly Ile Gly Trp Asp
    50                  55                  60

Arg Gly Pro Cys Val Gly Asn Thr Ala Ala Ile Ser Ser Ile Asn Tyr
65                  70                  75                  80

Pro Gln Ile Cys Leu Gln Asp Gly Pro Leu Gly Ile Arg Phe Gly Thr
                85                  90                  95

Gly Thr Thr Ala Phe Thr Pro Gly Val Gln Ala Ala Ser Thr Trp Asp
            100                 105                 110

Val Asp Leu Ile Arg Gln Arg Gly Ala Tyr Leu Gly Ala Glu Ala Lys
        115                 120                 125

Gly Cys Gly Ile His Ile Leu Leu Gly Pro Val Ala Gly Ala Leu Gly
130                 135                 140

Lys Ile Pro His Gly Gly Arg Asn Trp Glu Gly Phe Gly Ala Asp Pro
145                 150                 155                 160

Tyr Leu Ala Gly Ile Ala Met Lys Glu Thr Ile Glu Gly Ile Gln Ser
                165                 170                 175

Ala Gly Val Gln Ala Asn Ala Lys His Tyr Ile Ala Asn Glu Gln Glu
            180                 185                 190

Leu Asn Arg Glu Thr Met Ser Ser Asn Val Asp Asp Arg Thr Gln His
        195                 200                 205

Glu Leu Tyr Leu Trp Pro Phe Ala Asp Ala Val His Ala Asn Val Ala
    210                 215                 220

Ser Val Met Cys Ser Tyr Asn Lys Leu Asn Gly Thr Trp Ala Cys Glu
225                 230                 235                 240

Asn Asp Lys Ala Leu Asn Gln Ile Leu Lys Lys Glu Leu Gly Phe Gln
                245                 250                 255

Gly Tyr Val Leu Ser Asp Trp Asn Ala Gln His Ser Thr Ala Leu Ser
            260                 265                 270

Ala Asn Ser Gly Leu Asp Met Thr Met Pro Gly Thr Asp Phe Asn Gly
        275                 280                 285

Arg Asn Val Tyr Trp Gly Pro Gln Leu Asn Asn Ala Val Asn Ala Gly
    290                 295                 300

Gln Val Gln Arg Ser Arg Leu Asp Asp Met Cys Lys Arg Ile Leu Ala
305                 310                 315                 320

Gly Trp Tyr Leu Leu Gly Gln Asn Gln Gly Tyr Pro Ala Ile Asn Ile
                325                 330                 335

Arg Ala Asn Val Gln Gly Asn His Lys Glu Asn Val Arg Ala Val Ala
            340                 345                 350

Arg Asp Gly Ile Val Leu Leu Lys Asn Asp Gly Ile Leu Pro Leu Ser
        355                 360                 365

Lys Pro Arg Lys Ile Ala Val Val Gly Ser His Ser Val Asn Asn Pro
```

| | | | 370 | | | 375 | | | 380 | | |
|---|---|---|---|---|---|---|---|---|---|---|---|
| Gln | Gly | Ile | Asn | Ala | Cys | Val | Asp | Lys | Gly | Cys | Asn | Val | Gly | Thr | Leu |

Gln Gly Ile Asn Ala Cys Val Asp Lys Gly Cys Asn Val Gly Thr Leu
385                 390                 395                 400

Gly Met Gly Trp Gly Ser Gly Ser Val Asn Tyr Pro Tyr Leu Val Ser
            405                 410                 415

Pro Tyr Asp Ala Leu Arg Thr Arg Ala Gln Ala Asp Gly Thr Gln Ile
        420                 425                 430

Ser Leu His Asn Thr Asp Ser Thr Asn Gly Val Ser Asn Val Val Ser
            435                 440                 445

Asp Ala Asp Ala Val Val Val Ile Thr Ala Asp Ser Gly Glu Gly
        450                 455                 460

Tyr Ile Thr Val Glu Gly His Ala Gly Asp Arg Ser His Leu Asp Pro
465                 470                 475                 480

Trp His Asn Gly Asn Gln Leu Val Gln Ala Ala Ala Ala Asn Lys
            485                 490                 495

Asn Val Ile Val Val His Ser Val Gly Gln Ile Thr Leu Glu Thr
            500                 505                 510

Ile Leu Asn Thr Asn Gly Val Arg Ala Ile Val Trp Ala Gly Leu Pro
        515                 520                 525

Gly Gln Glu Asn Gly Asn Ala Leu Val Asp Val Leu Tyr Gly Leu Val
        530                 535                 540

Ser Pro Ser Gly Lys Leu Pro Tyr Thr Ile Gly Lys Arg Glu Ser Asp
545                 550                 555                 560

Tyr Gly Thr Ala Val Val Arg Gly Asp Asp Asn Phe Arg Glu Gly Leu
            565                 570                 575

Phe Val Asp Tyr Arg His Phe Asp Asn Ala Arg Ile Glu Pro Arg Tyr
            580                 585                 590

Glu Phe Gly Phe Gly Leu Ser Tyr Thr Asn Phe Thr Phe Ser Asp Ile
            595                 600                 605

Lys Ile Thr Ser Asn Val Lys Pro Gly Pro Ala Thr Gly Gln Thr Ile
            610                 615                 620

Pro Gly Gly Pro Ala Asp Leu Trp Glu Asp Val Ala Thr Val Thr Ala
625                 630                 635                 640

Thr Ile Thr Asn Ser Gly Ala Val Glu Gly Ala Glu Val Ala Gln Leu
            645                 650                 655

Tyr Ile Gly Leu Pro Ser Ser Ala Pro Ala Ser Pro Lys Gln Leu
            660                 665                 670

Arg Gly Phe Ser Lys Leu Lys Leu Ala Pro Gly Ala Ser Gly Thr Ala
            675                 680                 685

Thr Phe Asn Leu Arg Arg Arg Asp Leu Ser Tyr Trp Asp Thr Arg Leu
            690                 695                 700

Gln Asn Trp Val Val Pro Ser Gly Asn Phe Val Ser Val Gly Ala
705                 710                 715                 720

Ser Ser Arg Asp Ile Arg Leu Thr Gly Thr Ile Thr Ala
            725                 730

<210> SEQ ID NO 95
<211> LENGTH: 2551
<212> TYPE: DNA
<213> ORGANISM: Fusarium verticillioides

<400> SEQUENCE: 95
atgtttcctt cttccatatc ttgtttggcg gccctgagtc tgatgagcca gggtctacta     60
gctcagagcc aaccggaaaa tgtcatcacc gatgatacct acttctacgg tcaatcgcca    120

```
ccagtgtatc ctacacgtaa gcactctctc tgatttccca acgaaagcaa tactgatctc    180
ttgaccagcg gaacaggtag acaccggctc atgggctgcc gctgtagcca aagccaagaa    240
cttggtgtcc cagttgactc ttgaagagaa agtcaacttg actacaggag gccagacgac    300
caccggctgc tctggcttca tccctggcat tccccgtgta ggctttccag gactgtgttt    360
agcagacgct ggcaacggtg tccgcaacac agattatgtg agctcgtttc cctccgggat    420
tcatgtcggt gcaagctgga atccggagtt gacctacagc cggagctact acatgggtgc    480
tgaggccaaa gccaagggcg ttaacatcct tctcggtcca gtatttggac ctttgggccg    540
agtagttgaa ggtggacgca actgggaggg gttttccaat gatccctacc tggcgggtaa    600
attagggcat gaagctgtcg ccggtatcca agacgccgga gttgttgcat gcggaaaaca    660
tttccttgct caagagcagg agacccatag acttgcggcg tctgtcactg ggctgatgc     720 aatctcatca aatctcgatg acaagacact ccatgaatta tatctctggt aagcacatca    780
tatcttggct gagtagatga accttactaa cacccgaact gggcttttcg ctgatgcagt    840
ccacgccgga cttgccagtg tgatgtgcag ctacaacaga gcaaacaatt cacacgcctg    900
ccaaaactcg aagcttctca atggccttct caagggcgag ttaggattcc agggttttgt    960
cgtctcggac tggggcgcac agcaatctgg tatggcttca gcattggctg gcctggatgt   1020
tgtcatgccc agctcgatct tgtggggtgc caaccttacc cttggtgtga acaacggaac   1080
tattcccgag tcacaggttg acaatatggt tacacggtac gcgaagtctc agccttactt   1140
ctcaattctt ttgaactgac aatcgtgtag gctccttgca acttggtatc agttgaacca   1200
ggaccaagac accgaagccc caggtcacgg actcgctgcc aagctttggg agcctcaccc   1260
agtagtcgac gctcgcaacg caagctccaa gcctactatc tgggacggtg cagtcgaggg   1320
ccatgttctt gttaagaaca ccaacaacgc actgccattc aagcccaaca tgaaactcgt   1380
ttctttgttc ggatactctc acaaagctcc tgataagaac atcccagacc ccgcccaagg   1440
catgttctcc gcttggtcta tcggtgccca atccgccaac atcactgagc tgaacctcgg   1500 cttttctcgga aatttgagtc tcacatactc cgccatcgcg cccaacggaa ccatcatctc   1560
gggtggaggc tcgggtgcca gcgcttggac tctgttcagc tcacccttcg atgcattcgt   1620
ttctcgggcg aagaaagagg gtactgcgct tttctgggat tttgagagct gggatcctta   1680
tgtgaaccct acatctgaag cttgcatcgt tgctggtaat gcatgggcta gcgaaggctg   1740
ggatagacct gcaacctatg atgcctatac tgatgagctc atcaataacg tcgctgacaa   1800
gtgcgctaac actattgttg ttcttcacaa tgctggaaca cgacttgtgg atggcttctt   1860
tggtcacccc aacgtcaccg ctattatcta cgctcatctc ccaggtcagg atagtggaga   1920
tgctctggta tctttgctct atggcgatga gaacccatct ggtcgcctcc cttacaccgt   1980
tgcccgcaac gagacggatt atggtcacct gctgaagcca gacttgactc tcgcccccaa   2040
ccagtaccaa cactttcccc agtccgactt ctccgagggt attttcattg actaccgaca   2100
tttcgatgct aagaacatca cgcctcgctt cgagtttggt ttcggcttga gctacacaac   2160
ctttgagtac gctagtctcc agatctcaaa gtcccaggcc cagacaccgg aatacccagc   2220
tggtgctctt accgagggag gccgttcaga tttgtggac gtcgttgcta ctgtcacagc    2280
aagcgtcagg aacactgggt ctgtcgacgg caaggaggtt gcacagctat acgttggtgt   2340
tccaggtggt cctatgagac agctacgtgg ctttacgaaa ccagctatta aggctggaga   2400
gacggctaca gtgacctttg agcttactcg ccgcgacttg agtgtctggg atgttaatgc   2460
```

```
gcaggagtgg caacttcagc aaggcaacta tgctatctac gttggccgaa gtagtcgaga    2520
tttgcctctg caaagtacct tgagcatcta g                                   2551
```

<210> SEQ ID NO 96
<211> LENGTH: 780
<212> TYPE: PRT
<213> ORGANISM: Fusarium verticillioides

<400> SEQUENCE: 96

```
Met Phe Pro Ser Ser Ile Ser Cys Leu Ala Ala Leu Ser Leu Met Ser
1               5                   10                  15

Gln Gly Leu Leu Ala Gln Ser Gln Pro Glu Asn Val Ile Thr Asp Asp
                20                  25                  30

Thr Tyr Phe Tyr Gly Gln Ser Pro Val Tyr Pro Thr His Thr Gly
        35                  40                  45

Ser Trp Ala Ala Ala Val Ala Lys Ala Lys Asn Leu Val Ser Gln Leu
    50                  55                  60

Thr Leu Glu Glu Lys Val Asn Leu Thr Thr Gly Gly Gln Thr Thr Thr
65                  70                  75                  80

Gly Cys Ser Gly Phe Ile Pro Gly Ile Pro Arg Val Gly Phe Pro Gly
                85                  90                  95

Leu Cys Leu Ala Asp Ala Gly Asn Gly Val Arg Asn Thr Asp Tyr Val
            100                 105                 110

Ser Ser Phe Pro Ser Gly Ile His Val Gly Ala Ser Trp Asn Pro Glu
        115                 120                 125

Leu Thr Tyr Ser Arg Ser Tyr Tyr Met Gly Ala Glu Ala Lys Ala Lys
    130                 135                 140

Gly Val Asn Ile Leu Leu Gly Pro Val Phe Gly Pro Leu Gly Arg Val
145                 150                 155                 160

Val Glu Gly Gly Arg Asn Trp Glu Gly Phe Ser Asn Asp Pro Tyr Leu
                165                 170                 175

Ala Gly Lys Leu Gly His Glu Ala Val Ala Gly Ile Gln Asp Ala Gly
            180                 185                 190

Val Val Ala Cys Gly Lys His Phe Leu Ala Gln Glu Gln Glu Thr His
        195                 200                 205

Arg Leu Ala Ala Ser Val Thr Gly Ala Asp Ala Ile Ser Ser Asn Leu
    210                 215                 220

Asp Asp Lys Thr Leu His Glu Leu Tyr Leu Cys Val Met Cys Ser Tyr
225                 230                 235                 240

Asn Arg Ala Asn Asn Ser His Ala Cys Gln Asn Ser Lys Leu Leu Asn
                245                 250                 255

Gly Leu Leu Lys Gly Glu Leu Gly Phe Gln Gly Phe Val Val Ser Asp
            260                 265                 270

Trp Gly Ala Gln Gln Ser Gly Met Ala Ser Ala Leu Ala Gly Leu Asp
        275                 280                 285

Val Val Met Pro Ser Ser Ile Leu Trp Gly Ala Asn Leu Thr Leu Gly
    290                 295                 300

Val Asn Asn Gly Thr Ile Pro Glu Ser Gln Val Asp Asn Met Val Thr
305                 310                 315                 320

Arg Leu Leu Ala Thr Trp Tyr Gln Leu Asn Gln Asp Gln Asp Thr Glu
                325                 330                 335

Ala Pro Gly His Gly Leu Ala Ala Lys Leu Trp Glu Pro His Pro Val
            340                 345                 350

Val Asp Ala Arg Asn Ala Ser Ser Lys Pro Thr Ile Trp Asp Gly Ala
```

```
            355                 360                 365
Val Glu Gly His Val Leu Val Lys Asn Thr Asn Asn Ala Leu Pro Phe
            370                 375                 380
Lys Pro Asn Met Lys Leu Val Ser Leu Phe Gly Tyr Ser His Lys Ala
385                 390                 395                 400
Pro Asp Lys Asn Ile Pro Asp Pro Ala Gln Gly Met Phe Ser Ala Trp
                405                 410                 415
Ser Ile Gly Ala Gln Ser Ala Asn Ile Thr Glu Leu Asn Leu Gly Phe
                420                 425                 430
Leu Gly Asn Leu Ser Leu Thr Tyr Ser Ala Ile Ala Pro Asn Gly Thr
            435                 440                 445
Ile Ile Ser Gly Gly Ser Gly Ala Ser Ala Trp Thr Leu Phe Ser
450                 455                 460
Ser Pro Phe Asp Ala Phe Val Ser Arg Ala Lys Lys Glu Gly Thr Ala
465                 470                 475                 480
Leu Phe Trp Asp Phe Glu Ser Trp Asp Pro Tyr Val Asn Pro Thr Ser
                485                 490                 495
Glu Ala Cys Ile Val Ala Gly Asn Ala Trp Ala Ser Glu Gly Trp Asp
                500                 505                 510
Arg Pro Ala Thr Tyr Asp Ala Tyr Thr Asp Glu Leu Ile Asn Asn Val
            515                 520                 525
Ala Asp Lys Cys Ala Asn Thr Ile Val Val Leu His Asn Ala Gly Thr
            530                 535                 540
Arg Leu Val Asp Gly Phe Phe Gly His Pro Asn Val Thr Ala Ile Ile
545                 550                 555                 560
Tyr Ala His Leu Pro Gly Gln Asp Ser Gly Asp Ala Leu Val Ser Leu
                565                 570                 575
Leu Tyr Gly Asp Glu Asn Pro Ser Gly Arg Leu Pro Tyr Thr Val Ala
                580                 585                 590
Arg Asn Glu Thr Asp Tyr Gly His Leu Leu Lys Pro Asp Leu Thr Leu
            595                 600                 605
Ala Pro Asn Gln Tyr Gln His Phe Pro Gln Ser Asp Phe Ser Glu Gly
            610                 615                 620
Ile Phe Ile Asp Tyr Arg His Phe Asp Ala Lys Asn Ile Thr Pro Arg
625                 630                 635                 640
Phe Glu Phe Gly Phe Gly Leu Ser Tyr Thr Thr Phe Glu Tyr Ala Ser
                645                 650                 655
Leu Gln Ile Ser Lys Ser Gln Ala Gln Thr Pro Glu Tyr Pro Ala Gly
                660                 665                 670
Ala Leu Thr Glu Gly Gly Arg Ser Asp Leu Trp Asp Val Val Ala Thr
            675                 680                 685
Val Thr Ala Ser Val Arg Asn Thr Gly Ser Val Asp Gly Lys Glu Val
            690                 695                 700
Ala Gln Leu Tyr Val Gly Val Pro Gly Gly Pro Met Arg Gln Leu Arg
705                 710                 715                 720
Gly Phe Thr Lys Pro Ala Ile Lys Ala Gly Glu Thr Ala Thr Val Thr
                725                 730                 735
Phe Glu Leu Thr Arg Arg Asp Leu Ser Val Trp Asp Val Asn Ala Gln
                740                 745                 750
Glu Trp Gln Leu Gln Gln Gly Asn Tyr Ala Ile Tyr Val Gly Arg Ser
            755                 760                 765
Ser Arg Asp Leu Pro Leu Gln Ser Thr Leu Ser Ile
            770                 775                 780
```

<210> SEQ ID NO 97
<211> LENGTH: 2487
<212> TYPE: DNA
<213> ORGANISM: Fusarium verticillioides

<400> SEQUENCE: 97

```
atggctagca ttcgatctgt gttggtctcg ggtcttttgg ccgcgggtgt caatgcccaa      60
gcctacgatg cgagtgatcg cgctgaagat gctttcagct gggtccagcc caagaacacc     120
actattcttg gacagtacgg ccattcgcct cattaccctg ccagtatgtt caccaactac     180
accaagtgac actgaggctg tactgacatt ctagacaatg ctactggcaa gggctgggaa     240
gatgccttcg ccaaggctca aaactttgtc tcccaactaa ccctcgagga aaaggccgac     300
atggtcacag gaactccagg tccttgcgtc ggcaacatcg tcgccattcc ccgtctcaac     360
ttcaacggtc tctgtcttca cgacggcccc ctcgccatcc gagtagcaga ctacgccagt     420
gttttccccg ctggtgtatc agccgcttca tcgtgggaca aggacctcct ctaccagcgc     480
ggtctcgcca tgggtcaaga gttcaaggcc aagggtgctc acatcctcct cggccccgtc     540
gccggtcctc ttggccgctc ggcatactct ggtcgtaact gggagggttt ctcgccggac     600
ccttacctca ctggtattgc gatggaggag actatcatgg acatcaaga tgctggtgtt      660
caggctactg cgaagcactt tatcggtaat gagcaggagg tcatgcgaaa ccctactttt     720
gtcaaggatg ggtatattgg tgaggttgac aaggaggctc tttcgtctaa catggatgat     780
cgaaccatgc acgagcttta cctctggccc tttgccaatg ctgttcatgc caaggcttcc     840
agcatgatgt gctcgtacca gcgtctcaac ggctcctacg cctgccagaa ctcaaaggtc     900
ctcaacggaa ttctgcgtga tgagcttggt ttccagggct acgtcatgtc agattggggt     960
gccacccacg ccggtgttgc tgccatcaac agcggtctcg acatggacat gcccggtggt    1020
atcggtgcct acggaacata ctttaccaag tccttcttcg gcggcaacct cacccgcgcc    1080
gtcaccaacg gcaccctcga cgagacccgc gtcaacgaca tgatcacccg catcatgact    1140
ccctacttct ggctcggcca ggacaaggac tatccctccg tcgacccctc cagcggtgat    1200
ctcaacacct tcagccccaa gagctcctgg ttccgcgagt tcaacctcac cggcgagcgc    1260
agccgtgacg tccgcggtaa ccacggcgac ttgatccgca agcacggcgc cgagtctacc    1320
gtccttctca agaacgagaa gaacgccctt cccctcaaga gcccaagtc catcgctgtc     1380
tttggcaacg atgctggtga tatcactgag ggtttctaca accagaatga ctacgaattt    1440
ggcactcttg ttgctggtgg tggctctgga actggtcgtt tgacatacct tgtttcgcct    1500
ctagccgcca tcaatgctcg tgctaagcag gacggtactc ttgttcagca gtggatgaac    1560
aacactctta ttgctaccac caacgtcact gatctctgga tccctgctac tcccgatgtc    1620
tgcctcgttt tcttgaagac ttgggctgag gaggctgctg atcgtgagca cctctccgtt    1680
gactgggacg gtaatgatgt tgttgagtct gttgccaagt actgcaataa cactgtcgtc    1740
gtcactcact cttctggtat caacactctt ccttgggctg accaccccaa cgtcaccgct    1800
attctcgctg cccacttccc cggtcaggag tctggcaact ccctcgttga cctcctctac    1860
ggcgatgtca ccccctctgg tcgtcttccc tacaccatcg ccttcaacgg caccgactac    1920
aacgctcccc ccaccactgc cgtcaacacc accggcaagg aggactggca gtcttggttc    1980
gacgagaagc tcgagattga ctaccgctac ttcgacgcgc acaacatctc cgtccgctac    2040
gaattcggct tcggtctctc ctactccacc ttcgaaatct ccgacatctc cgctgagcca    2100
```

```
ctcgcatccg acattacctc ccagcccgag gatctccccg tgcagcccgg cggcaacccc    2160
gccctctggg agaccgtcta caacgtgacc gtctccgtct ccaacacggg caaggtcgac    2220
ggcgccactg tcccccagct atacgtgaca ttccccgaca gcgcgcctgc cggtacacca    2280
cccaagcagc tccgtgggtt cgacaaggtc ttccttgagg ctggcgagag caagagtgtc    2340
agctttgagc tgatgcgccg tgatctgagc tactgggata tcatttctca gaagtggctc    2400
atccctgagg gagagtttac tattcgtgtt ggattcagca gtcgggactt gaaggaggag    2460
acaaaggtta ctgttgttga ggcgtaa                                        2487
```

<210> SEQ ID NO 98
<211> LENGTH: 811
<212> TYPE: PRT
<213> ORGANISM: Fusarium verticillioides

<400> SEQUENCE: 98

```
Met Ala Ser Ile Arg Ser Val Leu Val Ser Gly Leu Leu Ala Ala Gly
1               5                   10                  15

Val Asn Ala Gln Ala Tyr Asp Ala Ser Asp Arg Ala Glu Asp Ala Phe
            20                  25                  30

Ser Trp Val Gln Pro Lys Asn Thr Thr Ile Leu Gly Gln Tyr Gly His
        35                  40                  45

Ser Pro His Tyr Pro Ala Asn Asn Ala Thr Gly Lys Gly Trp Glu Asp
    50                  55                  60

Ala Phe Ala Lys Ala Gln Asn Phe Val Ser Gln Leu Thr Leu Glu Glu
65                  70                  75                  80

Lys Ala Asp Met Val Thr Gly Thr Pro Gly Pro Cys Val Gly Asn Ile
                85                  90                  95

Val Ala Ile Pro Arg Leu Asn Phe Asn Gly Leu Cys Leu His Asp Gly
            100                 105                 110

Pro Leu Ala Ile Arg Val Ala Asp Tyr Ala Ser Val Phe Pro Ala Gly
        115                 120                 125

Val Ser Ala Ala Ser Ser Trp Asp Lys Asp Leu Leu Tyr Gln Arg Gly
    130                 135                 140

Leu Ala Met Gly Gln Glu Phe Lys Ala Lys Gly Ala His Ile Leu Leu
145                 150                 155                 160

Gly Pro Val Ala Gly Pro Leu Gly Arg Ser Ala Tyr Ser Gly Arg Asn
                165                 170                 175

Trp Glu Gly Phe Ser Pro Asp Pro Tyr Leu Thr Gly Ile Ala Met Glu
            180                 185                 190

Glu Thr Ile Met Gly His Gln Asp Ala Gly Val Gln Ala Thr Ala Lys
        195                 200                 205

His Phe Ile Gly Asn Glu Gln Glu Val Met Arg Asn Pro Thr Phe Val
    210                 215                 220

Lys Asp Gly Tyr Ile Gly Glu Val Asp Lys Glu Ala Leu Ser Ser Asn
225                 230                 235                 240

Met Asp Asp Arg Thr Met His Glu Leu Tyr Leu Trp Pro Phe Ala Asn
                245                 250                 255

Ala Val His Ala Lys Ala Ser Ser Met Met Cys Ser Tyr Gln Arg Leu
            260                 265                 270

Asn Gly Ser Tyr Ala Cys Gln Asn Ser Lys Val Leu Asn Gly Ile Leu
        275                 280                 285

Arg Asp Glu Leu Gly Phe Gln Gly Tyr Val Met Ser Asp Trp Gly Ala
    290                 295                 300
```

-continued

Thr His Ala Gly Val Ala Ala Ile Asn Ser Gly Leu Asp Met Asp Met
305                 310                 315                 320

Pro Gly Gly Ile Gly Ala Tyr Gly Thr Tyr Phe Thr Lys Ser Phe Phe
            325                 330                 335

Gly Gly Asn Leu Thr Arg Ala Val Thr Asn Gly Thr Leu Asp Glu Thr
        340                 345                 350

Arg Val Asn Asp Met Ile Thr Arg Ile Met Thr Pro Tyr Phe Trp Leu
    355                 360                 365

Gly Gln Asp Lys Asp Tyr Pro Ser Val Asp Pro Ser Gly Asp Leu
370                 375                 380

Asn Thr Phe Ser Pro Lys Ser Ser Trp Phe Arg Glu Phe Asn Leu Thr
385                 390                 395                 400

Gly Glu Arg Ser Arg Asp Val Arg Gly Asn His Gly Asp Leu Ile Arg
            405                 410                 415

Lys His Gly Ala Glu Ser Thr Val Leu Leu Lys Asn Glu Lys Asn Ala
            420                 425                 430

Leu Pro Leu Lys Lys Pro Lys Ser Ile Ala Val Phe Gly Asn Asp Ala
        435                 440                 445

Gly Asp Ile Thr Glu Gly Phe Tyr Asn Gln Asn Asp Tyr Glu Phe Gly
450                 455                 460

Thr Leu Val Ala Gly Gly Ser Gly Thr Gly Arg Leu Thr Tyr Leu
465                 470                 475                 480

Val Ser Pro Leu Ala Ala Ile Asn Ala Arg Ala Lys Gln Asp Gly Thr
            485                 490                 495

Leu Val Gln Gln Trp Met Asn Asn Thr Leu Ile Ala Thr Thr Asn Val
        500                 505                 510

Thr Asp Leu Trp Ile Pro Ala Thr Pro Asp Val Cys Leu Val Phe Leu
515                 520                 525

Lys Thr Trp Ala Glu Ala Ala Asp Arg Glu His Leu Ser Val Asp
530                 535                 540

Trp Asp Gly Asn Asp Val Val Glu Ser Val Ala Lys Tyr Cys Asn Asn
545                 550                 555                 560

Thr Val Val Thr His Ser Ser Gly Ile Asn Thr Leu Pro Trp Ala
            565                 570                 575

Asp His Pro Asn Val Thr Ala Ile Leu Ala Ala His Phe Pro Gly Gln
        580                 585                 590

Glu Ser Gly Asn Ser Leu Val Asp Leu Leu Tyr Gly Asp Val Asn Pro
            595                 600                 605

Ser Gly Arg Leu Pro Tyr Thr Ile Ala Phe Asn Gly Thr Asp Tyr Asn
    610                 615                 620

Ala Pro Pro Thr Thr Ala Val Asn Thr Gly Lys Glu Asp Trp Gln
625                 630                 635                 640

Ser Trp Phe Asp Glu Lys Leu Glu Ile Asp Tyr Arg Tyr Phe Asp Ala
            645                 650                 655

His Asn Ile Ser Val Arg Tyr Glu Phe Gly Phe Gly Leu Ser Tyr Ser
            660                 665                 670

Thr Phe Glu Ile Ser Asp Ile Ser Ala Glu Pro Leu Ala Ser Asp Ile
        675                 680                 685

Thr Ser Gln Pro Glu Asp Leu Pro Val Gln Pro Gly Gly Asn Pro Ala
            690                 695                 700

Leu Trp Glu Thr Val Tyr Asn Val Thr Val Ser Val Ser Asn Thr Gly
705                 710                 715                 720

Lys Val Asp Gly Ala Thr Val Pro Gln Leu Tyr Val Thr Phe Pro Asp

|         |         |         |         |         |         |         |         |         | 725     |
|---------|---------|---------|---------|---------|---------|---------|---------|---------|---------|
| Ser | Ala | Pro | Ala | Gly | Thr | Pro | Pro | Lys | Gln | Leu | Arg | Gly | Phe | Asp | Lys |
|     |     |     |     | 740 |     |     |     |     | 745 |     |     |     |     | 750 |     |

Val Phe Leu Glu Ala Gly Glu Ser Lys Ser Val Ser Phe Glu Leu Met
           755                 760                 765

Arg Arg Asp Leu Ser Tyr Trp Asp Ile Ile Ser Gln Lys Trp Leu Ile
       770                 775                 780

Pro Glu Gly Glu Phe Thr Ile Arg Val Gly Phe Ser Ser Arg Asp Leu
785                 790                 795                 800

Lys Glu Glu Thr Lys Val Thr Val Val Glu Ala
                805                 810

<210> SEQ ID NO 99
<211> LENGTH: 3269
<212> TYPE: DNA
<213> ORGANISM: Fusarium verticillioides

<400> SEQUENCE: 99

| atgaagctga attgggtcgc cgcagccctg tctataggtg ctgctggcac tgacagcgca | 60 |
| gttgctcttg cttctgcagt tccagacact ttggctggtg taaaggtcag tttttttca | 120 |
| ccatttcctc gtctaatctc agccttgttg ccatatcgcc cttgttcgct cggacgccac | 180 |
| gcaccagatc gcgatcattt cctcccttgc agccttggtt cctcttacga tcttccctcc | 240 |
| gcaattatca gcgcccttag tctacacaaa accccccgag acagtctttc attgagtttg | 300 |
| tcgacatcaa gttgcttctc aactgtgcat ttgcgtggct gtctacttct gcctctagac | 360 |
| aaccaaatct gggcgcaatt gaccgctcaa accttgttca ataaccttt tttattcgag | 420 |
| acgcacattt ataaatatgc cctttcaat aataccgact ttatgcgcgg cggctgctgt | 480 |
| ggcggttgat cagaaagctg acgctcaaaa ggttgtcacg agagatacac tcgcatactc | 540 |
| gccgcctcat tatccttcac catggatgga ccctaatgct gttggctggg aggaagctta | 600 |
| cgccaaagcc aagagctttg tgtcccaact cactctcatg gaaaaggtca acttgaccac | 660 |
| tggtgttggg taagcagctc cttgcaaaca gggtatctca atcccctcag ctaacaactt | 720 |
| ctcagatggc aaggcgaacg ctgtgtagga acgtgggat caattcctcg tctcggtatg | 780 |
| cgaggtctct gtctccagga tggtcctctt ggaattcgtc tgtccgacta caacagcgct | 840 |
| tttcccgctg gcaccacagc tggtgcttct tggagcaagt ctctctggta tgagagaggt | 900 |
| ctcctgatgg gcactgagtt caaggagaag ggtatcgata tcgctcttgg tcctgctact | 960 |
| ggacctcttg gtcgcactgc tgctggtgga cgaaactggg aaggcttcac cgttgatcct | 1020 |
| tatatggctg ccacgccat ggccgaggcc gtcaagggta ttcaagacgc aggtgtcatt | 1080 |
| gcttgtgcta agcattacat cgcaaacgag cagggtaagc cacttggacg atttgaggaa | 1140 |
| ttgacagaga actgacccctc ttgtagagca cttccgacag agtggcgagg tccagtcccg | 1200 |
| caagtacaac atctccgagt ctctctcctc caacctggat acaagacta tgcacgagct | 1260 |
| ctacgcctgg cccttcgctg acgccgtccg cgccggcgtc ggttccgtca tgtgctcgta | 1320 |
| caaccgagatc aacaactcgt acggttgcca gaactccaag ctcctcaacg gtatcctcaa | 1380 |
| ggacgagatg ggcttccagg gtttcgtcat gagcgattgg gcggcccagc ataccggtgc | 1440 |
| cgcttctgcc gtcgctggtc tcgatatgag catgcctggt gacactgcct cgacagcgg | 1500 |
| atacagcttc tggggcggaa acttgactct ggctgtcatc aacggaactg ttcccgcctg | 1560 |
| gcgagttgat gacatggctc tgcgaatcat gtctgccttc ttcaaggttg gaaagacgat | 1620 |

```
agaggatctt cccgacatca acttctcctc ctggacccgc gacaccttcg gcttcgtgca   1680
tacatttgct caagagaacc gcgagcaggt caactttgga gtcaacgtcc agcacgacca   1740
caagagccac atccgtgagg ccgctgccaa gggaagcgtc gtgctcaaga caccgggtc    1800
ccttcccctc aagaacccaa agttcctcgc tgtcattggt gaggacgccg gtcccaaccc   1860
tgctggaccc aatggttgtg gtgaccgtgg ttgcgataat ggtaccctgg ctatggcttg   1920
gggctcggga acttcccaat tcccttactt gatcaccccc gatcaagggc tctctaatcg   1980
agctactcaa gacggaactc gatatgagag catcttgacc aacaacgaat gggcttcagt   2040
acaagctctt gtcagccagc ctaacgtgac cgctatcgtt ttcgccaatg ccgactctgg   2100
tgagggatac attgaagtcg acggaaactt tggtgatcgc aagaacctca ccctctggca   2160
gcagggagac gagctcatca agaacgtgtc gtccatatgc cccaacacca ttgtagttct   2220
gcacaccgtc ggccctgtcc tactcgccga ctacgagaag aaccccaaca tcactgccat   2280
cgtctgggct ggtcttcccg gccaagagtc aggcaatgcc atcgctgatc tcctctacgg   2340
caaggtcagc cctggccgat ctcccttcac ttggggccgc acccgcgaga gctacggtac   2400
tgaggttctt tatgaggcga acaacggccg tggcgctcct caggatgact tctctgaggg   2460
tgtcttcatc gactaccgtc acttcgaccg acgatctcca agcaccgatg gaaagagctc   2520
tcccaacaac accgctgctc ctctctacga gttcggtcac ggtctatctt ggtccacctt   2580
tgagtactct gacctcaaca tccagaagaa cgtcgagaac ccctactctc ctcccgctgg   2640
ccagaccatc cccgccccaa cctttggcaa cttcagcaag aacctcaacg actacgtgtt   2700
ccccaagggc gtccgataca tctacaagtt catctacccc ttcctcaaca cctcctcatc   2760
cgccagcgag gcatccaacg atggtggcca gtttggtaag actgccgaag agttcctccc   2820
tcccaacgcc ctcaacggct cagcccagcc tcgtcttccc gcctctggtg ccccaggtgg   2880
taaccctcaa ttgtgggaca tcttgtacac cgtcacagcc acaatcacca acacaggcaa   2940
cgccacctcc gacgagattc cccagctgta tgtcagcctc ggtggcgaga acgagcccat   3000
ccgtgttctc cgcggtttcg accgtatcga gaacattgct cccggccaga gcgccatctt   3060
caacgctcaa ttgacccgtc gcgatctgag taactgggat acaaatgccc agaactgggt   3120
catcactgac catcccaaga ctgtctgggt tggaagcagc tctcgcaagc tgcctctcag   3180
cgccaagttg gagtaagaaa gccaaacaag ggttgttttt tggactgcaa ttttttggga   3240
ggacatagta gccgcgcgcc agttacgtc                                     3269
```

<210> SEQ ID NO 100
<211> LENGTH: 899
<212> TYPE: PRT
<213> ORGANISM: Fusarium verticillioides

<400> SEQUENCE: 100

```
Met Lys Leu Asn Trp Val Ala Ala Leu Ser Ile Gly Ala Ala Gly
1               5                   10                  15

Thr Asp Ser Ala Val Ala Leu Ala Ser Ala Val Pro Asp Thr Leu Ala
            20                  25                  30

Gly Val Lys Lys Ala Asp Ala Gln Lys Val Val Thr Arg Asp Thr Leu
        35                  40                  45

Ala Tyr Ser Pro Pro His Tyr Pro Ser Pro Trp Met Asp Pro Asn Ala
    50                  55                  60

Val Gly Trp Glu Glu Ala Tyr Ala Lys Ala Lys Ser Phe Val Ser Gln
65                  70                  75                  80
```

-continued

```
Leu Thr Leu Met Glu Lys Val Asn Leu Thr Thr Gly Val Gly Trp Gln
             85                  90                  95
Gly Glu Arg Cys Val Gly Asn Val Gly Ser Ile Pro Arg Leu Gly Met
        100                 105                 110
Arg Gly Leu Cys Leu Gln Asp Gly Pro Leu Gly Ile Arg Leu Ser Asp
            115                 120                 125
Tyr Asn Ser Ala Phe Pro Ala Gly Thr Thr Ala Gly Ala Ser Trp Ser
130                 135                 140
Lys Ser Leu Trp Tyr Glu Arg Gly Leu Leu Met Gly Thr Glu Phe Lys
145                 150                 155                 160
Glu Lys Gly Ile Asp Ile Ala Leu Gly Pro Ala Thr Gly Pro Leu Gly
                165                 170                 175
Arg Thr Ala Ala Gly Arg Asn Trp Glu Gly Phe Thr Val Asp Pro
            180                 185                 190
Tyr Met Ala Gly His Ala Met Ala Glu Ala Val Lys Gly Ile Gln Asp
            195                 200                 205
Ala Gly Val Ile Ala Cys Ala Lys His Tyr Ile Ala Asn Glu Gln Glu
            210                 215                 220
His Phe Arg Gln Ser Gly Glu Val Gln Ser Arg Lys Tyr Asn Ile Ser
225                 230                 235                 240
Glu Ser Leu Ser Ser Asn Leu Asp Asp Lys Thr Met His Glu Leu Tyr
                245                 250                 255
Ala Trp Pro Phe Ala Asp Ala Val Arg Ala Gly Val Gly Ser Val Met
            260                 265                 270
Cys Ser Tyr Asn Gln Ile Asn Asn Ser Tyr Gly Cys Gln Asn Ser Lys
            275                 280                 285
Leu Leu Asn Gly Ile Leu Lys Asp Glu Met Gly Phe Gln Gly Phe Val
            290                 295                 300
Met Ser Asp Trp Ala Ala Gln His Thr Gly Ala Ala Ser Ala Val Ala
305                 310                 315                 320
Gly Leu Asp Met Ser Met Pro Gly Asp Thr Ala Phe Asp Ser Gly Tyr
                325                 330                 335
Ser Phe Trp Gly Gly Asn Leu Thr Leu Ala Val Ile Asn Gly Thr Val
            340                 345                 350
Pro Ala Trp Arg Val Asp Asp Met Ala Leu Arg Ile Met Ser Ala Phe
            355                 360                 365
Phe Lys Val Gly Lys Thr Ile Glu Asp Leu Pro Asp Ile Asn Phe Ser
            370                 375                 380
Ser Trp Thr Arg Asp Thr Phe Gly Phe Val His Thr Phe Ala Gln Glu
385                 390                 395                 400
Asn Arg Glu Gln Val Asn Phe Gly Val Asn Val Gln His Asp His Lys
                405                 410                 415
Ser His Ile Arg Glu Ala Ala Lys Gly Ser Val Val Leu Lys Asn
            420                 425                 430
Thr Gly Ser Leu Pro Leu Lys Asn Pro Lys Phe Leu Ala Val Ile Gly
            435                 440                 445
Glu Asp Ala Gly Pro Asn Pro Ala Gly Pro Asn Gly Cys Gly Asp Arg
450                 455                 460
Gly Cys Asp Asn Gly Thr Leu Ala Met Ala Trp Gly Ser Gly Thr Ser
465                 470                 475                 480
Gln Phe Pro Tyr Leu Ile Thr Pro Asp Gln Gly Leu Ser Asn Arg Ala
                485                 490                 495
Thr Gln Asp Gly Thr Arg Tyr Glu Ser Ile Leu Thr Asn Asn Glu Trp
```

```
            500                 505                 510
Ala Ser Val Gln Ala Leu Val Ser Gln Pro Asn Val Thr Ala Ile Val
            515                 520                 525

Phe Ala Asn Ala Asp Ser Gly Glu Gly Tyr Ile Glu Val Asp Gly Asn
        530                 535                 540

Phe Gly Asp Arg Lys Asn Leu Thr Leu Trp Gln Gln Gly Asp Glu Leu
545                 550                 555                 560

Ile Lys Asn Val Ser Ser Ile Cys Pro Asn Thr Ile Val Val Leu His
            565                 570                 575

Thr Val Gly Pro Val Leu Leu Ala Asp Tyr Glu Lys Asn Pro Asn Ile
        580                 585                 590

Thr Ala Ile Val Trp Ala Gly Leu Pro Gly Gln Glu Ser Gly Asn Ala
        595                 600                 605

Ile Ala Asp Leu Leu Tyr Gly Lys Val Ser Pro Gly Arg Ser Pro Phe
        610                 615                 620

Thr Trp Gly Arg Thr Arg Glu Ser Tyr Gly Thr Glu Val Leu Tyr Glu
625                 630                 635                 640

Ala Asn Asn Gly Arg Gly Ala Pro Gln Asp Asp Phe Ser Glu Gly Val
            645                 650                 655

Phe Ile Asp Tyr Arg His Phe Asp Arg Arg Ser Pro Ser Thr Asp Gly
        660                 665                 670

Lys Ser Ser Pro Asn Asn Thr Ala Ala Pro Leu Tyr Glu Phe Gly His
        675                 680                 685

Gly Leu Ser Trp Ser Thr Phe Glu Tyr Ser Asp Leu Asn Ile Gln Lys
        690                 695                 700

Asn Val Glu Asn Pro Tyr Ser Pro Pro Ala Gly Gln Thr Ile Pro Ala
705                 710                 715                 720

Pro Thr Phe Gly Asn Phe Ser Lys Asn Leu Asp Tyr Val Phe Pro
            725                 730                 735

Lys Gly Val Arg Tyr Ile Tyr Lys Phe Ile Tyr Pro Phe Leu Asn Thr
            740                 745                 750

Ser Ser Ser Ala Ser Glu Ala Ser Asn Asp Gly Gly Gln Phe Gly Lys
        755                 760                 765

Thr Ala Glu Glu Phe Leu Pro Pro Asn Ala Leu Asn Gly Ser Ala Gln
        770                 775                 780

Pro Arg Leu Pro Ala Ser Gly Ala Pro Gly Asn Pro Gln Leu Trp
785                 790                 795                 800

Asp Ile Leu Tyr Thr Val Thr Ala Thr Ile Thr Asn Thr Gly Asn Ala
            805                 810                 815

Thr Ser Asp Glu Ile Pro Gln Leu Tyr Val Ser Leu Gly Gly Glu Asn
            820                 825                 830

Glu Pro Ile Arg Val Leu Arg Gly Phe Asp Arg Ile Glu Asn Ile Ala
        835                 840                 845

Pro Gly Gln Ser Ala Ile Phe Asn Ala Gln Leu Thr Arg Arg Asp Leu
        850                 855                 860

Ser Asn Trp Asp Thr Asn Ala Gln Asn Trp Val Ile Thr Asp His Pro
865                 870                 875                 880

Lys Thr Val Trp Val Gly Ser Ser Arg Lys Leu Pro Leu Ser Ala
            885                 890                 895

Lys Leu Glu

<210> SEQ ID NO 101
<211> LENGTH: 2370
```

<212> TYPE: DNA
<213> ORGANISM: Trichoderma reesei

<400> SEQUENCE: 101

```
atgcgttacc gaacagcagc tgcgctggca cttgccactg ggcccttgc tagggcagac      60
agtcagtata gctggtccca tactgggatg tgatatgtat cctggagaca ccatgctgac     120
tcttgaatca aggtagctca acatcggggg cctcggctga ggcagttgta cctcctgcag     180
ggactccatg gggaaccgcg tacgacaagg cgaaggccgc attggcaaag ctcaatctcc     240
aagataaggt cggcatcgtg agcggtgtcg gctggaacgg cggtccttgc gttggaaaca     300
catctccggc ctccaagatc agctatccat cgctatgcct tcaagacgga ccctcggtg     360
ttcgatactc gacaggcagc acagcctta cgccgggcgt tcaagcggcc tcgacgtggg     420
atgtcaattt gatccgcgaa cgtggacagt tcatcggtga ggaggtgaag gcctcgggga     480
ttcatgtcat acttggtcct gtggctgggc cgctgggaaa gactccgcag gcggtcgca     540
actgggaggg cttcggtgtc gatccatatc tcacgggcat tgccatgggt caaaccatca     600
acggcatcca gtcggtaggc gtgcaggcga cagcgaagca ctatatcctc aacgagcagg     660
agctcaatcg agaaaccatt tcgagcaacc cagatgaccg aactctccat gagctgtata     720
cttggccatt tgccgacgcg gttcaggcca atgtcgcttc tgtcatgtgc tcgtacaaca     780
aggtcaatac cacctgggcc tgcgaggatc agtacgcct gcagactgtg ctgaaagacc     840
agctggggtt cccaggctat gtcatgacgg actggaacgc acagcacacg actgtccaaa     900
gcgcgaattc tgggcttgac atgtcaatgc ctggcacaga cttcaacggt aacaatcggc     960
tctggggtcc agctctcacc aatgcggtaa atagcaatca ggtccccacg agcagagtcg    1020
acgatatggt gactcgtatc ctcgccgcat ggtacttgac aggccaggac caggcaggct    1080
atccgtcgtt caacatcagc agaaatgttc aaggaaacca caagaccaat gtcagggcaa    1140
ttgccaggga cggcatcgtt ctgctcaaga atgacgccaa catcctgccg ctcaagaagc    1200
ccgctagcat tgccgtcgtt ggatctgccg caatcattgg taaccacgcc agaaactcgc    1260
cctcgtgcaa cgacaaaggc tgcgacgacg gggccttggg catgggttgg ggttccggcg    1320
ccgtcaacta tccgtacttc gtcgcgccct acgatgccat caataccaga gcgtcttcgc    1380
agggcaccca ggttaccttg agcaacaccg acaacacgtc ctcaggcgca tctgcagcaa    1440
gaggaaagga cgtcgccatc gtcttcatca ccgccgactc gggtgaaggc tacatcaccg    1500
tggagggcaa cgcgggcgat cgcaacaacc tggatccgtg gcacaacggc aatgccctgg    1560
tccaggcggt ggccggtgcc aacagcaacg tcattgttgt tgtccactcc gttggcgcca    1620
tcattctgga gcagattctt gctcttccgc aggtcaaggc cgttgtctgg gcgggtcttc    1680
cttctcagga gagcggcaat gcgctcgtcg acgtgctgtg gggagatgtc agcccttctg    1740
gcaagctggt gtacaccatt gcgaagagcc ccaatgacta taacactcgc atcgtttccg    1800
gcggcagtga cagcttcagc gagggactgt tcatcgacta taagcacttc gacgacgcca    1860
atatcacgcc gcggtacgag ttcggctatg gactgtgtaa gtttgctaac ctgaacaatc    1920
tattagacag gttgactgac ggatgactgt ggaatgatag cttacaccaa gttcaactac    1980
tcacgcctct ccgtcttgtc gaccgccaag tctggtcctg cgactgggc cgttgtgccg     2040
ggaggcccga gtgatctgtt ccagaatgtc gcgacagtca ccgttgacat cgcaaactct    2100
ggccaagtga ctggtgccga ggtagcccag ctgtacatca cctacccatc ttcagcaccc    2160
aggaccctc cgaagcagct gcgaggcttt gccaagctga acctcacgcc tggtcagagc    2220
```

-continued

```
ggaacagcaa cgttcaacat ccgacgacga gatctcagct actgggacac ggcttcgcag    2280
aaatgggtgg tgccgtcggg gtcgtttggc atcagcgtgg gagcgagcag ccgggatatc    2340
aggctgacga gcactctgtc ggtagcgtag                                      2370
```

<210> SEQ ID NO 102
<211> LENGTH: 744
<212> TYPE: PRT
<213> ORGANISM: Trichoderma reesei

<400> SEQUENCE: 102

| Met | Arg | Tyr | Arg | Thr | Ala | Ala | Leu | Ala | Leu | Ala | Thr | Gly | Pro | Phe |
|---|---|---|---|---|---|---|---|---|---|---|---|---|---|---|
| 1 | | | | 5 | | | | | 10 | | | | | 15 |

| Ala | Arg | Ala | Asp | Ser | His | Ser | Thr | Ser | Gly | Ala | Ser | Ala | Glu | Ala | Val |
|---|---|---|---|---|---|---|---|---|---|---|---|---|---|---|---|
| | | | 20 | | | | 25 | | | | 30 | | | | |

Val Pro Pro Ala Gly Thr Pro Trp Gly Thr Ala Tyr Asp Lys Ala Lys
               35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

-continued

Asn Val Arg Ala Ile Ala Arg Asp Gly Ile Val Leu Lys Asn Asp
            355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
            450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
            530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
                580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
            610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
                660                 665                 670

Ser Ala Pro Arg Thr Pro Pro Lys Gln Leu Arg Gly Phe Ala Lys Leu
            675                 680                 685

Asn Leu Thr Pro Gly Gln Ser Gly Thr Ala Thr Phe Asn Ile Arg Arg
            690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 103
<211> LENGTH: 2625

```
<212> TYPE: DNA
<213> ORGANISM: Trichoderma reesei

<400> SEQUENCE: 103
atgaagacgt tgtcagtgtt tgctgccgcc cttttggcgg ccgtagctga ggccaatccc      60
tacccgcctc ctcactccaa ccaggcgtac tcgcctcctt tctacccttc gccatggatg     120
gaccccagtg ctccaggctg ggagcaagcc tatgcccaag ctaaggagtt cgtctcgggc     180
ttgactctct tggagaaggt caacctcacc accggtgttg ctggatgggt gagaagtgc      240
gttggaaacg ttggtaccgt gcctcgcttg ggcatgcgaa gtctttgcat gcaggacggc     300
cccctgggtc tccgattcaa cacgtacaac agcgctttca gcgttggctt gacggccgcc     360
gccagctgga gccgacacct ttgggttgac cgcggtaccg ctctgggctc cgaggcaaag     420
ggcaaggtgt cgatgttct tctcggaccc gtggctggcc ctctcggtcg caaccccaac     480
ggaggccgta acgtcgaggg tttcggctcg atccctatc tggcgggttt ggctctggcc     540
gataccgtga ccggaatcca gaacgcgggc accatcgcct gtgccaagca cttcctcctc     600
aacgagcagg agcatttccg ccaggtcggc gaagctaacg gttacggata ccccatcacc     660
gaggctctgt cttccaacgt tgatgacaag acgattcacg aggtgtacgg ctggcccttc     720
caggatgctg tcaaggctgg tgtcgggtcc ttcatgtgct cgtacaacca ggtcaacaac     780
tcgtacgctt gccaaaactc caagctcatc aacggcttgc tcaaggagga gtacggtttc     840
caaggctttg tcatgagcga ctggcaggcc cagcacacgg tgtcgcgtc tgctgttgcc     900
ggtctcgata tgaccatgcc tggtgacacc gccttcaaca ccggcgcatc ctactttgga     960
agcaacctga cgcttgctgt tctcaacggc accgtccccg agtggcgcat tgacgacatg    1020
gtgatgcgta tcatggctcc cttcttcaag gtgggcaaga cggttgacag cctcattgac    1080
accaactttg attcttggac caatggcgag tacggctacg ttcaggccgc cgtcaatgag    1140
aactggggaga aggtcaacta cggcgtcgat gtccgcgcca accatgcgaa ccacatccgc    1200
gaggttggcg ccaagggaac tgtcatcttc aagaacaacg gcatcctgcc ccttaagaag    1260
cccaagttcc tgaccgtcat tggtgaggat gctggcggca accctgccgg ccccaacggc    1320
tgcggtgacc gcggctgtga cgacggcact cttgccatgg agtggggatc tggtactacc    1380
aacttcccct acctcgtcac ccccgacgcg gccctgcaga gccaggctct ccaggacggc    1440
acccgctacg agagcatcct gtccaactac gccatctcgc agacccaggc gctcgtcagc    1500
cagcccgatg ccattgccat tgtctttgcc aactcggata gcggcgaggg ctacatcaac    1560
gtcgatggca acgagggcga ccgcaagaac ctgacgctgt ggaagaacgg cgacgatctg    1620
atcaagactg ttgctgctgt caaccccaag acgattgtcg tcatccactc gaccggcccc    1680
gtgattctca aggactacgc caaccacccc aacatctctg ccattctgtg ggccggtgct    1740
cctggccagg agtctggcaa ctcgctggtc gacattctgt acggcaagca gagcccgggc    1800
cgcactccct tcacctgggg cccgtcgctg gagagctacg gagttagtgt tatgaccacg    1860
cccaacaacg gcaacggcgc tccccaggat aacttcaacg agggcgcctt catcgactac    1920
cgctactttg acaaggtggc tcccggcaag cctcgcagct cggacaaggc tcccacgtac    1980
gagtttggct tcggactgtc gtggtcgacg ttcaagttct ccaacctcca catccagaag    2040
aacaatgtcg gccccatgag cccgcccaac ggcaagacga ttgcggctcc ctctctgggc    2100
agcttcagca gaaccttaa ggactatggc ttccccaaga cgttcgccg catcaaggag    2160
tttatctacc cctacctgag caccactacc tctggcaagg aggcgtcggg tgacgctcac    2220
```

```
tacggccaga ctgcgaagga gttcctcccc gccggtgccc tggacggcag ccctcagcct    2280
cgctctgcgg cctctggcga acccggcggc aaccgccagc tgtacgacat tctctacacc    2340
gtgacggcca ccattaccaa cacgggctcg gtcatggacg acgccgttcc ccagctgtac    2400
ctgagccacg gcgtcccaa cgagccgccc aaggtgctgc gtggcttcga ccgcatcgag    2460
cgcattgctc ccggccagag cgtcacgttc aaggcagacc tgacgcgccg tgacctgtcc    2520
aactgggaca cgaagaagca gcagtgggtc attaccgact accccaagac tgtgtacgtg    2580
ggcagctcct cgcgcgacct gccgctgagc gcccgcctgc catga                    2625
```

<210> SEQ ID NO 104
<211> LENGTH: 874
<212> TYPE: PRT
<213> ORGANISM: Trichoderma reesei

<400> SEQUENCE: 104

```
Met Lys Thr Leu Ser Val Phe Ala Ala Ala Leu Leu Ala Ala Val Ala
1               5                   10                  15

Glu Ala Asn Pro Tyr Pro Pro His Ser Asn Gln Ala Tyr Ser Pro
            20                  25                  30

Pro Phe Tyr Pro Ser Pro Trp Met Asp Pro Ser Ala Pro Gly Trp Glu
        35                  40                  45

Gln Ala Tyr Ala Gln Ala Lys Glu Phe Val Ser Gly Leu Thr Leu Leu
    50                  55                  60

Glu Lys Val Asn Leu Thr Thr Gly Val Gly Trp Met Gly Glu Lys Cys
65                  70                  75                  80

Val Gly Asn Val Gly Thr Val Pro Arg Leu Gly Met Arg Ser Leu Cys
                85                  90                  95

Met Gln Asp Gly Pro Leu Gly Leu Arg Phe Asn Thr Tyr Asn Ser Ala
            100                 105                 110

Phe Ser Val Gly Leu Thr Ala Ala Ala Ser Trp Ser Arg His Leu Trp
        115                 120                 125

Val Asp Arg Gly Thr Ala Leu Gly Ser Glu Ala Lys Gly Lys Gly Val
    130                 135                 140

Asp Val Leu Leu Gly Pro Val Ala Gly Pro Leu Gly Arg Asn Pro Asn
145                 150                 155                 160

Gly Gly Arg Asn Val Glu Gly Phe Gly Ser Asp Pro Tyr Leu Ala Gly
                165                 170                 175

Leu Ala Leu Ala Asp Thr Val Thr Gly Ile Gln Asn Ala Gly Thr Ile
            180                 185                 190

Ala Cys Ala Lys His Phe Leu Leu Asn Glu Gln Glu His Phe Arg Gln
        195                 200                 205

Val Gly Glu Ala Asn Gly Tyr Gly Tyr Pro Ile Thr Glu Ala Leu Ser
    210                 215                 220

Ser Asn Val Asp Asp Lys Thr Ile His Glu Val Tyr Gly Trp Pro Phe
225                 230                 235                 240

Gln Asp Ala Val Lys Ala Gly Val Gly Ser Phe Met Cys Ser Tyr Asn
                245                 250                 255

Gln Val Asn Asn Ser Tyr Ala Cys Gln Asn Ser Lys Leu Ile Asn Gly
            260                 265                 270

Leu Leu Lys Glu Glu Tyr Gly Phe Gln Gly Phe Val Met Ser Asp Trp
        275                 280                 285

Gln Ala Gln His Thr Gly Val Ala Ser Ala Val Ala Gly Leu Asp Met
    290                 295                 300
```

Thr Met Pro Gly Asp Thr Ala Phe Asn Thr Gly Ala Ser Tyr Phe Gly
305                 310                 315                 320

Ser Asn Leu Thr Leu Ala Val Leu Asn Gly Thr Val Pro Glu Trp Arg
            325                 330                 335

Ile Asp Asp Met Val Met Arg Ile Met Ala Pro Phe Phe Lys Val Gly
            340                 345                 350

Lys Thr Val Asp Ser Leu Ile Asp Thr Asn Phe Asp Ser Trp Thr Asn
            355                 360                 365

Gly Glu Tyr Gly Tyr Val Gln Ala Ala Val Asn Glu Asn Trp Glu Lys
            370                 375                 380

Val Asn Tyr Gly Val Asp Val Arg Ala Asn His Ala Asn His Ile Arg
385                 390                 395                 400

Glu Val Gly Ala Lys Gly Thr Val Ile Phe Lys Asn Asn Gly Ile Leu
            405                 410                 415

Pro Leu Lys Lys Pro Lys Phe Leu Thr Val Ile Gly Glu Asp Ala Gly
            420                 425                 430

Gly Asn Pro Ala Gly Pro Asn Gly Cys Gly Asp Arg Gly Cys Asp Asp
            435                 440                 445

Gly Thr Leu Ala Met Glu Trp Gly Ser Gly Thr Thr Asn Phe Pro Tyr
            450                 455                 460

Leu Val Thr Pro Asp Ala Ala Leu Gln Ser Gln Ala Leu Gln Asp Gly
465                 470                 475                 480

Thr Arg Tyr Glu Ser Ile Leu Ser Asn Tyr Ala Ile Ser Gln Thr Gln
            485                 490                 495

Ala Leu Val Ser Gln Pro Asp Ala Ile Ala Ile Val Phe Ala Asn Ser
            500                 505                 510

Asp Ser Gly Glu Gly Tyr Ile Asn Val Asp Gly Asn Glu Gly Asp Arg
            515                 520                 525

Lys Asn Leu Thr Leu Trp Lys Asn Gly Asp Asp Leu Ile Lys Thr Val
            530                 535                 540

Ala Ala Val Asn Pro Lys Thr Ile Val Ile His Ser Thr Gly Pro
545                 550                 555                 560

Val Ile Leu Lys Asp Tyr Ala Asn His Pro Asn Ile Ser Ala Ile Leu
            565                 570                 575

Trp Ala Gly Ala Pro Gly Gln Glu Ser Gly Asn Ser Leu Val Asp Ile
            580                 585                 590

Leu Tyr Gly Lys Gln Ser Pro Gly Arg Thr Pro Phe Thr Trp Gly Pro
            595                 600                 605

Ser Leu Glu Ser Tyr Gly Val Ser Val Met Thr Thr Pro Asn Asn Gly
            610                 615                 620

Asn Gly Ala Pro Gln Asp Asn Phe Asn Glu Gly Ala Phe Ile Asp Tyr
625                 630                 635                 640

Arg Tyr Phe Asp Lys Val Ala Pro Gly Lys Pro Arg Ser Ser Asp Lys
            645                 650                 655

Ala Pro Thr Tyr Glu Phe Gly Phe Gly Leu Ser Trp Ser Thr Phe Lys
            660                 665                 670

Phe Ser Asn Leu His Ile Gln Lys Asn Asn Val Gly Pro Met Ser Pro
            675                 680                 685

Pro Asn Gly Lys Thr Ile Ala Ala Pro Ser Leu Gly Ser Phe Ser Lys
            690                 695                 700

Asn Leu Lys Asp Tyr Gly Phe Pro Lys Asn Val Arg Arg Ile Lys Glu
705                 710                 715                 720

Phe Ile Tyr Pro Tyr Leu Ser Thr Thr Thr Ser Gly Lys Glu Ala Ser

```
                        725                 730                 735
Gly Asp Ala His Tyr Gly Gln Thr Ala Lys Glu Phe Leu Pro Ala Gly
                740                 745                 750

Ala Leu Asp Gly Ser Pro Gln Pro Arg Ser Ala Ser Gly Glu Pro
            755                 760                 765

Gly Gly Asn Arg Gln Leu Tyr Asp Ile Leu Tyr Thr Val Thr Ala Thr
        770                 775                 780

Ile Thr Asn Thr Gly Ser Val Met Asp Asp Ala Val Pro Gln Leu Tyr
785                 790                 795                 800

Leu Ser His Gly Gly Pro Asn Glu Pro Pro Lys Val Leu Arg Gly Phe
                805                 810                 815

Asp Arg Ile Glu Arg Ile Ala Pro Gly Gln Ser Val Thr Phe Lys Ala
                820                 825                 830

Asp Leu Thr Arg Arg Asp Leu Ser Asn Trp Asp Thr Lys Lys Gln Gln
                835                 840                 845

Trp Val Ile Thr Asp Tyr Pro Lys Thr Val Tyr Val Gly Ser Ser Ser
        850                 855                 860

Arg Asp Leu Pro Leu Ser Ala Arg Leu Pro
865                 870

<210> SEQ ID NO 105
<211> LENGTH: 2577
<212> TYPE: DNA
<213> ORGANISM: Artificial Sequence
<220> FEATURE:
<223> OTHER INFORMATION: synthetic codon optimized nucleotide sequence

<400> SEQUENCE: 105
atgcgcaacg gcctcctcaa ggtcgccgcc ttagccgctg ccagcgccgt caacggcgag      60
aacctcgcct acagccccccc cttctacccc agccctgggg ccaacggcca gggcgactgg    120
gccgaggcct accagaaggc cgtccagttc gtcagccagc tcaccctcgc cgagaaggtc    180
aacctcacca ccggcaccgg ctgggagcag gaccgctgcg tcggccaggt cggcagcatc    240
ccccgcttag gcttcccccgg cctctgcatg caggacagcc cctcggcgt ccgcgacacc    300 gactacaaca gcgccttccc ctgccggcgt taacgtcgcc ccacctggga ccgcaactta    360
gcctaccgca gaggcgtcgc catgggcgag aacaccgcg gcaagggcgt cgacgtccag    420
ttaggccccg tcgccggccc cttaggccgc tctcctgatg ccggccgcaa ctgggagggc    480 ttcgccccccg accccgtcct caccggcaac atgatggcca gcaccatcca gggcatccag    540
gatgctggcg tcattgcctg cgccaagcac ttcatcctct acgagcagga acacttccgc    600
cagggcgccc aggacggcta cgacatcagc gacagcatca gcgccaacgc gacgacaag    660 accatgcacg agttataccct ctggccccttc gccgatgccg tccgcgccgg tgtcggcagc    720
gtcatgtgca gctacaacca ggtcaacaac agctacgcct gcagcaacag ctacaccatg    780
aacaagctcc tcaagagcga gttaggcttc cagggcttcg tcatgaccga ctggggcggc    840
caccacagcg gcgtcggctc tgccctcgcc ggcctcgaca tgagcatgcc cggcgacatt    900
gccttcgaca gcggcacgtc tttctggggc accaacctca ccgttgccgt cctcaacggc    960
tccatccccg agtggcgcgt cgacgacatg ccgtccgca tcatgagcgc ctactacaag   1020
gtcggccgcg accgctacag cgtccccatc aacttcgaca gctggaccct cgacacctac   1080
ggccccgagc actacgccgt cggccagggc cagaccaaga tcaacgagca cgtcgacgtc   1140
cgcggcaacc acgccgagat catccacgag atcggcgccg cctccgccgt cctcctcaag   1200
```

```
aacaagggcg gcctccccct cactggcacc gagcgcttcg tcggtgtctt tggcaaggat   1260
gctggcagca accccggggg cgtcaacggc tgcagcgacc gcggctgcga caacggcacc   1320
ctcgccatgg gctggggcag cggcaccgcc aactttccct acctcgtcac ccccgagcag   1380
gccatccagc gcgaggtcct cagccgcaac ggcaccttca ccggcatcac cgacaacggc   1440
gccttagccg agatggccgc tgccgcctct caggccgaca cctgcctcgt ctttgccaac   1500
gccgactccg gcgagggcta catcaccgtc gatggcaacg agggcgaccg caagaacctc   1560
accctctggc agggcgccga ccaggtcatc cacaacgtca gcgccaactg caacaacacc   1620
gtcgtcgtct acacaccgt cggccccgtc ctcatcgacg actggtacga ccaccccaac   1680
gtcaccgcca tcctctgggc cggtttaccc ggtcaggaaa gcggcaacag cctcgtcgac   1740
gtcctctacg gccgcgtcaa ccccggcaag accccttca cctggggcag agcccgcgac   1800
gactatggcg cccctctcat cgtcaagcct aacaacggca agggcgcccc ccagcaggac   1860
ttcaccgagg gcatcttcat cgactaccgc cgcttcgaca gtacaacat cacccccatc   1920
tacgagttcg gcttcggcct cagctacacc accttcgagt tcagccagtt aaacgtccag   1980
cccatcaacg cccctcccta caccccgcc agcggcttta cgaaggccgc ccagagcttc   2040
ggccagccct ccaatgccag cgacaacctc tacctagcg acatcgagcg cgtccccctc   2100
tacatctacc cctggctcaa cagcaccgac ctcaaggcca gcgccaacga ccccgactac   2160
ggcctcccca ccgagaagta cgtcccccc aacgccacca cggcgaccc ccagcccatt   2220
gaccctgccg gcggtgcccc tggcggcaac cccagcctct acgagcccgt cgcccgcgtc   2280
accaccatca tcaccaacac cggcaaggtc accggcgacg aggtccccca gctctatgtc   2340
agcttaggcg ccctgacga cgcccccaag gtcctccgcg gcttcgaccg catcaccctc   2400
gcccctggcc agcagtacct ctggaccacc ccctcactc gccgcgacat cagcaactgg   2460
gaccccgtca cccagaactg ggtcgtcacc aactacacca agaccatcta cgtcggcaac   2520
agcagccgca acctcccct ccaggccccc ctcaagccct accccggcat ctgatga       2577
```

<210> SEQ ID NO 106
<211> LENGTH: 857
<212> TYPE: PRT
<213> ORGANISM: Talaromyces emersonii

<400> SEQUENCE: 106

```
Met Arg Asn Gly Leu Leu Lys Val Ala Ala Leu Ala Ala Ala Ser Ala
1               5                   10                  15

Val Asn Gly Glu Asn Leu Ala Tyr Ser Pro Pro Phe Tyr Pro Ser Pro
                20                  25                  30

Trp Ala Asn Gly Gln Gly Asp Trp Ala Glu Ala Tyr Gln Lys Ala Val
        35                  40                  45

Gln Phe Val Ser Gln Leu Thr Leu Ala Glu Lys Val Asn Leu Thr Thr
    50                  55                  60

Gly Thr Gly Trp Glu Gln Asp Arg Cys Val Gly Gln Val Gly Ser Ile
65                  70                  75                  80

Pro Arg Leu Gly Phe Pro Gly Leu Cys Met Gln Asp Ser Pro Leu Gly
                85                  90                  95

Val Arg Asp Thr Asp Tyr Asn Ser Ala Phe Pro Ala Gly Val Asn Val
                100                 105                 110

Ala Ala Thr Trp Asp Arg Asn Leu Ala Tyr Arg Arg Gly Val Ala Met
            115                 120                 125

Gly Glu Glu His Arg Gly Lys Gly Val Asp Val Gln Leu Gly Pro Val
```

```
                130              135              140
Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
                    165                 170                 175

Gln Gly Ile Gln Asp Ala Gly Val Ile Ala Cys Ala Lys His Phe Ile
                180                 185                 190

Leu Tyr Glu Gln Glu His Phe Arg Gln Gly Ala Gln Asp Gly Tyr Asp
                195                 200                 205

Ile Ser Asp Ser Ile Ser Ala Asn Ala Asp Lys Thr Met His Glu
210                 215                 220

Leu Tyr Leu Trp Pro Phe Ala Asp Ala Val Arg Ala Gly Val Gly Ser
225                 230                 235                 240

Val Met Cys Ser Tyr Asn Gln Val Asn Asn Ser Tyr Ala Cys Ser Asn
                    245                 250                 255

Ser Tyr Thr Met Asn Lys Leu Leu Lys Ser Glu Leu Gly Phe Gln Gly
                260                 265                 270

Phe Val Met Thr Asp Trp Gly His His Ser Gly Val Gly Ser Ala
                275                 280                 285

Leu Ala Gly Leu Asp Met Ser Met Pro Gly Asp Ile Ala Phe Asp Ser
290                 295                 300

Gly Thr Ser Phe Trp Gly Thr Asn Leu Thr Val Ala Val Leu Asn Gly
305                 310                 315                 320

Ser Ile Pro Glu Trp Arg Val Asp Asp Met Ala Val Arg Ile Met Ser
                    325                 330                 335

Ala Tyr Tyr Lys Val Gly Arg Asp Arg Tyr Ser Val Pro Ile Asn Phe
                340                 345                 350

Asp Ser Trp Thr Leu Asp Thr Tyr Gly Pro Glu His Tyr Ala Val Gly
                355                 360                 365

Gln Gly Gln Thr Lys Ile Asn Glu His Val Asp Val Arg Gly Asn His
                370                 375                 380

Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
                    405                 410                 415

Phe Gly Lys Asp Ala Gly Ser Asn Pro Trp Gly Val Asn Gly Cys Ser
                420                 425                 430

Asp Arg Gly Cys Asp Asn Gly Thr Leu Ala Met Gly Trp Gly Ser Gly
                435                 440                 445

Thr Ala Asn Phe Pro Tyr Leu Val Thr Pro Glu Gln Ala Ile Gln Arg
450                 455                 460

Glu Val Leu Ser Arg Asn Gly Thr Phe Thr Gly Ile Thr Asp Asn Gly
465                 470                 475                 480

Ala Leu Ala Glu Met Ala Ala Ala Ser Gln Ala Asp Thr Cys Leu
                485                 490                 495

Val Phe Ala Asn Ala Asp Ser Gly Glu Gly Tyr Ile Thr Val Asp Gly
                500                 505                 510

Asn Glu Gly Asp Arg Lys Asn Leu Thr Leu Trp Gln Gly Ala Asp Gln
                515                 520                 525

Val Ile His Asn Val Ser Ala Asn Cys Asn Asn Thr Val Val Val Leu
                530                 535                 540

His Thr Val Gly Pro Val Leu Ile Asp Asp Trp Tyr Asp His Pro Asn
545                 550                 555                 560
```

Val Thr Ala Ile Leu Trp Ala Gly Leu Pro Gly Gln Glu Ser Gly Asn
            565                 570                 575

Ser Leu Val Asp Val Leu Tyr Gly Arg Val Asn Pro Gly Lys Thr Pro
            580                 585                 590

Phe Thr Trp Gly Arg Ala Arg Asp Asp Tyr Gly Ala Pro Leu Ile Val
            595                 600                 605

Lys Pro Asn Asn Gly Lys Gly Ala Pro Gln Gln Asp Phe Thr Glu Gly
            610                 615                 620

Ile Phe Ile Asp Tyr Arg Arg Phe Asp Lys Tyr Asn Ile Thr Pro Ile
625                 630                 635                 640

Tyr Glu Phe Gly Phe Gly Leu Ser Tyr Thr Thr Phe Glu Phe Ser Gln
            645                 650                 655

Leu Asn Val Gln Pro Ile Asn Ala Pro Pro Tyr Thr Pro Ala Ser Gly
            660                 665                 670

Phe Thr Lys Ala Ala Gln Ser Phe Gly Gln Pro Ser Asn Ala Ser Asp
            675                 680                 685

Asn Leu Tyr Pro Ser Asp Ile Glu Arg Val Pro Leu Tyr Ile Tyr Pro
            690                 695                 700

Trp Leu Asn Ser Thr Asp Leu Lys Ala Ser Ala Asn Asp Pro Asp Tyr
705                 710                 715                 720

Gly Leu Pro Thr Glu Lys Tyr Val Pro Pro Asn Ala Thr Asn Gly Asp
            725                 730                 735

Pro Gln Pro Ile Asp Pro Ala Gly Gly Ala Pro Gly Gly Asn Pro Ser
            740                 745                 750

Leu Tyr Glu Pro Val Ala Arg Val Thr Thr Ile Ile Thr Asn Thr Gly
            755                 760                 765

Lys Val Thr Gly Asp Glu Val Pro Gln Leu Tyr Val Ser Leu Gly Gly
            770                 775                 780

Pro Asp Asp Ala Pro Lys Val Leu Arg Gly Phe Asp Arg Ile Thr Leu
785                 790                 795                 800

Ala Pro Gly Gln Gln Tyr Leu Trp Thr Thr Thr Leu Thr Arg Arg Asp
            805                 810                 815

Ile Ser Asn Trp Asp Pro Val Thr Gln Asn Trp Val Val Thr Asn Tyr
            820                 825                 830

Thr Lys Thr Ile Tyr Val Gly Asn Ser Ser Arg Asn Leu Pro Leu Gln
            835                 840                 845

Ala Pro Leu Lys Pro Tyr Pro Gly Ile
            850                 855

<210> SEQ ID NO 107
<211> LENGTH: 2586
<212> TYPE: DNA
<213> ORGANISM: Aspergillus niger

<400> SEQUENCE: 107
atgcgcttca ccagcatcga ggccgtcgcc ctcaccgccg tcagcctcgc cagcgccgac      60
gagttagcct acagccccca ctactacccc agccctggga ccaacggcca gggcgactgg     120
gccgaggcct accagcgcgc cgtcgacatc gtcagccaga tgaccctcgc cgagaaggtc     180
aacctcacca ccggcaccgg ctgggagtta gagttatgcg tcggccagac tggtggcgtc     240
ccccgcctcg cgatccccgg catgtgcgcc caggacagcc cctcggcgt ccgcgacagc     300 gactacaaca gcgccttccc tgccggcgtc aacgtcgccg ccacctggga caagaacctc     360
gcctacctcc gcggccaggc catgggccag gaattcagcg acaagggcgc cgacatccag     420

```
ttaggcccg ctgccggccc tttaggccgc tctcccgacg gcggcagaaa ctgggagggc    480
ttcagccccg accccgctct cagcggcgtc ctcttcgccg agactatcaa gggcatccag    540
gatgctggcg tcgtcgccac cgccaagcac tacattgcct acgagcagga acacttccgc    600
caggcccccg aggcccaggg ctacggcttc aacatcaccg agagcggcag cgccaacctc    660
gacgacaaga ccatgcacga gttataccct tggcccttcg ccgacgccat tagagctggc    720
gctggtgctg tcatgtgcag ctacaaccag atcaacaaca gctacggctg ccagaacagc    780
tacaccctca caagctcct caaggccgag ttaggcttcc agggcttcgt catgtccgac    840
tgggccgccc accacgccgg cgtcagcggc gccttagccg gcctcgacat gagcatgccc    900
ggcgacgtcg actacgacag cggcaccagc tactggggca ccaacctcac catcagcgtc    960
ctcaacggca ccgtccccca gtggcgcgtc gacgacatgg ccgtccgcat catggccgcc   1020
tactacaagg tcggccgcga ccgcctctgg accccccca acttcagcag ctggacccgc   1080
gacgagtacg gcttcaagta ctactacgtc agcgagggcc cctatgagaa ggtcaaccag   1140
ttcgtcaacg tccagcgcaa ccacagcgag ttaatccgcc gcatcggcgc cgacagcacc   1200
gtcctcctca gaacgacgg cgccctcccc ctcaccggca aggaacgcct cgtcgccctc   1260
atcggcgagg acgccggcag caacccctac ggcgccaacg gctgcagcga ccgcggctgc   1320
gacaacggca ccctcgccat gggctggggc agcggcaccg ccaacttccc ttacctcgtc   1380
accccccgagc aggccatcag caacgaggtc ctcaagaaca gaacggcgt ctttaccgcc   1440
accgacaact gggccatcga ccagatcgag gccttagcca agaccgcctc tgtcagcctc   1500
gtctttgtca cgccgacag cggcgagggc tacatcaacg tcgacggcaa cctcggcgac   1560
cgccgcaacc tcaccctctg gcgcaacggc gacaacgtca tcaaggccgc cgccagcaac   1620
tgcaacaaca ccatcgtcat catccacagc gtcggccccg tcctcgtcaa cgagtggtac   1680
gacaacccca acgtcaccgc catcctctgg ggcggcttac ccggccagga aagcggcaac   1740
agcctcgccg acgtcctcta cggccgcgtc aaccctggcg ccaagagccc cttcacctgg   1800
ggcaagaccc gcgaggccta tcaggactac ctctacaccg agcccaacaa cggcaacggc   1860
gcccccagg aagatttcgt cgagggcgtc tttatcgact accgcggctt tgacaagcgc   1920
aacgagactc ccatctacga gttcggctac ggcctcagct acaccacctt caactacagc   1980
aacctccagg tcgaggtcct cagcgcccct gcctacgagc cgccagcgg cgagactgag   2040
gccgccccca ccttcggcga ggtcggcaac gccagcgact acttataccc cgacggcctc   2100
cagcgcatca ccaagttcat ctaccccctgg ctcaacagca ccgacctcga ggccagcagc   2160
ggcgacgcct cttacggcca ggacgcctcc gactacctcc ccgagggtgc caccgacggc   2220
agcgctcagc ccatcttacc tgccggtggc ggtgctggcg gcaacccag actctacgac   2280
gagctgatcc gcgtcagcgt caccatcaag aacaccggca aggtcgctgg tgacgaggtc   2340
ccccagctct acgtcagctt aggcggcct aacgagccca agatcgtcct ccgccagttc   2400
gagcgcatca ccctccagcc cagcaaggaa actcagtgga gcaccaccct cactcgccgc   2460
gacctcgcca actggaacgt cgagactcag gactgggaga tcaccagcta ccccaagatg   2520
gtctttgccg gcagcagcag ccgcaagctc ccctccgcg ccagcctccc caccgtccac   2580
tgatga                                                              2586
```

<210> SEQ ID NO 108
<211> LENGTH: 860
<212> TYPE: PRT

-continued

<213> ORGANISM: Aspergillus niger

<400> SEQUENCE: 108

```
Met Arg Phe Thr Ser Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Glu Ala Tyr Gln Arg Ala Val
        35                  40                  45

Asp Ile Val Ser Gln Met Thr Leu Ala Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Ile Pro Gly Met Cys Ala Gln Asp Ser Pro Leu Gly
                85                  90                  95

Val Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
        195                 200                 205

Gly Phe Asn Ile Thr Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His Ala His Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Phe Lys Tyr Tyr
        355                 360                 365

Tyr Val Ser Glu Gly Pro Tyr Glu Lys Val Asn Gln Phe Val Asn Val
    370                 375                 380

Gln Arg Asn His Ser Glu Leu Ile Arg Arg Ile Gly Ala Asp Ser Thr
385                 390                 395                 400
```

-continued

Val Leu Leu Lys Asn Asp Gly Ala Leu Pro Leu Thr Gly Lys Glu Arg
            405                 410                 415

Leu Val Ala Leu Ile Gly Glu Asp Ala Gly Ser Asn Pro Tyr Gly Ala
        420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
    450                 455                 460

Ala Ile Ser Asn Glu Val Leu Lys Asn Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ser Asn Cys Asn Asn Thr
    530                 535                 540

Ile Val Ile Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Tyr Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Gln Val Glu Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Asp Gly Leu Gln Arg Ile Thr
    690                 695                 700

Lys Phe Ile Tyr Pro Trp Leu Asn Ser Thr Asp Leu Glu Ala Ser Ser
705                 710                 715                 720

Gly Asp Ala Ser Tyr Gly Gln Asp Ala Ser Asp Tyr Leu Pro Glu Gly
                725                 730                 735

Ala Thr Asp Gly Ser Ala Gln Pro Ile Leu Pro Ala Gly Gly Gly Ala
            740                 745                 750

Gly Gly Asn Pro Arg Leu Tyr Asp Glu Leu Ile Arg Val Ser Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Lys Glu Thr Gln Trp Ser Thr Thr
                805                 810                 815

Leu Thr Arg Arg Asp Leu Ala Asn Trp Asn Val Glu Thr Gln Asp Trp

|  |  | 820 |  |  | 825 |  |  | 830 |  |  |
|---|---|---|---|---|---|---|---|---|---|---|
| Glu | Ile | Thr | Ser | Tyr | Pro | Lys | Met | Val | Phe | Ala | Gly | Ser | Ser | Ser | Arg |
|  |  | 835 |  |  |  | 840 |  |  |  | 845 |

| Lys | Leu | Pro | Leu | Arg | Ala | Ser | Leu | Pro | Thr | Val | His |
|---|---|---|---|---|---|---|---|---|---|---|---|
|  |  | 850 |  |  |  | 855 |  |  |  | 860 |

<210> SEQ ID NO 109
<211> LENGTH: 3203
<212> TYPE: DNA
<213> ORGANISM: Fusarium oxysporum

<400> SEQUENCE: 109

```
atgaagctga actgggtcgc cgcagccctc tctataggtg ctgctggcac tgatggtgca      60
gttgctcttg cttctgaagt tccaggcact ttggctggtg taaaggtcgg ttttttttacc    120
atttcctcac ctaatctcag ccttgttgcc atatcgccct tattcgctcg gacgctacgc     180
accaaatcgc gatcatttcc tcccttgcag ccttgttttc ttttttcgat cttccctccg     240
caatcgccag cacccttagc ctacacaaaa accccccgaga cagtctcatt gagtttgtcg    300
acatcaagtt gcttctcaag tgtgcatttg cgtggctgtc tacttctgcc tctagaccac     360
caaatctggg cgcaattgat cgctcaaacc ttgttcgaat aagcctttta ttcgagacgt     420
ccaattttta cagagaatgt acctttcaat ataccgacg ttatgcgcgg cggtggctgc      480
tgtgatggtt gttgatcaga atactgacgc tcaaaaggtt gtcacgagag atacactcgc     540
acactcacct cctcactatc cttcaccatg gatggatcct aatgccattg gctgggagga    600
agcttacgcc aaagcaaaga actttgtgtc ccagctcact ctcctcgaaa ggtcaacttc     660
gaccactggt gttgggtaag tagctccttg cgaacagtgc atctcggtct ccttgactaa   720
cgactctctc aggtggcaag gcgaacgctg tgtaggaaac gtgggatcaa ttcctcgtct    780
tggtatgcga ggtcttttgc ttcaggatgg tcctcttgga attcgtctgt ccgattacaa    840
cagtgctttt cccgctggca ccacagctgg tgcttcttgg agcaagtctc tctggtatga    900
gagggggctct ctgatgggaa ctgagttcaa ggggaagggt atcgatatcg ctcttggccc    960
tgctactggt cctcttggcc gcactgctgc tggtggacga actgggagg ctttaccgt    1020
tgatccttat atggctggcc atgccatggc cgaggccgtc aagggcatcc aagacgcagg   1080
tgtcattgct tgtgctaagc attacatcgc aaacgagcaa ggtaagccaa ttggacggtt   1140
tgggaaatcg acagagaact gacccccttg tagagcactt ccgacagagt ggcgaggtcc   1200
agtcccgcaa gtacaacatc tccgagtctc tctcctccaa cctggacgac aagactttgc    1260
acgagctcta cgcctggccc tttgctgatg ccgtccgcgc tggcgtcggt tcagtcatgt   1320
gctcttacaa tcagatcaac aactcgtacg gttgccagaa ctccaagctc ctcaacggta   1380
tcctcaagga cgagatgggt ttccagggct tcgtcatgag cgattgggcg cccagcaca   1440
ccggtgctgc ttctgccgtc gctggtcttg atatgagcat gcctggtgac accgcgttcg   1500
acagtggata tagcttctgg ggtggaaacc tgactcttgc tgtcatcaac ggaactgttc   1560
ccgcctggcg agttgatgac atggctctgc gaatcatgtc ggccttcttc aaggttggaa   1620
agacggtaga ggacctcccc gacatcaact tctcctcctg acccgcgac accttcggct   1680
tcgtccaaac atttgctcaa gagaaccgcg aacaagtcaa ctttggagtt aacgtccagc   1740
acgaccacaa gaaccacatc cgtgagtctg ccgccaaggg aagcgtcatc ctcaagaaca   1800
ccggctccct tcccctcaac aatcccaagt tcctcgctgt cattggtgag gacgccggtc   1860
ccaacccctgc tggacccaat ggttgcggcg accgtggttg cgacaatggt accctggcta   1920
```

-continued

```
tggcttgggg ctcgggaact tctcaattcc cttacttgat cacacccgac caaggtctcc    1980
agaaccgagc tgcccaagac ggaactcgat atgagagcat cttgaccaac aacgaatggg    2040
cccagacaca ggctcttgtc agccaaccca acgtgaccgc tatcgttttt gccaacgccg    2100
actctggtga gggttacatt gaagtcgacg gaaacttcgg tgatcgcaag aacctcaccc    2160
tctggcaaca gggagacgag ctcatcaaga acgtctcgtc catctgcccc aacaccattg    2220
tcgttctgca taccgtcggc cctgtcctgc tcgccgacta cgagaagaac cccaacatca    2280
ccgccatcgt ctgggctggt cttccggcc aagagtctgg caatgccatc gctgatctcc     2340
tctacggcaa ggtaagccct ggccgatctc ccttcacttg gggccgcacc cgtgagagct    2400
acggtaccga ggttctttat gaggcgaaca acggccgtgg cgctcctcag gatgacttct    2460
cggagggtgt cttcattgac taccgtcact ttgatcgacg atctcccagc accgatggca    2520
agagcgctcc caacaacacc gctgctcctc tctacgagtt cggtcatggt ctgtcttgga    2580
ctacctttga gtattcagac ctcaacatcc agaagaacgt taactccacc tactctcctc    2640
ctgctggtca gaccattcct gccccaacct ttggcaactt cagcaagaac ctcaacgact    2700
acgtgttccc taagggtgtc cgatacatct acaagttcat ctaccccttc ctgaacactt    2760
cctcatccgc cagcgaggca tctaacgacg gcggccagtt tggtaagact gccgaagagt    2820
tcctacctcc aaacgccctc aacggctcag cccagcctcg tcttccctct tctggtgccc    2880
caggcggtaa ccctcaattg tgggatatcc tgtacaccgt cacagccaca atcaccaaca    2940
caggcaacgc cacctccgac gagattcccc agctgtatgt cagcctcggt ggcgagaacg    3000
aacccgttcg tgtcctccgc ggtttcgacc gtatcgagaa cattgctccc ggccagagcg    3060
ccatcttcaa cgctcaattg acccgtcgcg atctgagcaa ctgggatgtg gatgcccaga    3120
actgggttat caccgaccat ccaaagacgg tgtgggttgg aagtagttct cgcaagctgc    3180
ctctcagcgc caagttggaa taa                                            3203
```

<210> SEQ ID NO 110
<211> LENGTH: 899
<212> TYPE: PRT
<213> ORGANISM: Fusarium oxysporum

<400> SEQUENCE: 110

```
Met Lys Leu Asn Trp Val Ala Ala Leu Ser Ile Gly Ala Ala Gly
1               5                   10                  15

Thr Asp Gly Ala Val Ala Leu Ala Ser Glu Val Pro Gly Thr Leu Ala
            20                  25                  30

Gly Val Lys Asn Thr Asp Ala Gln Lys Val Val Thr Arg Asp Thr Leu
        35                  40                  45

Ala His Ser Pro Pro His Tyr Pro Ser Pro Trp Met Asp Pro Asn Ala
    50                  55                  60

Ile Gly Trp Glu Glu Ala Tyr Ala Lys Ala Lys Asn Phe Val Ser Gln
65                  70                  75                  80

Leu Thr Leu Leu Glu Lys Val Asn Leu Thr Thr Gly Val Gly Trp Gln
                85                  90                  95

Gly Glu Arg Cys Val Gly Asn Val Gly Ser Ile Pro Arg Leu Gly Met
            100                 105                 110

Arg Gly Leu Cys Leu Gln Asp Gly Pro Leu Gly Ile Arg Leu Ser Asp
        115                 120                 125

Tyr Asn Ser Ala Phe Pro Ala Gly Thr Thr Ala Gly Ala Ser Trp Ser
    130                 135                 140
```

-continued

Lys Ser Leu Trp Tyr Glu Arg Gly Leu Leu Met Gly Thr Glu Phe Lys
145                 150                 155                 160

Gly Lys Gly Ile Asp Ile Ala Leu Gly Pro Ala Thr Gly Pro Leu Gly
            165                 170                 175

Arg Thr Ala Ala Gly Gly Arg Asn Trp Glu Gly Phe Thr Val Asp Pro
        180                 185                 190

Tyr Met Ala Gly His Ala Met Ala Glu Ala Val Lys Gly Ile Gln Asp
            195                 200                 205

Ala Gly Val Ile Ala Cys Ala Lys His Tyr Ile Ala Asn Glu Gln Glu
        210                 215                 220

His Phe Arg Gln Ser Gly Glu Val Gln Ser Arg Lys Tyr Asn Ile Ser
225                 230                 235                 240

Glu Ser Leu Ser Ser Asn Leu Asp Asp Lys Thr Leu His Glu Leu Tyr
            245                 250                 255

Ala Trp Pro Phe Ala Asp Ala Val Arg Ala Gly Val Gly Ser Val Met
            260                 265                 270

Cys Ser Tyr Asn Gln Ile Asn Asn Ser Tyr Gly Cys Gln Asn Ser Lys
            275                 280                 285

Leu Leu Asn Gly Ile Leu Lys Asp Glu Met Gly Phe Gln Gly Phe Val
            290                 295                 300

Met Ser Asp Trp Ala Ala Gln His Thr Gly Ala Ala Ser Ala Val Ala
305                 310                 315                 320

Gly Leu Asp Met Ser Met Pro Gly Asp Thr Ala Phe Asp Ser Gly Tyr
                325                 330                 335

Ser Phe Trp Gly Gly Asn Leu Thr Leu Ala Val Ile Asn Gly Thr Val
            340                 345                 350

Pro Ala Trp Arg Val Asp Asp Met Ala Leu Arg Ile Met Ser Ala Phe
            355                 360                 365

Phe Lys Val Gly Lys Thr Val Glu Asp Leu Pro Asp Ile Asn Phe Ser
            370                 375                 380

Ser Trp Thr Arg Asp Thr Phe Gly Phe Val Gln Thr Phe Ala Gln Glu
385                 390                 395                 400

Asn Arg Glu Gln Val Asn Phe Gly Val Asn Val Gln His Asp His Lys
                405                 410                 415

Asn His Ile Arg Glu Ser Ala Ala Lys Gly Ser Val Ile Leu Lys Asn
            420                 425                 430

Thr Gly Ser Leu Pro Leu Asn Asn Pro Lys Phe Leu Ala Val Ile Gly
            435                 440                 445

Glu Asp Ala Gly Pro Asn Pro Ala Gly Pro Asn Gly Cys Gly Asp Arg
            450                 455                 460

Gly Cys Asp Asn Gly Thr Leu Ala Met Ala Trp Gly Ser Gly Thr Ser
465                 470                 475                 480

Gln Phe Pro Tyr Leu Ile Thr Pro Asp Gln Gly Leu Gln Asn Arg Ala
            485                 490                 495

Ala Gln Asp Gly Thr Arg Tyr Glu Ser Ile Leu Thr Asn Asn Glu Trp
            500                 505                 510

Ala Gln Thr Gln Ala Leu Val Ser Gln Pro Asn Val Thr Ala Ile Val
            515                 520                 525

Phe Ala Asn Ala Asp Ser Gly Glu Gly Tyr Ile Glu Val Asp Gly Asn
            530                 535                 540

Phe Gly Asp Arg Lys Asn Leu Thr Leu Trp Gln Gln Gly Asp Glu Leu
545                 550                 555                 560

Ile Lys Asn Val Ser Ser Ile Cys Pro Asn Thr Ile Val Val Leu His
            565                 570                 575

Thr Val Gly Pro Val Leu Leu Ala Asp Tyr Glu Lys Asn Pro Asn Ile
        580                 585                 590

Thr Ala Ile Val Trp Ala Gly Leu Pro Gly Gln Glu Ser Gly Asn Ala
        595                 600                 605

Ile Ala Asp Leu Leu Tyr Gly Lys Val Ser Pro Gly Arg Ser Pro Phe
    610                 615                 620

Thr Trp Gly Arg Thr Arg Glu Ser Tyr Gly Thr Glu Val Leu Tyr Glu
625                 630                 635                 640

Ala Asn Asn Gly Arg Gly Ala Pro Gln Asp Asp Phe Ser Glu Gly Val
                645                 650                 655

Phe Ile Asp Tyr Arg His Phe Asp Arg Arg Ser Pro Ser Thr Asp Gly
            660                 665                 670

Lys Ser Ala Pro Asn Asn Thr Ala Ala Pro Leu Tyr Glu Phe Gly His
        675                 680                 685

Gly Leu Ser Trp Thr Thr Phe Glu Tyr Ser Asp Leu Asn Ile Gln Lys
    690                 695                 700

Asn Val Asn Ser Thr Tyr Ser Pro Pro Ala Gly Gln Thr Ile Pro Ala
705                 710                 715                 720

Pro Thr Phe Gly Asn Phe Ser Lys Asn Leu Asn Asp Tyr Val Phe Pro
                725                 730                 735

Lys Gly Val Arg Tyr Ile Tyr Lys Phe Ile Tyr Pro Phe Leu Asn Thr
            740                 745                 750

Ser Ser Ser Ala Ser Glu Ala Ser Asn Asp Gly Gly Gln Phe Gly Lys
        755                 760                 765

Thr Ala Glu Glu Phe Leu Pro Pro Asn Ala Leu Asn Gly Ser Ala Gln
    770                 775                 780

Pro Arg Leu Pro Ser Ser Gly Ala Pro Gly Gly Asn Pro Gln Leu Trp
785                 790                 795                 800

Asp Ile Leu Tyr Thr Val Thr Ala Thr Ile Thr Asn Thr Gly Asn Ala
                805                 810                 815

Thr Ser Asp Glu Ile Pro Gln Leu Tyr Val Ser Leu Gly Gly Glu Asn
            820                 825                 830

Glu Pro Val Arg Val Leu Arg Gly Phe Asp Arg Ile Glu Asn Ile Ala
        835                 840                 845

Pro Gly Gln Ser Ala Ile Phe Asn Ala Gln Leu Thr Arg Arg Asp Leu
    850                 855                 860

Ser Asn Trp Asp Val Asp Ala Gln Asn Trp Val Ile Thr Asp His Pro
865                 870                 875                 880

Lys Thr Val Trp Val Gly Ser Ser Ser Arg Lys Leu Pro Leu Ser Ala
                885                 890                 895

Lys Leu Glu

<210> SEQ ID NO 111
<211> LENGTH: 3134
<212> TYPE: DNA
<213> ORGANISM: Gibberella zeae

<400> SEQUENCE: 111
atgaaggcca attggcttgc cgcggccgtt tatttggctg ctggcaccga tgctgcagtc      60
cctgacactt tggcaggagt caatgtaagc tactcttcaa tttcatctca tctcaacttt     120
gccaggccac aacaactttt cttcactcac gatcttttca ccataaacgc aacagtttca     180

```
caaaaaataa agcccaaatc atgtctctga tcgttgaact cgccatcttc gtttacatcg      240
cggttgtctt tttcttcttg tacttctcat tcgttgttgt tctctacatt ttcgactggc      300
tgtttagcct tgagattctt ctcactcccc gtgatgccta gatcactctc tgaggcgttt      360
aatctacttg tagagatgcg cctctcattt gttgtgtcgc tagtcgcgat agttgctgga      420
attgcagtcc ttgatcttcc tactgacact caaaagctcg ttgcgcggga cacactcgct      480
cactctcctc ctcactatcc ctcgccatgg atggaccta acgctgtcgg ctgggaggac      540
gcctacgcca aggccaagga ctttgtctcc cagatgactc tcctagaaaa ggtcaacttg      600
accactggtg ttgggtaagt aacgagcgac aagacgtcta caatccacta acacgatctc      660
tagatggcag ggcgaacgtt gtgttggaaa cgtgggatct atccctcgtc tcggtatgcg      720
aggcctctgt ctccaggatg gtcctctcgg aattcgcttc tccgactaca acagcgcttt      780
ccctactggt gtcaccgctg gtgcttcttg gagtaaggcc ctttggtacg agcgaggacg      840
attgatgggt accgagtta aggagaaggg tatcgatatt gctctcggcc ctgcaactgg      900
tcctctcggt cgccacgctg ctggtggacg aaactgggaa ggcttcactg tcgaccccta      960
cgccgctggc catgctatgg ctgagactgt caagggtatc caagattctg gagtcattgc     1020
ttgtgctaag cattacatcg caaacgagca aggtatgtac aggcccattc aatggcttca     1080
ggaacgaaaa ctaactctta atagaacact tccgtcaacg aggcgatgtc atgtctcaaa     1140
agttcaacat ttccgagtct ctgtcttcca accttgacga taagactatg cacgagctct     1200
acaactggcc tttcgccgac gccgtccgcg ccggtgttgg ctccattatg tgctcttaca     1260
accaggtcaa caactcatat gcttgccaga actccaagct cctcaacggc atcctcaagg     1320
acgagatggg tttccagggt ttcgtcatga gcgattggca ggctcagcac accggtgccg     1380
cctccgctgt tgccggtctt gacatgacca tgcctggtga caccgagttc aacactggct     1440
tcagcttctg gggtggaaac ctgaccctcg ctgttatcaa cggtactgtt cccgcctgga     1500
gaatcgacga catggctacc cgaattatgg ctgctttctt caaggttggc cgatctgttg     1560
aggaggaacc cgacatcaac ttctcagctt ggactcgtga tgagtatggc ttcgtccaga     1620
cctacgccca agagaaccga gaaaaggtca actttgctgt taatgtccag cacgaccaca     1680
agcgccacat tcgcgaggct ggcgcaaagg gatccgtcgt cctcaagaac actggctcac     1740
ttcctcttaa gaagccccag ttcctcgctg tcattggaga ggacgctggt tccaaccctg     1800
ccggacccaa cggttgcgct gaccgtggat gcgacaacgg tactcttgcc atggcatggg     1860
gttccggaac ctctcaattc ccctacccttg tcacccccga ccaaggcatc tcgctccagg     1920
ctattcagga cggtactcgt tatgagagca tcctcaacaa caaccagtgg ccccagacac     1980
aagctcttgt cagccagccc aacgtcaccg ccattgtctt tgccaatgcc gattctggtg     2040
agggctacat cgaggttgac ggcaactacg gcgaccgcaa gaacctcact ctgtggaagc     2100
aaggcgatga gctcatcaag aacgtctctg ctatctgccc caacaccatt gtggtccttc     2160
acaccgttgg ccccgtcctt ctaaccgagt ggcacaacaa cccaacatc accgccattg     2220 tttgggctgg tgtgcctgga caggagtccg gtaacgccat cgccgacatc tctacggca     2280 agaccagccc tggacgttct cccttcacct ggggtcgcac ttatgacagc tatgcacca     2340 aggttctcta caaggccaac aatggagagg gtgcccctca agaggacttt gtcgagggca     2400
acttcatcga ctaccgccac tttgaccgac aatcccccag caccaacgga aagagtgcca     2460
ccaacgactc ttctgctcct ctctacgagt tcggtttcgg tctgtcctgg actacctttg     2520
agtactctga tctcaaagtc gagtctgtca gcaacgcctc ttacagcccc tctgtcggaa     2580
```

-continued

```
acaccattcc tgccgctacc tacggcaact tcagcaagaa cctggacgat tacacattcc   2640
cctcaggtgt ccgatacctc tacaagttca tctacccta cctcaacacc tcttcctccg    2700
ctgagaaggc ttccggcgat gtcaagggca gatttggtga gaccggcgac gagttcctcc   2760
ctcccaacgc tctcaacggt tcatcgcagc ctcgtcttcc ttccagtggt gctcccggcg   2820
gtaaccctca gctctgggac attatgtaca ccgtcactgc caccatcacc aacactggtg   2880
acgctacctc ggatgaggtt ccccagctgt acgtcagcct cggtggtgag ggcgagcctg   2940
tccgtgtcct ccgtggcttc gagcgtcttg aaaacattgc tcctggtgag agtgccacat   3000
tcaccgctca gcttactcgc cgtgacctga gcaactggga cgtcaacgtc cagaactggg   3060
tcatcaccga tcacgccaag aagatctggg tcggcagcag ctctcgcaat ctgcccctca   3120
gcgccgacct gtag                                                    3134
```

<210> SEQ ID NO 112
<211> LENGTH: 886
<212> TYPE: PRT
<213> ORGANISM: Gibberella zeae

<400> SEQUENCE: 112

```
Met Lys Ala Asn Trp Leu Ala Ala Ala Val Tyr Leu Ala Ala Gly Thr
1               5                   10                  15

Asp Ala Ala Val Pro Asp Thr Leu Ala Gly Val Asn Leu Val Ala Arg
                20                  25                  30

Asp Thr Leu Ala His Ser Pro Pro His Tyr Pro Ser Pro Trp Met Asp
            35                  40                  45

Pro Asn Ala Val Gly Trp Glu Asp Ala Tyr Ala Lys Ala Lys Asp Phe
        50                  55                  60

Val Ser Gln Met Thr Leu Leu Glu Lys Val Asn Leu Thr Thr Gly Val
65                  70                  75                  80

Gly Trp Gln Gly Glu Arg Cys Val Gly Asn Val Gly Ser Ile Pro Arg
                85                  90                  95

Leu Gly Met Arg Gly Leu Cys Leu Gln Asp Gly Pro Leu Gly Ile Arg
            100                 105                 110

Phe Ser Asp Tyr Asn Ser Ala Phe Pro Thr Gly Val Thr Ala Gly Ala
        115                 120                 125

Ser Trp Ser Lys Ala Leu Trp Tyr Glu Arg Gly Arg Leu Met Gly Thr
    130                 135                 140

Glu Phe Lys Glu Lys Gly Ile Asp Ile Ala Leu Gly Pro Ala Thr Gly
145                 150                 155                 160

Pro Leu Gly Arg His Ala Ala Gly Gly Arg Asn Trp Glu Gly Phe Thr
                165                 170                 175

Val Asp Pro Tyr Ala Ala Gly His Ala Met Ala Glu Thr Val Lys Gly
            180                 185                 190

Ile Gln Asp Ser Gly Val Ile Ala Cys Ala Lys His Tyr Ile Ala Asn
        195                 200                 205

Glu Gln Glu His Phe Arg Gln Arg Gly Asp Val Met Ser Gln Lys Phe
    210                 215                 220

Asn Ile Ser Glu Ser Leu Ser Ser Asn Leu Asp Asp Lys Thr Met His
225                 230                 235                 240

Glu Leu Tyr Asn Trp Pro Phe Ala Asp Ala Val Arg Ala Gly Val Gly
                245                 250                 255

Ser Ile Met Cys Ser Tyr Asn Gln Val Asn Asn Ser Tyr Ala Cys Gln
            260                 265                 270
```

```
Asn Ser Lys Leu Leu Asn Gly Ile Leu Lys Asp Glu Met Gly Phe Gln
        275                 280                 285

Gly Phe Val Met Ser Asp Trp Gln Ala Gln His Thr Gly Ala Ala Ser
290                 295                 300

Ala Val Ala Gly Leu Asp Met Thr Met Pro Gly Asp Thr Glu Phe Asn
305                 310                 315                 320

Thr Gly Phe Ser Phe Trp Gly Gly Asn Leu Thr Leu Ala Val Ile Asn
                325                 330                 335

Gly Thr Val Pro Ala Trp Arg Ile Asp Asp Met Ala Thr Arg Ile Met
                340                 345                 350

Ala Ala Phe Phe Lys Val Gly Arg Ser Val Glu Glu Pro Asp Ile
                355                 360                 365

Asn Phe Ser Ala Trp Thr Arg Asp Glu Tyr Gly Phe Val Gln Thr Tyr
        370                 375                 380

Ala Gln Glu Asn Arg Glu Lys Val Asn Phe Ala Val Asn Val Gln His
385                 390                 395                 400

Asp His Lys Arg His Ile Arg Glu Ala Gly Ala Lys Gly Ser Val Val
                405                 410                 415

Leu Lys Asn Thr Gly Ser Leu Pro Leu Lys Lys Pro Gln Phe Leu Ala
                420                 425                 430

Val Ile Gly Glu Asp Ala Gly Ser Asn Pro Ala Gly Pro Asn Gly Cys
                435                 440                 445

Ala Asp Arg Gly Cys Asp Asn Gly Thr Leu Ala Met Ala Trp Gly Ser
        450                 455                 460

Gly Thr Ser Gln Phe Pro Tyr Leu Val Thr Pro Asp Gln Gly Ile Ser
465                 470                 475                 480

Leu Gln Ala Ile Gln Asp Gly Thr Arg Tyr Glu Ser Ile Leu Asn Asn
                485                 490                 495

Asn Gln Trp Pro Gln Thr Gln Ala Leu Val Ser Gln Pro Asn Val Thr
        500                 505                 510

Ala Ile Val Phe Ala Asn Ala Asp Ser Gly Glu Gly Tyr Ile Glu Val
        515                 520                 525

Asp Gly Asn Tyr Gly Asp Arg Lys Asn Leu Thr Leu Trp Lys Gln Gly
        530                 535                 540

Asp Glu Leu Ile Lys Asn Val Ser Ala Ile Cys Pro Asn Thr Ile Val
545                 550                 555                 560

Val Leu His Thr Val Gly Pro Val Leu Leu Thr Glu Trp His Asn Asn
                565                 570                 575

Pro Asn Ile Thr Ala Ile Val Trp Ala Gly Val Pro Gly Gln Glu Ser
        580                 585                 590

Gly Asn Ala Ile Ala Asp Ile Leu Tyr Gly Lys Thr Ser Pro Gly Arg
        595                 600                 605

Ser Pro Phe Thr Trp Gly Arg Thr Tyr Asp Ser Tyr Gly Thr Lys Val
        610                 615                 620

Leu Tyr Lys Ala Asn Asn Gly Glu Gly Ala Pro Gln Glu Asp Phe Val
625                 630                 635                 640

Glu Gly Asn Phe Ile Asp Tyr Arg His Phe Asp Arg Gln Ser Pro Ser
                645                 650                 655

Thr Asn Gly Lys Ser Ala Thr Asn Asp Ser Ser Ala Pro Leu Tyr Glu
                660                 665                 670

Phe Gly Phe Gly Leu Ser Trp Thr Thr Phe Glu Tyr Ser Asp Leu Lys
                675                 680                 685
```

| | | | | | | | | | | | |
|---|---|---|---|---|---|---|---|---|---|---|---|
|Val|Glu|Ser|Val|Ser|Asn|Ala|Ser|Tyr|Ser|Pro|Ser Val Gly Asn Thr|
| |690| | | |695| | | |700| | |

Ile Pro Ala Pro Thr Tyr Gly Asn Phe Ser Lys Asn Leu Asp Asp Tyr
705                 710                 715                 720

Thr Phe Pro Ser Gly Val Arg Tyr Leu Tyr Lys Phe Ile Tyr Pro Tyr
            725                 730                 735

Leu Asn Thr Ser Ser Ser Ala Glu Lys Ala Ser Gly Asp Val Lys Gly
            740                 745                 750

Arg Phe Gly Glu Thr Gly Asp Glu Phe Leu Pro Pro Asn Ala Leu Asn
            755                 760                 765

Gly Ser Ser Gln Pro Arg Leu Pro Ser Ser Gly Ala Pro Gly Gly Asn
770                 775                 780

Pro Gln Leu Trp Asp Ile Met Tyr Thr Val Thr Ala Thr Ile Thr Asn
785                 790                 795                 800

Thr Gly Asp Ala Thr Ser Asp Glu Val Pro Gln Leu Tyr Val Ser Leu
            805                 810                 815

Gly Gly Glu Gly Glu Pro Val Arg Val Leu Arg Gly Phe Glu Arg Leu
            820                 825                 830

Glu Asn Ile Ala Pro Gly Glu Ser Ala Thr Phe Thr Ala Gln Leu Thr
            835                 840                 845

Arg Arg Asp Leu Ser Asn Trp Asp Val Asn Val Gln Asn Trp Val Ile
850                 855                 860

Thr Asp His Ala Lys Lys Ile Trp Val Gly Ser Ser Arg Asn Leu
865                 870                 875                 880

Pro Leu Ser Ala Asp Leu
            885

<210> SEQ ID NO 113
<211> LENGTH: 2796
<212> TYPE: DNA
<213> ORGANISM: Nectria haematococca

<400> SEQUENCE: 113

```
atgcggttca ccgtccttct cgcggcattt tcggggcttg tccccatggt tggttcgcaa    60
gctgaccaga aaccactaca gctcggtgtg aacaataaca ctctggcgca ttcacctcct   120
cactatcctt cgccatggat ggatcctgct gctcctggct gggaggaagc ctatctcaag   180
gcgaaagatt ttgtttcaca gcttacccct cttgaaaagg tcaacttgac cactggtgtt   240
gggtgagtca cttgtttttcc tctctcctga cgtgacactt tgctttggcc tgcttcctat   300
atcgtctact agcattgcta acactcgagg cagatggatg ggcgaacgtt gcgtcggcaa   360
cgtgggttca ctccctcgtt ttggaatgcg tggtctctgc atgcaggatg gcccctcgg    420
catccgcttg tctgactata actctgcctt tcctactggt attacagctg gtgcctcttg   480
gagccgtgcc ctttggtacc aacgtggcct cctgatgggc accgagcatc gtgaaaaagg   540
catcgacgtt gcacttgggc ctgctactgg tcctcttggt cgtactccta ctggcggccg   600
caactgggag ggtttctcgg ttgatcccta cgttgctggc gttgccatgg ccgagactgt   660
tagcggcatt caagatggtg gtactatcgc ctgtgctaag cactacatcg gcaacgaaca   720
aggtatgcct cttcacttct cctcgctgat aaatctgctc acaacaacct agagcaccat   780
cgccaagccc ccgaatccat ggccgcggc tacaacatca ccgagtccct gtcgtcgaac   840
gttgatgaca agaccctcca cgagctctat tctctggccgt tcgcagatgc cgtcaaggct   900
ggtgttggtg ctatcatgtg ttcctaccag cagctgaaca actcttacgg ttgccaaaac   960
```

```
tctaagcttc tcaacggaat tctcaaggac gagctaggat tccagggctt cgtcatgagt    1020
gactggcaag cccaacatgc tggagctgct accgctgttg caggccttga catgaccatg    1080
cccggtgaca ctttgttcaa caccggatac agcttctggg gtggtaacct gaccctcgct    1140
gtagtcaatg cactgttcc cgactggcgt attgacgaca tggctatgag aatcatggca     1200
gctttcttca aggttggcaa gactgttgag gaccttcctg acatcaactt ttcttcttgg    1260
tctcgagaca cttttggcta cgttcaagcc gctgcccaag agaactggga acagatcaac    1320
ttcggagttg atgttcgtca cgaccacagc gaacacattc gactctcggc cgccaagggc    1380
accgtcctcc ttaagaactc tggctcattg cctctgaaga gcccaagtt ccttgccgtc     1440
gttggcgagg acgccggccc gaaccctgct ggccccaacg gctgtaacga ccgcggatgt    1500
aacaacggca ctctggccat gtcctggggc tcaggaacag cccagttccc ttacctcgtt    1560
actcccgact cagcgctaca gaaccaggct gtcctcgacg gcactcgcta cgagagtgtc    1620
ttgcggaaca accagtggga acagacacgc agtctcatta gccaacctaa cgtgacggct    1680
attgtgtttg ccaatgccaa ttccggagag ggatatatcg atgttgacgg caacgaaggc    1740
gatcggaaga atttgacctt gtggaacgag ggtgatgacc taattaagaa cgtctcctca    1800
atctgcccca acaccattgt tgttctgcac actgttggcc ctgtcatcct gacggaatgg    1860
tatgacaacc cgaacattac cgccatagtg tgggctggtg tacctggaca ggagtccggc    1920
aatgctcttg tggacatcct ttatggcaaa acaagccctg tcgctctcc cttcacatgg     1980
ggtcgcaccc gaaagagtta cggcactgat gtcctatacg agcccaacaa tggtcagggt    2040
gctcctcaag atgatttcac ggagggagtc tttatcgact atcgtcattt tgaccaggtt    2100
tctcctagca ccgacggcag caagtctaat gatgagtcca gtcccatcta cgagtttggc    2160
catggtctgt cctggaccac gtttgagtac tctgaactca acattcaagc tcacaacaag    2220
attcccttcg atcctcctat tggcgagacg attgccgctc cggtccttgg caactacagt    2280
accgaccttg ccgattacac gttccccgat ggaattcgct acatctacca gttcatctat    2340
ccctggttga atacttcttc ttccggaaga gaggcttctg gcgatcccga ctacggaaag    2400
acggccgaag agttcctgcc ccccggagct ctcgacgggt cagctcagcc gcgacctcca    2460
tcctctggtg ctccaggtgg aaaccctcat ctttgggatg tgttgtacac tgttagtgct    2520
atcatcacca acactggcaa cgccaccctc gacgagatcc gcagctcta cgttagtctc     2580
ggtggcgaga acgagcccgt ccgcgtcctt cgcgggttcg accgaattga gaacattgcg    2640
cctggccaga gtgtcagatt cacaactgac atcactcgcc gcgacctgag caactgggac    2700
gtcgtctctc agaactgggt cattacagac tacgagaaga ccgtatatgt cgggagcagc    2760
tcccgcaacc tgcctctcaa ggcaaccctg aagtaa                              2796
```

<210> SEQ ID NO 114
<211> LENGTH: 880
<212> TYPE: PRT
<213> ORGANISM: Nectria haematococca

<400> SEQUENCE: 114

Met Arg Phe Thr Val Leu Leu Ala Ala Phe Ser Gly Leu Val Pro Met
1               5                   10                  15

Val Gly Ser Gln Ala Asp Gln Lys Pro Leu Gln Leu Gly Val Asn Asn
            20                  25                  30

Asn Thr Leu Ala His Ser Pro Pro His Tyr Pro Ser Pro Trp Met Asp
        35                  40                  45

-continued

Pro Ala Ala Pro Gly Trp Glu Ala Tyr Leu Lys Ala Lys Asp Phe
 50                  55                  60

Val Ser Gln Leu Thr Leu Leu Glu Lys Val Asn Leu Thr Thr Gly Val
 65                  70                  75                  80

Gly Trp Met Gly Glu Arg Cys Val Gly Asn Val Gly Ser Leu Pro Arg
                 85                  90                  95

Phe Gly Met Arg Gly Leu Cys Met Gln Asp Gly Pro Leu Gly Ile Arg
            100                 105                 110

Leu Ser Asp Tyr Asn Ser Ala Phe Pro Thr Gly Ile Thr Ala Gly Ala
            115                 120                 125

Ser Trp Ser Arg Ala Leu Trp Tyr Gln Arg Gly Leu Leu Met Gly Thr
130                 135                 140

Glu His Arg Glu Lys Gly Ile Asp Val Ala Leu Gly Pro Ala Thr Gly
145                 150                 155                 160

Pro Leu Gly Arg Thr Pro Thr Gly Gly Arg Asn Trp Glu Gly Phe Ser
                165                 170                 175

Val Asp Pro Tyr Val Ala Gly Val Ala Met Ala Glu Thr Val Ser Gly
            180                 185                 190

Ile Gln Asp Gly Gly Thr Ile Ala Cys Ala Lys His Tyr Ile Gly Asn
            195                 200                 205

Glu Gln Glu His His Arg Gln Ala Pro Glu Ser Ile Gly Arg Gly Tyr
210                 215                 220

Asn Ile Thr Glu Ser Leu Ser Ser Asn Val Asp Asp Lys Thr Leu His
225                 230                 235                 240

Glu Leu Tyr Leu Trp Pro Phe Ala Asp Ala Val Lys Ala Gly Val Gly
                245                 250                 255

Ala Ile Met Cys Ser Tyr Gln Gln Leu Asn Asn Ser Tyr Gly Cys Gln
            260                 265                 270

Asn Ser Lys Leu Leu Asn Gly Ile Leu Lys Asp Glu Leu Gly Phe Gln
            275                 280                 285

Gly Phe Val Met Ser Asp Trp Gln Ala Gln His Ala Gly Ala Ala Thr
290                 295                 300

Ala Val Ala Gly Leu Asp Met Thr Met Pro Gly Asp Thr Leu Phe Asn
305                 310                 315                 320

Thr Gly Tyr Ser Phe Trp Gly Asn Leu Thr Leu Ala Val Val Asn
                325                 330                 335

Gly Thr Val Pro Asp Trp Arg Ile Asp Asp Met Ala Met Arg Ile Met
            340                 345                 350

Ala Ala Phe Phe Lys Val Gly Lys Thr Val Glu Asp Leu Pro Asp Ile
            355                 360                 365

Asn Phe Ser Ser Trp Ser Arg Asp Thr Phe Gly Tyr Val Gln Ala Ala
370                 375                 380

Ala Gln Glu Asn Trp Glu Gln Ile Asn Phe Gly Val Asp Val Arg His
385                 390                 395                 400

Asp His Ser Glu His Ile Arg Leu Ser Ala Ala Lys Gly Thr Val Leu
                405                 410                 415

Leu Lys Asn Ser Gly Ser Leu Pro Leu Lys Lys Pro Lys Phe Leu Ala
            420                 425                 430

Val Val Gly Glu Asp Ala Gly Pro Asn Pro Ala Gly Pro Asn Gly Cys
            435                 440                 445

Asn Asp Arg Gly Cys Asn Asn Gly Thr Leu Ala Met Ser Trp Gly Ser
450                 455                 460

Gly Thr Ala Gln Phe Pro Tyr Leu Val Thr Pro Asp Ser Ala Leu Gln

```
                465                 470                 475                 480
        Asn Gln Ala Val Leu Asp Gly Thr Arg Tyr Glu Ser Val Leu Arg Asn
                            485                 490                 495

Asn Gln Trp Glu Gln Thr Arg Ser Leu Ile Ser Gln Pro Asn Val Thr
                        500                 505                 510

Ala Ile Val Phe Ala Asn Ala Asn Ser Gly Glu Gly Tyr Ile Asp Val
                        515                 520                 525

Asp Gly Asn Glu Gly Asp Arg Lys Asn Leu Thr Leu Trp Asn Glu Gly
                    530                 535                 540

Asp Asp Leu Ile Lys Asn Val Ser Ser Ile Cys Pro Asn Thr Ile Val
        545                 550                 555                 560

Val Leu His Thr Val Gly Pro Val Ile Leu Thr Glu Trp Tyr Asp Asn
                            565                 570                 575

Pro Asn Ile Thr Ala Ile Val Trp Ala Gly Val Pro Gly Gln Glu Ser
                        580                 585                 590

Gly Asn Ala Leu Val Asp Ile Leu Tyr Gly Lys Thr Ser Pro Gly Arg
                        595                 600                 605

Ser Pro Phe Thr Trp Gly Arg Thr Arg Lys Ser Tyr Gly Thr Asp Val
                    610                 615                 620

Leu Tyr Glu Pro Asn Asn Gly Gln Gly Ala Pro Gln Asp Asp Phe Thr
        625                 630                 635                 640

Glu Gly Val Phe Ile Asp Tyr Arg His Phe Asp Gln Val Ser Pro Ser
                            645                 650                 655

Thr Asp Gly Ser Lys Ser Asn Asp Glu Ser Ser Pro Ile Tyr Glu Phe
                        660                 665                 670

Gly His Gly Leu Ser Trp Thr Thr Phe Glu Tyr Ser Glu Leu Asn Ile
                        675                 680                 685

Gln Ala His Asn Lys Ile Pro Phe Asp Pro Pro Ile Gly Glu Thr Ile
                    690                 695                 700

Ala Ala Pro Val Leu Gly Asn Tyr Ser Thr Asp Leu Ala Asp Tyr Thr
        705                 710                 715                 720

Phe Pro Asp Gly Ile Arg Tyr Ile Tyr Gln Phe Ile Tyr Pro Trp Leu
                            725                 730                 735

Asn Thr Ser Ser Ser Gly Arg Glu Ala Ser Gly Asp Pro Asp Tyr Gly
                        740                 745                 750

Lys Thr Ala Glu Glu Phe Leu Pro Pro Gly Ala Leu Asp Gly Ser Ala
                        755                 760                 765

Gln Pro Arg Pro Pro Ser Ser Gly Ala Pro Gly Gly Asn Pro His Leu
                    770                 775                 780

Trp Asp Val Leu Tyr Thr Val Ser Ala Ile Ile Thr Asn Thr Gly Asn
        785                 790                 795                 800

Ala Thr Ser Asp Glu Ile Pro Gln Leu Tyr Val Ser Leu Gly Gly Glu
                            805                 810                 815

Asn Glu Pro Val Arg Val Leu Arg Gly Phe Asp Arg Ile Glu Asn Ile
                        820                 825                 830

Ala Pro Gly Gln Ser Val Arg Phe Thr Thr Asp Ile Thr Arg Arg Asp
                        835                 840                 845

Leu Ser Asn Trp Asp Val Val Ser Gln Asn Trp Val Ile Thr Asp Tyr
                    850                 855                 860

Glu Lys Thr Val Tyr Val Gly Ser Ser Ser Arg Asn Leu Pro Leu Lys
        865                 870                 875                 880

<210> SEQ ID NO 115
```

<211> LENGTH: 3169
<212> TYPE: DNA
<213> ORGANISM: Verticillium dahliae

<400> SEQUENCE: 115
atgaagctga ccctcgctac tgccttactg gcagccagcg ggtgtgtctc tgcgggacaa 60
cccaagctca aggtacgtac ttgcctcttt ttcacaagga aaccaaaccc gcaccataat 120
ggtgattgag cagtcgtgct ttcctcaacc cgaatcaaac ccatgccgtg ttcgcgcatg 180
ccctttcgat cgtctgttgt gtgtgaaccc acgctcttca agcatcgcac atagcaccac 240
tccatcttca ttttcgagca atttcgggcc gcagagagcg gtctttcact tcaccacaat 300
cgttcatgcc tcgtgcccca ctgccatgtt tcttcccagt attctacttc tgagagcctt 360
gaccaccgtt gtcgacatct cgtcgccaag gctcgttgac acggactctg tttcccttgg 420
aattaatatt cgaaacaatg ctgaccagca tcctcagcgc cagactaaca gctctagcga 480
gctcgccttt tcccctccgc actacccttc tccatggatg aacccccaag cgactgggtg 540
ggaggacgcc tacgcccgtg ccagagaggt ggtagagcag atgactctgc tcgaaaaggt 600
caacctgacg acaggtgtcg ggtaagcttc acagaccccg tcttgccatc caaagtcatc 660
tgacagaatc ctagctggag cggtgatctc tgcgtcggaa acgtcggctc gatcccccga 720
atcggctgga gggggctttg tttgcaggat ggcccacagg gtatccgttt cgcggactac 780
gtctcgtact tcacttcgag ccagacagcc ggcgctacct gggaccgagg gcttctgtac 840
cagcgcgctc acgccattgg cgccgaagga gtagccaagg gcgtcgacgt cgtcctcggg 900
cccgccattg gccctctagg tcgccttccc gccggaggtc gtaactggga gggtttcgcc 960
gtggaccctt acctcagtgg cgttgctgtc gccgaatccg tcaggggcat ccaggatgct 1020
ggtgctattg ccaacgtcaa gcactacatc gtcaatgagc aggaacattt ccgccaggct 1080
ggcgaggctc aaggttacgg ctacgatgtc gacgaggcat tatcgtcgaa cgttgacgac 1140
aagaccatgc atgagcttta cctttggcca tttgcagacg ctgtccgtgc tggagccggc 1200
agtgtcatgt gttcttatca acaggtgggg gcaataccat tctctcctct ttccttgcag 1260
acagtgcact gaccgacctt ttttgcccaa gatcaacaac agttacggct gtcaaaactc 1320
acatcttctg aatgggctcc tcaaggacga actcggcttt caggggttcg tcctcagcga 1380
ttggcaagcg cagcatgctg gtgctgccac tgccgttgct ggacttgaca tggccatgcc 1440
cggtgacact cgcttcaaca ccggagtcgc cttctggggc gctaacctta ccaatgccat 1500
tttgaacggc accgttcccg aatatcggct cgatgacatg gccatgcgta ttatggcggc 1560
ctttttcaaa gttggaaaga ccctggacga tgttcctgac atcaacttct cgtcttggac 1620
aaaagacacc atcggcccgc tgcactgggc ggcccaggac aatgtgcagg tcatcaacca 1680
acacgttgat gtccgtcaag accacggcgc cctcattcgc accatcgctg cccgcggtac 1740
tgtcttacta aaaaatgagg gatcactgcc tctgaacaag ccgaaatttg ttgctgtcat 1800
tggtgaagat gctggccctc gtcctgttgg tcccaatggc tgccctgatc agggttgcaa 1860
taacggcact ctggctgctg gatggggatc tggcaccgcc agtttccctt atctcatcac 1920
tcctgatagt gctcttcagt ttcaagccgt ttcggatggc tcgcgatacg aaagcatcct 1980
cagcaactgg gattatgagc gcacagaggc cttggtttcc caggcggatg ctactgctct 2040
ggttttcgtc aatgcaaact ctggcgaagg atatatcagc gttgatggaa acgaaggtga 2100
tcgcaagaac ctcactctct ggaatggagg agacgagctt attcaacgag tcgctgcggc 2160
caacaacaac accatcgtca tcatccattc ggttggtccc gttctagtca ctgactggta 2220
cgagaatccc aatatcacgg ctatcatctg ggccggctta cccggacagg agtctggcaa 2280
ctctatcgcc gatattcttt acggccgcgt gaaccctggt ggcaagacac ctttcacctg 2340
gggtccaact gttgagagct acggcgttga cgtcctgaga gagcccaaca atggcaatgg 2400
tgctccccag agcgatttcg acgagggagt cttcatcgat taccgttggt ttgaccggca 2460
gtcgggtgtt gataacaatg catcagcgcc gaggaacagc agcagcagcc acgccccaat 2520
cttcgagttt ggctatggcc tttcgtacac aacctttgaa ttctccaatc ttcagattga 2580
gaggcatgac gttcacgatt acgtccctac cactgggcag acgagccctg cgccgagatt 2640
tggtgctaac tacagtacga actacgacga ctacgtcttt cccgagggcg aaatccgtta 2700
catctatcaa cacatctacc catacctcaa ttcctcagac ccaaaggagg cattggctga 2760
tcctaaatac ggccaaactg cagaagagtt cctcccagag ggcgctcttg atgcctcacc 2820
gcagcctagg ctcccagctt ctggagggcc cggaggcaac ccaatgcttt gggacgtcat 2880
attcacggtc accgcgaccg tgaccaacac gggtaaggtt gctggggacg aagtggcaca 2940
gctttacgtt tctcttggtg gacctgacga tccgattcga gtcctccgtg ggttcgaccg 3000
cattcacatc gcgcctggag cctcgcaaac cttccgtgcg gaactcacgc gccgggacct 3060
cagcaactgg gatgttgtca cgcaaaattg gttcatcagc cagtacgaaa agacggtctt 3120
tgtcgggagc tcatcccgaa acctccctct cagcactcgc ctcgaatag 3169

<210> SEQ ID NO 116
<211> LENGTH: 890
<212> TYPE: PRT
<213> ORGANISM: Verticillium dahliae

<400> SEQUENCE: 116

Met Lys Leu Thr Leu Ala Thr Ala Leu Leu Ala Ala Ser Gly Cys Val
1 5 10 15

Ser Ala Gly Gln Pro Lys Leu Lys His Pro Gln Arg Gln Thr Asn Ser
20 25 30

Ser Ser Glu Leu Ala Phe Ser Pro Pro His Tyr Pro Ser Pro Trp Met
35 40 45

Asn Pro Gln Ala Thr Gly Trp Glu Asp Ala Tyr Ala Arg Ala Arg Glu
50 55 60

Val Val Glu Gln Met Thr Leu Leu Glu Lys Val Asn Leu Thr Thr Gly
65 70 75 80

Val Gly Trp Ser Gly Asp Leu Cys Val Gly Asn Val Gly Ser Ile Pro
85 90 95

Arg Ile Gly Trp Arg Gly Leu Cys Leu Gln Asp Gly Pro Gln Gly Ile
100 105 110

Arg Phe Ala Asp Tyr Val Ser Tyr Phe Thr Ser Ser Gln Thr Ala Gly
115 120 125

Ala Thr Trp Asp Arg Gly Leu Leu Tyr Gln Arg Ala His Ala Ile Gly
130 135 140

Ala Glu Gly Val Ala Lys Gly Val Asp Val Val Leu Gly Pro Ala Ile
145 150 155 160

Gly Pro Leu Gly Arg Leu Pro Ala Gly Gly Arg Asn Trp Glu Gly Phe
165 170 175

Ala Val Asp Pro Tyr Leu Ser Gly Val Ala Val Ala Glu Ser Val Arg
180 185 190

Gly Ile Gln Asp Ala Gly Ala Ile Ala Asn Val Lys His Tyr Ile Val
195 200 205

```
Asn Glu Gln Glu His Phe Arg Gln Ala Gly Glu Ala Gln Gly Tyr Gly
    210                 215                 220

Tyr Asp Val Asp Glu Ala Leu Ser Ser Asn Val Asp Asp Lys Thr Met
225                 230                 235                 240

His Glu Leu Tyr Leu Trp Pro Phe Ala Asp Ala Val Arg Ala Gly Ala
                245                 250                 255

Gly Ser Val Met Cys Ser Tyr Gln Gln Ile Asn Asn Ser Tyr Gly Cys
            260                 265                 270

Gln Asn Ser His Leu Leu Asn Gly Leu Leu Lys Asp Glu Leu Gly Phe
        275                 280                 285

Gln Gly Phe Val Leu Ser Asp Trp Gln Ala Gln His Ala Gly Ala Ala
    290                 295                 300

Thr Ala Val Ala Gly Leu Asp Met Ala Met Pro Gly Asp Thr Arg Phe
305                 310                 315                 320

Asn Thr Gly Val Ala Phe Trp Gly Ala Asn Leu Thr Asn Ala Ile Leu
                325                 330                 335

Asn Gly Thr Val Pro Glu Tyr Arg Leu Asp Asp Met Ala Met Arg Ile
            340                 345                 350

Met Ala Ala Phe Phe Lys Val Gly Lys Thr Leu Asp Asp Val Pro Asp
        355                 360                 365

Ile Asn Phe Ser Ser Trp Thr Lys Asp Thr Ile Gly Pro Leu His Trp
    370                 375                 380

Ala Ala Gln Asp Asn Val Gln Val Ile Asn Gln His Val Asp Val Arg
385                 390                 395                 400

Gln Asp His Gly Ala Leu Ile Arg Thr Ile Ala Ala Arg Gly Thr Val
                405                 410                 415

Leu Leu Lys Asn Glu Gly Ser Leu Pro Leu Asn Lys Pro Lys Phe Val
            420                 425                 430

Ala Val Ile Gly Glu Asp Ala Gly Pro Arg Pro Val Gly Pro Asn Gly
        435                 440                 445

Cys Pro Asp Gln Gly Cys Asn Asn Gly Thr Leu Ala Ala Gly Trp Gly
    450                 455                 460

Ser Gly Thr Ala Ser Phe Pro Tyr Leu Ile Thr Pro Asp Ser Ala Leu
465                 470                 475                 480

Gln Phe Gln Ala Val Ser Asp Gly Ser Arg Tyr Glu Ser Ile Leu Ser
                485                 490                 495

Asn Trp Asp Tyr Glu Arg Thr Glu Ala Leu Val Ser Gln Ala Asp Ala
            500                 505                 510

Thr Ala Leu Val Phe Val Asn Ala Asn Ser Gly Glu Gly Tyr Ile Ser
        515                 520                 525

Val Asp Gly Asn Glu Gly Asp Arg Lys Asn Leu Thr Leu Trp Asn Gly
    530                 535                 540

Gly Asp Glu Leu Ile Gln Arg Val Ala Ala Asn Asn Thr Ile
545                 550                 555                 560

Val Ile Ile His Ser Val Gly Pro Val Leu Val Thr Asp Trp Tyr Glu
                565                 570                 575

Asn Pro Asn Ile Thr Ala Ile Ile Trp Ala Gly Leu Pro Gly Gln Glu
            580                 585                 590

Ser Gly Asn Ser Ile Ala Asp Ile Leu Tyr Gly Arg Val Asn Pro Gly
        595                 600                 605

Gly Lys Thr Pro Phe Thr Trp Gly Pro Thr Val Glu Ser Tyr Gly Val
    610                 615                 620
```

```
Asp Val Leu Arg Glu Pro Asn Asn Gly Asn Gly Ala Pro Gln Ser Asp
625                 630                 635                 640

Phe Asp Glu Gly Val Phe Ile Asp Tyr Arg Trp Phe Asp Arg Gln Ser
            645                 650                 655

Gly Val Asp Asn Asn Ala Ser Ala Pro Arg Asn Ser Ser Ser Ser His
        660                 665                 670

Ala Pro Ile Phe Glu Phe Gly Tyr Gly Leu Ser Tyr Thr Thr Phe Glu
        675                 680                 685

Phe Ser Asn Leu Gln Ile Glu Arg His Asp Val His Asp Tyr Val Pro
690                 695                 700

Thr Thr Gly Gln Thr Ser Pro Ala Pro Arg Phe Gly Ala Asn Tyr Ser
705                 710                 715                 720

Thr Asn Tyr Asp Asp Tyr Val Phe Pro Glu Gly Glu Ile Arg Tyr Ile
            725                 730                 735

Tyr Gln His Ile Tyr Pro Tyr Leu Asn Ser Ser Asp Pro Lys Glu Ala
        740                 745                 750

Leu Ala Asp Pro Lys Tyr Gly Gln Thr Ala Glu Glu Phe Leu Pro Glu
        755                 760                 765

Gly Ala Leu Asp Ala Ser Pro Gln Pro Arg Leu Pro Ala Ser Gly Gly
770                 775                 780

Pro Gly Gly Asn Pro Met Leu Trp Asp Val Ile Phe Thr Val Thr Ala
785                 790                 795                 800

Thr Val Thr Asn Thr Gly Lys Val Ala Gly Asp Val Ala Gln Leu
            805                 810                 815

Tyr Val Ser Leu Gly Gly Pro Asp Asp Pro Ile Arg Val Leu Arg Gly
        820                 825                 830

Phe Asp Arg Ile His Ile Ala Pro Gly Ala Ser Gln Thr Phe Arg Ala
        835                 840                 845

Glu Leu Thr Arg Arg Asp Leu Ser Asn Trp Asp Val Val Thr Gln Asn
850                 855                 860

Trp Phe Ile Ser Gln Tyr Glu Lys Thr Val Phe Val Gly Ser Ser Ser
865                 870                 875                 880

Arg Asn Leu Pro Leu Ser Thr Arg Leu Glu
            885                 890

<210> SEQ ID NO 117
<211> LENGTH: 2418
<212> TYPE: DNA
<213> ORGANISM: Podospora anserina

<400> SEQUENCE: 117
atgaaactca ataagccatt cctggccatt tatttggctt tcaacttggc cgaggcttcg      60
aaaactccgg attgcatcag tggtccgctg gcaaagacct ggcatgtgta caacggcg     120 tcacctcctg cgcgagcagc tgctcttgtg caggctttaa atatcacgga aaagcttgtg    180
aatctagtgg agtatgtcaa gtcaagagaa gctcctttag ggatttcaat tcagctaatc    240
actcctcata gcatgagcct cggtgcagaa aggatcggcc ttccagctta tgcttggtgg    300
aacgaagctc ttcatggtgt tgccgcgtcg cctggggtct ccttcaatca ggccggacaa    360
gaattctcac acgctacttc atttgcgaat actattacgc tagcagccgc ctttgacaat    420
gacctggttt acgaggtggc ggataccatc agcactgaag cgcgagcgtt cagcaatgcc    480
gagctcgctg gactggatta ctggacgcct aacatcaacc cgtacaaaga tccgagatgg    540
gggaggggcc atgaggtttg ttaccttagc cttcttttcc gtgccgtgca gttgctgaga    600
```

```
actcaaaaga cacccggaga agatccggta cacatcaaag gctacgtcca agcacttctc    660
gagggtctag aagggagaga caagatcaga aaggtgattg ccacttgtaa acactttgca    720
gcctatgatt tggagagatg gcaaggggct cttagataca ggttcaatgc tgttgtgacc    780
tcgcaggatc tttcggagta ctacctccaa ccgtttcaac aatgcgctcg agacagcaag    840
gtcgggtctt tcatgtgctc atataatgcg ctcaacggaa caccggcatg tgcaagcacg    900
tatttgatgg acgacatcct tcgaaaacac tggaattgga ccgagcacaa caactatata    960
acgagcgact gtaatgctat tcaggacttc ctccccaact ttcacaactt cagccaaact   1020
ccagctcaag ccgccgctga tgcttataac gccggtacag acaccgtctg tgaggtgcct   1080 ggatacccc cactcacaga tgtaatcgga gcatacaatc agtctctgct gtcagaggaa   1140
attatcgacc gagcacttcg cagattatac gaaggcctca tccgagctgg ctatctcgac   1200
tcagcctccc cacatccata caccaaaatc tcatggtccc aagtaaacac ccccaaagcc   1260
caagccctgg ctctccagtc cgccaccgac gggatagtcc ttctcaaaaa caacggcctc   1320
cttcccctag acctcaccaa caaaaccata gccctcatag ccactgggc caatgcaacc   1380 cgccaaatgc taggcggcta cagcggtatc ccccttact acgccaaccc aatctatgca   1440
gccacccagc tcaacgtcac ttttcatcac gccccaggac cggtgaacca gtcatctccc   1500
tccacaaatg acacctggac ctcccccgcc ctctccgcgg cttccaaatc ggatatcatc   1560
ctctacctcg gcggcaccga cctctccatc gcagccgaag accgagacag agactccatc   1620
gcctggccat ccgctcaact ttccttgtta acctccctcg cccagatggg aaaacccaca   1680
atcgtagcaa gactaggcga ccaagtagac gacaccccc tgctctccaa cccaaacatc   1740
tcctccatcc tatgggtagg ctacccaggc caatcaggcg aacagccct cttgaacatc   1800 atcaccggag tcagctcccc cgccgctcga ctgcccgtca cagtctaccc agaaacttac   1860
acctccctca tcccctgac agccatgtcc ctccgcccaa cctccgcccg cccaggccgg   1920
acttacaggt ggtacccctc cccgtgctc cccttcggcc acggcctcca ctacacaacc   1980
tttaccgcca aattcggcgt ctttgagtcc ctcaccatca acattgccga actcgtttcc   2040
aactgtaacg aacgatacct cgacctctgc cggttcccgc aggtgtccgt ctgggtgtcg   2100
aatacgggag aactcaaatc tgactatgtc gcccttgttt ttgtcagggg tgagtacgga   2160
ccggagccgt acccgatcaa gacgctggtg gggtacaagc ggataaggga tatcgagccg   2220
gggactacgg gggcggcgcc ggtgggggtg gtggtggggg atttggctag ggtggatttg   2280 gggggaata gggttttgtt tccggggaag tatgagtttc tgctggatgt ggaggggggg   2340
agggataggg ttgtgatcga gttggttggg gaggaggtgg tgttggagaa gttccctcag   2400
ccgcctgcgg cgggttga                                                 2418
```

<210> SEQ ID NO 118
<211> LENGTH: 805
<212> TYPE: PRT
<213> ORGANISM: Podospora anserina

<400> SEQUENCE: 118

Met Lys Leu Asn Lys Pro Phe Leu Ala Ile Tyr Leu Ala Phe Asn Leu
1               5                   10                  15

Ala Glu Ala Ser Lys Thr Pro Asp Cys Ile Ser Gly Pro Leu Ala Lys
                20                  25                  30

Thr Leu Ala Cys Asp Thr Thr Ala Ser Pro Pro Ala Arg Ala Ala Ala
            35                  40                  45

```
Leu Val Gln Ala Leu Asn Ile Thr Glu Lys Leu Val Asn Leu Val Glu
 50              55                  60

Tyr Val Lys Ser Arg Glu Ala Pro Leu Gly Ile Ser Ile Gln Leu Ile
 65              70                  75                  80

Thr Pro His Ser Met Ser Leu Gly Ala Glu Arg Ile Gly Leu Pro Ala
                 85                  90                  95

Tyr Ala Trp Trp Asn Glu Ala Leu His Gly Val Ala Ala Ser Pro Gly
                100                 105                 110

Val Ser Phe Asn Gln Ala Gly Gln Glu Phe Ser His Ala Thr Ser Phe
            115                 120                 125

Ala Asn Thr Ile Thr Leu Ala Ala Phe Asp Asn Asp Leu Val Tyr
    130                 135                 140

Glu Val Ala Asp Thr Ile Ser Thr Glu Ala Arg Ala Phe Ser Asn Ala
145                 150                 155                 160

Glu Leu Ala Gly Leu Asp Tyr Trp Thr Pro Asn Ile Asn Pro Tyr Lys
                165                 170                 175

Asp Pro Arg Trp Gly Arg Gly His Glu Val Cys Tyr Leu Ser Leu Leu
            180                 185                 190

Phe Arg Ala Val Gln Leu Leu Arg Thr Gln Lys Thr Pro Gly Glu Asp
    195                 200                 205

Pro Val His Ile Lys Gly Tyr Val Gln Ala Leu Leu Glu Gly Leu Glu
210                 215                 220

Gly Arg Asp Lys Ile Arg Lys Val Ile Ala Thr Cys Lys His Phe Ala
225                 230                 235                 240

Ala Tyr Asp Leu Glu Arg Trp Gln Gly Ala Leu Arg Tyr Arg Phe Asn
                245                 250                 255

Ala Val Val Thr Ser Gln Asp Leu Ser Glu Tyr Tyr Leu Gln Pro Phe
            260                 265                 270

Gln Gln Cys Ala Arg Asp Ser Lys Val Gly Ser Phe Met Cys Ser Tyr
    275                 280                 285

Asn Ala Leu Asn Gly Thr Pro Ala Cys Ala Ser Thr Tyr Leu Met Asp
    290                 295                 300

Asp Ile Leu Arg Lys His Trp Asn Trp Thr Glu His Asn Asn Tyr Ile
305                 310                 315                 320

Thr Ser Asp Cys Asn Ala Ile Gln Asp Phe Leu Pro Asn Phe His Asn
                325                 330                 335

Phe Ser Gln Thr Pro Ala Gln Ala Ala Asp Ala Tyr Asn Ala Gly
    340                 345                 350

Thr Asp Thr Val Cys Glu Val Pro Gly Tyr Pro Pro Leu Thr Asp Val
            355                 360                 365

Ile Gly Ala Tyr Asn Gln Ser Leu Leu Ser Glu Glu Ile Ile Asp Arg
    370                 375                 380

Ala Leu Arg Arg Leu Tyr Glu Gly Leu Ile Arg Ala Gly Tyr Leu Asp
385                 390                 395                 400

Ser Ala Ser Pro His Pro Tyr Thr Lys Ile Ser Trp Ser Gln Val Asn
                405                 410                 415

Thr Pro Lys Ala Gln Ala Leu Ala Leu Gln Ser Ala Thr Asp Gly Ile
            420                 425                 430

Val Leu Leu Lys Asn Asn Gly Leu Pro Leu Asp Leu Thr Asn Lys
    435                 440                 445

Thr Ile Ala Leu Ile Gly His Trp Ala Asn Ala Thr Arg Gln Met Leu
450                 455                 460

Gly Gly Tyr Ser Gly Ile Pro Pro Tyr Tyr Ala Asn Pro Ile Tyr Ala
```

```
            465                 470                 475                 480
Ala Thr Gln Leu Asn Val Thr Phe His His Ala Pro Gly Pro Val Asn
                    485                 490                 495

Gln Ser Ser Pro Ser Thr Asn Asp Thr Trp Thr Ser Pro Ala Leu Ser
            500                 505                 510

Ala Ala Ser Lys Ser Asp Ile Ile Leu Tyr Leu Gly Thr Asp Leu
            515                 520                 525

Ser Ile Ala Ala Glu Asp Arg Asp Arg Asp Ser Ile Ala Trp Pro Ser
            530                 535                 540

Ala Gln Leu Ser Leu Leu Thr Ser Leu Ala Gln Met Gly Lys Pro Thr
545                 550                 555                 560

Ile Val Ala Arg Leu Gly Asp Gln Val Asp Asp Thr Pro Leu Leu Ser
                    565                 570                 575

Asn Pro Asn Ile Ser Ser Ile Leu Trp Val Gly Tyr Pro Gly Gln Ser
                    580                 585                 590

Gly Gly Thr Ala Leu Leu Asn Ile Ile Thr Gly Val Ser Ser Pro Ala
            595                 600                 605

Ala Arg Leu Pro Val Thr Val Tyr Pro Glu Thr Tyr Thr Ser Leu Ile
            610                 615                 620

Pro Leu Thr Ala Met Ser Leu Arg Pro Thr Ser Ala Arg Pro Gly Arg
625                 630                 635                 640

Thr Tyr Arg Trp Tyr Pro Ser Pro Val Leu Pro Phe Gly His Gly Leu
                    645                 650                 655

His Tyr Thr Thr Phe Thr Ala Lys Phe Gly Val Phe Glu Ser Leu Thr
                    660                 665                 670

Ile Asn Ile Ala Glu Leu Val Ser Asn Cys Asn Glu Arg Tyr Leu Asp
            675                 680                 685

Leu Cys Arg Phe Pro Gln Val Ser Val Trp Val Ser Asn Thr Gly Glu
            690                 695                 700

Leu Lys Ser Asp Tyr Val Ala Leu Val Phe Val Arg Gly Glu Tyr Gly
705                 710                 715                 720

Pro Glu Pro Tyr Pro Ile Lys Thr Leu Val Gly Tyr Lys Arg Ile Arg
                    725                 730                 735

Asp Ile Glu Pro Gly Thr Thr Gly Ala Ala Pro Val Gly Val Val
            740                 745                 750

Gly Asp Leu Ala Arg Val Asp Leu Gly Gly Asn Arg Val Leu Phe Pro
            755                 760                 765

Gly Lys Tyr Glu Phe Leu Leu Asp Val Glu Gly Gly Arg Asp Arg Val
    770                 775                 780

Val Ile Glu Leu Val Gly Glu Val Val Leu Glu Lys Phe Pro Gln
785                 790                 795                 800

Pro Pro Ala Ala Gly
            805

<210> SEQ ID NO 119
<211> LENGTH: 721
<212> TYPE: PRT
<213> ORGANISM: Thermotoga neapolitana

<400> SEQUENCE: 119

Met Glu Lys Val Asn Glu Ile Leu Ser Gln Leu Thr Leu Glu Glu Lys
1               5                   10                  15

Val Lys Leu Val Val Gly Val Gly Leu Pro Gly Leu Phe Gly Asn Pro
            20                  25                  30
```

-continued

```
His Ser Arg Val Ala Gly Ala Gly Glu Thr His Pro Val Pro Arg
         35                  40                  45
Val Gly Leu Pro Ala Phe Val Leu Ala Asp Gly Pro Ala Gly Leu Arg
 50                  55                  60
Ile Asn Pro Thr Arg Glu Asn Asp Glu Asn Thr Tyr Tyr Thr Thr Ala
 65                  70                  75                  80
Phe Pro Val Glu Ile Met Leu Ala Ser Thr Trp Asn Arg Glu Leu Leu
                 85                  90                  95
Glu Glu Val Gly Lys Ala Met Gly Glu Val Arg Glu Tyr Gly Val
             100                 105                 110
Asp Val Leu Leu Ala Pro Ala Met Asn Ile His Arg Asn Pro Leu Cys
             115                 120                 125
Gly Arg Asn Phe Glu Tyr Tyr Ser Glu Asp Pro Val Leu Ser Gly Glu
130                 135                 140
Met Ala Ser Ser Phe Val Lys Gly Val Gln Ser Gln Gly Val Gly Ala
145                 150                 155                 160
Cys Ile Lys His Phe Val Ala Asn Asn Gln Glu Thr Asn Arg Met Val
                 165                 170                 175
Val Asp Thr Ile Val Ser Glu Arg Ala Leu Arg Glu Ile Tyr Leu Arg
             180                 185                 190
Gly Phe Glu Ile Ala Val Lys Lys Ser Lys Pro Trp Ser Val Met Ser
         195                 200                 205
Ala Tyr Asn Lys Leu Asn Gly Lys Tyr Cys Ser Gln Asn Glu Trp Leu
     210                 215                 220
Leu Lys Lys Val Leu Arg Glu Glu Trp Gly Phe Glu Gly Phe Val Met
225                 230                 235                 240
Ser Asp Trp Tyr Ala Gly Asp Asn Pro Val Glu Gln Leu Lys Ala Gly
                 245                 250                 255
Asn Asp Leu Ile Met Pro Gly Lys Ala Tyr Gln Val Asn Thr Glu Arg
             260                 265                 270
Arg Asp Glu Ile Glu Glu Ile Met Glu Ala Leu Lys Glu Gly Lys Leu
         275                 280                 285
Ser Glu Glu Val Leu Asp Glu Cys Val Arg Asn Ile Leu Lys Val Leu
     290                 295                 300
Val Asn Ala Pro Ser Phe Lys Asn Tyr Arg Tyr Ser Asn Lys Pro Asp
305                 310                 315                 320
Leu Glu Lys His Ala Lys Val Ala Tyr Glu Ala Gly Ala Glu Gly Val
                 325                 330                 335
Val Leu Leu Arg Asn Glu Glu Ala Leu Pro Leu Ser Glu Asn Ser Lys
             340                 345                 350
Ile Ala Leu Phe Gly Thr Gly Gln Ile Glu Thr Ile Lys Gly Gly Thr
         355                 360                 365
Gly Ser Gly Asp Thr His Pro Arg Tyr Ala Ile Ser Ile Leu Glu Gly
     370                 375                 380
Ile Lys Glu Arg Gly Leu Asn Phe Asp Glu Glu Leu Ala Lys Thr Tyr
385                 390                 395                 400
Glu Asp Tyr Ile Lys Lys Met Arg Glu Thr Glu Glu Tyr Lys Pro Arg
                 405                 410                 415
Arg Asp Ser Trp Gly Thr Ile Ile Lys Pro Lys Leu Pro Glu Asn Phe
             420                 425                 430
Leu Ser Glu Lys Glu Ile His Lys Leu Ala Lys Lys Asn Asp Val Ala
         435                 440                 445
Val Ile Val Ile Ser Arg Ile Ser Gly Glu Gly Tyr Asp Arg Lys Pro
```

```
                    450                 455                 460
Val Lys Gly Asp Phe Tyr Leu Ser Asp Asp Glu Thr Asp Leu Ile Lys
465                 470                 475                 480

Thr Val Ser Arg Glu Phe His Glu Gln Gly Lys Lys Val Ile Val Leu
                    485                 490                 495

Leu Asn Ile Gly Ser Pro Val Glu Val Val Ser Trp Arg Asp Leu Val
                500                 505                 510

Asp Gly Ile Leu Leu Val Trp Gln Ala Gly Gln Glu Thr Gly Arg Ile
            515                 520                 525

Val Ala Asp Val Leu Thr Gly Arg Ile Asn Pro Ser Gly Lys Leu Pro
530                 535                 540

Thr Thr Phe Pro Arg Asp Tyr Ser Asp Val Pro Ser Trp Thr Phe Pro
545                 550                 555                 560

Gly Glu Pro Lys Asp Asn Pro Gln Lys Val Val Tyr Glu Glu Asp Ile
                565                 570                 575

Tyr Val Gly Tyr Arg Tyr Tyr Asp Thr Phe Gly Val Glu Pro Ala Tyr
            580                 585                 590

Glu Phe Gly Tyr Gly Leu Ser Tyr Thr Thr Phe Glu Tyr Ser Asp Leu
            595                 600                 605

Asn Val Ser Phe Asp Gly Glu Thr Leu Arg Val Gln Tyr Arg Ile Glu
            610                 615                 620

Asn Thr Gly Gly Arg Ala Gly Lys Glu Val Ser Gln Val Tyr Ile Lys
625                 630                 635                 640

Ala Pro Lys Gly Lys Ile Asp Lys Pro Phe Gln Glu Leu Lys Ala Phe
                645                 650                 655

His Lys Thr Arg Leu Leu Asn Pro Gly Glu Ser Glu Glu Val Val Leu
            660                 665                 670

Glu Ile Pro Val Arg Asp Leu Ala Ser Phe Asn Gly Glu Glu Trp Val
            675                 680                 685

Val Glu Ala Gly Glu Tyr Glu Val Arg Val Gly Ala Ser Ser Arg Asn
            690                 695                 700

Ile Lys Leu Lys Gly Thr Phe Ser Val Gly Glu Glu Arg Arg Phe Lys
705                 710                 715                 720

Pro

<210> SEQ ID NO 120
<211> LENGTH: 17
<212> TYPE: PRT
<213> ORGANISM: Trichoderma reesei

<400> SEQUENCE: 120

Met Tyr Arg Lys Leu Ala Val Ile Ser Ala Phe Leu Ala Thr Ala Arg
1               5                   10                  15

Ala

<210> SEQ ID NO 121
<211> LENGTH: 28
<212> TYPE: DNA
<213> ORGANISM: Artificial Sequence
<220> FEATURE:
<223> OTHER INFORMATION: synthetic primer

<400> SEQUENCE: 121
caccatgaga tatagaacag ctgccgct                                    28

<210> SEQ ID NO 122
```

```
<211> LENGTH: 40
<212> TYPE: DNA
<213> ORGANISM: Artificial Sequence
<220> FEATURE:
<223> OTHER INFORMATION: synthetic primer

<400> SEQUENCE: 122
cgaccgccct gcggagtctt gcccagtggt cccgcgacag          40

<210> SEQ ID NO 123
<211> LENGTH: 40
<212> TYPE: DNA
<213> ORGANISM: Artificial Sequence
<220> FEATURE:
<223> OTHER INFORMATION: synthetic primer

<400> SEQUENCE: 123
ctgtcgcggg accactgggc aagactccgc agggcggtcg          40

<210> SEQ ID NO 124
<211> LENGTH: 20
<212> TYPE: DNA
<213> ORGANISM: Artificial Sequence
<220> FEATURE:
<223> OTHER INFORMATION: synthetic primer

<400> SEQUENCE: 124
cctacgctac cgacagagtg                                20

<210> SEQ ID NO 125
<211> LENGTH: 20
<212> TYPE: DNA
<213> ORGANISM: Artificial Sequence
<220> FEATURE:
<223> OTHER INFORMATION: synthetic primer

<400> SEQUENCE: 125
gtctagactg gaaacgcaac                                20

<210> SEQ ID NO 126
<211> LENGTH: 21
<212> TYPE: DNA
<213> ORGANISM: Artificial Sequence
<220> FEATURE:
<223> OTHER INFORMATION: synthetic primer

<400> SEQUENCE: 126
gagttgtgaa gtcggtaatc c                              21

<210> SEQ ID NO 127
<211> LENGTH: 35
<212> TYPE: DNA
<213> ORGANISM: Artificial Sequence
<220> FEATURE:
<223> OTHER INFORMATION: synthetic primer

<400> SEQUENCE: 127
caccatgaaa gcaaacgtca tcttgtgcct cctgg               35

<210> SEQ ID NO 128
<211> LENGTH: 43
<212> TYPE: DNA
<213> ORGANISM: Artificial Sequence
<220> FEATURE:
<223> OTHER INFORMATION: synthetic primer

<400> SEQUENCE: 128
```
ctattgtaag atgccaacaa tgctgttata tgccggcttg ggg 43

<210> SEQ ID NO 129
<211> LENGTH: 21
<212> TYPE: DNA
<213> ORGANISM: Artificial Sequence
<220> FEATURE:
<223> OTHER INFORMATION: synthetic primer

<400> SEQUENCE: 129
gagttgtgaa gtcggtaatc c 21

<210> SEQ ID NO 130
<211> LENGTH: 18
<212> TYPE: DNA
<213> ORGANISM: Artificial Sequence
<220> FEATURE:
<223> OTHER INFORMATION: synthetic primer

<400> SEQUENCE: 130
cacgaagagc ggcgattc 18

<210> SEQ ID NO 131
<211> LENGTH: 23
<212> TYPE: DNA
<213> ORGANISM: Artificial Sequence
<220> FEATURE:
<223> OTHER INFORMATION: synthetic primer

<400> SEQUENCE: 131
cacccatgct gctcaatctt cag 23

<210> SEQ ID NO 132
<211> LENGTH: 23
<212> TYPE: DNA
<213> ORGANISM: Artificial Sequence
<220> FEATURE:
<223> OTHER INFORMATION: synthetic primer

<400> SEQUENCE: 132
ttacgcagac ttggggtctt gag 23

<210> SEQ ID NO 133
<211> LENGTH: 20
<212> TYPE: DNA
<213> ORGANISM: Artificial Sequence
<220> FEATURE:
<223> OTHER INFORMATION: synthetic primer

<400> SEQUENCE: 133
gcttgagtgt atcgtgtaag 20

<210> SEQ ID NO 134
<211> LENGTH: 21
<212> TYPE: DNA
<213> ORGANISM: Artificial Sequence
<220> FEATURE:
<223> OTHER INFORMATION: synthetic primer

<400> SEQUENCE: 134
gcaacggcaa agccccactt c 21

<210> SEQ ID NO 135
<211> LENGTH: 32
<212> TYPE: DNA

```
<213> ORGANISM: Artificial Sequence
<220> FEATURE:
<223> OTHER INFORMATION: synthetic primer

<400> SEQUENCE: 135
gtagcggccg cctcatctca tctcatccat cc                                32

<210> SEQ ID NO 136
<211> LENGTH: 24
<212> TYPE: DNA
<213> ORGANISM: Artificial Sequence
<220> FEATURE:
<223> OTHER INFORMATION: synthetic primer

<400> SEQUENCE: 136
caccatgcag ctcaagtttc tgtc                                         24

<210> SEQ ID NO 137
<211> LENGTH: 32
<212> TYPE: DNA
<213> ORGANISM: Artificial Sequence
<220> FEATURE:
<223> OTHER INFORMATION: synthetic primer

<400> SEQUENCE: 137
ggttactagt caactgcccg ttctgtagcg ag                                32

<210> SEQ ID NO 138
<211> LENGTH: 29
<212> TYPE: DNA
<213> ORGANISM: Artificial Sequence
<220> FEATURE:
<223> OTHER INFORMATION: synthetic primer

<400> SEQUENCE: 138
catgcgatcg cgacgttttg gtcaggtcg                                    29

<210> SEQ ID NO 139
<211> LENGTH: 40
<212> TYPE: DNA
<213> ORGANISM: Artificial Sequence
<220> FEATURE:
<223> OTHER INFORMATION: synthetic primer

<400> SEQUENCE: 139
gacagaaact tgagctgcat ggtgtgggac aacaagaagg                        40

<210> SEQ ID NO 140
<211> LENGTH: 29
<212> TYPE: DNA
<213> ORGANISM: Artificial Sequence
<220> FEATURE:
<223> OTHER INFORMATION: synthetic primer

<400> SEQUENCE: 140
caccatggtt cgcttcagtt caatcctag                                    29

<210> SEQ ID NO 141
<211> LENGTH: 22
<212> TYPE: DNA
<213> ORGANISM: Artificial Sequence
<220> FEATURE:
<223> OTHER INFORMATION: synthetic primer

<400> SEQUENCE: 141
gtggctagaa gatatccaac ac                                           22
```

<210> SEQ ID NO 142
<211> LENGTH: 29
<212> TYPE: DNA
<213> ORGANISM: Artificial Sequence
<220> FEATURE:
<223> OTHER INFORMATION: synthetic primer

<400> SEQUENCE: 142
catgcgatcg cgacgttttg gtcaggtcg                              29

<210> SEQ ID NO 143
<211> LENGTH: 39
<212> TYPE: DNA
<213> ORGANISM: Artificial Sequence
<220> FEATURE:
<223> OTHER INFORMATION: synthetic primer

<400> SEQUENCE: 143
gaactgaagc gaaccatggt gtgggacaac aagaaggac                   39

<210> SEQ ID NO 144
<211> LENGTH: 21
<212> TYPE: DNA
<213> ORGANISM: Artificial Sequence
<220> FEATURE:
<223> OTHER INFORMATION: synthetic primer

<400> SEQUENCE: 144
gtagttatgc gcatgctaga c                                      21

<210> SEQ ID NO 145
<211> LENGTH: 22
<212> TYPE: DNA
<213> ORGANISM: Artificial Sequence
<220> FEATURE:
<223> OTHER INFORMATION: synthetic primer

<400> SEQUENCE: 145
gtggctagaa gatatccaac ac                                     22

<210> SEQ ID NO 146
<211> LENGTH: 21
<212> TYPE: DNA
<213> ORGANISM: Artificial Sequence
<220> FEATURE:
<223> OTHER INFORMATION: synthetic primer

<400> SEQUENCE: 146
gtagttatgc gcatgctaga c                                      21

<210> SEQ ID NO 147
<211> LENGTH: 28
<212> TYPE: DNA
<213> ORGANISM: Artificial Sequence
<220> FEATURE:
<223> OTHER INFORMATION: synthetic primer

<400> SEQUENCE: 147
ccggctcagt atcaaccact aagcacat                               28

<210> SEQ ID NO 148
<211> LENGTH: 250
<212> TYPE: PRT
<213> ORGANISM: Thermoascus aurantiacus

<400> SEQUENCE: 148

```
Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

Val Glu Leu Gln Trp Thr Pro Trp Pro Asp Ser His Gly Pro Val
            100                 105                 110

Ile Asn Tyr Leu Ala Pro Cys Asn Gly Asp Cys Ser Thr Val Asp Lys
        115                 120                 125

Thr Gln Leu Glu Phe Phe Lys Ile Ala Glu Ser Gly Leu Ile Asn Asp
    130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
    210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250
```

<210> SEQ ID NO 149
<211> LENGTH: 799
<212> TYPE: DNA
<213> ORGANISM: Thermoascus aurantiacus

<400> SEQUENCE: 149

```
atgtcctttt ccaagataat tgctactgcc ggcgttcttg cctctgcttc tctagtggct    60
ggccatggct tcgttcagaa catcgtgatt gatggtaaaa agtatgtcat gcaagacgc   120
acataagcgg caacagctga caatcgacag ttatggcggg tatctagtga accagtatcc   180
atacatgtcc aatcctccag aggtcatcgc ctggtctact acggcaactg atcttggatt   240
tgtggacggt actggatacc aaaccccaga tatcatctgc cataggggcg ccaagcctgg   300
agccctgact gctccagtct ctccaggagg aactgttgag cttcaatgga ctccatggcc   360
tgattctcac catggcccag ttatcaacta ccttgctccg tgcaatggtg attgttccac   420
tgtggataag acccaattag aattcttcaa aattgccgag agcggtctca tcaatgatga   480
caatcctcct gggatctggg cttcagacaa tctgatagca gccaacaaca gctggactgt   540
caccattcca accacaattg cacctggaaa ctatgttctg aggcatgaga ttattgctct   600
tcactcagct cagaaccagg atggtgccca gaactatccc cagtgcatca atctgcaggt   660
```

```
cactggaggt ggttctgata accctgctgg aactcttgga acggcactct accacgatac    720
cgatcctgga attctgatca acatctatca gaaactttcc agctatatca tccctggtcc    780
tcctctgtat actggttaa                                                 799
```

<210> SEQ ID NO 150
<211> LENGTH: 532
<212> TYPE: PRT
<213> ORGANISM: Aspergillus fumigatus

<400> SEQUENCE: 150

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
```

```
              340                 345                 350
Val Ser Gly Asn Ser Ile Thr Thr Glu Tyr Cys Thr Ala Gln Lys Ser
            355                 360                 365

Leu Phe Gln Asp Gln Asn Val Phe Glu Lys His Gly Gly Leu Glu Gly
        370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
            435                 440                 445

Val Val Tyr Ser Asn Ile Lys Val Gly Pro Ile Gly Ser Thr Phe Asn
        450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
            500                 505                 510

Thr Thr Cys Ala Ser Pro Tyr Thr Cys Gln Lys Leu Asn Asp Tyr Tyr
            515                 520                 525

Ser Gln Cys Leu
        530

<210> SEQ ID NO 151
<211> LENGTH: 452
<212> TYPE: PRT
<213> ORGANISM: Aspergillus fumigatus

<400> SEQUENCE: 151

Met His Gln Arg Ala Leu Leu Phe Ser Ala Leu Ala Val Ala Ala Asn
1               5                   10                  15

Ala Gln Gln Val Gly Thr Gln Thr Pro Glu Thr His Pro Pro Leu Thr
            20                  25                  30

Trp Gln Lys Cys Thr Ala Gly Ser Cys Ser Gln Gln Ser Gly Ser
        35                  40                  45

Val Val Ile Asp Ala Asn Trp Arg Trp Leu His Ser Thr Lys Asp Thr
    50                  55                  60

Thr Asn Cys Tyr Thr Gly Asn Thr Trp Asn Thr Glu Leu Cys Pro Asp
65                  70                  75                  80

Asn Glu Ser Cys Ala Gln Asn Cys Ala Leu Asp Gly Ala Asp Tyr Ala
                85                  90                  95

Gly Thr Tyr Gly Val Thr Thr Ser Gly Ser Glu Leu Lys Leu Ser Phe
            100                 105                 110

Val Thr Gly Ala Asn Val Gly Ser Arg Leu Tyr Leu Met Gln Asp Asp
        115                 120                 125

Glu Thr Tyr Gln His Phe Asn Leu Leu Asn His Glu Phe Thr Phe Asp
    130                 135                 140

Val Asp Val Ser Asn Leu Pro Cys Gly Leu Asn Gly Ala Leu Tyr Phe
145                 150                 155                 160

Val Ala Met Asp Ala Asp Gly Gly Met Ser Lys Tyr Pro Ser Asn Lys
                165                 170                 175
```

```
Ala Gly Ala Lys Tyr Gly Thr Gly Tyr Cys Asp Ser Gln Cys Pro Arg
            180                 185                 190

Asp Leu Lys Phe Ile Asn Gly Met Ala Asn Val Glu Gly Trp Glu Pro
            195                 200                 205

Ser Ser Ser Asp Lys Asn Ala Gly Val Gly Gly His Gly Ser Cys Cys
210                 215                 220

Pro Glu Met Asp Ile Trp Glu Ala Asn Ser Ile Ser Thr Ala Val Thr
225                 230                 235                 240

Pro His Pro Cys Asp Asp Val Ser Gln Thr Met Cys Ser Gly Asp Ala
            245                 250                 255

Cys Gly Gly Thr Tyr Ser Glu Ser Arg Tyr Ala Gly Thr Cys Asp Pro
            260                 265                 270

Asp Gly Cys Asp Phe Asn Pro Phe Arg Met Gly Asn Glu Ser Phe Tyr
            275                 280                 285

Gly Pro Gly Lys Ile Val Asp Thr Lys Ser Lys Met Thr Val Val Thr
            290                 295                 300

Gln Phe Ile Thr Ala Asp Gly Thr Asp Ser Gly Ala Leu Ser Glu Ile
305                 310                 315                 320

Lys Arg Leu Tyr Val Gln Asn Gly Lys Val Ile Ala Asn Ser Val Ser
            325                 330                 335

Asn Val Ala Gly Val Ser Gly Asn Ser Ile Thr Ser Asp Phe Cys Thr
            340                 345                 350

Ala Gln Lys Lys Ala Phe Gly Asp Glu Asp Ile Phe Ala Lys His Gly
            355                 360                 365

Gly Leu Ser Gly Met Gly Lys Ala Leu Ser Glu Met Val Leu Ile Met
370                 375                 380

Ser Ile Trp Asp Asp His His Ser Ser Met Met Trp Leu Asp Ser Thr
385                 390                 395                 400

Tyr Pro Thr Asp Ala Asp Pro Ser Lys Pro Gly Val Ala Arg Gly Thr
            405                 410                 415

Cys Glu His Gly Ala Gly Asp Pro Glu Asn Val Glu Ser Gln His Pro
            420                 425                 430

Asp Ala Ser Val Thr Phe Ser Asn Ile Lys Phe Gly Pro Ile Gly Ser
            435                 440                 445

Thr Tyr Glu Gly
450

<210> SEQ ID NO 152
<211> LENGTH: 450
<212> TYPE: PRT
<213> ORGANISM: Chaetosphaeridium globosum

<400> SEQUENCE: 152

Met Lys Gln Tyr Leu Gln Tyr Leu Ala Ala Ala Leu Pro Leu Met Ser
1               5                   10                  15

Leu Val Ser Ala Gln Gly Val Gly Thr Ser Thr Ser Glu Thr His Pro
            20                  25                  30

Lys Ile Thr Trp Lys Lys Cys Ser Gly Gly Ser Cys Ser Thr Val
            35                  40                  45

Asn Ala Glu Val Val Ile Asp Ala Asn Trp Arg Trp Leu His Asn Ala
50                  55                  60

Asp Ser Lys Asn Cys Tyr Asp Gly Asn Glu Trp Thr Asp Ala Cys Thr
65                  70                  75                  80

Ser Ser Asp Asp Cys Thr Ser Lys Cys Val Leu Glu Gly Ala Glu Tyr
                85                  90                  95
```

Gly Lys Thr Tyr Gly Ala Ser Thr Ser Gly Asp Ser Leu Ser Leu Lys
            100                 105                 110

Phe Leu Thr Lys His Glu Tyr Gly Thr Asn Ile Gly Ser Arg Phe Tyr
            115                 120                 125

Leu Met Asn Gly Ala Ser Lys Tyr Gln Met Phe Thr Leu Met Asn Asn
            130                 135                 140

Glu Phe Ala Phe Asp Val Asp Leu Ser Thr Val Glu Cys Gly Leu Asn
145                 150                 155                 160

Ser Ala Leu Tyr Phe Val Ala Met Glu Glu Asp Gly Met Ala Ser
                165                 170                 175

Tyr Ser Thr Asn Lys Ala Gly Ala Lys Tyr Gly Thr Tyr Cys Asp
                180                 185                 190

Ala Gln Cys Ala Arg Asp Leu Lys Phe Val Gly Gly Lys Ala Asn Tyr
        195                 200                 205

Asp Gly Trp Thr Pro Ser Ser Asn Asp Ala Asn Ala Gly Val Gly Ala
            210                 215                 220

Leu Gly Gly Cys Cys Ala Glu Ile Asp Val Trp Glu Ser Asn Ala His
225                 230                 235                 240

Ala Phe Ala Phe Thr Pro His Ala Cys Glu Asn Asn Asn Tyr His Val
                245                 250                 255

Cys Glu Asp Thr Thr Cys Gly Gly Thr Tyr Ser Glu Asp Arg Phe Ala
                260                 265                 270

Gly Asp Cys Asp Ala Asn Gly Cys Asp Tyr Asn Pro Tyr Arg Val Gly
            275                 280                 285

Asn Thr Asp Phe Tyr Gly Lys Gly Met Thr Val Asp Thr Ser Lys Lys
            290                 295                 300

Phe Thr Val Val Ser Gln Phe Gln Glu Asn Lys Leu Thr Gln Phe Phe
305                 310                 315                 320

Val Gln Asn Gly Lys Lys Ile Glu Ile Pro Gly Pro Lys His Glu Gly
                325                 330                 335

Leu Pro Thr Glu Ser Ser Asp Ile Thr Pro Glu Leu Cys Ser Ala Met
            340                 345                 350

Pro Glu Val Phe Gly Asp Arg Asp Arg Phe Ala Glu Val Gly Gly Phe
            355                 360                 365

Asp Ala Leu Asn Lys Ala Leu Ala Val Pro Met Val Leu Val Met Ser
370                 375                 380

Ile Trp Asp Asp His Tyr Ala Asn Met Leu Trp Leu Asp Ser Ser Tyr
385                 390                 395                 400

Pro Pro Glu Lys Ala Gly Thr Pro Gly Gly Asp Arg Gly Pro Cys Ala
                405                 410                 415

Gln Asp Ser Gly Val Pro Ser Glu Val Glu Ser Gln Tyr Pro Asp Ala
            420                 425                 430

Thr Val Val Trp Ser Asn Ile Arg Phe Gly Pro Ile Gly Ser Thr Val
            435                 440                 445

Gln Val
    450

<210> SEQ ID NO 153
<211> LENGTH: 452
<212> TYPE: PRT
<213> ORGANISM: Chaetosphaeridium globosum

<400> SEQUENCE: 153

Met Tyr Arg Gln Val Ala Thr Ala Leu Ser Phe Ala Ser Leu Val Leu

-continued

```
1               5                   10                  15
Gly Gln Gln Val Gly Thr Leu Thr Ala Glu Thr His Pro Ser Leu Pro
            20                  25                  30

Ile Glu Val Cys Thr Ala Pro Gly Ser Cys Thr Lys Glu Asp Thr Thr
            35                  40                  45

Val Val Leu Asp Ala Asn Trp Arg Trp Thr His Val Thr Asp Gly Tyr
    50                  55                  60

Thr Asn Cys Tyr Thr Gly Asn Ala Trp Asn Glu Thr Ala Cys Pro Asp
65                  70                  75                  80

Gly Lys Thr Cys Ala Ala Asn Cys Ala Ile Asp Gly Ala Glu Tyr Glu
                85                  90                  95

Lys Thr Tyr Gly Ile Thr Thr Pro Glu Glu Gly Ala Leu Arg Leu Asn
                100                 105                 110

Phe Val Thr Glu Ser Asn Val Gly Ser Arg Val Tyr Leu Met Ala Gly
            115                 120                 125

Glu Asp Lys Tyr Arg Leu Phe Asn Leu Leu Asn Lys Glu Phe Thr Met
            130                 135                 140

Asp Val Asp Val Ser Asn Leu Pro Cys Gly Leu Asn Gly Ala Val Tyr
145                 150                 155                 160

Phe Ser Glu Met Asp Glu Asp Gly Gly Met Ser Arg Phe Glu Gly Asn
                165                 170                 175

Lys Ala Gly Ala Lys Tyr Gly Thr Gly Tyr Cys Asp Ser Gln Cys Pro
                180                 185                 190

Arg Asp Ile Lys Phe Ile Asn Gly Glu Ala Asn Ser Glu Gly Trp Gly
            195                 200                 205

Gly Glu Asp Gly Asn Ser Gly Thr Gly Lys Tyr Gly Thr Cys Cys Ala
            210                 215                 220

Glu Met Asp Ile Trp Glu Ala Asn Leu Asp Ala Thr Ala Tyr Thr Pro
225                 230                 235                 240

His Pro Cys Lys Val Thr Glu Gln Thr Arg Cys Glu Asp Asp Thr Glu
                245                 250                 255

Cys Gly Ala Gly Asp Ala Arg Tyr Glu Gly Leu Cys Asp Arg Asp Gly
                260                 265                 270

Cys Asp Phe Asn Ser Phe Arg Leu Gly Asn Lys Glu Phe Tyr Gly Pro
            275                 280                 285

Glu Lys Thr Val Asp Thr Ser Lys Pro Phe Thr Leu Val Thr Gln Phe
            290                 295                 300

Val Thr Ala Asp Gly Thr Asp Thr Gly Ala Leu Gln Ser Ile Arg Arg
305                 310                 315                 320

Phe Tyr Val Gln Asp Gly Thr Val Ile Pro Asn Ser Glu Thr Val Val
                325                 330                 335

Glu Gly Val Asp Pro Thr Asn Glu Ile Thr Asp Phe Cys Ala Gln
                340                 345                 350

Gln Lys Thr Ala Phe Gly Asp Asn Asn His Phe Lys Thr Ile Gly Gly
            355                 360                 365

Leu Pro Ala Met Gly Lys Ser Leu Glu Lys Met Val Leu Val Leu Ser
    370                 375                 380

Ile Trp Asp Asp His Ala Val Tyr Met Asn Trp Leu Asp Ser Asn Tyr
385                 390                 395                 400

Pro Thr Asp Ala Asp Pro Thr Lys Pro Gly Val Ala Arg Gly Arg Cys
                405                 410                 415

Asp Pro Glu Ala Gly Val Pro Glu Thr Val Glu Ala Ala His Pro Asp
                420                 425                 430
```

Ala Tyr Val Ile Tyr Ser Asn Ile Lys Ile Gly Ala Leu Asn Ser Thr
            435                 440                 445

Phe Ala Ala Ala
    450

<210> SEQ ID NO 154
<211> LENGTH: 526
<212> TYPE: PRT
<213> ORGANISM: Thielavia terrestris

<400> SEQUENCE: 154

Met His Ala Lys Phe Ala Thr Leu Ala Ala Leu Val Ala Ser Ala Ala
1               5                   10                  15

Ala Gln Gln Ala Cys Thr Leu Thr Ala Glu Asn His Pro Thr Leu Ser
            20                  25                  30

Trp Ser Lys Cys Thr Ser Gly Gly Ser Cys Thr Ser Val Ser Gly Ser
        35                  40                  45

Val Thr Ile Asp Ala Asn Trp Arg Trp Thr His Gln Val Ser Ser Ser
    50                  55                  60

Thr Asn Cys Tyr Thr Gly Asn Glu Trp Asp Thr Ser Ile Cys Thr Asp
65                  70                  75                  80

Gly Ala Ser Cys Ala Ala Cys Cys Leu Asp Gly Ala Asp Tyr Ser
                85                  90                  95

Gly Thr Tyr Gly Ile Thr Thr Ser Gly Asn Ala Leu Ser Leu Gln Phe
            100                 105                 110

Val Thr Gln Gly Pro Tyr Ser Thr Asn Ile Gly Ser Arg Thr Tyr Leu
        115                 120                 125

Met Ala Ser Asp Thr Lys Tyr Gln Met Phe Thr Leu Leu Gly Asn Glu
    130                 135                 140

Phe Thr Phe Asp Val Asp Val Ser Gly Leu Gly Cys Gly Leu Asn Gly
145                 150                 155                 160

Ala Leu Tyr Phe Val Ser Met Asp Glu Asp Gly Gly Leu Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Asn Val
        195                 200                 205

Gly Trp Thr Pro Ser Ser Asn Asp Lys Asn Ala Gly Leu Gly Asn Tyr
    210                 215                 220

Gly Ser Cys Cys Ser Glu Met Asp Val Trp Glu Ala Asn Ser Ile Ser
225                 230                 235                 240

Ala Ala Tyr Thr Pro His Pro Cys Thr Thr Ile Gly Gln Thr Arg Cys
                245                 250                 255

Glu Gly Asp Asp Cys Gly Gly Thr Tyr Ser Thr Asp Arg Tyr Ala Gly
            260                 265                 270

Glu Cys Asp Pro Asp Gly Cys Asp Phe Asn Ser Tyr Arg Met Gly Asn
        275                 280                 285

Thr Thr Phe Tyr Gly Lys Gly Met Thr Val Asp Thr Ser Lys Lys Phe
    290                 295                 300

Thr Val Val Thr Gln Phe Leu Thr Asp Ser Ser Gly Asn Leu Ser Glu
305                 310                 315                 320

Ile Lys Arg Phe Tyr Val Gln Asn Gly Val Val Ile Pro Asn Ser Asn
                325                 330                 335

Ser Asn Ile Ala Gly Val Ser Gly Asn Ser Ile Thr Gln Ala Phe Cys

```
                340                 345                 350
Asp Ala Gln Lys Thr Ala Phe Gly Asp Thr Asn Val Phe Asp Gln Lys
                355                 360                 365
Gly Gly Leu Ala Gln Met Gly Lys Ala Leu Ala Gln Pro Met Val Leu
            370                 375                 380
Val Met Ser Leu Trp Asp Asp His Ala Val Asn Met Leu Trp Leu Asp
385                 390                 395                 400
Ser Thr Tyr Pro Thr Asp Ala Ala Gly Lys Pro Gly Ala Ala Arg Gly
                405                 410                 415
Thr Cys Pro Thr Thr Ser Gly Val Pro Ala Asp Val Glu Ser Gln Ala
            420                 425                 430
Pro Asn Ser Lys Val Ile Tyr Ser Asn Ile Arg Phe Gly Pro Ile Gly
            435                 440                 445
Ser Thr Val Ser Gly Leu Pro Gly Gly Ser Asn Pro Gly Gly Gly
            450                 455                 460
Ser Ser Ser Thr Thr Thr Thr Arg Pro Ala Thr Ser Thr Thr Ser
465                 470                 475                 480
Ser Ala Ser Ser Gly Pro Thr Gly Gly Thr Ala Ala His Trp Gly
                485                 490                 495
Gln Cys Gly Gly Ile Gly Trp Thr Gly Pro Thr Val Cys Ala Ser Pro
                500                 505                 510
Tyr Thr Cys Gln Lys Leu Asn Asp Trp Tyr Tyr Gln Cys Leu
            515                 520                 525

<210> SEQ ID NO 155
<211> LENGTH: 455
<212> TYPE: PRT
<213> ORGANISM: Thielavia terrestris

<400> SEQUENCE: 155

Met Leu Ser Lys Ile Leu Ala Leu Gly Ala Leu Ala Gly Ala Ala Val
1               5                   10                  15
Ala Gln Gln Ala Gly Thr Gln Thr Ala Glu Asn His Pro Lys Met Ser
                20                  25                  30
Trp Gln Lys Cys Ser Ser Gly Gly Ser Cys Thr Thr Val Gln Gly Glu
            35                  40                  45
Val Val Ile Asp Ser Asn Trp Arg Trp Val His Asp Lys Asn Gly Tyr
        50                  55                  60
Thr Asn Cys Tyr Thr Gly Asn Glu Trp Asn Thr Thr Ile Cys Ser Asp
65                  70                  75                  80
Ala Lys Ser Cys Ala Ala Asn Cys Ala Leu Asp Gly Ala Asp Tyr Ser
                85                  90                  95
Gly Thr Tyr Gly Val Thr Thr Ser Gly Asn Ala Leu Thr Leu Lys Phe
            100                 105                 110
Val Thr Lys Gly Ser Tyr Ser Thr Asn Ile Gly Ser Arg Leu Tyr Met
        115                 120                 125
Met Ala Ser Ser Thr Lys Tyr Gln Met Phe Thr Leu Leu Gly Asn Glu
    130                 135                 140
Phe Thr Phe Asp Val Asp Val Ser Lys Leu Gly Cys Gly Leu Asn Gly
145                 150                 155                 160
Ala Leu Tyr Phe Val Ala Met Asp Glu Asp Gly Gly Met Ser Lys Tyr
                165                 170                 175
Ser Ala Asn Lys Ala Gly Ala Lys Tyr Gly Thr Gly Tyr Cys Asp Ala
            180                 185                 190
```

```
Gln Cys Pro Arg Asp Leu Lys Phe Ile Asn Gly Gln Ala Asn Ser Ala
            195                 200                 205

Gln Trp Thr Pro Ser Ser Asn Asp Gln Asn Ala Gly Val Gly Gln Tyr
        210                 215                 220

Gly Ser Cys Cys Ala Glu Met Asp Ile Trp Tyr Ala Asn Ser Ile Ser
225                 230                 235                 240

Ala Ala Val Thr Pro His Pro Cys Glu Thr Val Gln His Gln Cys
                245                 250                 255

Glu Gly Asp Ser Cys Gly Gly Thr Tyr Ser Gly Asp Arg Tyr Gly Gly
            260                 265                 270

Asp Cys Asp Pro Asp Gly Cys Asp Phe Asn Ala Tyr Arg Gln Gly Val
        275                 280                 285

Lys Asp Phe Tyr Gly Pro Ser Met Thr Val Asp Thr Thr Lys Lys Phe
        290                 295                 300

Thr Val Val Thr Gln Phe Ile Lys Gly Ser Asp Gly Glu Leu Ser Glu
305                 310                 315                 320

Ile Lys Arg Phe Tyr Val Gln Asp Gly Lys Val Ile Glu Asn Ala Asn
                325                 330                 335

Ser Thr Ile Pro Asn Asn Pro Gly Asn Ser Ile Thr Pro Asp Phe Cys
                340                 345                 350

Lys Ala Gln Lys Val Ala Phe Gly Asp Arg Asp Val Phe Asn Glu Lys
            355                 360                 365

Gly Gly Phe Pro Gln Phe Ser Lys Ala Val Gln Thr Pro Met Val Leu
        370                 375                 380

Val Met Ser Leu Trp Asp Asp His Tyr Ala Asn Met Leu Trp Leu Asp
385                 390                 395                 400

Ser Thr Tyr Pro Val Asp Ala Asp Pro Ser Glu Pro Gly Lys Ala Arg
                405                 410                 415

Gly Thr Cys Asp Thr Ser Ser Gly Val Pro Lys Asp Val Glu Ala Asn
            420                 425                 430

Gln Ala Ser Asn Gln Val Ile Tyr Ser Asn Ile Lys Phe Gly Pro Ile
        435                 440                 445

Gly Ser Thr Phe Lys Gln Ser
    450                 455

<210> SEQ ID NO 156
<211> LENGTH: 482
<212> TYPE: PRT
<213> ORGANISM: Sporotrichum thermophile

<400> SEQUENCE: 156

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
                20                  25                  30

Gln Cys Gly Gly Asn Gly Trp Gln Gly Pro Thr Cys Cys Ala Ser Gly
            35                  40                  45

Ser Thr Cys Val Ala Gln Asn Glu Trp Tyr Ser Gln Cys Leu Pro Asn
    50                  55                  60

Ser Gln Val Thr Ser Thr Thr Pro Ser Ser Thr Thr Ser Gln
65                  70                  75                  80

Arg Ser Thr Ser Thr Ser Ser Thr Thr Arg Ser Gly Ser Ser Ser
                85                  90                  95

Ser Ser Ser Thr Thr Pro Pro Val Ser Ser Pro Val Thr Ser Ile
                100                 105                 110
```

Pro Gly Gly Ala Thr Ser Thr Ala Ser Tyr Ser Gly Asn Pro Phe Ser
            115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Gln Thr Leu Ser Gln Val Arg Ala Leu Asn Lys
                180                 185                 190

Ala Gly Ala Asn Pro Pro Tyr Ala Ala Gln Leu Val Val Tyr Asp Leu
            195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
            275                 280                 285

Gln Leu Asn Leu Pro Asn Val Ala Met Tyr Leu Asp Ala Gly His Ala
            290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
                340                 345                 350

Ser Tyr Thr Ser Pro Asn Pro Asn Tyr Asp Glu Lys His Tyr Ile Glu
            355                 360                 365

Ala Phe Ser Pro Leu Leu Asn Ser Ala Gly Phe Pro Ala Arg Phe Ile
            370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
                420                 425                 430

Gly Gly Glu Ser Asp Gly Thr Ser Asp Thr Ser Ala Ala Arg Tyr Asp
            435                 440                 445

Tyr His Cys Gly Leu Ser Asp Ala Leu Gln Pro Ala Pro Glu Ala Gly
            450                 455                 460

Gln Trp Phe Gln Ala Tyr Phe Glu Gln Leu Leu Thr Asn Ala Asn Pro
465                 470                 475                 480

Pro Phe

<210> SEQ ID NO 157
<211> LENGTH: 395
<212> TYPE: PRT
<213> ORGANISM: Sporotrichum thermophile

<400> SEQUENCE: 157

```
Met Lys Phe Val Gln Ser Ala Thr Leu Ala Phe Ala Ala Thr Ala Leu
1               5                   10                  15

Ala Ala Pro Ser Arg Thr Thr Pro Gln Lys Pro Arg Gln Ala Ser Ala
            20                  25                  30

Gly Cys Ala Ser Ala Val Thr Leu Asp Ala Ser Thr Asn Val Phe Gln
        35                  40                  45

Gln Tyr Thr Leu His Pro Asn Asn Phe Tyr Arg Ala Glu Val Glu Ala
    50                  55                  60

Ala Ala Glu Ala Ile Ser Asp Ser Ala Leu Ala Glu Lys Ala Arg Lys
65                  70                  75                  80

Val Ala Asp Val Gly Thr Phe Leu Trp Leu Asp Thr Ile Glu Asn Ile
                85                  90                  95

Gly Arg Leu Glu Pro Ala Leu Glu Asp Val Pro Cys Glu Asn Ile Val
                100                 105                 110

Gly Leu Val Ile Tyr Asp Leu Pro Gly Arg Asp Cys Ala Ala Lys Ala
            115                 120                 125

Ser Asn Gly Glu Leu Lys Val Gly Glu Leu Asp Arg Tyr Lys Thr Glu
        130                 135                 140

Tyr Ile Asp Lys Ile Ala Glu Ile Leu Lys Ala His Ser Asn Thr Ala
145                 150                 155                 160

Phe Ala Leu Val Ile Glu Pro Asp Ser Leu Pro Asn Leu Val Thr Asn
                165                 170                 175

Ser Asp Leu Gln Thr Cys Gln Gln Ser Ala Ser Gly Tyr Arg Glu Gly
                180                 185                 190

Val Ala Tyr Ala Leu Lys Gln Leu Asn Leu Pro Asn Val Val Met Tyr
            195                 200                 205

Ile Asp Ala Gly His Gly Gly Trp Leu Gly Trp Asp Ala Asn Leu Lys
210                 215                 220

Pro Gly Ala Gln Glu Leu Ala Ser Val Tyr Lys Ser Ala Gly Ser Pro
225                 230                 235                 240

Ser Gln Val Arg Gly Ile Ser Thr Asn Val Ala Gly Trp Asn Ala Trp
                245                 250                 255

Asp Gln Glu Pro Gly Glu Phe Ser Asp Ala Ser Asp Ala Gln Tyr Asn
                260                 265                 270

Lys Cys Gln Asn Glu Lys Ile Tyr Ile Asn Thr Phe Gly Ala Glu Leu
            275                 280                 285

Lys Ser Ala Gly Met Pro Asn His Ala Ile Ile Asp Thr Gly Arg Asn
        290                 295                 300

Gly Val Thr Gly Leu Arg Asp Glu Trp Gly Asp Trp Cys Asn Val Asn
305                 310                 315                 320

Gly Ala Gly Phe Gly Val Arg Pro Thr Ala Asn Thr Gly Asp Glu Leu
                325                 330                 335

Ala Asp Ala Phe Val Trp Val Lys Pro Gly Gly Glu Ser Asp Gly Thr
                340                 345                 350

Ser Asp Ser Ser Ala Ala Arg Tyr Asp Ser Phe Cys Gly Lys Pro Asp
            355                 360                 365

Ala Phe Lys Pro Ser Pro Glu Ala Gly Thr Trp Asn Gln Ala Tyr Phe
        370                 375                 380

Glu Met Leu Leu Lys Asn Ala Asn Pro Ser Phe
385                 390                 395

<210> SEQ ID NO 158
<211> LENGTH: 481
```

<212> TYPE: PRT
<213> ORGANISM: Thielavia terrestris

<400> SEQUENCE: 158

Met Ala Gln Lys Leu Leu Ala Ala Leu Ala Ala Ser Ala Leu
1               5                   10                  15

Ala Ala Pro Val Val Glu Glu Arg Gln Asn Cys Gly Ser Val Trp Ser
            20                  25                  30

Gln Cys Gly Gly Ile Gly Trp Ser Gly Ala Thr Cys Cys Ala Ser Gly
            35                  40                  45

Asn Thr Cys Val Glu Leu Asn Pro Tyr Tyr Ser Gln Cys Leu Pro Asn
        50                  55                  60

Ser Gln Val Thr Thr Ser Thr Ser Lys Thr Thr Ser Thr Thr Thr Arg
65                  70                  75                  80

Ser Ser Thr Thr Ser His Ser Ser Gly Pro Thr Ser Thr Ser Thr Thr
                85                  90                  95

Thr Thr Ser Ser Pro Val Val Thr Thr Pro Pro Ser Thr Ser Ile Pro
            100                 105                 110

Gly Gly Ala Ser Ser Thr Ala Ser Trp Ser Gly Asn Pro Phe Ser Gly
            115                 120                 125

Val Gln Met Trp Ala Asn Asp Tyr Tyr Ala Ser Glu Val Ser Ser Leu
        130                 135                 140

Ala Ile Pro Ser Met Thr Gly Ala Met Ala Thr Lys Ala Ala Glu Val
145                 150                 155                 160

Ala Lys Val Pro Ser Phe Gln Trp Leu Asp Arg Asn Val Thr Ile Asp
                165                 170                 175

Thr Leu Phe Ala His Thr Leu Ser Gln Ile Arg Ala Ala Asn Gln Lys
            180                 185                 190

Gly Ala Asn Pro Pro Tyr Ala Gly Ile Phe Val Val Tyr Asp Leu Pro
        195                 200                 205

Asp Arg Asp Cys Ala Ala Ala Ser Asn Gly Glu Phe Ser Ile Ala
210                 215                 220

Asn Asn Gly Ala Ala Asn Tyr Lys Thr Tyr Ile Asp Ala Ile Arg Ser
225                 230                 235                 240

Leu Val Ile Gln Tyr Ser Asp Ile Arg Ile Ile Phe Val Ile Glu Pro
                245                 250                 255

Asp Ser Leu Ala Asn Met Val Thr Asn Leu Asn Val Ala Lys Cys Ala
            260                 265                 270

Asn Ala Glu Ser Thr Tyr Lys Glu Leu Thr Val Tyr Ala Leu Gln Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Asn Leu Phe Ala
305                 310                 315                 320

Glu Ile Tyr Thr Ser Ala Gly Lys Pro Ala Ala Val Arg Gly Leu Ala
                325                 330                 335

Thr Asn Val Ala Asn Tyr Asn Gly Trp Ser Leu Ala Thr Pro Pro Ser
            340                 345                 350

Tyr Thr Gln Gly Asp Pro Asn Tyr Asp Glu Ser His Tyr Val Gln Ala
        355                 360                 365

Leu Ala Pro Leu Leu Thr Ala Asn Gly Phe Pro Ala His Phe Ile Thr
    370                 375                 380

Asp Thr Gly Arg Asn Gly Lys Gln Pro Thr Gly Gln Arg Gln Trp Gly
385                 390                 395                 400

```
Asp Trp Cys Asn Val Ile Gly Thr Gly Phe Gly Val Arg Pro Thr Thr
            405                 410                 415

Asn Thr Gly Leu Asp Ile Glu Asp Ala Phe Val Trp Val Lys Pro Gly
        420                 425                 430

Gly Glu Cys Asp Gly Thr Ser Asn Thr Thr Ser Pro Arg Tyr Asp Tyr
            435                 440                 445

His Cys Gly Leu Ser Asp Ala Leu Gln Pro Ala Pro Glu Ala Gly Thr
        450                 455                 460

Trp Phe Gln Ala Tyr Phe Glu Gln Leu Leu Thr Asn Ala Asn Pro Pro
465                 470                 475                 480

Phe

<210> SEQ ID NO 159
<211> LENGTH: 2394
<212> TYPE: DNA
<213> ORGANISM: Trichoderma reesei

<400> SEQUENCE: 159
```

| | |
|---|---:|
| atggtgaata acgcagctct tctcgccgcc ctgtcggctc tcctgcccac ggccctggcg | 60 |
| cagaacaatc aaacatacgc caactactct gctcagggcc agcctgatct ctaccccgag | 120 |
| acacttgcca cgctcacact ctcgttcccc gactgcgaac atggcccct caagaacaat | 180 |
| ctcgtctgtg actcatcggc cggctatgta gagcgagccc aggccctcat ctcgctcttc | 240 |
| accctcgagg agctcattct caacacgcaa aactcgggcc ccggcgtgcc tcgcctgggt | 300 |
| cttccgaact accaagtctg gaatgaggct ctgcacggct ggaccgcgc caacttcgcc | 360 |
| accaagggcg ccagttcga atgggcgacc tcgttcccca tgcccatcct cactacggcg | 420 |
| gccctcaacc gcacattgat ccaccagatt gccgacatca tctcgaccca gctcgagca | 480 |
| ttcagcaaca gcggccgtta cggtctcgac gtctatgcgc aaacgtcaa tggcttccga | 540 |
| agcccctct gggccgtgg ccaggagacg cccggcgaag acgcctttt cctcagctcc | 600 |
| gcctatactt acgagtacat cacgggcatc cagggtggcg tcgaccctga gcacctcaag | 660 |
| gttgccgcca cggtgaagca cttgccgga tacgacctcg agaactggaa caaccagtcc | 720 |
| cgtctcggtt tcgacgccat cataactcag caggacctct ccgaatacta cactccccag | 780 |
| ttcctcgctg cggcccgtta tgcaaagtca cgcagcttga tgtgcgcata caactccgtc | 840 |
| aacggcgtgc ccagctgtgc caacagcttc ttcctgcaga cgcttttgcg cgagagctgg | 900 |
| ggcttccccg aatggggata cgtctcgtcc gattgcgatg ccgtctacaa cgtttttcaac | 960 |
| cctcatgact acgccagcaa ccagtcgtca gccgccgcca gctcactgcg agccggcacc | 1020 |
| gatatcgact gcggtcagac ttacccgtgg cacctcaacg agtcctttgt ggccggcgaa | 1080 |
| gtctcccgcg gcgagatcga gcggtccgtc accgtctgt acgccaacct cgtccgtctc | 1140 |
| ggatacttcg acaagaagaa ccagtaccgc tcgctcggtt ggaaggatgt cgtcaagact | 1200 |
| gatgcctgga acatctcgta cgaggctgct gttgagggca tcgtcctgct caagaacgat | 1260 |
| ggcactctcc ctctgtccaa gaaggtgcgc agcattgctc tgatcggacc atgggccaat | 1320 |
| gccacaaccc aaatgcaagg caactactat ggccctgccc ataccctcat cagccctctg | 1380 |
| gaagctgcta agaaggccgg ctatcacgtc aactttgaac tcggcacaga gatcgccggc | 1440 |
| aacagcacca ctggctttgc caaggccatt gctgccgcca agaagtcgga tgccatcatc | 1500 |
| tacctcggtg gaattgacaa caccattgaa caggagggcg ctgaccgcac ggacattgct | 1560 |
| tggcccggta atcagctgga tctcatcaag cagctcagcg aggtcggcaa accccttgtc | 1620 |

```
gtcctgcaaa tgggcggtgg tcaggtagac tcatcctcgc tcaagagcaa caagaaggtc    1680
aactccctcg tctggggcgg atatcccggc cagtcgggag gcgttgccct cttcgacatt    1740
ctctctggca agcgtgctcc tgccggccga ctggtcacca ctcagtaccc ggctgagtat    1800
gttcaccaat tccccagaa tgacatgaac ctccgacccg atggaaagtc aaaccctgga    1860
cagacttaca tctggtacac cggcaaaccc gtctacgagt ttggcagtgg tctcttctac    1920
accaccttca aggagactct cgccagccac cccaagagcc tcaagttcaa cacctcatcg    1980
atcctctctg ctcctcaccc cggatacact tacagcgagc agattcccgt cttcaccttc    2040
gaggccaaca tcaagaactc gggcaagacg gagtccccat atacggccat gctgtttgtt    2100
cgcacaagca acgctggccc agccccgtac ccgaacaagt ggctcgtcgg attcgaccga    2160
cttgccgaca tcaagcctgg tcactcttcc aagctcagca tccccatccc tgtcagtgct    2220
ctcgcccgtg ttgattctca cggaaaccgg attgtatacc ccggcaagta tgagctagcc    2280
ttgaacaccg acgagtctgt gaagcttgag tttgagttgg tgggagaaga ggtaacgatt    2340
gagaactggc cgttggagga gcaacagatc aaggatgcta cacctgacgc ataa          2394
```

<210> SEQ ID NO 160
<211> LENGTH: 780
<212> TYPE: DNA
<213> ORGANISM: Trichoderma reesei

<400> SEQUENCE: 160

```
atggtctcct tcacctccct cctcgccggc gtcgccgcca tctcgggcgt cttggccgct     60
cccgccgccg aggtcgaatc cgtggctgtg agaagcgcc agacgattca gcccggcacg    120
ggctacaaca acggctactt ctactcgtac tggaacgatg ccacggcgg cgtgacgtac    180 accaatggtc ccggcgggca gttctccgtc aactggtcca actcgggcaa ctttgtcggc    240
ggcaagggat ggcagcccgg gaccaagaac aagtaagact acctactctt accccctttg    300
accaacacag cacaacacaa tacaacacat gtgactacca atcatggaat cggatctaac    360
agctgtgttt taaaaaaaag ggtcatcaac ttctcgggaa gctacaaccc caacggcaac    420
agctacctct ccgtgtacgg ctggtcccgc aaccccctga tcgagtacta catcgtcgag    480
aactttggca cctacaaccc gtccacgggc gccaccaagc tgggcgaggt cacctccgac    540
ggcagcgtct acgacattta ccgcacgcag cgcgtcaacc agccgtccat catcggcacc    600
gccacctttt accagtactg gtccgtccgc cgcaaccacc gctcgagcgg ctccgtcaac    660
acggcgaacc acttcaacgc gtgggctcag caaggcctga cgctcgggac gatggattac    720
cagattgttg ccgtggaggg ttactttagc tctggctctg cttccatcac cgtcagctaa    780
```

<210> SEQ ID NO 161
<211> LENGTH: 368
<212> TYPE: PRT
<213> ORGANISM: Thielavia terrestris

<400> SEQUENCE: 161

```
Met Pro Ser Phe Ala Ser Lys Thr Leu Leu Ser Thr Leu Ala Gly Ala
1               5                  10                  15

Ala Ser Val Ala Ala His Gly His Val Ser Asn Ile Val Ile Asn Gly
                20                  25                  30

Val Ser Tyr Gln Gly Tyr Asp Pro Thr Ser Phe Pro Tyr Met Gln Asn
            35                  40                  45

Pro Pro Ile Val Val Gly Trp Thr Ala Ala Asp Thr Asp Asn Gly Phe
```

```
            50                  55                  60
Val Ala Pro Asp Ala Phe Ala Ser Gly Asp Ile Ile Cys His Lys Asn
 65                  70                  75                  80

Ala Thr Asn Ala Lys Gly His Ala Val Val Ala Gly Asp Lys Ile
                 85                  90                  95

Phe Ile Gln Trp Asn Thr Trp Pro Glu Ser His His Gly Pro Val Ile
                100                 105                 110

Asp Tyr Leu Ala Ser Cys Gly Ser Ala Ser Cys Glu Thr Val Asp Lys
                115                 120                 125

Thr Lys Leu Glu Phe Phe Lys Ile Asp Glu Val Gly Leu Val Asp Gly
                130                 135                 140

Ser Ser Ala Pro Gly Val Trp Gly Ser Asp Gln Leu Ile Ala Asn Asn
145                 150                 155                 160

Asn Ser Trp Leu Val Glu Ile Pro Pro Thr Ile Ala Pro Gly Asn Tyr
                165                 170                 175

Val Leu Arg His Glu Ile Ile Ala Leu His Ser Ala Glu Asn Ala Asp
                180                 185                 190

Gly Ala Gln Asn Tyr Pro Gln Cys Phe Asn Leu Gln Ile Thr Gly Thr
                195                 200                 205

Gly Thr Ala Thr Pro Ser Gly Val Pro Gly Thr Ser Leu Tyr Thr Pro
                210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
                245                 250                 255

Ser Ser Ser Ala Ile Thr Ala Ser Gly Thr Ala Leu Thr Gly Ser Ala
                260                 265                 270

Thr Ala Pro Ala Ala Ala Ala Thr Thr Ser Thr Thr Asn Ala
                275                 280                 285

Ala Ala Ala Ala Thr Ser Ala Ala Ala Ala Gly Thr Ser Thr Thr
                290                 295                 300

Thr Thr Ser Ala Ala Val Val Gln Thr Ser Ser Ser Ser Ser
305                 310                 315                 320

Ala Pro Ser Ser Ala Ala Ala Ala Thr Thr Ala Ala Ala Ser
                325                 330                 335

Ala Arg Pro Thr Gly Cys Ser Ser Gly Arg Ser Arg Lys Gln Pro Arg
                340                 345                 350

Arg His Ala Arg Asp Met Val Val Ala Arg Gly Ala Glu Glu Ala Asn
                355                 360                 365

<210> SEQ ID NO 162
<211> LENGTH: 520
<212> TYPE: PRT
<213> ORGANISM: Artificial Sequence
<220> FEATURE:
<223> OTHER INFORMATION: synthetic consensus sequence
<220> FEATURE:
<221> NAME/KEY: misc_feature
<222> LOCATION: (19)..(21)
<223> OTHER INFORMATION: Xaa can be any naturally occurring amino acid
      or skipped
<220> FEATURE:
<221> NAME/KEY: misc_feature
<222> LOCATION: (37)..(37)
<223> OTHER INFORMATION: Xaa can be any naturally occurring amino acid
      or skipped
<220> FEATURE:
<221> NAME/KEY: misc_feature
<222> LOCATION: (46)..(46)
```

```
<223> OTHER INFORMATION: Xaa can be any naturally occurring amino acid
      or skipped
<220> FEATURE:
<221> NAME/KEY: misc_feature
<222> LOCATION: (49)..(49)
<223> OTHER INFORMATION: Xaa can be any naturally occurring amino acid
      or skipped
<220> FEATURE:
<221> NAME/KEY: misc_feature
<222> LOCATION: (53)..(56)
<223> OTHER INFORMATION: Xaa can be any naturally occurring amino acid
      or skipped
<220> FEATURE:
<221> NAME/KEY: misc_feature
<222> LOCATION: (73)..(73)
<223> OTHER INFORMATION: Xaa can be any naturally occurring amino acid
      or skipped
<220> FEATURE:
<221> NAME/KEY: misc_feature
<222> LOCATION: (109)..(111)
<223> OTHER INFORMATION: Xaa can be any naturally occurring amino acid
      or skipped
<220> FEATURE:
<221> NAME/KEY: misc_feature
<222> LOCATION: (128)..(134)
<223> OTHER INFORMATION: Xaa can be any naturally occurring amino acid
      or skipped
<220> FEATURE:
<221> NAME/KEY: misc_feature
<222> LOCATION: (139)..(140)
<223> OTHER INFORMATION: Xaa can be any naturally occurring amino acid
      or skipped
<220> FEATURE:
<221> NAME/KEY: misc_feature
<222> LOCATION: (154)..(163)
<223> OTHER INFORMATION: Xaa can be any naturally occurring amino acid
      or skipped
<220> FEATURE:
<221> NAME/KEY: misc_feature
<222> LOCATION: (167)..(172)
<223> OTHER INFORMATION: Xaa can be any naturally occurring amino acid
      or skipped
<220> FEATURE:
<221> NAME/KEY: misc_feature
<222> LOCATION: (220)..(225)
<223> OTHER INFORMATION: Xaa can be any naturally occurring amino acid
      or skipped
<220> FEATURE:
<221> NAME/KEY: misc_feature
<222> LOCATION: (244)..(245)
<223> OTHER INFORMATION: Xaa can be any naturally occurring amino acid
      or skipped
<220> FEATURE:
<221> NAME/KEY: misc_feature
<222> LOCATION: (247)..(247)
<223> OTHER INFORMATION: Xaa can be any naturally occurring amino acid
      or skipped
<220> FEATURE:
<221> NAME/KEY: misc_feature
<222> LOCATION: (253)..(255)
<223> OTHER INFORMATION: Xaa can be any naturally occurring amino acid
      or skipped
<220> FEATURE:
<221> NAME/KEY: misc_feature
<222> LOCATION: (257)..(272)
<223> OTHER INFORMATION: Xaa can be any naturally occurring amino acid
      or skipped
<220> FEATURE:
<221> NAME/KEY: misc_feature
<222> LOCATION: (275)..(275)
<223> OTHER INFORMATION: Xaa can be any naturally occurring amino acid
      or skipped
<220> FEATURE:
<221> NAME/KEY: misc_feature
<222> LOCATION: (290)..(296)
<223> OTHER INFORMATION: Xaa can be any naturally occurring amino acid
      or skipped
<220> FEATURE:
<221> NAME/KEY: misc_feature
```

```
<222> LOCATION: (298)..(299)
<223> OTHER INFORMATION: Xaa can be any naturally occurring amino acid
      or skipped
<220> FEATURE:
<221> NAME/KEY: misc_feature
<222> LOCATION: (301)..(301)
<223> OTHER INFORMATION: Xaa can be any naturally occurring amino acid
      or skipped
<220> FEATURE:
<221> NAME/KEY: misc_feature
<222> LOCATION: (313)..(313)
<223> OTHER INFORMATION: Xaa can be any naturally occurring amino acid
      or skipped
<220> FEATURE:
<221> NAME/KEY: misc_feature
<222> LOCATION: (321)..(321)
<223> OTHER INFORMATION: Xaa can be any naturally occurring amino acid
      or skipped
<220> FEATURE:
<221> NAME/KEY: misc_feature
<222> LOCATION: (324)..(334)
<223> OTHER INFORMATION: Xaa can be any naturally occurring amino acid
      or skipped
<220> FEATURE:
<221> NAME/KEY: misc_feature
<222> LOCATION: (338)..(339)
<223> OTHER INFORMATION: Xaa can be any naturally occurring amino acid
      or skipped
<220> FEATURE:
<221> NAME/KEY: misc_feature
<222> LOCATION: (342)..(342)
<223> OTHER INFORMATION: Xaa can be any naturally occurring amino acid
      or skipped
<220> FEATURE:
<221> NAME/KEY: misc_feature
<222> LOCATION: (351)..(351)
<223> OTHER INFORMATION: Xaa can be any naturally occurring amino acid
      or skipped
<220> FEATURE:
<221> NAME/KEY: misc_feature
<222> LOCATION: (353)..(353)
<223> OTHER INFORMATION: Xaa can be any naturally occurring amino acid
      or skipped
<220> FEATURE:
<221> NAME/KEY: misc_feature
<222> LOCATION: (355)..(355)
<223> OTHER INFORMATION: Xaa can be any naturally occurring amino acid
      or skipped
<220> FEATURE:
<221> NAME/KEY: misc_feature
<222> LOCATION: (359)..(364)
<223> OTHER INFORMATION: Xaa can be any naturally occurring amino acid
      or skipped
<220> FEATURE:
<221> NAME/KEY: misc_feature
<222> LOCATION: (366)..(368)
<223> OTHER INFORMATION: Xaa can be any naturally occurring amino acid
      or skipped
<220> FEATURE:
<221> NAME/KEY: misc_feature
<222> LOCATION: (370)..(383)
<223> OTHER INFORMATION: Xaa can be any naturally occurring amino acid
      or skipped
<220> FEATURE:
<221> NAME/KEY: misc_feature
<222> LOCATION: (385)..(386)
<223> OTHER INFORMATION: Xaa can be any naturally occurring amino acid
      or skipped
<220> FEATURE:
<221> NAME/KEY: misc_feature
<222> LOCATION: (388)..(388)
<223> OTHER INFORMATION: Xaa can be any naturally occurring amino acid
      or skipped
<220> FEATURE:
<221> NAME/KEY: misc_feature
<222> LOCATION: (392)..(396)
<223> OTHER INFORMATION: Xaa can be any naturally occurring amino acid
      or skipped
```

```
<220> FEATURE:
<221> NAME/KEY: misc_feature
<222> LOCATION: (398)..(399)
<223> OTHER INFORMATION: Xaa can be any naturally occurring amino acid
      or skipped
<220> FEATURE:
<221> NAME/KEY: misc_feature
<222> LOCATION: (401)..(446)
<223> OTHER INFORMATION: Xaa can be any naturally occurring amino acid
      or skipped
<220> FEATURE:
<221> NAME/KEY: misc_feature
<222> LOCATION: (453)..(453)
<223> OTHER INFORMATION: Xaa can be any naturally occurring amino acid
      or skipped
<220> FEATURE:
<221> NAME/KEY: misc_feature
<222> LOCATION: (455)..(457)
<223> OTHER INFORMATION: Xaa can be any naturally occurring amino acid
      or skipped
<220> FEATURE:
<221> NAME/KEY: misc_feature
<222> LOCATION: (460)..(460)
<223> OTHER INFORMATION: Xaa can be any naturally occurring amino acid
      or skipped
<220> FEATURE:
<221> NAME/KEY: misc_feature
<222> LOCATION: (462)..(463)
<223> OTHER INFORMATION: Xaa can be any naturally occurring amino acid
      or skipped
<220> FEATURE:
<221> NAME/KEY: misc_feature
<222> LOCATION: (466)..(466)
<223> OTHER INFORMATION: Xaa can be any naturally occurring amino acid
      or skipped
<220> FEATURE:
<221> NAME/KEY: misc_feature
<222> LOCATION: (468)..(468)
<223> OTHER INFORMATION: Xaa can be any naturally occurring amino acid
      or skipped
<220> FEATURE:
<221> NAME/KEY: misc_feature
<222> LOCATION: (470)..(497)
<223> OTHER INFORMATION: Xaa can be any naturally occurring amino acid
      or skipped
<220> FEATURE:
<221> NAME/KEY: misc_feature
<222> LOCATION: (499)..(510)
<223> OTHER INFORMATION: Xaa can be any naturally occurring amino acid
      or skipped
<220> FEATURE:
<221> NAME/KEY: misc_feature
<222> LOCATION: (515)..(520)
<223> OTHER INFORMATION: Xaa can be any naturally occurring amino acid
      or skipped

<400> SEQUENCE: 162

Met Lys Ser Ser Ala Ser Leu Leu Leu Ala Ala Leu Ala Gly Ala
1               5                   10                  15

Ala Ala Xaa Xaa Xaa Val Ala Ala His Gly His Val Val Asn Gly Val
            20                  25                  30

Ile Asn Gly Val Xaa Tyr Gln Gly Tyr Asp Pro Thr Thr Xaa Pro Tyr
                35                  40                  45

Xaa Asn Asn Pro Xaa Xaa Xaa Pro Ser Val Val Gly Trp Cys Asn
    50                  55                  60

Ala Gly Thr Asp Asn Gly Phe Val Xaa Pro Asp Ala Tyr Ala Ser Pro
65                  70                  75                  80

Asp Ile Ile Cys His Lys Gly Ala Thr Asn Ala Lys Gly His Ala Thr
                85                  90                  95

Val Ala Ala Gly Asp Lys Ile Ser Ile Gln Trp Thr Xaa Xaa Xaa Trp
                100                 105                 110
```

-continued

```
Pro Glu Ser His Lys Gly Pro Val Ile Asp Tyr Leu Ala Lys Cys Xaa
            115                 120                 125

Xaa Xaa Xaa Xaa Xaa Xaa Gly Gly Cys Thr Xaa Xaa Thr Val Asp Lys
        130                 135                 140

Thr Ser Leu Gly Trp Phe Lys Ile Asp Xaa Xaa Xaa Xaa Xaa Xaa Xaa
145                 150                 155                 160

Xaa Xaa Xaa Gly Val Gly Xaa Xaa Xaa Xaa Xaa Asp Pro Gly Val
            165                 170                 175

Trp Ala Thr Asp Asp Leu Ile Ala Asn Asn Ser Trp Leu Val Lys
            180                 185                 190

Ile Pro Ser Asp Ile Ala Pro Gly Asn Tyr Val Leu Arg His Glu Ile
        195                 200                 205

Ile Ala Leu His Ser Ala Gly Ser Ala Asn Gly Xaa Xaa Xaa Xaa Xaa
        210                 215                 220

Xaa Ala Gln Asn Tyr Pro Gln Cys Ala Asn Leu Gln Val Thr Gly Ser
225                 230                 235                 240

Gly Ser Ala Xaa Xaa Ser Xaa Pro Ser Gly Val Lys Xaa Xaa Xaa Pro
            245                 250                 255

Xaa Xaa Xaa Xaa Xaa Xaa Xaa Xaa Xaa Xaa Xaa Xaa Xaa Xaa Xaa
        260                 265                 270

Gly Thr Xaa Leu Tyr Lys Ala Thr Asp Pro Gly Ile Leu Val Asn Ile
        275                 280                 285

Tyr Xaa Xaa Xaa Xaa Xaa Xaa Xaa Ala Xaa Xaa Ser Xaa Tyr Thr Val
        290                 295                 300

Pro Gly Pro Ala Val Ile Thr Gly Xaa Ala Ser Ser Val Ala Gln Ser
305                 310                 315                 320

Xaa Ser Ala Xaa Xaa Xaa Xaa Xaa Xaa Xaa Xaa Xaa Xaa Xaa Thr Ala
            325                 330                 335

Thr Xaa Xaa Ala Val Xaa Pro Gly Gly Thr Ala Pro Ala Pro Xaa Ala
            340                 345                 350

Xaa Thr Xaa Ala Ser Thr Xaa Xaa Xaa Xaa Xaa Thr Xaa Xaa Xaa
            355                 360                 365

Thr Xaa Xaa Xaa Xaa Xaa Xaa Xaa Xaa Xaa Xaa Xaa Xaa Xaa Ala
370                 375                 380

Xaa Xaa Gly Xaa Ser Ala Pro Xaa Xaa Xaa Xaa Xaa Cys Xaa Xaa Ala
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Tyr Gly
            435                 440                 445

Gln Cys Gly Gly Xaa Gly Xaa Xaa Xaa Thr Gly Xaa Thr Xaa Xaa Cys
450                 455                 460

Ala Xaa Gly Xaa Thr Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Cys Xaa Xaa Xaa Xaa Xaa Xaa Xaa Xaa Xaa Xaa Tyr Tyr
        500                 505                 510

Ser Gln Xaa Xaa Xaa Xaa Xaa Xaa
            515                 520
```

METHOD FOR REDUCING VISCOSITY IN SACCHARIFICATION PROCESS

CROSS REFERENCE TO RELATED APPLICATIONS

This application is a continuation of and claims the benefit of priority to U.S. patent application Ser. No. 14/004,877, filed on Jan. 29, 2014, which was the National Stage Entry of International Patent Application No. PCT/US12/29445, filed on Mar. 16, 2012, which claims the benefit of U.S. Provisional Application No. 61/453,923, filed Mar. 17, 2011, the entireties of which are hereby incorporated by reference.

STATEMENT CONCERNING JOINT RESEARCH ACCRUEMENT

This invention arose from research conducted under a joint research agreement (as defined under 35 U.S.C. § 100(h) and 37 C.F.R. § 1.9(e)) between Danisco US Inc. and E. I. du Pont de Nemours and Company.

FIELD OF THE INVENTION

The present invention relates to compositions useful for hydrolyzing biomass, methods of using such compositions to hydrolyze biomass materials, and methods for reducing viscosity of biomass saccharification mixtures.

SEQUENCE LISTING

The content of the electronically submitted sequence listing in ASCII text (File Name: NB31556USCNT_SEQLIST.txt; Size: 472,257 bytes; and date of creation Feb. 23, 2016) is incorporated herein by reference in its entirety.

BACKGROUND OF THE INVENTION

Bioconversion of renewable lignocellulosic biomass to a fermentable sugar that is subsequently fermented to produce alcohol (e.g., ethanol) as an alternative to liquid fuels has attracted the intensive attention of researchers since the 1970s, when the oil crisis occurred (Bungay, H. R., "Energy: the biomass options". NY: Wiley; 1981; Olsson L, Hahn-Hagerdal B. Enzyme Microb Technol 1996, 18:312-31; Zaldivar, J et al., Appl Microbiol Biotechnol 2001, 56: 17-34; Galbe, M et al., Appl Microbiol Biotechnol 2002, 59:618-28). The production of sugars from lignocellulosic biomass materials has been known for some time, as has the subsequent fermentation and distillation of the sugars into ethanol. Much of the prior development occurred around the time of World War II when fuels were at a premium in such countries as Germany, Japan and the Soviet Union. These early processes were primarily directed to acid hydrolysis, which were complex in engineering and design, and were typically sensitive to small variations in the processes, such as to temperature, pressure and/or acid concentrations. A comprehensive discussion of these early processes is found in "Production of Sugars from Wood Using High-pressure Hydrogen Chloride", Biotechnology and Bioengineering, Volume XXV, at 2757-2773 (1983).

The abundant supply of petroleum in the period from World War II through the early 1970s slowed ethanol conversion research. However, due to the oil crisis of 1973, researchers increased their efforts to develop processes for the utilization of wood and agricultural byproducts for the production of ethanol. This research was especially important for development of ethanol as a gasoline additive to reduce the dependency of the United States upon foreign oil production, to increase the octane rating of fuels, and to reduce exhaust pollutants as an environmental measure.

Concurrently with the "oil crisis," the U.S. Environmental Protection Agency promulgated regulations requiring reduced lead additives. Insofar as ethanol is virtually a replacement of lead, some refineries have selected ethanol as the substitute for its capability of easy introduction into a refinery's operation without costly capital equipment investment.

The high pressure and high temperature gas saccharification processes developed decades ago continue to be improved. New and current research focuses greatly on enzymatic conversion processes, which employ enzymes from a variety of organisms, such as mesophilic and thermophilic fungi, yeast and bacteria, degrading cellulose into fermentable sugars. Uncertainty remains with these processes, mainly on their ability to be scaled up for commercialization and on the efficiency of ethanol production.

Cellulose and hemicellulose are the most abundant plant materials produced by photosynthesis. They can be degraded for use as an energy source by numerous microorganisms, including bacteria, yeast and fungi, which produce enzymes capable of hydrolysis of the polymeric substrates to monomeric sugars (Aro et al., 2001). Organisms are often restrictive with regard to which sugars they use, and this dictates which sugars are best to produce during conversion. As we approach the limits of non-renewable resources, we recognize the enormous potential of cellulose to become a major renewable energy resource (Krishna et al., 2001). The effective utilization of cellulose through biological processes can potentially overcome the shortage of foods, feeds, and fuels (Ohmiya et al., 1997).

Cellulases are enzymes that hydrolyze cellulose (beta-1, 4-glucan or beta D-glucosidic linkages) resulting in the formation of glucose, cellobiose, cellooligosaccharides, and the like. Cellulases have been traditionally divided into 3 major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG") (Knowles et al., 1987 and Shulein, 1988). Endoglucanases act mainly on the amorphous parts of the cellulose fiber, whereas cellobiohydrolases are also able to degrade crystalline cellulose.

Cellulases have also been shown to be useful in degradation of cellulose biomass to ethanol (wherein the cellulases degrade cellulose to glucose, and yeast or other microbes further ferment the glucose into ethanol), in the treatment of mechanical pulp (Pere et al., 1996), for use as a feed additive (WO 91/04673) and in grain wet milling Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Ethanol production from readily available sources of cellulose provides a stable, renewable fuel source.

Cellulases are produced by a number of bacteria, yeast and fungi. Certain fungi produce a complete cellulase system (i.e., a whole cellulase) capable of degrading crystalline forms of cellulose. A whole cellulase, especially one that is naturally occurring, is, however, not necessarily capable of achieving efficient degradation because it may not include all the components/activities required for this efficiency, for example, activities from each of the CBH, EG and BG classifications. (Filho et al., 1996). It is known that individual CBH, EG, and BG components alone do not bring about efficient hydrolysis, but the combination of EG-type cellulases and CBH-type cellulases interact to more efficiently degrade cellulose than either enzyme used alone (Wood, 1985; Baker et al., 1994; and Nieves et al., 1995).

Cellulases are known in the art to be useful in the treatment of textiles, for enhancing the cleaning ability of detergent compositions, for use as a softening agent, for improving the feel and appearance of cotton fabrics, and the like (Kumar et al., 1997). Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691, 178, and 5,776,757, and GB App. No. 1,358,599), have been described.

Hence, cellulases produced in fungi and bacteria have received significant attention. In particular, fermentation of *Trichoderma* spp. (e.g., *T. longibrachiatum* or *T. reesei*) has been shown to produce a complete cellulase system capable of degrading crystalline forms of cellulose. Over the years, *Trichoderma* cellulase production has been improved by classical mutagenesis, screening, selection and development of highly refined, large scale inexpensive fermentation conditions. While the multi-component cellulase system of *Trichoderma* spp. is able to hydrolyze cellulose to glucose, there are cellulases from other microorganisms, particularly bacterial strains, with different properties for efficient cellulose hydrolysis, and it would be advantageous to express these proteins in a filamentous fungus for industrial scale cellulase production. However, the results of many studies demonstrate that the yield of expressing bacterial enzymes from filamentous fungi is low (Jeeves et al., 1991).

Soluble sugars such as glucose and cellobiose have many uses for the production of chemicals and biological products. The optimization of cellulose hydrolysis allows for the use of less enzymes and improved cost effectiveness for the production of soluble sugars.

An efficient conversion of lignocellulosic biomass into fermentable sugars is key to producing bioethanol in a cost-effective and environmentally-friendly way. To reduce energy and processing cost, particularly for distillation, the minimum ethanol concentration produced by a viable process should be at least 4% (w/v). Such an increased ethanol concentration can be achieved by processing substrates having high dry matter of solids. However a common problem associated with saccharifying a high dry matter biomass is the high viscosity of the slurry, resulting in a slurry that is not pumpable or requires large energy input during handling. When dealing with handling of high solids, problems such as 1) insufficient mixing with limited mass transfer, 2) increasing concentration of inhibitors, such as acetic acid, furfural, 5-hydroxymethyl furfural, phenolic lignin degradation, 3) production inhibition, such as glucose, cellobiose, ethanol, and 4) fermentation microorganism viability, will occur. High viscosity limits the dry substance level in the process, increasing energy and water consumption, reducing the separation efficiency, evaporation and heat exchange, and ultimately, the ethanol yield. Reduction of viscosity is therefore beneficial, and enzymes play a key role in breaking down the soluble/insoluble compounds causing high viscosity.

Studies to increase solid loading and/or reduce viscosity of saccharification processes have taken place. For example, a number of studies utilized fed-batch operations in order to increase the solids level in the biomass substrate loading. A gravimetric mixing reactor design was used, which allowed batch enzymatic liquefaction and hydrolysis of pretreated wheat straw at up to 40% solids concentration. This fed-batch strategy sequentially loads the biomass substrate or substrate plus enzymes during enzymatic hydrolysis in order to achieve hydrolysis of a large amount of substrate, a relatively low viscosity during hydrolysis, and a relatively high glucose concentration during the process. Alternatively, enzymatic pre-hydrolysis of a lignocellulosic biomass for a period of time at the enzymes' optimum temperature, e.g., 50° C., can be carried out to reduce the viscosity of the slurry, enabling pumping and stirring. The decrease in viscosity during pre-hydrolysis makes the subsequent fermentation or SSF possible.

Despite the development of numerous approaches, there remains a need in the art for additional ways to reduce viscosity and improve yield of desirable fermentable sugars.

All references cited herein, including patents, patent applications, and publications, are incorporated by reference in their entirety.

SUMMARY OF INVENTION

The present disclosure is based, in part, on the surprising discovery that inclusion of a certain endoglucanase enzyme (e.g., a polypeptide having glycosyl hydrolase family 61 ("GH61")/endoglucanase activity, such as the *T. reesei* endoglucanase ("Eg4")) in a biomass saccharification mixture substantially reduces the viscosity of the mixture. The disclosure also pertains to the inclusion of such enzyme(s) to substantially improve the saccharification and the yields of desirable fermentable sugars from a given biomass substrate.

Provided herein are polypeptides having glycosyl hydrolase family 61 ("GH61")/endoglucanase activity. By "GH61/endoglucanase activity" it is meant that the polypeptide has a GH61 activity and/or an endoglucanase activity. In some aspects, the polypeptide is isolated. In some aspects, the polypeptide having GH61/endoglucanase activity (e.g., an isolated polypeptide) is a GH61 endoglucanase or an endoglucanase IV ("EG IV") from various species, or a polypeptide corresponding to (e.g., sharing homology with, sharing functional domains, sharing GH61 motif(s), and/or sharing conservative residues with) a GH61 endoglucanase (e.g., a *T. reesei* Eg4 polypeptide). Such species include *Trichoderma, Humicola, Fusarium, Aspergillus, Neurospora, Penicillium, Cephalosporium, Achlya, Podospora, Endothia, Mucor, Cochliobolus, Pyricularia, Chrysosporium, Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis care giea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium*

*purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei, Trichoderma viride, Geosmithia emersonii,* or *G. stearothermophilus.*

In some aspects, the polypeptide having GH61/endoglucanase activity (e.g., an isolated polypeptide) is a GH61 endoglucanase selected from the group consisting of the polypeptides with amino acid sequences shown in FIG. 1 of the present disclosure. For example, suitable GH61 endoglucanases include those that are represented by their GenBank Accession Numbers CAB97283.2, CAD70347.1, CAD21296.1, CAE81966.1, CAF05857.1, EAA26873.1, EAA29132.1, EAA30263.1, EAA33178.1, EAA33408.1, EAA34466.1, EAA36362.1, EAA29018.1, and EAA29347.1, or those that are named St61 from *S. thermophilum* 24630, St61A from *S. thermophilum* 23839c, St61B from *S. thermophilum* 46583, St61D from *S. thermophilum* 80312, Afu61a from *A. fumigatus* Afu3g03870 (NCBI Ref: XP_748707), an endoglucanase of NCBI Ref: XP_750843.1 from *A. fumigatus* Afu6g09540, an endoglucanase of *A. fumigatus* EDP47167, an endoglucanase of *T. terrestris* 16380, an endoglucanase of *T. terrestris* 155418, an endoglucanase of *T. terrestris* 68900, Cg61A (EAQ86340.1) from *C. globosum, T. reesei* Eg7, *T. reesei* Eg4, and an endoglucanase with GenBank Accession: XP_752040 from *A. fumigatus* Af293. In some aspects, the polypeptide having GH61/endoglucanase activity (e.g., isolated polypeptide) comprises an amino acid sequence that is at least about 60% (e.g., at least about 60%, 65%, 70%, 75%, 80%, 85%, 90%, 91%, 92%, 93%, 94%, 95%, 96%, 97%, 98%, 99%) sequence identity to any one of SEQ ID NOs: 1-29 and 148. In certain aspects, the polypeptide having GH61/endoglucanase activity (e.g., isolated polypeptide) comprises an amino acid sequence that comprises one or more sequence motif(s) selected from the group consisting of: (1) SEQ ID NOs:84 and 88; (2) SEQ ID NOs:85 and 88; (3) SEQ ID NO:86; (4) SEQ ID NO:87; (5) SEQ ID NOs:84, 88 and 89; (6) SEQ ID NOs:85, 88, and 89; (7) SEQ ID NOs: 84, 88, and 90; (8) SEQ ID NOs: 85, 88 and 90; (9) SEQ ID NOs:84, 88 and 91; (10) SEQ ID NOs: 85, 88 and 91; (11) SEQ ID NOs: 84, 88, 89 and 91; (12) SEQ ID NOs: 84, 88, 90 and 91; (13) SEQ ID NOs: 85, 88, 89 and 91: and (14) SEQ ID NOs: 85, 88, 90 and 91. In some embodiments, the polypeptide is at least about 100 (e.g., at least about 120, 130, 140, 150, 160, 170, 180, 190, 200, 220, 240, or more) amino acid residues in length.

In some aspects, the polypeptide having GH61/endoglucanase activity is a variant of a GH61 endoglucanase such as, for example, one selected from those listed in FIG. 1. Sutiable polypeptide include, e.g, GenBank Accession Number CAB97283.2, CAD70347.1, CAD21296.1, CAE81966.1, CAF05857.1, EAA26873.1, EAA29132.1, EAA30263.1, EAA33178.1, EAA33408.1, EAA34466.1, EAA36362.1, EAA29018.1, or EAA29347.1, or St61 of *S. thermophilum* 24630, St61A of *S. thermophilum* 23839c, St61B of *S. thermophilum* 46583, St61D of *S. thermophilum* 80312, Afu61a of *A. fumigatus* Afu3g03870 (NCBI Ref: XP_748707), an enzyme of *A. fumigatus* Afu6g09540 (NCBI Ref: XP_750843.1), an enzyme of *A. fumigatus* EDP47167, an enzyme of *T. terrestris* 16380, an enzyme of *T. terrestris* 155418, an enzyme of *T. terrestris* 68900, and *C. globosum* Cg61A (EAQ86340.1), *T. reesei* Eg7, *T. reesei* Eg4, and an enzyme of *A. fumigatus* Af293 (with GenBank Accession: XP_752040). In some aspects, the polypeptide having GH61/. endoglucanase activity is a variant of an enzyme comprising any one of SEQ ID NOs: 1-29 and 148. The poloypeptide having GH61/endoglucanase activity may be a variant of an enzyme having at least about 100 (e.g., at least about 110, 120, 130, 140, 150, 160, 170, 180, 190, 200, 220, 240 or more) amino acid residues in length, comprising one or more of the sequence motifs selected from: (1) SEQ ID NOs:84 and 88; (2) SEQ ID NOs:85 and 88; (3) SEQ ID NO:86; (4) SEQ ID NO:87; (5) SEQ ID NOs:84, 88 and 89; (6) SEQ ID NOs:85, 88, and 89; (7) SEQ ID NOs: 84, 88, and 90; (8) SEQ ID NOs: 85, 88 and 90; (9) SEQ ID NOs:84, 88 and 91; (10) SEQ ID NOs: 85, 88 and 91; (11) SEQ ID NOs: 84, 88, 89 and 91; (12) SEQ ID NOs: 84, 88, 90 and 91; (13) SEQ ID NOs: 85, 88, 89 and 91: and (14) SEQ ID NOs: 85, 88, 90 and 91. The polypeptide having GH61/endoglucanase activity may be a variant of a GH61 endoglucanase, wherein the variant has an amino acid sequence having at least about 60% (e.g., at least about any of 60%, 65%, 70%, 75%, 80%, 85%, 90%, 95%, 96%, 97%, 98%, or 99%) identity to any one of SEQ ID NOs:1-18.

In some aspects, the polypeptide having GH61/endoglucanase activity (e.g., an isolated polypeptide, including a variant of GH61 endoglucanase) has endoglucanase activity. The variant may comprise at least one motif (at least 1, 2, 3, 4, 5, 6, 7, or 8 motifs) selected from SEQ ID NOs:84-91. For the purpose of the present disclosure enzymes can be referred to by their functionalities. For example, an eodnglucanse polypeptide can also be referred as polypeptide having endoglucanase activity, or vise versa.

In some aspects, the polypeptide having GH61/endoglucanase activity (including a variant of GH61 endoglucanase) comprises one or more sequence motif(s) selected from: (1) SEQ ID NOs:84 and 88; (2) SEQ ID NOs:85 and 88; (3) SEQ ID NO:86; (4) SEQ ID NO:87; (5) SEQ ID NOs:84, 88 and 89; (6) SEQ ID NOs:85, 88, and 89; (7) SEQ ID NOs: 84, 88, and 90; (8) SEQ ID NOs: 85, 88 and 90; (9) SEQ ID NOs:84, 88 and 91; (10) SEQ ID NOs: 85, 88 and 91; (11) SEQ ID NOs: 84, 88, 89 and 91; (12) SEQ ID NOs: 84, 88, 90 and 91; (13) SEQ ID NOs: 85, 88, 89 and 91: and (14) SEQ ID NOs: 85, 88, 90 and 91.

In some aspects, the polypeptide having GH61/endoglucanase activity (including a variant) comprises a CBM domain (e.g., functional CBM domain). In some aspects, the polypeptide having GH61/endoglucanase activity (including a variant of GH61 endoglucanase) comprises a catalytic domain (e.g., functional catalytic domain).

Also provided herein are variants of EG IV polypeptides. For example, such variants can have at least about 60% (e.g., at least about 60%, 65%, 70%, 75%, 80%, 85%, 90%, 91%, 92%, 93%, 94%, 95%, 96%, 97%, 98%, 99%) sequence identity to any one of SEQ ID NOs: 1-29 and 148, or to a mature polypeptide thereof. For example, provided herein are variants of *T. reesei* Eg4 polypeptide. Such variants may have at least about 60% (e.g., at least about 60%, 65%, 70%, 75%, 80%, 85%, 88%, 90%, 92.5%, 95%, 96%, 97%, 98%, or 99%) sequence identity to residues 22 to 344 of SEQ ID NO:27. In some aspects, the polypeptide or a variant thereof is isolated. In some aspects, the polypeptide or a variant thereof has endoglucanase activity. In some aspects, the polypeptide or a variant thereof comprises residues corresponding to at least about 5 residues (e.g., at least about any of 6, 7, 8, 9, 10, 11, or 12) of H22, D61, G63, C77, H107, R177, E179, H184, Q193, C198, Y195, and Y232 of SEQ ID NO:27, or any corresponding conserved residues in any of the other polypeptides. In some aspects, the polypeptide or a variant thereof comprises residues corresponding to H22, D61, G63, C77, H107, R177, E179, H184, Q193, C198, Y195, and Y232 of SEQ ID NO:27. The polypeptide or a variant thereof may comprise residues corresponding to at least 5 residues (e.g., at least about any of 6, 7, 8, 9, 10, 11, 12, 13, 14, 15, 16, 17, 18, or 19) of G313, Q314, C315, G316, G317, S321, G322, P323, T324, C326, A327, T331, C332, N336, Y338, Y339, Q341, C342, and L343 of SEQ ID NO:27. In some aspects, the polypeptide or a variant thereof comprises residues corresponding to G313, Q314, C315, G316, G317, S321, G322, P323, T324, C326, A327, T331, C332, N336, Y338, Y339, Q341, C342, and L343 of SEQ ID NO:27. The polypeptide or a variant thereof may comprise a CBM domain (e.g., a functional CBM domain). In some aspects, the polypeptide or a variant thereof comprises a catalytic domain (e.g., a functional catalytic domain).

Also provided herein are nucleic acids or polynucleotides encoding any one of the polypeptides herein. For example, the disclosure provides polynucleotide encoding a polypeptide having at least about 60% (e.g., at least about 60%, 65%, 70%, 75%, 80%, 85%, 90%, 91%, 92%, 93%, 94%, 95%, 96%, 97%, 98%, 99%) sequence identity to any one of SEQ ID NOs: 1-29 and 148. For example, the disclosure provides herein isolated nucleic acids having at least about 60% (e.g., at least about 60%, 65%, 70%, 75%, 80%, 85%, 88%, 90%, 92.5%, 95%, 96%, 97%, 98%, or 99%) identity to SEQ ID NO:30. Also provided are expression cassettes, vectors, and cells comprising the nucleic acids described above.

Also provided herein are enzyme compositions (e.g., non-naturally occurring compositions) comprising a polypeptide having GH61/endoglucanase activity. In some aspects, the composition comprises a whole cellulase comprising the polypeptide having GH61/endoglucanase activity (e.g., T. reesei Eg4 or a variant thereof). The polypeptide having GH61/endoglucanase activity is, e.g., T. reesei endoglucanase IV ("T. reesei Eg4") or a variant thereof. A variant of T. reesei Eg4 can be any of the variants provided herein.

In some aspects, the enzyme composition is a cellulase composition. The enzyme composition may further comprise one or more hemicellulases, and thus can also be a hemicellulase composition. In some aspects, the enzyme composition comprises at least one (e.g., at least 2, 3, 4, 5, 6, 7, or 8) cellulase polypeptide(s). In some aspects, the at least one cellulase polypeptide is a polypeptide having endoglucanase activity, a polypeptide having cellobiohydrolase activity, or a polypeptide having β-glucosidase activity. In some aspects, the composition further comprises at least one (e.g., at least 2, 3, 4, 5, 6, 7, or 8) hemicellulase polypeptide(s). In some aspects, the at least one hemicellulase polypeptide is a polypeptide having xylanase activity, a polypeptide having β-xylosidase activity, or a polypeptide having L-α-arabinofuranosidase activity, or a polypeptide having combined xylanase/β-xylosidase activity, combined β-xylosidase/L-α-arabinofuranosidase activity, or combined xylanase/L-α-arabinofuranosidase activity activity. In some aspects, the composition comprises at least one (e.g., at least 2, 3, 4, 5, 6, 7, or 8) cellulase polypeptide(s) and at least one (e.g., at least 2, 3, 4, 5, 6, 7, or 8) hemicellulase polypeptide(s).

In some aspects, the enzyme composition comprises a polypeptide having GH61/endoglucanase activity and further comprises at least 1 (e.g., at least 2, 3, 4, or 5) polypeptide having endoglucanase activity, at least 1 (e.g., at least 2, 3, 4, or 5) polypeptide having cellobiohydrolase activity, at least 1 (e.g., at least 2, 3, 4, or 5) polypeptide having β-glucosidase activity, at least 1 (e.g., at least 2, 3, 4, or 5) polypeptide having xylanase activity, at least 1 (e.g., at least 2, 3, 4, or 5) polypeptide having β-xylosidase activity, and/or at least 1 (e.g., at least 2, 3, 4, or 5) polypeptide having L-α-arabinofuranosidase activity.

In some aspects, the composition comprises a polypeptide having GH61/endoglucanase activity (e.g., T. reesei Eg4 or a variant thereof) and at least one polypeptide having xylanase activity (e.g., T. reesei Xyn3, T. reesei Xyn2, AfuXyn2, AfuXyn5, or a variant thereof). In some aspects, the composition further comprises at least one polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, or a variant thereof). In some aspects, the composition further comprises at least one polypeptide having cellobiohydrolase activity (e.g., T. reesei CBH1, A. fumigatus 7A, 7B, C. globosum 7A, 7B, T. terrestris 7A, 7B, T. reesei CBH2, T. terrestris 6A, S. thermophile 6A, 6B, or a variant thereof). In some aspects, the composition further comprises at least one polypeptide having endoglucanase activity other than the GH61 enzyme (e.g., T. reesei EG1, T. reesei EG2, or a variant thereof).

The composition may comprise a polypeptide having GH61/endoglucanase activity (e.g., T. reesei Eg4 or a variant thereof) and at least 1 polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B or a variant thereof). The composition may comprise a polypeptide having GH61/endoglucanase activity and at least 1 polypeptide having cellobiohydrolase activity (e.g., T. reesei CBH1, A. fumigatus 7A, 7B, C. globosum 7A, 7B, T. terrestris 7A, 7B, T. reesei CBH2, T. terrestris 6A, S. thermophile 6A, 6B or a variant thereof). The composition may comprise a polypeptide having GH61/endoglucanase activity, and at least 1 polypeptide having endoglucanase activity (e.g., T. reesei EG1, T. reesei EG2 or a variant thereof). The composition may comprise a polypeptide having GH61/endoglucanase activity and at least 1 polypeptide having β-xylosidase activity (e.g., Fv3A, Fv43A, Pf43A, Fv43D, Fv39A, Fv43E, Fo43A, Fv43B, Pa51A, Gz43A, T. reesei Bxl1 or a variant thereof). The composition may comprise a polypeptide having GH61/endoglucanase activity and at least 1 polypeptide having L-α-arabinofuranosidase activity (e.g., Af43A, Fv43B, Pf51A, Pa51A, Fv51A or a variant thereof).

Any one of the compositions described herein may comprise a whole cellulase. For example, a composition is provided comprising a whole cellulase comprising a polypeptide having GH61/endoglucanase activity. Alternatively, a composition is provided comprising a whole cellulase plus a polypeptide having GH61/endoglucanase activity. In some aspects, a composition comprising a polypeptide having GH61/endoglucanase activity, and a polypeptide having endoglucanase activity other than the polypeptide having GH61/endoglucanase activity, a polypeptide having cellobiohydrolase activity, and a polypeptide having β-glucosidase activity is provided. The composition further comprises one or more hemicellulase polypeptides. For example, the composition may comprise one or more polypeptides having xylanase activity, one or more polypeptides having β-xylosidase activity, and/or one or more polypeptides having L-α-arabinofuranosidase activity. A composition may comprise a polypeptide having GH61/endoglucanase activity, at least one polypeptide having xylanase activity (e.g., T. reesei Xyn3, T. reesei Xyn2, AfuXyn2, AfuXyn5, or a variant thereof), and a whole cellulase. In some aspects, a composition comprising a polypeptide having GH61/endoglucanase activity, at least one polypeptide having xylanase activity (e.g., T. reesei Xyn3, T. reesei Xyn2, AfuXyn2, AfuXyn5, or a variant thereof), and at least one other polypeptide having hemicellulase activity is provided.

In some aspects, the whole cellulase comprises at least one polypeptide having endoglucanase activity (e.g., *T. reesei* EG1, *T. reesei* EG2, or a variant thereof) that is not the polypeptide having GH61/endoglucanase activity. The whole cellulase can comprise at least one polypeptide having cellobiohydrolase activity (e.g., *T. reesei* CBH1, *A. fumigatus* 7A, 7B, *C. globosum* 7A, 7B, *T. terrestris* 7A, 7B, *T. reesei* CBH2, *T. terrestris* 6A, *S. thermophile* 6A, 6B, or a variant thereof). The whole cellulase can comprise at least one polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, or a variant thereof).

In some aspects, in any one of the compositions described herein, the at least one polypeptide having endoglucanase activity but is not the one having GH61/endoglucanase activity is, e.g., *T. reesei* EG1 (or a variant thereof) and/or *T. reesei* EG2 (or a variant thereof). In some aspects, the at least one polypeptide having cellobiohydrolase activity is, e.g., *T. reesei* CBH1, *A. fumigatus* 7A, 7B, *C. globosum* 7A, 7B, *T. terrestris* 7A, 7B, *T. reesei* CBH2, *T. terrestris* 6A, *S. thermophile* 6A, 6B, or a variant thereof. In some aspects, the at least one polypeptide having β-glucosidase activity is, e.g., Fv3C, Pa3D, Fv3G, Fv3D, Tr3A, Tr3B, Te3A, An3A, Fo3A, Gz3A, Nh3A, Vd3A, Pa3G, and/or Tn3B, or variants thereof. In some aspects, the at least one polypeptide having xylanase activity is, e.g., *T. reesei* Xyn3, *T. reesei* Xyn2, AfuXyn2, and/or AfuXyn5, or variants thereof. In some aspects, the at least one polypeptide having β-xylosidase activity is, e.g., a Group 1 β-xylosidase or a Group 2 β-xylosidase, wherein the Group 1 β-xylosidase may be Fv3A, Fv43A polypeptide, or a variant thereof, and the Group 2 β-xylosidase may be Pf43A, Fv43D, Fv39A, Fv43E, Fo43A, Fv43B, Pa51A, Gz43A, *T. reesei* Bxl1 polypeptide, or a variant thereof. In some aspects, the at least one polypeptide having β-xylosidase activity is, e.g., Fv3A (or a variant thereof) and/or Fv43D (or a variant thereof). In some aspects, the at least one polypeptide having L-α-arabinofuranosidase activity may be Af43A, Fv43B, Pf51A, Pa51A, and/or Fv51A, or variants thereof.

In some aspects, a composition comprising an isolated polypeptide having GH61/endoglucanase activity (e.g., *T. reesei* Eg4 or a variant thereof) is provided. In some aspects, the polypeptide having GH61/endoglucanase activity (e.g., *T. reesei* Eg4 or a variant thereof) is expressed by a host cell, wherein the nucleic acid encoding the polypeptide having GH61/endoglucanase activity has been engineered into the host cell. For example, the polypeptide having GH61/endoglucanase activity is expressed by a host cell, and the nucleic acid encoding that polypeptide is heterologous to the host cell.

In some aspects, a composition is provided comprising a polypeptide having GH61/endoglucanase activity (e.g., *T. reesei* Eg4 or a variant thereof), and further comprising one or more cellulase polypeptides and/or one or more hemicellulase polypeptides, wherein the cellulase polypeptide and/or the hemicellulase polypeptide is expressed by a host cell, and the cellulase polypeptide and/or hemicellulase polypeptide is heterologous to the host cell. In some aspects, a composition comprising a polypeptide having GH61/endoglucanase activity and further comprising at least one cellulase polypeptide and/or at least one hemicellulase polypeptide is provided, and the cellulase polypeptide and/or the hemicellulase polypeptide is expressed by a host cell, and the cellulase polypeptide and/or hemicellulase polypeptide is endogenous to the host cell. In some aspects, the cellulase polypeptide comprises a polypeptide having endoglucanase activity (e.g., *T. reesei* EG1, *T. reesei* EG2, or a variant thereof) that is different from the polypeptide having GH61/endoglucanase activity, a polypeptide having cellobiohydrolase activity (e.g., *T. reesei* CBH1, *A. fumigatus* 7A, 7B, *C. globosum* 7A, 7B, *T. terrestris* 7A, 7B, *T. reesei* CBH2, *T. terrestris* 6A, *S. thermophile* 6A, 6B, or a variant thereof), or a polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, or a variant thereof). In some aspects, the hemicellulase polypeptide comprises a polypeptide having xylanase activity (e.g., *T. reesei* Xyn3, *T. reesei* Xyn2, AfuXyn2, AfuXyn5, or a variant thereof), a polypeptide having β-xylosidase activity (e.g., Fv3A, Fv43A, Pf43A, Fv43D, Fv39A, Fv43E, Fo43A, Fv43B, Pa51A, Gz43A, *T. reesei* Bxl1, or a variant thereof), or a polypeptide having L-α-arabinofuranosidase activity (e.g., Af43A, Fv43B, Pf51A, Pa51A, Fv51A, or a variant thereof).

In some aspects, the composition is prepared from a fermentation broth. In some aspects, the composition is prepared from the fermentation broth of an integrated strain (e.g., H3A/Eg4, #27, as described herein in the Examples), wherein the GH61 endoglucanase gene is integrated into the genetic materials of the host strain. In some aspects, the composition is prepared from the fermentation broth of a strain, wherein a nucleic acid encoding a polypeptide having GH61/endoglucanase activity (e.g., *T. reesei* Eg4 or a variant thereof) is heterologous to the host cell, wherein the GH61 endoglucanase has been, e.g., integrated into the strain, or expressed by a vector introduced into the host strain.

Any one of the compositions or methods provided herein comprising a polypeptide having GH61/endoglucanase activity (e.g., *T. reesei* Eg4 or a variant thereof) may be a whole cellulase. The composition may be a fermentation broth subject to minimum post-production processing (e.g., purification, filtration, a cell kill step, and/or ultrafiltration, etc), and is used as a whole broth formulation.

In some aspects, a composition (e.g., a non-naturally occurring composition) is provided comprising *T. reesei* Eg4, *T. reesei* Bgl1, *T. reesei* xyn3, Fv3A, Fv43D, and Fv51A, or respective variants thereof. The composition may be a whole cellulase. The composition may be a fermentation broth subject to minimum post-production processing (e.g., filtration, purification, ultrafiltration, a cell-kill step, etc), and is thus used as a whole broth formulation. In some aspects, the composition comprises an isolated *T. reesei* Eg4 or a variant thereof. In some aspects, the composition comprises at least one of an isolated *T. reesei* Bgl1, an isolated *T. reesei* xyn3, an isolated Fv3A, an isolated Fv43D, and an isolated Fv51A. For example, any of the above-mentioned polypeptides can be introduced into the composition by simple addition or mixing of purified or isolated polypeptides. Alternatively, the polypeptides herein can be expressed by the host strain using suitable recombinant techniques, and certain of the above-mentioned polypeptides may be overexpressed or underexpressed, as compared to their naturally-occurring levels in the host cell. In some aspects, genes encoding any one of the above-mentioned polypeptides can be integrated into the host strain. In some aspects, the composition of the present disclosure is prepared from a fermentation broth of the host strain. In some aspects, the composition is from the fermentation broth of an integrated strain (e.g., H3A/Eg4, #27, as described herein in the Examples). In some embodiments, the fermentation broth is subject to minimum post-production processing, and is used as a whole broth formulation. In some aspects, the nucleic acid encoding the GH61 endoglucanase is heterologous to the host cell. In some aspects, at least one of the nucleic acids encoding *T. reesei* Bgl1, *T. reesei* xyn3, Fv3A, Fv43D, or Fv51A is heterologous to the host cell expressing the GH61 endoglucanase of the invention. In some aspects, at least one nucleic acid encoding *T. reesei* Bgl1, *T. reesei* xyn3, Fv3A, Fv43D, or Fv51A is endogenous to the host cell expressing the GH61 endoglucanase.

The polypeptide having GH61/endoglucanase activity (e.g., *T. reesei* Eg4 or a variant thereof) may be present in an enzyme composition or in a biomass saccharification mixture in an amount sufficient to increase the yield of fermentable sugar(s) from hydrolysis of a biomass material (e.g., by at least about 5%, 10%, 15%, 20%, 25%, 30%, 35%, 40%, 45%, 50%, 60%, 70%, 80%, or 90%) as compared to the yield achieved by a control enzyme composition or a control biomass saccharification mixture that is comparable in terms of the types and concentrations of enzymatic or other components therein, but without the polypeptide(s) having GH61/endoglucanase activity. The polypeptide having GH61/endoglucanase activity may be present in the enzyme composition or in a biomass saccharification mixture in an amount sufficient to reduce the viscosity of the biomass saccharification mixture during hydrolysis of the biomass material therein (e.g., by at least about 5%, 10%, 15%, 20%, 25%, 30%, 35%, 40%, 45%, 50%, 60%, 70%, 80%, or 90%) as compared to the viscosity of a control mixture that is comparable in terms of the types and concentrations of enzymatic or other components therein, but without the polypeptide having GH61/endoglucanase activity. In some aspects, the enzyme composition or the biomass saccharification mixture comprises at least 1 polypeptide having endoglucanase activity, at least 1 polypeptide having cellobiohydrolase activity, at least 1 polypeptide having β-glucosidase activity, in total amounts that are sufficient to cause hydrolysis of the biomass material to which the polypeptides come into contact. The enzyme composition or the biomass saccharification mixture may further comprise at least 1 polypeptide having xylanase activity, at least 1 polypeptide having β-xylosidase activity, at least 1 polypeptide having L-α-arabinofuranosidase activity, and/or a whole cellulase, or a mixture thereof, in total amounts that are sufficient to cause hydrolysis of the biomass material to which the polypeptides come into contact.

In some aspects, the polypeptide having GH61/endoglucanase activity (e.g., *T. reesei* Eg4 or a variant thereof) is present in an amount that is about 0.1 wt. % to about 50 wt. % (e.g., about 0.5 wt. % to about 30 wt. %, about 1 wt. % to about 20 wt. %, about 5 wt. % to about 20 wt. %, about 7 wt. % to about 20 wt. %, or about 8 to about 15 wt. %) of the total weight of proteins in the enzyme composition or in the biomass saccharification mixture. For example the polypeptide having GH61/endoglucanase activity is present in an amount that is about 8 wt. %, about 10 wt. %, or about 12 wt. % of the total weight of proteins in the enzyme composition or in the biomass saccharification mixture. The enzyme composition or the biomass saccharification mixture may comprise more than one polypeptides having GH61/endoglucanase activity. For example, the enzyme composition or biomass saccharification mixture can comprise a *T. reesei* Eg4 or a variant thereof, as well as a *T. reesei* Eg7 (or a variant thereof), wherein the total amount of polypeptides having GH61/endoglucanase (Eg4+Eg7) activity is about 0.1 wt. % to about 50 wt. % (e.g., about 0.5 wt. % to about 30 wt. %, about 2 wt. % to about 20 wt. %, about 5 wt. % to about 20 wt. %, about 7 wt. % to about 20 wt. %, or about 8 wt. % to about 15 wt. %) of the total weight of proteins in the enzyme composition or in the biomass saccharification mixture. The polypeptide(s) having GH61/endoglucanase activity may be expressed from polynucleotides that are heterologous or endogenous to the host cell. Alternatively the polypeptide having GH61/endoglucanase activity can be introduced into the enzyme composition or the biomass saccharification mixture in an isolated or purified form.

In some aspects, a polypeptide having cellobiohydrolase activity (e.g., *T. reesei* CBH1, *A. fumigatus* 7A, 7B, *C. globosum* 7A, 7B, *T. terrestris* 7A, 7B, *T. reesei* CBH2, *T. terrestris* 6A, *S. thermophile* 6A, 6B, or a variant thereof) is present in an amount that is about 0.1 wt. % to about 80 wt. % (e.g., about 5 wt. % to about 70 wt. %, about 10 wt. % to about 60 wt. %, about 20 wt. % to about 50 wt. %, or about 25 wt. % to about 50 wt. %) of the total weight of proteins in the enzyme composition or the biomass saccharification mixture. The enzyme composition or biomass saccharification mixture may comprise more than one polypeptide having cellobiohydrolase activity (e.g., *T. reesei* CBH1, *A. fumigatus* 7A, 7B, *C. globosum* 7A, 7B, *T. terrestris* 7A, 7B, *T. reesei* CBH2, *T. terrestris* 6A, *S. thermophile* 6A, 6B, or a variant thereof), wherein the total amount of polypeptides having cellobiohydrolase activity is about 0.1 wt. % to about 80 wt. % (e.g., about 5 wt. % to about 70 wt. %, about 10 wt. % to about 60 wt. %, about 20 wt. % to about 50 wt. %, or about 25 wt. % to about 50 wt. %) of the total weight of proteins in the enzyme composition or the biomass saccharification mixture. The polypeptide having cellobiohydrolase activity is, in some aspects, expressed from a nucleic acid heterologous or endogenous to the host cell. In some aspects, the polypeptide having cellobiohydrolase activity can be introduced into the enzyme composition or biomass saccharification mixture in an isolated or purified form.

The enzyme composition or the biomass saccharification mixture may comprise one or more polypeptides having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B or a variant thereof), wherein the total amount of polypeptides having β-glucosidase activity is about 0.1 wt. % to about 50 wt. % (e.g., about 1 wt. % to about 30 wt. %, about 2 wt. % to about 20 wt. %, about 5 wt. % to about 20 wt. %, or about 8 wt. % to about 15 wt. %) of the total weight of proteins in the enzyme composition or biomass saccharification mixture. The polypeptide having β-glucosidase activity may be expressed from a nucleic acid heterologous or endogenous to the host cell. The polypeptide having β-glucosidase activity may alternatively be introduced into the enzyme composition or biomass saccharification mixture in an isolated or purified form.

In some aspects, the enzyme composition or biomass saccharification mixture can comprise one or more the polypeptides having xylanase activity (e.g., *T. reesei* Xyn3, *T. reesei* Xyn2, AfuXyn2, AfuXyn5, or a variant thereof), wherein the total amount of polypeptides having xylanase activity is about 0.1 wt. % to about 50 wt. % (e.g., about 1 wt. % to about 40 wt. %, about 4 wt. % to about 30 wt. %, about 5 wt. % to about 20 wt. %, or about 8 wt. % to about 15 wt. %) of the total weight of proteins in the enzyme composition or the biomass saccharification mixture. The polypeptide having xylanase activity can be expressed from a nucleic acid heterologous or endogenous to the host cell. In some aspects, the polypeptide having xylanase activity can be introduced or mixed into the enzyme composition or the biomass saccharification mixture in an isolated or purified form.

The enzyme composition or biomass saccharification mixture may comprise one or more polypeptides having L-α-arabinofuranosidase activity (e.g., Af43A, Fv43B, Pf51A, Pa51A, Fv51A, or a variant thereof), wherein the total amount of polypeptides having L-α-arabinofuranosidase activity is about 0.1 wt. % to about 50 wt. % (e.g., about 1 wt. % to about 40 wt. %, about 2 wt. % to about 30 wt. %, about 4 wt. % to about 20 wt. %, or about 5 wt. % to about 15 wt. %) of the total weight of proteins in the enzyme composition or the biomass saccharification mixture. The polypeptide having L-α-arabinofuranosidase activity may be expressed from a nucleic acid heterologous or endogenous to the host cell. In some aspects, the polypeptide having L-α-arabinofuranosidase activity can be introduced or mixed into the enzyme composition or the biomass saccharification mixture in an isolated or purified form.

The enzyme composition or the biomass saccharification mixture may comprise one or more polypeptides having β-xylosidase activity (e.g., Fv3A, Fv43A, Pf43A, Fv43D, Fv39A, Fv43E, Fo43A, Fv43B, Pa51A, Gz43A, T. reesei Bxl1 or a variant thereof), wherein the total amount of the polypeptides having β-xylosidase activity is about 0.1 wt. % to about 50 wt. % (e.g., about 1 wt. % to about 40 wt. %, about 4 wt. % to about 35 wt. %, about 5 wt. % to about 25 wt. %, or about 5 wt. % to about 20 wt. %) of the total weight of proteins in the enzyme composition or the biomass saccharification mixture. The polypeptide having β-xylosidase activity may be expressed from a nucleic acid heterologous or endogenous to the host cell. The polypeptide having β-xylosidase activity may alternatively be introduced into the enzyme composition or the biomass saccharification mixture in an isolated or purified form.

In some aspects, the enzyme composition provided herein may be a whole cellulase. The whole cellulase may comprise one or more polypeptides having endoglucanase activity (such as, e.g, T. reesei Eg4, Eg1, Eg2, Eg7, or a variant thereof) expressed from a nucleic acid heterologous or endogenous to the host cell. The whole cellulase may also comprise one or more polypeptides having cellobiohydrolase activity (e.g., T. reesei CBH1, A. fumigatus 7A, 7B, C. globosum 7A, 7B, T. terrestris 7A, 7B, T. reesei CBH2, T. terrestris 6A, S. thermophile 6A, 6B, or a variant thereof) expressed from a nucleic acid heterologous or endogenous to the host cell. The whole cellulase may further comprise one or more polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, or a variant thereof) expressed from a nucleic acid heterologous or endogenous to the host cell. The whole cellulase may be used in the form of a fermentation broth of the host cell. The broth can be subject to minimum post-production processing, including, e.g., filtration, purification, ultrafiltration, a cell-kill step, etc, and thus the broth may be used for biomass hydrolysis in a whole broth formulation.

In some aspects, the enzyme composition provided herein is capable of converting a biomass material into fermentable sugar(s) (e.g., glucose, xylose, arabinose, and/or cellobiose). In some aspects, the enzyme composition is capable of achieving at least about 0.1 (e.g., 0.1 to 0.4) fraction product as determined by the calcofluor assay described herein.

In some aspects, the enzyme composition can be a cellulase composition or a hemicellulase composition. The enzyme composition may comprise the polypeptide having GH61/endoglucanase activity and further may comprise one or more cellulase polypeptides and/or one or more hemicellulase polypeptides, wherein the one or more polypeptides having GH61/endoglucanase activity and the one or more cellulase polypeptides, and/or the one or more hemicellulase polypeptides are blended into a mixture before the mixture is used to contact and hydrolyze a biomass substrate in a biomass saccharification mixture.

In some aspects, the one or more polypeptides having GH61/endoglucanase activity, one or more cellulase polypeptides, and one or more hemicellulase polypeptide, are added to a biomass material, at different times. For example, a polypeptide having GH61/endoglucanase activity is added to a biomass material before, or after, a cellulase polypeptide and/or a hemicellulase polypeptide is added to the same biomass material.

In some aspects, a composition of the invention comprises at least one polypeptide having GH61/endoglucanase activity and a biomass material in, e.g., a mixture. For example, the composition may be a hydrolysis mixture, a fermentation broth/mixture, or a biomass saccharification mixture. The mixture may comprise one or more fermentable sugar(s).

Also provided herein are methods of hydrolyzing a biomass material comprising contacting the biomass material with an enzyme composition (e.g., a non-naturally occurring composition) comprising a polypeptide having GH61/endoglucanase activity, in an amount sufficient to hydrolyze the biomass material in the resulting biomass saccharification mixture.

Also provided herein are methods of reducing the viscosity of a biomass mixture, and/or a biomass saccharification mixture comprising contacting the mixture with an enzyme composition (e.g., a non-naturally occurring composition) comprising a polypeptide having GH61/endoglucanase activity, which is present in the composition in an amount sufficient to reduce the viscosity of the mixture. In some aspects, the biomass mixture or the biomass saccharification mixture comprises a biomass material, optionally also fermentable sugar(s), a whole cellulase and/or a composition comprising a polypeptide having cellulase activity and/or a polypeptide having hemicellulase activity. The viscosity of the mixture may be reduced by at least about 5%, (e.g., at least about 5%, 10%, 15%, 20%, 25%, 30%, 35%, 40%, 45%, 50%, 60%, 70%, 80%, or 90%) as compared to the viscosity of a control mixture comprising the same components at the same concentrations except that the polypeptide having GH61/endoglucanase activity is absent from the mixture. The biomass material may comprise hemicellulose, cellulose, or a mixture thereof. The biomass material may comprises glucan, xylan and/or lignin, or a mixture thereof.

In some aspects, the biomass material can suitably be treated or pre-treated with an acid or a base. In some aspects, the base is ammonia. The method of the invention may further comprise adjusting the pH of the biomass mixture to a pH of about 4.0 to about 6.5 (e.g., pH of about 4.5 to about 5.5). In some aspects, the method is performed at a pH of about 4.0 to about 6.5 (e.g., pH of about 4.5 to about 5.5). In some aspects, the method is performed for about 2 h to about 7 d (e.g., about 4 h to about 6 d, about 8 h to about 5 d, or about 8 h to about 3 d). This pH adjustment can suitably be made before putting the biomass mixture in contact with the polypeptides or the enzyme compositions.

In some aspects, the biomass material is present in a saccharification mixture in a high solids level, e.g., the biomass material in its solid state constitutes at least about 5 wt. % to about 60 wt. % (e.g., about 10 wt. % to about 50 wt. %, about 15 wt. % to about 40 wt. %, about 15 wt. % to about 30 wt. %, or about 20 wt. % to about 30 wt. %) of the total weight of enzymes plus biomass materials in the saccharification mixture. By the weight of the biomass material in its solid state, it is meant the weight of the biomass material in its dry state, its dry solid state, its natural state, or its unprocessed state, or before the biomass is contacted with the polypeptides in the enzyme composition. Preferably the biomass material in its solid state constitutes at least about 15 wt. %, and even more preferably at least about 20 wt. % or 25 wt. % of the total weight of enzymes plus biomass materials in the saccharification mixture.

In some aspects, the method comprises producing fermentable sugar(s). The amount of fermentable sugar(s) may be produced at an increased level using the method of the invention. For example, the amount of the fermentable sugar(s) produced using the methods or the compositions herein is increased by at least about 5% (e.g., at least about 5%, 10%, 15%, 20%, 25%, 30%, 35%, 40%, 45%, 50%, 60%, 70%, 80%, or 90%) as compared to the amount of the fermentable sugar(s) produced when the same biomass material is hydrolyzed by an enzyme composition comprising the same polypeptide components at the same concentrations, except that polypeptide having GH61/endoglucanase activity is absent.

In some aspects, the amount of the enzyme composition comprising a polypeptide having GH61/endoglucanase activity is sufficient to increase the yield of fermentable sugar(s) by at least about 5%, (e.g., at least about 5%, 10%, 15%, 20%, 25%, 30%, 35%, 40%, 45%, 50%, 60%, 70%, 80%, or 90%), as compared to the yield of fermentable sugar(s) from the same biomass material by an enzyme composition having the same components at the same concentrations, except that the polypeptide having GH61/endoglucanase activity is absent. In some aspects, the amount of the polypeptide having GH61/endoglucanase activity in the biomass saccharification mixture is sufficient to reduce the viscosity of the mixture by at least about 5% (e.g., at least about 5%, 10%, 15%, 20%, 25%, 30%, 35%, 40%, 45%, 50%, 60%, 70%, 80%, or 90%) as compared to the viscosity of a control biomass saccharification mixture comprising the same biomass and the same panel of polypeptides at the same concentrations, except that the polypeptide having GH61/endoglucanase activity is absent.

In some aspects, the amount of the composition comprising a polypeptide having GH61/endoglucanase activity used in a saccharification or hydrolysis process is about 0.1 mg to about 50 mg protein (e.g., about 0.2 mg to about 40 mg protein, about 0.5 mg to about 30 mg protein, about 1 mg to about 20 mg protein, or about 5 mg to about 15 mg protein) per gram of cellulose, hemicellulose, or a mixture of cellulose and hemicelluloses in the biomass material. The protein amount described herein refers to the weight of total protein in the enzyme composition or the biomass saccharification mixture. The proteins include a polypeptide having GH61/endoglucanase activity and may include other enzymes such as cellulase polypeptide(s) and/or hemicellulase polypeptide(s). In some aspects, the amount of the polypeptide having GH61/endoglucanase activity used in the hydrolysis or saccharification process is about 0.2 mg to about 30 mg (e.g., about 0.2 mg to about 20 mg, about 0.5 mg to about 10 mg, or about 1 mg to about 5 mg) protein per gram of cellulose, hemicellulose, or cellulose and hemicelluloses contained in the biomass material.

The enzyme composition or biomass saccharification mixture comprising a polypeptide having GH61/endoglucanase activity and at least 1 polypeptide having endoglucanase activity (e.g., T. reesei Eg1, T. reesei Eg2, and/or a variant thereof) in the hybrolysis or saccharification process may contain about 0.2 mg to about 30 mg (e.g., about 0.2 mg to about 20 mg, about 0.5 mg to about 10 mg, or about 1 mg to about 5 mg) protein per gram of cellulose, hemicellulose, or cellulose and hemicellulose in the biomass material.

The enzyme composition or biomass saccharification mixture comprising a polypeptide having GH61/endoglucanase activity and at least 1 polypeptide having cellobiohydrolase activity (e.g., T. reesei CBH1, A. fumigatus 7A, 7B, C. globosum 7A, 7B, T. terrestris 7A, 7B, T. reesei CBH2, T. terrestris 6A, S. thermophile 6A, 6B, or a variant thereof) in the hydrolysis or saccharification process may contain about 0.2 mg to about 30 mg (e.g., about 0.2 mg to about 20 mg, about 0.5 mg to about 10 mg, or about 1 mg to about 5 mg) protein per gram of cellulose, hemicellulose, or cellulose and hemicellulose in the biomass material.

In some aspects, the enzyme composition or biomass saccharification mixture comprising a polypeptide having GH61/endoglucanase activity and at least 1 polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, or a variant thereof) in the hydrolysis or saccharification process may contain about 0.2 mg to about 30 mg (e.g., about 0.2 mg to about 20 mg, about 0.5 mg to about 10 mg, or about 0.5 mg to about 5 mg) protein per gram of cellulose, hemicellulose, or cellulose and hemicellulose in the biomass material.

The enzyme composition or biomass saccharification mixture comprising a polypeptide having GH61/endoglucanase activity and at least 1 polypeptide having xylanase activity (e.g., T. reesei Xyn3, T. reesei Xyn2, AfuXyn2, AfuXyn5 or a variant thereof) in the hydrolysis or saccharification process may contain about 0.2 mg to about 30 mg (e.g., about 0.2 mg to about 20 mg, about 0.5 mg to about 10 mg, about 0.5 mg to about 5 mg) protein per gram of cellulose, hemicellulose, or cellulose and hemicellulose in the biomass material.

The enzyme composition or the biomass saccharification mixture comprising a polypeptide having GH61/endoglucanase activity and at least 1 polypeptide having β-xylosidase activity (e.g., Fv3A, Fv43A, Pf43A, Fv43D, Fv39A, Fv43E, Fo43A, Fv43B, Pa51A, Gz43A, T. reesei Bxl1, and/or a variant thereof) used in the hydrolysis or saccharification process may contain about 0.2 mg to about 30 mg (e.g., about 0.2 mg to about 20 mg, about 0.5 mg to about 10 mg, or about 0.5 mg to about 5 mg) protein per gram of cellulose, hemicellulose, or cellulose and hemicellulose in the biomass material.

The enzyme composition or the biomass saccharification mixture comprising a polypeptide having GH61/endoglucanase activity and at least 1 polypeptide having L-α-arabinofuranosidase activity (e.g., Af43A, Fv43B, Pf51A, Pa51A, Fv51A, and/or a variant thereof) used in the hydrolysis or saccharification process may contain about 0.2 mg to about 30 mg (e.g., about 0.2 mg to about 20 mg, about 0.5 mg to about 10 mg, or about 0.5 mg to about 5 mg) protein per gram of cellulose, hemicellulose, or cellulose and hemicellulose in the biomass material.

In some aspects, the method of the invention is performed at a temperature of about 30° C. to about 65° C. (e.g., about 35° C. to about 60° C., about 40° C. to about 60° C., or about 45° C. to about 55° C.).

The method of the invention may further comprise the step of contacting the biomass material with an enzyme composition comprising a whole cellulase. In some aspects, the step of further contacting the biomass material with a composition comprising a whole cellulase is performed before, after, or concurrently with contacting the biomass material with an enzyme composition comprising a polypeptide having GH61/endoglucanase activity.

In some aspects, the method of the invention further comprises the step contacting the biomass material with an enzyme composition comprising a polypeptide having cellulase activity and/or a polypeptide having hemicellulase activity. The step of contacting the biomass material with a composition comprising a polypeptide having cellulase activity and/or a polypeptide having hemicellulase activity may be performed before, after, or concurrently with contacting the biomass material with an enzyme composition comprising a polypeptide having GH61/endoglucanase activity.

In some aspect, the composition comprises the polypeptide having GH61/endoglucanase activity and further comprises at least 1 cellulase polypeptide and/or at least one hemicellulase polypeptide, wherein the polypeptide having GH61/endoglucanase activity and at least one cellulase polypeptide and/or at least 1 hemicellulase polypeptide are blended into a mixture before the mixture is used to contact the biomass material.

In some aspects, the composition comprises the polypeptide having GH61/endoglucanase activity and further comprises 1 or more cellulase polypeptides and/or 1 or more hemicellulase polypeptides, wherein the polypeptide having GH61/endoglucanase activity and 1 or more cellulase polypeptides and/or 1 or more hemicellulase polypeptides are added to the biomass material at different times. For example, the polypeptide having GH61/endoglucanase activity (e.g., T. reesei Eg4 or a variant thereof) is added before or after the 1 or more cellulase polypeptides and/or the 1 or more hemicellulase polypeptides are added.

In some aspects, methods of applying the invention in both an industrial setting and/or a commercial setting are contemplated. Accordingly a method or a method of manufacturing, marketing, or otherwise commercializing the instant compositions comprising suitable GH61 endoglucanases is within the purview of the disclosure. The method includes, for example, the application of the compositions or the GH61 endoglucanase polypeptides or variants thereof in a merchant enzyme supply model, wherein the enzymes and variants, as well as the compositions of the invention are supplied or sold to cellulosic sugar producers, certain ethanol (bioethanol) refineries or other bio-chemical or biomaterial manufacturers. The method can also be, in some aspects, the application of the compositions or the GH61 endoglucanase polypeptides or variants thereof in an on-site bio-refinery model, wherein the polypeptides or variants, or the non-naturally occurring cellulase and hemicellulase compositions of the invention are produced in an enzyme production system that is built by the enzyme manufacturer at a site that is located at or in the vicinity of the cellulosic sugar plant, bioethanol refineries or the bio-chemical/biomaterial manufacturers. In some aspects, suitable biomass substrates, preferably subject to appropriate pretreatments as described herein, can be hydrolyzed using the saccharification methods and the enzymes and/or enzyme compositions herein at or near the bioethanol refineries or the bio-chemical/biomaterial manufacturing facilities. The resulting fermentable sugars can then be subject to fermentation at the same facilities or at facilities in the vicinity.

It is to be understood that one, some, or all of the properties of the embodiments described herein may be combined to form other embodiments of the present invention. These and other aspects of the invention will become apparent to one of skill in the art.

BRIEF DESCRIPTION OF THE FIGURES

The skilled artisan will understand that the drawings are for illustration purposes only and are not intended to limit the scope of the present teachings in anyway.

FIGS. 1A-1E: FIG. 1A, FIG. 1B, FIG. 1C, FIG. 1D, and FIG. 1E depict certain amino acid sequences of various polypeptides having GH61/endoglucanase activity.

FIGS. 2A-2D: FIG. 2A, FIG. 2B, FIG. 2C, and FIG. 2D depict percent identity and divergence using ClustalV (PAM250) comparing a number of amino acid sequences of various polypeptides having GH61/endoglucanase activity, such as those presented in FIG. 1 (SEQ ID NOs: 1-28).

FIGS. 3A-3L: FIG. 3A, FIG. 3B, FIG. 3C, FIG. 3D, FIG. 3E, FIG. 3F, FIG. 3G, FIG. 3H, FIG. 3I, FIG. 3J, FIG. 3K, and FIG. 3L depict the alignment of various polypeptides having GH61/endoglucanase activity such as those presented in FIG. 1 (SEQ ID NOs: 1-28).

FIGS. 4A-4B: FIG. 4A depicts nucleotide sequence of T. reesei Eg4 (SEQ ID NO:30). FIG. 4B depicts amino acid sequence of T. reesei Eg4 (SEQ ID NO:27). The predicted signal sequence is underlined, the predicted conserved domains are in bold, and the predicted linker is in italic.

FIG. 5: depicts an amino acid sequence alignment of T. reesei Eg4 (TrEG4) (SEQ ID NO:27) with T. reesei Eg7 (TrEG7, or TrEGb) (SEQ ID NO:26) and TtEG (SEQ ID NO:29).

FIGS. 6A-6B: FIG. 6A provides conserved residues of T. reesei Eg4 (TrEg4), inferred from sequence alignment and the known structures of TrEG7 (crystal structure at Protein Data Bank Accession: pdb:2vtc) and TtEG (crystal structure at Protein Data Bank Accession: pdb:3EII). FIG. 6B provides conserved CBM domain residues inferred from sequence alignment with known sequences of Tr6A, and Tr7A.

FIG. 7 lists a number of amino acid sequence motifs of GH61 endoglucanases. Each of the "a" s in the sequence motifs represents an amino acid that may be any one of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine.

FIG. 8A depicts pENTR-TOPO-Bgl1-943/942 plasmid. FIG. 8B depicts pTrex3g 943/942 expression vector. FIG. 8C depicts pENTR/T. reesei Xyn3 plasmid. FIG. 8D depicts pTrex3g/T. reesei Xyn3 expression vector. FIG. 8E depicts pENTR-Fv3A plasmid. FIG. 8F depicts the pTrex6g plasmid. FIG. 8G depicts pTrex6g/Fv3A expression vector. FIG. 8H depicts TOPO Blunt/Pegl1-Fv43D plasmid. FIG. 8I depicts TOPO Blunt/Pegl1-Fv51A plasmid.

FIG. 9: provides the enzyme composition of T. reesei integrated strain H3A.

FIG. 10: lists the enzymes (purified or unpurified) that were individually added to each of the samples in Example 2, and the stock protein concentrations of these enzymes.

FIG. 11A depicts glucose release following saccharification of dilute ammonia pretreated corncob by adding enzyme compositions comprising various purified or non-purified enzymes of FIG. 10, which were added to T. reesei integrated strain H3A, in accordance with Example 2. FIG. 11B depicts cellobiose release following saccharification of dilute ammonia pretreated corncob by adding enzyme compositions comprising various purified or non-purified enzymes of FIG. 10, which were added to T. reesei integrated strain H3A, in accordance with Example 2; FIG. 11C depicts xylobiose release following saccharification of dilute ammonia pretreated corncob by adding enzyme compositions comprising various purified or non-purified enzymes of FIG. 10, which were added to T. reesei integrated strain H3A, in accordance with Example 2; FIG. 11D depicts xylose release following saccharification of dilute ammonia pretreated corncob by adding enzyme compositions comprising various purified or non-purified enzymes of FIG. 10, which were added to *T. reesei* integrated strain H3A, in accordance with Example 2.

FIG. 12A depicts the expression cassette Peg11-eg4-sucA, as described in Example 3; FIG. 12B depicts the plasmid map of pCR Blunt II TOPO containing expression cassette pEG1-EG4-sucA, as described in Example 3.

FIG. 15: provides a *T. reesei* Eg4 dosing chart for Example 4 (experiment 1). The sample "#27" is an H3A/Eg4 integrated strain as described in Example 4. The amounts of purified *T. reesei* Eg4 that were added were listed under "Sample Description" either by wt. % or by mass (in mg protein/g G+X).

FIG. 16A depicts the effect of *T. reesei* Eg4 on glucose release in saccharification of dilute ammonia pretreated corncob according to Example 4. FIG. 16B depicts the effect of *T. reesei* Eg4 on xylose release in saccharification of dilute ammonia pretreated corncob. The Y-axes of these figures refer to the concentrations of glucose or xylose released in the reaction mixtures. The X axes list the names/brief descriptions of the enzyme composition samples. This is according to Example 4 (experiment 1).

FIGS. 17A-17B: FIG. 17A provides another *T. reesei* Eg4 dosing chart for Example 4 (experiment 2). The samples are described similarly to those in FIG. 15. The amounts of purified *T. reesei* Eg4 that were added varied by smaller increments than those of Example 4, experiment 1 (above). FIG. 17B provides another *T. reesei* Eg4 dosing chart for Example 4 (experiment 3). The samples are described similarly to those in FIGS. 16 and 17A. The amounts of purified *T. reesei* Eg4 that were added varied by even finer increments than those of Example 4, experiments 1 and 2 (above)

FIG. 18A depicts the effect of *T. reesei* Eg4 in various amounts (0.05 mg/g to 1.0 mg/g) on glucose release from saccharification of dilute ammonia pretreated corncob, as described in Example 4. FIG. 18B depicts the effect of *T. reesei* Eg4 in various amounts (0.1 mg/g to 0.5 mg/g) on glucose release from saccharification of dilute ammonia pretreated corncob, as described in Example 4.

FIG. 20: provides percentage yield of xylose monomers released from dilute ammonia pretreated corncob using an enzyme composition comprising *T. reesei* Eg4, in accordance with Example 6.

FIG. 21: provides percentage yield of glucose monomer released from dilute ammonia pretreated corncob using an enzyme composition comprising *T. reesei* Eg4, in accordance with Example 6.

FIG. 22: provides yield (mg/ml) of total fermentable monomers released from dilute ammonia pretreated corncob using an enzyme composition comprising *T. reesei* Eg4, in accordance with Example 6.

FIG. 23: compares the amounts of glucose released as a result of hydrolysis by an enzyme composition without *T. reesei* Eg4 vs. one comprising *T. reesei* Eg4 at 0.53 mg/g. The experiment is described in Example 7.

FIG. 28: compares saccharification performance, in terms the amounts of glucose or xylose released, of enzyme compositions produced by the *T. reesei* integrated strain H3A and the integrated strain H3A/Eg4 (strain #27). This is according to Example 11.

FIG. 29: depicts the change in percent glucan and xylan conversion at increasing amounts of an enzyme composition produced by the *T. reesei* integrated strain H3A/Eg4 (strain #27). This is in accordance with the description of Example 12.

FIG. 30: is a table listing the effect of *T. reesei* Eg4 addition on dilute ammonia pretreated corncob saccharification. Experimental conditions are described in Example 13.

FIGS. 33A-33C: FIG. 33A, FIG. 33B, and FIG. 33C depict amounts for various enzyme compositions for saccharification. Experimental conditions are described in Example 14.

FIGS. 34A-34C: FIG. 34A, FIG. 34B, and FIG. 34C depict the amount of glucose, glucose+cellobiose, or xylose produced with each enzyme composition corresponding to FIG. 33. Experimental conditions are described in Example 14.

FIG. 35: depicts various ratios of CBH1, CBH2 and *T. reesei* Eg2 mixtures, as described in Example 15.

FIGS. 36A-36B: FIG. 36A and FIG. 36B depict glucan conversion (%) using various enzyme compositions. Experimental conditions are described in Example 15.

FIGS. 39A-39B: FIG. 39A depicts the amount of substrate and various enzymes used in the experiment of Example 22, with the result depicted in FIG. 37. FIG. 39B depicts the amount of substrate and various enzymes used in the experiment of Example 22, with the result depicted in FIG. 38.

FIGS. 49A-49E: FIG. 49A, FIG. 49B, FIG. 49C, FIG. 49D, and FIG. 49E provide a summary of the sequence identifies in the present disclosure.

FIGS. 50A-50B: FIG. 50A depicts nucleotide sequence encoding Fv3A (SEQ ID NO:35). FIG. 50B depicts Fv3A amino acid sequence (SEQ ID NO:36). The predicted signal sequence is underlined, and the predicted conserved domain is in bold.

FIGS. 51A-51B: FIG. 51A depicts nucleotide sequence encoding Pf43A (SEQ ID NO:37). FIG. 51B depicts Pf43A amino acid sequence (SEQ ID NO:38). The predicted signal sequence is underlined, the predicted conserved domain is in bold, the predicted carbohydrate binding module ("CBM") is in uppercase, and the predicted linker separating the CD and CBM is in italics.

FIG. 52A-52B: FIG. 52A depicts nucleotide sequence encoding Fv43E (SEQ ID NO:39). FIG. 52B depicts Fv43E amino acid sequence (SEQ ID NO:40). The predicted signal sequence is underlined, and the predicted conserved domain is in bold.

FIGS. 53A-53B: FIG. 53A depicts nucleotide sequence encoding Fv39A (SEQ ID NO:41). FIG. 53B depicts Fv39A amino acid sequence (SEQ ID NO:42). The predicted signal sequence is underlined, and the predicted conserved domain is in bold.

FIGS. 54A-54B: FIG. 54A depicts nucleotide sequence encoding Fv43A (SEQ ID NO:43). FIG. 54B depicts Fv43A amino acid sequence (SEQ ID NO:44). The predicted signal sequence is underlined, the predicted conserved domain in bold, the predicted CBM in uppercase, and the predicted linker connecting the conserved domain and CBM in italics.

FIGS. 55A-55B: FIG. 55A depicts nucleotide sequence encoding Fv43B (SEQ ID NO:45). FIG. 55B depicts Fv43B amino acid sequence (SEQ ID NO:46). The predicted signal sequence is underlined. The predicted conserved domain is in boldface type.

FIGS. 56A-56B: FIG. 56A depicts nucleotide sequence encoding Pa51A (SEQ ID NO:47). FIG. 56B depicts Pa51A amino acid sequence (SEQ ID NO:48). The predicted signal sequence is underlined. The predicted L-α-arabinofuranosidase conserved domain is in bold. For expression in *T. reesei*, the genomic DNA was codon optimized (see FIG. 73C).

FIGS. 57A-57B: FIG. 57A depicts nucleotide sequence encoding Gz43A (SEQ ID NO:49). FIG. 57B depicts Gz43A amino acid sequence (SEQ ID NO:50). The predicted signal sequence is underlined, and the predicted conserved domain is in bold. For expression in *T. reesei*, the predicted signal sequence was replaced by *T. reesei* CBH1 signal sequence (myrklavisaflatara (SEQ ID NO: 120)).

FIGS. 58A-58B: FIG. 58A depicts nucleotide sequence encoding Fo43A (SEQ ID NO:51). FIG. 58B depicts Fo43A amino acid sequence (SEQ ID NO:52). The predicted signal sequence is underlined, and the predicted conserved domain is in bold. For expression in *T. reesei*, the predicted signal sequence was replaced by *T. reesei* CBH1 signal sequence (myrklavisaflatara (SEQ ID NO:120))

FIGS. 59A-59B: FIG. 59A depicts nucleotide sequence encoding Af43A (SEQ ID NO:53). FIG. 59B depicts Af43A amino acid sequence (SEQ ID NO:54). The predicted conserved domain is in bold.

FIGS. 60A-60B: FIG. 60A depicts nucleotide sequence encoding Pf51A (SEQ ID NO:55). FIG. 60B depicts Pf51A amino acid sequence (SEQ ID NO:56). The predicted signal sequence is underlined, and the predicted L-α-arabinofuranosidase conserved domain in bold. For expression in *T. reesei*, the predicted signal sequence was replaced by a codon optimized the *T. reesei* CBH1 signal sequence (myrklavisaflatara (SEQ ID NO:120)) (underlined) and the Pf51A nucleotide sequence was codon optimized for expression.

FIGS. 61A-61B: FIG. 61A depicts nucleotide sequence encoding AfuXyn2 (SEQ ID NO:57). FIG. 61B depicts AfuXyn2 amino acid sequence (SEQ ID NO:58). The predicted signal sequence is underlined, and the predicted GH11 conserved domain in bold.

FIGS. 62A-62B: FIG. 62A depicts nucleotide sequence encoding AfuXyn5 (SEQ ID NO:59). FIG. 62B depicts AfuXyn5 amino acid sequence (SEQ ID NO:60). The predicted signal sequence is underlined, and the predicted GH11 conserved domain in bold. FIGS. 63A-63B: FIG. 63A depicts nucleotide sequence encoding Fv43D (SEQ ID NO:61). FIG. 63B depicts Fv43D amino acid sequence (SEQ ID NO:62). The predicted signal sequence is underlined. The predicted conserved domain is in bold.

FIGS. 64A-64B: FIG. 64A depicts nucleotide sequence encoding Pf43B (SEQ ID NO:63). FIG. 64B depicts Pf43B amino acid sequence (SEQ ID NO:64). The predicted signal sequence is underlined, and the predicted conserved domain is in bold.

FIGS. 65A-65B: FIG. 65A depicts nucleotide sequence encoding Fv51A (SEQ ID NO:65). FIG. 65B depicts Fv51A amino acid sequence (SEQ ID NO:66). The predicted signal sequence is underlined, and the predicted L-α-arabinofuranosidase conserved domain is in bold.

FIGS. 66A-66B: FIG. 66A depicts nucleotide sequence encoding Cg51B (SEQ ID NO:67). FIG. 66B depicts Cg51B amino acid sequence (SEQ ID NO:68). The predicted signal sequence corresponding is underlined, and the predicted conserved domain is in bold.

FIGS. 67A-67B: FIG. 67A depicts nucleotide sequence encoding Fv43C (SEQ ID NO:69). FIG. 67B depicts Fv43C amino acid sequence (SEQ ID NO:70). The predicted signal sequence is underlined, and the predicted conserved domain is in bold.

FIGS. 68A-68B: FIG. 68A depicts nucleotide sequence encoding Fv30A (SEQ ID NO:71). FIG. 68B depicts Fv30A amino acid sequence (SEQ ID NO:72). The predicted signal sequence is underlined.

FIGS. 69A-69B: FIG. 69A depicts nucleotide sequence encoding Fv43F (SEQ ID NO:73). FIG. 69B depicts Fv43F amino acid sequence (SEQ ID NO:74). The predicted signal sequence is underlined.

FIGS. 70A-70B: FIG. 70A depicts nucleotide sequence encoding T. reesei Xyn3 (SEQ ID NO:75). FIG. 70B depicts Xyn3 amino acid sequence (SEQ ID NO:76). The predicted signal sequence is underlined, and the predicted conserved domain is in bold.

FIGS. 71A-71B: FIG. 71A depicts amino acid sequence of T. reesei Xyn2 (SEQ ID NO:77). The signal sequence is underlined. The predicted conserved domain is in bold. The coding sequence can be found in Torronen et al. Biotechnology, 1992, 10:1461-65. FIG. 71B depicts the nucleotide sequence encoding Xyn2 (SEQ ID NO:160).

FIGS. 72A-72B: FIG. 72A depicts amino acid sequence of T. reesei Bxl1 (SEQ ID NO:78). The signal sequence is underlined. The predicted conserved domain is in bold. The coding sequence can be found in Margolles-Clark et al. Appl. Environ. Microbiol. 1996, 62(10):3840-46. FIG. 72B depicts nucleotide sequence encoding Bxl1 (SEQ ID NO: 159)

FIGS. 73A-73F: FIG. 73A depicts amino acid sequence of T. reesei Bgl1 (SEQ ID NO:79). The signal sequence is underlined. The predicted conserved domain is in bold. The coding sequence can be found in Barnett et al. Bio-Technology, 1991, 9(6):562-567. FIG. 73B depicts deduced cDNA for Pa51A (SEQ ID NO:80). FIG. 73C depicts codon optimized cDNA for Pa51A (SEQ ID NO:81). FIG. 73D: depicts coding sequence for a construct comprising a CBH1 signal sequence (underlined) upstream of genomic DNA encoding mature Gz43A (SEQ ID NO:82). FIG. 73E: depicts coding sequence for a construct comprising a CBH1 signal sequence (underlined) upstream of genomic DNA encoding mature Fo43A (SEQ ID NO:83). FIG. 73F: depicts codon optimized coding sequence for a construct comprising a CBH1 signal sequence (underlined) upstream of codon optimized DNA encoding mature Pf51A (SEQ ID NO:92).

FIGS. 74A-74B: FIG. 74A depicts nucleotide sequence encoding Pa3D (SEQ ID NO:93). FIG. 74B depicts amino acid sequence of Pa3D (SEQ ID NO:94). The predicted signal sequence is underlined, and the predicted conserved domains are in bold.

FIGS. 75A-75B: FIG. 75A depicts nucleotide sequence encoding Fv3G (SEQ ID NO:95). FIG. 75B depicts amino acid sequence of Fv3G (SEQ ID NO:96). The predicted signal sequence is underlined, and the predicted conserved domains are in bold.

FIGS. 76A-76B: FIG. 76A depicts nucleotide sequence encoding Fv3D (SEQ ID NO:97). FIG. 76B depicts amino acid sequence of Fv3D (SEQ ID NO:98). The predicted signal sequence is underlined, and the predicted conserved domains are in bold.

FIGS. 77A-77B: FIG. 77A depicts nucleotide sequence encoding Fv3C (SEQ ID NO:99). FIG. 77B depicts amino acid sequence of Fv3C (SEQ ID NO:100). The predicted signal sequence is underlined, and the predicted conserved domains are in bold.

FIGS. 78A-78B: FIG. 78A depicts nucleotide sequence encoding Tr3A (SEQ ID NO:101). FIG. 78B depicts amino acid sequence of Tr3A (SEQ ID NO:102). The predicted signal sequence is underlined, and the predicted conserved domains are in bold.

FIGS. 79A-79B: FIG. 79A depicts nucleotide sequence encoding Tr3B (SEQ ID NO:103). FIG. 79B depicts amino acid sequence of Tr3B (SEQ ID NO:104). The predicted signal sequence is underlined, and the predicted conserved domains are in bold.

FIGS. 80A-80B: FIG. 80A depicts nucleotide sequence encoding Te3A (SEQ ID NO:105). FIG. 80B depicts amino acid sequence of Te3A (SEQ ID NO:106). The predicted signal sequence is underlined, and the predicted conserved domains are in bold.

FIGS. 81A-81B: FIG. 81A depicts nucleotide sequence encoding An3A (SEQ ID NO:107). FIG. 81B depicts amino acid sequence of An3A (SEQ ID NO:108). The predicted signal sequence is underlined, and the predicted conserved domains are in bold.

FIGS. 82A-82B: FIG. 82A depicts nucleotide sequence encoding Fo3A (SEQ ID NO:109). FIG. 82B depicts amino acid sequence of Fo3A (SEQ ID NO:110). The predicted signal sequence is underlined, and the predicted conserved domains are in bold.

FIGS. 83A-83B: FIG. 83A depicts nucleotide sequence encoding Gz3A (SEQ ID NO:111). FIG. 83B depicts amino acid sequence of Gz3A (SEQ ID NO:112). The predicted signal sequence is underlined, and the predicted conserved domains are in bold.

FIGS. 84A-84B: FIG. 84A depicts nucleotide sequence encoding Nh3A (SEQ ID NO:113). FIG. 84B depicts amino acid sequence of Nh3A (SEQ ID NO:114). The predicted signal sequence is underlined, and the predicted conserved domains are in bold.

FIGS. 85A-85B: FIG. 85A depicts nucleotide sequence encoding Vd3A (SEQ ID NO:115). FIG. 85B depicts amino acid sequence of Vd3A (SEQ ID NO:116). The predicted signal sequence is underlined, and the predicted conserved domains are in bold.

FIGS. 86A-86B: FIG. 86A depicts nucleotide sequence encoding Pa3G (SEQ ID NO:117). FIG. 86B depicts amino acid sequence of Pa3G (SEQ ID NO:118). The predicted signal sequence is underlined, and the predicted conserved domains are in bold.

FIG. 87: depicts amino acid sequence encoding Tn3B (SEQ ID NO:119). The standard signal prediction program, Signal P (www.cbs.dtu.dk/services/SignalP/) provided no predicted signal.

FIG. 88: depicts a partial amino acid sequence alignment of the CBM domains of T. reesei Eg4 (SEQ ID NO:27) with Tr6A (SEQ ID NO:31) and with Tr7A (SEQ ID NO:32).

FIGS. 89A-89C: FIG. 89A depicts amino acid sequence of Eg6 (SEQ ID NO:33) from T. reesei. The bolded amino acid sequence is the predicted signal peptide sequence. FIG. 89B depicts amino acid sequence of S. coccosporum endoglucanase SEQ ID NO:34;

FIG. 89C depicts the nucleotide sequence encoding a GH61A from Thermoascus aurantiacus, SEQ ID NO:149.

FIGS. 90A-90I: FIG. 90A depicts amino acid sequence of Afu7A (SEQ ID NO:150), a homolog of CBH1 of T. reesei. FIG. 90B depicts amino acid sequence of Afu7B (SEQ ID NO:151), a homolog of CBH1 of T. reesei. FIG. 90C depicts amino acid sequence of Cg7A (SEQ ID NO:152), a homolog of CBH1 of T. reesei. FIG. 90D depicts amino acid sequence of Cg7B (SEQ ID NO:153), a homolog of CBH1 of T. reesei. FIG. 90E depicts amino acid sequence of Tt7A (SEQ ID NO:154), a homolog of CBH1 of T. reesei. FIG. 90F depicts amino acid sequence of Tt7B (SEQ ID NO:155), a homolog of CBH1 of T. reesei. FIG. 90G depicts amino acid sequence of St6A (SEQ ID NO:156), a homolog of CBH2 of T. reesei. FIG. 90H depicts amino acid sequence of St6B (SEQ ID NO:157), a homolog of CBH2 of *T. reesei*. FIG. 90I amino acid sequence of Tt6A (SEQ ID NO:158), a homolog of CBH2 of *T. reesei*.

DETAILED DESCRIPTION OF THE INVENTION

Figure 8A:
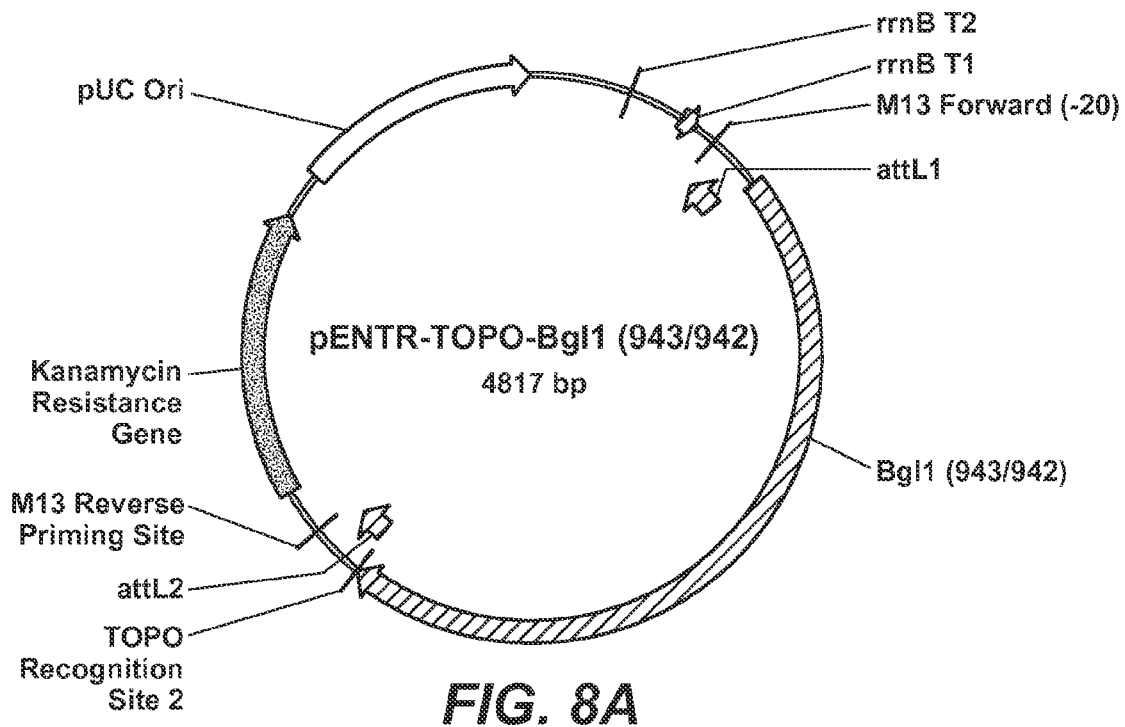
FIGS. 8A-8I.

Unless defined otherwise, all technical and scientific terms used herein have the meaning as commonly understood by a skilled person in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice of the present invention, the preferred methods and materials are described. Numeric ranges are inclusive of the numbers defining the range. The invention is not limited to the particular methodology, protocols, and reagents described, as these may vary.

The headings provided herein do not limit the various aspects or embodiments of the invention that can be had by reference to the specification as a whole. Accordingly the terms defined below are more fully defined by reference to the specification as a whole.

The present disclosure provides compositions comprising a polypeptide having glycosyl hydrolase family 61 ("GH61")/endoglucanase activity, polypeptides having GH61/endoglucanase activity, nucleotides encoding a polypeptide provided herein, vectors containing nucleotide provided herein, and cells containing nucleotide and/or vector provided herein. The present disclosure further provides methods of hydrolyzing a biomass material and methods of reducing the viscosity of a biomass-containing mixture using a composition provided herein.

The term "isolated" as used herein with respect to nucleic acids, such as DNA or RNA, refers to molecules separated from other DNAs or RNAs, respectively, which are present in the natural source of the nucleic acid. Moreover, by an "isolated nucleic acid" is meant to include nucleic acid fragments, which are not naturally occurring as fragments and would not be found in the natural state. The term "isolated" is also used herein to refer to polypeptides, which are isolated from other cellular proteins and is meant to encompass both purified and recombinant polypeptides. The term "isolated" as used herein also refers to a nucleic acid or polypeptide that may be substantially free of cellular material, viral material, or culture medium when produced by recombinant DNA techniques. The term "isolated" as used herein additionally refers to a nucleic acid or polypeptide that may be substantially free of chemical precursors or other chemicals when chemically synthesized.

As used herein, a "variant" of polypeptide X refers to a polypeptide having the amino acid sequence of polypeptide X with one or more altered amino acid residues. The variant may have conservative or nonconservative changes. Guidance in determining which amino acid residues may be substituted, inserted, or deleted without affecting biological activity may be found using computer programs known in the art, e.g., LASERGENE software (DNASTAR). A variant of the invention includes polypeptides comprising altered amino acid sequences in comparison with a precursor enzyme amino acid sequence, wherein the variant enzyme retains the characteristic cellulolytic nature of the precursor enzyme but may have altered properties in some specific aspects, e.g., an increased or decreased pH optimum, an increased or decreased oxidative stability; an increased or decreased thermostability, and increased or decreased level of specific activity towards one or more substrates, as compared to the precursor enzyme.

As used herein, a polypeptide or nucleic acid that is "heterologous" to a host cell refers to a polypeptide or nucleic acid that does not naturally occur in a host cell.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise.

It is understood that aspects and variations of the methods and compositions described herein include "consisting" and/or "consisting essentially of" aspects and variations.

Polypeptides

The disclosure provides polypeptides (e.g., isolated, synthetic, or recombinant polypeptides) having GH61/endoglucanase activity. For example, the present disclosure provides GH61 endoglucanases from various species or variants thereof, endoglucanase IV (or endoglucanase 4) polypeptides (also described herein as "Eg4" or "EG4", which are used interchangeably herein) from various species or variants thereof, and *Trichoderma reesei* Eg4 polypeptide or variants thereof. In some aspects, the polypeptide is isolated.

Glycoside hydrolase family 61 ("GH61") enzymes

Glycoside hydrolase family 61 ("GH61") enzymes have been identified in Eukaryota. A weak endoglucanase activity has been observed for Cel61A from *Hypocrea jecorina* (Karlsson et al, Eur J Biochem, 2001, 268(24):6498-6507), which is thus said to have GH61/endoglucanase activity. GH61 polypeptides potentiate enzymatic hydrolysis of lignocellulosic substrates by cellulases (Harris et al, 2010, Biochemistry, 49(15) 3305-16). Studies on homologous polypeptides involved in chitin degradation predict that GH61 polypeptides may employ an oxidative hydrolysis mechanism that requires an electron donor substrate and in which divalent metal ions are involved (Vaaje-Kolstad, 2010, Science, 330(6001), 219-22). This agrees with the observation that the synergistic effect of GH61 polypeptides on lignocellulosic substrate degradation is dependent on divalent ions (Harris et al, 2010, Biochemistry, 49(15) 3305-16). A number of available structures of GH61 polypeptides have divalent atoms bound by a number of conserved amino acid residues (Karkehabadi, 2008, J. Mol. Biol., 383(1) 144-54; Harris et al, 2010, Biochemistry, 49(15) 3305-16). It has been reported that the GH61 polypeptides have a flat surface at the metal binding site that is formed by conserved residues and might be involved in substrate binding (Karkehabadi, 2008, J. Mol. Biol., 383(1), 144-54).

The present disclosure provides polypeptides having GH61/endoglucanase activity (e.g., isolated polypeptide) which can be a GH61 endoglucanase or endoglucanase IV ("EG IV") from various species, or can also be a polypeptide from various species corresponding to (sharing homology with, sharing functional domains, sharing GH61 motif(s), and/or sharing conservative residues with) a GH61 endoglucanase (e.g., a *Trichoderma reesei* Eg4 polypeptide). Such species include *Trichoderma, Humicola, Fusarium, Aspergillus, Neurospora, Penicillium, Cephalosporium, Achlya, Podospora, Endothia, Mucor, Cochliobolus, Pyricularia, Chrysosporium, Aspergillus awamori, Aspergillus fumiga-*

*tus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei, Trichoderma viride, Geosmithia emersonii,* or *G. stearothermophilus.*

Polypeptides having GH61/endoglucanase activity include a number of GH61 endoglucanases listed in FIG. 1. For example, suitable GH61 endoglucanases include those comprising amino acid sequences that are at least about 60% identical to the various sequences listed in FIG. 1, including, for example, those represented by their GenBank Accession Numbers CAB97283.2, CAD70347.1, CAD21296.1, CAE81966.1, CAF05857.1, EAA26873.1, EAA29132.1, EAA30263.1, EAA33178.1, EAA33408.1, EAA34466.1, EAA36362.1, EAA29018.1, and EAA29347.1, or St61 from *S. thermophilum* 24630, St61A from *S. thermophilum* 23839c, St61B from *S. thermophilum* 46583, St61D from *S. thermophilum* 80312, Afu61a from *A. fumigatus* Afu3g03870 (NCBI Ref: XP_748707), an endoglucanase having NCBI Ref: XP_750843.1 from *A. fumigatus* Afu6g09540, an endoglucanase from *A. fumigatus* EDP47167, an endoglucanase from *T. terrestris* 16380, an endoglucanase from *T. terrestris* 155418, an endoglucanase from *T. terrestris* 68900, Cg61A (Accession Number EAQ86340.1) from *C. globosum, T. reesei* Eg7, *T. reesei* Eg4, and an endoglucanase with GenBank Accesssion Number XP_752040 from *A. fumigatus* Af293. In some aspects, a suitable GH61 endoglucanase polypeptide of the invention comprises an amino acid sequence of at least about 60% (e.g., at least about 60%, 65%, 70%, 75%, 80%, 85%, 90%, 91%, 92%, 93%, 94%, 95%, 96%, 97%, 98%, 99%) sequence identity to any one of SEQ ID NOs: 1-29 and 148. In some aspects, a suitable GH61 endoglucanase polypeptide of the invention comprises one or more of the amino acid sequence motifs selected from: (1) SEQ ID NOs:84 and 88; (2) SEQ ID NOs:85 and 88; (3) SEQ ID NO:86; (4) SEQ ID NO:87; (5) SEQ ID NOs:84, 88 and 89; (6) SEQ ID NOs:85, 88, and 89; (7) SEQ ID NOs: 84, 88, and 90; (8) SEQ ID NOs: 85, 88 and 90; (9) SEQ ID NOs:84, 88 and 91; (10) SEQ ID NOs: 85, 88 and 91; (11) SEQ ID NOs: 84, 88, 89 and 91; (12) SEQ ID NOs: 84, 88, 90 and 91; (13) SEQ ID NOs: 85, 88, 89 and 91: and (14) SEQ ID NOs: 85, 88, 90 and 91. The polypeptide may be at least 100 (e.g., 110, 120, 130, 140, 150, 160, 170, 180, 200, 220, 250 or more) residues in length.

Polypeptides having GH61/endoglucanase activity (e.g., isolated polypeptide) provided herein may also be a variant of a GH61 endoglucanase, e.g., any of the polypeptides with amino acid sequences shown FIG. 1 of the present disclosure. For example, suitable GH61 endoglucanases include those represented by their GenBank Accession Numbers CAB97283.2, CAD70347.1, CAD21296.1, CAE81966.1, CAF05857.1, EAA26873.1, EAA29132.1, EAA30263.1, EAA33178.1, EAA33408.1, EAA34466.1, EAA36362.1, EAA29018.1, and EAA29347.1, or St61 from *S. thermophilum* 24630, St61A from *S. thermophilum* 23839c, St61B from *S. thermophilum* 46583, St61D from *S. thermophilum* 80312, Afu61a from *A. fumigatus* Afu3g03870 (NCBI Ref: XP_748707), an endoglucanase with NCBI Ref: XP_750843.1 from *A. fumigatus* Afu6g09540, an endoglucanase from *A. fumigatus* EDP47167, an endoglucanase from *T. terrestris* 16380, an endoglucanase from *T. terrestris* 155418, an endoglucanase from *T. terrestris* 68900, Cg61A (EAQ86340.1) from *C. globosum, T. reesei* Eg7, *T. reesei* Eg4, and an endoglucanase with GenBank Accession: XP_752040 from *A. fumigatus* Af293. In some aspects, the polypeptide having GH61/endoglucanase activity (e.g., isolated polypeptide) is a variant of EG IV. In some aspects, the polypeptide having GH61/endoglucanase activity (e.g., isolated polypeptide) is a variant of a GH61 endoglucanase, wherein the variant has an amino acid sequence having at least about 60% (e.g., at least about 60%, 65%, 70%, 75%, 80%, 85%, 90%, 95%, 96%, 97%, 98%, or 99%) identity as any one of the amino acid sequences SEQ ID NOs: 1-29 and 148.

Figure 3C:
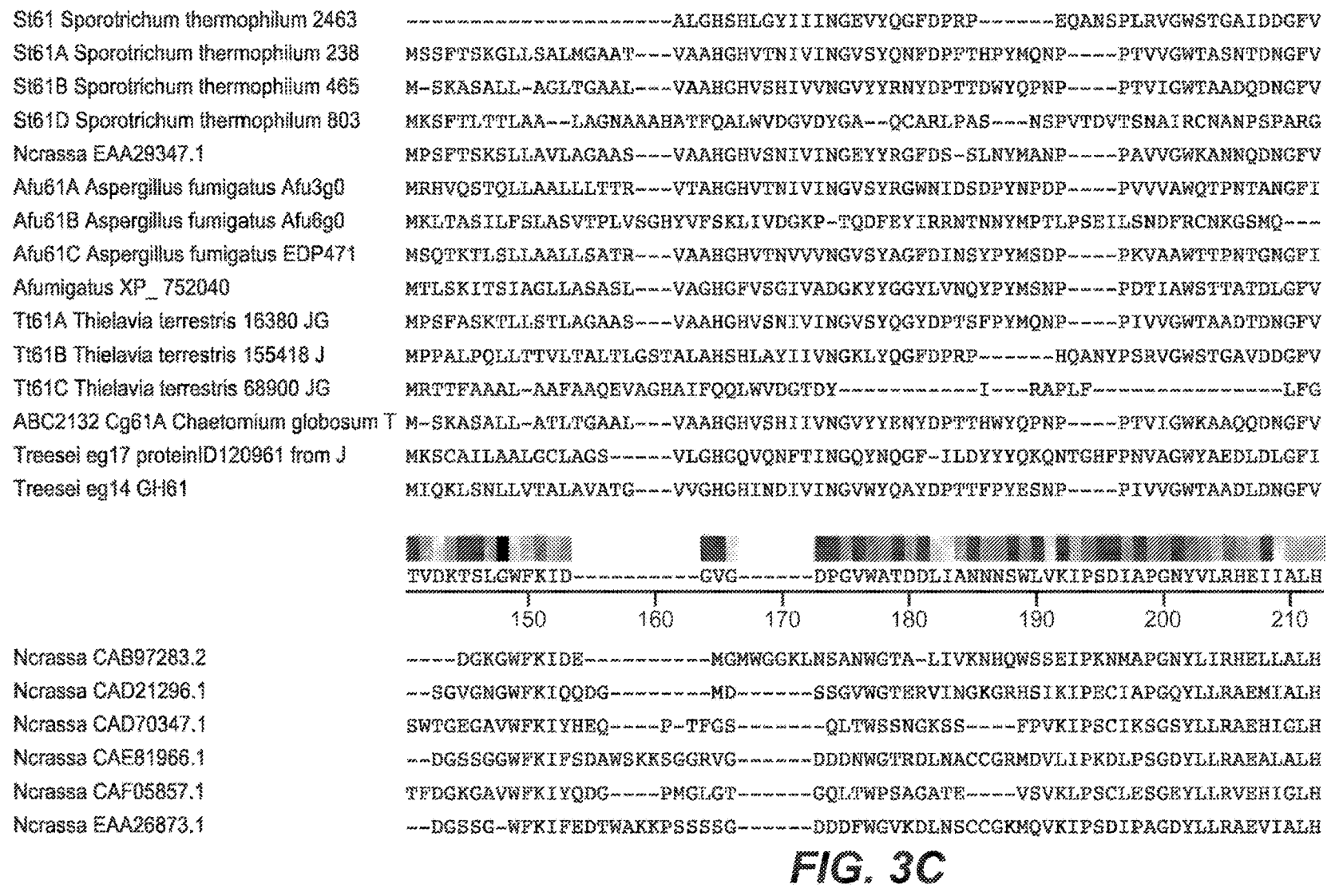

An alignment using amino acid sequences SEQ ID NOs: 1-29 and 148 was performed and the alignment result is shown in FIG. 3. FIG. 2 shows the percent identity and divergence results from comparison of the amino acid sequences of the polypeptides. The alignment indicated that the GH61 endoglucanase polypeptides share certain sequence motifs, and such motifs are shown in FIG. 7 of the present disclosure.

Accordingly, the present disclosure provides polypeptides (e.g., isolated, synthetic, or recombinant polypeptides) having GH61/endoglucanase activity, which may be a GH61 endoglucanase or a variant thereof, and the variant may comprise at least one motif (at least any of 2, 3, 4, 5, 6, 7, or 8) selected from SEQ ID NOs:84-91. Each of the "a" s in sequence motifs with SEQ ID NOs:84-91 (described in FIG. 7) represents an amino acid that may be any one of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine. For example, in some aspects, the disclosure provides polypeptides (e.g., isolated, synthetic, or recombinant polypeptides) comprising at least one sequence motif, such as at least one (e.g., 2, 3, 4, 5, 6, 7, or 8) of SEQ ID NOs: 84, 85, 86, 87, 88, 89, 90, and 91. In some aspects, the disclosure provides polypeptides (e.g., isolated, synthetic, or recombinant polypeptides) comprising one or more of the sequence motifs selected from the group consisting of: (1) SEQ ID NOs:84 and 88; (2) SEQ ID NOs:85 and 88; (3) SEQ ID NO:86; (4) SEQ ID NO:87; (5) SEQ ID NOs:84, 88 and 89; (6) SEQ ID NOs:85, 88, and 89; (7) SEQ ID NOs: 84, 88, and 90; (8) SEQ ID NOs: 85, 88 and 90; (9) SEQ ID NOs:84, 88 and 91; (10) SEQ ID NOs: 85, 88 and 91; (11) SEQ ID NOs: 84, 88, 89 and 91; (12) SEQ ID NOs: 84, 88, 90 and 91; (13) SEQ ID NOs: 85, 88, 89 and 91: and (14) SEQ ID NOs: 85, 88, 90 and 91, over a region of at least about 10, e.g., at least about any of 15, 20, 25, 30, 35, 40, 45, 50, 55, 60, 65, 70, 75, 80, 85, 90, 95, 100, 125, 150, 175, 200, 225, 250, 275, 300, 325, or 350 residues, or over the full length of the immature polypeptide, the full length mature polypeptide, the full length of the conserved domain, and/or the full length CBM. The conserved domain can be a predicted catalytic domain ("CD"). Exemplary polypeptides also include fragments of at least about 10, e.g., at least about any of 15, 20, 25, 30, 35, 40, 45, 50, 75, 80, 85, 90, 95, 100, 150, 200, 250, 300, 350, 400, 450, 500, 550, or 600 residues in length. The fragments can comprise a conserved domain and/or a CBM. Where a fragment comprises a conserved domain and a CBM of an enzyme, the fragment optionally includes a linker separating the two. The linker can be a native linker or a heterologous linker. In some aspects, the polypeptide has GH61/endoglucanase activity.

In some aspects, the polypeptide having GH61/endoglucanase activity is a GH61 endoglucanase or a variant thereof, an enzyme comprising any one of SEQ ID NOs: 1-29 and 148, or a variant thereof, an EG IV or a variant thereof, or a T. reesei Eg4 or a variant thereof. A variant described here has endoglucanase activity. The polypeptide having GH61/endoglucanase activity (including a variant) may comprise a CBM domain (e.g., functional CBM domain). The polypeptide having GH61/endoglucanase activity (including a variant) may comprise a catalytic domain (e.g., function catalytic domain).

T. reesei Eg4 is a GH61 endoglucanase polypeptide. The amino acid sequence of T. reesei Eg4 (SEQ ID NO:27) is shown in FIGS. 1, 4B and 5. SEQ ID NO:27 is the sequence of the immature T. reesei Eg4. T. reesei Eg4 has a predicted signal sequence corresponding to residues 1 to 21 of SEQ ID NO:27 (underlined); cleavage of the signal sequence is predicted to yield a mature polypeptide having a sequence corresponding to residues 22 to 344 of SEQ ID NO:27. The predicted conserved domains correspond to residues 22-256 and 307-343 of SEQ ID NO:27, with the latter being the predicted carbohydrate-binding domain (CBM). T. reesei Eg4 was shown to have endoglucanse activity in, for example, an enzymatic assay using carboxy methyl cellulose as substrates. Methods of measuring endoglucanse activity are also known to one skilled in the art.

The disclosure further provides a variant of Trichoderma reesei Eg4 polypeptide, which may comprise a sequence having at least about 60% (e.g., at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) sequence identity to at least about 50 (e.g., at least about 55, 60, 65, 70, 75, 100, 125, 150, 175, 200, 250, or 300) contiguous amino acid residues among residues 22 to 344 of SEQ ID NO:27. For example, the disclosure provides variants of T. reesei Eg4 polypeptide. Such variants may have at least about 70% (e.g., at least about 70%, 75%, 80%, 85%, 88%, 90%, 92.5%, 95%, 96%, 97%, 98%, or 99%) identity to residues 22 to 344 of SEQ ID NO:27. The polypeptide or a variant thereof may be isolated. The polypeptide or a variant thereof may have endoglucanase activity.

T. reesei Eg4 residues H22, H107, H184, Q193, and Y195 were predicted to function as metal coordinator residues; residues D61 and G63 were predicted to be conserved surface residues; and residue Y232 were predicted to be involved in activity, based on an amino acid sequence alignment of a number of known endoglucanases, e.g., an endoglucanase from T. terrestris (Accession No. ACE10234, also termed "TtEG" herein) (SEQ ID NO:29), and another endoglucanse Eg7 (Accession No. ADA26043.1) from T. reesei (also termed "TrEGb" or "TrEG7" herein), with T. reesei Eg4 (see, FIG. 5). The predicted conserved residues in T. reesei Eg4 A are shown in FIGS. 6A and 6B. A variant of T. reesei Eg4 polypeptide may be unaltered, as compared to a native T. reesei Eg4, at residues H22, H107, H184, Q193, Y195, D61, G63, and Y232. A variant of T. reesei Eg4 polypeptide may be unaltered in at least 60%, 70%, 80%, 90%, 95%, 98%, or 99% of the amino acid residues that are conserved among TrEGb, TtEG, and T. reesei Eg4, as shown in the alignment of FIG. 5. A variant of T. reesei Eg4 polypeptide may comprise the entire predicted conserved domains of native T. reesei Eg4. See FIGS. 5 and 6. An exemplary variant of T. reesei Eg4 polypeptide comprises a sequence having at least about any of 70%, 75%, 80%, 85%, 86%, 87%, 88%, 89%, 90%, 91%, 92%, 93%, 94%, 95%, 96%, 97%, 98%, 99%, or 100% identity to the mature T. reesei Eg4 sequence shown in FIG. 4B (e.g., residues 22 to 344 of SEQ ID NO:27). In some aspects, the variant of T. reesei Eg4 polypeptide has endoglucanse (e.g., endoglucanse IV (EGIV)) activity.

In some aspects, a variant of T. reesei Eg4 polypeptide has endoglucanase activity and comprises an amino acid sequence with at least about any of 60%, 65%, 70%, 75%, 80%, 85%, 86%, 87%, 88%, 89%, 90%, 91%, 92%, 93%, 94%, 95%, 96%, 97%, 98%, 99% or 100% sequence identity to the amino acid sequence of SEQ ID NO:27, or to residues (i) 22-255, (ii) 22-343, (iii) 307-343, (iv) 307-344, or (v) 22-344 of SEQ ID NO:27.

In some aspects, the polypeptide or a variant thereof comprises residues corresponding to at least about 3 residues (e.g., at least about any of 4, 5, 6, 7, 8, 9, 10, 11, or 12) of H22, D61, G63, C77, H107, R177, E179, H184, Q193, C198, Y195, and Y232 of SEQ ID NO:27. In some aspects, the polypeptide or a variant thereof comprises residues corresponding to H22, D61, G63, C77, H107, R177, E179, H184, Q193, C198, Y195, and Y232 of SEQ ID NO:27. In some aspects, the polypeptide or a variant thereof comprises residues corresponding to at least 3 residues (e.g., at least about any of 4, 5, 6, 7, 8, 9, 10, 11, 12, 13, 14, 15, 16, 17, 18, or 19) of G313, Q314, C315, G316, G317, S321, G322, P323, T324, C326, A327, T331, C332, N336, Y338, Y339, Q341, C342, and L343 of SEQ ID NO:27. In some aspects, the polypeptide or a variant thereof comprises residues corresponding to G313, Q314, C315, G316, G317, S321, G322, P323, T324, C326, A327, T331, C332, N336, Y338, Y339, Q341, C342, and L343 of SEQ ID NO:27. In some aspects, the polypeptide or a variant thereof comprises a CBM domain (e.g., functional CBM domain). In some aspects, the polypeptide or a variant thereof comprises a catalytic domain (e.g., functional catalytic domain). The polypeptide suitably has endoglucanase activity.

A variant of GH61 endoglucanase, an endoglucanase comprising any one of SEQ ID NOs:1-29 and 148, an EG IV, or Trichoderma reesei Eg4 polypeptide may be made using amino acid substitution. Conservative substitutions are shown in the table below under the heading of "conservative substitutions". Substitutions may also be exemplary substitution shown in the table below.

TABLE 1

Amino Acid Substitutions.

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |

TABLE 1-continued

Amino Acid Substitutions.

| Original Residue | Conservative Substitutions | Exemplary Substitutions |
|---|---|---|
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the enzymatic properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class. Any cysteine residue not involved in maintaining the proper conformation of the polypeptide also may be substituted, generally with serine, to improve the oxidative stability of the molecule and prevent aberrant cross-linking. Conversely, cysteine bond(s) may be added to the polypeptide to improve its stability.

In some aspects, a polypeptide (e.g., isolated, synthetic, or recombinant polypeptide) having GH61/endoglucanase activity is a fusion or chimeric polypeptide that includes a domain of a polypeptide of the present disclosure attached to one or more fusion segments, which are typically heterologous to the polypeptide (e.g., derived from a different source than the polypeptide of the disclosure). Suitable fusion or chimeric segments include, without limitation, segments that can enhance a polypeptide's stability, provide other desirable biological activity or enhanced levels of desirable biological activity, and/or facilitate purification of the polypeptide (e.g., by affinity chromatography). A suitable fusion segment can be a domain of any size that has the desired function (e.g., imparts increased stability, solubility, action or biological activity; and/or simplifies purification of a polypeptide). A fusion or hybrid polypeptide of the invention can be constructed from two or more fusion or chimeric segments, each of which or at least two of which are derived from a different source or microorganism. Fusion or hybrid segments can be joined to amino and/or carboxyl termini of the domain(s) of a polypeptide of the present disclosure. The fusion segments can be susceptible to cleavage. There may be some advantage in having this susceptibility, for example, it may enable straight-forward recovery of the polypeptide of interest. Fusion polypeptides may be produced by culturing a recombinant cell transfected with a fusion nucleic acid that encodes a polypeptide, which includes a fusion segment attached to either the carboxyl or amino terminal end, or fusion segments attached to both the carboxyl and amino terminal ends, of a polypeptide, or a domain thereof.

Accordingly, polypeptides of the present disclosure also include expression products of gene fusions (e.g., an overexpressed, soluble, and active form of expression product), of mutagenized genes (e.g., genes having codon modifications to enhance gene transcription and translation), and of truncated genes (e.g., genes having signal sequences removed or substituted with a heterologous signal sequence).

Glycosyl hydrolases that utilize insoluble substrates are often modular enzymes. They may comprise catalytic modules appended to one or more non-catalytic carbohydrate-binding domains (CBMs). In nature, CBMs are thought to promote the glycosyl hydrolase's interaction with its target substrate polysaccharide. Thus, the disclosure provides chimeric enzymes having altered substrate specificity; including, for example, chimeric enzymes having multiple substrates as a result of "spliced-in" heterologous CBMs. The heterologous CBMs of the chimeric enzymes of the disclosure can also be designed to be modular, such that they are appended to a catalytic module or catalytic domain (a "CD", e.g., at an active site), which can likewise be heterologous or homologous to the glycosyl hydrolase.

Thus, the disclosure provides peptides and polypeptides consisting of, or comprising, CBM/CD modules, which can be homologously paired or joined to form chimeric (heterologous) CBM/CD pairs. Thus, these chimeric polypeptides/peptides can be used to improve or alter the performance of an enzyme of interest.

In some aspects, there is provided a polypeptide having GH61/endoglucanase activity, which comprises at least one CD and/or CBM of any one of the polypeptides with sequences shown in FIG. 1 of the present disclosure. For example, suitable GH61 endoglucanase polypeptides of FIG. 1 includes those that are represented by their GenBank Accession Numbers CAB97283.2, CAD70347.1, CAD21296.1, CAE81966.1, CAF05857.1, EAA26873.1, EAA29132.1, EAA30263.1, EAA33178.1, EAA33408.1, EAA34466.1, EAA36362.1, EAA29018.1, and EAA29347.1, or St61 from *S. thermophilum* 24630, St61A from *S. thermophilum* 23839c, St61B from *S. thermophilum* 46583, St61D from *S. thermophilum* 80312, Afu61a from *A. fumigatus* Afu3g03870 (NCBI Ref: XP_748707), an endoglucanase of NCBI Ref: XP_750843.1 from *A. fumigatus* Afu6g09540, an endoglucanase of *A. fumigatus* EDP47167, an endoglucanase of *T. terrestris* 16380, an endoglucanase of *T. terrestris* 155418, an endoglucanase of *T. terrestris* 68900, Cg61A (EAQ86340.1) from *C. globosum*, *T. reesei* Eg7, *T. reesei* Eg4, and an endoglucanase with GenBank Accession: XP_752040 from *A. fumigatus* Af293. The polypeptide may suitably be a fusion polypeptide comprising functional domains from two or more different polypeptides (e.g., a CBM from one polypeptide linked to a CD from another polypeptide).

The polypeptides of the disclosure can suitably be obtained and/or used in "substantially pure" form. For example, a polypeptide of the disclosure constitutes at least about 80 wt. % (e.g., at least about any of 85 wt. %, 90 wt. %, 91 wt. %, 92 wt. %, 93 wt. %, 94 wt. %, 95 wt. %, 96 wt. %, 97 wt. %, 98 wt. %, or 99 wt. %) of the total protein in a given composition, which also includes other ingredients such as a buffer or solution.

Also the polypeptides of the disclosure may suitably be obtained and/or used in culture broths (e.g., a filamentous fungal culture broth). The culture broth may be an engineered enzyme composition, e.g., the culture broth may be produced by a recombinant host cell engineered to express a heterologous polypeptide of the disclosure, or by a recombinant host cell engineered to express an endogenous polypeptide of the disclosure in greater or lesser amounts than the endogenous expression levels (e.g., in an amount that is 1-, 2-, 3-, 4-, 5-, or more-fold greater or less than the endogenous expression levels). Furthermore, the culture broths may be produced by certain "integrated" host cell strains that are engineered to express a plurality of the polypeptides of the disclosure in desired ratios. Nucleic acids, expression cassettes, vectors, and host cells The disclosure provides nucleic acids (e.g., isolated, synthetic or recombinant nucleic acids) encoding polypeptides provided above, e.g., polypeptides having GH61/endoglucanase activity, GH61 endoglucanase or a variant thereof, EG IV or a variant thereof, *T. reesei* Eg4 or a variant thereof. In certain aspects, the disclosure provides nucleic acids (e.g., isolated, synthetic or recombinant nucleic acids) encoding a polypeptide comprising any one of SEQ ID NOs:1-29 and 148, or a polypeptide having at least about 60%, 65%, 70%, 75%, 80%, 85%, 86%, 87%, 88%, 89%, 90%, 91%, 92%, 93%, 94%, 95%, 96%, 97%, 98%, 99% or 100% identity to any one of SEQ ID NOs: 1-29 and 148.

In certain aspects, the disclosure provides nucleic acids (e.g., isolated, synthetic or recombinant nucleic acids) encoding any one of the polypeptides having GH61/endoglucanase activity (including a variant of a GH61 endoglucanase) comprising one or more sequence motif selected from: (1) SEQ ID NOs:84 and 88; (2) SEQ ID NOs:85 and 88; (3) SEQ ID NO:86; (4) SEQ ID NO:87; (5) SEQ ID NOs:84, 88 and 89; (6) SEQ ID NOs:85, 88, and 89; (7) SEQ ID NOs: 84, 88, and 90; (8) SEQ ID NOs: 85, 88 and 90; (9) SEQ ID NOs:84, 88 and 91; (10) SEQ ID NOs: 85, 88 and 91; (11) SEQ ID NOs: 84, 88, 89 and 91; (12) SEQ ID NOs: 84, 88, 90 and 91; (13) SEQ ID NOs: 85, 88, 89 and 91: and (14) SEQ ID NOs: 85, 88, 90 and 91. The disclosure further provides nucleic acids (e.g., isolated, synthetic or recombinant nucleic acids) encoding a polypeptide having GH61/endoglucanase activity (including a variant of a GH61 endoglucanase) that comprises a CBM domain (e.g., functional CBM domain) and/or catalytic domain (e.g., functional catalytic domain).

The disclosure further provides nucleic acids (e.g., isolated, synthetic or recombinant nucleic acids) encoding variants of *T. reesei* Eg4 polypeptide. Such variants may have at least about 60% (e.g., at least about any of 60%, 65%, 70%, 75%, 80%, 85%, 88%, 90%, 92.5%, 95%, 96%, 97%, 98%, or 99%) sequence identity to residues 22 to 344 of SEQ ID NO:27. In some aspects, the polypeptide or a variant thereof has endoglucanase activity. The polypeptide or a variant thereof may comprise residues corresponding to at least about 5 residues (e.g., at least about any of 6, 7, 8, 9, 10, 11, or 12) of H22, D61, G63, C77, H107, R177, E179, H184, Q193, C198, Y195, and Y232 of SEQ ID NO:27. The polypeptide or a variant thereof may comprise residues corresponding to H22, D61, G63, C77, H107, R177, E179, H184, Q193, C198, Y195, and Y232 of SEQ ID NO:27. The polypeptide or a variant thereof may comprise residues corresponding to at least 5 residues (e.g., at least about any of 6, 7, 8, 9, 10, 11, 12, 13, 14, 15, 16, 17, 18, or 19) of G313, Q314, C315, G316, G317, S321, G322, P323, T324, C326, A327, T331, C332, N336, Y338, Y339, Q341, C342, and L343 of SEQ ID NO:27. In some aspects, the polypeptide or a variant thereof comprises residues corresponding to G313, Q314, C315, G316, G317, S321, G322, P323, T324, C326, A327, T331, C332, N336, Y338, Y339, Q341, C342, and L343 of SEQ ID NO:27.

The disclosure provides nucleic acids (e.g., isolated, synthetic or recombinant nucleic acids) comprising a nucleic acid sequence having at least about 70%, e.g., at least about any of 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, or 99%, or complete (100%) identity to nucleic acid sequence SEQ ID NO:30, over a region of at least about 10, e.g., at least about any of 15, 20, 25, 30, 35, 40, 45, 50, 75, 100, 150, 200, 250, 300, 350, 400, 450, 500, 550, 600, 650, 700, 750, 800, 850, 900, 950, 1000, or 1050 nucleotides. In some aspects, the disclosure provides nucleic acids encoding any one of the polypeptides provided herein. Also provided herein are isolated nucleic acids having at least about 80% (e.g., at least about any of 85%, 88%, 90%, 92.5%, 95%, 96%, 97%, 98%, or 99%) identity to SEQ ID NO:30.

In some aspects, there is provided a nucleic acid (e.g., isolated, synthetic or recombinant nucleic acid) encoding a polypeptide comprising an amino acid sequence with at least 75%, 80%, 85%, 90%, 91%, 92%, 93%, 94%, 95%, 96%, 97%, 98%, 99% or 100% sequence identity to the amino acid sequence of SEQ ID NO:27, or to residues (i) 22-255, (ii) 22-343, (iii) 307-343, (iv) 307-344, or (v) 22-344 of SEQ ID NO:27. In some aspects, there is provided a nucleic acid (e.g., isolated, synthetic or recombinant nucleic acid) having at least 70% (e.g., at least 70%, 75%, 80%, 85%, 90%, 91%, 92%, 93%, 94%, 95%, 96%, 97%, 98%, 99% or more) sequence identity to SEQ ID NO:30, or a nucleic acid that is capable of hybridizing under high stringency conditions to a complement of SEQ ID NO:30, or to a fragment thereof. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6. Aqueous and nonaqueous methods are described in that reference and either method can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2.×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions unless otherwise specified.

The disclosure also provides expression cassettes and/or vectors comprising any of the above-described nucleic acids. The nucleic acid encoding a polypeptide such as an enzyme of the disclosure may be operably linked to a promoter. Specifically where recombinant expression in a filamentous fungal host is desired, the promoter can be a filamentous fungal promoter. The nucleic acids can be, e.g., under the control of heterologous promoters. The nucleic acids can also be expressed under the control of constitutive or inducible promoters. Examples of promoters that can be used include, but are not limited to, a cellulase promoter, a xylanase promoter, the 1818 promoter (previously identified as a highly expressed protein by EST mapping Trichoderma). For example, the promoter can suitably be a cellobiohydrolase, endoglucanase, or β-glucosidase promoter. A particularly suitable promoter can be, for example, a T. reesei cellobiohydrolase, endoglucanase, or β-glucosidase promoter. For example, the promoter is a cellobiohydrolase I (cbh1) promoter. Non-limiting examples of promoters include a cbh1, cbh2, egl1, egl2, egl3, egl4, egl5, pki1, gpd1, xyn1, or xyn2 promoter. Additional non-limiting examples of promoters include a T. reesei cbh1, cbh2, egl1, egl2, egl3, egl4, egl5, pki1, gpd1, xyn1, or xyn2 promoter.

As used herein, the term "operably linked" means that selected nucleotide sequence (e.g., encoding a polypeptide described herein) is in proximity with a promoter to allow the promoter to regulate expression of the selected DNA. In addition, the promoter is located upstream of the selected nucleotide sequence in terms of the direction of transcription and translation. By "operably linked" is meant that a nucleotide sequence and a regulatory sequence(s) are connected in such a way as to permit gene expression when the appropriate molecules (e.g., transcriptional activator proteins) are bound to the regulatory sequence(s).

The present disclosure further provides host cells containing any of the polynucleotides vectors, or expression cassettes described herein. The present disclosure also provides host cells that can be used to express one or more polypeptides of the disclosure. Suitable host cells include cells of any microorganism (e.g., cells of a bacterium, a protist, an alga, a fungus (e.g., a yeast or filamentous fungus), or other microbe), and are preferably cells of a bacterium, a yeast, or a filamentous fungus.

Suitable host cells of the bacterial genera include, but are not limited to, cells of *Escherichia, Bacillus, Lactobacillus, Pseudomonas*, and *Streptomyces*. Suitable cells of bacterial species include, e.g., cells of *Escherichia coli, Bacillus subtilis, Bacillus licheniformis, Lactobacillus brevis, Pseudomonas aeruginosa*, or *Streptomyces lividans*.

Suitable host cells of the genera of yeast include, but are not limited to, cells of *Saccharomyces, Schizosaccharomyces, Candida, Hansenula, Pichia, Kluyveromyces*, and *Phaffia*. Suitable cells of yeast species include, but are not limited to, cells of *Saccharomyces cerevisiae, Schizosaccharomyces pombe, Candida albicans, Hansenula polymorpha, Pichia pastoris, P. canadensis, Kluyveromyces marxianus*, and *Phaffia rhodozyma*.

Suitable host cells of filamentous fungi include all filamentous forms of the subdivision Eumycotina. Suitable cells of filamentous fungal genera include, but are not limited to, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*. Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

The disclosure provides a host cell, e.g., a recombinant fungal host cell or a recombinant filamentous fungus, engineered to recombinantly express a polypeptide having GH61/endoglucanase activity (e.g., T. reesei Eg4 or a variant thereof).

The present disclosure also provides a recombinant host cell e.g., a recombinant fungal host cell or a recombinant microorganism, e.g., a filamentous fungus, such as a recombinant T. reesei, that is engineered to recombinantly express T. reesei Xyn3, T. reesei Bgl1 (also termed "Tr3A"), Fv3A, Fv43D, and Fv51A polypeptides. For example, the recombinant host cell is suitably a T. reesei host cell. The recombinant fungus is suitably a recombinant T. reesei. The disclosure provides, for example, a T. reesei host cell engineered to recombinantly express T. reesei Eg4, T. reesei Xyn3, T. reesei Bgl1, Fv3A, Fv43D, and Fv51A polypeptides. Alternatively the present disclosure also provides a recombinant host cell or a recombinant microorganism that is, e.g., an *Aspergillus* (such as an *A. oryzae, A. niger*) host cell or a recombinant *Aspergillus* engineered to recombinantly express the polypeptides described herein.

Additionally the disclosure provides a recombinant host cell or recombinant organism that is engineered to express an enzyme blend comprising suitable enzymes in ratios suitable for saccharification. The recombinant host cell is, for example, a fungal host cell or a bacterial host cell. The recombinant fungus is, e.g., a recombinant T. reesei, A. oryzae, A. niger, or yeast. The recombinant fungal host cell may be, e.g., a T. reesei, A. oryzae, A. niger, or yeast cell. The recombinant bacterial host cell may be, e.g., a *Bascillus subtilis*, or an *E. coli* cell. The recombinant bacterial organism may be, e.g., a *Bascillus subtilis* or an *E. coli*. Examples of enzyme ratios/amounts present in suitable enzyme blends are described herein such as below.

Compositions

The disclosure also provides compositions (e.g., non-naturally occurring compositions) such as enzyme compositions containing cellulase(s) and/or hemicellulase(s), which can be used to hydrolyze biomass material and/or reduce the viscosity of biomass mixture (e.g., biomass saccharification mixture containing enzyme and substrate).

Cellulases include enzymes capable of hydrolyzing cellulose (beta-1,4-glucan or beta D-glucosidic linkages) polymers to glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and β-glucosidases (β-D-glucoside glucohydrolase; EC 3.2.1.21) ("BG") (Knowles et al., 1987, Trends in Biotechnology 5(9):255-261; Shulein, 1988, Methods in Enzymology, 160:234-242). Endoglucanases act mainly on the amorphous parts of the cellulose fiber, whereas cellobiohydrolases are also able to degrade crystalline cellulose. Hemicellulases include, for example, xylanases, β-xylosidases, and L-α-arabinofuranosidases.

The composition of the invention may be a multi-enzyme blend, comprising more than one enzyme. The enzyme composition of the invention can suitably include one or more additional enzymes derived from other microorganisms, plants, or organisms. Synergistic enzyme combinations and related methods are contemplated. The disclosure includes methods for identifying the optimum ratios of the enzymes included in the enzyme compositions for degrading various types of biomass materials. These methods include, e.g., tests to identify the optimum proportion or relative weights of enzymes to be included in the enzyme composition of the invention in order to effectuate efficient conversion of various substrates (e.g., lignocellulosic substrates) to their constituent fermentable sugars.

The cell walls of higher plants are comprised of a variety of carbohydrate polymer (CP) components. These CP interact through covalent and non-covalent means, providing the structural integrity required to form rigid cell walls and resist turgor pressure in plants. The major CP found in plants is cellulose, which forms the structural backbone of the cell wall. During cellulose biosynthesis, chains of poly-β-1,4-D-glucose self associate through hydrogen bonding and hydrophobic interactions to form cellulose microfibrils, which further self-associate to form larger fibrils. Cellulose microfibrils are often irregular structurally and contain regions of varying crystallinity. The degree of crystallinity of cellulose fibrils depends on how tightly ordered the hydrogen bonding is between and among its component cellulose chains. Areas with less-ordered bonding, and therefore more accessible glucose chains, are referred to as amorphous regions. The general model for cellulose depolymerization to glucose involves a minimum of three distinct enzymatic activities. Endoglucanases cleave cellulose chains internally to shorter chains in a process that increases the number of accessible ends, which are more susceptible to exoglucanase activity than the intact cellulose chains. These exoglucanases (e.g., cellobiohydrolases) are specific for either reducing ends or non-reducing ends, liberating, in most cases, cellobiose, the dimer of glucose. The accumulating cellobiose is then subject to cleavage by cellobiases (e.g., β-1,4-glucosidases) to glucose. Cellulose contains only anhydro-glucose. In contrast, hemicellulose contains a number of different sugar monomers. For instance, aside from glucose, sugar monomers in hemicellulose can also include xylose, mannose, galactose, rhamnose, and arabinose. Hemicelluloses mostly contain D-pentose sugars and occasionally small amounts of L-sugars. Xylose is typically present in the largest amount, but mannuronic acid and galacturonic acid also tend to be present. Hemicelluloses include xylan, glucuronoxylan, arabinoxylan, glucomannan, and xyloglucan.

The compositions (e.g., enzymes and multi-enzyme compositions) of the disclosure can be used for saccharification of cellulose materials (e.g., glucan) and/or hemicellulose materials (e.g., xylan, arabinoxylan, and xylan- or arabinoxylan-containing substrates). The enzyme blend/composition is suitably a non-naturally occurring composition.

The enzyme compositions provided herein may comprise a mixture of xylan-hydrolyzing, hemicellulose- and/or cellulose-hydrolyzing enzymes, which include at least one, several, or all of a cellulase, including a glucanase; a cellobiohydrolase; an L-α-arabinofuranosidase; a xylanase; a β-glucosidase; and a β-xylosidase. The present disclosure also provides enzyme compositions that may be non-naturally occurring compositions. As used herein, the term "enzyme compositions" refers to: (1) a composition made by combining component enzymes, whether in the form of a fermentation broth or partially or completely isolated or purified; (2) a composition produced by an organism modified to express one or more component enzymes; in certain embodiments, the organism used to express one or more component enzymes can be modified to delete one or more genes; in certain other embodiments, the organism used to express one or more component enzymes can further comprise proteins affecting xylan hydrolysis, hemicellulose hydrolysis, and/or cellulose hydrolysis; (3) a composition made by combining component enzymes simultaneously, separately, or sequentially during a saccharification or fermentation reaction; (4) an enzyme mixture produced in situ, e.g., during a saccharification or fermentation reaction; (5) a composition produced in accordance with any or all of the above (1)-(4).

The term "fermentation broth" as used herein refers to an enzyme preparation produced by fermentation that undergoes no or minimal recovery and/or purification subsequent to fermentation. For example, microbial cultures are grown to saturation, incubated under carbon-limiting conditions to allow protein synthesis (e.g., expression of enzymes). Then, once the enzyme(s) are secreted into the cell culture media, the fermentation broths can be used. The fermentation broths of the disclosure can contain unfractionated or fractionated contents of the fermentation materials derived at the end of the fermentation. For example, the fermentation broths of the invention are unfractionated and comprise the spent culture medium and cell debris present after the microbial cells (e.g., filamentous fungal cells) undergo a fermentation process. The fermentation broth can suitably contain the spent cell culture media, extracellular enzymes, and live or killed microbial cells. Alternatively, the fermentation broths can be fractionated to remove the microbial cells. In those cases, the fermentation broths can, for example, comprise the spent cell culture media and the extracellular enzymes.

The enzyme compositions such as cellulase compositions provided herein may be capable of achieving at least 0.1 (e.g. 0.1 to 0.4) fraction product as determined by the calcofluor assay. All chemicals used were of analytical grade. Avicel PH-101 was purchased from FMC BioPolymer (Philadelphia, Pa.). Cellobiose and calcofluor white were purchased from Sigma (St. Louise, Mo.). Phosphoric acid swollen cellulose (PASC) was prepared from Avicel PH-101 using an adapted protocol of Walseth, TAPPI 1971, 35:228 and Wood, Biochem. J. 1971, 121:353-362. In short, Avicel was solubilized in concentrated phosphoric acid then precipitated using cold deionized water. After the cellulose is collected and washed with more water to neutralize the pH, it was diluted to 1% solids in 50 mM sodium acetate pH5. All enzyme dilutions were made into 50 mM sodium acetate buffer, pH5.0. GC220 Cellulase (Danisco US Inc., Genencor) was diluted to 2.5, 5, 10, and 15 mg protein/G PASC, to produce a linear calibration curve. Samples to be tested were diluted to fall within the range of the calibration curve, i.e. to obtain a response of 0.1 to 0.4 fraction product. 150 μL of cold 1% PASC was added to 20 μL of enzyme solution in 96-well microtiter plates. The plate was covered and incubated for 2 h at 50° C., 200 rpm in an Innova incubator/shaker. The reaction was quenched with 100 μL of 50 μg/mL Calcofluor in 100 mM Glycine, pH10. Fluorescence was read on a fluorescence microplate reader (SpectraMax M5 by Molecular Devices) at excitation wavelength Ex=365 nm and emission wavelength Em=435 nm. The result is expressed as the fraction product according to the equation:

FP=1−(Fl sample−Fl buffer w/cellobiose)/(Fl zero enzyme−Fl buffer w/cellobiose), wherein FP is fraction product, and Fl=fluorescence units.

Any of the enzymes described specifically herein can be combined with any one or more of the enzymes described herein or with any other available and suitable enzymes, to produce a suitable multi-enzyme blend/composition. The disclosure is not restricted or limited to the specific exemplary combinations listed below.

Exemplary Compositions

There are provided non-naturally occurring compositions comprising a polypeptide having GH61/endoglucanase activity. The invention also provides a non-naturally occurring composition comprising whole cellulase comprising a polypeptide having GH61/endoglucanase activity (e.g., whole cellulase enriched with a polypeptide having GH61/endoglucanase activity such as endoglucanase IV (e.g., *T. reesei* Eg4 polypeptide-enriched whole cellulase)). The polypeptide having GH61/endoglucanase activity may be any polypeptide having GH61/endoglucanase activity provided herein. In some aspects, the polypeptide having GH61/endoglucanase activity is *T. reesei* Eg4 or a variant thereof. A variant of *T. reesei* Eg4 can be any of the variants provided above.

Endoglucanase is referred to herein as "Eg" or "Egl," interchangeably, in the present disclosure including figures.

As used herein, the term "naturally occurring composition" refers to a composition produced by a naturally occurring source, comprising one or more enzymatic components or activities, wherein each of the components or activities is found at the ratio and level produced by the naturally-occurring source as it is found in nature, untouched, unmodified by the human hand. Accordingly, a naturally occurring composition is, e.g., one that is produced by an organism unmodified with respect to the cellulolytic or hemicellulolytic enzymes such that the ratio or levels of the component enzymes are unaltered from that produced by the native organism in its native environment. A "non-naturally occurring composition," on the other hand, refers to a composition produced by: (1) combining component cellulolytic or hemicelluloytic enzymes either in a naturally occurring ratio or a non-naturally occurring, i.e., altered, ratio; or (2) modifying an organism to express, overexpress or underexpress one or more endogeneous or exogenous enzymes; or (3) modifying an organism such that at least one endogenous enzyme is deleted. A "non-naturally occurring composition" also refers to a composition produced by a naturally-occurring, unmodified organism, but cultured in a man-made medium or environment that is different from the organism's native environment such that the amounts of enzymes in the composition differ from those existing in a composition made by a native organism grown in its native habitat.

Any one of GH61 endoglucanase polypeptides or a variant thereof may be used in any of the compositions described herein. A suitable GH61 endoglucanase may include one of the polypeptides shown in FIG. 1 of the present disclosure. Suitable GH61 endoglucanases include those that are represented by their GenBank Accession Numbers CAB97283.2, CAD70347.1, CAD21296.1, CAE81966.1, CAF05857.1, EAA26873.1, EAA29132.1, EAA30263.1, EAA33178.1, EAA33408.1, EAA34466.1, EAA36362.1, EAA29018.1, and EAA29347.1, or St61 from *S. thermophilum* 24630, St61A from *S. thermophilum* 23839c, St61B from *S. thermophilum* 46583, St61D from *S. thermophilum* 80312, Afu61a from *A. fumigatus* Afu3g03870 (NCBI Ref: XP_748707), an endoglucanase of NCBI Ref: XP_750843.1 from *A. fumigatus* Afu6g09540, an endoglucanase of *A. fumigatus* EDP47167, an endoglucanase of *T. terrestris* 16380, an endoglucanase of *T. terrestris* 155418, an endoglucanase of *T. terrestris* 68900, Cg61A (EAQ86340.1) from *C. globosum*, *T. reesei* Eg7, *T. reesei* Eg4, and an endoglucanase with GenBank Accession: XP_752040 from *A. fumigatus* Af293. In some aspects, the polypeptide having GH61/endoglucanase activity (e.g., isolated polypeptide) is a variant of GH61 endoglucanase or EG IV.

In some aspects, the polypeptide having GH61/endoglucanase activity (including a variant of GH61 endoglucanase) is one comprising any one of SEQ ID NOs: 1-29 and 148, or one that comprises a polypeptide having at least about 60%, 65%, 70%, 75%, 80%, 85%, 90%, 92.5%, 95%, 96%, 97%, 98%, or 99% sequence identity to any one of SEQ ID NOs: 1-29 and 148. In some aspects, the polypeptide having GH61/endoglucanase activity (including a variant of GH61 endoglucanase) may comprise at least one motif (at least any of 2, 3, 4, 5, 6, 7, or 8) selected from SEQ ID NOs:84-91. It may comprise one or more sequence motif(s) selected from the group consisting of: (1) SEQ ID NOs:84 and 88; (2) SEQ ID NOs:85 and 88; (3) SEQ ID NO:86; (4) SEQ ID NO:87; (5) SEQ ID NOs:84, 88 and 89; (6) SEQ ID NOs:85, 88, and 89; (7) SEQ ID NOs: 84, 88, and 90; (8) SEQ ID NOs: 85, 88 and 90; (9) SEQ ID NOs:84, 88 and 91; (10) SEQ ID NOs: 85, 88 and 91; (11) SEQ ID NOs: 84, 88, 89 and 91; (12) SEQ ID NOs: 84, 88, 90 and 91; (13) SEQ ID NOs: 85, 88, 89 and 91: and (14) SEQ ID NOs: 85, 88, 90 and 91.

In some aspects of any one of the compositions or methods described herein, the polypeptide having GH61/endoglucanase activity (including a variant of GH61 endoglucanase) may have at least about 60% (e.g., at least about any of 60%, 65%, 70%, 75%, 80%, 85%, 88%, 90%, 92.5%, 95%, 96%, 97%, 98%, or 99%) sequence identity to residues 22 to 344 of SEQ ID NO:27. In some aspects, the polypeptide or a variant thereof comprises residues corresponding to at least about 5 residues (e.g., at least about any of 6, 7, 8, 9, 10, 11, or 12) of H22, D61, G63, C77, H107, R177, E179, H184, Q193, C198, Y195, and Y232 of SEQ ID NO:27. In some aspects, the polypeptide or a variant thereof comprises residues corresponding to H22, D61, G63, C77, H107, R177, E179, H184, Q193, C198, Y195, and Y232 of SEQ ID NO:27. In some aspects, the polypeptide or a variant thereof comprises residues corresponding to at least 5 residues (e.g., at least about any of 6, 7, 8, 9, 10, 11, 12, 13, 14, 15, 16, 17, 18, or 19) of G313, Q314, C315, G316, G317, S321, G322, P323, T324, C326, A327, T331, C332, N336, Y338, Y339, Q341, C342, and L343 of SEQ ID NO:27. In some aspects, the polypeptide or a variant thereof comprises residues corresponding to G313, Q314, C315, G316, G317, S321, G322, P323, T324, C326, A327, T331, C332, N336, Y338, Y339, Q341, C342, and L343 of SEQ ID NO:27. In some aspects, the polypeptide or a variant thereof comprises a CBM domain (e.g., functional CBM domain). In some aspects, the polypeptide or a variant thereof comprises a catalytic domain (e.g., functional catalytic domain). In some aspects, the polypeptide or a variant thereof is isolated. In some aspects, the polypeptide or a variant thereof has endoglucanase activity.

In some aspects, the polypeptide having GH61/endoglucanase activity is endoglucanase IV, for example, a *T. reesei*

Eg4 polypeptide or a variant thereof. For example, the disclosure provides non-naturally occurring compositions comprising a *T. reesei* Eg4 polypeptide or a variant thereof. A variant of *T. reesei* Eg4 polypeptide can be any one of the variants of *T. reesei* Eg4 polypeptide described herein. In some aspects, the polypeptide having GH61/endoglucanase activity includes amino acid sequence SEQ ID NO:27 or residues 22 to 344 of SEQ ID NO:27.

In some aspects, there is provided a composition comprising an isolated (or substantially purified) polypeptide having glycosyl hydrolase family 61 ("GH61")/endoglucanase activity (e.g., *T. reesei* Eg4 or a variant thereof). Methods of producing polypeptide, recovering the polypeptide, and isolating or purifying the polypeptide are known to one of skill in the art.

In some aspects of any of the compositions or methods described herein, the polypeptide having GH61/endoglucanase activity (e.g., *T. reesei* Eg4 or a variant thereof) is expressed from a host cell, wherein the nucleic acid encoding the polypeptide having GH61/endoglucanase activity has been engineered into the host cell. In some aspects, the polypeptide having GH61/endoglucanase activity (e.g., *T. reesei* Eg4 or a variant thereof) is heterologous to the host cell expressing the polypeptide having GH61/endoglucanase activity.

The present disclosure provides compositions comprising a polypeptide having GH61/endoglucanase activity and comprising at least one cellulase polypeptide and/or at least one hemicellulase polypeptide, or a mixture thereof. In some aspects, the composition comprises at least one (e.g., at least 2, 3, 4, 5, 6, 7, or 8) cellulase polypeptide(s). In some aspects, the cellulase polypeptide is a polypeptide having endoglucanase activity, a polypeptide having cellobiohydrolase activity, or a polypeptide having β-glucosidase activity. In some aspects, the composition comprises at least one (e.g., at least 2, 3, 4, 5, 6, 7, or 8) hemicellulase polypeptide(s). In some aspects, the hemicellulase polypeptide is a polypeptide having xylanase activity, a polypeptide having β-xylosidase activity, or a polypeptide having L-α-arabinofuranosidase activity. In some aspects, the composition further comprises at least one (e.g., at least 2, 3, 4, 5, 6, 7, or 8) cellulase polypeptide(s) and at least one (e.g., at least 2, 3, 4, 5, 6, 7, or 8) hemicellulase polypeptide(s). Varying amounts for polypeptide(s) included in the compositions provided herein are provided below in "Amount of component(s) in compositions" section.

Cellulases and hemicellulases for use in accordance with the methods and compositions of the disclosure can be obtained from, or produced recombinantly from, inter alia, one or more of the following organisms: *Crinipellis scapella, Macrophomina phaseolina, Myceliophthora thermophila, Sordaria fimicola, Volutella colletotrichoides, Thielavia terrestris, Acremonium* sp., *Exidia glandulosa, Fomes fomentarius, Spongipellis* sp., *Rhizophlyctis rosea, Rhizomucor pusillus, Phycomyces niteus, Chaetostylum fresenii, Diplodia gossypina, Ulospora bilgramii, Saccobolus dilutellus, Penicillium verruculosum, Penicillium chrysogenum, Thermomyces verrucosus, Diaporthe syngenesia, Colletotrichum lagenarium, Nigrospora* sp., *Xylaria hypoxylon, Nectria pinea, Sordaria macrospora, Thielavia thermophila, Chaetomium mororum, Chaetomium virscens, Chaetomium brasiliensis, Chaetomium cunicolorum, Syspastospora boninensis, Cladorrhinum foecundissimum, Scytalidium thermophila, Gliocladium catenulatum, Fusarium oxysporum* ssp. *lycopersici, Fusarium oxysporum* ssp. *passiflora, Fusarium solani, Fusarium anguioides, Fusarium poae, Humicola nigrescens, Humicola grisea, Panaeolus retirugis, Trametes sanguinea, Schizophyllum commune, Trichothecium roseum, Microsphaeropsis* sp., *Acsobolus stictoideus* spej., *Poronia punctata, Nodulisporum* sp., *Trichoderma* sp. (e.g., *Trichoderma reesei*) and *Cylindrocarpon* sp.

In the present disclosure, the cellulase or hemicellulase may be prepared from any known microorganism cultivation method(s), resulting in the expression of enzymes capable of hydrolyzing a cellulosic material. Fermentation may include shake flask cultivation, small- or large-scale fermentation, such as continuous, batch, fed-batch, or solid state fermentations in laboratory or industrial fermenters performed in a suitable medium and under conditions allowing the cellulase to be expressed or isolated. Generally, the microorganism is cultivated in a cell culture medium suitable for production of enzymes capable of hydrolyzing a cellulosic material. The cultivation takes place in a suitable nutrient medium comprising carbon and nitrogen sources and inorganic salts, using procedures known in the art. Suitable culture media, temperature ranges and other conditions suitable for growth and cellulase production are known in the art. As a non-limiting example, the normal temperature range for the production of cellulases by *T. reesei* is 24° C. to 28° C.

The present disclosure provides non-naturally occurring compositions comprising a polypeptide having GH61/endoglucanase activity (e.g., endoglucanase IV polypeptide such as *T. reesei* Eg4 polypeptide or a variant thereof), wherein the composition further comprises at least 1 polypeptide having endoglucanase activity (e.g., at least 2, 3, 4, or 5 polypeptides having endoglucanase activity), at least 1 polypeptide having cellobiohydrolase activity (e.g., at least 2, 3, 4, or 5 polypeptides having cellobiohydrolase activity), at least 1 polypeptide having glucosidase activity (e.g., β-glucosidase) (e.g., at least 2, 3, 4, or 5 polypeptides having β-glucosidase activity), at least 1 polypeptide having xylanase activity (e.g., at least 2, 3, 4, or 5 polypeptides having xylanase activity), at least 1 polypeptide having xylosidase activity (e.g., β-xylosidase) (e.g., at least 2, 3, 4, or 5 polypeptides having β-xylosidase activity), and/or at least 1 polypeptide having arabinofuranosidase activity (e.g., L-α-arabinofuranosidase) (e.g., at least 2, 3, 4, or 5 polypeptides having L-α-arabinofuranosidase activity). Varying amounts for polypeptide(s) included in the compositions provided herein are provided below in "Amount of component(s) in compositions" section.

The present disclosure provides non-naturally occurring compositions comprising whole cellulase comprising a polypeptide having GH61/endoglucanase activity (e.g., whole cellulase enriched with endoglucanase IV polypeptide, such as, e.g., *T. reesei* Eg4 polypeptide or a variant thereof), wherein the composition further comprises at least 1 polypeptide having endoglucanase activity (e.g., at least 2, 3, 4, or 5 polypeptides having endoglucanase activity), at least 1 polypeptide having cellobiohydrolase activity (e.g., at least 2, 3, 4, or 5 polypeptides having cellobiohydrolase activity), at least 1 polypeptide having glucosidase activity (e.g., β-glucosidase) (e.g., at least 2, 3, 4, or 5 polypeptides having β-glucosidase activity), at least 1 polypeptide having xylanase activity (e.g., at least 2, 3, 4, or 5 polypeptides having xylanase activity), at least one polypeptide having xylosidase activity (e.g., β-xylosidase) (e.g., at least 2, 3, 4, or 5 polypeptides having β-xylosidase activity), and/or at least one polypeptide having arabinofuranosidase activity (e.g., L-α-arabinofuranosidase) (e.g., at least 2, 3, 4, or 5 polypeptides having L-α-arabinofuranosidase activity). Varying amounts for polypeptide(s) included in the compositions provided herein are provided below in "Amount of component(s) in compositions" section.

In some aspects, the composition comprises a polypeptide having GH61/endoglucanase activity (e.g., T. reesei Eg4 or a variant thereof) and at least 1 polypeptide having xylanase activity (e.g., T. reesei Xyn3, T. reesei Xyn2, AfuXyn2, AfuXyn5, or a variant thereof). In some aspects, the polypeptide having xylanase activity is T. reesei Xyn3. The composition may further comprise at least 1 polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, and/or Tn3B). The composition may further comprise at least 1 polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, and/or a variant thereof). The composition may further comprise at least 1 polypeptide having cellobiohydrolase activity (e.g., T. reesei CBH1, A. fumigatus 7A, 7B, C. globosum 7A, 7B, T. terrestris 7A, 7B, T. reesei CBH2, T. terrestris 6A, S. thermophile 6A, 6B, or a variant thereof). The composition may further comprise at least 1 polypeptide having endoglucanase activity (e.g., T. reesei EG1 (or a variant thereof) and/or T. reesei EG2 (or a variant thereof)).

In some aspects, the composition comprises a polypeptide having GH61/endoglucanase activity (e.g., T. reesei Eg4 or a variant thereof) and at least 1 polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, or a variant thereof). The composition may comprise a polypeptide having GH61/endoglucanase activity (e.g., T. reesei Eg4 or a variant thereof) and at least 1 polypeptide (or at least 2 polypeptides) having cellobiohydrolase activity (e.g., T. reesei CBH1, A. fumigatus 7A, 7B, C. globosum 7A, 7B, T. terrestris 7A, 7B, T. reesei CBH2, T. terrestris 6A, S. thermophile 6A, 6B, or a variant thereof). The composition may comprise a polypeptide having GH61/endoglucanase activity (e.g., T. reesei Eg4 or a variant thereof) and further comprises at least 1 polypeptide (or at least 2 polypeptides) having endoglucanase activity (e.g., T. reesei EG1 (or a variant thereof) and/or T. reesei EG2 (or a variant thereof)). The composition may comprise a polypeptide having GH61/endoglucanase activity (e.g., T. reesei Eg4 or a variant thereof) and at least 1 polypeptide (or at least two polypeptides) having β-xylosidase activity (e.g., Fv3A, Fv43A, Pf43A, Fv43D, Fv39A, Fv43E, Fo43A, Fv43B, Pa51A, Gz43A, and/or T. reesei Bxl1). The composition may comprise a polypeptide having GH61/endoglucanase activity (e.g., T. reesei Eg4 or a variant thereof) and at least 1 polypeptide (or at least 2 polypeptides) having β-xylosidase activity (e.g., Fv3A, Fv43A, Pf43A, Fv43D, Fv39A, Fv43E, Fo43A, Fv43B, Pa51A, Gz43A, T. reesei Bxl1, and/or a variant thereof). The composition may comprise a polypeptide having GH61/endoglucanase activity (e.g., T. reesei Eg4 or a variant thereof) and at least one polypeptide (at least 2 polypeptides) having L-α-arabinofuranosidase activity (e.g., Af43A, Fv43B, Pf51A, Pa51A, Fv51A, or a variant thereof).

In some aspects, any of the polypeptides described herein (e.g., polypeptide having endoglucanase activity, polypeptide having cellobiohydrolase activity, polypeptide having glucosidase activity (e.g., β-glucosidase), polypeptide having xylanase activity, polypeptide having xylosidase activity (e.g., β-xylosidase), or polypeptide having arabinofuranosidase activity (e.g., L-α-arabinofuranosidase)) may be a component of a whole cellulase such as a whole cellulase described herein. Any of the polypeptides described herein may be produced by expressing an endogenous or exogenous gene encoding the corresponding polypeptide(s). The polypeptide(s) can be, in some circumstances, overexpressed or underexpressed.

Regarding any of the compositions described above, varying amounts for polypeptide(s) included in the compositions are provided below in "Amount of component(s) in compositions" section.

Polypeptide Having Endoglucanase Activity

A polypeptide having endoglucanase activity includes a polypeptide that catalyzes the cleavage of internal β-1,4 linkages. Endoglucanase ("EG") refers to a group of cellulase enzymes classified as EC 3.2.1.4. An EG enzyme hydrolyzes internal beta-1,4 glucosidic bonds of the cellulose. EG catalyzes endohydrolysis of 1,4-beta-D-glycosidic linkages in cellulose, cellulose derivatives (for example, carboxy methyl cellulose), lichenin, beta-1,4 bonds in mixed beta-1,3 glucans such as cereal beta-D-glucans or xyloglucans, and other plant material containing cellulosic components. EG activity can be determined using carboxymethyl cellulose (CMC) hydrolysis according to the procedure of Ghose, 1987, Pure and Appl. Chem. 59: 257-268. In some aspects, at least one polypeptide having endoglucanase activity includes T. reesei EG1 (GenBank Accession No. HM641862.1) and/or T. reesei EG2 polypeptide (GenBank Accession No. ABA64553.1).

A thermostable T. terrestris endoglucanase (Kvesitadaze et al., Applied Biochem. Biotech. 1995, 50:137-143) is, in another example, used in the methods and compositions of the present disclosure. Moreover, a T. reesei EG3 (GenBank Accession No. AAA34213.1) (Okada et al. Appl. Environ. Microbiol. 1988, 64:555-563), EG5 (GenBank Accession No. AAP57754) (Saloheimo et al. Molecular Microbiology 1994, 13:219-228), EG6 (FIG. 89A) (U.S. Patent Publication No. 20070213249), or EG7 (GenBank Accession No. AAP57753) (U.S. Patent Publication No. 20090170181), an A. cellulolyticus E1 endoglucanase (Swiss-Prot entry P54583.1) (U.S. Pat. No. 5,536,655), a H. insolens endoglucanase V (EGV) (Protein Data Bank entry 4ENG), a S. coccosporum endoglucanase (FIG. 89B) (U.S. Patent Publication No. 20070111278), an A. aculeatus endoglucanase F1-CMC (Swiss-Prot entry P22669.1) (Ooi et al. Nucleic Acid Res. 1990, 18:5884), an A. kawachii IFO 4308 endoglucanase CMCase-1 (Swiss-Prot entry Q96WQ8.1) (Sakamoto et al. Curr. Genet. 1995, 27:435-439), an E. carotovora endoglucanase CelS (GenBank Accession No. AAA24817.1) (Saarilahti et al. Gene 1990, 90:9-14); or an A. thermophilum ALK04245 endoglucanase (U.S. Patent Publication No. 20070148732) can also be used. Additional suitable endoglucanases are described in, e.g., WO 91/17243, WO 91/17244, WO 91/10732, U.S. Pat. No. 6,001,639. A polypeptide having endoglucanase activity may be a variant of any one of the endoglucases provided herein.

Polypeptide Having Cellobiohydrolase Activity

A polypeptide having cellobiohydrolase activity includes a polypeptide having 1,4-D-glucan cellobiohydrolase (E.C. 3.2.1.91) activity which catalyzes the hydrolysis of 1,4-beta-D-glucosidic linkages in cellulose, cellotetriose, or any beta-1,4-linked glucose containing polymer, releasing cellobiose from the ends of the chain. For purposes of the present invention, cellobiohydrolase activity can be determined by release of water-soluble reducing sugar from cellulose as measured by the PHBAH method of Lever et al., 1972, Anal. Biochem. 47: 273-279. A distinction between the exoglucanase mode of attack of a cellobiohydrolase and the endoglucanase mode of attack can be made by a similar measurement of reducing sugar release from substituted cellulose such as carboxymethyl cellulose or hydroxyethyl cellulose (Ghose, 1987, Pure & Appl. Chem. 59: 257-268). A true cellobiohydrolase will have a very high ratio of activity on unsubstituted versus substituted cellulose (Bailey et al, 1993, Biotechnol. Appl. Biochem. 17: 65-76).

Suitable CBHs can be selected from *A. bisporus* CBH1 (Swiss Prot Accession No. Q92400), *A. aculeatus* CBH1 (Swiss Prot Accession No. 059843), *A. nidulans* CBHA (GenBank Accession No. AF420019) or CBHB (GenBank Accession No. AF420020), *A. niger* CBHA (GenBank Accession No. AF156268) or CBHB (GenBank Accession No. AF156269), *C. purpurea* CBH1 (Swiss Prot Accession No. 000082), *C. carbonarum* CBH1 (Swiss Prot Accession No. Q00328), *C. parasitica* CBH1 (Swiss Prot Accession No. Q00548), *F. oxysporum* CBH1 (Cel7A) (Swiss Prot Accession No. P46238), *H. grisea* CBH1.2 (GenBank Accession No. U50594), *H. grisea* var. *thermoidea* CBH1 (GenBank Accession No. D63515), CBHI.2 (GenBank Accession No. AF123441), or exo1 (GenBank Accession No. AB003105), *M. albomyces* Cel7B (GenBank Accession No. AJ515705), *N. crassa* CBHI (GenBank Accession No. X77778), *P. funiculosum* CBHI (Cel7A) (GenBank Accession No. AJ312295) (U.S. Patent Publication No. 20070148730), *P. janthinellum* CBHI (GenBank Accession No. S56178), *P. chrysosporium* CBH (GenBank Accession No. M22220), or CBHI-2 (Cel7D) (GenBank Accession No. L22656), *T. emersonii* CBH1A (GenBank Accession No. AF439935), *T. viride* CBH1 (GenBank Accession No. X53931), or *V. volvacea* V14 CBH1 (GenBank Accession No. AF156693). A polypeptide having cellobiohydrolase activity may be a variant of any one of CBHs provided herein.

In some aspects, at least one polypeptide having cellobiohydrolase activity includes *T. reesei* CBH 1 (Swiss-Prot entry P62694.1) (or a variant thereof) and/or *T. reesei* CBH2 (Swiss-Prot entry P07987.1) (or a variant thereof) polypeptide. See Shoemaker et al. Bio/Technology 1983, 1:691-696; see also Teeri et al. Bio/Technology 1983, 1:696-699, *A. fumigatus* 7A, 7B, *C. globosum* 7A, 7B, *T. terrestris* 7A, 7B, which are *T. reesei* CBH1 homologs; *T. terrestris* 6A, *S. thermophile* 6A, 6B, which are *T. reesei* CBH2 homologs, or a variant thereof.

Polypeptide Having Glucosidase Activity

A polypeptide having glucosidase activity includes a polypeptide having beta-D-glucoside glucohydrolase (E.C. 3.2.1.21) activity which catalyzes the hydrolysis of cellobiose with the release of beta-D-glucose. For purposes of the present invention, β-glucosidase activity may be measured by methods known in the art, e.g., HPLC. A polypeptide having glucosidase activity includes members of certain GH families, including, without limitation, members of GH families 1, 3, 9 or 48, which catalyze the hydrolysis of cellobiose to release β-D-glucose. A polypeptide having glucosidase activity includes β-glucosidase such as β-glucosidase obtained from a number of microorganisms, by recombinant means, or be purchased from commercial sources. Examples of β-glucosidases from microorganisms include, without limitation, ones from bacteria and fungi. For example, a β-glucosidase is suitably obtained from a filamentous fungus. In some aspects, at least one polypeptide having glucosidase activity (e.g., β-glucosidase activity) is a *T. reesei* Bgl1 polypeptide.

The β-glucosidases can be obtained, or produced recombinantly, from, inter alia, *A. aculeatus* (Kawaguchi et al. Gene 1996, 173: 287-288), *A. kawachi* (Iwashita et al. Appl. Environ. Microbiol. 1999, 65: 5546-5553), *A. oryzae* (WO 2002/095014), *C. biazotea* (Wong et al. Gene, 1998, 207: 79-86), *P. funiculosum* (WO 2004/078919), *S. fibuligera* (Machida et al. Appl. Environ. Microbiol. 1988, 54: 3147-3155), *S. pombe* (Wood et al. Nature 2002, 415: 871-880), or *T. reesei* (e.g., β-glucosidase 1 (U.S. Pat. No. 6,022,725), β-glucosidase 3 (U.S. Pat. No. 6,982,159), β-glucosidase 4 (U.S. Pat. No. 7,045,332), β-glucosidase 5 (U.S. Pat. No. 7,005,289), β-glucosidase 6 (U.S. Publication No. 20060258554), β-glucosidase 7 (U.S. Publication No. 20060258554)). A polypeptide having β-glucosidases activity may be a variant of any one of β-glucosidases provided herein.

The β-glucosidase can be produced by expressing an endogenous or exogenous gene encoding a β-glucosidase. For example, β-glucosidase can be secreted into the extracellular space e.g., by Gram-positive organisms (e.g., *Bacillus* or Actinomycetes), or a eukaryotic hosts (e.g., *Trichoderma, Aspergillus, Saccharomyces*, or *Pichia*). The β-glucosidase can be, in some circumstances, overexpressed or underexpressed.

The β-glucosidase can also be obtained from commercial sources. Examples of commercial β-glucosidase preparation suitable for use include, e.g., *T. reesei* β-glucosidase in Accellerase® BG (Danisco US Inc., Genencor); NOVOZYM™ 188 (a β-glucosidase from *A. niger*); *Agrobacterium* sp. β-glucosidase, and *T. maritima* β-glucosidase from Megazyme (Megazyme International Ireland Ltd., Ireland.).

β-glucosidase activity can be determined by a number of suitable means known in the art, such as the assay described by Chen et al., in Biochimica et Biophysica Acta 1992, 121:54-60, wherein 1 pNPG denotes 1 μmoL of Nitrophenol liberated from 4-nitrophenyl-β-D-glucopyranoside in 10 min at 50° C. (122° F.) and pH 4.8.

Polypeptide Having Xylanase Activity

Xylanase activity may be measured by using colorimetric azo-birchwood xylan assay (S-AXBL, Megazyme International Ireland Ltd., Ireland).

A polypeptide having xylanase activity may include Group A xylanases, selected from, e.g., Xyn, Xyn2, AfuXyn2, and/or AfuXyn5 polypeptide, or a variant thereof.

Any of the compositions described herein may optionally comprise one or more xylanases in addition to or in place of the one or more Group A xylanases. Any xylanase (EC 3.2.1.8) can be used as the additional one or more xylanases. Suitable xylanases include, e.g., *C. saccharolyticum* xylanase (Luthi et al. 1990, Appl. Environ. Microbiol. 56(9):2677-2683), *T. maritima* xylanase (Winterhalter & Liebel, 1995, Appl. Environ. Microbiol. 61(5):1810-1815), *Thermatoga* Sp. Strain FJSS-B.1 xylanase (Simpson et al. 1991, Biochem. J. 277, 413-417), *B. circulans* xylanase (BcX) (U.S. Pat. No. 5,405,769), *A. niger* xylanase (Kinoshita et al. 1995, Journal of Fermentation and Bioengineering 79(5):422-428), *S. lividans* xylanase (Shareck et al. 1991, Gene 107:75-82; Morosoli et al. 1986 Biochem. J. 239:587-592; Kluepfel et al. 1990, Biochem. J. 287:45-50), *B. subtilis* xylanase (Bernier et al. 1983, Gene 26(1):59-65), *C. fimi* xylanase (Clarke et al., 1996, FEMS Microbiology Letters 139:27-35), *P. fluorescens* xylanase (Gilbert et al. 1988, Journal of General Microbiology 134:3239-3247), *C. thermocellum* xylanase (Dominguez et al., 1995, Nature Structural Biology 2:569-576), *B. pumilus* xylanase (Nuyens et al. Applied Microbiology and Biotechnology 2001, 56:431-434; Yang et al. 1998, Nucleic Acids Res. 16(14B): 7187), *C. acetobutylicum* P262 xylanase (Zappe et al. 1990, Nucleic Acids Res. 18(8):2179), or *T. harzianum* xylanase (Rose et al. 1987, J. Mol. Biol. 194(4):755-756). A polypeptide having xylanase activity may be a variant of any one of the xylanases provided herein.

Polypeptide Having Xylosidase (e.g., β-Xylosidase) Activity

Xylosidase (e.g., β-xylosidase) activity may be measured by using chromogenic substrate 4-nitrophenyl beta-D-xylopyranoside (pNPX, Sigma-Aldrich N2132).

A polypeptide having xylosidase (e.g., β-xylosidase) activity may be a Group 1 β-xylosidase enzyme (e.g., Fv3A or Fv43A) or a Group 2 β-xylosidase enzyme (e.g., Pf43A, Fv43D, Fv39A, Fv43E, Fo43A, Fv43B, Pa51A, Gz43A, T. reesei Bxl1, or a variant thereof). In some aspects, any of the composition provided herein may suitably comprise one or more Group 1 β-xylosidases and one or more Group 2 β-xylosidases.

Any of the composition provided herein such as the enzyme blends/compositions of the disclosure can optionally comprise one or more β-xylosidases, in addition to or in place of the Group 1 and/or Group 2 β-xylosidases above. Any β-xylosidase (EC 3.2.1.37) can be used as the additional β-xylosidases. Suitable β-xylosidases include, for example, T. emersonii Bxl1 (Reen et al. 2003, Biochem Biophys Res Commun 305(3):579-85), G. stearothermophilus β-xylosidases (Shallom et al. 2005, Biochemistry 44:387-397), S. thermophilum β-xylosidases (Zanoelo et al. 2004, J. Ind. Microbiol. Biotechnol. 31:170-176), T. lignorum β-xylosidases (Schmidt, 1998, Methods Enzymol. 160: 662-671), A. awamori xylosidases (Kurakake et al. 2005, Biochim Biophys. Acta 1726:272-279), A. versicolor β-xylosidases (Andrade et al. 2004, Process Biochem. 39:1931-1938), Streptomyces sp. β-xylosidases (Pinphanichakarn et al. 2004, World J. Microbiol. Biotechnol. 20:727-733), T. maritima β-xylosidases (Xue and Shao, 2004, Biotechnol. Lett. 26:1511-1515), Trichoderma sp. SY β-xylosidases (Kim et al. 2004, J. Microbiol. Biotechnol. 14:643-645), A. niger β-xylosidases (Oguntimein and Reilly, 1980, Biotechnol. Bioeng. 22:1143-1154), or P. wortmanni β-xylosidases (Matsuo et al. 1987, Agric. Biol. Chem. 51:2367-2379). A polypeptide having xylosidase (e.g., β-xylosidase) activity may be a variant of any one of the xylosidases provided herein.

Arabinofuranosidase activity may be measured by chromogenic substrate 4-nitrophenyl alpha-L-arabinofuranoside (pNPA, Sigma-Aldrich N3641).

Any one of the compositions provided herein such as the enzyme blends/compositions of the disclosure can, for example, suitably comprise at least one polypeptide having arabinofuranosidase activity (e.g., L-α-arabinofuranosidase activity) such as L-α-arabinofuranosidases. The L-α-arabinofuranosidase may be, for example, Af43A, Fv43B, Pf51A, Pa51A, Fv51A, or a variant thereof.

The enzyme blends/compositions of the disclosure may optionally comprise one or more L-α-arabinofuranosidases in addition to or in place of the foregoing L-α-arabinofuranosidases. L-α-arabinofuranosidases (EC 3.2.1.55) from any suitable organism can be used as the additional L-α-arabinofuranosidases. Suitable L-α-arabinofuranosidases include, e.g., L-α-arabinofuranosidases of A. oryzae (Numan & Bhosle, J. Ind. Microbiol. Biotechnol. 2006, 33:247-260), A. sojae (Oshima et al. J. Appl. Glycosci. 2005, 52:261-265), B. brevis (Numan & Bhosle, J. Ind. Microbiol. Biotechnol. 2006, 33:247-260), B. stearothermophilus (Kim et al., J. Microbiol. Biotechnol. 2004, 14:474-482), B. breve (Shin et al., Appl. Environ. Microbiol. 2003, 69:7116-7123), B. longum (Margolies et al., Appl. Environ. Microbiol. 2003, 69:5096-5103), C. thermocellum (Taylor et al., Biochem. J. 2006, 395:31-37), F. oxysporum (Panagiotou et al., Can. J. Microbiol. 2003, 49:639-644), F. oxysporum f. sp. dianthi (Numan & Bhosle, J. Ind. Microbiol. Biotechnol. 2006, 33:247-260), G. stearothermophilus T-6 (Shallom et al., J. Biol. Chem. 2002, 277:43667-43673), H. vulgare (Lee et al., J. Biol. Chem. 2003, 278:5377-5387), P. chrysogenum (Sakamoto et al., Biophys. Acta 2003, 1621:204-210), Penicillium sp. (Rahman et al., Can. J. Microbiol. 2003, 49:58-64), P. cellulosa (Numan & Bhosle, J. Ind. Microbiol. Biotechnol. 2006, 33:247-260), R. pusillus (Rahman et al., Carbohydr. Res. 2003, 338:1469-1476), S. chartreusis, S. thermoviolacus, T. ethanolicus, T. xylanilyticus (Numan & Bhosle, J. Ind. Microbiol. Biotechnol. 2006, 33:247-260), Tfusca (Tuncer and Ball, Folia Microbiol. 2003, (Praha) 48:168-172), T. maritima (Miyazaki, Extremophiles 2005, 9:399-406), Trichoderma sp. SY (Jung et al. Agric. Chem. Biotechnol. 2005, 48:7-10), A. kawachii (Koseki et al., Biochim Biophys. Acta 2006, 1760:1458-1464), F. oxysporum f. sp. dianthi (Chacon-Martinez et al., Physiol. Mol. Plant Pathol. 2004, 64:201-208), T. xylanilyticus (Debeche et al., Protein Eng. 2002, 15:21-28), H. insolens, M. giganteus (Sorensen et al., Biotechnol. Frog. 2007, 23:100-107), or R. sativus (Kotake et al. J. Exp. Bot. 2006, 57:2353-2362). A polypeptide having arabinofuranosidase activity may be a variant of any one of the arabinofuranosidases described herein.

In some aspects of any one of the compositions described herein, the at least one polypeptide having endoglucanase activity comprises T. reesei EG1 (or a variant thereof) and/or T. reesei EG2 (or a variant thereof). In some aspects of any one of the compositions described herein, the at least one polypeptide having cellobiohydrolase ("CBH") activity comprises T. reesei CBH1, A. fumigatus 7A, 7B, C. globosum 7A, 7B, T. terrestris 7A, 7B, T. reesei CBH2, T. terrestris 6A, S. thermophile 6A, 6B, or a variant thereof. In some aspects of any one of the compositions described herein, the at least one polypeptide having β-glucosidase activity comprises Fv3C, Pa3D, Fv3G, Fv3D, Tr3A, Tr3B, Te3A, An3A, Fo3A, Gz3A, Nh3A, Vd3A, Pa3G, and/or Tn3B. In some aspects of any one of the compositions described herein, the at least one polypeptide having β-glucosidase activity comprises Fv3C, Pa3D, Fv3G, Fv3D, Tr3A, Tr3B, Te3A, An3A, Fo3A, Gz3A, Nh3A, Vd3A, Pa3G, Tn3B, and/or a variant thereof. In some aspects of any one of the compositions described herein, the at least one polypeptide having xylanase activity comprises T. reesei Xyn3, T. reesei Xyn2, AfuXyn2, and/or AfuXyn5. In some aspects of any one of the compositions described herein, the at least one polypeptide having xylanase activity comprises T. reesei Xyn3, T. reesei Xyn2, AfuXyn2, AfuXyn5, and/or a variant thereof. In some aspects of any one of the compositions described herein, the at least one polypeptide having β-xylosidase activity is a Group 1 β-xylosidase or a Group 2 β-xylosidase, wherein the Group 1 β-xylosidase comprises Fv3A, Fv43A, or a variant thereof, and the Group 2 β-xylosidase comprises Pf43A, Fv43D, Fv39A, Fv43E, Fo43A, Fv43B, Pa51A, Gz43A, T. reesei Bxl1, or a variant thereof. In some aspects, the at least one polypeptide having β-xylosidase activity comprises F. verticillioides Fv3A, F. verticillioides Fv43D, or a variant thereof. In some aspects of any one of the compositions described herein, the at least one polypeptide having L-α-arabinofuranosidase activity comprises Af43A, Fv43B, Pf51A, Pa51A, and/or Fv51A. In some aspects of any one of the compositions described herein, the at least one polypeptide having L-α-arabinofuranosidase activity comprises Af43A, Fv43B, Pf51A, Pa51A, Fv51A, and/or a variant thereof.

Whole Cellulase

Any of the compositions provided here such as enzyme blends/compositions of the disclosure may comprise whole cellulase.

As used herein, a "whole cellulase" refers to either a naturally occurring or a non-naturally occurring cellulase-containing composition comprising at least 3 different enzyme types: (1) an endoglucanase, (2) a cellobiohydrolase, and (3) a β-glucosidase, or comprising at least 3 different enzymatic activities: (1) an endoglucanase activity, which catalyzes the cleavage of internal β-1,4 linkages, resulting in shorter glucooligosaccharides, (2) a cellobiohydrolase activity, which catalyzes an "exo"-type release of cellobiose units 03-1,4 glucose-glucose disaccharide), and (3) a β-glucosidase activity, which catalyzes the release of glucose monomer from short cellooligosaccharides (e.g., cellobiose). The whole cellulase may comprise at least one polypeptide having endoglucanase activity (e.g., EG2 (or a variant thereof) and/or EG4 (or a variant thereof)), at least one polypeptide having cellobiohydrolase activity (e.g., CBH1 (or a variant thereof) and/or CBH2 (or a variant thereof)), and at least one polypeptide having β-glucosidase activity (e.g., Bgl1 or a variant thereof).

A "naturally occurring cellulase-containing" composition is one produced by a naturally occurring source, which comprises one or more cellobiohydrolase-type, one or more endoglucanase-type, and one or more β-glucosidase-type components or activities, wherein each of these components or activities is found at the ratio and level produced in nature, untouched by the human hand. Accordingly, a naturally occurring cellulase-containing composition is, for example, one that is produced by an organism unmodified with respect to the cellulolytic enzymes such that the ratio or levels of the component enzymes are unaltered from that produced by the native organism in nature. A "non-naturally occurring cellulase-containing composition" refers to a composition produced by: (1) combining component cellulolytic enzymes either in a naturally occurring ratio or a non-naturally occurring, i.e., altered, ratio; or (2) modifying an organism to overexpress or underexpress one or more cellulolytic enzymes; or (3) modifying an organism such that at least one cellulolytic enzyme is deleted. A "non-naturally occurring cellulase containing" composition can also refer to a composition resulting from adjusting the culture conditions for a naturally-occurring organism, such that the naturally-occurring organism grows under a non-native condition, and produces an altered level or ratio of enzymes. Accordingly, in some embodiments, the whole cellulase preparation of the present disclosure can have one or more EGs and/or CBHs and/or β-glucosidases deleted and/or overexpressed.

In some aspects, there is provided a non-naturally occurring composition comprising a polypeptide having GH61/endoglucanase activity (e.g., endoglucanase IV polypeptide such as *T. reesei* Eg4 polypeptide or a variant thereof) or a non-naturally occurring composition comprising a polypeptide having GH61/endoglucanase activity (e.g., whole cellulase enriched with endoglucanase IV polypeptide such as *T. reesei* Eg4 polypeptide or a variant thereof), wherein the composition further comprises a whole cellulase, at least 1 polypeptide having endoglucanase activity (e.g., at least 2, 3, 4, or 5 polypeptides having endoglucanase activity), at least 1 polypeptide having cellobiohydrolase activity (e.g., at least 2, 3, 4, or 5 polypeptides having cellobiohydrolase activity), at least 1 polypeptide having glucosidase activity (e.g., β-glucosidase) (e.g., at least 2, 3, 4, or 5 polypeptides having β-glucosidase activity), at least 1 polypeptide having xylanase activity (e.g., at least 2, 3, 4, or 5 polypeptides having xylanase activity), at least 1 polypeptide having xylosidase activity (e.g., β-xylosidase) (e.g., at least 2, 3, 4, or 5 polypeptides having β-xylosidase activity), and/or at least 1 polypeptide having arabinofuranosidase activity (e.g., L-α-arabinofuranosidase) (e.g., at least 2, 3, 4, or 5 polypeptides having L-α-arabino-furanosidase activity). The polypeptides having various enzyme activities are described above.

In some aspects, the whole cellulase comprises at least 1 polypeptide having endoglucanase activity such as *T. reesei* EG1, *T. reesei* EG2, or a variant thereof. In some aspects, the whole cellulase comprises at least one polypeptide having cellobiohydrolase activity such as *T. reesei* CBH1, *T. reesei* CBH2, or a variant thereof. In some aspects, the whole cellulase comprises at least 1 polypeptide having β-glucosidase activity such as Fv3C, Pa3D, Fv3G, Fv3D, Tr3A, Tr3B, Te3A, An3A, Fo3A, Gz3A, Nh3A, Vd3A, Pa3G, Tn3B, or a variant thereof.

In the present disclosure, a whole cellulase preparation can be from any microorganism that is capable of hydrolyzing a cellulosic material. In some embodiments, the whole cellulase preparation is a fungal or bacterial whole cellulase. For example, the whole cellulase preparation can be from an *Acremonium*, *Aspergillus*, *Chrysosporium*, *Emericella*, *Fusarium*, *Humicola*, *Mucor*, *Myceliophthora*, *Neurospora*, *Penicillium*, *Scytalidium*, *Thielavia*, *Tolypocladium*, *Trichoderma*, or yeast species.

The whole cellulase preparation may be, e.g., an *Aspergillus aculeatus*, *Aspergillus awamori*, *Aspergillus foetidus*, *Aspergillus japonicus*, *Aspergillus nidulays*, *Aspergillus niger*, or *Aspergillus oryzae* whole cellulase. Moreover, the whole cellulase preparation may be a *Fusarium bactridioides*, *Fusarium cerealis*, *Fusarium crookwellenoe*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* whole cellulase preparation. The whole cellulase preparation may also be a *Chrysosporium lucknowence*, *Humicola insolens*, *Humicola lanuginosa*, *Mucor miehei*, *Myceliophthora thermophila*, *Neurospora crassa*, *Penicillium purpurogenum*, *Penicillium funiculosum*, *Scytalidium thermophilum*, or *Thielavia terrestris* whole cellulase preparation. The whole cellulase preparation may also be a *Trichoderma harzianum*, *Trichoderma koningii*, *Trichoderma longibrachiatum*, *Trichoderma reesei* (e.g., RL-P37 (Sheir-Neiss G et al. Appl. Microbiol. Biotechnology, 1984, 20, pp. 46-53), QM9414 (ATCC No. 26921), NRRL 15709, ATCC 13631, 56764, 56466, 56767), or a *Trichoderma viride* (e.g., ATCC 32098 and 32086) whole cellulase preparation.

The whole cellulase preparation can be integrated strain *T. reesei* H3A or H3A/Eg4 #27 (as described in the Examples herein) preparation.

The whole cellulase preparation can suitably be a *T. reesei* RutC30 whole cellulase preparation, which is available from the American Type Culture Collection as *T. reesei* ATCC 56765. For example, the whole cellulase preparation can also suitably be a whole cellulase of *P. funiculosum*, which is available from the American Type Culture Collection as *P. funiculosum* ATCC Number: 10446.

The whole cellulase preparation can also be obtained from commercial sources. Examples of commercial cellulase preparations suitable for use in the methods and compositions of the present disclosure include, for example, CEL-LUCLAST™ and Cellic™ (Novozymes A/S) and LAMINEX™ BG, IndiAge™ 44L, Primafast™ 100, Primafast™ 200, Spezyme™ CP, Accellerase® 1000 and Accellerase® 1500 (Danisco US. Inc., Genencor).

Suitable whole cellulase preparations can be made using any known microorganism cultivation methods, especially fermentation, resulting in the expression of enzymes capable of hydrolyzing a cellulosic material. As used herein, "fermentation" refers to shake flask cultivation, small- or large-scale fermentation, such as continuous, batch, fed-batch, or solid state fermentations in laboratory or industrial fermenters performed in a suitable medium and under conditions that allow the cellulase and/or enzymes of interest to be expressed and/or isolated. Generally the microorganism is cultivated in a cell culture medium suitable for production of enzymes capable of hydrolyzing a cellulosic material. The cultivation takes place in a nutrient medium comprising carbon and nitrogen sources and inorganic salts, using known procedures and variations. Culture media, temperature ranges and other conditions for growth and cellulase production are known. As a non-limiting example, a typical temperature range for the production of cellulases by $T.$ $reesei$ is 24° C. to 28° C.

The whole cellulase preparation can be used as it is produced by fermentation with no or minimal recovery and/or purification. In that sense, the whole cellulase preparation can be used in a whole broth formulation. For example, once cellulases are secreted into the cell culture medium, the cell culture medium containing the cellulases can be used directly. The whole cellulase preparation can comprise the unfractionated contents of fermentation material, including the spent cell culture medium, extracellular enzymes and cells. On the other hand, the whole cellulase preparation can also be subject to further processing in a number of routine steps, e.g., precipitation, centrifugation, affinity chromatography, filtration, or the like. For example, the whole cellulase preparation can be concentrated, and then used without further purification. The whole cellulase preparation can, e.g., be formulated to comprise certain chemical agents that decrease cell viability or kill the cells after fermentation. The cells can for example be lysed or permeabilized using known methods.

The endoglucanase activity of the whole cellulase preparation can be determined using carboxymethyl cellulose (CMC) as a substrate. A suitable assay measures the production of reducing ends created by the enzyme mixture acting on CMC wherein 1 unit is the amount of enzyme that liberates 1 µmoL of product/min (Ghose, T. K., Pure & Appl. Chem. 1987, 59, pp. 257-268).

The whole cellulase may be enriched with a polypeptide having GH61/endoglucanase activity, e.g., an EG IV-enriched (such as, e.g., enriched with $T. reesei$ Eg4 polypeptide or a variant thereof) cellulase. The EG IV-enriched whole cellulase generally comprises an EG IV polypeptide (such as, e.g., $T. reesei$ Eg4 polypeptide or a variant thereof) and a whole cellulase preparation. The EG IV-enriched whole cellulase compositions can be produced by recombinant means. For example, such a whole cellulase preparation can be achieved by expressing an EG IV in a microorganism capable of producing a whole cellulase. The EG IV-enriched whole cellulase composition can also, e.g., comprise a whole cellulase preparation and an EG IV (such as, e.g., $T. reesei$ Eg4 polypeptide or a variant thereof). For instance, the EG IV-enriched (e.g., enriched with $T. reesei$ Eg4 polypeptide or a variant thereof) whole cellulase composition can suitably comprise at least 0.1 wt. %, 1 wt. %, 2 wt. %, 5 wt. %, 7 wt. %, 10 wt. %, 15 wt. % or 20 wt. %, and up to 25 wt. %, 30 wt. %, 35 wt. %, 40 wt. %, or 50 wt. % EG IV based on the total weight of proteins in that blend/composition.

The whole cellulase can be a β-glucosidase-enriched cellulase. The β-glucosidase-enriched whole cellulase generally comprises a β-glucosidase and a whole cellulase preparation. The β-glucosidase-enriched whole cellulase compositions can be produced by recombinant means. For example, such a whole cellulase preparation can be achieved by expressing a β-glucosidase in a microorganism capable of producing a whole cellulase. The β-glucosidase-enriched whole cellulase composition can also, e.g., comprise a whole cellulase preparation and a β-glucosidase. For instance, the β-glucosidase-enriched whole cellulase composition can suitably comprise at least 0.1 wt. %, 1 wt. %, 2 wt. %, 5 wt. %, 7 wt. %, 10 wt. %, 15 wt. % or 20 wt. %, and up to 25 wt. %, 30 wt. %, 35 wt. %, 40 wt. %, or 50 wt. % β-glucosidase based on the total weight of proteins in that blend/composition.

Certain fungi produce complete cellulase systems, including exo-cellobiohydrolases or CBH-type cellulases, endoglucanases or EG-type cellulases and β-glucosidase or BG-type cellulases (Schulein, 1988). However, sometimes these systems lack CBH-type cellulases, e.g., bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

In some aspects, the cellulase is used as is produced by fermentation with no or minimal recovery and/or purification. For example, once cellulases are secreted by a cell into the cell culture medium, the cell culture medium containing the cellulases can be used. In some aspects, the whole cellulase preparation comprises the unfractionated contents of fermentation material, including cell culture medium, extracellular enzymes and cells. Alternatively, the whole cellulase preparation can be processed by any convenient method, e.g., by precipitation, centrifugation, affinity, filtration or any other method known in the art. In some aspects, the whole cellulase preparation can be concentrated, for example, and then used without further purification. In some aspects, the whole cellulase preparation comprises chemical agents that decrease cell viability or kills the cells. In some aspects, the cells are lysed or permeabilized using methods known in the art.

A composition is provided comprising a polypeptide having GH61/endoglucanase activity (e.g., $T. reesei$ Eg4 or a variant thereof) and further comprising at least one cellulase polypeptide and/or at least one hemicellulase polypeptide, wherein the cellulase polypeptide and/or the hemicellulase polypeptide is heterologous to the host cell expressing the cellulase polypeptide and/or the hemicellulase polypeptide. In some aspects, there is provided a composition comprising a polypeptide having GH61/endoglucanase activity (e.g., $T. reesei$ Eg4 or a variant thereof) and further comprising at least 1 cellulase polypeptide and/or at least 1 hemicellulase polypeptide, wherein the cellulase polypeptide and/or the hemicellulase polypeptide is expressed from a host cell, and wherein cellulase polypeptide and/or a hemicellulase polypeptide is endogenous to the host cell. The cellulase polypeptide may comprise a polypeptide having endoglucanase activity (e.g., $T. reesei$ EG1 or a variant thereof, *T. reesei* EG2 or a variant thereof), a polypeptide having cellobiohydrolase activity (e.g., *T. reesei* CBH1, *A. fumigatus* 7A, 7B, *C. globosum* 7A, 7B, *T. terrestris* 7A, 7B, *T. reesei* CBH2, *T. terrestris* 6A, *S. thermophile* 6A, 6B, or a variant thereof), or a polypeptide having β-glucosidase activity (e.g., Fv3C, Pa3D, Fv3G, Fv3D, Tr3A, Tr3B, Te3A, An3A, Fo3A, Gz3A, Nh3A, Vd3A, Pa3G, Tn3B, or a variant thereof). The hemicellulase polypeptide may comprise a polypeptide having xylanase activity (e.g., *T. reesei* Xyn3, *T. reesei* Xyn2, AfuXyn2, AfuXyn5, or a variant thereof), a having β-xylosidase activity (e.g., Fv3A, Fv43A, Pf43A, Fv43D, Fv39A, Fv43E, Fo43A, Fv43B, Pa51A, Gz43A, *T. reesei* Bxl1, or a variant thereof), or a polypeptide having L-α-arabinofuranosidase activity (e.g., Af43A, Fv43B, Pf51A, Pa51A, Fv51A, or a variant thereof).

In some aspects, the composition is from fermentation broth. The composition may be from the fermentation broth of a strain, wherein a nucleic acid encoding a polypeptide having GH61/endoglucanase activity (e.g., *T. reesei* Eg4 or a variant thereof) is heterologous to the host cell expressing the polypeptide having GH61/endoglucanase activity (e.g., integrated into the strain or expressed from a vector in the host strain). The composition may be from the fermentation broth of an integrated strain (e.g., H3A/Eg4, #27 as in Examples).

The composition comprising a polypeptide having GH61/endoglucanase activity (e.g., *T. reesei* Eg4 or a variant thereof) may comprise whole cellulase. Thus, a composition is provided (e.g., a non-naturally occurring composition) comprising *T. reesei* Eg4 (or a variant thereof), *T. reesei* Bgl1 (or a variant thereof), *T. reesei* xyn3 (or a variant thereof), Fv3A (or a variant thereof), Fv43D (or a variant thereof), and Fv51A (or a variant thereof).

In some aspects, the composition comprises isolated *T. reesei* Eg4. In some aspects, the composition comprises at least one (at least 2, 3, 4, or 5) of isolated *T. reesei* Bgl1, isolated *T. reesei* xyn3, isolated Fv3A, isolated Fv43D, and isolated Fv51A.

In some aspects, the composition is from fermentation broth. In some aspects, the composition is from the fermentation broth of an integrated strain (e.g., H3A/Eg4, #27 as described herein in the Examples). The *T. reesei* Eg4 or the nucleic acid encoding *T. reesei* Eg4 may be heterologous to the host cell expressing *T. reesei* Eg4. At least one nucleic acid encoding *T. reesei* Bgl1, *T. reesei* xyn3, Fv3A, Fv43D, Fv51A, or a variant thereof may be heterologous to the host cell such as the host cell expressing *T. reesei* Eg4. In some aspects, at least one nucleic acid encoding *T. reesei* Bgl1, *T. reesei* xyn3, Fv3A, Fv43D, Fv51A, or a variant thereof is endogenous to the host cell such as the host cell expressing *T. reesei* Eg4.

Regarding any of the compositions described above, varying amounts of the polypeptide(s) included in the compositions are described below in "Amount of component(s) in compositions" section.

Amount of Component(s) in Compositions

A non-naturally occurring composition comprising a polypeptide having GH61/endoglucanase activity (or a non-naturally occurring composition comprising whole cellulase comprising a polypeptide having GH61/endoglucanase activity) provided herein may comprise various components as described herein, wherein each component is present in the composition in various amount.

In some aspects of any one of the compositions or methods provided herein, the polypeptide having GH61/endoglucanase activity (e.g., *T. reesei* Eg4 or a variant thereof) is present in the composition in an amount sufficient to increase the yield of fermentable sugar(s) from hydrolysis of biomass material (e.g., by at least about any of 5%, 10%, 15%, 20%, 25%, 30%, 35%, 40%, 45%, 50%, 60%, 70%, 80%, or 90%) compared to the yield in the absence of the polypeptide having GH61/endoglucanase activity (e.g., *T. reesei* Eg4 or a variant thereof). Any one of the compositions or methods provided herein, the polypeptide having GH61/endoglucanase activity (e.g., *T. reesei* Eg4 or a variant thereof) may be present in the composition in an amount sufficient to reduce the viscosity of a biomass mixture during hydrolysis of a biomass material (e.g., by at least about any of 5%, 10%, 15%, 20%, 25%, 30%, 35%, 40%, 45%, 50%, 60%, 70%, 80%, or 90%) compared to the viscosity of the biomass mixture during hydrolysis in the absence of the polypeptide having GH61/endoglucanase activity (e.g., *T. reesei* Eg4 or a variant thereof). The composition may further comprise at least 1 polypeptide having endoglucanase activity, at least 1 polypeptide having cellobiohydrolase activity, at least 1 polypeptide having β-glucosidase activity, at least 1 polypeptide having xylanase activity, at least 1 polypeptide having β-xylosidase activity, at least 1 polypeptide having L-α-arabinofuranosidase activity, and/or whole cellulase, or a mixture thereof. The amount of polypeptide(s) having endoglucanase activity, the amount of polypeptide(s) having cellobiohydrolase activity, the amount of polypeptide(s) having β-glucosidase activity, the amount of polypeptide(s) having xylanase activity, the amount of polypeptide(s) having β-xylosidase activity, the amount of polypeptide(s) having L-α-arabinofuranosidase activity, or the amount of whole cellulase is sufficient to increase the yield of fermentable sugar(s) from hydrolysis of biomass material (e.g., by at least about any of 5%, 10%, 15%, 20%, 25%, 30%, 35%, 40%, 45%, 50%, 60%, 70%, 80%, or 90%) compared to the yield in the absence of the polypeptide having GH61/endoglucanase activity (e.g., *T. reesei* Eg4 or a variant thereof), the polypeptide(s) having endoglucanase activity, the polypeptide(s) having cellobiohydrolase activity, the polypeptide(s) having β-glucosidase activity, the polypeptide(s) having xylanase activity, the polypeptide(s) having β-xylosidase activity, the polypeptide(s) having L-α-arabinofuranosidase activity, or the whole cellulase. In some aspects, the amount of polypeptide(s) having endoglucanase activity, the amount of polypeptide(s) having cellobiohydrolase activity, the amount of polypeptide(s) having β-glucosidase activity, the amount of polypeptide(s) having xylanase activity, the amount of polypeptide(s) having L-α-arabinofuranosidase activity, or the amount of whole cellulase is sufficient to reduce the viscosity of a biomass mixture during hydrolysis of a biomass material (e.g., by at least about any of 5%, 10%, 15%, 20%, 25%, 30%, 35%, 40%, 45%, 50%, 60%, 70%, 80%, or 90%) compared to the viscosity of a biomass mixture in the absence of the polypeptide having GH61/endoglucanase activity (e.g., *T. reesei* Eg4 or a variant thereof), the polypeptide(s) having endoglucanase activity, the polypeptide(s) having cellobiohydrolase activity, the polypeptide(s) having β-glucosidase activity, the polypeptide(s) having xylanase activity, the polypeptide(s) having β-xylosidase activity, the polypeptide(s) having L-α-arabinofuranosidase activity, or the whole cellulase.

A polypeptide having GH61/endoglucanase activity (such as EG IV including *T. reesei* Eg4 polypeptide or a variant thereof) may be present in any of the compositions described herein (such as in any of the enzyme blends/compositions provided herein) in an amount that is at least about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, or 50 wt. % of the total weight of proteins in the composition. In some aspects, a polypeptide having GH61/endoglucanase activity (such as EG IV including, e.g., *T. reesei* Eg4 polypeptide or a variant thereof) may be present in any of the compositions described herein (such as in any of the enzyme blends/ compositions provided herein) in an amount that is no more than about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of proteins in the composition. A polypeptide having GH61/endoglucanase activity (such as EG IV including, e.g., *T. reesei* Eg4 polypeptide or a variant thereof) may be present in any of the compositions described herein (such as in any of the enzyme blends/compositions provided herein) in an amount that has a range having upper limit and lower limit. For example, lower limit for a polypeptide having GH61/endoglucanase activity is about any of 0.01 wt. %, 1 wt. %, 2 wt. %, 3 wt. %, 4 wt. %, 5 wt. %, 6 wt. % 7 wt. %, 8 wt. %, 9 wt. %, 10 wt. %, 12 wt. %, 15 wt. %, 20 wt. %, 25 wt. %, 30 wt. %, 40 wt. %, 45 wt. %, or 50 wt. % of the total weight of proteins in the composition. Upper limit for a polypeptide having GH61/endoglucanase activity may be about any of 10 wt, %, 15 wt, %, 20 wt. %, 25 wt. %, 30 wt. %, 35 wt. %, 40 wt. %, 50 wt. %, 55 wt. %, 60 wt. %, 65 wt. % or 70 wt. % of the total weight of proteins in the composition. In some aspects, a polypeptide having GH61/endoglucanase activity (such as EG IV including, e.g., *T. reesei* Eg4 polypeptide or a variant thereof) may be present in any of the compositions described herein (such as in any of the enzyme blends/compositions provided herein) in an amount that is about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of proteins in the composition. The polypeptide having GH61/endoglucanase activity (e.g., *T. reesei* Eg4 or a variant thereof) may be present in about 10 wt. % or 12 wt. % of the total weight of proteins in the composition. The composition may have at least two polypeptides having endoglucanase activity (e.g., *T. reesei* Eg4, *T. reesei* Eg1, and/or *T. reesei* Eg2, or a variant thereof), where the total amount of polypeptides having endoglucanase activity is about 0.1 to about 50 wt. % (e.g., about 0.5 to about 45 wt. %, about 1 to about 30 wt. %, about 2 to about 20 wt. %, about 5 to about 20 wt. %, or about 8 to about 15 wt. %) of the total weight of proteins in the composition. The polypeptide having GH61/endoglucanase activity may be heterologous or endogenous to the host cell expressing the polypeptide having GH61/endoglucanase activity. The polypeptide having GH61/endoglucanase activity included in the composition may be isolated.

In some aspects, the enzyme composition (e.g., the enzyme composition) described herein is whole cellulase composition comprising a polypeptide having GH61/endoglucanase activity. In some aspects, a polypeptide having GH61/endoglucanase activity (such as EG IV including, e.g., *T. reesei* Eg4 polypeptide or a variant thereof) may be present in an amount that is at least about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, or 50 wt. % of the total weight of the whole cellulase. In some aspects, a polypeptide having GH61/endoglucanase activity (such as EG IV including, e.g., *T. reesei* Eg4 polypeptide or a variant thereof) may be present in an amount that is no more than about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of the whole cellulase. In some aspects, a polypeptide having GH61/endoglucanase activity (such as EG IV including, e.g., *T. reesei* Eg4 polypeptide or a variant thereof) may be present in an amount that has a lower limit of about any of 0.01 wt. %, 1 wt. %, 2 wt. %, 3 wt. %, 4 wt. %, 5 wt. %, 6 wt. % 7 wt. %, 8 wt. %, 9 wt. %, 10 wt. %, 12 wt. %, 15 wt. %, 20 wt. %, 25 wt. %, 30 wt. %, 40 wt. %, 45 wt. %, or 50 wt. % of the total weight of the whole cellulase and a upper limit of about any of 10 wt, %, 15 wt, %, 20 wt. %, 25 wt. %, 30 wt. %, 35 wt. %, 40 wt. %, 50 wt. %, 55 wt. %, 60 wt. %, 65 wt. % or 70 wt. % of the total weight of the whole cellulase. In some aspects, a polypeptide having GH61/endoglucanase activity (such as EG IV including, e.g., *T. reesei* Eg4 polypeptide or a variant thereof) may be present in an amount that is about 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 13 wt. %, 14 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of the whole cellulase. In some aspects, a polypeptide having GH61/endoglucanase activity (such as EG IV including, e.g., *T. reesei* Eg4 polypeptide or a variant thereof) is present in an amount that is about 10 wt. % or 12 wt. % of the total weight of the whole cellulase.

In some aspects, any of the compostions provided herein may comprise at least one polypetide having endoglucanase activity (e.g., in addition to a polypeptide having GH61/endoglucanase activity) including *T. reesei* Eg1 or a variant thereof and/or *T. reesei* Eg2 or a variant thereof. In some aspects, the total amount of the polypeptide(s) having endoglucanase activity may be present in any of the compositions described herein (such as in any of the enzyme blends/compositions provided herein) in an amount that is at least about 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, or 50 wt. % of the total weight of proteins in the composition. In some aspects, the total amount of the polypeptide(s) having endoglucanase activity may be present in any of the compositions described herein (such as in any of the enzyme blends/compositions provided herein) in an amount that is no more than about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of proteins in the composition. In some aspects, the total amount of the polypeptide(s) having endoglucanase activity may be present in any of the compositions described herein (such as in any of the enzyme blends/compositions provided herein) in an amount that has a range having upper limit and lower limit. For example, lower limit for the total amount of the polypeptide(s) having endoglucanase activity is about any of 0.01 wt. %, 1 wt. %, 2 wt. %, 3 wt. %, 4 wt. %, 5 wt. %, 6 wt. % 7 wt. %, 8 wt. %, 9 wt. %, 10 wt. %, 12 wt. %, 15 wt. %, 20 wt. %, 25 wt. %, 30 wt. %, 40 wt. %, 45 wt. %, or 50 wt. % of the total weight of proteins in the composition. Upper limit for the total amount of the polypeptide(s) having endoglucanase activity may be about any of 10 wt, %, 15 wt, %, 20 wt. %, 25 wt. %, 30 wt. %, 35 wt. %, 40 wt. %, 50 wt. %, 55 wt. %, 60 wt. %, 65 wt. % or 70 wt. % of the total weight of proteins in the composition. In some aspects, the total amount of the polypeptide(s) having endoglucanase activity may be present in any of the compositions described herein (such as in any of the enzyme blends/compositions provided herein) in an amount that is about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of proteins in the composition.

In some aspects, any of the compostions provided herein may comprise one or more polypeptide with various enzyme activity, such as polypeptide(s) having cellobiohydrolase activity, polypeptide(s) having glucosidase activity (e.g., β-glucosidase), polypeptide(s) having xylanase activity, polypeptide(s) having xylosidase activity, and/or polypeptide(s) having arabinofuranosidase activity. In some aspects, there may be multiple polypeptides having the same enzyme activity. Each of the polypeptides mentioned above (or the total amount of the polypeptides having a specific enzyme activity, e.g., total amount of the polypeptides having cellobiohydrolase activity, glucosidase activity (e.g., β-glucosidase), xylanase activity, xylosidase activity, or arabinofuranosidase activity) may be present in any of the compositions described herein (such as in any of the enzyme blends/compositions provided herein) in an amount that is at least about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, or 50 wt. % of the total weight of proteins in the composition. In some aspects, each of the polypeptides mentioned above (or the total amount of the polypeptides having a specific enzyme activity, e.g., total amount of the polypeptides having cellobiohydrolase activity, glucosidase activity (e.g., β-glucosidase), xylanase activity, xylosidase activity, or arabinofuranosidase activity) may be no more than about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of proteins in the composition. Each of the polypeptides mentioned above (or the total amount of the polypeptides having a specific enzyme activity, e.g., total amount of the polypeptides having cellobiohydrolase activity, glucosidase activity (e.g., β-glucosidase), xylanase activity, xylosidase activity, or arabinofuranosidase activity) may be present in any of the compositions described herein (such as in any of the enzyme blends/compositions provided herein) in an amount that has a range having upper and lower limits. For example, lower limit for the total amount of the polypeptide(s) having endoglucanase activity is about any of 0.01 wt. %, 1 wt. %, 2 wt. %, 3 wt. %, 4 wt. %, 5 wt. %, 6 wt. % 7 wt. %, 8 wt. %, 9 wt. %, 10 wt. %, 12 wt. %, 15 wt. %, 20 wt. %, 25 wt. %, 30 wt. %, 40 wt. %, 45 wt. %, or 50 wt. % of the total weight of proteins in the composition. Upper limit may be about any of 10 wt, %, 15 wt, %, 20 wt. %, 25 wt. %, 30 wt. %, 35 wt. %, 40 wt. %, 50 wt. %, 55 wt. %, 60 wt. %, 65 wt. % or 70 wt. % of the total weight of proteins in the composition. In some aspects, each of the polypeptides mentioned above (or the total amount of the polypeptides having a specific enzyme activity, e.g., total amount of the polypeptides having cellobiohydrolase activity, glucosidase activity (e.g., β-glucosidase), xylanase activity, xylosidase activity, or arabinofuranosidase activity) may be present in any of the compositions described herein (such as in any of the enzyme blends/compositions provided herein) in an amount that is about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, or 80 wt. % of the total weight of proteins in the composition.

In some aspects, any of the compostions provided herein may further comprise whole cellulase. The whole cellulase may be present in any of the compositions described herein (such as in any of the enzyme blends/compositions provided herein) in an amount that is at least about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, or 95 wt. % of the total weight of proteins in the composition. The whole cellulase may be present in any of the compositions described herein (such as in any of the enzyme blends/compositions provided herein) in an amount that is no more than about any of 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, or 95 wt. % of the total weight of proteins in the composition. The whole cellulase may be present in any of the compositions described herein (such as in any of the enzyme blends/compositions provided herein) in an amount that is about any of 1 wt. %, 2 wt. %, 3 wt. %, 4 wt. %, 5 wt. %, 6 wt. % 7 wt. %, 8 wt. %, 9 wt. %, 10 wt. %, 11 wt. %, 12 wt. %, 15 wt. %, 20 wt. %, 25 wt. %, 30 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. %, or 95 wt. % of the total weight of proteins in the composition.

In some aspects of any one of the compositions or methods provided herein, the polypeptide having cellobiohydrolase activity (e.g., *T. reesei* CBH1, *T. reesei* CBH2, or a variant thereof) is present in an amount that is about 0.1 to about 70 wt. % (e.g., about 0.5 to about 60 wt. %, about 5 to about 70 wt. %, about 10 to about 60 wt. %, about 20 to about 50 wt. %, or about 30 to about 50 wt. %) of the total weight of proteins in the composition. In some aspects, the composition has at least two polypeptides having cellobiohydrolase activity (e.g., *T. reesei* CBH1 (or a variant thereof) and *T. reesei* CBH2 (or a variant thereof)), wherein the total amount of polypeptides having cellobiohydrolase activity is about 0.1 to about 70 wt. % (e.g., about 0.5 to about 60 wt. %, about 5 to about 70 wt. %, about 10 to about 60 wt. %, about 20 to about 50 wt. %, or about 30 to about 50 wt. %) of the total weight of proteins in the composition. The polypeptide having cellobiohydrolase activity may be expressed from a nucleic acid heterologous or endogenous to the host cell. In some aspects, the polypeptide having cellobiohydrolase activity included in the composition is isolated.

In some aspects of any one of the compositions or methods provided herein, the polypeptide having β-glucosidase activity (e.g., an Fv3C, a Pa3D, an Fv3G, an Fv3D, a Tr3A, a Tr3B, a Te3A, an An3A, an Fo3A, a Gz3A, an Nh3A, a Vd3A, a Pa3G, a Tn3B, or a variant thereof) is present in an amount that is about 0.1 to about 50 wt. % (e.g., about 0.5 to about 40 wt. %, about 1 to about 30 wt. %, about 2 to about 20 wt. %, about 5 to about 20 wt. %, or about 8 to about 15 wt. %) of the total weight of proteins in the composition. In some aspects, the composition has at least two polypeptides having β-glucosidase activity, wherein the total amount of polypeptides having β-glucosidase activity is about 0.1 to about 50 wt. % (e.g., about 0.5 to about 40 wt. % about 1 to about 30 wt. %, about 2 to about 20 wt. %, about 5 to about 20 wt. %, or about 8 to about 15 wt. %) of the total weight of proteins in the composition. The polypeptide having β-glucosidase activity may be expressed from a nucleic acid heterologous or endogenous to the host cell. In some aspects, the polypeptide having β-glucosidase activity included in the composition is isolated.

Any one of the compositions or methods provided herein, the polypeptide having xylanase activity (e.g., T. reesei Xyn3, T. reesei Xyn2, an AfuXyn2, an AfuXyn5, or a variant thereof) may be present in an amount that is about 0.1 to about 50 wt. % (e.g., about 0.5 to about 40 wt. %, about 1 to about 40 wt. %, about 4 to about 30 wt. %, about 5 to about 20 wt. %, or about 8 to about 15 wt. %) of the total weight of proteins in the composition. The composition may have at least 2 polypeptides having xylanase activity, wherein the total amount of polypeptides having xylanase activity is about 0.1 to about 50 wt. % (e.g., about 0.5 to about 40 wt. %, about 1 to about 40 wt. %, about 4 to about 30 wt. %, about 5 to about 20 wt. %, or about 8 to about 15 wt. %) of the total weight of proteins in the composition. The polypeptide having xylanase activity may be expressed from a nucleic acid heterologous or endogenous to the host cell. The polypeptide having xylanase activity included in the composition may be isolated.

Any one of the compositions or methods provided herein, the polypeptide having L-α-arabinofuranosidase activity (e.g., an Af43A, an Fv43B, a Pf51A, a Pa51A, an Fv51A, or a variant thereof) may be present in an amount that is about 0.1 to about 50 wt. % (e.g., about 0.5 to about 45 wt. %, about 1 to about 40 wt. %, about 2 to about 30 wt. %, about 4 to about 20 wt. %, or about 5 to about 15 wt. %) of the total weight of enzymes in the composition. The composition may have at least 2 polypeptides having L-α-arabinofuranosidase activity, wherein the total amount of polypeptides having L-α-arabinofuranosidase activity is about 0.1 to about 50 wt. % (e.g., about 0.5 to about 45 wt. %, about 1 to about 40 wt. %, about 2 to about 30 wt. %, about 4 to about 20 wt. %, or about 5 to about 15 wt. %) of the total weight of proteins in the composition. The polypeptide having L-α-arabinofuranosidase activity may be expressed from a nucleic acid heterologous or heterologous to the host cell. The polypeptide having L-α-arabinofuranosidase activity included in the composition may be isolated.

Any one of the compositions or methods provided herein, the polypeptide having β-xylosidase activity (e.g., Fv3A, Fv43A, a Pf43A, an Fv43D, an Fv39A, an Fv43E, an Fo43A, an Fv43B, a Pa51A, a Gz43A, a T. reesei Bxl1, or a variant thereof) may be present in an amount that is about 0.1 to about 50 wt. % (e.g., about 0.5 to about 45 wt. %, about 1 to about 40 wt. %, about 4 to about 35 wt. %, about 5 to about 25 wt. %, or about 5 to about 20 wt. %) of the total weight of enzymes in the composition. The composition may have at least 2 polypeptides having β-xylosidase activity, wherein the total amount of polypeptides having β-xylosidase activity is about 0.1 to about 50 wt. % (e.g., about 0.5 to about 45 wt. %, about 1 to about 40 wt. %, about 4 to about 35 wt. %, about 5 to about 25 wt. %, or about 5 to about 20 wt. %) of the total weight of proteins in the composition. The polypeptide having β-xylosidase activity may be expressed from a nucleic acid heterologous or endogenous to the host cell. The polypeptide having β-xylosidase activity included in the composition may be isolated.

Any one of the compositions or methods provided herein, the whole cellulase in the composition may be about 0.1 to about 100 wt. % (e.g., about 1 to about 95 wt. %, about 5 to about 90 wt. %, about 10 to about 85 wt. %, about 20 to about 80 wt. %, or about 30 to about 75 wt. %) of the total weight of proteins in the composition. The whole cellulase may comprise at least 1 polypeptide having endoglucanase activity (such as T. reesei Eg4 or a variant thereof, T. reesei Eg1 or a variant thereof, T. reesei Eg2 or a variant thereof) expressed from a nucleic acid heterologous or endogenous to the host cell. The whole cellulase may comprise at least 1 polypeptide having cellobiohydrolase activity (e.g., T. reesei CBH1 or a variant thereof, T. reesei CBH2 or a variant thereof) expressed from a nucleic acid heterologous or endogenous to the host cell. The whole cellulase may comprise at least one polypeptide having β-glucosidase activity (e.g., an Fv3C, a Pa3D, an Fv3G, an Fv3D, a Tr3A, a Tr3B, a Te3A, an An3A, an Fo3A, a Gz3A, an Nh3A, a Vd3A, a Pa3G, a Tn3B, or a variant thereof) expressed from a nucleic acid heterologous or endogenous to the host cell.

In some aspects, the composition of the invention is capable of converting a biomass material into fermentable sugar(s) (e.g., glucose, xylose, arabinose, and/or cellobiose). In some aspects, the composition is capable of achieving at least 0.1 (e.g., 0.1 to 0.4) fraction product as determined by the calcofluor assay.

In some aspects, the composition comprises the polypeptide having GH61/endoglucanase activity (e.g., T. reesei Eg4 or a variant thereof) and further comprises at least one cellulase polypeptide and/or at least one hemicellulase polypeptide, wherein the polypeptide having GH61/endoglucanase activity (e.g., T. reesei Eg4 or a variant thereof) and at least one cellulase polypeptide and/or at least one hemicellulase polypeptide are mixed together before contacting a biomass material.

In some aspects, the composition comprises a polypeptide having GH61/endoglucanase activity (e.g., T. reesei Eg4 or a variant thereof) and further comprises at least one cellulase polypeptide and/or at least one hemicellulase polypeptide, wherein the polypeptide having GH61/endoglucanase activity (e.g., T. reesei Eg4 or a variant thereof) and at least one cellulase polypeptide and/or at least one hemicellulase polypeptide are added to a biomass material at different times (e.g., a polypeptide having GH61/endoglucanase activity is added to a biomass material before or after the at least one cellulase polypeptide and/or at least one hemicellulase polypeptide is added to the biomass material).

In some aspects, the composition comprising a polypeptide having GH61/endoglucanase activity (e.g., T. reesei Eg4 or a variant thereof) is a mixture comprising a biomass material, e.g., the composition is a hydrolysis mixture, a fermentation mixture, or a saccharification mixture. Such mixture may further include fermentable sugar(s).

Other Components

The enzyme compositions of the disclosure may suitably further comprise 1 or more accessory proteins. Examples of accessory proteins include, without limitation, mannanases (e.g., endomannanases, exomannanases, and β-mannosidases), galactanases (e.g., endo- and exo-galactanases), arabinases (e.g., endo-arabinases and exo-arabinases), ligninases, amylases, glucuronidases, proteases, esterases (e.g., ferulic acid esterases, acetyl xylan esterases, coumaric acid esterases or pectin methyl esterases), lipases, other glycoside hydrolases, xyloglucanases, CIP1, CIP2, swollenins, expansins, and cellulose disrupting proteins. For example, the cellulose disrupting proteins are cellulose binding modules.

Methods and Processes

The disclosure provides methods and processes for biomass saccharification, using enzymes, enzyme blends/compositions of the disclosure. In particular, the disclosure provides methods and processes for using any one of the polypeptides or compositions provided herein for hydrolyzing a biomass material. Further, the disclosure provides methods of using any one of the polypeptides or compositions provided herein for reducing the viscosity of a biomass mixture (e.g., a biomass mixture containing biomass substrate and enzyme during saccharification process). In some aspects, there are provided methods of hydrolyzing a biomass material comprising contacting the biomass material with a non-naturally occurring composition comprising a polypeptide having GH61/endoglucanase activity. In some aspects, the polypeptide is in an amount sufficient to hydrolyze the biomass material.

The term "biomass," as used herein, refers to any composition comprising cellulose and/or hemicellulose (including lignin in lignocellulosic biomass materials). As used herein, biomass includes, without limitation, seeds, grains, tubers, plant waste or byproducts of food processing or industrial processing (e.g., stalks), corn (including, e.g., cobs, stover, and the like), grasses (including, e.g., Indian grass, such as *Sorghastrum nutans*; or, switchgrass, e.g., *Panicum* species, such as *Panicum virgatum*), perennial canes (e.g., giant reeds), wood (including, e.g., wood chips, processing waste), paper (including paper waste), pulp, and recycled paper (including, e.g., newspaper, printer paper, and the like). Other biomass materials include, without limitation, potatoes, soybean (e.g., rapeseed), barley, rye, oats, wheat, beets, and sugar cane bagasse. Suitable lignocellulosic biomass materials include, without limitation, seeds, grains, tubers, plant waste or byproducts of food processing or industrial processing (e.g., stalks), corn (including, e.g., cobs, stover, and the like), grasses (e.g., Indian grass, such as *Sorghastrum nutans*; or, switchgrass, e.g., *Panicum* species, such as *Panicum virgatum*), perennial canes, e.g., giant reeds, wood (including, e.g., wood chips, processing waste), paper, pulp, recycled paper (e.g., newspaper), wood pulp, or sawdust. Examples of grasses include, without limitation, Indian grass or switchgrass. Examples of reeds include, without limitation, certain perennial canes such as giant reeds. Examples of paper waste include, without limitation, discarded or used photocopy paper, computer printer paper, notebook paper, notepad paper, typewriter paper, newspapers, magazines, cardboard and paper-based packaging materials.

The saccharified biomass can be made into a number of bio-based products, via processes such as, e.g., microbial fermentation and/or chemical synthesis. As used herein, "microbial fermentation" refers to a process of growing and harvesting fermenting microorganisms under suitable conditions. The fermenting microorganism can be any microorganism suitable for use in a desired fermentation process for the production of bio-based products. Suitable fermenting microorganisms include, without limitation, filamentous fungi, yeast, and bacteria. The saccharified biomass can, e.g., be made it into a fuel (e.g., a biofuel such as a bioethanol, biobutanol, biomethanol, a biopropanol, a biodiesel, a jet fuel, or the like) via fermentation and/or chemical synthesis. The saccharified biomass can, e.g., also be made into a commodity chemical (e.g., ascorbic acid, isoprene, 1,3-propanediol), lipids, amino acids, proteins, and enzymes, via fermentation and/or chemical synthesis.

Biomass material may include cellulose, hemicellulose, or a mixture thereof. For example, a biomass material may include glucan and/or xylan.

In some aspects, there are provided methods of reducing the viscosity of a biomass mixture comprising contacting the biomass mixture with non-naturally occurring composition comprising a polypeptide having GH61/endoglucanase activity. The polypeptide is in an amount sufficient to reduce the viscosity. The biomass mixture may comprise biomass material (e.g., pretreated biomass material). The biomass mixture may comprise an enzyme composition such as any of the enzyme compositions provided herein or a mixture thereof.

In some aspects, any of the polypeptides, compositions provided herein may be used to hydrolyze substrate such as a biomass material or reduce the viscosity of a substrate-enzyme mixture during saccharification process. The substrate may be a biomass material. The substrate may be isolated cellulose or isolated hemicellulose. The substrate may be glucan and/or xylan. In some aspects, the biomass material is pretreated biomass material.

Pretreatment of Biomass Material

Prior to saccharification, a biomass material is preferably subject to one or more pretreatment step(s) in order to render xylan, hemicellulose, cellulose and/or lignin material more accessible or susceptable to enzymes and thus more amenable to hydrolysis by the enzyme(s) and/or enzyme blends/compositions of the disclosure.

Pretreatment may include chemical, physical, and biological pretreatment. For example, physical pretreatment techniques can include without limitation various types of milling, crushing, steaming/steam explosion, irradiation and hydrothermolysis. Chemical pretreatment techniques can include without limitation dilute acid, alkaline, organic solvent, ammonia, sulfur dioxide, carbon dioxide, and pH-controlled hydrothermolysis. Biological pretreatment techniques can include without limitation applying lignin-solubilizing microorganisms. The pretreatment can occur from several minutes to several hours, such as from about 1 hour to about 120.

In some aspects, any of the methods or processes provided herein may further comprise pretreating the biomass material, such as pretreating the biomass with acid or base. The acid or base may be ammonia, sodium hydroxide, or phosphoric acid. The method may further comprise pretreating the biomass material with ammonia. The pretreatment may be steam explosion, pulping, grinding, acid hydrolysis, or combinations thereof.

In one embodiment, the pretreatment may be by elevated temperature and the addition of either of dilute acid, concentrated acid or dilute alkali solution. The pretreatment solution can added for a time sufficient to at least partially hydrolyze the hemicellulose components and then neutralized In an exemplary embodiment, the pretreatment entails subjecting biomass material to a catalyst comprising a dilute solution of a strong acid and a metal salt in a reactor. The biomass material can, e.g., be a raw material or a dried material. This pretreatment can lower the activation energy, or the temperature, of cellulose hydrolysis, ultimately allowing higher yields of fermentable sugars. See, e.g., U.S. Pat. Nos. 6,660,506; 6,423,145.

Another exemplary pretreatment method entails hydrolyzing biomass by subjecting the biomass material to a first hydrolysis step in an aqueous medium at a temperature and a pressure chosen to effectuate primarily depolymerization of hemicellulose without achieving significant depolymerization of cellulose into glucose. This step yields a slurry in which the liquid aqueous phase contains dissolved monosaccharides resulting from depolymerization of hemicellulose, and a solid phase containing cellulose and lignin. The slurry is then subject to a second hydrolysis step under conditions that allow a major portion of the cellulose to be depolymerized, yielding a liquid aqueous phase containing dissolved/soluble depolymerization products of cellulose. See, e.g., U.S. Pat. No. 5,536,325.

A further example of method involves processing a biomass material by one or more stages of dilute acid hydrolysis using about 0.4% to about 2% of a strong acid; followed by treating the unreacted solid lignocellulosic component of the acid hydrolyzed material with alkaline delignification. See, e.g., U.S. Pat. No. 6,409,841.

Another example of pretreatment method comprises prehydrolyzing biomass (e.g., lignocellulosic materials) in a prehydrolysis reactor; adding an acidic liquid to the solid lignocellulosic material to make a mixture; heating the mixture to reaction temperature; maintaining reaction temperature for a period of time sufficient to fractionate the lingo-cellulosic material into a solubilized portion containing at least about 20% of the lignin from the lignocellulosic material, and a solid fraction containing cellulose; separating the solubilized portion from the solid fraction, and removing the solubilized portion while at or near reaction temperature; and recovering the solubilized portion. The cellulose in the solid fraction is rendered more amenable to enzymatic digestion. See, e.g., U.S. Pat. No. 5,705,369.

Further pretreatment methods can involve the use of hydrogen peroxide $H_2O_2$. See Gould, 1984, Biotech, and Bioengr. 26:46-52.

Pretreatment can also comprise contacting a biomass material with stoichiometric amounts of sodium hydroxide and ammonium hydroxide at a very low concentration. See Teixeira et al., 1999, Appl. Biochem. and Biotech. 77-79: 19-34. Pretreatment can also comprise contacting a lignocellulose with a chemical (e.g., a base, such as sodium carbonate or potassium hydroxide) at a pH of about 9 to about 14 at moderate temperature, pressure, and pH. See PCT Publication WO2004/081185.

Ammonia may be used in a pretreatment method. Such a pretreatment method comprises subjecting a biomass material to low ammonia concentration under conditions of high solids. See, e.g., U.S. Patent Publication 20070031918, PCT publication WO 06110901.

Saccharification Process and Viscosity Reduction

The present disclosure provides methods of reducing the viscosity of a biomass mixture comprising contacting the biomass mixture with a composition (e.g., a non-naturally occurring composition) comprising a polypeptide having glycosyl hydrolase family 61 ("GH61") endoglucanase activity in an amount sufficient to reduce the viscosity of the biomass mixture. In some aspects, the biomass mixture comprises a biomass material, fermentable sugar(s), whole cellulase, a composition comprising a polypeptide having cellulase activity, and/or a polypeptide having hemicellulase activity. In some aspects, the viscosity is reduced by at least about 5%, (e.g., at least about any of 5%, 10%, 15%, 20%, 25%, 30%, 35%, 40%, 45%, 50%, 60%, 70%, 80%, or 90%) compared to the viscosity of a biomass mixture in the absence of a polypeptide having GH61/endoglucanase activity (e.g., *T. reesei* Eg4 or a variant thereof). In some aspects of any of the methods described herein, the biomass material comprises hemicellulose, cellulose, or a mixture thereof. In some aspects, the biomass material comprises glucan, xylan and/or lignin.

The methods and processes provided herein may be performed under various conditions. For example, any of the methods provided herein may be performed at a pH in the range of pH of about 3.5 to about 7.0, for example, pH of about 4.0 to about 6.5, pH of about 4.4 to about 6.0, pH of about 4.8 to about 5.6, or about 4.5 to about 5.5. The saccharification mixture containing biomass material may be adjusted to the desired pH using base or acid (such as sulfuric acid) according to any of the methods known to one of ordinary skill in the art. For example, the pretreated biomass material may be added with base or acid (such as sulfuric acid) to achieve the desired pH for saccharification. Any of the methods for hydrolyzing a biomass material or reducing the viscosity of the biomass mixture may be conducted at a pH of about 4.8 to about 5.6 (e.g., pH of about any of 4.8, 4.9, 5.0, 5.1, 5.2, 5.3, 5.4, 5.5, or 5.6). In some aspects, the method further comprises adjusting the pH of the biomass mixture to a pH of about 4.0 to about 6.5 (e.g., pH of about 4.5 to about 5.5).

The methods and processes provided herein may be performed for any length of time, e.g., 1 hour, 2 hours, 4 hours, 8 hours, 12 hours, 18 hours, 24 hours, 2 days, 3 days, 4 days, 5 days, 6 days, 7 days, 8 days, 10 days, 14 days, 3 weeks, or 4 weeks. After any of the saccharification time described herein, the amount of fermentable sugar(s) is increased and/or the viscosity of the saccharification mixture is reduced. In some aspects, the method is performed for about 2 hours to about 7 days (e.g., about 4 hours to about 6 days, about 8 hours to about 5 days, or about 8 hours to about 3 days).

A composition (e.g., a non-naturally occurring composition) comprising polypeptide having GH61/endoglucanase activity (e.g., EG IV such as *T. reesei* Eg4 or a variant thereof) may be added after the biomass material is pretreated. A composition (e.g., a non-naturally occurring composition) comprising polypeptide having GH61/endoglucanase activity (e.g., EG IV such as *T. reesei* Eg4 or a variant thereof) may be added to the biomass material before or after another enzyme composition (such as an enzyme composition comprising hemicellulose, cellulase, or whole cellulase) is added to the biomass material. A composition (e.g., a non-naturally occurring composition) comprising polypeptide having GH61/endoglucanase activity (e.g., EG IV such as *T. reesei* Eg4 or a variant thereof) may be added to the biomass mixture containing (a) biomass material and/or fermentable sugars and (b) enzyme (such as hemicellulase or cellulase including whole cellulase). In some aspects, a composition (e.g., a non-naturally occurring composition) comprising polypeptide having GH61/endoglucanase activity (e.g., EG IV such as *T. reesei* Eg4 or a variant thereof) is added to the biomass mixture, wherein the biomass material has been hydrolyzed for a period of time (such as about any of 5 minutes, 10 minutes, 30 minutes, 1 hour, 2 hours, 4 hours, 8 hours, 12 hours, 18 hours, 24 hours, 2 days, 3 days, 4 days, or 5 days).

A composition (e.g., a non-naturally occurring composition) comprising isolated polypeptide having GH61/endoglucanase activity (e.g., EG IV such as *T. reesei* Eg4 or a variant thereof) may be added to biomass material during saccharification. A composition (e.g., a non-naturally occurring composition) comprising whole cellulase may be added to biomass material during saccharification, where the whole cellulase comprises a polypeptide having GH61/endoglucanase activity (e.g., EG IV such as *T. reesei* Eg4 or a variant thereof).

A biomass material used in any one of the methods may be in liquid form, solid form, or a mixture thereof. A biomass material used in any one of the methods may be wet form, dry form, a material having various degree of moisture, or a mixture thereof. A biomass material used in any one of the methods may be in a dry solid form (such as a dry solid form as a starting material). The biomass material may be processed into any of the following forms: wet form, dry form, solid form, liquid form, or a mixture thereof according to any method known to one skilled in the art.

A biomass material used in any of the methods may be present in the saccharification mixture in an amount of at least about any of 0.5 wt. %, 1 wt. %, 5 wt. %, 10 wt. %, 15 wt. %, 20 wt. %, 25 wt. %, 30 wt. %, 35 wt. %, 40 wt. %, 45 wt. %, 50 wt. %, 55 wt. %, or 60 wt. % of total weight of hydrolysis mixture or saccharification mixture, wherein the amount of the biomass material refers to the weight amount of the biomass material in its solid state (or the biomass material in its dry state, its dry solid state, its natural state, or its unprocessed state). The biomass material may also be in an amount of about 0.5 wt. % to about 55 wt. %, 1 wt. % to about 40 wt. %, 5 wt. % to about 60 wt. %, about 10 wt. % to about 55 wt. %, about 10 wt. % to about 50 wt. %, about 15 wt. % to about 50 wt. %, about 15 wt. % to about 40 wt. %, about 15 wt. % to about 35 wt. %, about 15 wt. % to about 30 wt. %, about 20 wt. % to about 35 wt. %, or about 20 wt. % to about 30 wt. % of a hydrolyzing mixture containing biomass material, wherein the amount of the biomass material refers to the weight amount of the biomass material in its solid state (or the biomass material in its dry state, its dry solid state, its natural state, or its unprocessed state). A biomass material used in any of the methods may be present in the saccharification mixture in an amount of about any of 0.5 wt. %, 1 wt. %. 5 wt. %, 10 wt. %, 15 wt. %, 20 wt. %, 25 wt. %, 30 wt. %, 35 wt. %, 40 wt. %, 45 wt. %, 50 wt. %, 55 wt. %, or 60 wt. % of total weight of hydrolysis mixture or saccharification mixture, wherein the amount of the biomass material refers to the weight amount of the biomass material in its solid state (or the biomass material in its dry state, its dry solid state, its natural state, or its unprocessed state).

The hydrolysis mixture or saccharification mixture includes biomass material, enzyme(s) (e.g., any one of polypeptides provided herein), enzyme composition (e.g., any one of the compositions provided herein), and/or other components such as components necessary for saccharification.

Any of the compositions provided herein may be used in the methods described herein such as any one of the compositions provided above in the "Exemplary compositions" section. The amount of any of the compositions described herein used in any one of the methods provided herein may be in the range of about 0.05 mg to about 50 mg, about 0.1 mg to about 40 mg, about 0.2 mg to about 30 mg, about 0.5 mg to about 25 mg, about 1 mg to about 25 mg, about 2 mg to about 25 mg, about 5 mg to about 25 mg, or about 10 mg to about 25 mg protein per gram of cellulose, hemicellulose, or a mixture of cellulose and hemicellulose contained in the biomass material. A non-naturally occurring composition comprising a polypeptide having GH61/endoglucanase activity (e.g., EG IV such as $T.$ $reesei$ Eg4 or a variant thereof) used in any one of the methods for hydrolyzing a biomass material and/or methods for reducing the viscosity of the biomass mixture may be in an amount of about 0.05 mg to about 50 mg, about 0.1 mg to about 40 mg, about 0.2 mg to about 30 mg, about 0.5 mg to about 25 mg, about 1 mg to about 25 mg, about 2 mg to about 25 mg, about 5 mg to about 25 mg, or about 10 mg to about 25 mg protein per gram of cellulose, hemicellulose, or a mixture of cellulose and hemicellulose contained in the substrate such as biomass material.

In some aspects, a non-naturally occurring composition comprising a polypeptide having GH61/endoglucanase activity (e.g., EG IV such as $T.$ $reesei$ Eg4 or a variant thereof) used in any of the methods for hydrolyzing a biomass material and/or methods for reducing the viscosity of the biomass mixture is in an amount of at least about any of 0.05 mg, 0.1 mg, 0.2 mg, 0.5 mg, 1 mg, 2 mg, 5 mg, 7.5 mg, 10 mg, 12 mg, 14 mg, 15 mg, 16 mg, 17.5 mg, 18 mg, 20 mg, 22.5 mg, 25 mg, 27. g mg, 30 mg, 35 mg, 40 mg, 45 mg, or 50 mg protein per gram of cellulose, hemicellulose, or a mixture of cellulose and hemicellulose contained in the substrate such as biomass material. In some aspects, a non-naturally occurring composition comprising a polypeptide having GH61/endoglucanase activity (e.g., EG IV such as $T.$ $reesei$ Eg4 or a variant thereof) used in any of the methods for hydrolyzing a biomass material and/or methods for reducing the viscosity of the biomass mixture is in an amount of no more than about any of 0.1 mg, 0.2 mg, 0.5 mg, 1 mg, 2 mg, 5 mg, 7.5 mg, 10 mg, 12 mg, 14 mg, 15 mg, 16 mg, 17.5 mg, 18 mg, 20 mg, 22.5 mg, 25 mg, 27.5 g mg, 30 mg, 35 mg, 40 mg, 45 mg, 50 mg, 55 mg, 60 mg, 65 mg, 75 mg, or 100 mg protein per gram of cellulose, hemicellulose, or a mixture of cellulose and hemicellulose contained in the substrate such as biomass material. In some aspects, a non-naturally occurring composition comprising a polypeptide having GH61/endoglucanase activity (e.g., EG IV such as $T.$ $reesei$ Eg4 or a variant thereof) used in any of the methods for hydrolyzing a biomass material and/or methods for reducing the viscosity of the biomass mixture is in an amount of about any of 0.05 mg, 0.1 mg, 0.2 mg, 0.5 mg, 1 mg, 2 mg, 5 mg, 7.5 mg, 10 mg, 12 mg, 14 mg, 15 mg, 16 mg, 17.5 mg, 18 mg, 20 mg, 22.5 mg, 25 mg, 27.5 g mg, 30 mg, 35 mg, 40 mg, 45 mg, or 50 mg protein per gram of cellulose, hemicellulose, or a mixture of cellulose and hemicellulose contained in the substrate such as biomass material. The amount of cellulose, hemicellulose, or a mixture of cellulose and hemicellulose contained in the substrate such as biomass material may be calculated using any methods known to one skilled in the art. The biomass material may comprise glucan, xylan, and/or lignin.

In some aspects of any of the methods described herein, the amount of the composition comprising a polypeptide having GH61/endoglucanase activity (e.g., $T.$ $reesei$ Eg4 or a variant thereof) is about 0.1 mg to about 50 mg protein (e.g., about 0.2 mg to about 40 mg protein, about 0.5 mg to about 30 mg protein, about 1 mg to about 20 mg protein, or about 5 mg to about 15 mg protein) per gram of cellulose, hemicellulose, or a mixture of cellulose and hemicellulose contained in the biomass material. The protein amount described herein refers to the weight of total protein in the composition. The proteins include a polypeptide having GH61/endoglucanase activity (e.g., $T.$ $reesei$ Eg4 or a variant thereof) and may also include other enzymes such as cellulase polypeptide(s) and/or hemicellulase polypeptide(s) in the composition.

In some aspects of any of the methods described herein, the amount of the polypeptide having GH61/endoglucanase activity (e.g., $T.$ $reesei$ Eg4 or a variant thereof) is about 0.2 mg to about 30 mg (e.g., about 0.2 mg to about 20 mg protein, about 0.5 mg to about 10 mg protein, or about 1 mg to about 5 mg protein) per gram of cellulose, hemicellulose, or a mixture of cellulose and hemicellulose contained in the biomass material.

In some aspects of any of the methods described herein, the composition comprises a polypeptide having GH61/endoglucanase activity (e.g., T. reesei Eg4 or a variant thereof) and at least one polypeptide having endoglucanase activity (e.g., T. reesei Eg1, T. reesei Eg2, and/or a variant thereof), wherein the total amount of the polypeptides having endoglucanase activity is about 0.2 mg to about 30 mg (e.g., about 0.2 mg to about 20 mg protein, about 0.5 mg to about 10 mg protein, or about 1 mg to about 5 mg protein) per gram of cellulose, hemicellulose, or a mixture of cellulose and hemicellulose contained in the biomass material.

In some aspects, the composition comprises a polypeptide having GH61/endoglucanase activity (e.g., T. reesei Eg4 or a variant thereof) and at least one polypeptide having cellobiohydrolase activity (e.g., T. reesei CBH1, T. reesei CBH2, and/or a variant thereof), wherein the amount of the polypeptide(s) having cellobiohydrolase activity is about 0.2 mg to about 30 mg (e.g., about 0.2 mg to about 20 mg protein, about 0.5 mg to about 10 mg protein, or about 1 mg to about 5 mg protein) per gram of cellulose, hemicellulose, or a mixture of cellulose and hemicellulose contained in the biomass material.

In some aspects of any of the methods described herein, the composition comprises a polypeptide having GH61/endoglucanase activity (e.g., T. reesei Eg4 or a variant thereof) and at least one polypeptide having β-glucosidase activity (e.g., an Fv3C, a Pa3D, an Fv3G, an Fv3D, a Tr3A, a Tr3B, a Te3A, an An3A, an Fo3A, a Gz3A, an Nh3A, a Vd3A, a Pa3G, a Tn3B, or a variant thereof), wherein the amount of the polypeptide(s) having β-glucosidase activity is about 0.2 mg to about 30 mg (e.g., about 0.2 mg to about 20 mg protein, about 0.5 mg to about 10 mg protein, or about 0.5 mg to about 5 mg protein) per gram of cellulose, hemicellulose, or a mixture of cellulose and hemicellulose contained in the biomass material.

In some aspects, the composition comprises a polypeptide having GH61/endoglucanase activity (e.g., T. reesei Eg4 or a variant thereof) and at least one polypeptide having xylanase activity (e.g., T. reesei Xyn3, T. reesei Xyn2, an AfuXyn2, an AfuXyn5, or a variant thereof), wherein the amount of the polypeptide(s) having xylanase activity is about 0.2 mg to about 30 mg (e.g., about 0.2 mg to about 20 mg protein, about 0.5 mg to about 10 mg protein, or about 0.5 mg to about 5 mg protein) per gram of cellulose, hemicellulose, or a mixture of cellulose and hemicellulose contained in the biomass material.

In some aspects, the composition comprises a polypeptide having GH61/endoglucanase activity (e.g., T. reesei Eg4 or a variant thereof) and at least one polypeptide having β-xylosidase activity (e.g., Fv3A, Fv43A, a Pf43A, an Fv43D, an Fv39A, an Fv43E, an Fo43A, an Fv43B, a Pa51A, a Gz43A, a T. reesei Bxl1, or a variant thereof), wherein the amount of the polypeptide(s) having β-xylosidase activity is about 0.2 mg to about 30 mg (e.g., about 0.2 mg to about 20 mg protein, about 0.5 mg to about 10 mg protein, or about 0.5 mg to about 5 mg protein) per gram of cellulose, hemicellulose, or a mixture of cellulose and hemicellulose contained in the biomass material.

In some aspects, the composition comprises a polypeptide having GH61/endoglucanase activity (e.g., T. reesei Eg4 or a variant thereof) and at least one polypeptide having L-α-arabinofuranosidase activity (e.g., an Af43A, an Fv43B, a Pf51A, a Pa51A, an Fv51A, or a variant thereof), wherein the amount of the polypeptide(s) having L-α-arabinofuranosidase activity is about 0.2 mg to about 30 mg (e.g., about 0.2 mg to about 20 mg protein, about 0.5 mg to about 10 mg protein, or about 0.5 mg to about 5 mg protein) per gram of cellulose, hemicellulose, or a mixture of cellulose and hemicellulose contained in the biomass material.

In any one of the methods provided herein, the viscosity of the biomass mixture may be reduced by at least about any of 5%, 10%, 15%, 20%, 25%, 30%, 35%, 40%, 45%, 50%, 55%, 60%, 65%, 70%, 75%, 80%, 85%, 90%, or 95% compared to the viscosity of the biomass mixture in the absence of an enzyme composition provided herein. For example, there are provided methods of reducing the viscosity of a biomass mixture comprising contacting the biomass mixture with a non-naturally occurring composition comprising a polypeptide having GH61/endoglucanase activity (e.g., EG IV such as T. reesei Eg4 or a variant thereof), wherein the viscosity is reduced by at least about any of 5%, 10%, 15%, 20%, 25%, 30%, 35%, 40%, 45%, 50%, 55%, 60%, 65%, 70%, 75%, 80%, 85%, 90%, or 95% compared to the viscosity of the biomass mixture in the absence of a polypeptide having GH61/endoglucanase activity (e.g., EG IV such as T. reesei Eg4 or a variant thereof). In some aspects, the viscosity is reduced by about any of 5%, 10%, 15%, 20%, 25%, 30%, 35%, 40%, 45%, 50%, 55%, 60%, 65%, 70%, 75%, 80%, 85%, 90%, or 95% compared to the viscosity of the biomass mixture in the absence of a polypeptide having GH61/endoglucanase activity (e.g., EG IV such as T. reesei Eg4 or a variant thereof). The reduction of viscosity described herein is seen after a certain period of saccharification. For example, the reduction of viscosity is seen after 30 minutes, 1 hour, 2 hours, 4 hours, 8 hours, 12 hours, 18 hours, 24 hours, 2 days, 3 days, 4 days, or 5 days saccharification. Methods of measuring viscosity are known in the art. For example, viscosity may be measured by human eyes, or be measured by a viscometer such as Brookfield viscometer (Brookfield Engineering, Inc). For example, viscosity of saccharification reaction mixture can be measured using a viscosity meter with ammonia-pretreated corncob as substrates. A viscosity meter can measure the resistance (torque) it takes to turn a spindle at a constant rate in the slurry.

The methods provided herein may be conducted at a temperature that is suitable for saccharification. For example, any one of the methods described herein may be performed at about 20° C. to about 75° C., about 25° C. to about 70° C., about 30° C. to about 65° C., about 35° C. to about 60° C., about 37° C. to about 60° C., about 40° C. to about 60° C., about 40° C. to about 55° C., about 40° C. to about 50° C., or about 45° C. to about 50° C. In some aspects, any one of the methods described herein may be performed at about 20° C., about 25° C., about 30° C., about 35° C., about 37° C., about 40° C., about 45° C., about 48° C., about 50° C., about 55° C., about 60° C., about 65° C., about 70° C., or about 75° C.

In some aspects of any of the methods described herein, the method comprises producing fermentable sugar(s), wherein the amount of the fermentable sugar(s) is increased by at least about 5% (e.g., at least about any of 5%, 10%, 15%, 20%, 25%, 30%, 35%, 40%, 45%, 50%, 60%, 70%, 80%, or 90%) compared to the amount of the fermentable sugar(s) produced in the absence of a polypeptide having GH61/endoglucanase activity (e.g., T. reesei Eg4 or a variant thereof).

Also provided herein are methods of increasing the amount of fermentable sugar(s) (and/or increasing the conversion from a biomass material to fermentable sugar(s) such as glucan conversion) by using a composition (e.g., a non-naturally occurring composition) comprising a polypeptide having GH61/endoglucanase activity (e.g., EG IV such as T. reesei Eg4 or a variant thereof) during hydrolysis of biomass material. There are various fermentable sugars produced from hydrolysis of biomass material, including but are not limited to, glucose, xylose, and/or cellobiose. In some aspects, the amount of fermentable sugar(s) produced from hydrolysis of biomass material may be increased by at least about any of 5%, 10%, 15%, 20%, 25%, 30%, 35%, 40%, 45%, 50%, 55%, 60%, 65%, 70%, 75%, 80%, 85%, 90%, or 95% compared to the amount of fermentable sugar(s) in the absence of an enzyme composition provided herein. For example, there are provided methods of increasing the amount of fermentable sugar(s) comprising contacting the biomass material with a non-naturally occurring composition comprising a polypeptide having GH61/endoglucanase activity (e.g., EG IV such as *T. reesei* Eg4 or a variant thereof) (to start or further a saccharification process), wherein the amount of fermentable sugar(s) from saccharification is increased by at least about any of 5%, 10%, 15%, 20%, 25%, 30%, 35%, 40%, 45%, 50%, 55%, 60%, 65%, 70%, 75%, 80%, 85%, 90%, or 95% compared to the amount of fermentable sugar(s) from saccharification in the absence of a polypeptide having GH61/endoglucanase activity (e.g., EG IV such as *T. reesei* Eg4 or a variant thereof). In some aspects, the amount of fermentable sugar(s) from saccharification is increased by about any of 5%, 10%, 15%, 20%, 25%, 30%, 35%, 40%, 45%, 50%, 55%, 60%, 65%, 70%, 75%, 80%, 85%, 90%, or 95% compared to the amount of fermentable sugar(s) from saccharification in the absence of a polypeptide having GH61/endoglucanase activity (e.g., EG IV such as *T. reesei* Eg4 or a variant thereof). The increase in amount of fermentable sugar(s) produced from hydrolysis of biomass material described herein is seen after a certain period of saccharification. For example, the increase in amount of fermentable sugar(s) is seen after 30 minutes, 1 hour, 2 hours, 4 hours, 8 hours, 12 hours, 18 hours, 24 hours, 2 days, 3 days, 4 days, or 5 days saccharification. Methods of measuring amount of fermentable sugar(s) and/or glucan conversion are known to a person skilled in the art.

The reduction in viscosity of saccharification mixture may correlate with improved yield of desirable fermentable sugars.

In some aspects, the method further comprises the step of contacting the biomass material with a composition comprising whole cellulase. In some aspects, the step of further contacting the biomass material with a composition comprising whole cellulase is performed before, after, or concurrently with contacting the biomass material with composition comprising a polypeptide having glycosyl hydrolase family 61 ("GH61") endoglucanase activity (e.g., *T. reesei* Eg4 or a variant thereof).

In some aspects of any of the methods described herein, the method comprises the step of further contacting the biomass material with a composition comprising a polypeptide having cellulase activity and/or a polypeptide having hemicellulase activity. In some aspects, the step of further contacting the biomass material with a composition comprising a polypeptide having cellulase activity and/or a polypeptide having hemicellulase activity is performed before, after, or concurrently with contacting the biomass material with composition comprising a polypeptide having glycosyl hydrolase family 61 ("GH61") endoglucanase activity (e.g., *T. reesei* Eg4 or a variant thereof).

In some aspects, the composition comprises the polypeptide having GH61/endoglucanase activity (e.g., *T. reesei* Eg4 or a variant thereof) and further comprises at least one cellulase polypeptide and/or at least one hemicellulase polypeptide, wherein the polypeptide having GH61/endoglucanase activity (e.g., *T. reesei* Eg4 or a variant thereof) and at least one cellulase polypeptide and/or at least one hemicellulase polypeptide are mixed together before contacting the biomass material with a composition comprising the polypeptide having GH61/endoglucanase activity (e.g., *T. reesei* Eg4 or a variant thereof).

In some aspects, the composition comprises the polypeptide having GH61/endoglucanase activity (e.g., *T. reesei* Eg4 or a variant thereof) and further comprises at least one cellulase polypeptide and/or at least one hemicellulase polypeptide, wherein the polypeptide having GH61/endoglucanase activity (e.g., *T. reesei* Eg4 or a variant thereof) and at least one cellulase polypeptide and/or at least one hemicellulase polypeptide are added to the biomass material at different times (e.g., the polypeptide having GH61/endoglucanase activity (e.g., *T. reesei* Eg4 or a variant thereof) is added before or after at least one cellulase polypeptide and/or at least one hemicellulase polypeptide is added to the biomass material).

Enhanced cellulose conversion may be achieved at higher temperatures using the CBH polypeptides described in, for example, any one of the following US Patent Publications US20050054039, US20050037459, US20060205042, US20050048619A1 and US20060218671. Methods of over-expressing β-glucosidase are known in the art. See, e.g., U.S. Pat. No. 6,022,725. See also, e.g., US Patent Publication 20050214920.

The methods of the present disclosure can be used in the production of monosaccharides, disaccharides, and polysaccharides as chemical, fermentation feedstocks for microorganism, and inducers for the production of proteins, organic products, chemicals and fuels, plastics, and other products or intermediates. In particular, the value of processing residues (dried distillers grain, spent grains from brewing, sugarcane bagasse, etc.) can be increased by partial or complete solubilization of cellulose or hemicellulose. In addition to ethanol, chemicals that can be produced from cellulose and hemicellulose include, acetone, acetate, glycine, lysine, organic acids (e.g., lactic acid), 1,3-propanediol, butanediol, glycerol, ethylene glycol, furfural, polyhydroxyalkanoates, cis, cis-muconic acid, animal feed and xylose.

Business Methods

The cellulase and/or hemicellulase compositions of the disclosure can be further used in industrial and/or commercial settings. Accordingly a method or a method of manufacturing, marketing, or otherwise commercializing the instant non-naturally occurring cellulase and/or hemicellulase compositions is also contemplated.

In a specific embodiment, the non-naturally occurring cellulase and/or hemicellulase compositions of the invention, for example, comprising one or more of the GH61 endoglucanases or variants thereof as described herein, can be supplied or sold to certan ethanol (bioethanol) refineries or other bio-chemical or bio-material manufacturers. In a first example, the non-naturally occurring cellulase and/or hemicellulase compositions can be manufactured in an enzyme manufacturing facility that is specialized in manufacturing enzymes at an industrial scale. The non-naturally occurring cellulase and/or hemicellulase compositions can then be packaged or sold to customers of the enzyme manufacturer. This operational strategy is termed the "merchant enzyme supply model" herein.

In another operational strategy, the non-naturally occurring cellulase and hemicellulase compositions of the invention can be produced in a state of the art enzyme production system that is built by the enzyme manufacturer at a site that is located at or in the vicinity of the bioethanol refineries or the bio-chemical/biomaterial manufacturers ("on-site"). In some embodiments, an enzyme supply agreement is executed by the enzyme manufactuer and the bioethanol refinerie or the bio-chemical/biomaterial manufacturer. The enzyme manufacturer designs, controls and operates the enzyme production system on site, utilizing the host cell, expression, and production methods as described herein to produce the non-naturally-occurring cellulase and/or hemicellulase compositions. In certain embodiments, suitable biomass, preferably subject to appropriate pretreatments as described herein, can be hydrolyzed using the saccharification methods and the enzymes and/or enzyme compositions herein at or near the bioethanol refineries or the bio-chemical/biomaterial manufacturing facilities. The resulting fermentable sugars can then be subject to fermentation at the same facilities or at facilities in the vicinity. This operational strategy is termed the "on-site biorefinery model" herein.

The on-site biorefinery model provides certain advantages over the merchant enzyme supply model, incuding, e.g., the provision of a self-sufficient operation, allowing minimal reliance on enzyme supply from merchant enzyme suppliers. This in turn allows the bioethanol refineries or the bio-chemical/biomaterial manufacturers to better control enzyme supply based on real-time or nearly real-time demand. In certain embodiments, it is contemplated that an on-site enzyme production facility can be shared between two or among two or more bioethanol refineries and/or the bio-chemical/biomaterial manufacturers who are located near to each other, reducing the cost of transporting and storing enzymes. Moreover, this allows more immediate "drop-in" technology improvements at the enzyme production facility on-site, reducing the time lag between the improvements of enzyme compositions to a higher yield of fermentable sugars and ultimately, bioethanol or biochemicals.

The on-site biorefinery model has more general applicability in the industrial production and commercialization of bioethanols and biochemicals, in that it can be used to manufacture, supply, and produce not only the cellulase and non-naturally occurring hemicellulase compositions of the present disclosure but also those enzymes and enzyme compositions that process starch (e.g., corn) to allow for more efficient and effective direct conversion of starch to bioethanol or bio-chemicals. The starch-processing enzymes can, in certain embodiments, be produced in the on-site biorefinery, then quickly and easily integrated into the bioethanol refinery or the biochemical/biomaterial manufacturing facility in order to produce bioethanol.

Thus in certain aspects, the invention also pertains to certain business method of applying the enzymes (e.g., certain GH61 endoglucanases and variants thereof), cells, compositions (e.g., comprising a suitable GH61 endoglucanase or a variant thereof), and processes herein in the manufacturing and marketing of certain bioethanol, biofuel, biochemicals or other biomaterials. In some embodiments, the invention prertains to the application of such enzymes, cells, compositions and processes in an on-site biorefinery model. In other embodiments, the invention pertains to the application of such enzymes, cells, compositions and processes in a merchant enzyme supply model.

Relatedly, the disclosure provides the use of the enzymes and/or the enzyme compositions of the invention in a commercial setting. For example, the enzymes and/or enzyme compositions of the disclosure can be sold in a suitable market place together with instructions for typical or preferred methods of using the enzymes and/or compositions. Accordingly the enzymes and/or enzyme compositions of the disclosure can be used or commercialized within a merchant enzyme supplier model, where the enzymes and/or enzyme compositions of the disclosure are sold to a manufacturer of bioethanol, a fuel refinery, or a biochemical or biomaterials manufacturer in the business of producing fuels or bio-products. In some aspects, the enzyme and/or enzyme composition of the disclosure can be marketed or commercialized using an on-site bio-refinery model, wherein the enzyme and/or enzyme composition is produced or prepared in a facility at or near to a fuel refinery or biochemical/biomaterial manufacturer's facility, and the enzyme and/or enzyme composition of the invention is tailored to the specific needs of the fuel refinery or biochemical/biomaterial manufacturer on a real-time basis. Moreover, the disclosure relates to providing these manufacturers with technical support and/or instructions for using the enzymes and.or enzyme compositions such that the desired bio-product (e.g., biofuel, bio-chemicals, bio-materials, etc) can be manufactured and marketed.

The following are examples of the methods and compositions of the invention. It is understood that various other embodiments may be practiced, given the general description provided above.

EXAMPLES

Example 1: Assays/Methods

The following assays/methods were generally used in the Examples described below. Any deviations from the protocols provided below are indicated in specific Examples.

A. Pretreatment of Biomass Substrates

Corncob, corn stover and switch grass were pretreated prior to enzymatic hydrolysis according to the methods and processing ranges described in International Patent Publication WO06110901A (unless otherwise noted). These references for pretreatment are also included in the disclosures of US Patent Application Publications 20070031918-A1, 20070031919-A1, 20070031953-A1, and/or 20070037259-A1.

Ammonia fiber explosion treated (AFEX) corn stover was obtained from Michigan Biotechnology Institute International (MBI). The composition of the corn stover was determined by MBI (Teymouri, F et al. Applied Biochemistry and Biotechnology, 2004, 113:951-963) using the National Renewable Energy Laboratory (NREL) procedure, NREL LAP-002. NREL procedures are available at: www.nrel.gov/biomass/analytical_procedures.html.

The FPP pulp and paper substrates were obtained from SMURFIT KAPPA CELLULOSE DU PIN, France.

Steam Expanded Sugar-cane Bagasse (SEB) was obtained from SunOpta (Glasser, W G et al. Biomass and Bioenergy 1998, 14(3): 219-235; Jollez, P et al. Advances in thermochemical biomass conversion, 1994, 2:1659-1669).

B. Compositional Analysis of Biomass

The 2-step acid hydrolysis method described in Determination of structural carbohydrates and lignin in the biomass (National Renewable Energy Laboratory, Golden, Colo. 2008 www.nrel.gov/biomass/pdfs/42618.pdf) was used to measure the composition of biomass substrates. Using this method, enzymatic hydrolysis results were reported herein in terms of percent conversion with respect to the theoretical yield from the starting glucan and xylan content of the substrate.

C. Total Protein Assay

The BCA protein assay is a colorimetric assay that measures protein concentration with a spectrophotometer.

The BCA Protein Assay Kit (Pierce Chemical, Product #23227) was used according to the manufacturer's suggestion. Enzyme dilutions were prepared in test tubes using 50 mM sodium acetate pH 5 buffer. Diluted enzyme solution (0.1 mL) was added to 2 mL Eppendorf centrifuge tubes containing 1 mL 15% tricholoroacetic acid (TCA). The tubes were vortexed and placed in an ice bath for 10 min. The samples were then centrifuged at 14,000 rpm for 6 min. The supernatant was poured out, the pellet was resuspended in 1 mL 0.1 N NaOH, and the tubes vortexed until the pellet dissolved. BSA standard solutions were prepared from a stock solution of 2 mg/mL. BCA working solution was prepared by mixing 0.5 mL Reagent B with 25 mL Reagent A. 0.1 mL of the enzyme resuspended sample was added to 3 Eppendorf centrifuge tubes. Two (2) mL Pierce BCA working solution was added to each sample and BSA standard Eppendorf tubes. All tubes were incubated in a 37° C. waterbath for 30 min. The samples were then cooled to room temperature (15 min) and the absorbance measured at 562 nm in a spectrophotometer.

Average values for the protein absorbance for each standard were calculated. The average protein standard was plotted, absorbance on x-axis and concentration (mg/mL) on the y-axis. The points were fit to a linear equation:

$$y = mx + b$$

The raw concentration of the enzyme samples was calculated by substituting the absorbance for the x-value. The total protein concentration was calculated by multiplying with the dilution factor.

The total protein of purified samples was determined by A280 (Pace, C N, et al. *Protein Science*, 1995, 4:2411-2423).

The total protein content of fermentation products was sometimes measured as total nitrogen by combustion, capture and measurement of released nitrogen, either by Kjeldahl (rtech laboratories, www.rtechlabs.com) or in-house by the DUMAS method (TruSpec CN, www.leco.com) (Sader, A. P. O. et al., Archives of Veterinary Science, 2004, 9(2):73-79). For complex protein-containing samples, e.g. fermentation broths, an average 16% N content, and the conversion factor of 6.25 for nitrogen to protein was used. In some cases, total precipitable protein was measured to remove interfering non-protein nitrogen. A 12.5% final TCA concentration was used and the protein-containing TCA pellet was resuspended in 0.1 M NaOH.

In some cases, Coomassie Plus—the Better Bradford Assay (Thermo Scientific, Rockford, Ill. product #23238) was used according to manufacturer recommendation. In other cases, total protein was measured using the Biuret method as modified by Weichselbaum and Gornall using Bovine Serum Albumin as a calibrator (Weichselbaum, T. Amer. J. Clin. Path. 1960, 16:40; Gornall, A. et al. J. Biol. Chem. 1949, 177:752).

D. Glucose Determination Using ABTS

The ABTS (2, 2'-azino-bis(3-ethylenethiazoline-6)-sulfonic acid) assay for glucose determination is based on the principle that in the presence of $O_2$, glucose oxidase catalyzes the oxidation of glucose while producing stoichiometric amounts of hydrogen peroxide ($H_2O_2$). This reaction is followed by the horse radish peroxidase (HRP) catalyzed oxidation of ABTS which linearly correlates to the concentration of $H_2O_2$. The emergence of oxidized ABTS is indicated by the evolution of a green color, which is quantified at an OD of 405 nm A mixture of ABTS powder (Sigma, #A1888-5g 2.74 mg/mL), 0.1 U/mL HRP (100 U/mL, Sigma, #P8375) and 1 U/mL Glucose Oxidase, (OxyGO® HP L5000, 5000 U/mL, Genencor Division, Danisco USA) was prepared in 50 mM Na Acetate Buffer, pH 5.0 and kept in the dark (substrate). Glucose standards (0, 2, 4, 6, 8, 10 nmol) were prepared in 50 mM Na Acetate Buffer, pH 5.0 and 10 μL of each standard was added to a 96-well flat bottom MTP in triplicate. Ten (10) μL of serially diluted samples were also added to the MTP. One hundred (100) μL of ABTS substrate solution was added to each well and the plate was placed on a spectrophotometric plate reader to kinetically read oxidation of ABTS for 5 min at 405 nm.

Alternately absorbance at 405 nm was measured after 15-30 min of incubation followed by quenching of the reaction with 50 mM Na Acetate Buffer, pH 5.0 containing 2% SDS.

E. Sugar Analysis by HPLC

Samples from biomass saccharification were prepared by centrifugation to clear insoluble material, filtration through a 0.22 μm nylon filter (Spin-X centrifuge tube filter, Corning Incorporated, Corning, N.Y.) and dilution to an appropriate concentration of soluble sugars with distilled water. Monomer sugars were determined on a Shodex Sugar SH-G SH1011, 8×300 mm with a 6×50 mm SH-1011P guard column (www.shodex.net). Solvent was 0.01 N $H_2SO_4$ run at 0.6 mL/min Column temperature was 50° C. and detection was by refractive index. Alternately, sugars were analyzed using a Biorad Aminex HPX-87H column with a Waters 2410 refractive index detector. The analysis time was 20 min, the injection volume was 20 μL of diluted sample, the mobile phase was 0.01 N sulfuric acid, 0.2 μm filtered and degassed, the flow rate was 0.6 mL/min and the column temperature was 60° C. External standards of glucose, xylose and arabinose were run with each sample set.

Oligomeric sugars were separated by size exclusion chromatography in HPLC using a Tosoh Biosep G2000PW column 7.5 mmx60 cm (www.tosohbioscience.de). The solvent was distilled water at 0.6 mL/min and the column was run at room temperature. Six carbon sugar standards used for size calibration were: stachyose, raffinose, cellobiose and glucose; and 5 carbon sugars were: xylohexose, xylopentose, xylotetrose, xylotriose, xylobiose and xylose. Xylo-oligomers were obtained from Megazyme (www.megazyme.com). Detection was by refractive index and when reported quantitatively results are either as peak area units or relative peak areas by percent.

Total soluble sugars were determined by hydrolysis of the centrifuged and filter clarified samples described above. The clarified sample was diluted 1 to 1 with 0.8 N $H_2SO_4$ and the resulting solution was autoclaved in a capped vial for a total cycle time of 1 h at 121° C. Results are reported without correction for loss of monomer sugar during the hydrolysis.

F. Oligomer Preparation from Cob and Enzyme Assays

Oligomers from *T. reesei* Xyn3 hydrolysis of corncobs were prepared by incubating 8 mg *T. reesei* Xyn3 per g Glucan+Xylan with 250 g dry weight of dilute ammonia pretreated corncob in 50 mM pH 5.0 Na Acetate buffer (pH adjusted with 1 N sulfuric acid). The reaction proceeded for 72 h at 48° C., 180 rpm rotary shaking. The supernatant was centrifuged 9,000×G, then filtered through 0.22 μm Nalgene filters to recover the soluble sugars. For subsequent enzyme assays, 100 μL aliquots of the *T. reesei* Xyn3 oligomer-containing supernatant were incubated with 1 μg/μL of either *T. reesei* integrated strain H3A, 1 μg/μL of *T. reesei* integrated strain H3A/EG4#27 or water control in Eppendorf tubes at 48° C. for 2.5 h. The supernatants were then diluted 4× with ice cold MilliQ water, filtered, and analyzed by HPLC for sugar release from the oligomers.

G. Corncob Saccharification Assay

For a typical example herein, unless otherwise specifically described with the particular examples, corncob saccharification was performed in a microtiter plate format in accordance with the following procedures. The biomass substrate, e.g., a dilute ammonia pretreated corncob, was diluted in water and pH-adjusted with sulfuric acid to create a pH 5, 7% cellulose slurry that was then used directly without further processing in the assays. Enzyme samples were loaded based on mg total protein per g of cellulose (as determined using conventional compositional analysis methods, such as, for example, using the method described in Example 1A above) in the substrate (e.g., the corncob). The enzymes were then diluted in 50 mM sodium acetate, pH 5.0, to obtain the desired loading concentration. Forty (40) µL of enzyme solution were added to 70 mg of dilute-ammonia pretreated corncob at 7% cellulose per well (equivalent to 4.5% cellulose final per well). The assay plates were covered with aluminum plate sealers, mixed at room temperature and incubated at 50° C., 200 rpm, for 3 days ("3d"). At the end of the incubation period, the saccharification reaction was quenched by adding to each well 100 µL of a 100 mM glycine buffer, pH10.0. The plate was centrifuged for 5 min at 3,000 rpm. Ten (10) µL of the supernatant was then added to 200 µL of MilliQ water in a 96-well HPLC plate and the soluble sugars were measured using HPLC.

Example 2: Construction of an Integrated Expression Strain of *Trichoderma reesei*

An integrated expression strain of *Trichoderma reesei* was constructed that co-expressed five genes: *T. reesei* β-glucosidase gene bgl1, *T. reesei* endoxylanase gene xyn3, *F. verticillioides* β-xylosidase gene fv3A, *F. verticillioides* β-xylosidase gene fv43D, and *F. verticillioides* α-arabinofuranosidase gene fv51A.

The construction of the expression cassettes for these different genes and the transformation of *T. reesei* are described below.

A. Construction of the β-Glucosidase Expression Vector

The N-terminal portion of the native *T. reesei* β-glucosidase gene bgl1 was codon optimized by DNA 2.0 (Menlo Park, USA). This synthesized portion comprised of the first 447 bases of the coding region. This fragment was PCR amplified using primers SK943 and SK941. The remaining region of the native bgl1 gene was PCR amplified from a genomic DNA sample extracted from *T. reesei* strain RL-P37 (Sheir-Neiss, G et al. Appl. Microbiol. Biotechnol. 1984, 20:46-53), using primer SK940 and SK942. These two PCR fragments of the bgl1 gene were fused together in a fusion PCR reaction, using primers SK943 and SK942:

```
Forward Primer SK943:
                              (SEQ ID NO: 121)
(5'-CACCATGAGATATAGAACAGCTGCCGCT-3')

Reverse Primer SK941:
                              (SEQ ID NO: 122)
(5'-CGACCGCCCTGCGGAGTCTTGCCCAGTGGTCCCGCGACAG-3')

Forward Primer (SK940):
                              (SEQ ID NO: 123)
(5'-CTGTCGCGGGACCACTGGGCAAGACTCCGCAGGGCGGTCG-3')

Reverse Primer (SK942):
                              (SEQ ID NO: 124)
(5'-CCTACGCTACCGACAGAGTG-3')
```

Figure 8B:
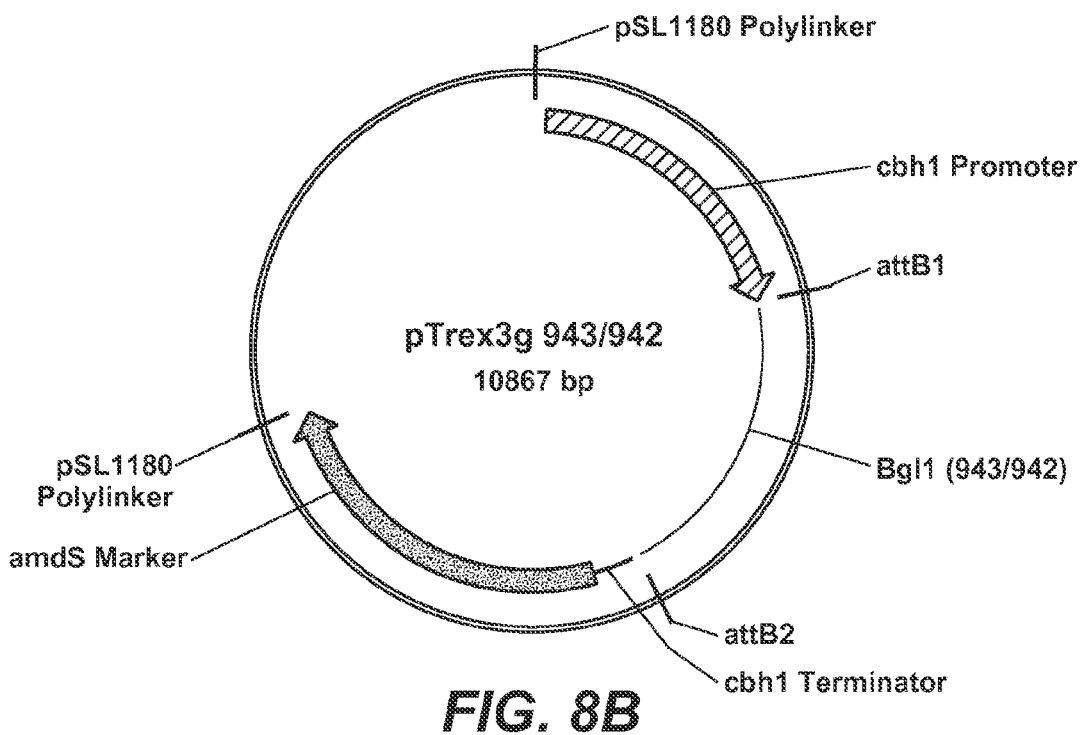

The resulting fusion PCR fragments were cloned into the Gateway® Entry vector pENTR™/D-TOPO®, and transformed into *E. coli* One Shot® TOP10 Chemically Competent cells (Invitrogen) resulting in the intermediate vector, pENTR-TOPO-Bgl1-(943/942) (FIG. 8A). The nucleotide sequence of the inserted DNA was determined. The pENTR-943/942 vector with the correct bgl1 sequence was recombined with pTrex3g using a LR Clonase® reaction protocol outlined by Invitrogen. The LR clonase reaction mixture was transformed into *E. coli* One Shot® TOP10 Chemically Competent cells (Invitrogen), resulting in the final expression vector, pTrex3g 943/942 (FIG. 8B). The vector also contains the *Aspergillus nidulans* amdS gene, encoding acetamidase, as a selectable marker for transformation of *T. reesei*. The expression cassette was amplified by PCR with primers SK745 and SK771 to generate product for transformation of *T. reesei*.

Forward Primer SK771: (5'-GTCTAGACTGGAAACG-CAAC-3') (SEQ ID NO:125)

Reverse Primer SK745: (5'-GAGTTGTGAAGTCGG-TAATCC-3') (SEQ ID NO:126)

B. Construction of the Endoxylanase Expression Cassette

The native *T. reesei* endoxylanase gene xyn3 was PCR amplified from a genomic DNA sample extracted from *T. reesei*, using primers xyn3F-2 and xyn3R-2.

```
Forward Primer xyn3F-2:
                              (SEQ ID NO: 127)
(5'-CACCATGAAAGCAAACGTCATCTTGTGCCTCCTGG-3')

Reverse Primer (xyn3R-2):
                              (SEQ ID NO: 128)
(5'-CTATTGTAAGATGCCAACAATGCTGTTATATGCCGGCTTGGG

G-3')
```

Figure 8C:
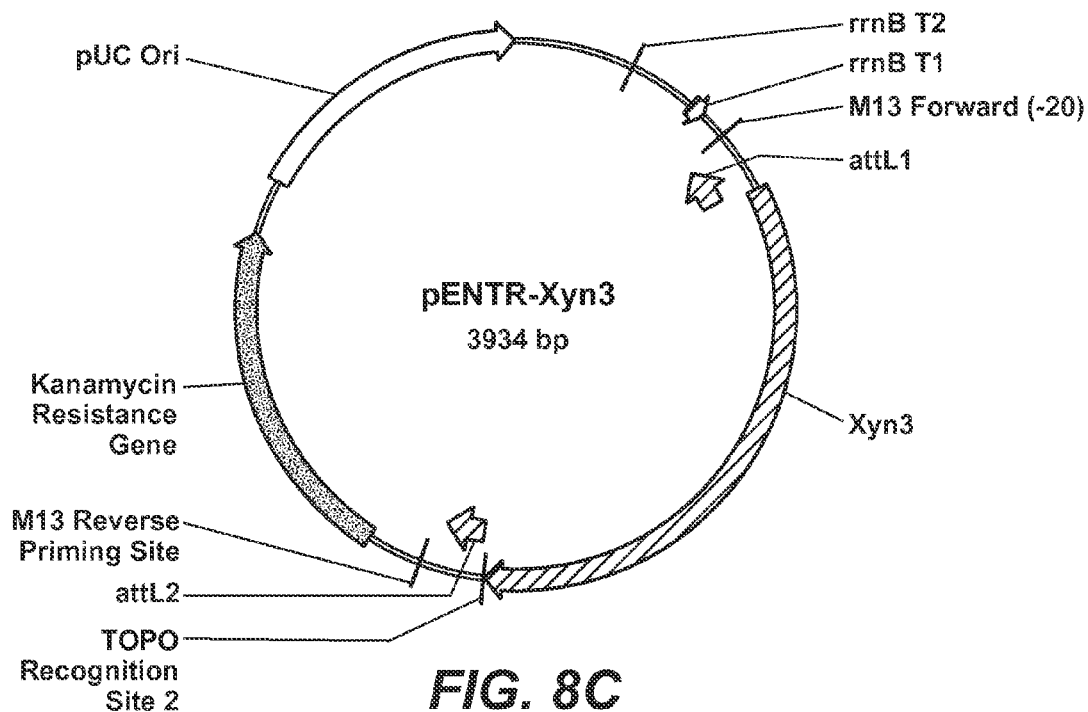
Figure 8D:
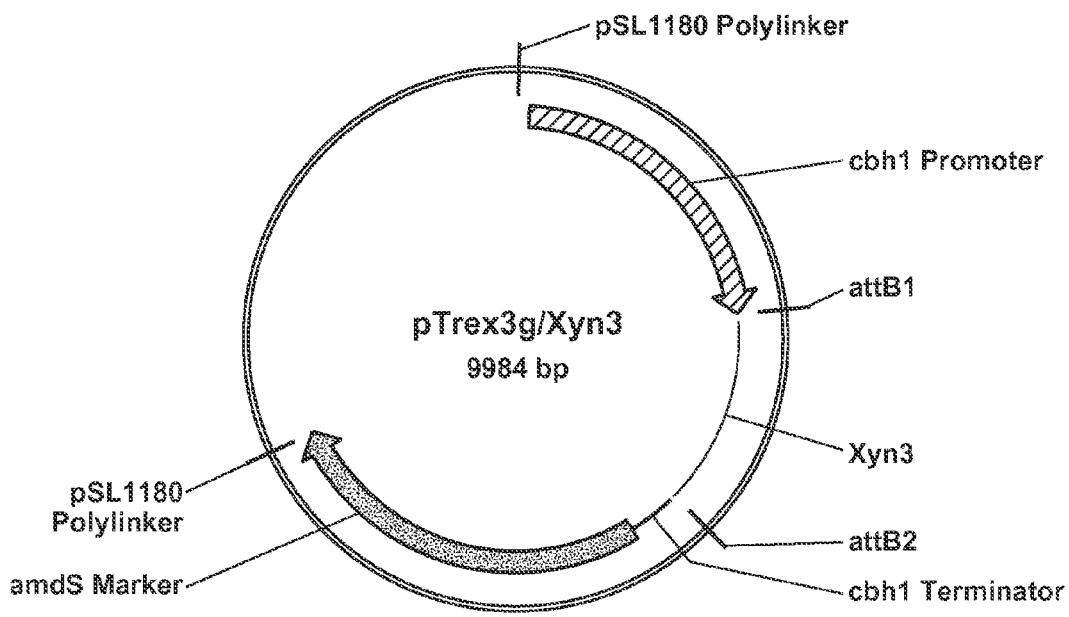

The resulting PCR fragments were cloned into the Gateway® Entry vector pENTR™/D-TOPO®, and transformed into *E. coli* One Shot® TOP10 Chemically FIG. 8C). The nucleotide sequence of the inserted DNA was determined. The pENTR/Xyn3 vector with the correct xyn3 sequence was recombined with pTrex3g using a LR Clonase® reaction protocol outlined by Invitrogen. The LR clonase reaction mixture was transformed into *E. coli* One Shot® TOP10 Chemically Competent cells (Invitrogen), resulting in the final expression vector, pTrex3g/Xyn3 (FIG. 8D). The vector also contains the *Aspergillus nidulans* amdS gene, encoding acetamidase, as a selectable marker for transformation of *T. reesei*. The expression cassette was amplified by PCR with primers SK745 and SK822 to generate product for transformation of *T. reesei*.

```
Forward Primer SK745:
                              (SEQ ID NO: 129)
(5'-GAGTTGTGAAGTCGGTAATCC-3')

Reverse Primer SK822:
                              (SEQ ID NO: 130)
(5'-CACGAAGAGCGGCGATTC-3')
```

C. Construction of the β-Xylosidase Fv3A Expression Vector

The *F. verticillioides* β-xylosidase fv3A gene was amplified from a *F. verticillioides* genomic DNA sample using the primers MH124 and MH125.

Forward Primer MH124:
(SEQ ID NO: 131)
(5'-CAC CCA TGC TGC TCA ATC TTC AG-3')

Reverse Primer MH125:
(SEQ ID NO: 132)
(5'-TTA CGC AGA CTT GGG GTC TTG AG-3')

Figure 8E:
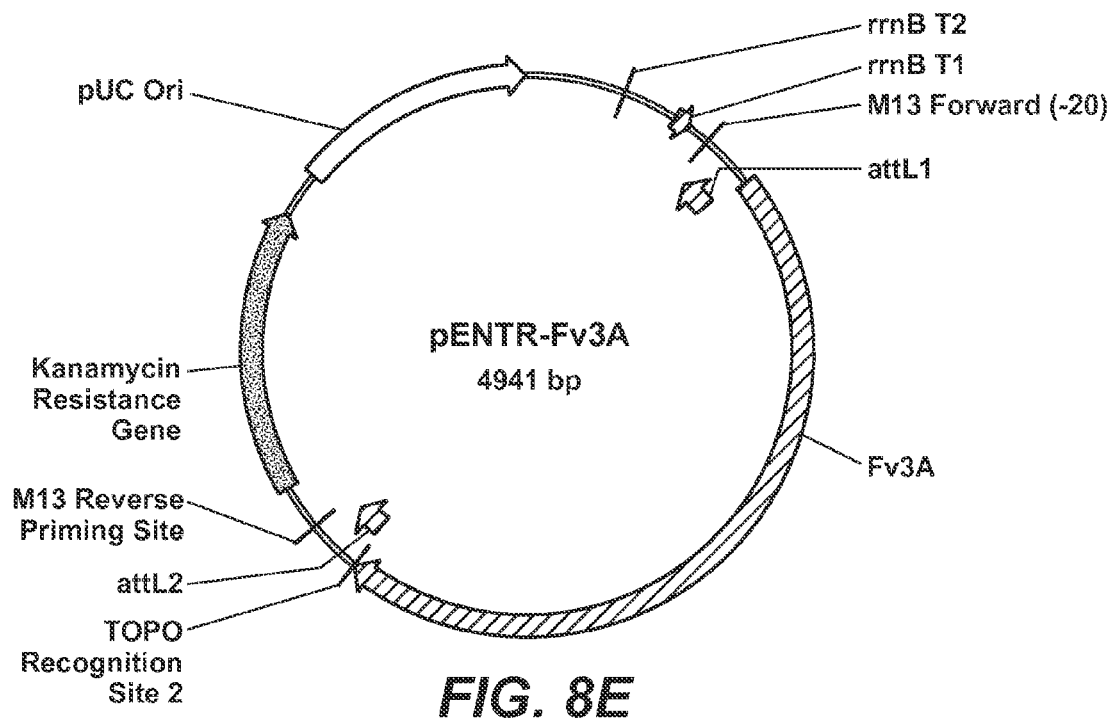
Figure 8F:
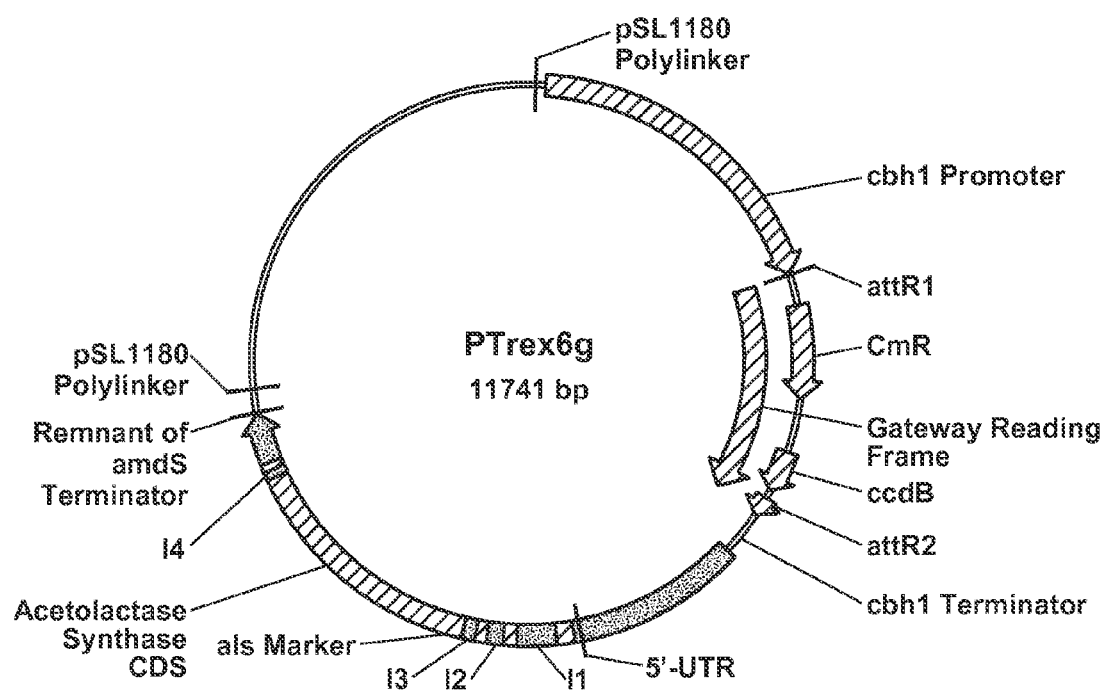
Figure 8G:
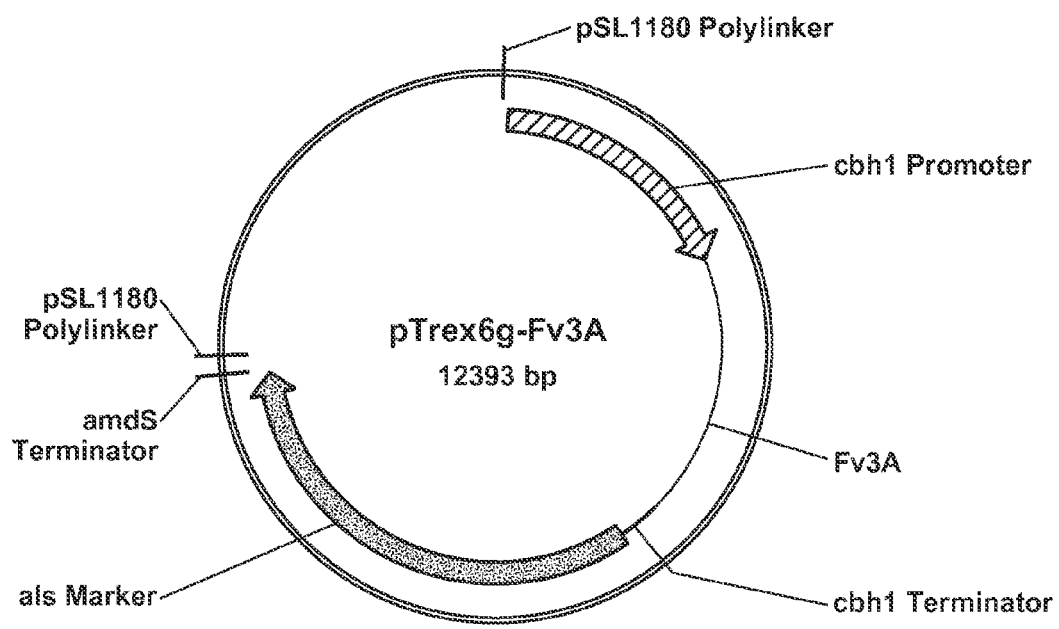

The PCR fragments were cloned into the Gateway® Entry vector pENTR™/D-TOPO®, and transformed into *E. coli* One Shot® TOP10 Chemically Competent cells (Invitrogen) resulting in the intermediate vector, pENTR-Fv3A (FIG. 8E). The nucleotide sequence of the inserted DNA was determined. The pENTR-Fv3A vector with the correct fv3A sequence was recombined with pTrex6g (FIG. 8F) using a LR Clonase® reaction protocol outlined by Invitrogen. The LR clonase reaction mixture was transformed into *E. coli* One Shot® TOP10 Chemically Competent cells (Invitrogen), resulting in the final expression vector, pTrex6g/Fv3A (FIG. 8G). The vector also contains a chlorimuron ethyl resistant mutant of the native *T. reesei* acetolactate synthase (als) gene, designated alsR, which is used together with its native promoter and terminator as a selectable marker for transformation of *T. reesei* (WO2008/039370 A1). The expression cassette was PCR amplified with primers SK1334, SK1335 and SK1299 to generate product for transformation of *T. reesei*.

Forward Primer SK1334:
(SEQ ID NO: 133)
(5'-GCTTGAGTGTATCGTGTAAG-3')

Forward Primer SK1335:
(SEQ ID NO: 134)
(5'-GCAACGGCAAAGCCCCACTTC-3')

Reverse Primer SK1299:
(SEQ ID NO: 135)
(5'-GTAGCGGCCGCCTCATCTCATCTCATCCATCC-3')

D. Construction of the β-Xylosidase Fv43D Expression Cassette

Figure 8H:
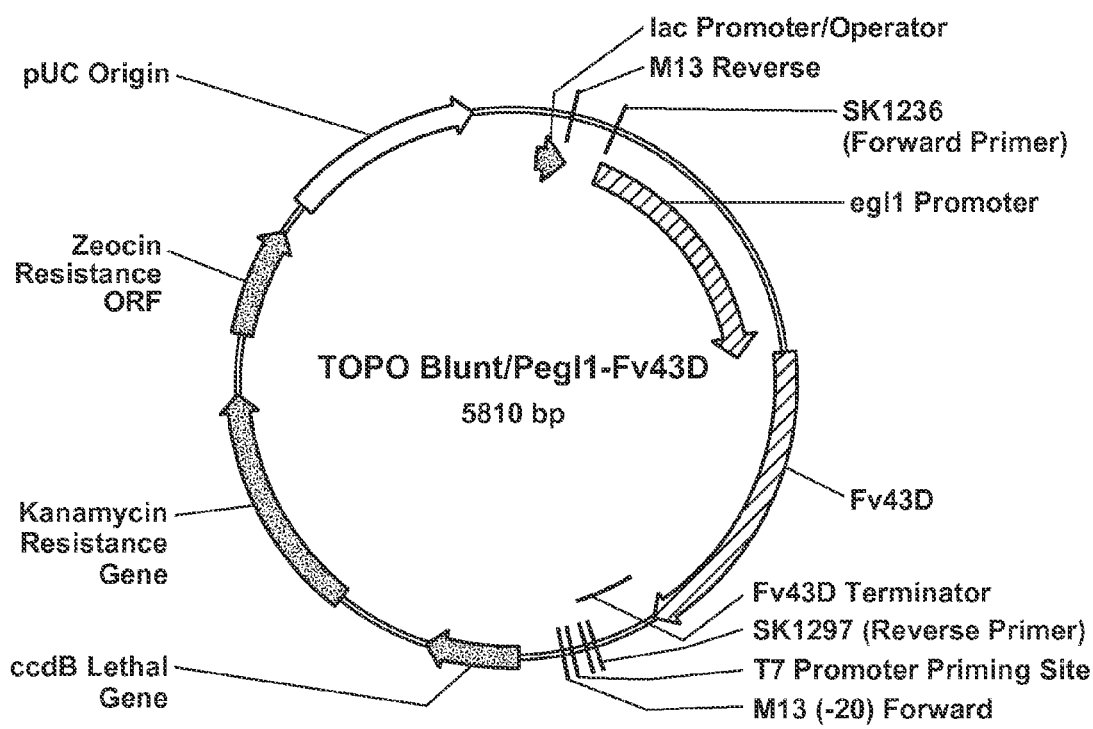

For the construction of the *F. verticillioides* β-xylosidase Fv43D expression cassette, the fv43D gene product was amplified from a *F. verticillioides* genomic DNA sample using the primers SK1322 and SK1297. A region of the promoter of the endoglucanase gene egl1 was amplified by PCR from a *T. reesei* genomic DNA sample extracted from strain RL-P37, using the primers SK1236 and SK1321. These two PCR amplified DNA fragments were subsequently fused together in a fusion PCR reaction using the primers SK1236 and SK1297. The resulting fusion PCR fragment was cloned into pCR-Blunt II-TOPO vector (Invitrogen) to give the plasmid TOPO Blunt/Pegl1-Fv43D (FIG. 8H) and *E. coli* One Shot® TOP10 Chemically Competent cells (Invitrogen) were transformed using this plasmid. Plasmid DNA was extracted from several *E. coli* clones and confirmed by restriction digest.

Forward Primer SK1322:
(SEQ ID NO: 136)
(5'-CACCATGCAGCTCAAGTTTCTGTC-3')

Reverse Primer SK1297:
(SEQ ID NO: 137)
(5'-GGTTACTAGTCAACTGCCCGTTCTGTAGCGAG-3')

Forward Primer SK1236:
(SEQ ID NO: 138)
(5'-CATGCGATCGCGACGTTTTGGTCAGGTCG-3')

Reverse Primer SK1321:
(SEQ ID NO: 139)
(5'-GACAGAAACTTGAGCTGCATGGTGTGGGACAACAAGAAGG-3')

The expression cassette was PCR amplified from TOPO Blunt/Pegl1-Fv43D with primers SK1236 and SK1297 to generate product for transformation of *T. reesei*.

E. Construction of the α-Arabinofuranosidase Expression Cassette

Figure 8I:
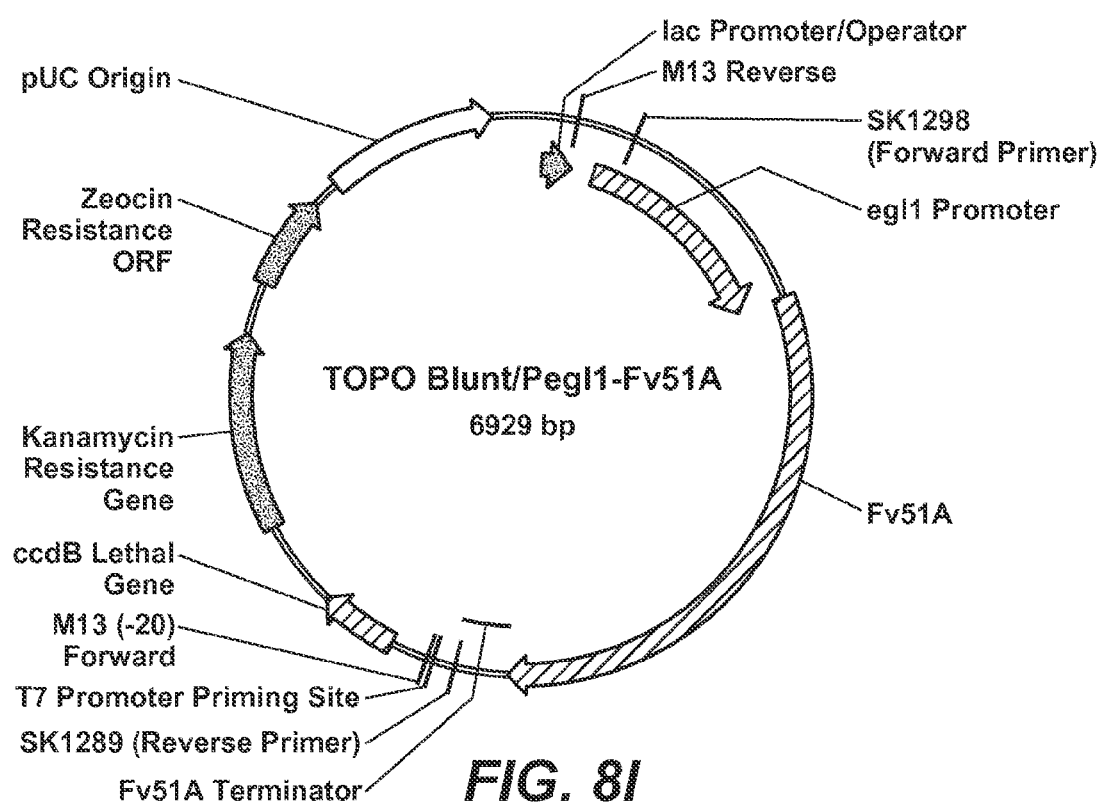
Figure 11A:
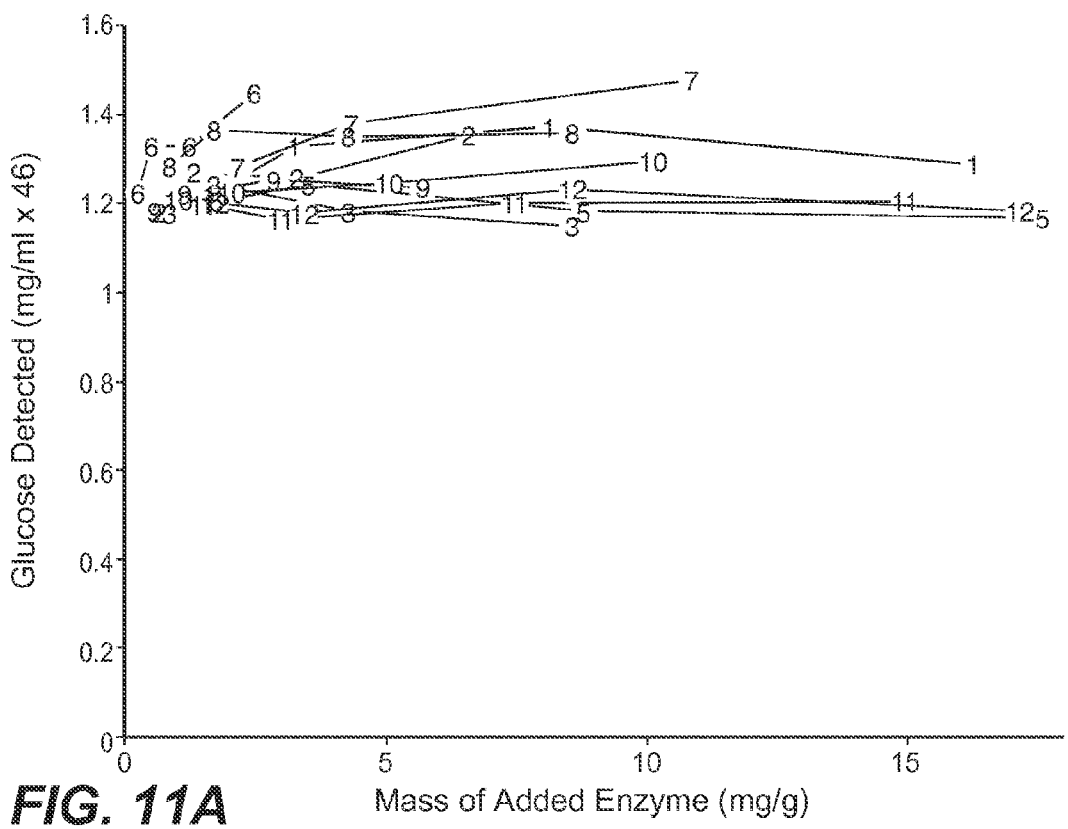
FIGS. 11A-11D.
Figure 11B:
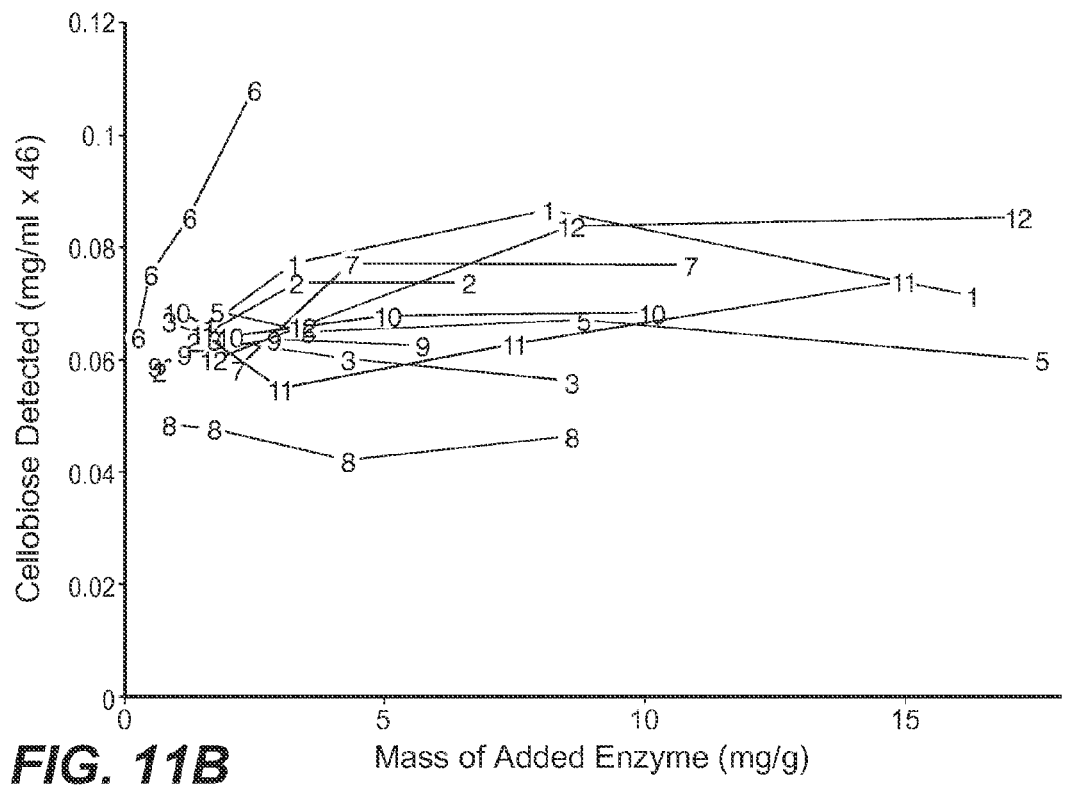
Figure 11C:
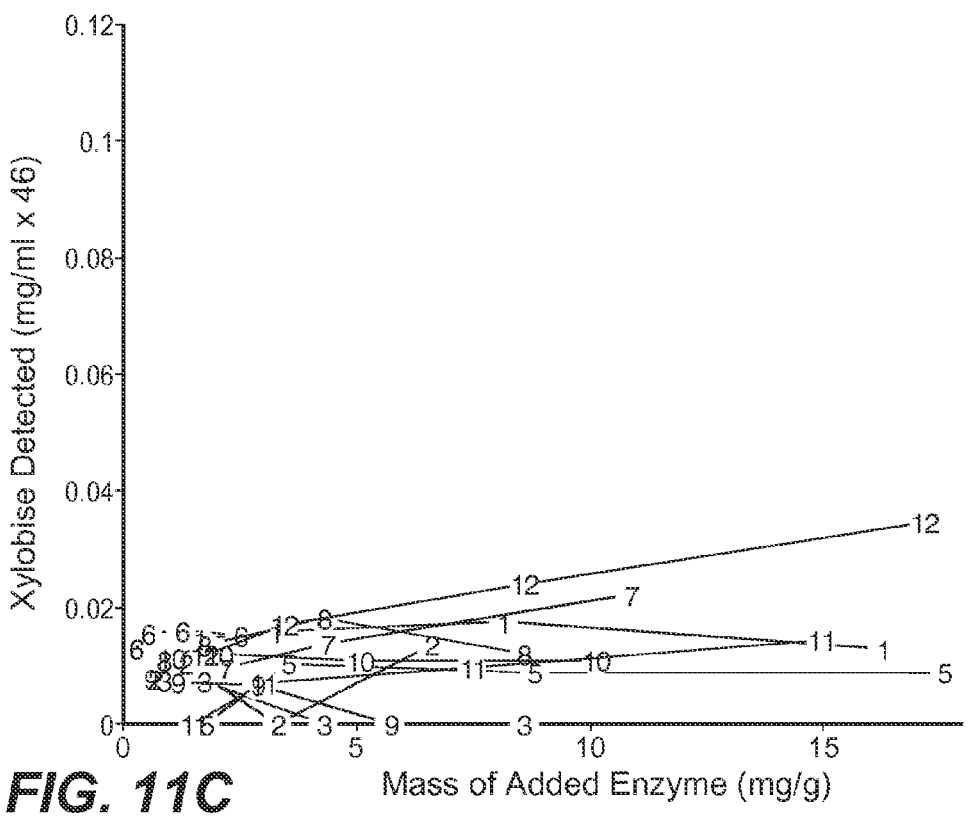
Figure 11D:
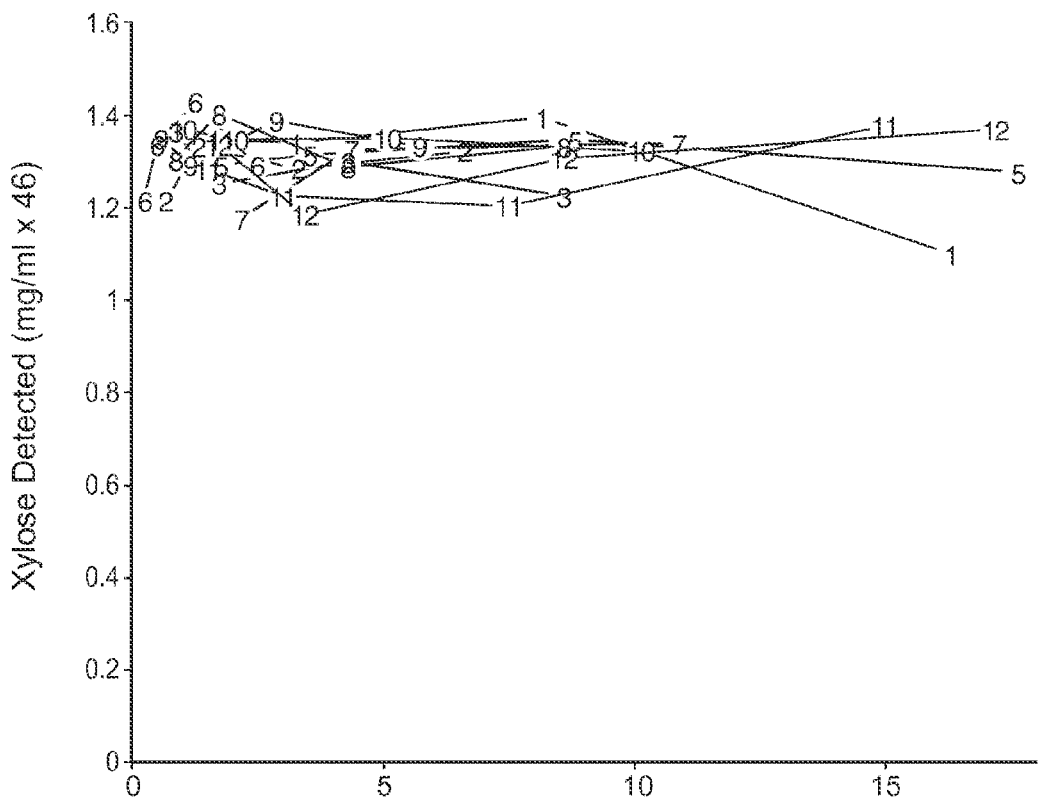

For the construction of the *F. verticillioides* α-arabinofuranosidase gene fv51A expression cassette, the fv51A gene product was amplified from *F. verticillioides* genomic DNA using the primers SK1159 and SK1289. A region of the promoter of the endoglucanase gene egl1 was amplified by PCR from a *T. reesei* genomic DNA sample extracted from strain RL-P37, using the primers SK1236 and SK1262. These two PCR amplified DNA fragments were subsequently fused together in a fusion PCR reaction using the primers SK1236 and SK1289. The resulting fusion PCR fragment was cloned into pCR-Blunt II-TOPO vector (Invitrogen) to give the plasmid TOPO Blunt/Pegl1-Fv51A (FIG. 8I) and *E. coli* One Shot® TOP10 Chemically Competent cells (Invitrogen) were transformed using this plasmid.

Forward Primer SK1159:
(SEQ ID NO: 140)
(5'-CACCATGGTTCGCTTCAGTTCAATCCTAG-3')

Reverse Primer SK1289:
(SEQ ID NO: 141)
(5'-GTGGCTAGAAGATATCCAACAC-3')

Forward Primer SK1236:
(SEQ ID NO: 142)
(5'-CATGCGATCGCGACGTTTTGGTCAGGTCG-3')

Reverse Primer SK1262:
(SEQ ID NO: 143)
(5'-GAACTGAAGCGAACCATGGTGTGGGACAACAAGAAGGAC-3')

The expression cassette was PCR amplified with primers SK1298 and SK1289 to generate product for transformation of *T. reesei*.

Forward Primer SK1298:
(SEQ ID NO: 144)
(5'-GTAGTTATGCGCATGCTAGAC-3')

Reverse Primer SK1289:
(SEQ ID NO: 145)
(5'-GTGGCTAGAAGATATCCAACAC-3')

F. Co-Transformation of *T. reesei* Expression Cassettes for β-Glucosidase and Endoxylanase A *Trichoderma reesei* mutant strain, derived from RL-P37 (Sheir-Neiss, G et al. Appl. Microbiol. Biotechnol. 1984, 20:46-53), and selected for high cellulase production was co-transformed with the β-glucosidase expression cassette (cbh1 promoter, Treesei β-glucosidase1 gene, cbh1 terminator, and amdS marker), and the endoxylanase expression cassette (cbh1 promoter, *T. reesei* xyn3, and cbh1 terminator) using PEG-mediated transformation (Penttila, M et al. Gene 1987, 61(2):155-64). Numerous transformants were isolated and examined for β-glucosidase and endoxylanase production. One transformant called *T. reesei* strain #229 was used for transformation with the other expression cassettes.

G. Co-Transformation of *T. reesei* Strain #229 with Expression Cassettes for Two β-Xylosidases and an α-Arabinofuranosidase

*T. reesei* strain #229 was co-transformed with the β-xylosidase fv3A expression cassette (cbh1 promoter, fv3A gene, cbh1 terminator, and alsR marker), the β-xylosidase fv43D expression cassette (egl1 promoter, fv43D gene, native fv43D terminator), and the fv51A α-arabinofuranosidase expression cassette (egl1 promoter, fv51A gene, fv51A native terminator) using electroporation (see e.g. WO 08153712). Transformants were selected on Vogels agar plates containing chlorimuron ethyl (80 ppm). Vogels agar was prepared as follows, per liter.

| 50 × Vogels Stock Solution (recipe below) | 20 mL |
|---|---|
| BBL Agar | 20 g |
| With deionized H₂O bring to post-sterile addition: | 980 mL |
| 50% Glucose | 20 mL |

| 50 × Vogels Stock Solution, per liter: | |
|---|---|
| In 750 mL deionized H2O, dissolve successively: | |
| Na$_3$Citrate*2H$_2$O | 125 g |
| KH$_2$PO$_4$ (Anhydrous) | 250 g |
| NH$_4$NO$_3$ (Anhydrous) | 100 g |
| MgSO$_4$*7H$_2$O | 10 g |
| CaCl$_2$*2H$_2$O | 5 g |

| Vogels Trace Element Solution (recipe below) | 5 mL |
|---|---|
| d-Biotin | 0.1 g |
| With deionized H$_2$O, | bring to 1 L |

| Vogels Trace Element Solution: | |
|---|---|
| Citric Acid | 50 g |
| ZnSO$_4$•*7H$_2$O | 50 g |
| Fe(NH$_4$)2SO$_4$•*6H$_2$O | 10 g |
| CuSO$_4$•5H$_2$O | 2.5 g |
| MnSO$_4$•4H$_2$O | 0.5 g |
| H$_3$BO$_3$ | 0.5 g |
| Na$_2$MoO$_4$•2H$_2$O | 0.5 g |

Numerous transformants were isolated and examined for β-xylosidase and L-α-arabinofuranosidase production. Transformants were also screened for biomass conversion performance according to the cob saccharification assay described in Example 1 (supra). Examples of *T. reesei* integrated expression strains described herein are H3A, 39A, A10A, 11A, and G9A, which express all of the genes for *T. reesei* beta-glucosidase 1, *T. reesei* Xyn3, Fv3A, Fv51A, and Fv43D, at different ratios. Other integrated *T. reesei* strains include those wherein most of the genes for *T. reesei* beta-glucosidase 1, *T. reesei* Xyn3, Fv3A, Fv51A, and Fv43D, were expressed at different ratios. For example, one lacked overexpressed *T. reesei* Xyn3; another lacked Fv51A, as determined by Western Blot; two others lacked Fv3A, one lacked overexpressed Bgl1 (e.g. strain H3A-5).

H. Composition of *T. reesei* Integrated Strain H3A

Fermentation of the *T. reesei* integrated strain H3A yields the following proteins *T. reesei* Xyn3, *T. reesei* Bgl1, Fv3A, Fv51A, and Fv43D, at ratios determined as described herein and shown in FIG. 9.

I. Protein Analysis by HPLC

Liquid chromatography (LC) and mass spectroscopy (MS) were performed to separate, identify, and quantify the enzymes contained in fermentation broths. Enzyme samples were first treated with a recombinantly expressed endoH glycosidase from *S. plicatus* (e.g., NEB P0702L). EndoH was used at a ratio of 0.01-0.03 μg endoH protein per μg sample total protein and incubated for 3 h at 37° C., pH 4.5-6.0 to enzymatically remove N-linked gycosylation prior to HPLC analysis. Approximately 50 μg of protein was then injected for hydrophobic interaction chromatography using an Agilent 1100 HPLC system with an HIC-phenyl column and a high-to-low salt gradient over 35 min. The gradient was achieved using high salt buffer A: 4 M ammonium sulphate containing 20 mM potassium phosphate pH 6.75 and low salt buffer B: 20 mM potassium phosphate pH 6.75. Peaks were detected with UV light at 222 nm and fractions were collected and identified by mass spectroscopy. Protein concentrations are reported as the percent of each peak area relative to the total integrated area of the sample.

J. Effect of Addition of Purified Proteins to the Fermentation Broth of *T. reesei* Integrated Strain H3A on Saccharification of Dilute Ammonia Pretreated Corncob Purified proteins (and one unpurified protein) were serially diluted from stock solution and added to a fermentation broth of *T. reesei* integrated strain H3A to determine their benefit to saccharification of pretreated biomass. Dilute ammonia pretreated corncob was loaded into microtiter plate (MTP) wells at 20% solids (w/w) (~5 mg of cellulose per well), pH 5. H3A protein (in the form of fermentation broth) was added to each well at 20 mg protein/g cellulose. Volumes of 10, 5, 2, and 1 μL of each of the diluted proteins (FIG. 10) were added into individual wells, and water was added such that the liquid addition to each well was a total of 10 μL. Reference wells included additions of either 10 μL water or dilutions of additional H3A fermentation broth. The MTP were sealed with foil and incubated at 50° C. with 200 RPM shaking in an Innova incubator shaker for three days. The samples were quenched with 100 μL of 100 mM glycine pH 10. The quenched samples were covered with a plastic seal and centrifuged 3000 RPM for 5 min at 4° C. An aliquot (5 μL) of the quenched reactions was diluted with 100 μL of water and the concentration of glucose produced in the reactions was determined using HPLC. The glucose data was plotted as a function of the protein concentration added to the 20 mg/g of H3A (the concentrations of the protein additions were variable due to different starting concentrations and additions by volume). Results are shown in FIGS. 11A-11D.

Example 3: Construction of *T. reesei* Strains

A. Construction of and Screening for *T. reesei* Strain H3A/EG4#27

Figure 12A:
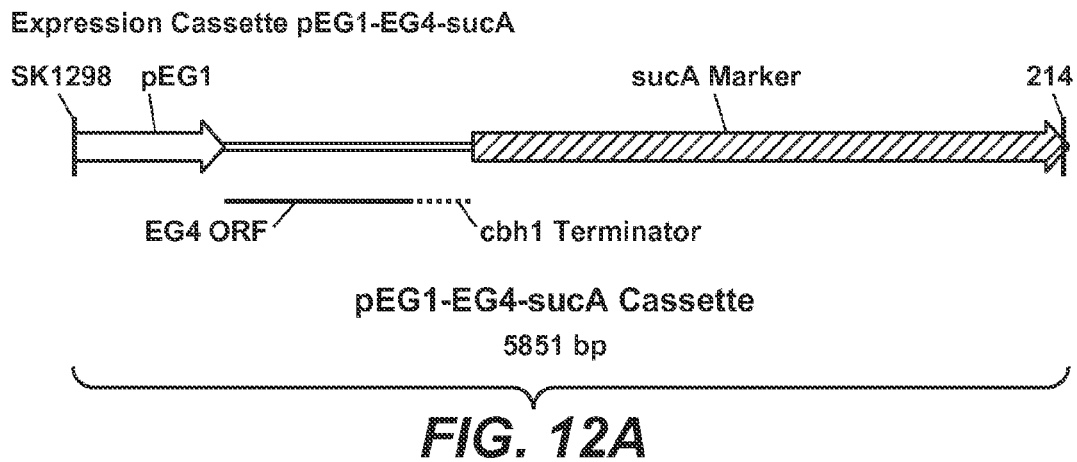
FIGS. 12A-12B.
Figure 12B:
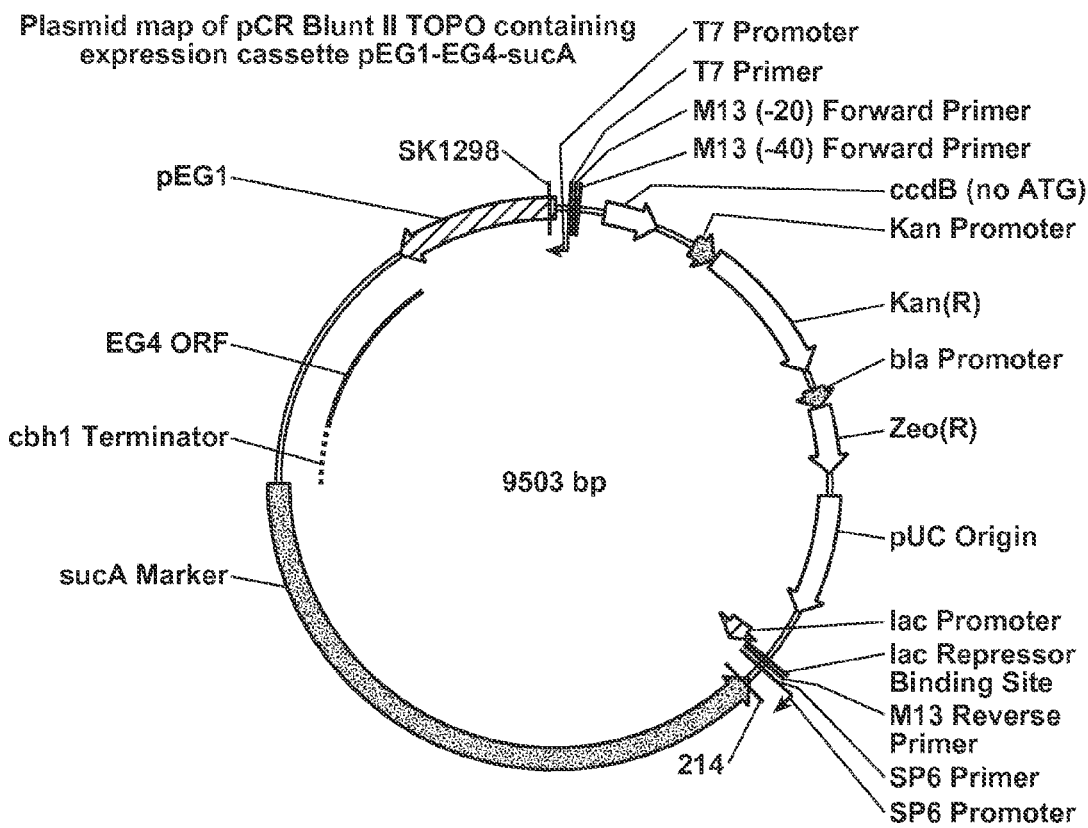

An expression cassette containing the *T. reesei* egl1 (also termed "Cel 7B") promoter, *T. reesei* eg4 (also termed "TrEG4", or "Cel 61A") open reading frame, and cbh1 (Cel 7A) terminator sequence (FIG. 12A) from *Trichoderma reesei*, and sucA selectable marker (see, Boddy et al., Curr. Genet. 1993, 24:60-66) from *Aspergillus niger* was cloned into pCR Blunt II TOPO (Invitrogen) (FIG. 12B).

The expression cassette Pegl1-eg4-sucA was amplified by PCR with the primers:

```
SK1298:
                                   (SEQ ID NO: 146)
5'-GTAGTTATGCGCATGCTAGAC-3'

214:
                                   (SEQ ID NO: 147)
5'-CCGGCTCAGTATCAACCACTAAGCACAT-3'
```

Pfu Ultra II (Stratagene) was used as the polymerase for the PCR reaction. The products of the PCR reaction were purified with the QIAquick PCR purification kit (Qiagen) as per the manufacturer's protocol. The products of the PCR reaction were then concentrated using a speed vac to 1-3 µg/µL. The *T. reesei* host strain to be transformed (H3A) was grown to full sporulation on potato dextrose agar plates for 5 d at 28° C. Spores from 2 plates were harvested with MilliQ water and filtered through a 40 µM cell strainer (BD Falcon). Spores were transferred to a 50 mL conical tube and washed 3 times by repeated centrifugation with 50 mL water. A final wash with 1.1 M sorbitol solution was carried out. The spores were resuspended in a small volume (less than 2 times the pellet volume) using 1.1 M sorbitol solution. The spore suspension was then kept on ice. Spore suspension (60 µL) was mixed with 10-20 µg of DNA, and transferred into the electroporation cuvette (E-shot, 0.1 cm standard electroporation cuvette from Invitrogen). The spores were electroporated using the Biorad Gene Pulser Xcell with settings of 16 kV/cm, 25 µF, 400Ω. After electroporation, 1 mL of 1.1.M sorbitol solution was added to the spore suspension. The spore suspension was plated on Vogel's agar (see example 2G), containing 2% sucrose as the carbon source.

The transformation plates were incubated at 30° C. for 5-7 d. The initial transformants were restreaked onto secondary Vogel's agar plates with sucrose and grown at 30° C. for an additional 5-7 d. Single colonies growing on secondary selection plates were then grown in wells of microtiter plates using the method described in WO/2009/114380. The supernatants were analyzed on SDS-PAGE to check for expression levels prior to saccharification performance screening.

A total of 94 transformants overexpressed EG4 in strain H3A. Two H3A control strains were grown in microtiter plates along with the H3A/EG4 strains. Performance screening of *T. reesei* strains expressing EG4 protein was performed using ammonia pretreated corncob. The dilute ammonia pretreated corncob was suspended in water and adjusted to pH 5.0 with sulfuric acid to achieve 7% cellulose. The slurry was dispensed into a flat bottom 96 well microtiter plate (Nunc, 269787) and centrifuged at 3,000 rpm for 5 min.

Corncob saccharification reactions were initiated by adding 20 µL of H3A or H3A/EG4 strain culture broth per well of substrate. The corncob saccharification reactions were sealed with aluminum (E&K scientific) and mixed for 5 min at 650 rpm, 24° C. The plate was then placed in an Innova incubator at 50° C. and 200 rpm for 72 h. At the end of 72-h saccharification, the reactions were quenched by adding 100 µL of 100 mM glycine, pH 10.0. The plate was then mixed thoroughly and centrifuged at 3,000 rpm for 5 min. Supernatant (10 µL) was added to 200 µL of water in an HPLC 96-well microtiter plate (Agilent, 5042-1385). Glucose, xylose, cellobiose and xylobiose concentrations were measured by HPLC using an Aminex HPX-87P column (300 mm×7.8 mm, 125-0098) pre-fitted with guard column.

Figure 13:
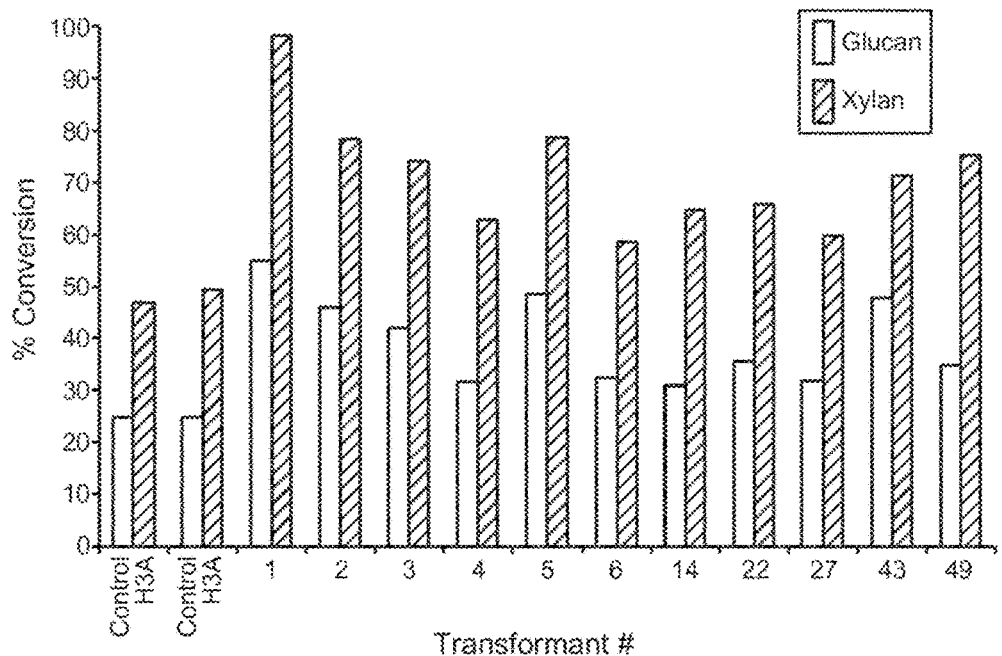
FIG. 13: depicts the amount or percentage of glucan and xylan conversion to cellobiose, glucose, xylobiose and xylose by an enzyme composition comprising enzymes produced by the *T. reesei* integrated strain H3A transformants expressing *T. reesei* Eg4, in accordance with Example 3.

The screening on corncob identified the following H3A/EG4 strains as having improved glucan and xylan conversion compared to the H3A control strains: 1, 2, 3, 4, 5, 6, 14, 22, 27, 43, and 49 (FIG. 13).

Figure 14:
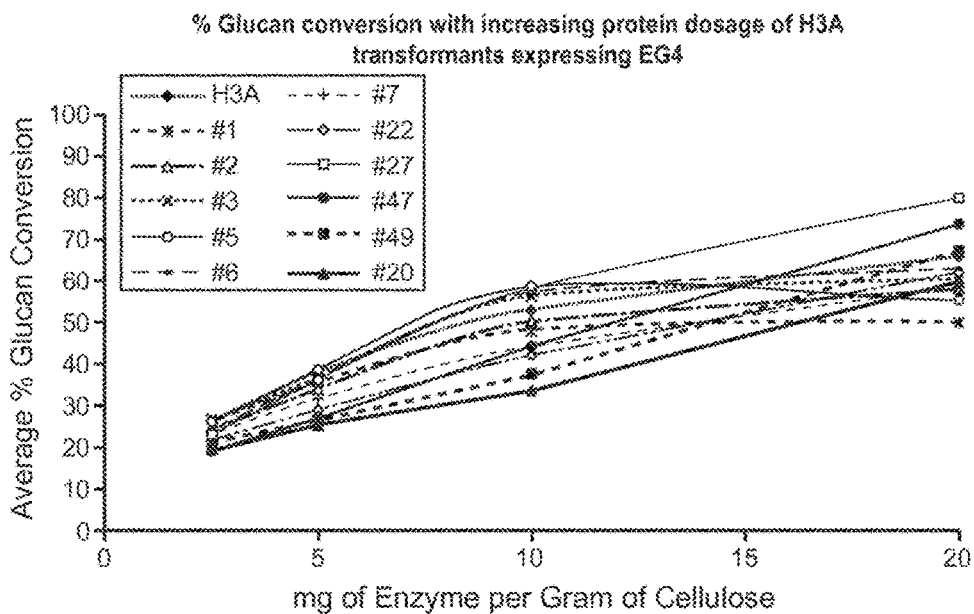
FIG. 14: depicts the increased percent glucan conversion observed using an increasing amount of an enzyme composition produced by H3A transformants expressing *T. reesei* Eg4. The experimental details are described in Example 3.

Select H3A/EG4 strains were re-grown in shake flasks. A total of 30 mL of protein culture filtrate was collected per shake flask per strain. The culture filtrates were concentrated 10-fold using 10 kDa membrane centrifugal concentrators (Sartorious, VS2001) and the total protein concentration was determined by BCA as described in Example 1C. A corncob saccharification reaction was performed using 2.5, 5, 10, or 20 mg protein from H3A/EG4 strain samples per g of cellulose per well of corncob substrate. An H3A strain produced at 14 L fermentation scale and a previously identified low performance sample (H3A/EG4 strain #20) produced at shake flask scale were included as controls. The saccharification reactions were carried out as described in Example 4 (below). Increased glucan conversion with increased protein dose was observed with culture supernatant from all of the EG4 expressing strains (FIG. 14). *T. reesei* integrated strain H3A/EG4#27 was used in additional saccharification reactions, and the strain was purified by streaking a single colony onto a potato dextrose plate from which a single colony was isolated.

Example 4: Range of *T. reesei* EG4 Concentrations for Improved Saccharification of Dilute Ammonia Pretreated Corncob To determine preferred dosing, hydrolysis of dilute ammonia pretreated corncob (25% solids, 8.7% cellulose, 7.3% xylan) was conducted at pH 5.3 using fermentation broth from either *T. reesei* integrated strain H3A/EG4 #27 or H3A with purified EG4 added to the reaction mix. The total loading of *T. reesei* integrated strain H3A/EG4 #27 or H3A was 14 mg protein per gram of glucan (G) and xylan (X).

The reaction mix (total mass 5 g) was loaded into 20 mL scintillation vials in a total reaction volume of 5 mL according to the dosing chart in FIGS. 15, 17A and 17B.

Figure 16A:
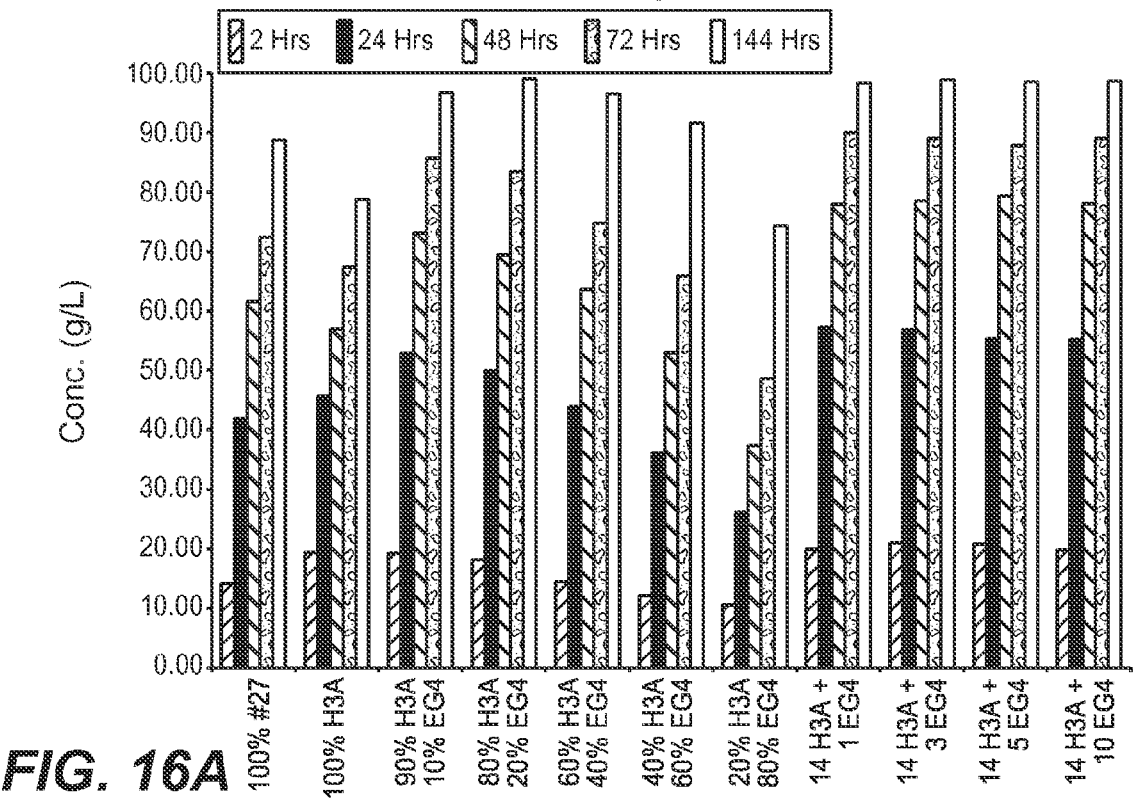
FIGS. 16A-16B.
Figure 16B:
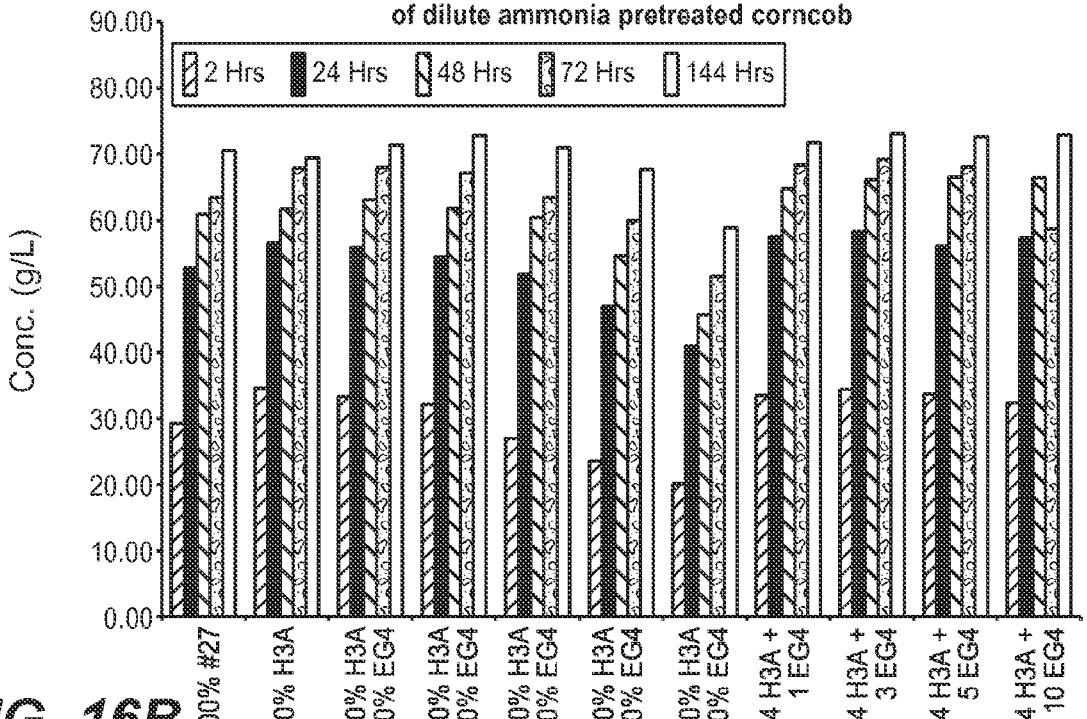

The set up for experiment 1 is shown in FIG. 15. MilliQ Water and 6 N Sulfuric acid were mixed in a conical tube and added to the respective vials and the vials were swirled to mix the contents. Enzymes samples were added to the vials and the vials incubated for 6 d at 50° C. At various time points, 100 µL of sample was removed from the vials diluted with 900 µL 5 mM sulfuric acid, vortexed, centrifuged and the supernatant was used to measure the concentrations of soluble sugars using HPLC. The results of glucan and xylan conversion are shown in FIGS. 16A and 16B, respectively.

Figure 18A:
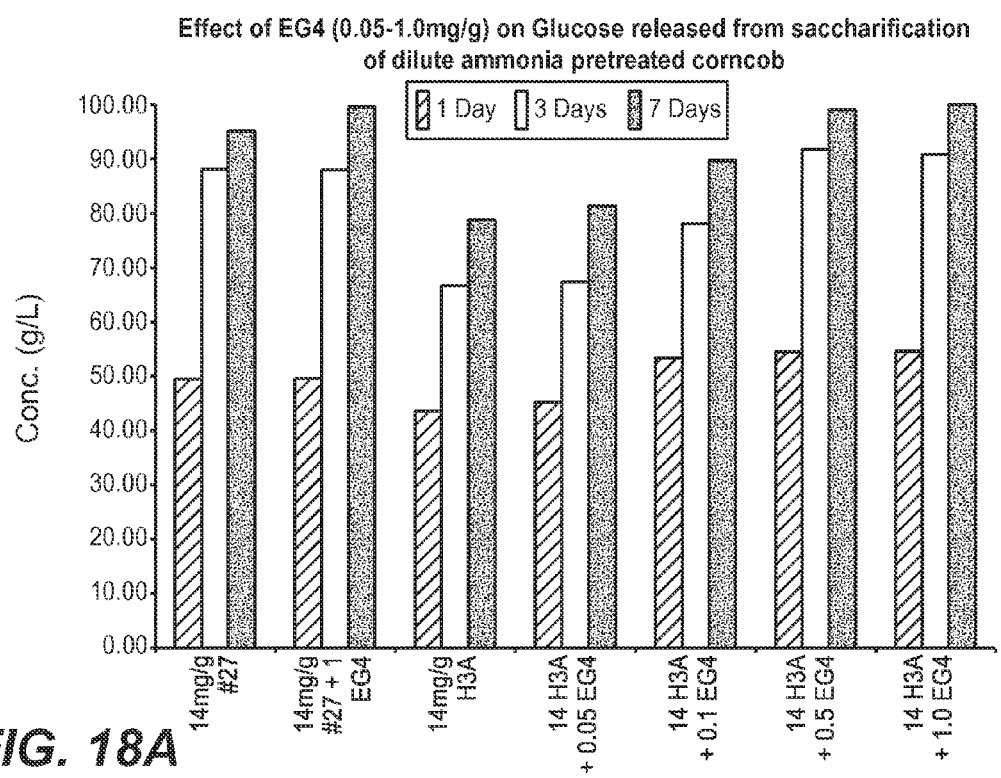
FIGS. 18A-18B.

The set up for experiment 2 is shown in FIG. 17A. To further determine the preferred EG4 concentration, saccharification of dilute ammonia corncob (25% solids, 8.7% cellulose, 7.3% xylan) was conducted at pH 5.3 using fermentation broth from either *T. reesei* integrated strain H3A/EG4 #27 or H3A with purified EG4 added (ranging from 0.05 to 1.0 mg protein/g G+X) to the reaction mix. The total loading of *T. reesei* integrated strain H3A/EG4 #27 or H3A was 14 mg protein/g glucan+xylan. The experimental results are shown in FIG. 18A.

The set up for experiment 3 is shown in FIG. 17B. To pinpoint the preferred concentration range of *T. reesei* Eg4 yet further, dilute ammonia corncob (25% solids, 8.7% cellulose, and 7.3% xylan) was hydrolyzed at pH 5.3 using *T. reesei* integrated strain H3A/EG4 #27 or H3A with purified EG4 added at concentrations ranging from 0.1-0.5 mg protein/g G+X. The total loading of *T. reesei* integrated strain H3A/EG4 #27 or H3A was 14 mg protein per g of glucan and xylan.

Figure 18B:
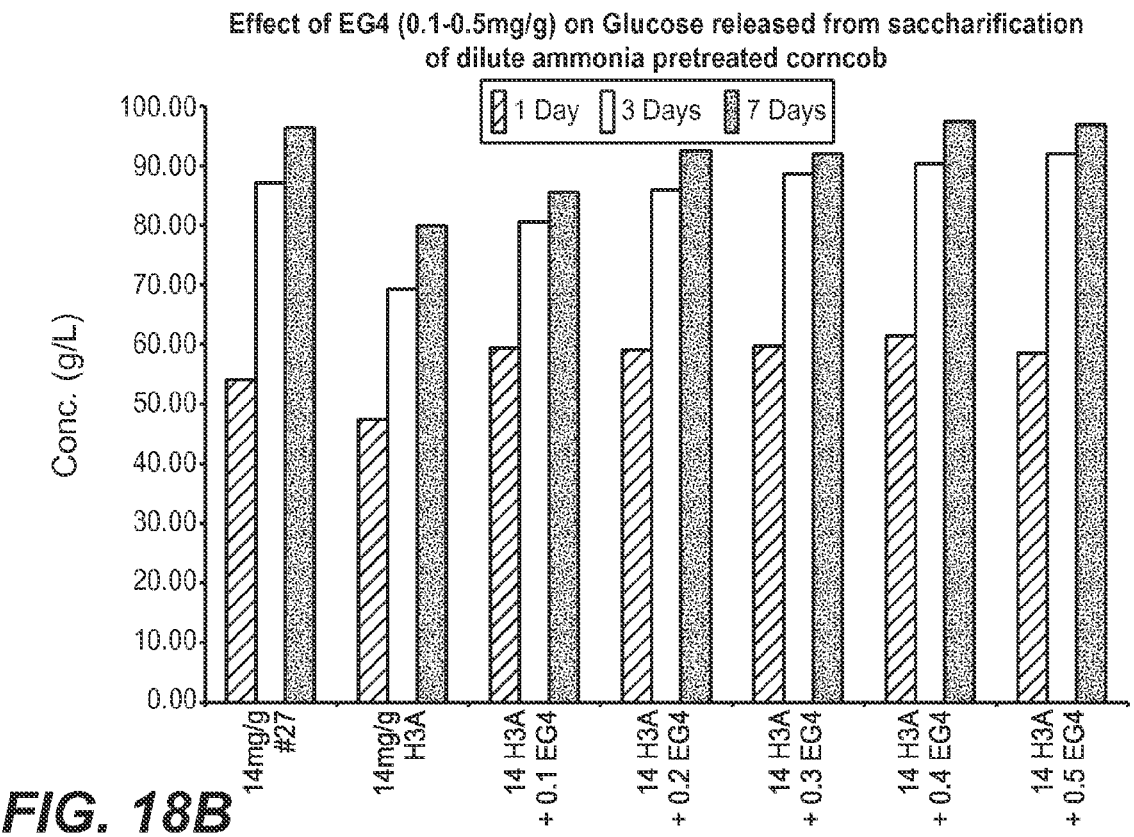

Results are shown in FIG. 18B.

Figure 19:
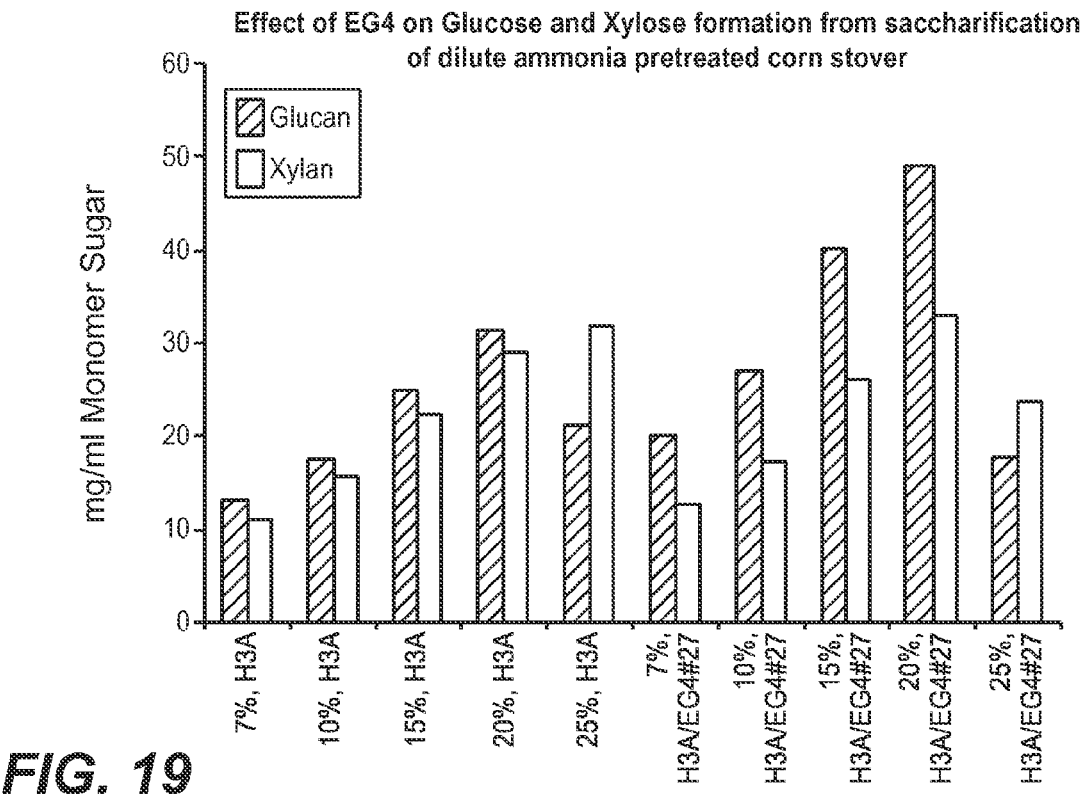
FIG. 19: depicts the effect of *T. reesei* Eg4 in an enzyme composition on glucose/xylose release from saccharification of different solid loadings of dilute ammonia pretreated corn stover, as described in Example 5. The solid loading is listed on the x-axis as #%.

Example 5: Effect of *T. reesei* Eg4 on Saccharification of Dilute Ammonia Pretreated Corn Stover at Different Solid Loadings Dilute ammonia pre-treated corn stover was incubated with fermentation broth from *T. reesei* integrated strain H3A or H3A/EG4#27 (14 mg protein/g glucan and xylan) at 7, 10, 15, 20 and 25% solids (% S) for three days at 50° C., pH 5.3 (5 g total wet biomass in 20 mL vials). The reactions were carried out as described in Example 4 above. Glucose and xylose were analyzed by HPLC. Results are shown in FIG. 19. All samples up to 20% solids were visibly liquefied on day 1.

Example 6: Effect of Overexpression of *T. reesei* EG4 on Hydrolysis of Dilute Ammonia Pretreated Corncob The effect of overexpression of *T. reesei* Eg4 in strain H3A on saccharification of dilute ammonia pretreated corncob was tested using fermentation broths from strains H3A/EG4 #27 and H3A. Corncob saccharification at 3 g scale was performed in 20 mL glass vials as follows. Enzyme preparation, 1 N sulfuric acid and 50 mM pH 5.0 sodium acetate buffer (with 0.01% sodium azide and 5 mM $MnCl_2$) were added to give a final slurry of 3 g total reaction, 22% dry solids, pH 5.0 with enzyme loadings varying between 1.7 and 21.0 mg total protein per gram Glucan+Xylan. All saccharification vials were incubated at 48° C. with 180 rpm rotation. After 72 h, 12 mL of filtered MilliQ water was added to each vial to dilute the entire saccharification reaction 5-fold. The samples were centrifuged at 14,000×g for 5 min, then filtered through a 0.22 µm nylon filter (Spin-X centrifuge tube filter, Corning Incorporated, Corning, N.Y.) and further diluted 4-fold with filtered MilliQ water to create a final 20× dilution. 20 µL injections were analyzed by HPLC to measure the sugars released.

Overexpression or addition of *T. reesei* Eg4 led to enhanced xylose and glucose monomer release as compared to H3A alone (FIGS. 20 and 21). Addition of H3A/EG4#27 at different doses led to an increased yield of xylose as compared to strain H3A, or compared to Eg4+a constant 1.12 mg Xyn3 per g Glucan+Xylan (FIG. 20).

Addition of H3A/EG4#27 at different doses led to an increased yield of glucose compared to strain H3A or compared to Eg4+a constant 1.12 mg Xyn3 per g Glucan+Xylan (FIG. 21).

The effect of *T. reesei* Eg4 on total fermentable monomer (xylose, glucose and arabinose) release by integrated strains H3A/EG4#27 or H3A is illustrated in the FIG. 22. The H3A/EG4#27 integrated strain led to enhanced total fermentable monomer release compared to the integrated strain H3A, or compared to Eg4+1.12 mg Xyn3/g Glucan+Xylan.

Example 7: Purified *T. reesei* EG4 Leads to Glucose Release in Dilute Ammonia Pretreated Corncob The effect of purified *T. reesei* Eg4 on the concentration of sugars released was tested using 1.05 g dilute ammonia pretreated corncob in the presence or absence of 0.53 mg Xyn3 per g Glucan+Xylan. The experiments were performed as described in Example 6. Results are shown in FIG. 23. The data indicate that purified *T. reesei* Eg4 leads to release of glucose monomer without the action of other cellulases such as endoglucanases, cellobiohydrolases and β-glucosidases.

Figure 24:
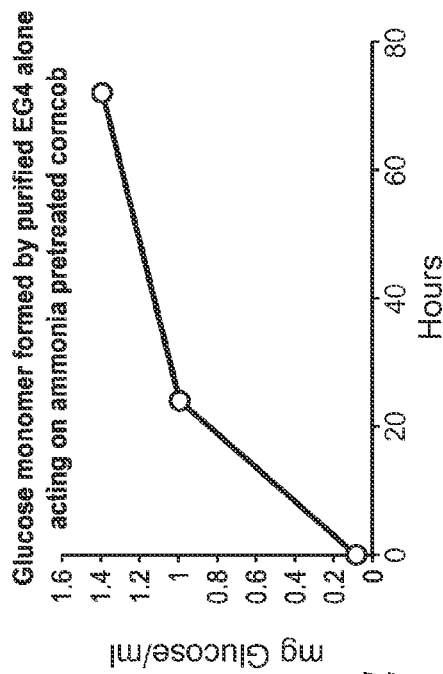
FIG. 24: depicts the glucose monomer release as a result of treating ammonia pretreated corncob using purified *T. reesei* Eg4 alone, according to Example 7.

Saccharification experiments were also conducted using dilute ammonia pretreated corncob with purified Eg4 added alone (no Xyn3 added). 3.3 µL of purified Eg4 (15.3 mg/mL) was added to 872 µL 50 mM, pH 5.0 sodium acetate buffer (included 0.01% sodium azide and 5 mM $MnCl_2$), 165 mg of dilute ammonia pretreated corncob (67.3% dry solids, 111 mg dry solids added) and 16.5 µL of 1 N sulfuric acid in 5 mL vials. The vials were incubated at 48° C. and rotated at 180 rpm. Periodically, 20 µL aliquots were removed, diluted 10-fold with filter sterilized double distilled water and filtered through a nylon filter before analysis for glucose released on a Dionex Ion Chromatography system. Authentic glucose solutions were used as external standards. Results are shown in FIG. 24, indicating that addition of purified Eg4 leads to release of glucose monomer from dilute ammonia pretreated corncobs over 72 h incubation at 48° C. in the absence of other cellulases or endoxylanase.

Example 8: Saccharification Performance of *T. reesei* Integrated Strains H3A and H3A/EG4 #27 on Various Substrates In this experiment, fermentation broth from *T. reesei* integrated strain H3A or H3A/EG4#27, dosed at 14 mg protein per g of glucan+xylan, was tested for saccharification performance on different substrates including: dilute ammonia pretreated corncob, washed dilute ammonia pretreated corncob, ammonia fiber expanded corn stover (AFEX CS), Steam Expanded Sugarcane Bagasse (SEB), and Kraft-pretreated paper pulps FPP27 (Softwood Industrial Unbleached Pulp delignified-Kappa 13.5, Glucan 81.9%, Xylan 8.0%, Klason Lignin 1.9%), FPP-31 (Hardwood Unbleached Pulp delignified-Kappa 10.1, Glucan 75.1%, Xylan 19.1%, Klason Lignin 2.2%), and FPP-37 (Softwood Unbleached Pulp air dried-Kappa 82, Glucan 71.4%, Xylan 8.7%, Klason Lignin 11.3%).

Figure 25:
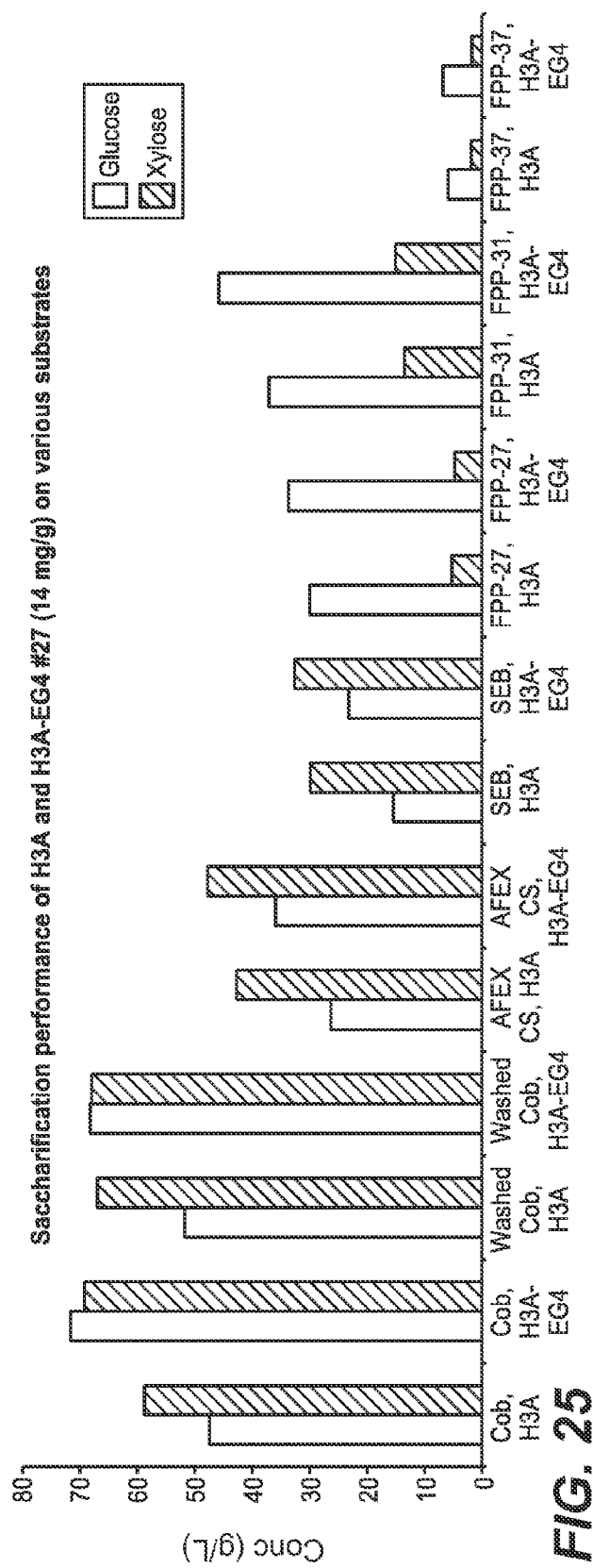
FIG. 25: depicts and compares the saccharification performance of the enzyme compositions produced by the *T. reesei* integrated strain H3A and the integrated strain H3A/Eg4 (strain #27), at an enzyme dosage of 14 mg/g. This is according to the description of Example 8.

The saccharification reactions were set up in 25 mL glass vials with final mass of 10 g in 0.1 M Sodium Citrate Buffer, pH 5.0 and incubated at 50° C., 200 rpm for 6 d. At the end of 6 d, 100 µL aliquots were diluted 1:10 in 5 mM sulfuric acid and the samples analyzed by HPLC to determine glucose and xylose formation. Results are shown in FIG. 25.

Figure 26:
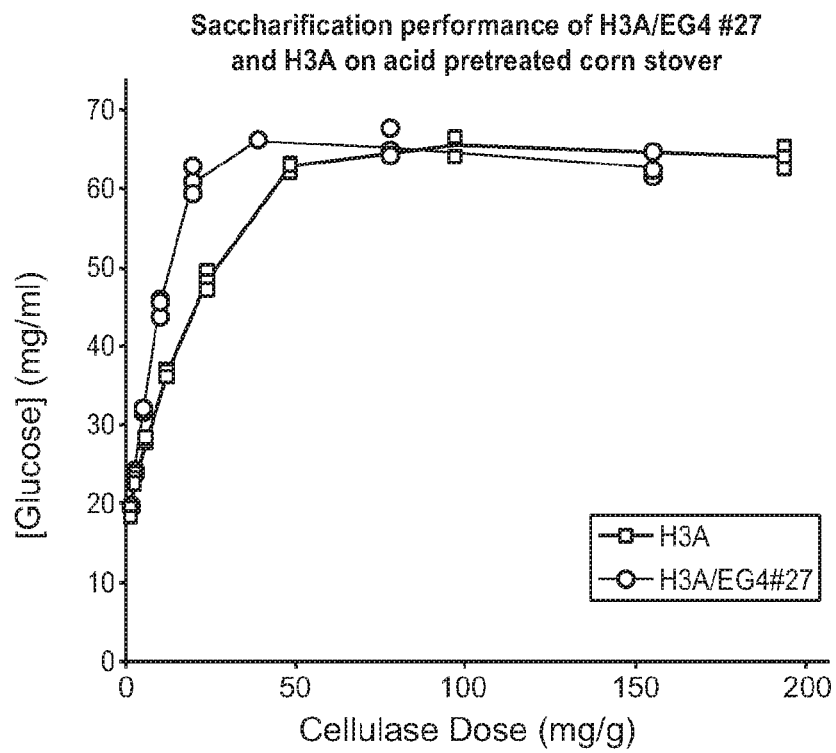
FIG. 26: depicts the saccharification performance of the enzyme compositions produced by the *T. reesei* integrated strain H3A and the integrated strain H3A/Eg4 (strain #27), at various enzyme dosages, on acid pretreated corn stover. This is according to the description of Example 9.

Example 9: Effect of *T. reesei* EG4 on Saccharification of Acid Pretreated Corn Stover The effect of Eg4 on saccharification of acid pretreated corn stover was tested. Corn stover pretreated with dilute sulfuric acid (Schell, D J, et al., *Appl. Biochem. Biotechnol.* 2003, 105(1-3):69-85) was obtained from NREL, adjusted to 20% solids and conditioned to a pH 5.0 with the addition of soda ash solution. Saccharification of the pretreated substrate was performed in a microtiter plate using 20% total solids. Total protein in the fermentation broths was measured by the Biuret assay (see Example 1 above). Increasing amounts of fermentation broth from *T. reesei* integrated strains H3A/EG4 #27 and H3A were added to the substrate and saccharification performance was measured following incubation at 50° C., 5 d, 200 RPM shaking. Glucose formation (mg/g) was measured using HPLC. Results are shown in FIG. 26.

Figure 27:
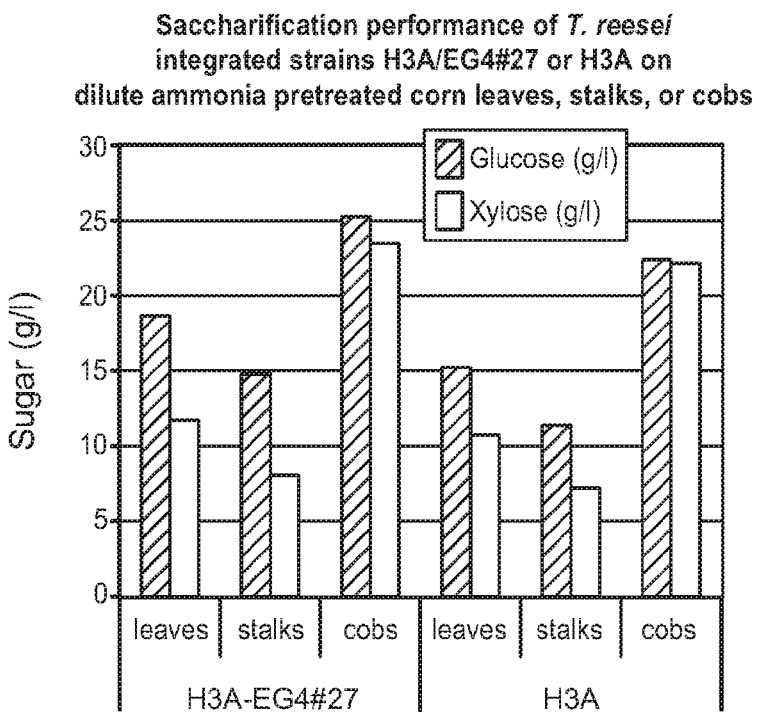
FIG. 27: depicts the saccharification performance of the enzyme compositions produced by the *T. reesei* integrated strain H3A and the integrated strain H3A/Eg4 (strain #27) on dilute ammonia pretreated corn leaves, stalks, or cobs, according to Example 10.

Example 10: Saccharification Performance of *T. reesei* Integrated Strains H3A and H3A/EG4#27 on Dilute Ammonia Pretreated Corn Leaves, Stalks, and Cobs Saccharification performance of *T. reesei* integrated strains H3A and H3A/EG4#27 was compared on dilute ammonia pretreated corn stover leaves, stalks, or cobs. Pretreatment was performed as described in WO06110901A. Five (5) g total mass (7% solids) was hydrolyzed in 20 mL vials at pH 5.3 (pH adjusted with 6 N $H_2SO_4$) using 14 mg protein per g of glucan+xylan. Saccharification reactions were carried out at 50° C. and samples analyzed by HPLC for glucose and xylose released on day 4. Results are shown in FIG. 27.

Example 11: Saccharification Performance on Dilute Ammonia Pretreated Corncob in Response to Overexpressed EG4 from *T. reesei*

Saccharification reactions at 3 g scale were performed using dilute ammonia pretreated corncob. Sufficient pretreated cob preparation was measured into 20 mL glass vials to give 0.75 g dry solid. Enzyme preparation, 1 N sulfuric acid and 50 mM pH 5.0 sodium acetate buffer (with 0.01% sodium azide) were added to give final slurry of 3 g total reaction, 25% dry solids, pH 5.0. Extra cellular protein (fermentation broth) from the *T. reesei* integrated strain H3A was added at 14 mg protein/g (glucan+xylan) either with or without an additional 5% of the 14 mg protein load as the unpurified culture supernatant from a *T. reesei* strain (Δcbh1 Δcbh2 Δeg1 Δeg2) (See International publication WO 05/001036) over expressing Eg4. The saccharification reactions were incubated for 72 h at 50° C. Following incubation, the reaction contents were diluted 3-fold, filtered and analyzed by HPLC for glucose and xylose concentration. The results are shown in FIG. 28. Addition of Eg4 protein in the form of extracelluar protein from a *T. reesei* strain over expressing Eg4 to H3A substantially increased the release of monomer glucose and slightly increased the release of monomer xylose.

Example 12: Saccharification Performance of Strain H3A/EG4#27 on Ammonia Pretreated Switchgrass The saccharification performance of strain H3A/EG4#27 on ammonia pretreated switchgrass (International Patent Publication WO06110901A) at increasing protein doses was compared to that of strain H3A (18.5% solids). Pretreated switchgrass preparations were measured into 20 mL glass vials to give 0.925 g of dry solid. 1 N sulfuric acid and 50 mM pH 5.3 sodium acetate buffer (with 0.01% sodium azide) were added to give final slurry of 5 grams total reaction. The enzyme dosages of H3A tested were 14, 20, and 30 mg/g (glucan+xylan); and the dosages of H3A-EG4 #27 were 5, 8, 11, 14, 20, and 30 mg/g (glucan+xylan). The reactions were incubated at 50° C. for 3 d. Following incubation, the reaction contents were diluted 3-fold, filtered and analyzed by HPLC for glucose and xylose concentration. The conversion of glucan and xylan were calculated based on the composition of the switchgrass substrate. The results (FIG. 29) indicate that the performance of H3A-EG4 #27 is more effective for glucan conversion than H3A at the same enzyme dosages.

Example 13: Effect of *T. reesei* EG4 Additions on Corncob Saccharification and on CMC and Cellobiose Hydrolysis

A. Corncob Saccharification

Dilute ammonia pretreated corncob was adjusted to 20% solids, 7% cellulose and 65 mg was dispensed per well in a microtiter plate. Saccharification reactions were initiated by adding 35 μL of 50 mM sodium acetate (pH 5.0) buffer containing *T. reesei* CBH1 at 5 mg protein/g glucan (final) and the relevant enzymes (CBH1 or Eg4), at final concentrations of 0, 1, 2, 3, 4 and 5 mg/g glucan. An Eg4 control received only EG4 at the same doses and as such, the total added protein in these wells was less. The microtiter plates were sealed with an aluminum plate seal (E&K scientific) and mixed for 2 min at 600 rpm, 24° C. The plate was then placed in an Innova incubator at 50° C. and 200 rpm for 72 h.

At the end of 72-h saccharification, the plate was quenched by adding 100 μL of 100 mM glycine, pH 10.0. The plate was then centrifuged at 3000 rpm for 5 min. Supernatant (20 μL) was added to 100 μL of water in HPLC 96 well microtiter plate (Agilent 5042-1385). Glucose and cellobiose concentrations were measured by HPLC using Aminex HPX-87P column (300 mm×7.8 mm, 125-0098) pre-fitted with guard column. % glucan conversion was calculated by 100×(mg cellobiose+mg glucose)/total glucan in substrate (FIG. 30).

B. CMC Hydrolysis

Carboxymethylcellulose (CMC, Sigma C4888) was diluted to 1% with 50 mM Sodium Acetate, pH 5.0. Hydrolysis reactions were initiated by separately adding each of three *T. reesei* purified enzymes—EG4, EG1 and CBH1 at final concentrations of 20, 10, 5, 2.5, 1.25 and 0 mg/g to 100 μL of 1% CMC in a 96-well microtiter plate (NUNC #269787). Sodium acetate, pH 5.0 50 mM was added to each well to a final volume of 150 μL. The CMC hydrolysis reactions were sealed with an aluminum plate seal (E&K scientific) and mixed for 2 min at 600 rpm, 24° C. The plate was then placed in an Innova incubator at 50° C. and 200 rpm for 30 min.

Figure 31:
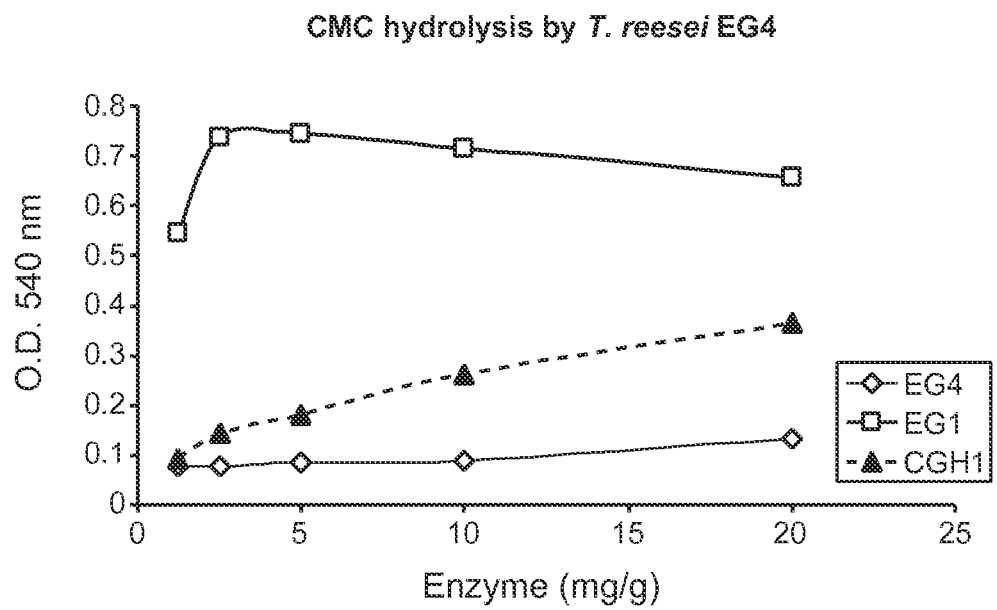
FIG. 31: depicts CMC hydrolysis by *T. reesei* Eg4. Experimental conditions are described in Example 13.

At the end of 30 min incubation, the plate was put in ice water for 10 min to stop the reaction, and samples were transferred to eppendorf tubes. To each tube was added 375 μL of dinitrosalicylic acid (DNS) solution (see below). Samples were then boiled for 10 min and O.D was measured at 540 nm by SpectraMAX 250 (Molecular Devices). Results are shown in FIG. 31.

DNS Solution:
40 g 3.5-Dinitrosalicylic acid (Sigma, D0550)
8 g Phenol
2 g Sodium sulfite ($Na_2SO_3$)
800 g Na—K tartarate (Rochelle salt)
Add all the above to 2 L of 2% NaOH
Stir overnight, covered with aluminum foil
Add distilled deionized water to a final volume of 4 L
Mix well
Store in a dark bottle, refrigerated

C. Cellobiose Hydrolysis

Cellobiose was diluted to 5 g/L with 50 mM Sodium Acetate, pH 5.0. Hydrolysis reactions were initiated by separately adding each of two enzymes—EG4 and BGL1 at final concentrations of 20, 10, 5, 2.5, and 0 mg/g to 100 μL cellobiose solution at 5 g/L. Sodium acetate, pH 5.0 was added to each well to a final volume of 120 μL. The reaction plates were sealed with an aluminum plate seal (E&K scientific) and mixed for 2 min at 600 rpm, 24° C. The plate was then placed in an Innova incubator at 50° C. and 200 rpm for 2 h.

Figure 32:
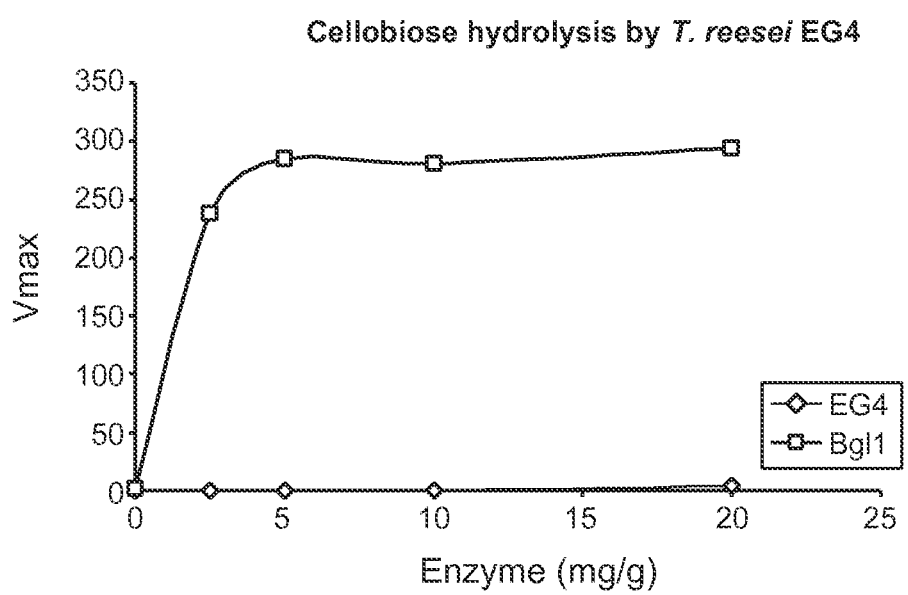
FIG. 32: depicts cellobiose hydrolysis by *T. reesei* Eg4. Experimental conditions are described in Example 13.

At the end of the 2 h hydrolysis step, the plate was quenched by adding 100 μL of 100 mM glycine, pH 10.0. The plate was then centrifuged at 3000 rpm for 5 min. Glucose concentration was measured by ABTS (2,2'-azino-bis 3-ethylbenzothiazoline-6-sulfonic acid) assay (Example 1). Ten (10) μL of supernatant was added to 90 μL ABTS solution in a 96-well microtiter plate (Corning costar 9017 EIA/RIA plate, 96 well flat bottom, medium binding). OD 420 nm was measured by SpectraMAX 250, Molecular Devices. Results are shown in FIG. 32.

Example 14: Purified EG4 Improves Glucose Production from Dilute Ammonia Pretreated Corncob when Mixed with Various Cellulase Mixtures The effect of purified Eg4 combined with purified cellulases (*T. reesei* EG1, EG2, CBH1, CBH2, and Bgl1) on the concentration of sugars released was tested using 1.05 g dilute ammonia pretreated corncob in the presence of 0.53 mg *T. reesei* Xyn3 per g of Glucan+Xylan. 1.06-g reactions were set up in 5 mL vials containing 0.111 g dry cob solids (10.5% solids). Enzyme preparation (FIG. 33), 1 N sulfuric acid and 50 mM pH 5.0 sodium acetate buffer (with 0.01% sodium azide and 5 mM $MnCl_2$) were added to give the final reaction weight. The reaction vials were incubated at 48° C. with 180 rpm rotation. After 72 h, filtered MilliQ water was added to dilute each saccharification reaction by 5-fold. The samples were centrifuged at 14,000×g for 5 min, then filtered through a 0.22 μm nylon filter (Spin-X centrifuge tube filter, Corning Incorporated, Corning, N.Y.) and further diluted 4-fold with filtered Milli-Q water to create a final 20× dilution. Twenty (20) μL injections were analyzed by HPLC to measure the sugars released (glucose, cellobiose, and xylose).

Figures 33A, 34A:
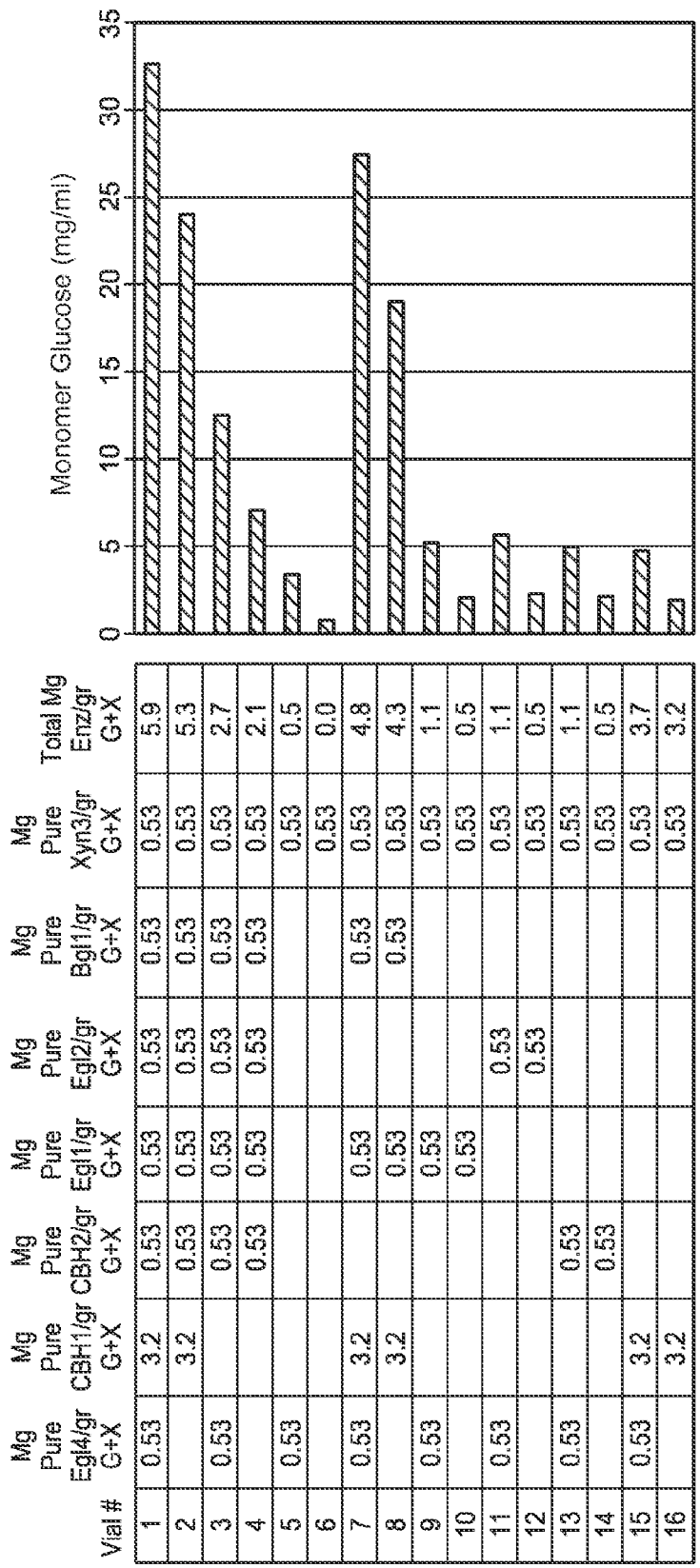

FIG. 34 shows glucose (A), glucose+cellobiose (B), or xylose (C) produced with each combination. Purified Eg4 improved the performance of individual cellulases and mixtures. When all of the purified cellulases were present, addition of 0.53 mg Eg4 per g Glucan+Xylan improved the conversion by almost 40% Improvement was also seen when Eg4 was added to a combination of CBH1, Egl1 and Bgl1. When individual cellulases were present with the cob, the absolute amounts of total glucose release were substantially lower than resulted from the experiment wherein combinations of cellulases were present with the cob, but in each case, the percent improvement in the presence of Eg4 was significant. Addition of *T. reesei* Eg4 to purified cellulases resulted in the following percent improvements in total Glucose release-Bgl1 (121%), Egl2 (112%), CBH2 (239%) and CBH1 (71%). This shows that Eg4 had a significant and broad effect to improve cellulase performance on biomass.

Example 15: Effects Observed when EG4 was Mixed with CBH1, CBH2, and EG2-Substrate: Dilute Ammonia Pretreated Corncob Dilute ammonia pretreated corncob saccharification reactions were prepared by adding enzyme mixtures as follows to corncob (65 mg per well of 20% solids, 7% cellulose) in 96-well MTPs (VWR). Eighty (80) μL of 50 mM sodium acetate (pH 5.0), 1 mg Bgl1/g glucan, and 0.5 mg Xyn3/g glucan background were also added to all wells.

To test the effect of mixing Eg4 individually with CBH1, CBH2 and EG2, each of CBH1, CBH2, and EG2 was added at 0, 1.25, 2.5, 5, 10 and 20 mg/g glucan, and EG4 was added at concentrations of 20, 18.75, 17.5, 15, 10 and 0 mg/g glucan to the respective wells, making the total proteins in individual wells 20 mg/g glucan. The control wells received only CBH1 or CBH2 or EG2 or EG4 at the same doses, as such the total added proteins in these wells were less than 20 mg/g.

To test the effect of Eg4 on combinations of cellulases, mixtures of CBH1, CBH2 and EG2 at different ratios (see, FIG. 35) were added at 0, 1.25, 2.5, 5, 10 and 20 mg protein/g glucan, and EG4 was added to the mixtures at concentrations of 20, 18.75, 17.5, 15, 10 and 0 mg protein/g glucan, such that the total proteins in individual wells was 20 mg protein/g glucan. As above, control wells received only one added protein so the total protein addition was less than 20 mg protein/g.

The corncob saccharification reactions were sealed with an aluminum plate seal (E&K scientific) and mixed for 2 min at 600 rpm, 24° C. The plate was then placed in an Innova 44 incubator shaker (New Brunswick Scientific) at 50° C. and 200 rpm for 72 h. At the end of the 72-h saccharification step, the plate was quenched by adding 100 μL of 100 mM glycine, pH 10.0. The plate was then centrifuged at 3000 rpm for 5 min (Rotanta 460R Centrifuge, Hettich Zentrifugen). Twenty (20) μL of supernatant was added to 100 μL of water in an HPLC 96-well microtiter plate (Agilent, 5042-1385). Glucose and cellobiose concentrations were measured by HPLC using an Aminex HPX-87P column (300 mm×7.8 mm, 125-0098) and guard column (BioRad).

Figure 36B:

The results were indicated in the table of FIG. 36, wherein the glucan conversion (%) is defined as 100×(glucose+cellulobiose)/total glucan.

This experiment indicates that Eg4, when added to a CBH1, CBH2 and/or EG2, was beneficial in improving saccharification of dilute ammonia pretreated corncob. Moreover, the highest improvement was observed when Eg4 and the other enzyme (CBH1, CBH2, or EG2) were added to the saccharification mixture in an equal amount. It was also observed that the effect of Eg4 is substantial on the CBH1 and CBH2 mixture. The optimum improvement by Eg4 was observed when the amount of Eg4 to CBH1 and CBH2 was 1:1.

Example 16: EG4 Improves Saccharification Performance of Various Cellulase Compositions The total protein concentration of commercial cellulase enzyme preparations Spezyme® CP, Accellerase®1500, and Accellerase® DUET (Genencor Division, Danisco US) were determined by the modified Biuret assay (described herein).

Purified *T. reesei* EG4 was added to each enzyme preparation, and the samples were then assayed for saccharification performance using a 25% solids loading of ammonia pretreated corncob, at a dose of 14 mg of total protein per g of substrate glucan and xylan (5 mg EG4 per g of glucan and xylan, plus 9 mg whole cellulase per g of glucan and xylan). The saccharification reaction was carried out using 5 g of total reaction mixture in a 20 mL vial at pH 5, with incubation at 50° C. in a rotary shaker set to 200 rpm for 7 d. The saccharification samples were diluted 10× with 5 mM sulfuric acid, filtered through a 0.2 μm filter before injection into the HPLC. HPLC analysis was performed using a BioRad Aminex HPX-87H ion exclusion column (300 mm×7.8 mm)

Figure 40:
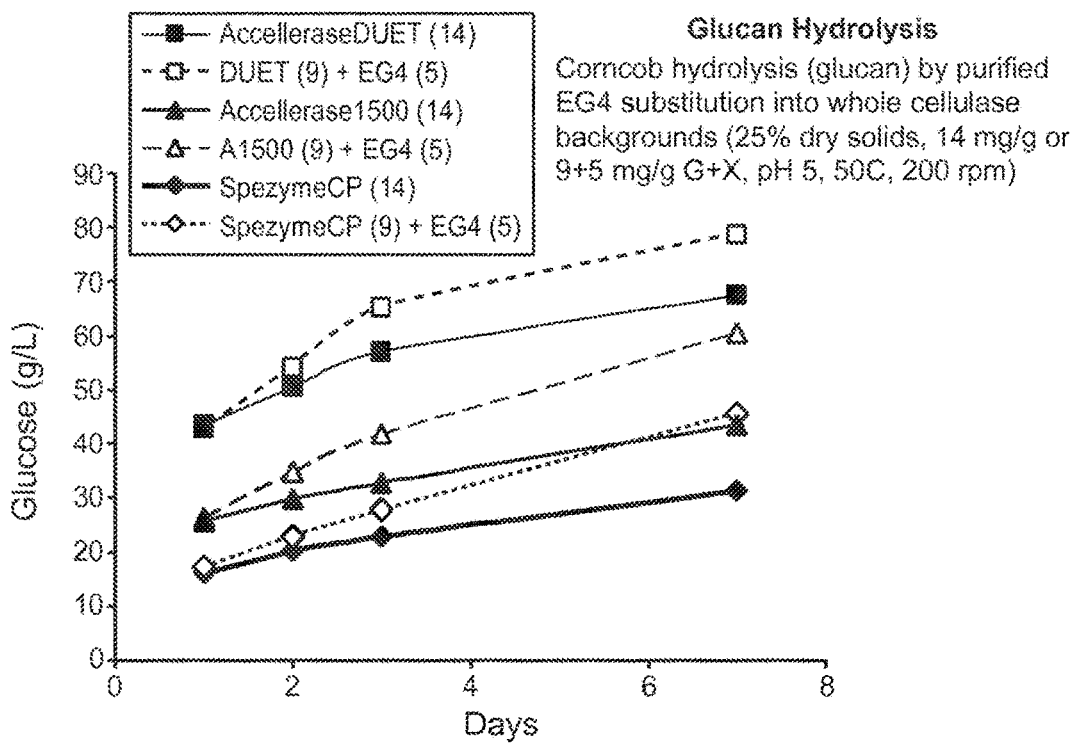
FIG. 40: depicts glucose production from corncob hydrolysis using various enzyme compositions, in accordance with the experiments described in Example 16.
Figure 41:
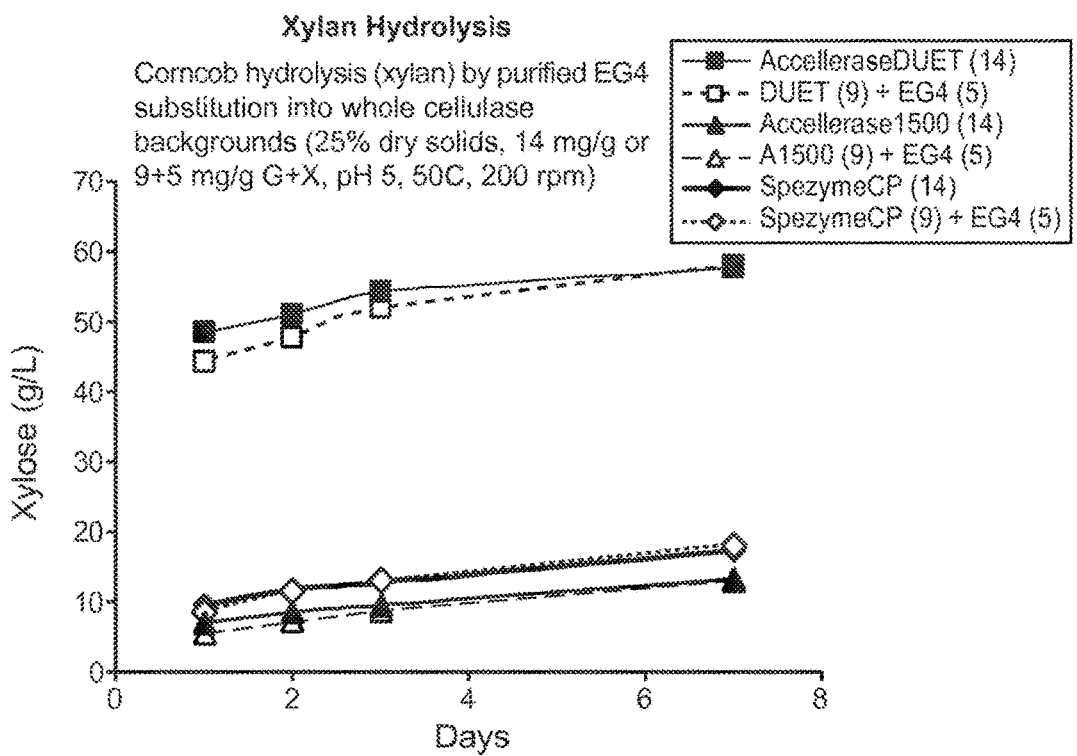
FIG. 41: depicts xylose production from corncob hydrolysis using various enzyme compositions in accordance with the description of Example 16.

Substitution of purified EG4 into whole cellulases improved glucan conversion in all tested cellulase products as illustrated in FIG. 40. As illustrated in FIG. 41, xylan conversion did not appear to be affected by the Eg4 substitution.

Example 17: Reduction of Viscosity in Biomass Saccharification

Biomass used in this experiment was Inbicon acidified steam-expansion pretreated wheat straw, with the following composition (Table 2):

| Component ID | Inbicon wheat straw Mean |
| --- | --- |
| Glucan | 55.0% |
| Xylan | 5.0% |
| Galactan | |
| Arabinan | |
| Mannan | |
| Klason Lignin | 31.0% |
| Acid soluble lignin | |
| Ash | 4.0% |
| Starch | |
| Mass Balance Closure | 95.0% |

Figure 42:
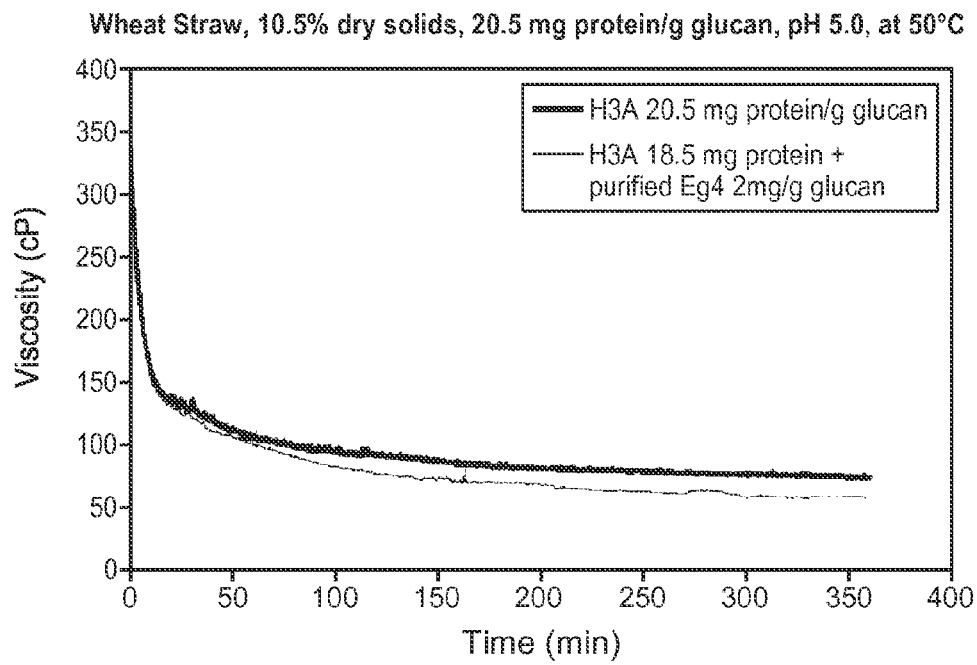
FIG. 42: depicts viscosity of saccharification mixture using H3A and H3A added with purified Eg4 over time in accordance with the description of Example 17.

The pre-treated wheat straw was diluted into water and pH-adjusted with sulfuric acid to pH5.0, and a solid level of 10.5% of that was mixed with, in a first sample, a fermentation broth of a *T. reesei* H3A strain (FIG. 9) at a total protein concentration of 20.5 mg protein/g cellulose in the biomass substrate at 50° C., or in a second sample, the fermentation broth of *T. reesei* H3A (FIG. 9) at a total protein concentration of 18.5 mg protein/g cellulose in the biomass substrate, and 2 mg/g cellulose of purified *T. reesei* Eg4. Viscosity reduction was measured using a Brookfield viscometer (Brookfield Engineering, Inc), monitoring viscosity change up to about 6 h. Results are indicated in FIG. 42.

Example 18: Reduction of Viscosity in Biomass Saccharification

Biomass used in this experiment was dilute acid pretreated corn stover from NREL (unwashed PCS).

Figure 43:
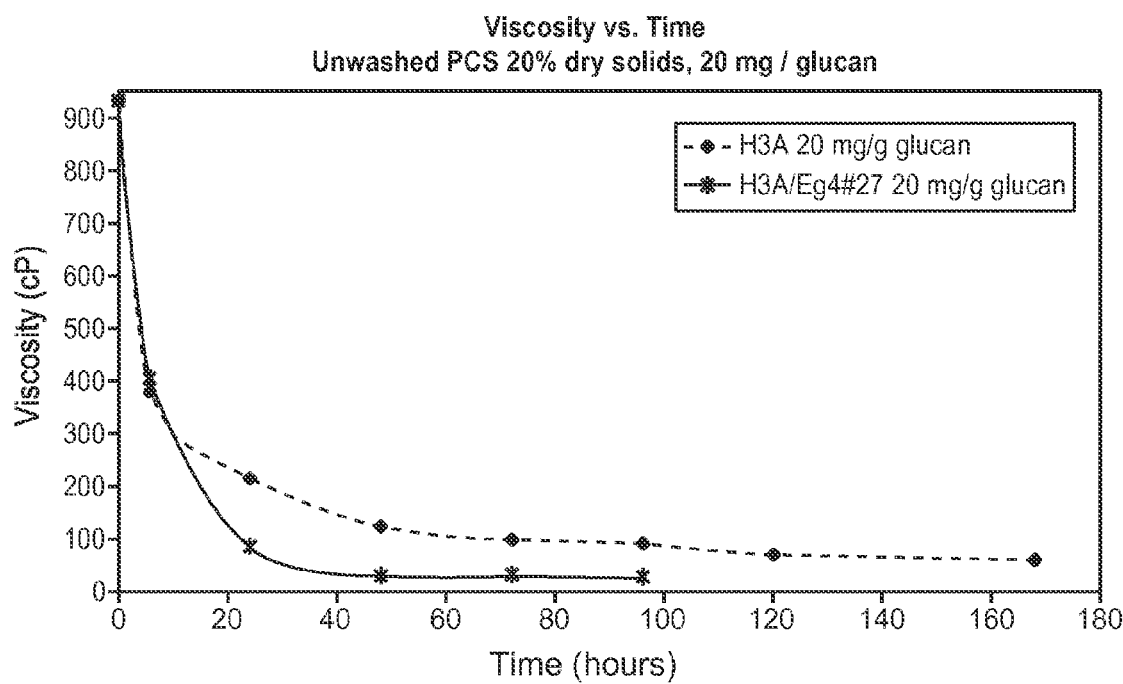
FIG. 43: depicts viscosity of saccharification mixture using H3A and H3A/Eg4#27 over time in accordance with the description of Example 18.

The unwashed pretreated corn stover was mixed, at a temperature of 50° C., pH of 5.0, and a solid level of 20% dry solids with, in a first sample, a fermentation broth of a *T. reesei* H3A strain (FIG. 9) at a total protein concentration of 20 mg/g cellulose in the biomass substrate, and in a second sample, a fermentation broth of *T. reesei* H3A/Eg4 #27 integrated strain, also at 20 mg/g cellulose. Viscosity reduction was measured using a Brookfield viscometer (Brookfield Engineering, Inc.), monitoring viscosity change for up to over 160 h. The results are indicated in FIG. 43.

Example 19: Reduction of Viscosity in Biomass Saccharification

Biomass used in this experiment was dilute ammonia pretreated corncob.

Figure 44:
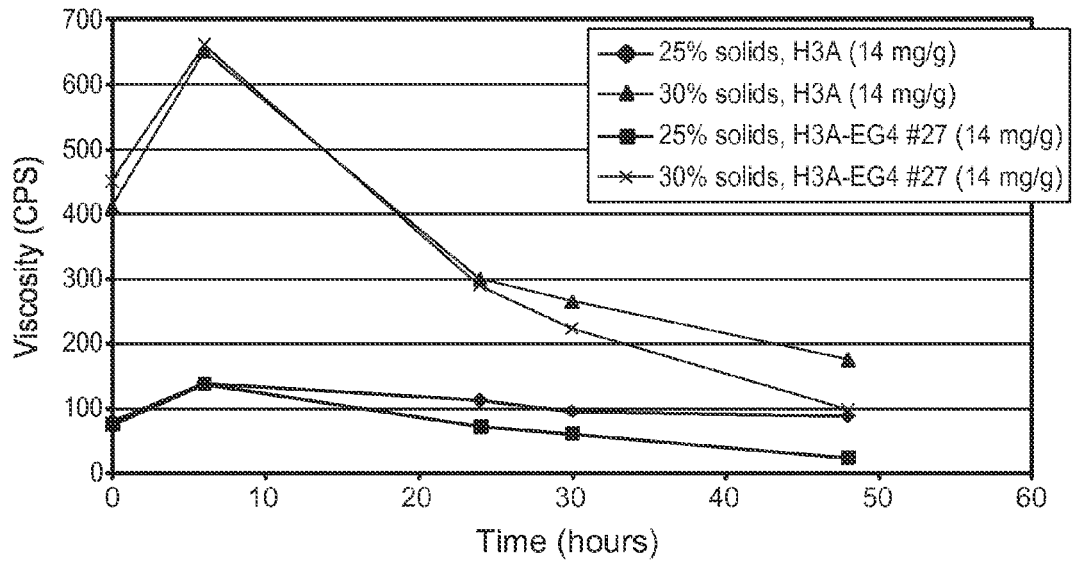
FIG. 44: depicts viscosity of saccharification of dilute ammonia pretreated corncob at 25% and 30% solids, using fermentation broths of H3A or of H3A/Eg4#27 broth at 14 mg/g cellulose, in accordance with the description of Example 19.

The dilute ammonia pretreated corncob was mixed with enzyme compositions at two solid loading conditions: 25% dry solids and 30% dry solids. Specifically, the pretreated biomass was mixed at 50° C. and pH 5.0 with 14 mg protein/g cellulose from a fermentation broth of either a *T. reesei* H3A (FIG. 9) or H3A/Eg4 #27 strain. Viscosity reduction was measured using a Brookfield Viscometer (Brookfield Engineering, Inc.). The results are indicated in FIG. 44.

Example 20: Determining the Effects of Various Cellulases on Viscosity Reduction and Glucose Production in Saccharification Process This study used various viscosity reducing enzymes, such as OPTIMASH™ BG, OPTIMASH™ TBG, OPTIMASH™ VR; or beta-glucosidase such as Accellerase® BG, in the presence of Accellerase® DUET in the saccharification process and determined the effects of these viscosity reducing enzymes in glucose production and viscosity reduction. Enzyme composition produced from H3A/EG4 integrated strain #27 was also included. Accellerase® 1500, Accellerase® DUET, Accellerase® BG, OPTIMASH™ BG, OPTIMASH™ TBG, and OPTIMASH™ VR were products available from Danisco US Inc., Genencor.

Pretreated wheat straw as described above was used. The composition analysis was performed and is listed in Table 2 (see Example 17).

The saccharification process was performed by incubating the pretreated wheat straw (25% dry matter) with various enzymes in reaction chambers. See, Larsen et al., The IBUS Process-Lignocellulosic Bioethanol Close to A commercial Reality, (2008) Chem. Eng. Tech. 31(5):765-772. The experimental conditions are shown in Tables 3 and 4. In each chamber, the total mass was 10 kg. The initial pH of the wheat straw was about 3.50 and was adjusted by adding $Na_2CO_3$ to pH 5.0. Glucose concentration was measured over time and cellulose conversion was calculated.

TABLE 3

| Experimental condition | Enzymes | Cellulase Loading mL/g cellulose | Viscosity Enzyme g/kg dry matter |
| --- | --- | --- | --- |
| 1 | Accellerase ® 1500 batch 1 | 0.22 | 0 |
| 2 | Accellerase ® DUET | 0.15 | 0 |
| 3 | Accellerase ® DUET | 0.25 | 0 |
| 4 | Accellerase ® DUET + Optimash ™ BG | 0.15 | 6 |
| 5 | Accellerase ® DUET + Optimash ™ TBG | 0.15 | 6 |
| 6 | Accellerase ® DUET + Optimash ™ VR | 0.15 | 6 |

TABLE 4

| Experimental condition | Enzymes | Cellulase Loading mL/g cellulose | Viscosity Enzyme g/kg dry matter |
| --- | --- | --- | --- |
| 7 | Accellerase ® 1500 (batch 1) | 0.22 | 0 |
| 8 | Accellerase ® 1500 (batch 2) | 0.22 | 0 |
| 9 | Accellerase ® DUET | 0.15 | 0 |
| 10 | Accellerase ® DUET + Accellerase ® BG | 0.15 | 0.1 |
| 11 | Accellerase ® DUET + Accellerase ® BG | 0.15 | 6 |
| 12 | H3A/Eg4#27 | 0.15 | 0 |

Experimental conditions 1-6 were conducted on the first day ("Day 1"), and experimental conditions 7-12 were conducted on the second day ("Day 2").

Figure 45:
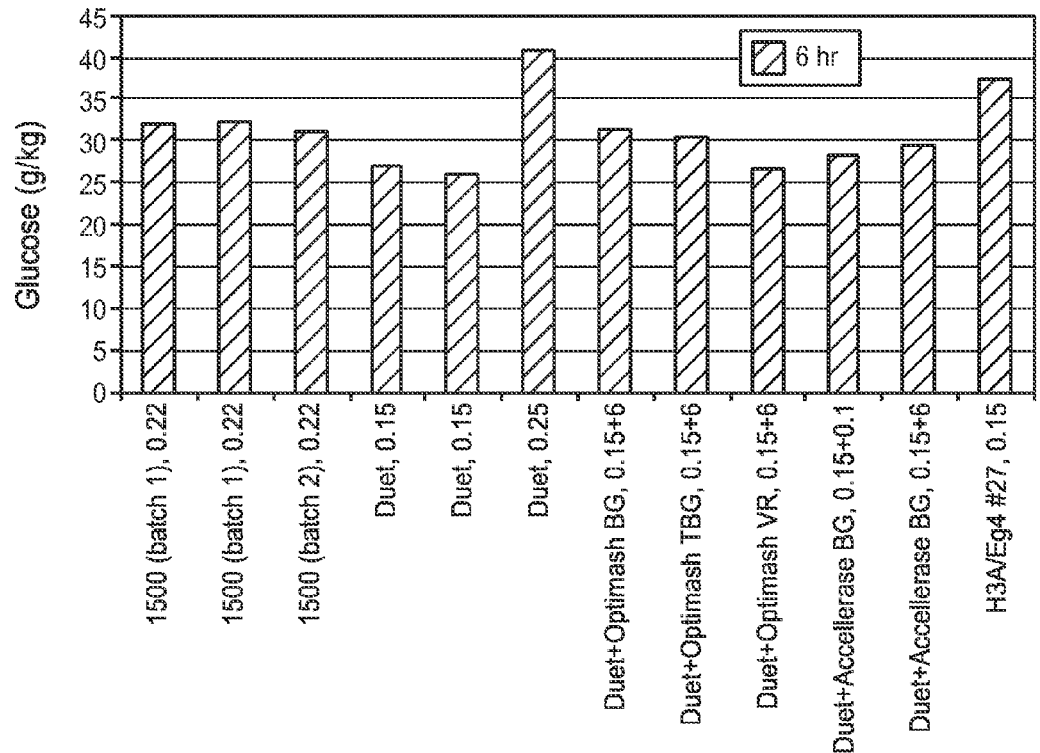
FIG. 45: depicts glucose concentration in 6-h saccharification, 25% dry matter, 50° C., pH5.0 using various enzyme compositions according to Example 20.

The glucose concentration was measured after 6 hour saccharification for each experimental condition. Accellerase® DUET at 0.25 mL/g cellulose resulted in 40.8 g glucose/kg after 6-h saccharification. See FIG. 45. The glucose concentration for Accellerase® DUET+OPTIMASH BG (or TBG) (0.15+6) (i.e., 0.15 mL Accellerase® DUET/g cellulose+6 g OPTIMASH BG (or TBG)/kg dry matter) was similar to the glucose concentration for Accellerase® 1500 at 0.22 mL/g cellulose. See FIG. 45. The glucose concentration for Accellerase® DUET+Accellerase BG at 0.15+6 (i.e., 0.15 mL Accellerase® DUET/g cellulose+6 g Accellerase BG/kg dry matter) was similar to the glucose concentration for Accellerase® 1500 at 0.22 mL/g cellulose and higher than the glucose concentration for Accellerase® DUET at 0.15 mL/g cellulose. See FIG. 45. High concentration of Accellerase® BG was able to reduce the viscosity of the saccharification reaction mixture. Using the enzyme composition produced from fermenting H3A/EG4 #27, at an amount of 0.15 mL/g cellulose yielded 37.5 g/kg glucose after 6-h saccharification, which was substantially higher than the glucose production for Accellerase® 1500 at 0.22 mL/g cellulose and Accellerase® DUET at 0.15 mL/g cellulose. See FIG. 45.

Figure 46:
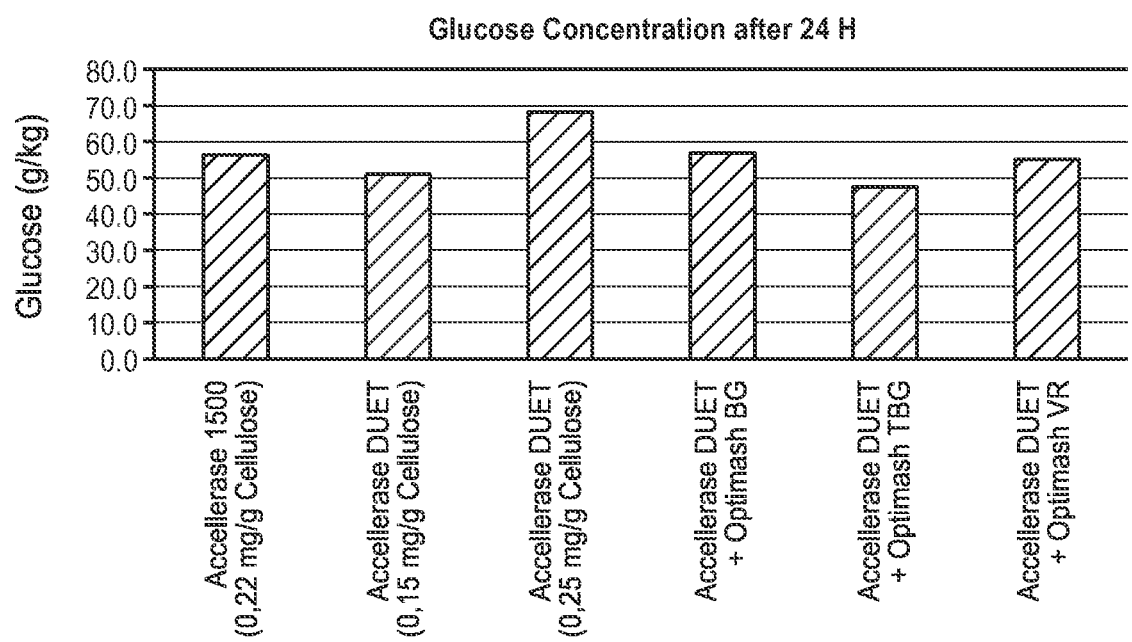
FIG. 46: depicts glucose concentration in 24-hour saccharification, 25% dry matter, 50° C., pH5.0 using various enzyme compositions according to Example 20.
Figure 47:
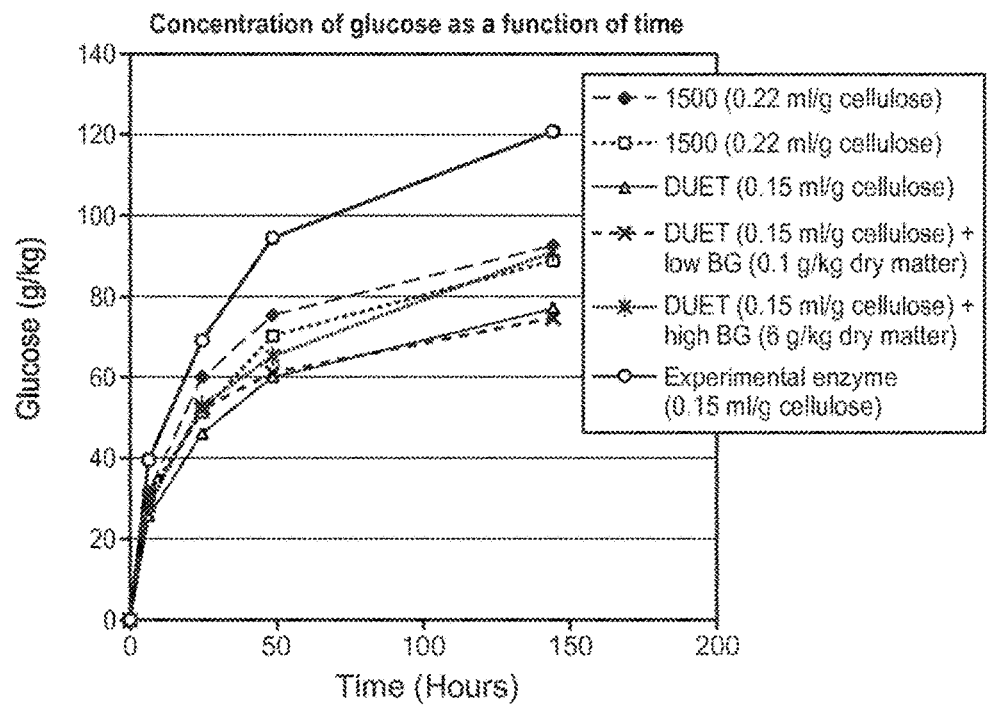
FIG. 47: depicts glucose concentration in saccharification over time, 25% dry matter, 50° C., pH5.0 using various enzyme compositions according to Example 20.
Figure 48:
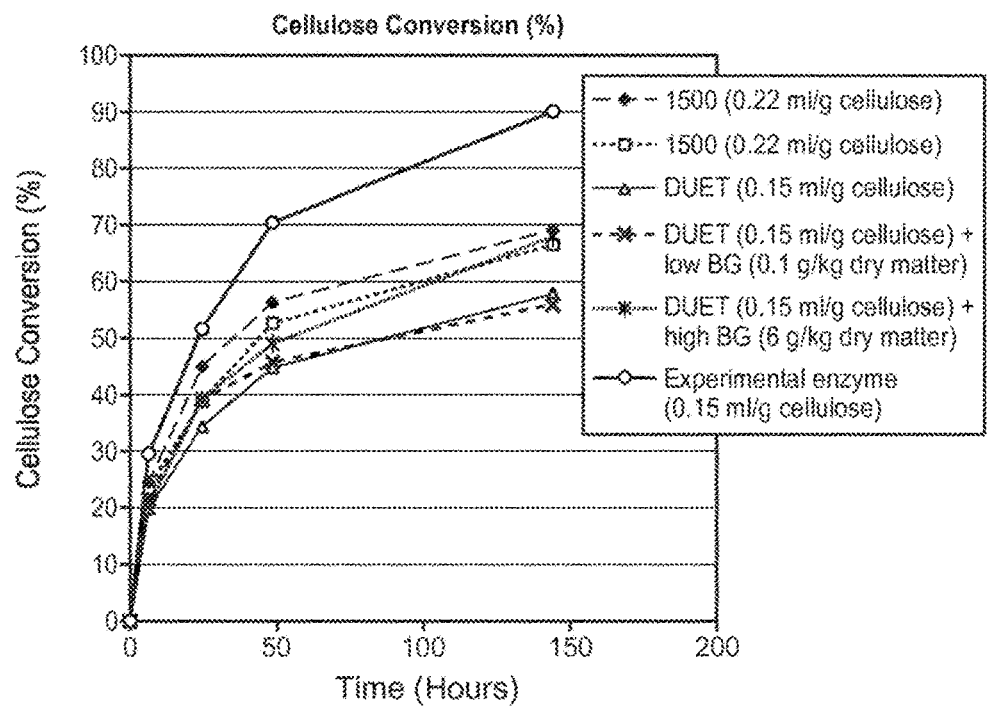
FIG. 48: depicts glucan conversion in saccharification over time, 25% dry matter, 50° C., pH5.0 using various enzyme compositions according to Example 20.

Glucose concentrations for various experimental conditions of Day 1's experiment were measured again after 24-h saccharification. See FIG. 46. The glucose concentration and cellulose conversion were measured over time for experimental conditions 7-12 on Day 2's experiment and results are shown in FIGS. 47 and 48.

Viscosity was observed by eye on Day 1's experiment after 6-h saccharification and is summarized in Table 6. More "+" indicates less viscous saccharification reaction mixture. In general, less viscous saccharification reaction mixture (e.g., thinner slurry) correlated with more glucose production.

TABLE 6

Viscosity observation for Day 1's experiment at 6-h

| Experimental condition | Enzymes | Viscosity Observation | Glucose (g/kg) |
|---|---|---|---|
| 1 | Accellerase ® 1500, 0.22 | ++ | 32.1 |
| 2 | Accellerase ® DUET, 0.15 | + | 27 |
| 3 | Accellerase ® DUET, 0.25 | ++++ | 40.8 |
| 4 | Accellerase ® DUET + Optimash BG | ++ | 31.4 |
| 5 | Accellerase ® DUET + Optimash TBG | + | 30.6 |
| 6 | Accellerase ® DUET + Optimash VR | +++ | 26.7 |

Viscosity of the saccharification reaction mixtures in various chambers on Day 2's experiment was observed by eye with reference to the visibility of the metal parts in each chamber. After 6-day of saccharification at 50° C., the saccharification mixture in chamber 3 (Experimental condition 9, Accellerase® DUET at 0.15 mL/g cellulose) was more viscous than the saccharification mixture in chamber 1 (Experimental condition 7) or 2 (Experimental condition 8, Accellerase® 1500 at 0.22 mL/g cellulose). Metal parts in chamber 3 could not be seen. The viscosity of the saccharification mixture in chamber 4 (Experimental condition 10, Accellerase DUET® at 0.15 mL/g cellulose+Accellerase® BG at 0.1 g/kg dry matter) was reduced compared to the viscosity of the saccharification mixture in chamber 3 (Accellerase® DUET at 0.15 mL/g cellulose). The viscosity of the saccharification mixture in chamber 5 (Experimental condition 11, Accellerase DUET® at 0.15 mL/g cellulose+ Accellerase BG at 6 g/kg dry matter) was more reduced compared to the viscosity of the saccharification mixture in chamber 4 (Accellerase® DUET at 0.15 mL/g cellulose+ Accellerase BG at 0.1 g/kg dry matter). Even with a high amount of Accellerase BG, the saccharification mixture (chamber 5, Accellerase DUET® at 0.15 mL/g cellulose+ Accellerase BG at 6 g/kg dry matter) was still more viscous than Accellerase® 1500 at 0.22 mL/g cellulose (chambers 1 and 2). However, with the addition of the enzyme composition produced from fermenting H3A/EG4 #27, it was surprisingly found that the viscosity of the saccharification mixture (chamber 6) was substantially reduced compared to the viscosity of the saccharification mixture in chamber 4 or 5. Metal parts in chamber 6 could be seen.

Example 21: Determining the Effects of Various Cellulases on Viscosity Reduction and Glucose Production in Saccharification Process A saccharification process was performed by incubating Inbicon pretreated wheat straw (25% dry matter) with various enzymes in reaction chambers. The experimental conditions are shown in Table 7. In each chamber, the total mass is 10 kg. The initial pH of the wheat straw was about 3.50 and was adjusted by adding $Na_2CO_3$ to pH 5.0. Accellerase® 1500, Accellerase® DUET, Accellerase® BG, Optimash™ BG, and Primafast® LUNA are products available from Genecor.

TABLE 7

| Experimental condition | Enzymes | Cellulase Loading mL/g cellulose | Viscosity Enzyme g/kg dry matter |
|---|---|---|---|
| 1 | Accellerase ® DUET | 0.15 | 0 |
| 2 | Accellerase ® 1500 | 0.22 | 0 |
| 3 | Accellerase ® DUET + Optimash BG | 0.15 | 1 |
| 4 | Accellerase ® DUET + Optimash BG | 0.15 | 2 |
| 5 | Accellerase ® DUET + Primafast LUNA | 0.15 | 1 |
| 6 | Accellerase ® DUET + Primafast LUNA | 0.15 | 2 |
| 7 | Accellerase ® DUET + Accellerase ® BG | 0.15 | 1 |
| 8 | Accellerase ® DUET + Accellerase ® BG | 0.15 | 2 |

TABLE 7-continued

| Experimental condition | Enzymes | Cellulase Loading mL/g cellulose | Viscosity Enzyme g/kg dry matter |
|---|---|---|---|
| 9 | Accellerase ® DUET + Optimash BG + Accellerase ® BG | 0.15 | 1 for Optimash BG; 1 for Accellerase ® BG |
| 10 | Accellerase ® DUET + Accellerase ® 1500 | 0.15 for Accellerase ® DUET; 0.22 for Accellerase ® 1500 | 0 |
| 11 | H3A/Eg4#27 + Optimash BG | 0.15 | 1 |
| 12 | H3A/Eg4#27 + Optimash BG | 0.15 | 2 |
| 13 | H3A/Eg4#27 + Primafast Luna | 0.15 | 1 |
| 14 | H3A/Eg4#27 + Primafast Luna | 0.15 | 2 |
| 15 | H3A/Eg4 #27 + Accellerase ® BG | 0.15 | 1 |
| 16 | H3A/Eg4#27 + Accellerase ® BG | 0.15 | 2 |

Glucose concentration was measured after 6 h, 24 h, 50 h, and 6 d of saccharification. Viscosity of saccharification reaction mixture was observed by eye and measured by a viscosity meter using methods known to one skilled in the art after 6 h, 24 h, 50 h, and 6 d of saccharification.

It was found that the glucose production of each of the experimental conditions 3-16 was increased compared to the glucose production of experimental condition 1. It was further found that the viscosity of each of the experimental conditions 3-16 was reduced compared to the viscosity of experimental condition 1.

This study also examined the glucose production and viscosity reduction in a saccharification process with the same experimental conditions as above but after a prolonged pre-hydrolysis time (such as 6 h, 9 h, 12 h, 24 h).

Example 22: Ascorbic Acid Effect on Avicel Hydrolysis by CBH1 and EG4

Crystalline cellulose (50 μL of 10% Avicel in 50 mM Sodium Acetate, pH 5.0) reactions were initiated by mixing together combinations of purified *T. reesei* CBH1 (5 mg/g final concentration), purified *T. reesei* Eg4 (10 mg/g final concentration), ascorbic acid (50 mM stock, 8.8 g/L final concentration) and manganese solution (10 mM final concentration) as described listed in FIG. 39A. Fifty (50) mM sodium acetate buffer, pH 5.0, was added to each sample to a final volume of 300 μL.

Figure 37:
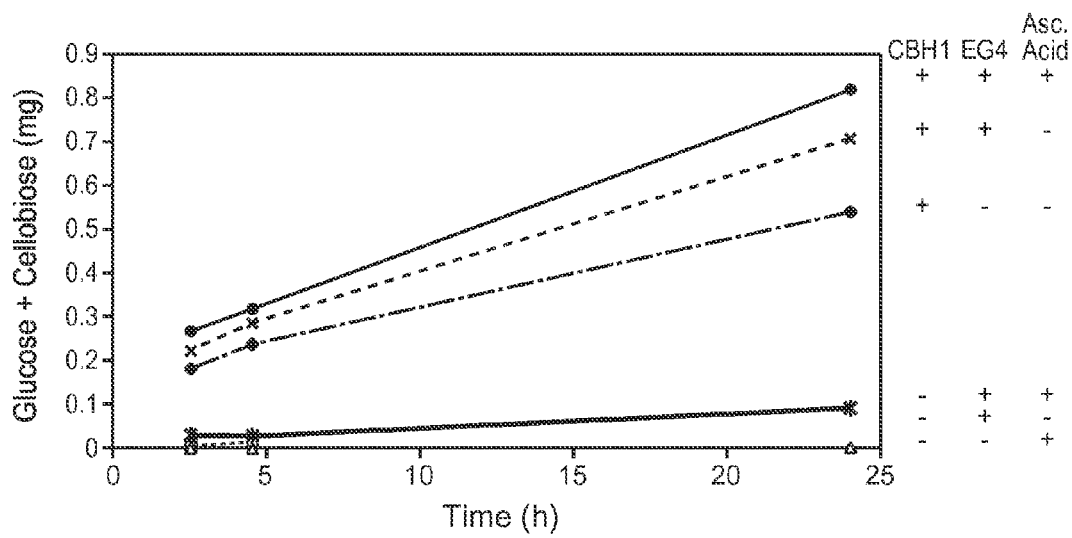
FIG. 37 depicts the effect of ascorbic acid when a composition comprising *T. reesei* Eg4 is used to treat Avicel in the presence or absence of CBH I, according to Example 22.

Reaction eppendorf tubes were vortexed and then placed in an Innova 44 incubator (New Brunswick Scientific) at 50° C., 200 rpm. Fifty (50) μL samples were taken from each tube at three time points (2.5, 4.5, 24 h) and quenched with 50 μL of 100 mM glycine buffer, pH 10.0. Samples were centrifuged at 3000 rpm for 5 minutes (Rotanta 460R Centrifuge, Hettich Zentrifugen) and supernatant (20 μL) was added to 100 μL of water in an HPLC 96-well microtiter plate (Agilent, 5042-1385). Glucose and cellobiose concentrations were measured by HPLC using Aminex HPX-87P column (300 mm×7.8 mm, 125-0098) pre-fitted with guard column. The results are shown in FIG. 37.

Next ascorbic acid effect on Avicel hydrolysis by CBH2 and EG4 was measured. Crystalline cellulose (80 μL of 10% Avicel in 50 mM Sodium Acetate, pH 5.0) reactions were initiated by mixing together combinations of purified *T. reesei* CBH2 (5 mg/g final concentration), purified *T. reesei* Eg4 (10 mg/g final concentration), ascorbic acid (50 mM stock, 8.8 g/l final concentration) and manganese solution (10 mM final concentration) as listed in FIG. 39B. Fifty (50) mM sodium acetate buffer, pH 5.0, was added to each sample to a final volume of 500 μL.

Figure 38:
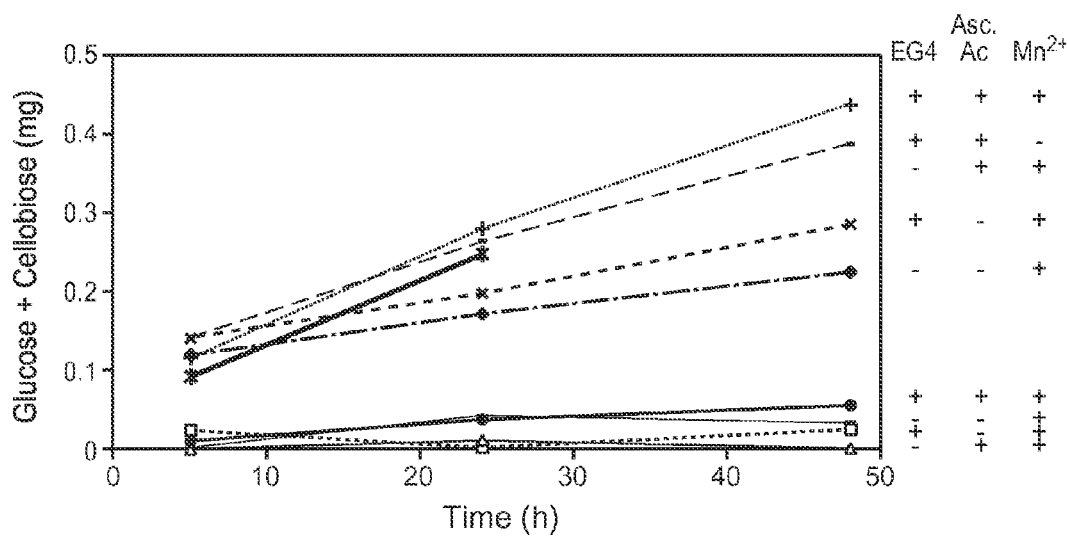
FIG. 38: depicts the effect of ascorbic acid on a composition comprising *T. reesei* Eg4 is used to treat Avicel in the presence/absence of CBH II, according to Example 22

Reaction eppendorf tubes were vortexed and then placed in an Innova 44 incubator (New Brunswick Scientific) at 50° C., 200 rpm. Fifty (50) μL samples were taken from each tube at three time points (5, 24, 48 h) and quenched with 50 μL of 100 mM glycine buffer, pH 10.0. Samples were centrifuged at 3000 rpm for 5 minutes (Rotanta 460R Centrifuge, Hettich Zentrifugen) and supernatant (20 μL) was added to 100 μL of water in an HPLC 96-well microtiter plate (Agilent, 5042-1385). Glucose and cellobiose concentrations were measured by HPLC using Aminex HPX-87P column (300 mm×7.8 mm, 125-0098) pre-fitted with guard column. Results are shown in FIG. 38.

What is claimed is:

1. A biomass saccharification mixture comprising:
   a. a pretreated biomass material; and
   b. a non-naturally occurring enzyme composition comprising a glycosyl hydrolase family 61 ("GH61") polypeptide having GH61/endoglucanase activity, wherein the GH61 polypeptide
      i) has at least 65% in sequence identity to residues 22-344 of SEQ ID NO:27; or
      ii) is encoded by a polynucleotide sequence or a complement thereof that has at least 65% sequence identity to SEQ ID NO:30; or
      iii) is encoded by a polynucleotide sequence that hybridizes under high stringency conditions to a sequence that is complementary to SEQ ID NO:30;
   wherein the enzyme composition is a whole cellulase comprising at least one polypeptide having cellobiohydrolase activity, at least one polypeptide having endoglucanase activity that is different from the GH61 polypeptide, and at least one polypeptide having beta-glucosidase activity and wherein the whole cellulase is derived from a host cell containing a heterologous expression cassette comprising a nucleic acid encoding the GH61 polypeptide, wherein the GH61 polypeptide is present in the whole cellulase in an amount of at least 6 wt % and no more than 50 wt % based on the total weight of protein in the whole cellulase and wherein said biomass saccharification mixture has a lower viscosity than a biomass saccharification mixture without the GH61 polypeptide and/or is capable of increasing the level of saccharification in the mixture as compared to the level of saccharification in a mixture having no or a lower level of GH-61 polypeptide.

2. The biomass saccharification mixture of claim 1, wherein the level of saccharification is measured by the yield of fermentable sugar after the mixture is incubated for a period of time sufficient to cause saccharification of the biomass.

3. The biomass saccharification mixture of claim 1 wherein the GH61 polypeptide having GH61/endoglucanase activity is derived from a filamentous fungus.

4. The biomass saccharification mixture of claim 3, wherein the filamentous fungus is one selected from the group: *Trichoderma, Humicola, Fusarium, Aspergillus, Neurospora, Penicillium, Cephalosporium, Achlya, Podospora, Endothia, Mucor, Cochliobolus, Pyricularia, Chrysosporium, Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei, Trichoderma viride, Geosmithia emersonii,* or *G. stearothermophilus.*

5. The biomass saccharification mixture of claim 1, wherein the at least one polypeptide having cellobiohydrolase activity is *T. reesei* CBH1, Af7A (SEQ ID NO:150), Af7B (SEQ ID NO:151), Cg7A (SEQ ID NO:152), Cg7B (SEQ ID NO:153), Tt7A (SEQ ID NO:154), Tt7B (SEQ ID NO:155), *T. reesei* CBH2, Tt6A (SEQ ID NO:156), St6A (SEQ ID NO:157), St6B (SEQ ID NO:158), ora variant thereof having at least 90% sequence identity thereto.

6. The biomass saccharification mixture of claim 1, wherein the at least one polypeptide having beta-glucosidase activity is:
   a. Fv3C (SEQ ID NO:100), Pa3D (SEQ ID NO:94), Fv3G (SEQ ID NO:96), Fv3D (SEQ ID NO:98), Tr3A (SEQ ID NO:102), Tr3B (SEQ ID NO:104), Te3A (SEQ ID NO:106), An3A (SEQ ID NO:108), Fo3A (SEQ ID NO:110), Gz3A (SEQ ID NO:112), Nh3A (SEQ ID NO:114), Vd3A (SEQ ID NO:116), Pa3G (SEQ ID NO:118), Tn3B (SEQ ID NO:119), or a variant thereof having at least 90% sequence identity thereto; or
   b. a polypeptide encoded by a polynucleotide (1) having at least 90% sequence identity to SEQ ID NO:99, 93, 95, 97, 101, 103, 105, 107, 109, 111, 113, 115, or 117; or (2) that hybridizes under high stringency conditions to a sequence that is complementary to SEQ ID NO: 99, 93, 95, 97, 101, 103, 105, 107, 109, 111, 113, 115, or 117.

7. The biomass saccharification mixture of claim 1, wherein the enzyme composition further comprises: (1) a polypeptide having xylanase activity, (2) a polypeptide having beta-xylosidase activity; and (3) a polypeptide having L-alpha-arabinofuranosidase activity.

8. The biomass saccharification mixture of claim 7, wherein the polypeptide having xylanase activity is:
   a. *T. reesei* Xyn3 (SEQ ID NO:76), *T. reesei* Xyn2 (SEQ ID NO:77), AfuXyn2 (SEQ ID NO:58), AfuXyn5 (SEQ ID NO:60), or a variant thereof having at least 90% sequence identity thereto; or
   b. a polypeptide encoded by a polynucleotide (1) having at least 90% sequence identity to SEQ ID NO:75, 57, or 59; or (2) that hybridizes under high stringency conditions to a sequence that is complementary to SEQ ID NO: 75, 57, or 59.

9. The biomass saccharification mixture of claim 7, wherein the at least one polypeptide having beta-xylosidase activity is:
   a. Fv3A (SEQ ID NO:36), Fv43A (SEQ ID NO:44), Pf43A (SEQ ID NO:38), Fv43D (SEQ ID NO:62), Fv39A (SEQ ID NO:42), Fv43E (SEQ ID NO:40), Fo43A (SEQ ID NO:52), Fv43B (SEQ ID NO:46), Pa51A (SEQ ID NO:48), Gz43A (SEQ ID NO:50), *T. reesei* Bxl1 (SEQ ID NO:78), or a variant thereof having at least 90% sequence identity thereto; or
   b. a polypeptide encoded by a polynucleotide (1) having at least 90% sequence identity to SEQ ID NO:35, 43, 37, 61, 41, 39, 51, 45, 47, 49, or 159; or (2) that hybridizes under high stringency conditions to a sequence that is complementary to SEQ ID NO: 35, 43, 37, 61, 41, 39, 51, 45, 47, 49, or 159.

10. The biomass saccharification mixture of claim 7, wherein the at least one polypeptide having L-alpha-arabinofuranosidase activity is:

a. Af43A (SEQ ID NO:54), Fv43B (SEQ ID NO:46), Pf51A (SEQ ID NO:56), Pa51A (SEQ ID NO:48), Fv51A (SEQ ID NO:66), or a variant thereof having at least 90% sequence identity thereto; or b. a polypeptide encoded by a polynucleotide (1) having at least 90% sequence identity to SEQ ID NO:53, 45, 55, 47, or 65; or (2) that hybridizes under high stringency conditions to a sequence that is complementary to SEQ ID NO: 53, 45, 55, 47, or 65.

11. The biomass saccharification mixture of claim 7, wherein the GH61 polypeptide is present in the whole cellulase in an amount of at least 8 wt % and no more than 35 wt % based on the total weight of protein in the whole cellulase.

12. The biomass saccharification mixture of claim 1, wherein the pretreated biomass material is subjected to pretreatment with an acid or a base, and wherein the pretreated biomass is adjusted to pH of about 4.0 to 6.5 before mixing with the enzyme composition.

13. The biomass saccharification mixture of claim 1, wherein the biomass material is present in the mixture in an amount of about 5 wt. % to about 60 wt. %, about 10 wt. % to about 50 wt. %, about 15 wt. % to about 40 wt. %, about 15 wt. % to about 30 wt. %, or about 20 wt. % to about 30 wt. %, referring to the amount of biomass material in its solid state relative to the total weight of the mixture.

14. A method of hydrolyzing a biomass material comprising incubating the biomass saccharification mixture of claim 1, under conditions suitable for hydrolyzing the biomass materials in the biomass saccharification mixture and for a sufficient period of time.

15. The method of claim 14, wherein the conditions suitable for hydrolyzing the biomass materials in the biomass saccharification mixture comprises: (1) a pH of about 3.5 to about 7.0; (2) for a duration of about 2 hours or longer; and/or (3) a temperature of about 20° C. to about 75° C.; or wherein the sufficient period of time comprises a time period of about 8 hours to about 72 hours.

16. The method of claim 14, wherein at any given time above 2 hours, the amount of fermentable sugars is produced by the biomass saccharifcation mixture is increased by at least about 5% as compared to the amount of fermentable sugars produced by a control biomass saccharification mixture comprising the same amount and type of biomass material, and the same composition of enzyme components but in the absence of the GH-61 polypeptide having GH61/endoglucanase activity.

17. The method of claim 14, wherein the viscosity of the biomass saccharification mixture is reduced by at least about 5%, about 10%, about 15%, about 20%, about 25%, about 30%, or about 35%, as compared to the viscosity of the control biomass saccharification mixture comprising the same amount and type of biomass material, and the same composition of enzyme components but in the absence of the GH61 polypeptide having GH61/endoglucanase activity.

18. A method of using the composition of claim 1 to convert a biomass material into fermentable sugars in a merchant enzyme supply model or an on-site bio-refinery model.

19. The biomass saccharification mixture of claim 1, wherein the polypeptide having endoglucanase activity is comprises *T. reesei* EG1 or *T. reesei* EG2.

* * * * *